US007960157B2

(12) United States Patent
Borns

(10) Patent No.: US 7,960,157 B2
(45) **Date of Patent: *Jun. 14, 2011**

(54) DNA POLYMERASE BLENDS AND USES THEREOF

(75) Inventor: Michael Borns, Escondido, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 1930 days.

This patent is subject to a terminal disclaimer.

(21) Appl. No.: 10/702,400

(22) Filed: Nov. 5, 2003

(65) Prior Publication Data

US 2004/0197800 A1 Oct. 7, 2004

Related U.S. Application Data

(63) Continuation of application No. 10/324,846, filed on Dec. 20, 2002, now abandoned.

(51) Int. Cl.
*C12N 9/12* (2006.01)
*C12P 19/34* (2006.01)

(52) U.S. Cl. ...... 435/194; 435/183; 435/69.7; 435/91.1; 530/350

(58) Field of Classification Search .................. 435/194
See application file for complete search history.

(56) References Cited

U.S. PATENT DOCUMENTS

| | | | | |
|---|---|---|---|---|
| 5,489,523 | A | 2/1996 | Mathur | 435/194 |
| 5,556,772 | A | 9/1996 | Sorge et al. | 435/91.2 |
| 5,834,285 | A | 11/1998 | Comb et al. | 435/194 |
| 5,972,603 | A | 10/1999 | Bedford et al. | 435/6 |
| 6,228,628 | B1 | 5/2001 | Gelfand et al. | 435/194 |
| 2002/0119461 | A1 | 8/2002 | Chatterjee | 435/6 |
| 2002/0164618 | A1 | 11/2002 | Callen et al. | 435/6 |

FOREIGN PATENT DOCUMENTS

| | | |
|---|---|---|
| JP | 11089588 | 4/1999 |
| JP | 2001269188 | 10/2001 |
| WO | WO9729209 | 8/1997 |
| WO | WO0118213 | 3/2001 |
| WO | 0132887 | 5/2001 |
| WO | WO0161015 | 8/2001 |
| WO | WO01/92501 | 12/2001 |
| WO | 0204022 | 1/2002 |
| WO | WO0234936 | 5/2002 |
| WO | 03060144 | 7/2003 |
| WO | 2004038007 | 5/2004 |
| WO | 2004087868 | 10/2004 |

OTHER PUBLICATIONS

Ngo et al. in The Protein Folding Problem and Tertiary Structure Prediction, 1994, Merz et al. (ed.), Birkhauser, Boston, MA, pp. 433 and 492-495.*
Komori et al., Protein Engineering, vol. 13, No. 1, pp. 41-47, 2000.*
International Search Report (PCT/US03/40421).
Bedford, et. al., PNAS (1997); v. 94, pp. 479-484.
Lim, et. al., J. Biol. Chem, (1999), v. 274(53): 38197-38203.
Motz, M., et al., J. Biol. Chem, (May 3, 2002); 277 (18); 16179-88.
Barnes, Wayne M., "PCR amplification of up to 35-kb DNA with high fidelity and high yield from γ bacteriophage templates," Proc. Natl. Acad. Sci. USA, Mar. 1994, vol. 91, pp. 2216-2220.
Pavlov, et al., "Helix-hairpin-helix motifs confer salt resistance and processivity on chimeric DNA polymerases," Proc. Natl. Acad. Sci. USA, Oct. 2002, vol. 99, No. 21, pp. 13510-13515.
Shimazaki, et al., "Over-expression of human DNA polymerase lambda in *E. coli* and characterization of the recombinant enzyme," Genes to Cells, Jul. 2002, vol. 7, pp. 639-651.
Supplementary Partial European Search Report, EP03797055, May 24, 2006.
Fogg, Mark J., et al., "Structural Basis for Uracil Recognition by Archaeal Family B DNA Polymerases", Nature Structural Biology, (2002) vol. 9, No. 12, pp. 922-927.

* cited by examiner

*Primary Examiner* — Richard G Hutson

(57) ABSTRACT

The present invention discloses novel blends of chimeric and non-chimeric thermostable DNA polymerases for use in PCR, DNA sequencing and mutagenesis protocols. The invention allows for PCR reactions with shorter extension times that will facilitate PCR amplification of genomic DNA templates and improve the efficacy of long PCR.

25 Claims, 298 Drawing Sheets

Oligonucleotide Primers for QuikChange Mutagenesis

V93E#1 5'-gAACATCCCCAAgATgAACCCACTATTAgAgAAAAAg-3' (SEQ ID NO: 5)

V93E#2 5'-CTTTTTCTCTAATAgTgggTTCATCTTggggATgTTC-3' (SEQ ID NO: 6)

V93R#1 5'-gAACATCCCCAAgATAgACCCACTATTAgAgAAAAAg-3' (SEQ ID NO: 7)

V93R#2 5'-CTTTTTCTCTAATAgTgggTCTATCTTggggATgTTC-3' (SEQ ID NO: 8)

V93N#1 5'-gAACATCCCCAAgATAACCCCACTATTAgAgAAAAAg-3' (SEQ ID NO: 9)

V93N#2 5'-CTTTTTCTCTAATAgTggggTTATCTTggggATgTTC-3' (SEQ ID NO: 10)

V93H#1 5'-gAACATCCCCAAgATCACCCCACTATTAgAgAAAAAg-3' (SEQ ID NO: 11)

V93H#2 5'-CTTTTTCTCTAATAgTggggTgATCTTggggATgTTC-3' (SEQ ID NO: 12)

V93X (for saturation mutagenesis; obtained V93G and V93L mutants from library)

5'-(Phosphate)gAACATCCCCAAgATNNKCCCACTATTAgAgAAAAAg-3' (SEQ ID NO: 13)

V93K#1 5'-gAACATCCCCAAgATAAACCCACTATTAgAg-3' (SEQ ID NO: 14)

V93K#2 5'-CTCTAATAgTgggTTTATCTTggggATgTTC-3' (SEQ ID NO: 15)

QCM#1 5'-(Phosphate)gAACATCCCCAAgATgCACCCACTATTAgAgAAAAAg- 3'(SEQ ID NO: 16)'

Alanine

QCM#2 5'-(Phosphate)gAACATCCCCAAgATgACCCCACTATTAgAgAAAAAg-3'(SEQ ID NO: 17)

Aspartic Acid

QCM#3 5'-(Phosphate)gAACATCCCCAAgATTgCCCCCACTATTAgAgAAAAAg-3' (SEQ ID NO: 18)

Cysteine

QCM#4 5'-(Phosphate)gAACATCCCCAAgATATACCCACTATTAgAgAAAAAg-3' (SEQ ID NO: 19)

Isoleucine

QCM#5 5'-(Phosphate)gAACATCCCCAAgATATgCCCACTATTAgAgAAAAAg-3' (SEQ ID NO: 20)

Methionine

QCM#6 5'-(Phosphate)gAACATCCCCAAgATTTCCCCACTATTAgAgAAAAAg-3' (SEQ ID NO: 21)

Phenylalanine

QCM#7 5'-(Phosphate)gAACATCCCCAAgATCCTCCCACTATTAgAgAAAAAg-3' (SEQ ID NO: 22)

Proline

QCM#8 5'-(Phosphate)gAACATCCCCAAgATAgCCCCACTATTAgAgAAAAAg-3' (SEQ ID NO: 23)

FIG. 1B

Serine

QCM#9 5'-(Phosphate)gAACATCCCCAAgATACACCCACTATTAgAgAAAAAg-3' (SEQ ID NO: 24)

Threonine

QCM#10 5'-(Phosphate)gAACATCCCCAAgATTACCCCACTATTAgAgAAAAAg-3' (SEQ ID NO: 25)

Tyrosine

QCM#11 5'-(Phosphate)g AACATCCCCAAgATTggCCCACTATTAgAgAAAAAg-3' (SEQ ID NO: 26)

Tryptophan

FIG. 1C

PFU DNA POLYMERASE

V93R MUTANT: NNN = AGA, AGG, CGA, CGC, CGG, CGT (ALL POSSIBLE CODONS FOR ARGININE) (SEQ ID NO: 27)

V93E MUTANT: NNN = GAA, GAG (ALL CODONS FOR GLUTAMIC ACID) (SEQ ID NO: 28)

```
ATGATTTTAG ATGTGGATTA CATAACTGAA GAAGGAAAAC CTGTTATTAG GCTATTCAAA 60
AAAGAGAACG GAAAATTTAA GATAGAGCAT GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC CAAGATNNNC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GATATAGAAA CCCTCTATCA CGAAGGAGAA GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
```

FIG. 4A-1

```
GAACTCGGGA AAGAATTCCT TCCAATGGAA ATTCAGCTTT CAAGATTAGT TGGACAACCT 1020
TTATGGGATG TTTCAAGGTC AAGCACAGGG AACCTTGTAG AGTGGTTCTT ACTTAGGAAA 1080
GCCTACGAAA GAAACGAAGT AGCTCCAAAC AAGCCAAGTG AAGAGGAGTA TCAAAGAAGG 1140
CTCAGGGAGA GCTACACAGG TGGATTCGTT AAAGAGCCAG AAAAGGGGTT GTGGGAAAAC 1200
ATAGTATACC TAGATTTTAG AGCCCTATAT CCCTCGATTA TAATTACCCA CAATGTTTCT 1260
CCCGATACTC TAAATCTTGA GGGATGCAAG AACTATGATA TCGCTCCTCA AGTAGGCCAC 1320
AAGTTCTGCA AGGACATCCC TGGTTTTATA CCAAGTCTCT TGGGACATTT GTTAGAGGAA 1380
AGACAAAAGA TTAAGACAAA AATGAAGGAA ACTCAAGATC CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA GAAAAGTTTG GATTTAAAGT CCTCTACATT 1620
GACACTGATG GTCTCTATGC AACTATCCCA GGAGGAGAAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
GAAGGAAAAG TCATTACTCG TGGTTTAGAG ATAGTTAGGA GAGATTGGAG TGAAATTGCA 1860
AAAGAAACTC AAGCTAGAGT TTTGGAGACA ATACTAAAAC ACGGAGATGT TGAAGAAGCT 1920
GTGAGAATAG TAAAAGAAGT AATACAAAAG CTTGCCAATT ATGAAATTCC ACCAGAGAAG 1980
CTCGCAATAT ATGAGCAGAT AACAAGACCA TTACATGAGT ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA GAATATTACA TGGAGAACCA GGTTCTTCCA 2220
GCGGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCCTAG 2328
```

FIG. 4A-2

PFU DNA POLYMERASE

G387P Mutant (CCN is the codon for Proline where N = C, G, A, or T)

V93R MUTANT: NNN = AGA, AGG, CGA, CGC, CGG, CGT (ALL POSSIBLE CODONS FOR ARGININE) (SEQ ID NO: 29)

V93E MUTANT: NNN = GAA, GAG (ALL CODONS FOR GLUTAMIC ACID) (SEQ ID NO: 30)

```
ATGATTTTAG ATGTGGATTA CATAACTGAA GAAGGAAAAC CTGTTATTAG GCTATTCAAA 60
AAAGAGAACG GAAAATTTAA GATAGAGCAT GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC CAAGATNNNC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GATATAGAAA CCCTCTATCA CGAAGGAGAA GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA ATTCAGCTTT CAAGATTAGT TGGACAACCT 1020
```

FIG. 4A-3

```
TTATGGGATG TTTCAAGGTC AAGCACAGGG AACCTTGTAG AGTGGTTCTT ACTTAGGAAA 1080
GCCTACGAAA GAAACGAAGT AGCTCCAAAC AAGCCAAGTG AAGAGGAGTA TCAAAGAAGG 1140
CTCAGGGAGA GCTACACACC NGGATTCGTT AAAGAGCCAG AAAAGGGGTT GTGGGAAAAC 1200
ATAGTATACC TAGATTTTAG AGCCCTATAT CCCTCGATTA TAATTACCCA CAATGTTTCT 1260
CCCGATACTC TAAATCTTGA GGGATGCAAG AACTATGATA TCGCTCCTCA AGTAGGCCAC 1320
AAGTTCTGCA AGGACATCCC TGGTTTTATA CCAAGTCTCT TGGGACATTT GTTAGAGGAA 1380
AGACAAAAGA TTAAGACAAA AATGAAGGAA ACTCAAGATC CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA GAAAAGTTTG GATTTAAAGT CCTCTACATT 1620
GACACTGATG GTCTCTATGC AACTATCCCA GGAGGAGAAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
GAAGGAAAAG TCATTACTCG TGGTTTAGAG ATAGTTAGGA GAGATTGGAG TGAAATTGCA 1860
AAAGAAACTC AAGCTAGAGT TTTGGAGACA ATACTAAAAC ACGGAGATGT TGAAGAAGCT 1920
GTGAGAATAG TAAAAGAAGT AATACAAAAG CTTGCCAATT ATGAAATTCC ACCAGAGAAG 1980
CTCGCAATAT ATGAGCAGAT AACAAGACCA TTACATGAGT ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA GAATATTACA TGGAGAACCA GGTTCTTCCA 2220
GCGGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCCTAG 2328
```

FIG. 4A-4

PFU DNA POLYMERASE

D141A/E143A Mutant (GCN is the codon for alanine where N = C, G, A, or T)

V93R MUTANT: NNN = AGA, AGG, CGA, CGC, CGG, CGT (ALL POSSIBLE CODONS FOR ARGININE) (SEQ ID NO: 31)

V93E MUTANT: NNN = GAA, GAG (ALL CODONS FOR GLUTAMIC ACID) (SEQ ID NO: 32)

ATGATTTTAG ATGTGGATTA CATAACTGAA GAAGGAAAAC CTGTTATTAG GCTATTCAAA 60
AAAGAGAACG GAAAATTTAA GATAGAGCAT GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC CAAGATNNNC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GCNATAGCNA CCCTCTATCA CGAAGGAGAA GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960

FIG. 4A-5

```
GAACTCGGGA AAGAATTCCT TCCAATGGAA ATTCAGCTTT CAAGATTAGT TGGACAACCT 1020
TTATGGGATG TTTCAAGGTC AAGCACAGGG AACCTTGTAG AGTGGTTCTT ACTTAGGAAA 1080
GCCTACGAAA GAAACGAAGT AGCTCCAAAC AAGCCAAGTG AAGAGGAGTA TCAAAGAAGG 1140
CTCAGGGAGA GCTACACAGGTGGATTCGTT AAAGAGCCAG AAAAGGGGTT GTGGGAAAAC 1200
ATAGTATACC TAGATTTTAG AGCCCTATAT CCCTCGATTA TAATTACCCA CAATGTTTCT 1260
CCCGATACTC TAAATCTTGA GGGATGCAAG AACTATGATA TCGCTCCTCA AGTAGGCCAC 1320
AAGTTCTGCA AGGACATCCC TGGTTTTATA CCAAGTCTCT TGGGACATTT GTTAGAGGAA 1380
AGACAAAAGA TTAAGACAAA AATGAAGGAA ACTCAAGATC CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA GAAAAGTTTG GATTTAAAGT CCTCTACATT 1620
GACACTGATG GTCTCTATGC AACTATCCCA GGAGGAGAAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT ACGAAGAAGA GGTATGCAGT AATAGATGAA 1800
GAAGGAAAAG TCATTACTCG TGGTTTAGAG ATAGTTAGGA GAGATTGGAG TGAAATTGCA 1860
AAAGAAACTC AAGCTAGAGT TTTGGAGACA ATACTAAAAC ACGGAGATGT TGAAGAAGCT 1920
GTGAGAATAG TAAAAGAAGT AATACAAAAG CTTGCCAATT ATGAAATTCC ACCAGAGAAG 1980
CTCGCAATAT ATGAGCAGAT AACAAGACCA TTACATGAGT ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA GAATATTACA TGGAGAACCA GGTTCTTCCA 2220
GCGGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCCTAG 2328
```

FIG. 4A-6

KOD DNA POLYMERASE

V93R MUTANT: NNN = AGA, AGG, CGA, CGC, CGG, CGT (ALL POSSIBLE CODONS FOR ARGININE) (SEQ ID NO: 33)

V93E MUTANT: NNN = GAA, GAG (ALL CODONS FOR GLUTAMIC ACID) (SEQ ID NO: 34)

```
ATGATCCTCG ACACTGACTA CATAACCGAG GATGGAAAGC CTGTCATAAG AATTTTCAAG 60
AAGGAAAACG GCGAGTTTAA GATTGAGTAC GACCGGACTT TTGAACCCTA CTTCTACGCC 120
CTCCTGAAGG ACGATTCTGC CATTGAGGAA GTCAAGAAGA TAACCGCCGA GAGGCACGGG 180
ACGGTTGTAA CGGTTAAGCG GGTTGAAAAG GTTCAGAAGA AGTTCCTCGG GAGACCAGTT 240
GAGGTCTGGA AACTCTACTT TACTCATCCG CAGGAC<u>NNN</u>C CAGCGATAAG GGACAAGATA 300
CGAGAGCATC CAGCAGTTAT TGACATCTAC GAGTACGACA TACCCTTCGC CAAGCGCTAC 360
CTCATAGACA AGGGATTAGT GCCAATGGAA GGCGACGAGG AGCTGAAAAT GCTCGCCTTC 420
GACATTGAAA CTCTCTACCA TGAGGGCGAG GAGTTCGCCG AGGGGCCAAT CCTTATGATA 480
AGCTACGCCG ACGAGGAAGG GGCCAGGGTG ATAACTTGGA AGAACGTGGA TCTCCCCTAC 540
GTTGACGTCG TCTCGACGGA GAGGGAGATG ATAAAGCGCT TCCTCCGTGT TGTGAAGGAG 600
AAAGACCCGG ACGTTCTCAT AACCTACAAC GGCGACAACT TCGACTTCGC CTATCTGAAA 660
AAGCGCTGTG AAAAGCTCGG AATAAACTTC GCCCTCGGAA GGGATGGAAG CGAGCCGAAG 720
ATTCAGAGGA TGGGCGACAG GTTTGCCGTC GAAGTGAAGG GACGGATACA CTTCGATCTC 780
TATCCTGTGA TAAGACGGAC GATAAACCTG CCCACATACA CGCTTGAGGC CGTTTATGAA 840
GCCGTCTTCG GTCAGCCGAA GGAGAAGGTT TACGCTGAGG AAATAACCAC AGCCTGGGAA 900
ACCGGCGAGA ACCTTGAGAG AGTCGCCCGC TACTCGATGG AAGATGCGAA GGTCACATAC 960
GAGCTTGGGA AGGAGTTCCT TCCGATGGAG GCCCAGCTTT CTCGCTTAAT CGGCCAGTCC 1020
CTCTGGGACG TCTCCCGCTC CAGCACTGGC AACCTCGTTG AGTGGTTCCT CCTCAGGAAG 1080
```

FIG. 4A-7

```
GCCTATGAGA GGAATGAGCT GGCCCCGAAC AAGCCCGATG AAAAGGAGCT GGCCAGAAGA 1140
CGGCAGAGCT ATGAAGGAGG CTATGTAAAA GAGCCCGAGA GAGGGTTGTG GGAGAACATA 1200
GTGTACCTAG ATTTTAGATC CCTGTACCCC TCAATCATCA TCACCCACAA CGTCTCGCCG 1260
GATACGCTCA ACAGAGAAGG ATGCAAGGAA TATGACGTTG CCCCACAGGT CGGCCACCGC 1320
TTCTGCAAGG ACTTCCCAGG ATTTATCCCG AGCCTGCTTG GAGACCTCCT AGAGGAGAGG 1380
CAGAAGATAA AGAAGAAGAT GAAGGCCACG ATTGACCCGA TCGAGAGGAA GCTCCTCGAT 1440
TACAGGCAGA GGGCCATCAA GATCCTGGCA AACAGCTACT ACGGTTACTA CGGCTATGCA 1500
AGGGCGCGCT GGTACTGCAA GGAGTGTGCA GAGAGCGTAA CGGCCTGGGG AAGGGAGTAC 1560
ATAACGATGA CCATCAAGGA GATAGAGGAA AAGTACGGCT TTAAGGTAAT CTACAGCGAC 1620
ACCGACGGAT TTTTTGCCAC AATACCTGGA GCCGATGCTG AAACCGTCAA AAAGAAGGCT 1680
ATGGAGTTCC TCAAGTATAT CAACGCCAAA CTTCCGGGCG CGCTTGAGCT CGAGTACGAG 1740
GGCTTCTACA AACGCGGCTT CTTCGTCACG AAGAAGAAGT ATGCGGTGAT AGACGAGGAA 1800
GGCAAGATAA CAACGCGCGG ACTTGAGATT GTGAGGCGTG ACTGGAGCGA GATAGCGAAA 1860
GAGACGCAGG CGAGGGTTCT TGAAGCTTTG CTAAAGGACG GTGACGTCGA GAAGGCCGTG 1920
AGGATAGTCA AAGAAGTTAC CGAAAAGCTG AGCAAGTACG AGGTTCCGCC GGAGAAGCTG 1980
GTGATCCACG AGCAGATAAC GAGGGATTTA AAGGACTACA AGGCAACCGG TCCCCACGTT 2040
GCCGTTGCCA AGAGGTTGGC CGCGAGAGGA GTCAAAATAC GCCCTGGAAC GGTGATAAGC 2100
TACATCGTGC TCAAGGGCTC TGGGAGGATA GGCGACAGGG CGATACCGTT CGACGAGTTC 2160
GACCCGACGA AGCACAAGTA CGACGCCGAG TACTACATTG AGAACCAGGT TCTCCCAGCC 2220
GTTGAGAGAA TTCTGAGAGC CTTCGGTTAC CGCAAGGAAG ACCTGCGCTA CCAGAAGACG 2280
AGACAGGTTG GTTTGAGTGC TTGGCTGAAG CCGAAGGGAA CTTGA  2325
```

FIG. 4A-8

Vent DNA POLYMERASE
V93R MUTANT: NNN = AGA, AGG, CGA, CGC, CGG, CGT (ALL POSSIBLE CODONS FOR ARGININE) (SEQ ID NO: 35)
V93E MUTANT: NNN = GAA, GAG (ALL CODONS FOR GLUTAMIC ACID) (SEQ ID NO: 36)

ATGATACTGG ACACTGATTA CATAACAAAA GATGGCAAGC CTATAATCCG AATTTTTAAG 60
AAAGAGAACG GGGAGTTTAA AATAGAACTT GACCCTCATT TTCAGCCCTA TATATATGCT 120
CTTCTCAAAG ATGACTCCGC TATTGAGGAG ATAAAGGCAA TAAAGGGCGA GAGACATGGA 180
AAAACTGTGA GAGTGCTCGA TGCAGTGAAA GTCAGGAAAA AATTTTTGGG AAGGGAAGTT 240
GAAGTCTGGA AGCTCATTTT CGAGCATCCC CAAGACNNNC CAGCTATGCG GGGCAAAATA 300
AGGGAACATC CAGCTGTGGT TGACATTTAC GAATATGACA TACCCTTTGC CAAGCGTTAT 360
CTCATAGACA AGGGCTTGAT TCCCATGGAG GGAGACGAGG AGCTTAAGCT CCTTGCCTTT 420
GATATTGAAA CGTTTTATCA TGAGGGAGAT GAATTTGGAA AGGGCGAGAT AATAATGATT 480
AGTTATGCCG ATGAAGAAGA GGCCAGAGTA ATCACATGGA AAAATATCGA TTTGCCGTAT 540
GTCGATGTTG TGTCCAATGA AAGAGAAATG ATAAAGCGTT TTGTTCAAGT TGTTAAAGAA 600
AAAGACCCCG ATGTGATAAT AACTTACAAT GGGGACAATT TTGATTTGCC GTATCTCATA 660
AAACGGGCAG AAAAGCTGGG AGTTCGGCTT GTCTTAGGAA GGGACAAAGA ACATCCCGAA 720
CCCAAGATTC AGAGGATGGG TGATAGTTTT GCTGTGGAAA TCAAGGGTAG AATCCACTTT 780
GATCTTTTCC CAGTTGTGCG AAGGACGATA AACCTCCCAA CGTATACGCT TGAGGCAGTT 840
TATGAAGCAG TTTTAGGAAA AACCAAAAGC AAATTAGGAG CAGAGGAAAT TGCCGCTATA 900
TGGGAAACAG AAGAAAGCAT GAAAAAACTA GCCCAGTACT CAATGGAAGA TGCTAGGGCA 960
ACGTATGAGC TCGGGAAGGA ATTCTTCCCC ATGGAAGCTG AGCTGGCAAA GCTGATAGGT 1020
CAAAGTGTAT GGGACGTCTC GAGATCAAGC ACCGGCAACC TCGTGGAGTG GTATCTTTTA 1080

FIG. 4A-9

```
AGGGTGGCAT ACGCGAGGAA TGAACTTGCA CCGAACAAAC CTGATGAGGA AGAGTATAAA 1140
CGGCGCTTAA GAACAACTTA CCTGGGAGGA TATGTAAAAG AGCCAGAAAA AGGTTTGTGG 1200
GAAAATATCA TTTATTTGGA TTTCCGCAGT CTGTACCCTT CAATAATAGT TACTCACAAC 1260
GTATCCCCAG ATACCCTTGA AAAAGAGGGC TGTAAGAATT ACGATGTTGC TCCGATAGTA 1320
GGATATAGGT TCTGCAAGGA CTTTCCGGGC TTTATTCCCT CCATACTCGG GGACTTAATT 1380
GCAATGAGGC AAGATATAAA GAAGAAAATG AAATCCACAA TTGACCCGAT CGAAAAGAAA 1440
ATGCTCGATT ATAGGCAAAG GGCTATTAAA TTGCTTGCAA ACAGCTATTA CGGCTATATG 1500
GGGTATCCTA AGGCAAGATG GTACTCGAAG GAATGTGCTG AAAGCGTTAC CGCATGGGGG 1560
AGACACTACA TAGAGATGAC GATAAGAGAA ATAGAGGAAA AGTTCGGCTT TAAGGTTCTT 1620
TATGCGGACA CTGACGGCTT TTATGCCACA ATACCCGGGG AAAAGCCTGA ACTCATTAAA 1680
AAGAAAGCCA AGGAATTCCT AAACTACATA AACTCCAAAC TTCCAGGTCT GCTTGAGCTT 1740
GAGTATGAGG GCTTTTACTT GAGAGGATTC TTTGTTACAA AAAAGCGCTA TGCAGTCATA 1800
GATGAAGAGG GCAGGATAAC AACAAGGGGC TTGGAAGTAG TAAGGAGAGA TTGGAGTGAG 1860
ATAGCTAAGG AGACTCAGGC AAAGGTTTTA GAGGCTATAC TTAAAGAGGG AAGTGTTGAA 1920
AAAGCTGTAG AAGTTGTTAG AGATGTTGTA GAGAAAATAG CAAAATACAG GGTTCCACTT 1980
GAAAAGCTTG TTATCCATGA GCAGATTACC AGGGATTTAA AGGACTACAA AGCCATTGGC 2040
CCTCATGTCG CGATAGCAAA AAGACTTGCC GCAAGAGGGA TAAAAGTGAA ACCGGGCACA 2100
ATAATAAGCT ATATCGTTCT CAAAGGGAGC GGAAAGATAA GCGATAGGGT AATTTTACTT 2160
ACAGAATACG ATCCTAGAAA ACACAAGTAC GATCCGGACT ACTACATAGA AAACCAAGTT 2220
TTGCCGGCAG TACTTAGGAT ACTCGAAGCG TTTGGATACA GAAAGGAGGA TTTAAGGTAT 2280
CAAAGCTCAA AACAAACCGG CTTAGATGCA TGGCTCAAGA GGTAG 2325
```

FIG. 4A-10

Deep Vent
V93R MUTANT: NNN = AGA, AGG, CGA, CGC, CGG, CGT (ALL POSSIBLE CODONS FOR ARGININE) (SEQ ID NO: 37)
V93E MUTANT: NNN = GAA, GAG (ALL CODONS FOR GLUTAMIC ACID) (SEQ ID NO: 38)

```
ATGATACTTG ACGCTGACTA CATCACCGAG GATGGGAAGC CGATTATAAG GATTTTCAAG    60
AAAGAAAACG GCGAGTTTAA GGTTGAGTAC GACAGAAACT TTAGACCTTA CATTTACGCT   120
CTCCTCAAAG ATGACTCGCA GATTGATGAG GTTAGGAAGA TAACCGCCGA GAGGCATGGG   180
AAGATAGTGA GAATTATAGA TGCCGAAAAG GTAAGGAAGA AGTTCCTGGG GAGGCCGATT   240
GAGGTATGGA GGCTGTACTT TGAACACCCT CAGGACNNNC CCGCAATAAG GGATAAGATA   300
AGAGAGCATT CCGCAGTTAT TGACATCTTT GAGTACGACA TTCCGTTCGC GAAGAGGTAC   360
CTAATAGACA AAGGCCTAAT TCCAATGGAA GGCGATGAAG AGCTCAAGTT GCTCGCATTT   420
GACATAGAAA CCCTCTATCA CGAAGGGGAG GAGTTCGCGA AGGGGCCCAT TATAATGATA   480
AGCTATGCTG ATGAGGAAGA AGCCAAAGTC ATAACGTGGA AAAAGATCGA TCTCCCGTAC   540
GTCGAGGTAG TTTCCAGCGA GAGGGAGATG ATAAAGCGGT TCCTCAAGGT GATAAGGGAG   600
AAAGATCCCG ATGTTATAAT TACCTACAAC GGCGATTCTT TCGACCTTCC CTATCTAGTT   660
AAGAGGGCCG AAAAGCTCGG GATAAAGCTA CCCCTGGGAA GGGACGGTAG TGAGCCAAAG   720
ATGCAGAGGC TTGGGGATAT GACAGCGGTG GAGATAAAGG GAAGGATACA CTTTGACCTC   780
TACCACGTGA TTAGGAGAAC GATAAACCTC CCAACATACA CCCTCGAGGC AGTTTATGAG   840
GCAATCTTCG GAAAGCCAAA GGAGAAAGTT TACGCTCACG AGATAGCTGA GGCCTGGGAG   900
ACTGGAAAGG GACTGGAGAG AGTTGCAAAG TATTCAATGG AGGATGCAAA GGTAACGTAC   960
GAGCTCGGTA GGGAGTTCTT CCCAATGGAG GCCCAGCTTT CAAGGTTAGT CGGCCAGCCC  1020
CTGTGGGATG TTTCTAGGTC TTCAACTGGC AACTTGGTGG AGTGGTACCT CCTCAGGAAG  1080
```

FIG. 4A-11

```
GCCTACGAGA GGAATGAATT GGCTCCAAAC AAGCCGGATG AGAGGGAGTA CGAGAGAAGG  1140
CTAAGGGAGA GCTACGCTGG GGGATACGTT AAGGAGCCGG AGAAAGGGCT CTGGGAGGGG  1200
TTAGTTTCCC TAGATTTCAG GAGCCTGTAC CCCTCGATAA TAATCACCCA TAACGTCTCA  1260
CCGGATACGC TGAACAGGGA AGGGTGTAGG GAATACGATG TCGCCCCAGA GGTTGGGCAC  1320
AAGTTCTGCA AGGACTTCCC GGGGTTTATC CCCAGCCTGC TCAAGAGGTT ATTGGATGAA  1380
AGGCAAGAAA TAAAAAGGAA GATGAAAGCT TCTAAAGACC CAATCGAGAA GAAGATGCTT  1440
GATTACAGGC AACGGGCAAT CAAAATCCTG GCAAACAGCT ATTATGGGTA TTATGGGTAC  1500
GCAAAAGCCC GTTGGTACTG TAAGGAGTGC GCAGAGAGCG TTACGGCCTG GGGGAGGGAA  1560
TATATAGAGT TCGTAAGGAA GGAACTGGAG GAAAAGTTCG GGTTCAAAGT CTTATACATA  1620
GACACAGATG GACTCTACGC CACAATTCCT GGGGCAAAAC CCGAGGAGAT AAAGAAGAAA  1680
GCCCTAGAGT TCGTAGATTA TATAAACGCC AAGCTCCCAG GGCTGTTGGA GCTTGAGTAC  1740
GAGGGCTTCT ACGTGAGAGG GTTCTTCGTG ACGAAGAAGA AGTATGCGTT GATAGATGAG  1800
GAAGGGAAGA TAATCACTAG GGGGCTTGAA ATAGTCAGGA GGGACTGGAG CGAAATAGCC  1860
AAAGAAACCC AAGCAAAAGT CCTAGAGGCT ATCCTAAAGC ATGGCAACGT TGAGGAGGCA  1920
GTAAAGATAG TTAAGGAGGT AACTGAAAAG CTGAGCAAGT ACGAAATACC TCCAGAAAAG  1980
CTAGTTATTT ACGAGCAGAT CACGAGGCCC CTTCACGAGT ACAAGGCTAT AGGTCCGCAC  2040
GTTGCCGTGG CAAAAAGGTT AGCCGCTAGA GGAGTAAAGG TGAGGCCTGG CATGGTGATA  2100
GGGTACATAG TGCTGAGGGG AGACGGGCCA ATAAGCAAGA GGGCTATCCT TGCAGAGGAG  2160
TTCGATCTCA GGAAGCATAA GTATGACGCT GAGTATTACA TAGAAAATCA GGTTTTACCT  2220
GCCGTTCTTA GAATATTAGA GGCCTTTGGG TACAGGAAAG AAGACCTCAG GTGGCAGAAG  2280
ACTAAACAGA CAGGTCTTAC GGCATGGCTT AACATCAAGA AGAAGTAA              2328
```

FIG. 4A-12

JDF-3
V93R MUTANT: NNN = AGA, AGG, CGA, CGC, CGG, CGT (ALL POSSIBLE CODONS
FOR ARGININE) (SEQ ID NO: 39)
V93E MUTANT: NNN = GAA, GAG (ALL CODONS FOR GLUTAMIC ACID) (SEQ ID NO: 40)
ATGATCCTTGACGTTGATTACATCACCGAGAATGGAAAGCCCGTCATCAGGGTCTTCAAGAAGGAGAACGGCGAGTTCA
GGATTGAATACGACCGCGAGTTCGAGCCCTACTTCTACGCGCTCCTCAGGGACGACTCTGCCATCGAAGAAATCAAAAA
GATAACCGCGGAGAGGCACGGCAGGGTCGTTAAGGTTAAGCGCGCGGAGAAGGTGAAGAAAAAGTTCCTCGGCAGGTCT
GTGGAGGTCTGGGTCCTCTACTTCACGCACCCGCAGGAC<u>NNN</u>CCGGCAATCCGCGACAAAATAAGGAAGCACCCCGCGG
TCATCGACATCTACGAGTACGACATACCCTTCGCCAAGCGCTACCTCATAGACAAGGGCCTAATCCCGATGGAAGGTGA
GGAAGAGCTTAAACTCATGTCCTTCGACATCGAGACGCTCTACCACGAGGGAGAAGAGTTTGGAACCGGGCCGATTCTG
ATGATAAGCTACGCCGATGAAAGCGAGGCGCGCGTGATAACCTGGAAGAAGATCGACCTTCCTTACGTTGAGGTTGTCT
CCACCGAGAAGGAGATGATTAAGCGCTTCTTGAGGGTCGTTAAGGAGAAGGACCCGGACGTGCTGATAACATACAACGG
CGACAACTTCGACTTCGCCTACCTGAAAAAGCGCTGTGAGAAGCTTGGCGTGAGCTTTACCCTCGGGAGGGACGGGAGC
GAGCCGAAGATACAGCGCATGGGGGACAGGTTTGCGGTCGAGGTGAAGGGCAGGGTACACTTCGACCTTTATCCAGTCA
TAAGGCGCACCATAAACCTCCCGACCTACACCCTTGAGGCTGTATACGAGGCGGTTTTCGGCAAGCCCAAGGAGAAGGT
CTACGCCGAGGAGATAGCCACCGCCTGGGAGACCGGCGAGGGGCTTGAGAGGGTCGCGCGCTACTCGATGGAGGACGCG
AGGGTTACCTACGAGCTTGGCAGGGAGTTCTTCCCGATGGAGGCCCAGCTTTCCAGGCTCATCGGCCAAGGCCTCTGGG
ACGTTTCCCGCTCCAGCACCGGCAACCTCGTCGAGTGGTTCCTCCTAAGGAAGGCCTACGAGAGGAACGAACTCGCTCC
CAACAAGCCCGACGAGAGGGAGCTGGCGAGGAGAAGGGGGGGCTACgcCGGTGGCTACGTCAAGGAGCCGGAGCGGGGA
CTGTGGGACAATATCGTGTATCTAGACTTTCGTAGTCTCTACCCTTCAATCATAATCACCCACAACGTCTCGCCAGATA
CGCTCAACCGCGAGGGGTGTAGGAGCTACGACGTTGCCCCCGAGGTCGGTCACAAGTTCTGCAAGGACTTCCCCGGCTT

FIG. 4A-13

CATTCCGAGCCTGCTCGGAAACCTGCTGGAGGAAAGGCAGAAGATAAAGAGGAAGATGAAGGCAACTCTCGACCCGCTG
GAGAAGAATCTCCTCGATTACAGGCAACGCGCCATCAAGATTCTCGCCAACAGCTACTACGGCTACTACGGCTATGCCA
GGGCAAGATGGTACTGCAGGGAGTGCGCCGAGAGCGTTACGGCATGGGGAAGGGAGTACATCGAAATGGTCATCAGAGA
GCTTGAGGAAAAGTTCGGTTTTAAAGTCCTCTATGCAGACACAGACGGTCTCCATGCCACCATTCCTGGAGCGGACGCT
GAAACAGTCAAGAAAAAGGCAATGGAGTTCTTAAACTATATCAATCCCAAACTGCCCGGCCTTCTCGAACTCGAATACG
AGGGCTTCTACGTCAGGGGCTTCTTCGTCACGAAGAAAAAGTACGCGGTCATCGACGAGGAGGGCAAGATAACCACGCG
CGGGCTTGAGATAGTCAGGCGCGACTGGAGCGAGATAGCGAAGGAGACGCAGGCGAGGGTTTTGGAGGCGATACTCAGG
CACGGTGACGTTGAAGAGGCCGTCAGAATTGTCAGGGAAGTCACCGAAAAGCTGAGCAAGTACGAGGTTCCGCCGGAGA
AGCTGGTTATCCACGAGCAGATAACGCGCGAGCTCAAGGACTACAAGGCCACCGGCCCGCACGTAGCCATAGCGAAgcG
TTTGGCCGCCAGAGGTGTTAAAATCCGGCCCGGAACTGTGATAAGCTACATCGTTCTGAAGGGCTCCGGAAGGATAGGC
GACAGGGCGATTCCCTTCGACGAGTTCGACCCGACGAAGCACAAGTACGATGCGGACTACTACATCGAGAACCAGGTTC
TGCCGGCAGTTGAGAGAATCCTCAGGGCCTTCGGCTACCGCAAGGAAGACCTGCGCTACCAGAAGACGAGGCAGGTCGG
GCTTGGCGCGTGGCTGAAGCCGAAGGGGAAGAAGAAGTGA

FIG. 4A-14

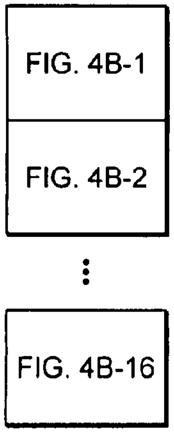

FIG. 4B

```
>Pfu V93R (SEQ ID NO:41)
MILDVDYITEEGKPVIRLFKKENGKFKIEHDRTFRPYIYALLRDDSKIEEVKKITGERHGKIVRIVDVEKVEKKFLG
KPITVWKLYLEHPQDRPTIREKVREHPAVVDIFEYDIPFAKRYLIDKGLIPMEGEEELKILAFDIETLYHEGEEFGK
GPIIMISYADENEAKVITWKNIDLPYVEVVSSEREMIKRFLRIIREKDPDIIVTYNGDSFDFPYLAKRAEKLGIKLT
IGRDGSEPKMQRIGDMTAVEVKGRIHFDLYHVITRTINLPTYTLEAVYEAIFGKPKEKVYADEIAKAWESGENLERV
AKYSMEDAKATYELGKEFLPMEIQLSRLVGQPLWDVSRSSTGNLVEWFLLRKAYERNEVAPNKPSEEEYQRRLRESY
TGGFVKEPEKGLWENIVYLDFRALYPSIIITHNVSPDTLNLEGCKNYDIAPQVGHKFCKDIPGFIPSLLGHLLEERQ
KIKTKMKETQDPIEKILLDYRQKAIKLLANSFYGYYGYAKARWYCKECAESVTAWGRKYIELVWKELEEKFGFKVLY
IDTDGLYATIPGGESEEIKKKALEFVKYINSKLPGLLELEYEGFYKRGFFVTKKRYAVIDEEGKVITRGLEIVRRDW
SEIAKETQARVLETILKHGDVEEAVRIVKEVIQKLANYEIPPEKLAIYEQITRPLHEYKAIGPHVAVAKKLAAKGVK
IKPGMVIGYIVLRGDGPISNRAILAEEYDPKKHKYDAEYYIENQVLPAVLRILEGFGYRKEDLRYQKTRQVGLTSWL
NIKKS //
```

FIG. 4B-1

>Pfu V93E (SEQ ID NO:42)
MILDVDYITEEGKPVIRLFKKENGKFKIEHDRTFRPYIYALLRDDSKIEEVKKITGERHGKIVRIVDVEKVEKKFLG
KPITVWKLYLEHPQDEPTIREKVREHPAVVDIFEYDIPFAKRYLIDKGLIPMEGEEELKILAFDIETLYHEGEEFGK
GPIIMISYADENEAKVITWKNIDLPYVEVVSSEREMIKRFLRIIREKDPDIIVTYNGDSFDFPYLAKRAEKLGIKLT
IGRDGSEPKMQRIGDMTAVEVKGRIHFDLYHVITRTINLPTYTLEAVYEAIFGKPKEKVYADEIAKAWESGENLERV
AKYSMEDAKATYELGKEFLPMEIQLSRLVGQPLWDVSRSSTGNLVEWFLLRKAYERNEVAPNKPSEEEYQRRLRESY
TGGFVKEPEKGLWENIVYLDFRALYPSIIITHNVSPDTLNLEGCKNYDIAPQVGHKFCKDIPGFIPSLLGHLLEERQ
KIKTKMKETQDPIEKILLDYRQKAIKLLANSFYGYYGYAKARWYCKECAESVTAWGRKYIELVWKELEEKFGFKVLY
IDTDGLYATIPGGESEEIKKKALEFVKYINSKLPGLLELEYEGFYKRGFFVTKKRYAVIDEEGKVITRGLEIVRRDW
SEIAKETQARVLETILKHGDVEEAVRIVKEVIQKLANYEIPPEKLAIYEQITRPLHEYKAIGPHVAVAKKLAAKGVK
IKPGMVIGYIVLRGDGPISNRAILAEEYDPKKHKYDAEYYIENQVLPAVLRILEGFGYRKEDLRYQKTRQVGLTSWL
NIKKS

FIG. 4B-2

>Pfu V93R/G387P (SEQ ID NO:43)
MILDVDYITEEGKPVIRLFKKENGKFKIEHDRTFRPYIYALLRDDSKIEEVKKITGERHGKIVRIVDVEKVEKKFLG
KPITVWKLYLEHPQDRPTIREKVREHPAVVDIFEYDIPFAKRYLIDKGLIPMEGEEELKILAFDIETLYHEGEEFGK
GPIIMISYADENEAKVITWKNIDLPYVEVVSSEREMIKRFLRIIREKDPDIIVTYNGDSFDFPYLAKRAEKLGIKLT
IGRDGSEPKMQRIGDMTAVEVKGRIHFDLYHVITRTINLPTYTLEAVYEAIFGKPKEKVYADEIAKAWESGENLERV
AKYSMEDAKATYELGKEFLPMEIQLSRLVGQPLWDVSRSSTGNLVEWFLLRKAYERNEVAPNKPSEEEYQRRLRESY
TPGFVKEPEKGLWENIVYLDFRALYPSIIITHNVSPDTLNLEGCKNYDIAPQVGHKFCKDIPGFIPSLLGHLLEERQ
KIKTKMKETQDPIEKILLDYRQKAIKLLANSFYGYYGYAKARWYCKECAESVTAWGRKYIELVWKELEEKFGFKVLY
IDTDGLYATIPGGESEEIKKKALEFVKYINSKLPGLLELEYEGFYKRGFFVTKKRYAVIDEEGKVITRGLEIVRRDW
SEIAKETQARVLETILKHGDVEEAVRIVKEVIQKLANYEIPPEKLAIYEQITRPLHEYKAIGPHVAVAKKLAAKGVK
IKPGMVIGYIVLRGDGPISNRAILAEEYDPKKHKYDAEYYIENQVLPAVLRILEGFGYRKEDLRYQKTRQVGLTSWL
NIKKS

FIG. 4B-3

>Pfu V93R/D141A/E143A(SEQ ID NO:44)
MILDVDYITEEGKPVIRLFKKENGKFKIEHDRTFRPYIYALLRDDSKIEEVKKITGERHGKIVRIVDVEKVEKKFLG
KPITVWKLYLEHPQDRPTIREKVREHPAVVDIFEYDIPFAKRYLIDKGLIPMEGEEELKILAFAIATLYHEGEEFGK
GPIIMISYADENEAKVITWKNIDLPYVEVVSSEREMIKRFLRIIREKDPDIIVTYNGDSFDFPYLAKRAEKLGIKLT
IGRDGSEPKMQRIGDMTAVEVKGRIHFDLYHVITRTINLPTYTLEAVYEAIFGKPKEKVYADEIAKAWESGENLERV
AKYSMEDAKATYELGKEFLPMEIQLSRLVGQPLWDVSRSSTGNLVEWFLLRKAYERNEVAPNKPSEEEYQRRLRESY
TGGFVKEPEKGLWENIVYLDFRALYPSIIITHNVSPDTLNLEGCKNYDIAPQVGHKFCKDIPGFIPSLLGHLLEERQ
KIKTKMKETQDPIEKILLDYRQKAIKLLANSFYGYYGYAKARWYCKECAESVTAWGRKYIELVWKELEEKFGFKVLY
IDTDGLYATIPGGESEEIKKKALEFVKYINSKLPGLLELEYEGFYKRGFFVTKKRYAVIDEEGKVITRGLEIVRRDW
SEIAKETQARVLETILKHGDVEEAVRIVKEVIQKLANYEIPPEKLAIYEQITRPLHEYKAIGPHVAVAKKLAAKGVK
IKPGMVIGYIVLRGDGPISNRAILAEEYDPKKHKYDAEYYIENQVLPAVLRILEGFGYRKEDLRYQKTRQVGLTSWL
NIKKS

FIG. 4B-4

>Pfu V93E/G387P(SEQ ID NO:45)

MILDVDYITEEGKPVIRLFKKENGKFKIEHDRTFRPYIYALLRDDSKIEEVKKITGERHGKIVRIVDVEKVEKKFLG
KPITVWKLYLEHPQDEPTIREKVREHPAVVDIFEYDIPFAKRYLIDKGLIPMEGEEELKILAFDIETLYHEGEEFGK
GPIIMISYADENEAKVITWKNIDLPYVEVVSSEREMIKRFLRIIREKDPDIIVTYNGDSFDFPYLAKRAEKLGIKLT
IGRDGSEPKMQRIGDMTAVEVKGRIHFDLYHVITRTINLPTYTLEAVYEAIFGKPKEKVYADEIAKAWESGENLERV
AKYSMEDAKATYELGKEFLPMEIQLSRLVGQPLWDVSRSSTGNLVEWFLLRKAYERNEVAPNKPSEEEYQRRLRESY
TPGFVKEPEKGLWENIVYLDFRALYPSIIITHNVSPDTLNLEGCKNYDIAPQVGHKFCKDIPGFIPSLLGHLLEERQ
KIKTKMKETQDPIEKILLDYRQKAIKLLANSFYGYYGYAKARWYCKECAESVTAWGRKYIELVWKELEEKFGFKVLY
IDTDGLYATIPGGESEEIKKKALEFVKYINSKLPGLLELEYEGFYKRGFFVTKKRYAVIDEEGKVITRGLEIVRRDW
SEIAKETQARVLETILKHGDVEEAVRIVKEVIQKLANYEIPPEKLAIYEQITRPLHEYKAIGPHVAVAKKLAAKGVK
IKPGMVIGYIVLRGDGPISNRAILAEEYDPKKHKYDAEYYIENQVLPAVLRILEGFGYRKEDLRYQKTRQVGLTSWL
NIKKS

FIG. 4B-5

>Pfu V93E/D141A/E143A(SEQ ID NO:46)
MILDVDYITEEGKPVIRLFKKENGKFKIEHDRTFRPYIYALLRDDSKIEEVKKITGERHGKIVRIVDVEKVEKKFLG
KPITVWKLYLEHPQDRPTIREKVREHPAVVDIFEYDIPFAKRYLIDKGLIPMEGEEELKILAFAIATLYHEGEEFGK
GPIIMISYADENEAKVITWKNIDLPYVEVVSSEREMIKRFLRIIREKDPDIIVTYNGDSFDFPYLAKRAEKLGIKLT
IGRDGSEPKMQRIGDMTAVEVKGRIHFDLYHVITRTINLPTYTLEAVYEAIFGKPKEKVYADEIAKAWESGENLERV
AKYSMEDAKATYELGKEFLPMEIQLSRLVGQPLWDVSRSSTGNLVEWFLLRKAYERNEVAPNKPSEEEYQRRLRESY
TGGFVKEPEKGLWENIVYLDFRALYPSIIITHNVSPDTLNLEGCKNYDIAPQVGHKFCKDIPGFIPSLLGHLLEERQ
KIKTKMKETQDPIEKILLDYRQKAIKLLANSFYGYYGYAKARWYCKECAESVTAWGRKYIELVWKELEEKFGFKVLY
IDTDGLYATIPGGESEEIKKKALEFVKYINSKLPGLLELEYEGFYKRGFFVTKKRYAVIDEEGKVITRGLEIVRRDW
SEIAKETQARVLETILKHGDVEEAVRIVKEVIQKLANYEIPPEKLAIYEQITRPLHEYKAIGPHVAVAKKLAAKGVK
IKPGMVIGYIVLRGDGPISNRAILAEEYDPKKHKYDAEYYIENQVLPAVLRILEGFGYRKEDLRYQKTRQVGLTSWL
NIKKS

FIG. 4B-6

>DEEP VENT V93R(SEQ ID NO:47)
MILDADYITEDGKPIIRIFKKENGEFKVEYDRNFRPYIYALLKDDSQIDEVRKITAERHGKIVRIIDAEKVRKKFLG
RPIEVWRLYFEHPQDRPAIRDKIREHSAVIDIFEYDIPFAKRYLIDKGLIPMEGDEELKLLAFDIETLYHEGEEFAK
GPIIMISYADEEEAKVITWKKIDLPYVEVVSSEREMIKRFLKVIREKDPDVIITYNGDSFDLPYLVKRAEKLGIKLP
LGRDGSEPKMQRLGDMTAVEIKGRIHFDLYHVIRRTINLPTYTLEAVYEAIFGKPKEKVYAHEIAEAWETGKGLERV
AKYSMEDAKVTYELGREFFPMEAQLSRLVGQPLWDVSRSSTGNLVEWYLLRKAYERNELAPNKPDEREYERRLRESY
AGGYVKEPEKGLWEGLVSLDFRSLYPSIIITHNVSPDTLNREGCREYDVAPEVGHKFCKDFPGFIPSLLKRLLDERQ
EIKRKMKASKDPIEKKMLDYRQRAIKILANSYYGYYGYAKARWYCKECAESVTAWGREYIEFVRKELEEKFGFKVLY
IDTDGLYATIPGAKPEEIKKKALEFVDYINAKLPGLLELEYEGFYVRGFFVTKKKYALIDEEGKIITRGLEIVRRDW
SEIAKETQAKVLEAILKHGNVEEAVKIVKEVTEKLSKYEIPPEKLVIYEQITRPLHEYKAIGPHVAVAKRLAARGVK
VRPGMVIGYIVLRGDGPISKRAILAEEFDLRKHKYDAEYYIENQVLPAVLRILEAFGYRKEDLRWQKTKQTGLTAWL
NIKKK

FIG. 4B-7

>DEEP VENT V93E(SEQ ID NO:48)
MILDADYITEDGKPIIRIFKKENGEFKVEYDRNFRPYIYALLKDDSQIDEVRKITAERHGKIVRIIDAEKVRKKFLG
RPIEVWRLYFEHPQDEPAIRDKIREHSAVIDIFEYDIPFAKRYLIDKGLIPMEGDEELKLLAFDIETLYHEGEEFAK
GPIIMISYADEEEAKVITWKKIDLPYVEVVSSEREMIKRFLKVIREKDPDVIITYNGDSFDLPYLVKRAEKLGIKLP
LGRDGSEPKMQRLGDMTAVEIKGRIHFDLYHVIRRTINLPTYTLEAVYEAIFGKPKEKVYAHEIAEAWETGKGLERV
AKYSMEDAKVTYELGREFFPMEAQLSRLVGQPLWDVSRSSTGNLVEWYLLRKAYERNELAPNKPDEREYERRLRESY
AGGYVKEPEKGLWEGLVSLDFRSLYPSIIITHNVSPDTLNREGCREYDVAPEVGHKFCKDFPGFIPSLLKRLLDERQ
EIKRKMKASKDPIEKKMLDYRQRAIKILANSYYGYYGYAKARWYCKECAESVTAWGREYIEFVRKELEEKFGFKVLY
IDTDGLYATIPGAKPEEIKKKALEFVDYINAKLPGLLELEYEGFYVRGFFVTKKKYALIDEEGKIITRGLEIVRRDW
SEIAKETQAKVLEAILKHGNVEEAVKIVKEVTEKLSKYEIPPEKLVIYEQITRPLHEYKAIGPHVAVAKRLAARGVK
VRPGMVIGYIVLRGDGPISKRAILAEEFDLRKHKYDAEYYIENQVLPAVLRILEAFGYRKEDLRWQKTKQTGLTAWL
NIKKK

FIG. 4B-8

>TGO V93R(SEQ ID NO:49)
MILDTDYITEDGKPVIRIFKKENGEFKIDYDRNFEPYIYALLKDDSAIEDVKKITAERHGTTVRVVRAEKVKKKFLG
RPIEVWKLYFTHPQDRPAIRDKIKEHPAVVDIYEYDIPFAKRYLIDKGLIPMEGDEELKMLAFDIETLYHEGEEFAE
GPILMISYADEEGARVITWKNIDLPYVDVVSTEKEMIKRFLKVVKEKDPDVLITYNGDNFDFAYLKKRSEKLGVKFI
LGREGSEPKIQRMGDRFAVEVKGRIHFDLYPVIRRTINLPTYTLEAVYEAIFGQPKEKVYAEEIAQAWETGEGLERV
ARYSMEDAKVTYELGKEFFPMEAQLSRLVGQSLWDVSRSSTGNLVEWFLLRKAYERNELAPNKPDERELARRRESYA
GGYVKEPERGLWENIVYLDFRSLYPSIIITHNVSPDTLNREGCEEYDVAPQVGHKFCKDFPGFIPSLLGDLLEERQK
VKKKMKATIDPIEKKLLDYRQRAIKILANSFYGYYGYAKARWYCKECAESVTAWGRQYIETTIREIEEKFGFKVLYA
DTDGFFATIPGADAETVKKKAKEFLDYINAKLPGLLELEYEGFYKRGFFVTKKKYAVIDEEDKITTRGLEIVRRDWS
EIAKETQARVLEAILKHGDVEEAVRIVKEVTEKLSKYEVPPEKLVIYEQITRDLKDYKATGPHVAVAKRLAARGIKI
RPGTVISYIVLKGSGRIGDRAIPFDEFDPAKHKYDAEYYIENQVLPAVERILRAFGYRKEDLRYQKTRQVGLGAWLK
PKT

FIG. 4B-9

>TGO V93E(SEQ ID NO:50)
MILDTDYITEDGKPVIRIFKKENGEFKIDYDRNFEPYIYALLKDDSAIEDVKKITAERHGTTVRVVRAEKVKKKFLG
RPIEVWKLYFTHPQDEPAIRDKIKEHPAVVDIYEYDIPFAKRYLIDKGLIPMEGDEELKMLAFDIETLYHEGEEFAE
GPILMISYADEEGARVITWKNIDLPYVDVVSTEKEMIKRFLKVVKEKDPDVLITYNGDNFDFAYLKKRSEKLGVKFI
LGREGSEPKIQRMGDRFAVEVKGRIHFDLYPVIRRTINLPTYTLEAVYEAIFGQPKEKVYAEEIAQAWETGEGLERV
ARYSMEDAKVTYELGKEFFPMEAQLSRLVGQSLWDVSRSSTGNLVEWFLLRKAYERNELAPNKPDERELARRRESYA
GGYVKEPERGLWENIVYLDFRSLYPSIIITHNVSPDTLNREGCEEYDVAPQVGHKFCKDFPGFIPSLLGDLLEERQK
VKKKMKATIDPIEKKLLDYRQRAIKILANSFYGYYGYAKARWYCKECAESVTAWGRQYIETTIREIEEKFGFKVLYA
DTDGFFATIPGADAETVKKKAKEFLDYINAKLPGLLELEYEGFYKRGFFVTKKKYAVIDEEDKITTRGLEIVRRDWS
EIAKETQARVLEAILKHGDVEEAVRIVKEVTEKLSKYEVPPEKLVIYEQITRDLKDYKATGPHVAVAKRLAARGIKI
RPGTVISYIVLKGSGRIGDRAIPFDEFDPAKHKYDAEYYIENQVLPAVERILRAFGYRKEDLRYQKTRQVGLGAWLK
PKT

FIG. 4B-10

>KOD V93R(SEQ ID NO:51)
MILDTDYITEDGKPVIRIFKKENGEFKIEYDRTFEPYFYALLKDDSAIEEVKKITAERHGTVVTVKRVEKVQKKFLG
RPVEVWKLYFTHPQDRPAIRDKIREHGAVIDIYEYDIPFAKRYLIDKGLVPMEGDEELKMLAFDIQTLYHEGEEFAE
GPILMISYADEEGARVITWKNVDLPYVDVVSTEREMIKRFLRVVKEKDPDVLITYNGDNFDFAYLKKRCEKLGINFA
LGRDGSEPKIQRMGDRFAVEVKGRIHFDLYPVIRRTINLPTYTLEAVYEAVFGQPKEKVYAEEITPAWETGENLERV
ARYSMEDAKVTYELGKEFLPMEAQLSRLIGQSLWDVSRSSTGNLVEWFLLRKAYERNELAPNKPDEKELARRRQSYE
GGYVKEPERGLWENIVYLDFRSLYPSIIITHNVSPDTLNREGCKEYDVAPQVGHRFCKDFPGFIPSLLGDLLEERQK
IKKKMKATIDPIERKLLDYRQRAIKILANSYYGYYGYARARWYCKECAESVTAWGREYITMTIKEIEEKYGFKVIYS
DTDGFFATIPGADAETVKKKAMEFLNYINAKLPGALELEYEGFYKRGFFVTKKKYAVIDEEGKITTRGLEIVRRDWS
EIAKETQARVLEALLKDGDVEKAVRIVKEVTEKLSKYEVPPEKLVIHEQITRDLKDYKATGPHVAVAKRLAARGVKI
RPGTVISYIVLKGSGRIGDRAIPFDEFDPTKHKYDAEYYIENQVLPAVERILRAFGYRKEDLRYQKTRQVGLSAWLK
PKGT

FIG. 4B-11

>KOD V93E(SEQ ID NO:52)
MILDTDYITEDGKPVIRIFKKENGEFKIEYDRTFEPYFYALLKDDSAIEEVKKITAERHGTVVTVKRVEKVQKKFLG
RPVEVWKLYFTHPQDEPAIRDKIREHGAVIDIYEYDIPFAKRYLIDKGLVPMEGDEELKMLAFDIQTLYHEGEEFAE
GPILMISYADEEGARVITWKNVDLPYVDVVSTEREMIKRFLRVVKEKDPDVLITYNGDNFDFAYLKKRCEKLGINFA
LGRDGSEPKIQRMGDRFAVEVKGRIHFDLYPVIRRTINLPTYTLEAVYEAVFGQPKEKVYAEEITPAWETGENLERV
ARYSMEDAKVTYELGKEFLPMEAQLSRLIGQSLWDVSRSSTGNLVEWFLLRKAYERNELAPNKPDEKELARRRQSYE
GGYVKEPERGLWENIVYLDFRSLYPSIIITHNVSPDTLNREGCKEYDVAPQVGHRFCKDFPGFIPSLLGDLLEERQK
IKKKMKATIDPIERKLLDYRQRAIKILANSYYGYYGYARARWYCKECAESVTAWGREYITMTIKEIEEKYGFKVIYS
DTDGFFATIPGADAETVKKKAMEFLNYINAKLPGALELEYEGFYKRGFFVTKKKYAVIDEEGKITTRGLEIVRRDWS
EIAKETQARVLEALLKDGDVEKAVRIVKEVTEKLSKYEVPPEKLVIHEQITRDLKDYKATGPHVAVAKRLAARGVKI
RPGTVISYIVLKGSGRIGDRAIPFDEFDPTKHKYDAEYYIENQVLPAVERILRAFGYRKEDLRYQKTRQVGLSAWLK
PKGT

FIG. 4B-12

>VENT V93R(SEQ ID NO:53)
MILDTDYITKDGKPIIRIFKKENGEFKIELDPHFQPYIYALLKDDSAIEEIKAIKGERHGKTVRVLDAVKVRKKFLG
REVEVWKLIFEHPQDRPAMRGKIREHPAVVDIYEYDIPFAKRYLIDKGLIPMEGDEELKLLAFDIETFYHEGDEFGK
GEIIMISYADEEEARVITWKNIDLPYVDVVSNEREMIKRFVQVVKEKDPDVIITYNGDNFDLPYLIKRAEKLGVRLV
LGRDKEHPEPKIORMGDSFAVEIKGRIHFDLFPVVRRTINLPTYTLEAVYEAVLGKTKSKLGAEEIAAIWETEESMK
KLAQYSMEDARATYELGKEFFPMEAELAKLIGQSVWDVSRSSTGNLVEWYLLRVAYARNELAPNKPDEEEYKRRLRT
TYLGGYVKEPEKGLWENIIYLDFRSLYPSIIVTHNVSPDTLEKEGCKNYDVAPIVGYRFCKDFPGFIPSILGDLIAM
RQDIKKKMKSTIDPIEKKMLDYRQRAIKLLANSYYGYMGYPKARWYSKECAESVTAWGRHYIEMTIREIEEKFGFKV
LYADTDGFYATIPGEKPELIKKKAKEFLNYINSKLPGLLELEYEGFYLRGFFVTKKRYAVIDEEGRITTRGLEVVRR
DWSEIAKETQAKVLEAILKEGSVEKAVEVVRDVVEKIAKYRVPLEKLVIHEQITRDLKDYKAIGPHVAIAKRLAARG
IKVKPGTIISYIVLKGSGKISDRVILLTEYDPRKHKYDPDYYIENQVLPAVLRILEAFGYRKEDLRYQSSKQTGLDA
WLKR

FIG. 4B-13

>VENT V93E(SEQ ID NO:54)
MILDTDYITKDGKPIIRIFKKENGEFKIELDPHFQPYIYALLKDDSAIEEIKAIKGERHGKTVRVLDAVKVRKKFLG
REVEVWKLIFEHPQDEPAMRGKIREHPAVVDIYEYDIPFAKRYLIDKGLIPMEGDEELKLLAFDIETFYHEGDEFGK
GEIIMISYADEEEARVITWKNIDLPYVDVVSNEREMIKRFVQVVKEKDPDVIITYNGDNFDLPYLIKRAEKLGVRLV
LGRDKEHPEPKIQRMGDSFAVEIKGRIHFDLFPVVRRTINLPTYTLEAVYEAVLGKTKSKLGAEEIAAIWETEESMK
KLAQYSMEDARATYELGKEFFPMEAELAKLIGQSVWDVSRSSTGNLVEWYLLRVAYARNELAPNKPDEEEYKRRLRT
TYLGGYVKEPEKGLWENIIYLDFRSLYPSIIVTHNVSPDTLEKEGCKNYDVAPIVGYRFCKDFPGFIPSILGDLIAM
RQDIKKKMKSTIDPIEKKMLDYRQRAIKLLANSYYGYMGYPKARWYSKECAESVTAWGRHYIEMTIREIEEKFGFKV
LYADTDGFYATIPGEKPELIKKKAKEFLNYINSKLPGLLELEYEGFYLRGFFVTKKRYAVIDEEGRITTRGLEVVRR
DWSEIAKETQAKVLEAILKEGSVEKAVEVVRDVVEKIAKYRVPLEKLVIHEQITRDLKDYKAIGPHVAIAKRLAARG
IKVKPGTIISYIVLKGSGKISDRVILLTEYDPRKHKYDPDYYIENQVLPAVLRILEAFGYRKEDLRYQSSKQTGLDA
WLKR

FIG. 4B-14

>JDF-3 V93R(SEQ ID NO:55)
MILDVDYITENGKPVIRVFKKENGEFRIEYDREFEPYFYALLRDDSAIEEIKKITAERHGRVVKVKRAEKVKKKFLGR
SVEVWVLYFTHPQDRPAIRDKIRKHPAVIDIYEYDIPFAKRYLIDKGLIPMEGEEELKLMSFDIETLYHEGEEFGTGP
ILMISYADESEARVITWKKIDLPYVEVVSTEKEMIKRFLRVVKEKDPDVLITYNGDNFDFAYLKKRCEKLGVSFTLGR
DGSEPKIQRMGDRFAVEVKGRVHFDLYPVIRRTINLPTYTLEAVYEAVFGKPKEKVYAEEIATAWETGEGLERVARYS
MEDARVTYELGREFFPMEAQLSRLIGQGLWDVSRSSTGNLVEWFLLRKAYERNELAPNKPDERELARRRGGYAGGYVK
EPERGLWDNIVYLDFRSLYPSIIITHNVSPDTLNREGCRSYDVAPEVGHKFCKDFPGFIPSLLGNLLEERQKIKRKMK
ATLDPLEKNLLDYRQRAIKILANSYYGYYGYARARWYCRECAESVTAWGREYIEMVIRELEEKFGFKVLYADTDGLHA
TIPGADAETVKKKAMEFLNYINPKLPGLLELEYEGFYVRGFFVTKKKYAVIDEEGKITTRGLEIVRRDWSEIAKETQA
RVLEAILRHGDVEEAVRIVREVTEKLSKYEVPPEKLVIHEQITRELKDYKATGPHVAIAKRLAARGVKIRPGTVISYI
VLKGSGRIGDRAIPFDEFDPTKHKYDADYYIENQVLPAVERILRAFGYRKEDLRYQKTRQVGLGAWLKPKGKKK

FIG. 4B-15

>JDF-3 V93E(SEQ ID NO:56)

MILDVDYITENGKPVIRVFKKENGEFRIEYDREFEPYFYALLRDDSAIEEIKKITAERHGRVVKVKRAEKVKKKFLGR
SVEVWVLYFTHPQDEPAIRDKIRKHPAVIDIYEYDIPFAKRYLIDKGLIPMEGEEELKLMSFDIETLYHEGEEFGTGP
ILMISYADESEARVITWKKIDLPYVEVVSTEKEMIKRFLRVVKEKDPDVLITYNGDNFDFAYLKKRCEKLGVSFTLGR
DGSEPKIQRMGDRFAVEVKGRVHFDLYPVIRRTINLPTYTLEAVYEAVFGKPKEKVYAEEIATAWETGEGLERVARYS
MEDARVTYELGREFFPMEAQLSRLIGQGLWDVSRSSTGNLVEWFLLRKAYERNELAPNKPDERELARRRGGYAGGYVK
EPERGLWDNIVYLDFRSLYPSIIITHNVSPDTLNREGCRSYDVAPEVGHKFCKDFPGFIPSLLGNLLEERQKIKRKMK
ATLDPLEKNLLDYRQRAIKILANSYYGYYGYARARWYCRECAESVTAWGREYIEMVIRELEEKFGFKVLYADTDGLHA
TIPGADAETVKKKAMEFLNYINPKLPGLLELEYEGFYVRGFFVTKKKYAVIDEEGKITTRGLEIVRRDWSEIAKETQA
RVLEAILRHGDVEEAVRIVREVTEKLSKYEVPPEKLVIHEQITRELKDYKATGPHVAIAKRLAARGVKIRPGTVISYI
VLKGSGRIGDRAIPFDEFDPTKHKYDADYYIENQVLPAVERILRAFGYRKEDLRYQKTRQVGLGAWLKPKGKKK

FIG. 4B-16

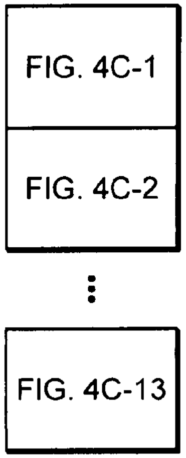

FIG. 4C

Tgo 93:
NNN = AGA, AGG, CGA, CGC, CGG, CGT (R)
(NUCLEOTIDE SEQUENCE: SEQ ID NO: 57; AMINO ACID SEQUENCE: SEQ ID NO: 58)

NNN = GAA, GAG (E)
(NUCLEOTIDE SEQUENCE: SEQ ID NO: 59; AMINO ACID SEQUENCE: SEQ ID NO: 60)

```
5'
atg atc ctc gat aca gac tac ata act gag gat gga aag ccc gtc atc       48
Met Ile Leu Asp Thr Asp Tyr Ile Thr Glu Asp Gly Lys Pro Val Ile
1               5                   10                  15

agg atc ttc aag aag gag aac ggc gag ttc aaa ata gac tac gac aga       96
Arg Ile Phe Lys Lys Glu Asn Gly Glu Phe Lys Ile Asp Tyr Asp Arg
            20                  25                  30

aac ttt gag cca tac atc tac gcg ctc ttg aag gac gac tct gcg att      144
Asn Phe Glu Pro Tyr Ile Tyr Ala Leu Leu Lys Asp Asp Ser Ala Ile
        35                  40                  45
```

FIG. 4C-1

```
gag gac gtc aag aag ata act gcc gag agg cac ggc act acc gtt agg      192
Glu Asp Val Lys Lys Ile Thr Ala Glu Arg His Gly Thr Thr Val Arg
    50                  55                  60

gtt gtc agg gcc gag aaa gtg aag aag aag ttc cta ggc agg ccg ata      240
Val Val Arg Ala Glu Lys Val Lys Lys Lys Phe Leu Gly Arg Pro Ile
65                  70                  75                  80

gag gtc tgg aag ctc tac ttc act cac ccc cag gac nnn ccc gca atc      288
Glu Val Trp Lys Leu Tyr Phe Thr His Pro Gln Asp Xaa Pro Ala Ile
                85                  90                  95

agg gac aag ata aag gag cat cct gcc gtt gtg gac atc tac gag tac      336
Arg Asp Lys Ile Lys Glu His Pro Ala Val Val Asp Ile Tyr Glu Tyr
            100                 105                 110
```

FIG. 4C-2

```
gac atc ccc ttc gcg aag cgc tac ctc ata gac aaa ggc tta atc ccg      384
Asp Ile Pro Phe Ala Lys Arg Tyr Leu Ile Asp Lys Gly Leu Ile Pro
        115                 120                 125

atg gag ggc gac gag gaa ctt aag atg ctc gcc ttc gac atc gag acg      432
Met Glu Gly Asp Glu Glu Leu Lys Met Leu Ala Phe Asp Ile Glu Thr
    130                 135                 140

ctc tat cac gag ggc gag gag ttc gcc gaa ggg cct atc ctg atg ata      480
Leu Tyr His Glu Gly Glu Glu Phe Ala Glu Gly Pro Ile Leu Met Ile
145                 150                 155                 160

agc tac gcc gac gag gaa ggg gcg cgc gtt att acc tgg aag aat atc      528
Ser Tyr Ala Asp Glu Glu Gly Ala Arg Val Ile Thr Trp Lys Asn Ile
                165                 170                 175
```

FIG. 4C-3

```
gac ctt ccc tat gtc gac gtc gtt tcc acc gag aag gag atg ata aag      576
Asp Leu Pro Tyr Val Asp Val Val Ser Thr Glu Lys Glu Met Ile Lys
            180                 185                 190

cgc ttc ctc aag gtc gtc aag gaa aag gat ccc gac gtc ctc ata acc      624
Arg Phe Leu Lys Val Val Lys Glu Lys Asp Pro Asp Val Leu Ile Thr
        195                 200                 205

tac aac ggc gac aac ttc gac ttc gcc tac ctc aag aag cgc tcc gag      672
Tyr Asn Gly Asp Asn Phe Asp Phe Ala Tyr Leu Lys Lys Arg Ser Glu
    210                 215                 220

aag ctc gga gtc aag ttc atc ctc gga agg gaa ggg agc gag ccg aaa      720
Lys Leu Gly Val Lys Phe Ile Leu Gly Arg Glu Gly Ser Glu Pro Lys
225                 230                 235                 240
```

FIG. 4C-4

```
atc cag cgc atg ggc gat cgc ttt gcg gtg gag gtc aag gga agg att      768
Ile Gln Arg Met Gly Asp Arg Phe Ala Val Glu Val Lys Gly Arg Ile
                245                 250                 255

cac ttc gac ctc tac ccc gtc att agg aga acg att aac ctc ccc act      816
His Phe Asp Leu Tyr Pro Val Ile Arg Arg Thr Ile Asn Leu Pro Thr
            260                 265                 270

tac acc ctt gag gca gta tat gaa gcc atc ttt gga cag ccg aag gag      864
Tyr Thr Leu Glu Ala Val Tyr Glu Ala Ile Phe Gly Gln Pro Lys Glu
        275                 280                 285

aag gtc tac gct gag gag ata gcg cag gcc tgg gaa acg ggc gag gga      912
Lys Val Tyr Ala Glu Glu Ile Ala Gln Ala Trp Glu Thr Gly Glu Gly
    290                 295                 300
```

FIG. 4C-5

```
tta gaa agg gtg gcc cgc tac tcg atg gag gac gca aag gta acc tat      960
Leu Glu Arg Val Ala Arg Tyr Ser Met Glu Asp Ala Lys Val Thr Tyr
305                 310                 315                 320

gaa ctc gga aaa gag ttc ttc cct atg gaa gcc cag ctc tcg cgc ctc     1008
Glu Leu Gly Lys Glu Phe Phe Pro Met Glu Ala Gln Leu Ser Arg Leu
                325                 330                 335

gta ggc cag agc ctc tgg gat gta tct cgc tcg agt acc gga aac ctc     1056
Val Gly Gln Ser Leu Trp Asp Val Ser Arg Ser Ser Thr Gly Asn Leu
            340                 345                 350

gtc gag tgg ttt ttg ctg agg aag gcc tac gag agg aat gaa ctt gca     1104
Val Glu Trp Phe Leu Leu Arg Lys Ala Tyr Glu Arg Asn Glu Leu Ala
        355                 360                 365
```

FIG. 4C-6

```
cca aac aag ccg gac gag agg gag ctg gca aga aga agg gag agc tac      1152
Pro Asn Lys Pro Asp Glu Arg Glu Leu Ala Arg Arg Arg Glu Ser Tyr
    370                 375                 380

gcg ggt gga tac gtc aag gag ccc gaa agg gga ctg tgg gag aac atc      1200
Ala Gly Gly Tyr Val Lys Glu Pro Glu Arg Gly Leu Trp Glu Asn Ile
385                 390                 395                 400

gtg tat ctg gac ttc cgc tcc ctg tat cct tcg ata ata atc acc cat      1248
Val Tyr Leu Asp Phe Arg Ser Leu Tyr Pro Ser Ile Ile Ile Thr His
                405                 410                 415

aac gtc tcc cct gat aca ctc aac agg gag ggt tgt gag gag tac gac      1296
Asn Val Ser Pro Asp Thr Leu Asn Arg Glu Gly Cys Glu Glu Tyr Asp
            420                 425                 430
```

FIG. 4C-7

```
gtg gct cct cag gta ggc cat aag ttc tgc aag gac ttc ccc ggc ttc      1344
Val Ala Pro Gln Val Gly His Lys Phe Cys Lys Asp Phe Pro Gly Phe
        435                 440                 445

atc cca agc ctc ctc gga gac ctc ttg gag gag aga cag aag gta aag      1392
Ile Pro Ser Leu Leu Gly Asp Leu Leu Glu Glu Arg Gln Lys Val Lys
    450                 455                 460

aag aag atg aag gcc act ata gac cca atc gag aag aaa ctc ctc gat      1440
Lys Lys Met Lys Ala Thr Ile Asp Pro Ile Glu Lys Lys Leu Leu Asp
465                 470                 475                 480

tac agg caa cga gca atc aaa atc ctt gct aat agc ttc tac ggt tac      1488
Tyr Arg Gln Arg Ala Ile Lys Ile Leu Ala Asn Ser Phe Tyr Gly Tyr
                485                 490                 495
```

FIG. 4C-8

```
tac ggc tat gca aag gcc cgc tgg tac tgc aag gag tgc gcc gag agc      1536
Tyr Gly Tyr Ala Lys Ala Arg Trp Tyr Cys Lys Glu Cys Ala Glu Ser
            500                 505                 510

gtt acc gct tgg ggc agg cag tac atc gag acc acg ata agg gaa ata      1584
Val Thr Ala Trp Gly Arg Gln Tyr Ile Glu Thr Thr Ile Arg Glu Ile
        515                 520                 525

gag gag aaa ttt ggc ttt aaa gtc ctc tac gcg gac aca gat gga ttt      1632
Glu Glu Lys Phe Gly Phe Lys Val Leu Tyr Ala Asp Thr Asp Gly Phe
    530                 535                 540

ttc gca aca ata cct gga gcg gac gcc gaa acc gtc aaa aag aag gca      1680
Phe Ala Thr Ile Pro Gly Ala Asp Ala Glu Thr Val Lys Lys Lys Ala
545                 550                 555                 560
```

FIG. 4C-9

```
aag gag ttc ctg gac tac atc aac gcc aaa ctg ccc ggc ctg ctc gaa      1728
Lys Glu Phe Leu Asp Tyr Ile Asn Ala Lys Leu Pro Gly Leu Leu Glu
                565                 570                 575

ctc gaa tac gag ggc ttc tac aag cgc ggc ttc ttc gtg acg aag aag      1776
Leu Glu Tyr Glu Gly Phe Tyr Lys Arg Gly Phe Phe Val Thr Lys Lys
            580                 585                 590

aag tac gcg gtt ata gac gag gag gac aag ata acg acg cgc ggg ctt      1824
Lys Tyr Ala Val Ile Asp Glu Glu Asp Lys Ile Thr Thr Arg Gly Leu
        595                 600                 605

gaa ata gtt agg cgt gac tgg agc gag ata gcg aag gag acg cag gcg      1872
Glu Ile Val Arg Arg Asp Trp Ser Glu Ile Ala Lys Glu Thr Gln Ala
    610                 615                 620
```

FIG. 4C-10

```
agg gtt ctt gag gcg ata cta aag cac ggt gac gtt gaa gaa gcg gta    1920
Arg Val Leu Glu Ala Ile Leu Lys His Gly Asp Val Glu Glu Ala Val
625                 630                 635                 640

agg att gtc aaa gag gtt acg gag aag ctg agc aag tac gag gtt cca    1968
Arg Ile Val Lys Glu Val Thr Glu Lys Leu Ser Lys Tyr Glu Val Pro
                645                 650                 655

ccg gag aag ctg gtc atc tac gag cag ata acc cgc gac ctg aag gac    2016
Pro Glu Lys Leu Val Ile Tyr Glu Gln Ile Thr Arg Asp Leu Lys Asp
            660                 665                 670

tac aag gcc acc ggg ccg cat gtg gct gtt gca aaa cgc ctc gcc gca    2064
Tyr Lys Ala Thr Gly Pro His Val Ala Val Ala Lys Arg Leu Ala Ala
        675                 680                 685
```

FIG. 4C-11

```
agg ggg ata aaa atc cgg ccc gga acg gtc ata agc tac atc gtg ctc      2112
Arg Gly Ile Lys Ile Arg Pro Gly Thr Val Ile Ser Tyr Ile Val Leu
    690                 695                 700

aaa ggc tcg gga agg att ggg gac agg gct ata ccc ttt gac gaa ttt      2160
Lys Gly Ser Gly Arg Ile Gly Asp Arg Ala Ile Pro Phe Asp Glu Phe
705                 710                 715                 720

gac ccg gca aag cac aag tac gat gca gaa tac tac atc gag aac cag      2208
Asp Pro Ala Lys His Lys Tyr Asp Ala Glu Tyr Tyr Ile Glu Asn Gln
                725                 730                 735

gtt ctt cca gct gtg gag agg att ctg agg gcc ttt ggt tac cgt aaa      2256
Val Leu Pro Ala Val Glu Arg Ile Leu Arg Ala Phe Gly Tyr Arg Lys
            740                 745                 750
```

FIG. 4C-12

```
gaa gat tta agg tat cag aaa acg cgg cag gtt ggc ttg ggg gcg tgg     2304
Glu Asp Leu Arg Tyr Gln Lys Thr Arg Gln Val Gly Leu Gly Ala Trp
        755                 760                 765

cta aaa cct aag aca tga                                             2322
Leu Lys Pro Lys Thr
```

Tgo93 (R): nnn = AGA, AGG, CGA, CGC, CGG, CGT (R)
Tgo 93 (R) amino acid sequence
Tgo 93 (E): nnn = GAA, GAG (E)
Tgo 93 (E)amino acid sequence
Tgo93 (D): nnn = GAT, GAC (D)
Tgo 93 (D) amino acid sequence
Tgo93 (K): nnn = AAA, AAG (K)
Tgo 93 (K) amino acid sequence
Tgo93 (Q): nnn = CAA, CAG (Q)
Tgo 93 (Q) amino acid sequence
Tgo93 (N): nnn = AAC, AAU (N)
Tgo 93 (N) amino acid sequence

FIG. 4C-13

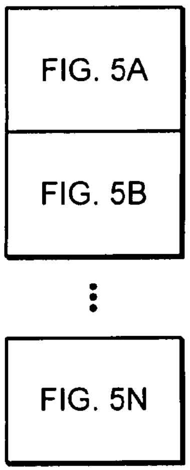

FIG. 5

PURIFIED THERMOSTABLE PYROCOCCUS FURIOSUS DNA POLYMERASE I

AMINO ACID SEQUENCE (SEQ ID NO: 62)

```
Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60
```

FIG. 5A

```
Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160
```

FIG. 5B

Ser Tyr Ala Asp Glu Asn Glu Ala Lys Val Ile Thr Trp Lys Asn Ile
165 170 175

Asp Leu Pro Tyr Val Glu Val Val Ser Ser Glu Arg Glu Met Ile Lys
180 185 190

Arg Phe Leu Arg Ile Ile Arg Glu Lys Asp Pro Asp Ile Ile Val Thr
195 200 205

Tyr Asn Gly Asp Ser Phe Asp Phe Pro Tyr Leu Ala Lys Arg Ala Glu
210 215 220

Lys Leu Gly Ile Lys Leu Thr Ile Gly Arg Asp Gly Ser Glu Pro Lys
225 230 235 240

Met Gln Arg Ile Gly Asp Met Thr Ala Val Glu Val Lys Gly Arg Ile
245 250 255

FIG. 5C

```
His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350
```

FIG. 5D

Val Glu Trp Phe Leu Leu Arg Lys Ala Tyr Glu Arg Asn Glu Val Ala
355 360 365

Pro Asn Lys Pro Ser Glu Glu Glu Tyr Gln Arg Arg Leu Arg Glu Ser
370 375 380

Tyr Thr Gly Gly Phe Val Lys Glu Pro Glu Lys Gly Leu Trp Glu Asn
385 390 395 400

Ile Val Tyr Leu Asp Phe Arg Ala Leu Tyr Pro Ser Ile Ile Ile Thr
405 410 415

His Asn Val Ser Pro Asp Thr Leu Asn Leu Glu Gly Cys Lys Asn Tyr
420 425 430

Asp Ile Ala Pro Gln Val Gly His Lys Phe Cys Lys Asp Ile Pro Gly
435 440 445

FIG. 5E

```
Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
    530                 535                 540
```

FIG. 5F

```
Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Thr Ile Leu Lys His Gly Asp Val Glu Glu Ala
625                 630                 635                 640
```

FIG. 5G

```
Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735
```

FIG. 5H

```
Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser
    770                 775
```

PURIFIED THERMOSTABLE PYROCOCCUS FURIOSUS DNA POLYMERASE I

NUCLEOTIDE SEQUENCE (SEQ ID NO: 61)

```
ccctggtcct gggtccacat atatgttctt actcgccttt atgaagaatc ccccagtcgc     60
tctaacctgg gttatagtga caaatcttcc tccaccaccg cccaagaagg ttatttctat    120
```

FIG. 5I

```
caactctaca cctcccctat tttctctctt atgagatttt taagtatagt tatagagaag    180
gttttatact ccaaactgag ttagtagata tgtggggagc ataatgattt tagatgtgga    240
ttacataact gaagaaggaa aacctgttat taggctattc aaaaaagaga acggaaaatt    300
taagatagag catgatagaa cttttagacc atacatttac gctcttctca gggatgattc    360
aaagattgaa gaagttaaga aaataacggg ggaaaggcat ggaaagattg tgagaattgt    420
tgatgtagag aaggttgaga aaaagtttct cggcaagcct attaccgtgt ggaaacttta    480
tttggaacat ccccaagatg ttcccactat tagagaaaaa gttagagaac atccagcagt    540
tgtggacatc ttcgaatacg atattccatt tgcaaagaga tacctcatcg acaaaggcct    600
aataccaatg gagggggaag aagagctaaa gattcttgcc ttcgatatag aaaccctcta    660
tcacgaagga gaagagtttg gaaaaggccc aattataatg attagttatg cagatgaaaa    720
tgaagcaaag gtgattactt ggaaaaacat agatcttcca tacgttgagg ttgtatcaag    780
```

FIG. 5J

```
cgagagagag atgataaaga gatttctcag gattatcagg gagaaggatc ctgacattat    840
agttacttat aatggagact cattcgactt cccatattta gcgaaaaggg cagaaaaact    900
tgggattaaa ttaaccattg gaagagatgg aagcgagccc aagatgcaga gaataggcga    960
tatgacggct gtagaagtca agggaagaat acatttcgac ttgtatcatg taataacaag   1020
gacaataaat ctcccaacat acacactaga ggctgtatat gaagcaattt ttggaaagcc   1080
aaaggagaag gtatacgccg acgagatagc aaaagcctgg gaaagtggag agaaccttga   1140
gagagttgcc aaatactcga tggaagatgc aaaggcaact tatgaactcg ggaaagaatt   1200
ccttccaatg gaaattcagc tttcaagatt agttggacaa cctttatggg atgtttcaag   1260
gtcaagcaca gggaaccttg tagagtggtt cttacttagg aaagcctacg aaagaaacga   1320
agtagctcca aacaagccaa gtgaagagga gtatcaaaga aggctcaggg agagctacac   1380
aggtggattc gttaaagagc cagaaaaggg gttgtgggaa aacatagtat acctagattt   1440
tagagcccta tatccctcga ttataattac ccacaatgtt tctcccgata ctctaaatct   1500
```

FIG. 5K

```
tgagggatgc aagaactatg atatcgctcc tcaagtaggc cacaagttct gcaaggacat   1560
ccctggtttt ataccaagtc tcttgggaca tttgttagag gaaagacaaa agattaagac   1620
aaaaatgaag gaaactcaag atcctataga aaaaatactc cttgactata gacaaaaagc   1680
gataaaactc ttagcaaatt ctttctacgg atattatggc tatgcaaaag caagatggta   1740
ctgtaaggag tgtgctgaga gcgttactgc ctggggaaga aagtacatcg agttagtatg   1800
gaaggagctc gaagaaaagt ttggatttaa agtcctctac attgacactg atggtctcta   1860
tgcaactatc ccaggaggag aaagtgagga aataaagaaa aaggctctag aatttgtaaa   1920
atacataaat tcaaagctcc ctggactgct agagcttgaa tatgaagggt tttataagag   1980
gggattcttc gttacgaaga agaggtatgc agtaatagat gaagaaggaa aagtcattac   2040
tcgtggttta gagatagtta ggagagattg gagtgaaatt gcaaaagaaa ctcaagctag   2100
agttttggag acaatactaa aacacggaga tgttgaagaa gctgtgagaa tagtaaaaga   2160
```

FIG. 5L

```
agtaatacaa aagcttgcca attatgaaat tccaccagag aagctcgcaa tatatgagca   2220
gataacaaga ccattacatg agtataaggc gataggtcct cacgtagctg ttgcaaagaa   2280
actagctgct aaaggagtta aaataaagcc aggaatggta attggataca tagtacttag   2340
aggcgatggt ccaattagca atagggcaat tctagctgag gaatacgatc ccaaaaagca   2400
caagtatgac gcagaatatt acattgagaa ccaggttctt ccagcggtac ttaggatatt   2460
ggagggattt ggatacagaa aggaagacct cagataccaa aagacaagac aagtcggcct   2520
aacttcctgg cttaacatta aaaaatccta gaaaagcgat agatatcaac ttttattctt   2580
tctaaccttt ttctatgaaa gaagaactga gcaggaatta ccagttcttc cgttatttta   2640
tgggtaatta aaaacccatg ctcttgggag aatcttcgaa taaaatccct aacttcaggc   2700
tttgctaagt gaatagaata aacaacatca ctcacttcaa acgccttcgt tagaaatggt   2760
ctatctgcat gcttctctgg ctcggaanng gaggattcat aacaacagta tcaacattct   2820
cagagaattg agaaacatca gaaactttga cttctacaac atttctaact ttgcaactct   2880
```

FIG. 5M

```
tcaagatttt ctaaaagaat tttaacggcc tcctcgtcaa tttcgacgac gtagatcttt   2940
tttgctccaa gcagagccgc tccaatggat aacacccctg ttcccgcacc caagtccgct   3000
acaatttttt ccttgtatct cctaatgtat aagcaagcca aaggagagta gatgctacct   3060
ttccgggagt tttgtattgc tctagccaag gtttgggatt tttgaatcct ttaactctgg   3120
aaagtataat ttcaagctcc ttcttcttca tgacagatga aaaattgttt tgtctctttt   3180
taacttttac agaaataact gtctcaaatt atgacaactc ttgacatttt tacttcatta   3240
ccagggtaat gtttttaagt atgaaatttt tctttcatag aggaggnnnn nngtcctctc   3300
ctcgatttcc ttggttgtgc tccatatgat aagcttccaa agtgggtgtt cagactttta   3360
gacactcaaa taccagacga caatggtgtg ctcactcaag ccccatatgg gttgagaaaa   3420
gtagaagcgg cactactcag atgcttcccc aggaatgagg ttgttgtagc tcntcccnga   3480
aagattgaga tgttcttgg                                                3499
```

FIG. 5N

Polymerase activity and Temperature optimum of Pfu N terminal truncation mutants

| Pfu clone # | Truncated after Pfu residue | Relative DNA polymerase activity | Temperature Optimum |
|---|---|---|---|
| 61 | H30 | Moderate | 65° |
| 72 | V66 | Similar to wild type | 70° |
| 81 | P128 | Low | Not tested |
| 92 | I158 | Low | Not tested |
| 3 | G125 | Similar to wild type | Not tested |
| 13/14 | K201 | low | 65° |

FIG. 7

Pyrococcus furiosus gene for archaeal histone (HMf-like)
(ACCESSION No: AB013081)
Nucleotide sequence (SEQ ID NO: 63)
Amino acid sequence (SEQ ID NO: 64)

```
 M   M   G   E   L   P   I   A   P   V   D   R   L   I   R   K   A   G      18
ATG ATG GGA GAA TTA CCA ATT GCC CCA GTT GAC AGA CTT ATA AGA AAG GCT GGT     54

 A   Q   R   V   S   E   Q   A   A   K   V   L   A   E   H   L   E   E      36
GCT CAG AGA GTT AGC GAG CAA GCA GCT AAG GTA CTT GCA GAG CAC CTT GAG GAA    108

 K   A   I   E   I   A   K   K   A   V   D   L   A   K   H   A   G   R      54
AAA GCT ATT GAG ATC GCA AAA AAG GCA GTA GAT CTT GCA AAG CAC GCA GGT AGA    162

 K   T   V   K   V   E   D   I   K   L   A   I   K   S   *                  69
AAG ACC GTT AAG GTC GAA GAC ATT AAG CTC GCA ATT AAG AGC TGA                207
```

| FIG. 8B-1 |
|---|
| FIG. 8B-2 |
| ⋮ |
| FIG. 8B-7 |

(HMf-like)-Taq DNA polymerase fusion protein

Nucleotide sequence (SEQ ID NO: 63) // Nucleotide sequence (SEQ ID NO: 65)
Amino acid sequence (SEQ ID NO: 64) // Amino acid sequence (SEQ ID NO: 66)

```
 M   M   G   E   L   P   I   A   P   V   D   R   L   I   R   K   A   G     18
ATG ATG GGA GAA TTA CCA ATT GCC CCA GTT GAC AGA CTT ATA AGA AAG GCT GGT    54

 A   Q   R   V   S   E   Q   A   A   K   V   L   A   E   H   L   E   E     36
GCT CAG AGA GTT AGC GAG CAA GCA GCT AAG GTA CTT GCA GAG CAC CTT GAG GAA   108

 K   A   I   E   I   A   K   K   A   V   D   L   A   K   H   A   G   R     54
AAA GCT ATT GAG ATC GCA AAA AAG GCA GTA GAT CTT GCA AAG CAC GCA GGT AGA   162

 K   T   V   K   V   E   D   I   K   L   A   I   K   S                     69
AAG ACC GTT AAG GTC GAA GAC ATT AAG CTC GCA ATT AAG AGC

    G   G   G
// GGC GGC GGT
```

FIG. 8B-1

```
 V   T   S   G   M   L   P   L   F   E   P   K   G   R   V   L   L   V
GTC ACT AGT GGG ATG CTG CCC CTC TTT GAG CCC AAG GGC CGG GTC CTC CTG GTG

 D   G   H   H   L   A   Y   R   T   F   H   A   L   K   G   L   T   T
GAC GGC CAC CAC CTG GCC TAC CGC ACC TTC CAC GCC CTG AAG GGC CTC ACC ACC

 S   R   G   E   P   V   Q   A   V   Y   G   F   A   K   S   L   L   K
AGC CGG GGG GAG CCG GTG CAG GCG GTC TAC GGC TTC GCC AAG AGC CTC CTC AAG

 A   L   K   E   D   G   D   A   V   I   V   V   F   D   A   K   A   P
GCC CTC AAG GAG GAC GGG GAC GCG GTG ATC GTG GTC TTT GAC GCC AAG GCC CCC

 S   F   R   H   E   A   Y   G   G   Y   K   A   G   R   A   P   T   P
TCC TTC CGC CAC GAG GCC TAC GGG GGG TAC AAG GCG GGC CGG GCC CCC ACG CCA

 E   D   F   P   R   Q   L   A   L   I   K   E   L   V   D   L   L   G
GAG GAC TTT CCC CGG CAA CTC GCC CTC ATC AAG GAG CTG GTG GAC CTC CTG GGG

 L   A   R   L   E   V   P   G   Y   E   A   D   D   V   L   A   S   L
CTG GCG CGC CTC GAG GTC CCG GGC TAC GAG GCG GAC GAC GTC CTG GCC AGC CTG

 A   K   K   A   E   K   E   G   Y   E   V   R   I   L   T   A   D   K
GCC AAG AAG GCG GAA AAG GAG GGC TAC GAG GTC CGC ATC CTC ACC GCC GAC AAA
```

FIG. 8B-2

```
 D   L   Y   Q   L   L   S   D   R   I   H   V   L   H   P   E   G   Y
GAC CTT TAC CAG CTC CTT TCC GAC CGC ATC CAC GTC CTC CAC CCC GAG GGG TAC

 L   I   T   P   A   W   L   W   E   K   Y   G   L   R   P   D   Q   W
CTC ATC ACC CCG GCC TGG CTT TGG GAA AAG TAC GGC CTG AGG CCC GAC CAG TGG

 A   D   Y   R   A   L   T   G   D   E   S   D   N   L   P   G   V   K
GCC GAC TAC CGG GCC CTG ACC GGG GAC GAG TCC GAC AAC CTT CCC GGG GTC AAG

 G   I   G   E   K   T   A   R   K   L   L   E   E   W   G   S   L   E
GGC ATC GGG GAG AAG ACG GCG AGG AAG CTT CTG GAG GAG TGG GGG AGC CTG GAA

 A   L   L   K   N   L   D   R   L   K   P   A   I   R   E   K   I   L
GCC CTC CTC AAG AAC CTG GAC CGG CTG AAG CCC GCC ATC CGG GAG AAG ATC CTG

 A   H   M   D   D   L   K   L   S   W   D   L   A   K   V   R   T   D
GCC CAC ATG GAC GAT CTG AAG CTC TCC TGG GAC CTG GCC AAG GTG CGC ACC GAC

 L   P   L   E   V   D   F   A   K   R   R   E   P   D   R   E   R   L
CTG CCC CTG GAG GTG GAC TTC GCC AAA AGG CGG GAG CCC GAC CGG GAG AGG CTT

 R   A   F   L   E   R   L   E   F   G   S   L   L   H   E   F   G   L
AGG GCC TTT CTG GAG AGG CTT GAG TTT GGC AGC CTC CTC CAC GAG TTC GGC CTT
```

FIG. 8B-3

```
 L   E   S   P   K   A   L   E   E   A   P   W   P   P   P   E   G   A
CTG GAA AGC CCC AAG GCC CTG GAG GAG GCC CCC TGG CCC CCG CCG GAA GGG GCC

 F   V   G   F   V   L   S   R   K   E   P   M   W   A   D   L   L   A
TTC GTG GGC TTT GTG CTT TCC CGC AAG GAG CCC ATG TGG GCC GAT CTT CTG GCC

 L   A   A   A   R   G   G   R   V   H   R   A   P   E   P   Y   K   A
CTG GCC GCC GCC AGG GGG GGC CGG GTC CAC CGG GCC CCC GAG CCT TAT AAA GCC

 L   R   D   L   K   E   A   R   G   L   L   A   K   D   L   S   V   L
CTC AGG GAC CTG AAG GAG GCG CGG GGG CTT CTC GCC AAA GAC CTG AGC GTT CTG

 A   L   R   E   G   L   G   L   P   P   G   D   D   P   M   L   L   A
GCC CTG AGG GAA GGC CTT GGC CTC CCG CCC GGC GAC GAC CCC ATG CTC CTC GCC

 Y   L   L   D   P   S   N   T   T   P   E   G   V   A   R   R   Y   G
TAC CTC CTG GAC CCT TCC AAC ACC ACC CCC GAG GGG GTG GCC CGG CGC TAC GGC

 G   E   W   T   E   E   A   G   E   R   A   A   L   S   E   R   L   F
GGG GAG TGG ACG GAG GAG GCG GGG GAG CGG GCC GCC CTT TCC GAG AGG CTC TTC

 A   N   L   W   G   R   L   E   G   E   E   R   L   L   W   L   Y   R
GCC AAC CTG TGG GGG AGG CTT GAG GGG GAG GAG AGG CTC CTT TGG CTT TAC CGG
```

FIG. 8B-4

```
 E   V   E   R   P   L   S   A   V   L   A   H   M   E   A   T   G   V
GAG GTG GAG AGG CCC CTT TCC GCT GTC CTG GCC CAC ATG GAG GCC ACG GGG GTG

 R   L   D   V   A   Y   L   R   A   L   S   L   E   V   A   E   E   I
CGC CTG GAC GTG GCC TAT CTC AGG GCC TTG TCC CTG GAG GTG GCC GAG GAG ATC

 A   R   L   E   A   E   V   F   R   L   A   G   H   P   F   N   L   N
GCC CGC CTC GAG GCC GAG GTC TTC CGC CTG GCC GGC CAC CCC TTC AAC CTC AAC

 S   R   D   Q   L   E   R   V   L   F   D   E   L   G   L   P   A   I
TCC CGG GAC CAG CTG GAA AGG GTC CTC TTT GAC GAG CTA GGG CTT CCC GCC ATC

 G   K   T   E   K   T   G   K   R   S   T   S   A   A   V   L   E   A
GGC AAG ACG GAG AAG ACC GGC AAG CGC TCC ACC AGC GCC GCC GTC CTG GAG GCC

 L   R   E   A   H   P   I   V   E   K   I   L   Q   Y   R   E   L   T
CTC CGC GAG GCC CAC CCC ATC GTG GAG AAG ATC CTG CAG TAC CGG GAG CTC ACC

 K   L   K   S   T   Y   I   D   P   L   P   D   L   I   H   P   R   T
AAG CTG AAG AGC ACC TAC ATT GAC CCC TTG CCG GAC CTC ATC CAC CCC AGG ACG

 G   R   L   H   T   R   F   N   Q   T   A   T   A   T   G   R   L   S
GGC CGC CTC CAC ACC CGC TTC AAC CAG ACG GCC ACG GCC ACG GGC AGG CTA AGT
```

FIG. 8B-5

```
 S   S   D   P   N   L   Q   N   I   P   V   R   T   P   L   G   Q   R
AGC TCC GAT CCC AAC CTC CAG AAC ATC CCC GTC CGC ACC CCG CTT GGG CAG AGG

 I   R   R   A   F   I   A   E   E   G   W   L   L   V   A   L   D   Y
ATC CGC CGG GCC TTC ATC GCC GAG GAG GGG TGG CTA TTG GTG GCC CTG GAC TAT

 S   Q   I   E   L   R   V   L   A   H   L   S   G   D   E   N   L   I
AGC CAG ATA GAG CTC AGG GTG CTG GCC CAC CTC TCC GGC GAC GAG AAC CTG ATC

 R   V   F   Q   E   G   R   D   I   H   T   E   T   A   S   W   M   F
CGG GTC TTC CAG GAG GGG CGG GAC ATC CAC ACG GAG ACC GCC AGC TGG ATG TTC

 G   V   P   R   E   A   V   D   P   L   M   R   R   A   A   K   T   I
GGC GTC CCC CGG GAG GCC GTG GAC CCC CTG ATG CGC CGG GCG GCC AAG ACC ATC

 N   F   G   V   L   Y   G   M   S   A   H   R   L   S   Q   E   L   A
AAC TTC GGG GTC CTC TAC GGC ATG TCG GCC CAC CGC CTC TCC CAG GAG CTA GCC

 I   P   Y   E   E   A   Q   A   F   I   E   R   Y   F   Q   S   F   P
ATC CCT TAC GAG GAG GCC CAG GCC TTC ATT GAG CGC TAC TTT CAG AGC TTC CCC

 K   V   R   A   W   I   E   K   T   L   E   E   G   R   R   R   G   Y
AAG GTG CGG GCC TGG ATT GAG AAG ACC CTG GAG GAG GGC AGG AGG CGG GGG TAC
```

FIG. 8B-6

```
 V   E   T   L   F   G   R   R   R   Y   V   P   D   L   E   A   R   V
GTG GAG ACC CTC TTC GGC CGC CGC CGC TAC GTG CCA GAC CTA GAG GCC CGG GTG

 K   S   V   R   E   A   A   E   R   M   A   F   N   M   P   V   Q   G
AAG AGC GTG CGG GAG GCG GCC GAG CGC ATG GCC TTC AAC ATG CCC GTC CAG GGC

 T   A   A   D   L   M   K   L   A   M   V   K   L   F   P   R   L   E
ACC GCC GCC GAC CTC ATG AAG CTG GCT ATG GTG AAG CTC TTC CCC AGG CTG GAG

 E   M   G   A   R   M   L   L   Q   V   H   D   E   L   V   L   E   A
GAA ATG GGG GCC AGG ATG CTC CTT CAG GTC CAC GAC GAG CTG GTC CTC GAG GCC

 P   K   E   R   A   E   A   V   A   R   L   A   K   E   V   M   E   G
CCA AAA GAG AGG GCG GAG GCC GTG GCC CGG CTG GCC AAG GAG GTC ATG GAG GGG

 V   Y   P   L   A   V   P   L   E   V   E   V   G   I   G   E   D   W
GTG TAT CCC CTG GCC GTG CCC CTG GAG GTG GAG GTG GGG ATA GGG GAG GAC TGG

 L   S   A   K   E   G   I   D   G   R   G   G   G   G   H   H   H   H
CTC TCC GCC AAG GAG GGC ATT GAT GGC CGC GGC GGA GGC GGG CAT CAT CAT CAT

 H   H   *
CAT CAT TAA
```

| FIG. 8C-1 |
| --- |
| FIG. 8C-2 |
| ⋮ |
| FIG. 8C-7 |

Taq DNA polymerase- (HMf-like) fusion protein

Nucleotide sequence (SEQ ID NO: 65) //Nucleotide sequence (SEQ ID NO: 63)
Amino acid sequence (SEQ ID NO: 66) /Amino acid sequence (SEQ ID NO: 64)

```
    G   G   G
 // GGC GGC GGT

V   T   S   G   M   L   P   L   F   E   P   K   G   R   V   L   L   V
GTC ACT AGT GGG ATG CTG CCC CTC TTT GAG CCC AAG GGC CGG GTC CTC CTG GTG

D   G   H   H   L   A   Y   R   T   F   H   A   L   K   G   L   T   T
GAC GGC CAC CAC CTG GCC TAC CGC ACC TTC CAC GCC CTG AAG GGC CTC ACC ACC

S   R   G   E   P   V   Q   A   V   Y   G   F   A   K   S   L   L   K
AGC CGG GGG GAG CCG GTG CAG GCG GTC TAC GGC TTC GCC AAG AGC CTC CTC AAG

A   L   K   E   D   G   D   A   V   I   V   V   F   D   A   K   A   P
GCC CTC AAG GAG GAC GGG GAC GCG GTG ATC GTG GTC TTT GAC GCC AAG GCC CCC

S   F   R   H   E   A   Y   G   G   Y   K   A   G   R   A   P   T   P
TCC TTC CGC CAC GAG GCC TAC GGG GGG TAC AAG GCG GGC CGG GCC CCC ACG CCA
```

FIG. 8C-1

```
 E   D   F   P   R   Q   L   A   L   I   K   E   L   V   D   L   L   G
GAG GAC TTT CCC CGG CAA CTC GCC CTC ATC AAG GAG CTG GTG GAC CTC CTG GGG

 L   A   R   L   E   V   P   G   Y   E   A   D   D   V   L   A   S   L
CTG GCG CGC CTC GAG GTC CCG GGC TAC GAG GCG GAC GAC GTC CTG GCC AGC CTG

 A   K   K   A   E   K   E   G   Y   E   V   R   I   L   T   A   D   K
GCC AAG AAG GCG GAA AAG GAG GGC TAC GAG GTC CGC ATC CTC ACC GCC GAC AAA

 D   L   Y   Q   L   L   S   D   R   I   H   V   L   H   P   E   G   Y
GAC CTT TAC CAG CTC CTT TCC GAC CGC ATC CAC GTC CTC CAC CCC GAG GGG TAC

 L   I   T   P   A   W   L   W   E   K   Y   G   L   R   P   D   Q   W
CTC ATC ACC CCG GCC TGG CTT TGG GAA AAG TAC GGC CTG AGG CCC GAC CAG TGG

 A   D   Y   R   A   L   T   G   D   E   S   D   N   L   P   G   V   K
GCC GAC TAC CGG GCC CTG ACC GGG GAC GAG TCC GAC AAC CTT CCC GGG GTC AAG

 G   I   G   E   K   T   A   R   K   L   L   E   E   W   G   S   L   E
GGC ATC GGG GAG AAG ACG GCG AGG AAG CTT CTG GAG GAG TGG GGG AGC CTG GAA

 A   L   L   K   N   L   D   R   L   K   P   A   I   R   E   K   I   L
GCC CTC CTC AAG AAC CTG GAC CGG CTG AAG CCC GCC ATC CGG GAG AAG ATC CTG
```

FIG. 8C-2

```
 A   H   M   D   D   L   K   L   S   W   D   L   A   K   V   R   T   D
GCC CAC ATG GAC GAT CTG AAG CTC TCC TGG GAC CTG GCC AAG GTG CGC ACC GAC

 L   P   L   E   V   D   F   A   K   R   R   E   P   D   R   E   R   L
CTG CCC CTG GAG GTG GAC TTC GCC AAA AGG CGG GAG CCC GAC CGG GAG AGG CTT

 R   A   F   L   E   R   L   E   F   G   S   L   L   H   E   F   G   L
AGG GCC TTT CTG GAG AGG CTT GAG TTT GGC AGC CTC CTC CAC GAG TTC GGC CTT

 L   E   S   P   K   A   L   E   E   A   P   W   P   P   P   E   G   A
CTG GAA AGC CCC AAG GCC CTG GAG GAG GCC CCC TGG CCC CCG CCG GAA GGG GCC

 F   V   G   F   V   L   S   R   K   E   P   M   W   A   D   L   L   A
TTC GTG GGC TTT GTG CTT TCC CGC AAG GAG CCC ATG TGG GCC GAT CTT CTG GCC

 L   A   A   A   R   G   G   R   V   H   R   A   P   E   P   Y   K   A
CTG GCC GCC GCC AGG GGG GGC CGG GTC CAC CGG GCC CCC GAG CCT TAT AAA GCC

 L   R   D   L   K   E   A   R   G   L   L   A   K   D   L   S   V   L
CTC AGG GAC CTG AAG GAG GCG CGG GGG CTT CTC GCC AAA GAC CTG AGC GTT CTG

 A   L   R   E   G   L   G   L   P   P   G   D   D   P   M   L   L   A
GCC CTG AGG GAA GGC CTT GGC CTC CCG CCC GGC GAC GAC CCC ATG CTC CTC GCC
```

FIG. 8C-3

```
 Y   L   L   D   P   S   N   T   T   P   E   G   V   A   R   R   Y   G
TAC CTC CTG GAC CCT TCC AAC ACC ACC CCC GAG GGG GTG GCC CGG CGC TAC GGC

 G   E   W   T   E   E   A   G   E   R   A   A   L   S   E   R   L   F
GGG GAG TGG ACG GAG GAG GCG GGG GAG CGG GCC GCC CTT TCC GAG AGG CTC TTC

 A   N   L   W   G   R   L   E   G   E   E   R   L   L   W   L   Y   R
GCC AAC CTG TGG GGG AGG CTT GAG GGG GAG GAG AGG CTC CTT TGG CTT TAC CGG

 E   V   E   R   P   L   S   A   V   L   A   H   M   E   A   T   G   V
GAG GTG GAG AGG CCC CTT TCC GCT GTC CTG GCC CAC ATG GAG GCC ACG GGG GTG

 R   L   D   V   A   Y   L   R   A   L   S   L   E   V   A   E   E   I
CGC CTG GAC GTG GCC TAT CTC AGG GCC TTG TCC CTG GAG GTG GCC GAG GAG ATC

 A   R   L   E   A   E   V   F   R   L   A   G   H   P   F   N   L   N
GCC CGC CTC GAG GCC GAG GTC TTC CGC CTG GCC GGC CAC CCC TTC AAC CTC AAC

 S   R   D   Q   L   E   R   V   L   F   D   E   L   G   L   P   A   I
TCC CGG GAC CAG CTG GAA AGG GTC CTC TTT GAC GAG CTA GGG CTT CCC GCC ATC

 G   K   T   E   K   T   G   K   R   S   T   S   A   A   V   L   E   A
GGC AAG ACG GAG AAG ACC GGC AAG CGC TCC ACC AGC GCC GCC GTC CTG GAG GCC
```

FIG. 8C-4

```
 L   R   E   A   H   P   I   V   E   K   I   L   Q   Y   R   E   L   T
CTC CGC GAG GCC CAC CCC ATC GTG GAG AAG ATC CTG CAG TAC CGG GAG CTC ACC

 K   L   K   S   T   Y   I   D   P   L   P   D   L   I   H   P   R   T
AAG CTG AAG AGC ACC TAC ATT GAC CCC TTG CCG GAC CTC ATC CAC CCC AGG ACG

 G   R   L   H   T   R   F   N   Q   T   A   T   A   T   G   R   L   S
GGC CGC CTC CAC ACC CGC TTC AAC CAG ACG GCC ACG GCC ACG GGC AGG CTA AGT

 S   S   D   P   N   L   Q   N   I   P   V   R   T   P   L   G   Q   R
AGC TCC GAT CCC AAC CTC CAG AAC ATC CCC GTC CGC ACC CCG CTT GGG CAG AGG

 I   R   R   A   F   I   A   E   E   G   W   L   L   V   A   L   D   Y
ATC CGC CGG GCC TTC ATC GCC GAG GAG GGG TGG CTA TTG GTG GCC CTG GAC TAT

 S   Q   I   E   L   R   V   L   A   H   L   S   G   D   E   N   L   I
AGC CAG ATA GAG CTC AGG GTG CTG GCC CAC CTC TCC GGC GAC GAG AAC CTG ATC

 R   V   F   Q   E   G   R   D   I   H   T   E   T   A   S   W   M   F
CGG GTC TTC CAG GAG GGG CGG GAC ATC CAC ACG GAG ACC GCC AGC TGG ATG TTC

 G   V   P   R   E   A   V   D   P   L   M   R   R   A   A   K   T   I
GGC GTC CCC CGG GAG GCC GTG GAC CCC CTG ATG CGC CGG GCG GCC AAG ACC ATC
```

FIG. 8C-5

```
 N   F   G   V   L   Y   G   M   S   A   H   R   L   S   Q   E   L   A
AAC TTC GGG GTC CTC TAC GGC ATG TCG GCC CAC CGC CTC TCC CAG GAG CTA GCC

 I   P   Y   E   E   A   Q   A   F   I   E   R   Y   F   Q   S   F   P
ATC CCT TAC GAG GAG GCC CAG GCC TTC ATT GAG CGC TAC TTT CAG AGC TTC CCC

 K   V   R   A   W   I   E   K   T   L   E   E   G   R   R   R   G   Y
AAG GTG CGG GCC TGG ATT GAG AAG ACC CTG GAG GAG GGC AGG AGG CGG GGG TAC

 V   E   T   L   F   G   R   R   R   Y   V   P   D   L   E   A   R   V
GTG GAG ACC CTC TTC GGC CGC CGC CGC TAC GTG CCA GAC CTA GAG GCC CGG GTG

 K   S   V   R   E   A   A   E   R   M   A   F   N   M   P   V   Q   G
AAG AGC GTG CGG GAG GCG GCC GAG CGC ATG GCC TTC AAC ATG CCC GTC CAG GGC

 T   A   A   D   L   M   K   L   A   M   V   K   L   F   P   R   L   E
ACC GCC GCC GAC CTC ATG AAG CTG GCT ATG GTG AAG CTC TTC CCC AGG CTG GAG

 E   M   G   A   R   M   L   L   Q   V   H   D   E   L   V   L   E   A
GAA ATG GGG GCC AGG ATG CTC CTT CAG GTC CAC GAC GAG CTG GTC CTC GAG GCC

 P   K   E   R   A   E   A   V   A   R   L   A   K   E   V   M   E   G
CCA AAA GAG AGG GCG GAG GCC GTG GCC CGG CTG GCC AAG GAG GTC ATG GAG GGG
```

FIG. 8C-6

```
 V   Y   P   L   A   V   P   L   E   V   E   V   G   I   G   E   D   W
GTG TAT CCC CTG GCC GTG CCC CTG GAG GTG GAG GTG GGG ATA GGG GAG GAC TGG

 L   S   A   K   E   G   I   D   G   R   G   G   G   G   H   H   H   H
CTC TCC GCC AAG GAG GGC ATT GAT GGC CGC GGC GGA GGC GGG CAT CAT CAT CAT

 H   H   //
CAT CAT  //

 M   M   G   E   L   P   I   A   P   V   D   R   L   I   R   K   A   G
ATG ATG GGA GAA TTA CCA ATT GCC CCA GTT GAC AGA CTT ATA AGA AAG GCT GGT

 A   Q   R   V   S   E   Q   A   A   K   V   L   A   E   H   L   E   E
GCT CAG AGA GTT AGC GAG CAA GCA GCT AAG GTA CTT GCA GAG CAC CTT GAG GAA

 K   A   I   E   I   A   K   K   A   V   D   L   A   K   H   A   G   R
AAA GCT ATT GAG ATC GCA AAA AAG GCA GTA GAT CTT GCA AAG CAC GCA GGT AGA

 K   T   V   K   V   E   D   I   K   L   A   I   K   S   *
AAG ACC GTT AAG GTC GAA GAC ATT AAG CTC GCA ATT AAG AGC TGA
```

<u>Pfu DNA Polymerase (WT) -(HMf-like) fusion protein</u>

Nucleotide sequence (SEQ ID NO: 61) //Nucleotide sequence (SEQ ID NO: 63)

//
```
ccctggtcct gggtccacat atatgttctt actcgccttt atgaagaatc ccccagtcgc

tctaacctgg gttatagtga caaatcttcc tccaccaccg cccaagaagg ttatttctat
```

FIG. 8D-1 caactctaca cctcccctat tttctctctt atgagatttt taagtatagt tatagagaag gttttatact ccaaactgag ttagtagata tgtggggagc ataatgattt tagatgtgga ttacataact gaagaaggaa aacctgttat taggctattc aaaaaagaga acggaaaatt taagatagag catgatagaa cttttagacc atacatttac gctcttctca gggatgattc aaagattgaa gaagttaaga aaataacggg ggaaaggcat ggaaagattg tgagaattgt tgatgtagag aaggttgaga aaaagtttct cggcaagcct attaccgtgt ggaaacttta tttggaacat ccccaagatg ttcccactat tagagaaaaa gttagagaac atccagcagt tgtggacatc ttcgaatacg atattccatt tgcaaagaga tacctcatcg acaaaggcct aataccaatg gagggggaag aagagctaaa gattcttgcc ttcgatatag aaaccctcta tcacgaagga gaagagtttg gaaaaggccc aattataatg attagttatg cagatgaaaa tgaagcaaag gtgattactt ggaaaaacat agatcttcca tacgttgagg ttgtatcaag cgagagagag atgataaaga gatttctcag gattatcagg gagaaggatc ctgacattat

FIG. 8D-2 agttacttat aatggagact cattcgactt cccatattta gcgaaaaggg cagaaaaact tgggattaaa ttaaccattg gaagagatgg aagcgagccc aagatgcaga gaataggcga tatgacggct gtagaagtca agggaagaat acatttcgac ttgtatcatg taataacaag gacaataaat ctcccaacat acacactaga ggctgtatat gaagcaattt ttggaaagcc aaaggagaag gtatacgccg acgagatagc aaaagcctgg gaaagtggag agaaccttga gagagttgcc aaatactcga tggaagatgc aaaggcaact tatgaactcg ggaaagaatt ccttccaatg gaaattcagc tttcaagatt agttggacaa cctttatggg atgtttcaag gtcaagcaca gggaaccttg tagagtggtt cttacttagg aaagcctacg aaagaaacga agtagctcca aacaagccaa gtgaagagga gtatcaaaga aggctcaggg agagctacac aggtggattc gttaaagagc cagaaaaggg gttgtgggaa aacatagtat acctagattt tagagcccta tatccctcga ttataattac ccacaatgtt tctcccgata ctctaaatct tgagggatgc aagaactatg atatcgctcc tcaagtaggc cacaagttct gcaaggacat

FIG. 8D-3 ccctggtttt ataccaagtc tcttgggaca tttgttagag gaaagacaaa agattaagac aaaaatgaag gaaactcaag atcctataga aaaaatactc cttgactata gacaaaaagc gataaaactc ttagcaaatt ctttctacgg atattatggc tatgcaaaag caagatggta ctgtaaggag tgtgctgaga gcgttactgc ctggggaaga aagtacatcg agttagtatg gaaggagctc gaagaaaagt ttggatttaa agtcctctac attgacactg atggtctcta tgcaactatc ccaggaggag aaagtgagga aataaagaaa aaggctctag aatttgtaaa atacataaat tcaaagctcc ctggactgct agagcttgaa tatgaagggt tttataagag gggattcttc gttacgaaga agaggtatgc agtaatagat gaagaaggaa aagtcattac tcgtggttta gagatagtta ggagagattg gagtgaaatt gcaaaagaaa ctcaagctag agttttggag acaatactaa aacacggaga tgttgaagaa gctgtgagaa tagtaaaaga agtaatacaa aagcttgcca attatgaaat tccaccagag aagctcgcaa tatatgagca gataacaaga ccattacatg agtataaggc gataggtcct cacgtagctg ttgcaaagaa

FIG. 8D-4 actagctgct aaaggagtta aaataaagcc aggaatggta attggataca tagtacttag aggcgatggt ccaattagca atagggcaat tctagctgag gaatacgatc ccaaaaagca caagtatgac gcagaatatt acattgagaa ccaggttctt ccagcggtac ttaggatatt ggagggattt ggatacagaa aggaagacct cagataccaa aagacaagac aagtcggcct aacttcctgg cttaacatta aaaaatccta gaaaagcgat agatatcaac ttttattctt tctaaccttt ttctatgaaa gaagaactga gcaggaatta ccagttcttc cgttatttta tgggtaatta aaaacccatg ctcttgggag aatcttcgaa taaaatccct aacttcaggc tttgctaagt gaatagaata aacaacatca ctcacttcaa acgccttcgt tagaaatggt ctatctgcat gcttctctgg ctcggaanng gaggattcat aacaacagta tcaacattct cagagaattg agaaacatca gaaactttga cttctacaac atttctaact ttgcaactct tcaagatttt ctaaaagaat tttaacggcc tcctcgtcaa tttcgacgac gtagatcttt tttgctccaa gcagagccgc tccaatggat aacacccctg ttcccgcacc caagtccgct

FIG. 8D-5

```
acaatttttt ccttgtatct cctaatgtat aagcaagcca aaggagagta gatgctacct

ttccgggagt tttgtattgc tctagccaag gtttgggatt tttgaatcct ttaactctgg

aaagtataat ttcaagctcc ttcttcttca tgacagatga aaaattgttt tgtctctttt

taacttttac agaaataact gtctcaaatt atgacaactc ttgacatttt tacttcatta

ccagggtaat gtttttaagt atgaaatttt tctttcatag aggaggnnnn nngtcctctc

ctcgatttcc ttggttgtgc tccatatgat aagcttccaa agtgggtgtt cagactttta

gacactcaaa taccagacga caatggtgtg ctcactcaag ccccatatgg gttgagaaaa

gtagaagcgg cactactcag atgcttcccc aggaatgagg ttgttgtagc tcntcccnga

aagattgaga tgttcttgg  //

//ATG ATG GGA GAA TTA CCA ATT GCC CCA GTT GAC AGA CTT ATA AGA AAG GCT GGT    54
  GCT CAG AGA GTT AGC GAG CAA GCA GCT AAG GTA CTT GCA GAG CAC CTT GAG GAA   108
  AAA GCT ATT GAG ATC GCA AAA AAG GCA GTA GAT CTT GCA AAG CAC GCA GGT AGA   162
  AAG ACC GTT AAG GTC GAA GAC ATT AAG CTC GCA ATT AAG AGC TGA
```

| |
|---|
| FIG. 8E-1 |
| FIG. 8E-2 |
| ⋮ |
| FIG. 8E-6 |

(HMf-like) - Pfu DNA Polymerase (WT) fusion protein

Nucleotide sequence (SEQ ID NO: 63) //Nucleotide sequence (SEQ ID NO: 61)

```
ATG ATG GGA GAA TTA CCA ATT GCC CCA GTT GAC AGA CTT ATA AGA AAG GCT GGT    54
GCT CAG AGA GTT AGC GAG CAA GCA GCT AAG GTA CTT GCA GAG CAC CTT GAG GAA   108
AAA GCT ATT GAG ATC GCA AAA AAG GCA GTA GAT CTT GCA AAG CAC GCA GGT AGA   162
AAG ACC GTT AAG GTC GAA GAC ATT AAG CTC GCA ATT AAG AGC //
```

FIG. 8E-1 ccctggtcct gggtccacat atatgttctt actcgccttt atgaagaatc ccccagtcgc tctaacctgg gttatagtga caaatcttcc tccaccaccg cccaagaagg ttatttctat caactctaca cctcccctat tttctctctt atgagatttt taagtatagt tatagagaag gttttatact ccaaactgag ttagtagata tgtggggagc ataatgattt tagatgtgga ttacataact gaagaaggaa aacctgttat taggctattc aaaaaagaga acggaaaatt taagatagag catgatagaa cttttagacc atacatttac gctcttctca gggatgattc aaagattgaa gaagttaaga aaataacggg ggaaaggcat ggaaagattg tgagaattgt tgatgtagag aaggttgaga aaaagtttct cggcaagcct attaccgtgt ggaaacttta tttggaacat ccccaagatg ttcccactat tagagaaaaa gttagagaac atccagcagt tgtggacatc ttcgaatacg atattccatt tgcaaagaga tacctcatcg acaaaggcct aataccaatg gagggggaag aagagctaaa gattcttgcc ttcgatatag aaaccctcta

FIG. 8E-2 tcacgaagga gaagagtttg gaaaaggccc aattataatg attagttatg cagatgaaaa tgaagcaaag gtgattactt ggaaaaacat agatcttcca tacgttgagg ttgtatcaag cgagagagag atgataaaga gatttctcag gattatcagg gagaaggatc ctgacattat agttacttat aatggagact cattcgactt cccatattta gcgaaaaggg cagaaaaact tgggattaaa ttaaccattg gaagagatgg aagcgagccc aagatgcaga gaataggcga tatgacggct gtagaagtca agggaagaat acatttcgac ttgtatcatg taataacaag gacaataaat ctcccaacat acacactaga ggctgtatat gaagcaattt ttggaaagcc aaaggagaag gtatacgccg acgagatagc aaaagcctgg gaaagtggag agaaccttga gagagttgcc aaatactcga tggaagatgc aaaggcaact tatgaactcg ggaaagaatt ccttccaatg gaaattcagc tttcaagatt agttggacaa cctttatggg atgtttcaag gtcaagcaca gggaaccttg tagagtggtt cttacttagg aaagcctacg aaagaaacga agtagctcca aacaagccaa gtgaagagga gtatcaaaga aggctcaggg agagctacac

FIG. 8E-3 aggtggattc gttaaagagc cagaaaaggg gttgtgggaa aacatagtat acctagattt tagagcccta tatccctcga ttataattac ccacaatgtt tctcccgata ctctaaatct tgagggatgc aagaactatg atatcgctcc tcaagtaggc cacaagttct gcaaggacat ccctggtttt ataccaagtc tcttgggaca tttgttagag gaaagacaaa agattaagac aaaaatgaag gaaactcaag atcctataga aaaaatactc cttgactata gacaaaaagc gataaaactc ttagcaaatt ctttctacgg atattatggc tatgcaaaag caagatggta ctgtaaggag tgtgctgaga gcgttactgc ctggggaaga aagtacatcg agttagtatg gaaggagctc gaagaaaagt ttggatttaa agtcctctac attgacactg atggtctcta tgcaactatc ccaggaggag aaagtgagga aataaagaaa aaggctctag aatttgtaaa atacataaat tcaaagctcc ctggactgct agagcttgaa tatgaagggt tttataagag gggattcttc gttacgaaga agaggtatgc agtaatagat gaagaaggaa aagtcattac tcgtggttta gagatagtta ggagagattg gagtgaaatt gcaaaagaaa ctcaagctag

FIG. 8E-4 agttttggag acaatactaa aacacggaga tgttgaagaa gctgtgagaa tagtaaaaga
agtaatacaa aagcttgcca attatgaaat tccaccagag aagctcgcaa tatatgagca
gataacaaga ccattacatg agtataaggc gataggtcct cacgtagctg ttgcaaagaa
actagctgct aaaggagtta aaataaagcc aggaatggta attggataca tagtacttag
aggcgatggt ccaattagca atagggcaat tctagctgag gaatacgatc ccaaaaagca
caagtatgac gcagaatatt acattgagaa ccaggttctt ccagcggtac ttaggatatt
ggagggattt ggatacagaa aggaagacct cagataccaa aagacaagac aagtcggcct
aacttcctgg cttaacatta aaaaatccta gaaaagcgat agatatcaac ttttattctt
tctaaccttt ttctatgaaa gaagaactga gcaggaatta ccagttcttc cgttatttta
tgggtaatta aaaacccatg ctcttgggag aatcttcgaa taaaatccct aacttcaggc
tttgctaagt gaatagaata aacaacatca ctcacttcaa acgccttcgt tagaaatggt
ctatctgcat gcttctctgg ctcggaanng gaggattcat aacaacagta tcaacattct

FIG. 8E-5

```
cagagaattg agaaacatca gaaactttga cttctacaac atttctaact ttgcaactct
tcaagatttt ctaaaagaat tttaacggcc tcctcgtcaa tttcgacgac gtagatcttt
tttgctccaa gcagagccgc tccaatggat aacacccctg ttcccgcacc caagtccgct
acaatttttt ccttgtatct cctaatgtat aagcaagcca aaggagagta gatgctacct
ttccgggagt tttgtattgc tctagccaag gtttgggatt tttgaatcct ttaactctgg
aaagtataat ttcaagctcc ttcttcttca tgacagatga aaaattgttt tgtctctttt
taacttttac agaaataact gtctcaaatt atgacaactc ttgacatttt tacttcatta
ccagggtaat gtttttaagt atgaaatttt tctttcatag aggaggnnnn nngtcctctc
ctcgatttcc ttggttgtgc tccatatgat aagcttccaa agtgggtgtt cagactttta
gacactcaaa taccagacga caatggtgtg ctcactcaag ccccatatgg gttgagaaaa
gtagaagcgg cactactcag atgcttcccc aggaatgagg ttgttgtagc tcntcccnga
aagattgaga tgttcttgg  //   TGA
```

| FIG. 8F-1 |
| --- |
| FIG. 8F-2 |

(HMf-like) - PFU DNA POLYMERASE (V93 R OR E) fusion protein

Nucleotide sequence (SEQ ID NO: 63) // Nucleotide sequence (SEQ ID NO: 27)
Nucleotide sequence (SEQ ID NO: 63) //Nucleotide sequence (SEQ ID NO: 28)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATG ATG GGA GAA TTA CCA ATT GCC CCA GTT GAC AGA CTT ATA AGA AAG GCT GGT    54
GCT CAG AGA GTT AGC GAG CAA GCA GCT AAG GTA CTT GCA GAG CAC CTT GAG GAA   108
AAA GCT ATT GAG ATC GCA AAA AAG GCA GTA GAT CTT GCA AAG CAC GCA GGT AGA   162
AAG ACC GTT AAG GTC GAA GAC ATT AAG CTC GCA ATT AAG AGC //

//ATGATTTTAG ATGTGGATTA CATAACTGAA GAAGGAAAAC CTGTTATTAG GCTATTCAAA 60
AAAGAGAACG GAAAATTTAA GATAGAGCAT
GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC
CAAGATXXXC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GATATAGAAA CCCTCTATCA CGAAGGAGAA
```

FIG. 8F-1

GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT
GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC
CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA
ATTCAGCTTT CAAGATTAGT TGGACAACCT 1020
TTATGGGATG TTTCAAGGTC AAGCACAGGG AACCTTGTAG AGTGGTTCTT ACTTAGGAAA
1080 GCCTACGAAA GAAACGAAGT AGCTCCAAAC AAGCCAAGTG AAGAGGAGTA TCAAAGAAGG 1140 CTCAGGGAGA GCTACACAGG
TGGATTCGTT AAAGAGCCAG AAAAGGGGTT GTGGGAAAAC 1200
ATAGTATACC TAGATTTTAG AGCCCTATAT CCCTCGATTA TAATTACCCA
CAATGTTTCT 1260 CCCGATACTC TAAATCTTGA GGGATGCAAG AACTATGATA TCGCTCCTCA AGTAGGCCAC 1320 AAGTTCTGCA
AGGACATCCC TGGTTTTATA CCAAGTCTCT TGGGACATTT GTTAGAGGAA 1380
AGACAAAAGA TTAAGACAAA AATGAAGGAA ACTCAAGATC
CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA
GAAAAGTTTG GATTTAAAGT CCTCTACATT 1620
GACACTGATG GTCTCTATGC AACTATCCCA GGAGGAGAAA GTGAGGAAAT AAAGAAAAAG
1680 GCTCTAGAAT TTGTAAAATA CATAAATTCA AAGCTCCCTG GACTGCTAGA GCTTGAATAT 1740 GAAGGGTTTT ATAAGAGGGG
ATTCTTCGTT ACGAAGAAGA GGTATGCAGT AATAGATGAA 1800
GAAGGAAAAG TCATTACTCG TGGTTTAGAG ATAGTTAGGA GAGATTGGAG
TGAAATTGCA 1860 AAAGAAACTC AAGCTAGAGT TTTGGAGACA ATACTAAAAC ACGGAGATGT TGAAGAAGCT 1920 GTGAGAATAG
TAAAAGAAGT AATACAAAAG CTTGCCAATT ATGAAATTCC ACCAGAGAAG 1980
CTCGCAATAT ATGAGCAGAT AACAAGACCA TTACATGAGT
ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA
GAATATTACA TGGAGAACCA GGTTCTTCCA 2220
GCGGTACTTA GGATATTGGA GGGATTTGGA TACAGAAAGG AAGACCTCAG ATACCAAAAG
2280 ACAAGACAAG TCGGCCTAAC TTCCTGGCTT AACATTAAAA AATCC // 2328
// TGA

| FIG. 8G-1 |
|---|
| FIG. 8G-2 |

PFU DNA POLYMERASE (V93 R OR E)-(HMf-like) fusion protein

Nucleotide sequence (SEQ ID NO: 27) // Nucleotide sequence (SEQ ID NO: 63)
Nucleotide sequence (SEQ ID NO: 28) // Nucleotide sequence (SEQ ID NO: 63)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATTTTAG ATGTGGATTA CATAACTGAA GAAGGAAAAC CTGTTATTAG GCTATTCAAA 60
AAAGAGAACG GAAAATTTAA GATAGAGCAT
GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC
CAAGATXXXC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GATATAGAAA CCCTCTATCA CGAAGGAGAA
GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT
GGAGACTCAT TCGCATTCCC ATATTTAGCG 660
AAAAGGGCAG AAAAACTTGG GATTAAATTA ACCATTGGAA GAGATGGAAG CGAGCCCAAG 720
```

FIG. 8G-1

```
ATGCAGAGAA TAGGCGATAT GACGGCTGTA GAAGTCAAGG GAAGAATACA TTTCGACTTG 780
TATCATGTAA TAACAAGGAC AATAAATCTC
CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA
ATTCAGCTTT CAAGATTAGT TGGACAACCT 1020
TTATGGGATG TTTCAAGGTC AAGCACAGGG AACCTTGTAG AGTGGTTCTT ACTTAGGAAA
1080 GCCTACGAAA GAAACGAAGT AGCTCCAAAC AAGCCAAGTG AAGAGGAGTA TCAAAGAAGG 1140 CTCAGGGAGA GCTACACAGG
TGGATTCGTT AAAGAGCCAG AAAAGGGGTT GTGGGAAAAC 1200
ATAGTATACC TAGATTTTAG AGCCCTATAT CCCTCGATTA TAATTACCCA
CAATGTTTCT 1260 CCCGATACTC TAAATCTTGA GGGATGCAAG AACTATGATA TCGCTCCTCA AGTAGGCCAC 1320 AAGTTCTGCA
AGGACATCCC TGGTTTTATA CCAAGTCTCT TGGGACATTT GTTAGAGGAA 1380
AGACAAAAGA TTAAGACAAA AATGAAGGAA ACTCAAGATC
CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA
GAAAAGTTTG GATTTAAAGT CCTCTACATT 1620
GACACTGATG GTCTCTATGC AACTATCCCA GGAGGAGAAA GTGAGGAAAT AAAGAAAAAG
1680 GCTCTAGAAT TTGTAAAATA CATAAATTCA AAGCTCCCTG GACTGCTAGA GCTTGAATAT 1740 GAAGGGTTTT ATAAGAGGGG
ATTCTTCGTT ACGAAGAAGA GGTATGCAGT AATAGATGAA 1800
GAAGGAAAAG TCATTACTCG TGGTTTAGAG ATAGTTAGGA GAGATTGGAG
TGAAATTGCA 1860 AAAGAAACTC AAGCTAGAGT TTTGGAGACA ATACTAAAAC ACGGAGATGT TGAAGAAGCT 1920 GTGAGAATAG
TAAAAGAAGT AATACAAAAG CTTGCCAATT ATGAAATTCC ACCAGAGAAG 1980
CTCGCAATAT ATGAGCAGAT AACAAGACCA TTACATGAGT
ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA
GAATATTACA TGGAGAACCA GGTTCTTCCA 2220
GCGGTACTTA GGATATTGGA GGGATTTGGA TACAGAAAGG AAGACCTCAG ATACCAAAAG
2280 ACAAGACAAG TCGGCCTAAC TTCCTGGCTT AACATTAAAA AATCC //          2328
   //ATG ATG GGA GAA TTA CCA ATT GCC CCA GTT GAC AGA CTT ATA AGA AAG GCT GGT     54
   GCT CAG AGA GTT AGC GAG CAA GCA GCT AAG GTA CTT GCA GAG CAC CTT GAG GAA    108
   AAA GCT ATT GAG ATC GCA AAA AAG GCA GTA GAT CTT GCA AAG CAC GCA GGT AGA    162
   AAG ACC GTT AAG GTC GAA GAC ATT AAG CTC GCA ATT AAG AGC TGA
```

| FIG. 8H-1 |
|---|
| FIG. 8H-2 |

PFU DNA POLYMERASE (G387P/V93R OR E) -(HMf-like) fusion protein

Nucleotide sequence (SEQ ID NO: 29) // Nucleotide sequence (SEQ ID NO: 63)
Nucleotide sequence (SEQ ID NO: 30) // Nucleotide sequence (SEQ ID NO: 63)

G387P Mutant (CCN is the codon for Proline where N = C, G, A, or T)
V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATTTTAG ATGTGGATTA CATAACTGAA GAAGGAAAAC CTGTTATTAG GCTATTCAAA 60
AAAGAGAACG GAAAATTTAA GATAGAGCAT
GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC
CAAGATXXXC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GATATAGAAA CCCTCTATCA CGAAGGAGAA
GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT
GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC
CCAACATACA CACTAGAGGC TGTATATGAA 840
GCAATTTTTG GAAAGCCAAA GGAGAAGGTA TACGCCGACG AGATAGCAAA AGCCTGGGAA 900
```

FIG. 8H-1

AGTGGAGAGA ACCTTGAGAG AGTTGCCAAA TACTCGATGG AAGATGCAAA GGCAACTTAT 960
GAACTCGGGA AAGAATTCCT TCCAATGGAA
ATTCAGCTTT CAAGATTAGT TGGACAACCT 1020
TTATGGGATG TTTCAAGGTC AAGCACAGGG AACCTTGTAG AGTGGTTCTT ACTTAGGAAA
1080 GCCTACGAAA GAAACGAAGT AGCTCCAAAC AAGCCAAGTG AAGAGGAGTA TCAAAGAAGG 1140 CTCAGGGAGA GCTACACACC
NGGATTCGTT AAAGAGCCAG AAAAGGGGTT GTGGGAAAAC 1200
ATAGTATACC TAGATTTTAG AGCCCTATAT CCCTCGATTA TAATTACCCA
CAATGTTTCT 1260 CCCGATACTC TAAATCTTGA GGGATGCAAG AACTATGATA TCGCTCCTCA AGTAGGCCAC 1320 AAGTTCTGCA
AGGACATCCC TGGTTTTATA CCAAGTCTCT TGGGACATTT GTTAGAGGAA 1380
AGACAAAAGA TTAAGACAAA AATGAAGGAA ACTCAAGATC
CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA
GAAAAGTTTG GATTTAAAGT CCTCTACATT 1620
GACACTGATG GTCTCTATGC AACTATCCCA GGAGGAGAAA GTGAGGAAAT AAAGAAAAAG
1680 GCTCTAGAAT TTGTAAAATA CATAAATTCA AAGCTCCCTG GACTGCTAGA GCTTGAATAT 1740 GAAGGGTTTT ATAAGAGGGG
ATTCTTCGTT ACGAAGAAGA GGTATGCAGT AATAGATGAA 1800
GAAGGAAAAG TCATTACTCG TGGTTTAGAG ATAGTTAGGA GAGATTGGAG
TGAAATTGCA 1860 AAAGAAACTC AAGCTAGAGT TTTGGAGACA ATACTAAAAC ACGGAGATGT TGAAGAAGCT 1920 GTGAGAATAG
TAAAAGAAGT AATACAAAAG CTTGCCAATT ATGAAATTCC ACCAGAGAAG 1980
CTCGCAATAT ATGAGCAGAT AACAAGACCA TTACATGAGT
ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA
GAATATTACA TGGAGAACCA GGTTCTTCCA 2220
GCGGTACTTA GGATATTGGA GGGATTTGGA TACAGAAAGG AAGACCTCAG ATACCAAAAG
2280 ACAAGACAAG TCGGCCTAAC TTCCTGGCTT AACATTAAAA AATCC // 2328

//ATG ATG GGA GAA TTA CCA ATT GCC CCA GTT GAC AGA CTT ATA AGA AAG GCT GGT 54
GCT CAG AGA GTT AGC GAG CAA GCA GCT AAG GTA CTT GCA GAG CAC CTT GAG GAA 108
AAA GCT ATT GAG ATC GCA AAA AAG GCA GTA GAT CTT GCA AAG CAC GCA GGT AGA 162
AAG ACC GTT AAG GTC GAA GAC ATT AAG CTC GCA ATT AAG AGC TGA

| FIG. 8I-1 |
|---|
| FIG. 8I-2 |

(HMf-like) - PFU DNA POLYMERASE (G387P/V93R OR E) fusion protein

Nucleotide sequence (SEQ ID NO: 63) // Nucleotide sequence (SEQ ID NO: 29)
Nucleotide sequence (SEQ ID NO: 63) // Nucleotide sequence (SEQ ID NO: 30)

G387P Mutant (CCN is the codon for Proline where N = C, G, A, or T)
V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATG ATG GGA GAA TTA CCA ATT GCC CCA GTT GAC AGA CTT ATA AGA AAG GCT GGT     54
   GCT CAG AGA GTT AGC GAG CAA GCA GCT AAG GTA CTT GCA GAG CAC CTT GAG GAA   108
   AAA GCT ATT GAG ATC GCA AAA AAG GCA GTA GAT CTT GCA AAG CAC GCA GGT AGA   162
   AAG ACC GTT AAG GTC GAA GAC ATT AAG CTC GCA ATT AAG AGC //

//ATGATTTTAG ATGTGGATTA CATAACTGAA GAAGGAAAAC CTGTTATTAG GCTATTCAAA 60
AAAGAGAACG GAAAATTTAA GATAGAGCAT
GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC
CAAGATXXXC CCACTATTAG AGAAAAAGTT 300
AGAGAACATC CAGCAGTTGT GGACATCTTC GAATACGATA TTCCATTTGC AAAGAGATAC 360
```

FIG. 8I-1

CTCATCGACA AAGGCCTAAT ACCAATGGAG GGGGAAGAAG AGCTAAAGAT TCTTGCCTTC 420
GATATAGAAA CCCTCTATCA CGAAGGAGAA
GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT
GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC
CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA
ATTCAGCTTT CAAGATTAGT TGGACAACCT 1020
TTATGGGATG TTTCAAGGTC AAGCACAGGG AACCTTGTAG AGTGGTTCTT ACTTAGGAAA
1080 GCCTACGAAA GAAACGAAGT AGCTCCAAAC AAGCCAAGTG AAGAGGAGTA TCAAAGAAGG 1140 CTCAGGGAGA GCTACACACC
NGGATTCGTT AAAGAGCCAG AAAAGGGGTT GTGGGAAAAC 1200
ATAGTATACC TAGATTTTAG AGCCCTATAT CCCTCGATTA TAATTACCCA
CAATGTTTCT 1260 CCCGATACTC TAAATCTTGA GGGATGCAAG AACTATGATA TCGCTCCTCA AGTAGGCCAC 1320 AAGTTCTGCA
AGGACATCCC TGGTTTTATA CCAAGTCTCT TGGGACATTT GTTAGAGGAA 1380
AGACAAAAGA TTAAGACAAA AATGAAGGAA ACTCAAGATC
CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA
GAAAAGTTTG GATTTAAAGT CCTCTACATT 1620
GACACTGATG GTCTCTATGC AACTATCCCA GGAGGAGAAA GTGAGGAAAT AAAGAAAAAG
1680 GCTCTAGAAT TTGTAAAATA CATAAATTCA AAGCTCCCTG GACTGCTAGA GCTTGAATAT 1740 GAAGGGTTTT ATAAGAGGGG
ATTCTTCGTT ACGAAGAAGA GGTATGCAGT AATAGATGAA 1800
GAAGGAAAAG TCATTACTCG TGGTTTAGAG ATAGTTAGGA GAGATTGGAG
TGAAATTGCA 1860 AAAGAAACTC AAGCTAGAGT TTTGGAGACA ATACTAAAAC ACGGAGATGT TGAAGAAGCT 1920 GTGAGAATAG
TAAAAGAAGT AATACAAAAG CTTGCCAATT ATGAAATTCC ACCAGAGAAG 1980
CTCGCAATAT ATGAGCAGAT AACAAGACCA TTACATGAGT
ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA
GAATATTACA TGGAGAACCA GGTTCTTCCA 2220
GCGGTACTTA GGATATTGGA GGGATTTGGA TACAGAAAGG AAGACCTCAG ATACCAAAAG
2280 ACAAGACAAG TCGGCCTAAC TTCCTGGCTT AACATTAAAA AATCC //TAG 2328

| FIG. 8J-1 |
|---|
| FIG. 8J-2 |

(HMF-LIKE)-PFU DNA POLYMERASE(D141A/E143A/V93R OR E) fusion protein

Nucleotide sequence (SEQ ID NO: 63) // Nucleotide sequence (SEQ ID NO: 31)
Nucleotide sequence (SEQ ID NO: 63) // Nucleotide sequence (SEQ ID NO: 32)

D141A/E143A Mutant (GCN is the codon for alanine where N = C, G, A, or T)
V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
//ATG ATG GGA GAA TTA CCA ATT GCC CCA GTT GAC AGA CTT ATA AGA AAG GCT GGT    54
   GCT CAG AGA GTT AGC GAG CAA GCA GCT AAG GTA CTT GCA GAG CAC CTT GAG GAA   108
   AAA GCT ATT GAG ATC GCA AAA AAG GCA GTA GAT CTT GCA AAG CAC GCA GGT AGA   162
   AAG ACC GTT AAG GTC GAA GAC ATT AAG CTC GCA ATT AAG AGC //

//ATGATTTTAG ATGTGGATTA CATAACTGAA GAAGGAAAAC CTGTTATTAG GCTATTCAAA 60
AAAGAGAACG GAAAATTTAA GATAGAGCAT
GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC
CAAGATXXXC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GCNATAGCNA CCCTCTATCA CGAAGGAGAA
GAGTTTGGAA AAGGCCCAAT TATAATGATT 480
AGTTATGCAG ATGAAAATGA AGCAAAGGTG ATTACTTGGA AAAACATAGA TCTTCCATAC 540
```

FIG. 8J-1

GTTGAGGTTG TATCAAGCGA GAGAGAGATG ATAAAGAGAT TTCTCAGGAT TATCAGGGAG 600
AAGGATCCTG ACATTATAGT TACTTATAAT
GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC
CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA
ATTCAGCTTT CAAGATTAGT TGGACAACCT 1020
TTATGGGATG TTTCAAGGTC AAGCACAGGG AACCTTGTAG AGTGGTTCTT ACTTAGGAAA
1080 GCCTACGAAA GAAACGAAGT AGCTCCAAAC AAGCCAAGTG AAGAGGAGTA TCAAAGAAGG 1140 CTCAGGGAGA GCTACACA GGT
GGATTCGTT AAAGAGCCAG AAAAGGGGTT GTGGGAAAAC 1200
ATAGTATACC TAGATTTTAG AGCCCTATAT CCCTCGATTA TAATTACCCA
CAATGTTTCT 1260 CCCGATACTC TAAATCTTGA GGGATGCAAG AACTATGATA TCGCTCCTCA AGTAGGCCAC 1320 AAGTTCTGCA
AGGACATCCC TGGTTTTATA CCAAGTCTCT TGGGACATTT GTTAGAGGAA 1380
AGACAAAAGA TTAAGACAAA AATGAAGGAA ACTCAAGATC
CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA
GAAAAGTTTG GATTTAAAGT CCTCTACATT 1620
GACACTGATG GTCTCTATGC AACTATCCCA GGAGGAGAAA GTGAGGAAAT AAAGAAAAAG
1680 GCTCTAGAAT TTGTAAAATA CATAAATTCA AAGCTCCCTG GACTGCTAGA GCTTGAATAT 1740 GAAGGGTTTT ATAAGAGGGG
ATTCTTCGTT ACGAAGAAGA GGTATGCAGT AATAGATGAA 1800
GAAGGAAAAG TCATTACTCG TGGTTTAGAG ATAGTTAGGA GAGATTGGAG
TGAAATTGCA 1860 AAAGAAACTC AAGCTAGAGT TTTGGAGACA ATACTAAAAC ACGGAGATGT TGAAGAAGCT 1920 GTGAGAATAG
TAAAAGAAGT AATACAAAAG CTTGCCAATT ATGAAATTCC ACCAGAGAAG 1980
CTCGCAATAT ATGAGCAGAT AACAAGACCA TTACATGAGT
ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA
GAATATTACA TGGAGAACCA GGTTCTTCCA 2220
GCGGTACTTA GGATATTGGA GGGATTTGGA TACAGAAAGG AAGACCTCAG ATACCAAAAG
2280 ACAAGACAAG TCGGCCTAAC TTCCTGGCTT AACATTAAAA AATCC // 2328

TGA

| FIG. 8K-1 |
|---|
| FIG. 8K-2 |

PFU DNA POLYMERASE(D141A/E143A/V93R OR E) - (HMF-LIKE) fusion protein

Nucleotide sequence (SEQ ID NO: 31) // Nucleotide sequence (SEQ ID NO: 63)
Nucleotide sequence (SEQ ID NO: 32) // Nucleotide sequence (SEQ ID NO: 63)

D141A/E143A Mutant (GCN is the codon for alanine where N = C, G, A, or T)
V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATTTTAG ATGTGGATTA CATAACTGAA GAAGGAAAAC CTGTTATTAG GCTATTCAAA 60
AAAGAGAACG GAAAATTTAA GATAGAGCAT
GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC
CAAGATXXXC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GCNATAGCNA CCCTCTATCA CGAAGGAGAA
GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT
GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC
```

FIG. 8K-1

CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA
ATTCAGCTTT CAAGATTAGT TGGACAACCT 1020
TTATGGGATG TTTCAAGGTC AAGCACAGGG AACCTTGTAG AGTGGTTCTT ACTTAGGAAA
1080 GCCTACGAAA GAAACGAAGT AGCTCCAAAC AAGCCAAGTG AAGAGGAGTA TCAAAGAAGG 1140 CTCAGGGAGA GCTACACA
GGTGGATTCGTT AAAGAGCCAG AAAAGGGGTT GTGGGAAAAC 1200
ATAGTATACC TAGATTTTAG AGCCCTATAT CCCTCGATTA TAATTACCCA
CAATGTTTCT 1260 CCCGATACTC TAAATCTTGA GGGATGCAAG AACTATGATA TCGCTCCTCA AGTAGGCCAC 1320 AAGTTCTGCA
AGGACATCCC TGGTTTTATA CCAAGTCTCT TGGGACATTT GTTAGAGGAA 1380
AGACAAAAGA TTAAGACAAA AATGAAGGAA ACTCAAGATC
CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA
GAAAAGTTTG GATTTAAAGT CCTCTACATT 1620
GACACTGATG GTCTCTATGC AACTATCCCA GGAGGAGAAA GTGAGGAAAT AAAGAAAAAG
1680 GCTCTAGAAT TTGTAAAATA CATAAATTCA AAGCTCCCTG GACTGCTAGA GCTTGAATAT 1740 GAAGGGTTTT ATAAGAGGGG
ATTCTTCGTT ACGAAGAAGA GGTATGCAGT AATAGATGAA 1800
GAAGGAAAAG TCATTACTCG TGGTTTAGAG ATAGTTAGGA GAGATTGGAG
TGAAATTGCA 1860 AAAGAAACTC AAGCTAGAGT TTTGGAGACA ATACTAAAAC ACGGAGATGT TGAAGAAGCT 1920 GTGAGAATAG
TAAAAGAAGT AATACAAAAG CTTGCCAATT ATGAAATTCC ACCAGAGAAG 1980
CTCGCAATAT ATGAGCAGAT AACAAGACCA TTACATGAGT
ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA
GAATATTACA TGGAGAACCA GGTTCTTCCA 2220
GCGGTACTTA GGATATTGGA GGGATTTGGA TACAGAAAGG AAGACCTCAG ATACCAAAAG
2280 ACAAGACAAG TCGGCCTAAC TTCCTGGCTT AACATTAAAA AATCC // 2328

//ATG ATG GGA GAA TTA CCA ATT GCC CCA GTT GAC AGA CTT ATA AGA AAG GCT GGT 54
GCT CAG AGA GTT AGC GAG CAA GCA GCT AAG GTA CTT GCA GAG CAC CTT GAG GAA 108
AAA GCT ATT GAG ATC GCA AAA AAG GCA GTA GAT CTT GCA AAG CAC GCA GGT AGA 162
AAG ACC GTT AAG GTC GAA GAC ATT AAG CTC GCA ATT AAG AGC TGA

| |
|---|
| FIG. 8L-1 |
| FIG. 8L-2 |
| FIG. 8L-3 |

KOD DNA POLYMERASE - (HMf-like) fusion protein

Nucleotide sequence (SEQ ID NO: 33) // Nucleotide sequence (SEQ ID NO: 63)
Nucleotide sequence (SEQ ID NO: 34) // Nucleotide sequence (SEQ ID NO: 63)

FIG. 8L-1

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATCCTCG ACACTGACTA CATAACCGAG GATGGAAAGC CTGTCATAAG AATTTTCAAG 60
AAGGAAAACG GCGAGTTTAA GATTGAGTAC GACCGGACTT TTGAACCCTA CTTCTACGCC 120
CTCCTGAAGG ACGATTCTGC CATTGAGGAA GTCAAGAAGA TAACCGCCGA GAGGCACGGG 180
ACGGTTGTAA CGGTTAAGCG GGTTGAAAAG GTTCAGAAGA AGTTCCTCGG GAGACCAGTT 240
GAGGTCTGGA AACTCTACTT TACTCATCCG CAGGACXXXC CAGCGATAAG GGACAAGATA 300
CGAGAGCATC CAGCAGTTAT TGACATCTAC GAGTACGACA TACCCTTCGC CAAGCGCTAC 360
CTCATAGACA AGGGATTAGT GCCAATGGAA GGCGACGAGG AGCTGAAAAT GCTCGCCTTC 420
GACATTGAAA CTCTCTACCA TGAGGGCGAG GAGTTCGCCG AGGGGCCAAT CCTTATGATA 480
AGCTACGCCG ACGAGGAAGG GGCCAGGGTG ATAACTTGGA AGAACGTGGA TCTCCCCTAC 540
GTTGACGTCG TCTCGACGGA GAGGGAGATG ATAAAGCGCT TCCTCCGTGT TGTGAAGGAG 600
AAAGACCCGG ACGTTCTCAT AACCTACAAC GGCGACAACT TCGACTTCGC CTATCTGAAA 660
AAGCGCTGTG AAAAGCTCGG AATAAACTTC GCCCTCGGAA GGGATGGAAG CGAGCCGAAG 720
ATTCAGAGGA TGGGCGACAG GTTTGCCGTC GAAGTGAAGG GACGGATACA CTTCGATCTC 780
TATCCTGTGA TAAGACGGAC GATAAACCTG CCCACATACA CGCTTGAGGC CGTTTATGAA 840
GCCGTCTTCG GTCAGCCGAA GGAGAAGGTT TACGCTGAGG AAATAACCAC AGCCTGGGAA 900
ACCGGCGAGA ACCTTGAGAG AGTCGCCCGC TACTCGATGG AAGATGCGAA GGTCACATAC 960
GAGCTTGGGA AGGAGTTCCT TCCGATGGAG GCCCAGCTTT CTCGCTTAAT CGGCCAGTCC 1020
CTCTGGGACG TCTCCCGCTC CAGCACTGGC AACCTCGTTG AGTGGTTCCT CCTCAGGAAG 1080
GCCTATGAGA GGAATGAGCT GGCCCCGAAC AAGCCCGATG AAAAGGAGCT GGCCAGAAGA 1140
CGGCAGAGCT ATGAAGGAGG CTATGTAAAA GAGCCCGAGA GAGGGTTGTG GGAGAACATA 1200
```

FIG. 8L-2

```
GTGTACCTAG ATTTTAGATC CCTGTACCCC TCAATCATCA TCACCCACAA CGTCTCGCCG 1260
GATACGCTCA ACAGAGAAGG ATGCAAGGAA TATGACGTTG CCCCACAGGT CGGCCACCGC 1320
TTCTGCAAGG ACTTCCCAGG ATTTATCCCG AGCCTGCTTG GAGACCTCCT AGAGGAGAGG 1380
CAGAAGATAA AGAAGAAGAT GAAGGCCACG ATTGACCCGA TCGAGAGGAA GCTCCTCGAT 1440
TACAGGCAGA GGGCCATCAA GATCCTGGCA AACAGCTACT ACGGTTACTA CGGCTATGCA 1500
AGGGCGCGCT GGTACTGCAA GGAGTGTGCA GAGAGCGTAA CGGCCTGGGG AAGGGAGTAC 1560
ATAACGATGA CCATCAAGGA GATAGAGGAA AAGTACGGCT TTAAGGTAAT CTACAGCGAC 1620
ACCGACGGAT TTTTTGCCAC AATACCTGGA GCCGATGCTG AAACCGTCAA AAAGAAGGCT 1680
ATGGAGTTCC TCAAGTATAT CAACGCCAAA CTTCCGGGCG CGCTTGAGCT CGAGTACGAG 1740
GGCTTCTACA AACGCGGCTT CTTCGTCACG AAGAAGAAGT ATGCGGTGAT AGACGAGGAA 1800
GGCAAGATAA CAACGCGCGG ACTTGAGATT GTGAGGCGTG ACTGGAGCGA GATAGCGAAA 1860
GAGACGCAGG CGAGGGTTCT TGAAGCTTTG CTAAAGGACG GTGACGTCGA GAAGGCCGTG 1920
AGGATAGTCA AAGAAGTTAC CGAAAAGCTG AGCAAGTACG AGGTTCCGCC GGAGAAGCTG 1980
GTGATCCACG AGCAGATAAC GAGGGATTTA AAGGACTACA AGGCAACCGG TCCCCACGTT 2040
GCCGTTGCCA AGAGGTTGGC CGCGAGAGGA GTCAAAATAC GCCCTGGAAC GGTGATAAGC 2100
TACATCGTGC TCAAGGGCTC TGGGAGGATA GGCGACAGGG CGATACCGTT CGACGAGTTC 2160
GACCCGACGA AGCACAAGTA CGACGCCGAG TACTACATTG AGAACCAGGT TCTCCCAGCC 2220
GTTGAGAGAA TTCTGAGAGC CTTCGGTTAC CGCAAGGAAG ACCTGCGCTA CCAGAAGACG 2280
AGACAGGTTG GTTTGAGTGC TTGGCTGAAG CCGAAGGGAA CT  2325
//ATG ATG GGA GAA TTA CCA ATT GCC CCA GTT GAC AGA CTT ATA AGA AAG GCT GGT     54
   GCT CAG AGA GTT AGC GAG CAA GCA GCT AAG GTA CTT GCA GAG CAC CTT GAG GAA    108
   AAA GCT ATT GAG ATC GCA AAA AAG GCA GTA GAT CTT GCA AAG CAC GCA GGT AGA    162
   AAG ACC GTT AAG GTC GAA GAC ATT AAG CTC GCA ATT AAG AGC TGA
```

| |
|---|
| FIG. 8M-1 |
| FIG. 8M-2 |
| FIG. 8M-3 |

(HMf-like) - KOD DNA POLYMERASE fusion protein

Nucleotide sequence (SEQ ID NO: 63) // Nucleotide sequence (SEQ ID NO: 33)
Nucleotide sequence (SEQ ID NO: 63) // Nucleotide sequence (SEQ ID NO: 34)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

FIG. 8M-1

```
//ATG ATG GGA GAA TTA CCA ATT GCC CCA GTT GAC AGA CTT ATA AGA AAG GCT GGT    54
  GCT CAG AGA GTT AGC GAG CAA GCA GCT AAG GTA CTT GCA GAG CAC CTT GAG GAA   108
  AAA GCT ATT GAG ATC GCA AAA AAG GCA GTA GAT CTT GCA AAG CAC GCA GGT AGA   162
  AAG ACC GTT AAG GTC GAA GAC ATT AAG CTC GCA ATT AAG AGC //

//ATGATCCTCG ACACTGACTA CATAACCGAG GATGGAAAGC CTGTCATAAG AATTTTCAAG 60
AAGGAAAACG GCGAGTTTAA GATTGAGTAC GACCGGACTT TTGAACCCTA CTTCTACGCC 120
CTCCTGAAGG ACGATTCTGC CATTGAGGAA GTCAAGAAGA TAACCGCCGA GAGGCACGGG 180
ACGGTTGTAA CGGTTAAGCG GGTTGAAAAG GTTCAGAAGA AGTTCCTCGG GAGACCAGTT 240
GAGGTCTGGA AACTCTACTT TACTCATCCG CAGGACXXXC CAGCGATAAG GGACAAGATA 300
CGAGAGCATC CAGCAGTTAT TGACATCTAC GAGTACGACA TACCCTTCGC CAAGCGCTAC 360
CTCATAGACA AGGGATTAGT GCCAATGGAA GGCGACGAGG AGCTGAAAAT GCTCGCCTTC 420
GACATTGAAA CTCTCTACCA TGAGGGCGAG GAGTTCGCCG AGGGGCCAAT CCTTATGATA 480
AGCTACGCCG ACGAGGAAGG GGCCAGGGTG ATAACTTGGA AGAACGTGGA TCTCCCCTAC 540
GTTGACGTCG TCTCGACGGA GAGGGAGATG ATAAAGCGCT TCCTCCGTGT TGTGAAGGAG 600
AAAGACCCGG ACGTTCTCAT AACCTACAAC GGCGACAACT TCGACTTCGC CTATCTGAAA 660
AAGCGCTGTG AAAAGCTCGG AATAAACTTC GCCCTCGGAA GGGATGGAAG CGAGCCGAAG 720
ATTCAGAGGA TGGGCGACAG GTTTGCCGTC GAAGTGAAGG GACGGATACA CTTCGATCTC 780
TATCCTGTGA TAAGACGGAC GATAAACCTG CCCACATACA CGCTTGAGGC CGTTTATGAA 840
GCCGTCTTCG GTCAGCCGAA GGAGAAGGTT TACGCTGAGG AAATAACCAC AGCCTGGGAA 900
ACCGGCGAGA ACCTTGAGAG AGTCGCCCGC TACTCGATGG AAGATGCGAA GGTCACATAC 960
GAGCTTGGGA AGGAGTTCCT TCCGATGGAG GCCCAGCTTT CTCGCTTAAT CGGCCAGTCC 1020
```

FIG. 8M-2

```
CTCTGGGACG TCTCCCGCTC CAGCACTGGC AACCTCGTTG AGTGGTTCCT CCTCAGGAAG 1080
GCCTATGAGA GGAATGAGCT GGCCCCGAAC AAGCCCGATG AAAAGGAGCT GGCCAGAAGA 1140
CGGCAGAGCT ATGAAGGAGG CTATGTAAAA GAGCCCGAGA GAGGGTTGTG GGAGAACATA 1200
GTGTACCTAG ATTTTAGATC CCTGTACCCC TCAATCATCA TCACCCACAA CGTCTCGCCG 1260
GATACGCTCA ACAGAGAAGG ATGCAAGGAA TATGACGTTG CCCCACAGGT CGGCCACCGC 1320
TTCTGCAAGG ACTTCCCAGG ATTTATCCCG AGCCTGCTTG GAGACCTCCT AGAGGAGAGG 1380
CAGAAGATAA AGAAGAAGAT GAAGGCCACG ATTGACCCGA TCGAGAGGAA GCTCCTCGAT 1440
TACAGGCAGA GGGCCATCAA GATCCTGGCA AACAGCTACT ACGGTTACTA CGGCTATGCA 1500
AGGGCGCGCT GGTACTGCAA GGAGTGTGCA GAGAGCGTAA CGGCCTGGGG AAGGGAGTAC 1560
ATAACGATGA CCATCAAGGA GATAGAGGAA AAGTACGGCT TTAAGGTAAT CTACAGCGAC 1620
ACCGACGGAT TTTTTGCCAC AATACCTGGA GCCGATGCTG AAACCGTCAA AAAGAAGGCT 1680
ATGGAGTTCC TCAAGTATAT CAACGCCAAA CTTCCGGGCG CGCTTGAGCT CGAGTACGAG 1740
GGCTTCTACA AACGCGGCTT CTTCGTCACG AAGAAGAAGT ATGCGGTGAT AGACGAGGAA 1800
GGCAAGATAA CAACGCGCGG ACTTGAGATT GTGAGGCGTG ACTGGAGCGA GATAGCGAAA 1860
GAGACGCAGG CGAGGGTTCT TGAAGCTTTG CTAAAGGACG GTGACGTCGA GAAGGCCGTG 1920
AGGATAGTCA AAGAAGTTAC CGAAAAGCTG AGCAAGTACG AGGTTCCGCC GGAGAAGCTG 1980
GTGATCCACG AGCAGATAAC GAGGGATTTA AAGGACTACA AGGCAACCGG TCCCCACGTT 2040
GCCGTTGCCA AGAGGTTGGC CGCGAGAGGA GTCAAAATAC GCCCTGGAAC GGTGATAAGC 2100
TACATCGTGC TCAAGGGCTC TGGGAGGATA GGCGACAGGG CGATACCGTT CGACGAGTTC 2160
GACCCGACGA AGCACAAGTA CGACGCCGAG TACTACATTG AGAACCAGGT TCTCCCAGCC 2220
GTTGAGAGAA TTCTGAGAGC CTTCGGTTAC CGCAAGGAAG ACCTGCGCTA CCAGAAGACG 2280
AGACAGGTTG GTTTGAGTGC TTGGCTGAAG CCGAAGGGAA CT //TAG 2325
```

| |
|---|
| FIG. 8N-1 |
| FIG. 8N-2 |
| FIG. 8N-3 |

(HMf-like)-Vent DNA POLYMERASE FUSION PROTEIN

Nucleotide sequence (SEQ ID NO: 63) // Nucleotide sequence (SEQ ID NO: 35)
Nucleotide sequence (SEQ ID NO: 63) // Nucleotide sequence (SEQ ID NO: 36)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

FIG. 8N-1

//ATG ATG GGA GAA TTA CCA ATT GCC CCA GTT GAC AGA CTT ATA AGA AAG GCT GGT 54
GCT CAG AGA GTT AGC GAG CAA GCA GCT AAG GTA CTT GCA GAG CAC CTT GAG GAA 108
AAA GCT ATT GAG ATC GCA AAA AAG GCA GTA GAT CTT GCA AAG CAC GCA GGT AGA 162
AAG ACC GTT AAG GTC GAA GAC ATT AAG CTC GCA ATT AAG AGC //

ATGATACTGG ACACTGATTA CATAACAAAA GATGGCAAGC CTATAATCCG AATTTTTAAG 60
AAAGAGAACG GGGAGTTTAA AATAGAACTT GACCCTCATT TTCAGCCCTA TATATATGCT 120
CTTCTCAAAG ATGACTCCGC TATTGAGGAG ATAAAGGCAA TAAAGGGCGA GAGACATGGA 180
AAAACTGTGA GAGTGCTCGA TGCAGTGAAA GTCAGGAAAA AATTTTTGGG AAGGGAAGTT 240
GAAGTCTGGA AGCTCATTTT CGAGCATCCC CAAGACXXXC CAGCTATGCG GGGCAAAATA 300
AGGGAACATC CAGCTGTGGT TGACATTTAC GAATATGACA TACCCTTTGC CAAGCGTTAT 360
CTCATAGACA AGGGCTTGAT TCCCATGGAG GGAGACGAGG AGCTTAAGCT CCTTGCCTTT 420
GATATTGAAA CGTTTTATCA TGAGGGAGAT GAATTTGGAA AGGGCGAGAT AATAATGATT 480
AGTTATGCCG ATGAAGAAGA GGCCAGAGTA ATCACATGGA AAAATATCGA TTTGCCGTAT 540
GTCGATGTTG TGTCCAATGA AAGAGAAATG ATAAAGCGTT TTGTTCAAGT TGTTAAAGAA 600
AAAGACCCCG ATGTGATAAT AACTTACAAT GGGGACAATT TTGATTTGCC GTATCTCATA 660
AAACGGGCAG AAAAGCTGGG AGTTCGGCTT GTCTTAGGAA GGGACAAAGA ACATCCCGAA 720
CCCAAGATTC AGAGGATGGG TGATAGTTTT GCTGTGGAAA TCAAGGGTAG AATCCACTTT 780
GATCTTTTCC CAGTTGTGCG AAGGACGATA AACCTCCCAA CGTATACGCT TGAGGCAGTT 840
TATGAAGCAG TTTTAGGAAA AACCAAAAGC AAATTAGGAG CAGAGGAAAT TGCCGCTATA 900
TGGGAAACAG AAGAAAGCAT GAAAAAACTA GCCCAGTACT CAATGGAAGA TGCTAGGGCA 960

FIG. 8N-2

```
ACGTATGAGC TCGGGAAGGA ATTCTTCCCC ATGGAAGCTG AGCTGGCAAA GCTGATAGGT 1020
CAAAGTGTAT GGGACGTCTC GAGATCAAGC ACCGGCAACC TCGTGGAGTG GTATCTTTTA 1080
AGGGTGGCAT ACGCGAGGAA TGAACTTGCA CCGAACAAAC CTGATGAGGA AGAGTATAAA 1140
CGGCGCTTAA GAACAACTTA CCTGGGAGGA TATGTAAAAG AGCCAGAAAA AGGTTTGTGG 1200
GAAAATATCA TTTATTTGGA TTTCCGCAGT CTGTACCCTT CAATAATAGT TACTCACAAC 1260
GTATCCCCAG ATACCCTTGA AAAAGAGGGC TGTAAGAATT ACGATGTTGC TCCGATAGTA 1320
GGATATAGGT TCTGCAAGGA CTTTCCGGGC TTTATTCCCT CCATACTCGG GGACTTAATT 1380
GCAATGAGGC AAGATATAAA GAAGAAAATG AAATCCACAA TTGACCCGAT CGAAAAGAAA 1440
ATGCTCGATT ATAGGCAAAG GGCTATTAAA TTGCTTGCAA ACAGCTATTA CGGCTATATG 1500
GGGTATCCTA AGGCAAGATG GTACTCGAAG GAATGTGCTG AAAGCGTTAC CGCATGGGGG 1560
AGACACTACA TAGAGATGAC GATAAGAGAA ATAGAGGAAA AGTTCGGCTT TAAGGTTCTT 1620
TATGCGGACA CTGACGGCTT TTATGCCACA ATACCCGGGG AAAAGCCTGA ACTCATTAAA 1680
AAGAAAGCCA AGGAATTCCT AAACTACATA AACTCCAAAC TTCCAGGTCT GCTTGAGCTT 1740
GAGTATGAGG GCTTTTACTT GAGAGGATTC TTTGTTACAA AAAAGCGCTA TGCAGTCATA 1800
GATGAAGAGG GCAGGATAAC AACAAGGGGC TTGGAAGTAG TAAGGAGAGA TTGGAGTGAG 1860
ATAGCTAAGG AGACTCAGGC AAAGGTTTTA GAGGCTATAC TTAAAGAGGG AAGTGTTGAA 1920
AAAGCTGTAG AAGTTGTTAG AGATGTTGTA GAGAAAATAG CAAAATACAG GGTTCCACTT 1980
GAAAAGCTTG TTATCCATGA GCAGATTACC AGGGATTTAA AGGACTACAA AGCCATTGGC 2040
CCTCATGTCG CGATAGCAAA AAGACTTGCC GCAAGAGGGA TAAAAGTGAA ACCGGGCACA 2100
ATAATAAGCT ATATCGTTCT CAAAGGGAGC GGAAAGATAA GCGATAGGGT AATTTTACTT 2160
ACAGAATACG ATCCTAGAAA ACACAAGTAC GATCCGGACT ACTACATAGA AAACCAAGTT 2220
TTGCCGGCAG TACTTAGGAT ACTCGAAGCG TTTGGATACA GAAAGGAGGA TTTAAGGTAT 2280
CAAAGCTCAA AACAAACCGG CTTAGATGCA TGGCTCAAGA GGTAG 2325
```

| |
|---|
| FIG. 8O-1 |
| FIG. 8O-2 |
| FIG. 8O-3 |

Vent DNA POLYMERASE - (HMf-like) FUSION PROTEIN

Nucleotide sequence (SEQ ID NO: 35) // Nucleotide sequence (SEQ ID NO: 63)
Nucleotide sequence (SEQ ID NO: 36) // Nucleotide sequence (SEQ ID NO: 63)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATACTGG ACACTGATTA CATAACAAAA GATGGCAAGC CTATAATCCG AATTTTTAAG 60
AAAGAGAACG GGGAGTTTAA AATAGAACTT GACCCTCATT TTCAGCCCTA TATATATGCT 120
```

FIG. 8O-1

```
CTTCTCAAAG ATGACTCCGC TATTGAGGAG ATAAAGGCAA TAAAGGGCGA GAGACATGGA 180
AAAACTGTGA GAGTGCTCGA TGCAGTGAAA GTCAGGAAAA AATTTTTGGG AAGGGAAGTT 240
GAAGTCTGGA AGCTCATTTT CGAGCATCCC CAAGACXXXC CAGCTATGCG GGGCAAAATA 300
AGGGAACATC CAGCTGTGGT TGACATTTAC GAATATGACA TACCCTTTGC CAAGCGTTAT 360
CTCATAGACA AGGGCTTGAT TCCCATGGAG GGAGACGAGG AGCTTAAGCT CCTTGCCTTT 420
GATATTGAAA CGTTTTATCA TGAGGGAGAT GAATTTGGAA AGGGCGAGAT AATAATGATT 480
AGTTATGCCG ATGAAGAAGA GGCCAGAGTA ATCACATGGA AAAATATCGA TTTGCCGTAT 540
GTCGATGTTG TGTCCAATGA AAGAGAAATG ATAAAGCGTT TTGTTCAAGT TGTTAAAGAA 600
AAAGACCCCG ATGTGATAAT AACTTACAAT GGGGACAATT TTGATTTGCC GTATCTCATA 660
AAACGGGCAG AAAAGCTGGG AGTTCGGCTT GTCTTAGGAA GGGACAAAGA ACATCCCGAA 720
CCCAAGATTC AGAGGATGGG TGATAGTTTT GCTGTGGAAA TCAAGGGTAG AATCCACTTT 780
GATCTTTTCC CAGTTGTGCG AAGGACGATA AACCTCCCAA CGTATACGCT TGAGGCAGTT 840
TATGAAGCAG TTTTAGGAAA AACCAAAAGC AAATTAGGAG CAGAGGAAAT TGCCGCTATA 900
TGGGAAACAG AAGAAAGCAT GAAAAAACTA GCCCAGTACT CAATGGAAGA TGCTAGGGCA 960
ACGTATGAGC TCGGGAAGGA ATTCTTCCCC ATGGAAGCTG AGCTGGCAAA GCTGATAGGT 1020
CAAAGTGTAT GGGACGTCTC GAGATCAAGC ACCGGCAACC TCGTGGAGTG GTATCTTTTA 1080
AGGGTGGCAT ACGCGAGGAA TGAACTTGCA CCGAACAAAC CTGATGAGGA AGAGTATAAA 1140
CGGCGCTTAA GAACAACTTA CCTGGGAGGA TATGTAAAAG AGCCAGAAAA AGGTTTGTGG 1200
GAAAATATCA TTTATTTGGA TTTCCGCAGT CTGTACCCTT CAATAATAGT TACTCACAAC 1260
GTATCCCCAG ATACCCTTGA AAAAGAGGGC TGTAAGAATT ACGATGTTGC TCCGATAGTA 1320
GGATATAGGT TCTGCAAGGA CTTTCCGGGC TTTATTCCCT CCATACTCGG GGACTTAATT 1380
```

FIG. 8O-2

```
GCAATGAGGC AAGATATAAA GAAGAAAATG AAATCCACAA TTGACCCGAT CGAAAAGAAA 1440
ATGCTCGATT ATAGGCAAAG GGCTATTAAA TTGCTTGCAA ACAGCTATTA CGGCTATATG 1500
GGGTATCCTA AGGCAAGATG GTACTCGAAG GAATGTGCTG AAAGCGTTAC CGCATGGGGG 1560
AGACACTACA TAGAGATGAC GATAAGAGAA ATAGAGGAAA AGTTCGGCTT TAAGGTTCTT 1620
TATGCGGACA CTGACGGCTT TTATGCCACA ATACCCGGGG AAAAGCCTGA ACTCATTAAA 1680
AAGAAAGCCA AGGAATTCCT AAACTACATA AACTCCAAAC TTCCAGGTCT GCTTGAGCTT 1740
GAGTATGAGG GCTTTTACTT GAGAGGATTC TTTGTTACAA AAAAGCGCTA TGCAGTCATA 1800
GATGAAGAGG GCAGGATAAC AACAAGGGGC TTGGAAGTAG TAAGGAGAGA TTGGAGTGAG 1860
ATAGCTAAGG AGACTCAGGC AAAGGTTTTA GAGGCTATAC TTAAAGAGGG AAGTGTTGAA 1920
AAAGCTGTAG AAGTTGTTAG AGATGTTGTA GAGAAAATAG CAAAATACAG GGTTCCACTT 1980
GAAAAGCTTG TTATCCATGA GCAGATTACC AGGGATTTAA AGGACTACAA AGCCATTGGC 2040
CCTCATGTCG CGATAGCAAA AAGACTTGCC GCAAGAGGGA TAAAAGTGAA ACCGGGCACA 2100
ATAATAAGCT ATATCGTTCT CAAAGGGAGC GGAAAGATAA GCGATAGGGT AATTTTACTT 2160
ACAGAATACG ATCCTAGAAA ACACAAGTAC GATCCGGACT ACTACATAGA AAACCAAGTT 2220
TTGCCGGCAG TACTTAGGAT ACTCGAAGCG TTTGGATACA GAAAGGAGGA TTTAAGGTAT 2280
CAAAGCTCAA AACAAACCGG CTTAGATGCA TGGCTCAAGA GG 2325 //

//ATG ATG GGA GAA TTA CCA ATT GCC CCA GTT GAC AGA CTT ATA AGA AAG GCT GGT     54
   GCT CAG AGA GTT AGC GAG CAA GCA GCT AAG GTA CTT GCA GAG CAC CTT GAG GAA    108
   AAA GCT ATT GAG ATC GCA AAA AAG GCA GTA GAT CTT GCA AAG CAC GCA GGT AGA    162
   AAG ACC GTT AAG GTC GAA GAC ATT AAG CTC GCA ATT AAG AGC TGA
```

| FIG. 8P-1 |
|---|
| FIG. 8P-2 |
| FIG. 8P-3 |

Deep Vent- (HMf-like) DNA polymerase fusion protein

Nucleotide sequence (SEQ ID NO: 37) // Nucleotide sequence (SEQ ID NO: 63)
Nucleotide sequence (SEQ ID NO: 38) // Nucleotide sequence (SEQ ID NO: 63)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATACTTG ACGCTGACTA CATCACCGAG GATGGGAAGC CGATTATAAG GATTTTCAAG    60
```

FIG. 8P-1

```
AAAGAAAACG GCGAGTTTAA GGTTGAGTAC GACAGAAACT TTAGACCTTA CATTTACGCT  120
CTCCTCAAAG ATGACTCGCA GATTGATGAG GTTAGGAAGA TAACCGCCGA GAGGCATGGG  180
AAGATAGTGA GAATTATAGA TGCCGAAAAG GTAAGGAAGA AGTTCCTGGG GAGGCCGATT  240
GAGGTATGGA GGCTGTACTT TGAACACCCT CAGGACXXXC CCGCAATAAG GGATAAGATA  300
AGAGAGCATT CCGCAGTTAT TGACATCTTT GAGTACGACA TTCCGTTCGC GAAGAGGTAC  360
CTAATAGACA AAGGCCTAAT TCCAATGGAA GGCGATGAAG AGCTCAAGTT GCTCGCATTT  420
GACATAGAAA CCCTCTATCA CGAAGGGGAG GAGTTCGCGA AGGGGCCCAT TATAATGATA  480
AGCTATGCTG ATGAGGAAGA AGCCAAAGTC ATAACGTGGA AAAAGATCGA TCTCCCGTAC  540
GTCGAGGTAG TTTCCAGCGA GAGGGAGATG ATAAAGCGGT TCCTCAAGGT GATAAGGGAG  600
AAAGATCCCG ATGTTATAAT TACCTACAAC GGCGATTCTT TCGACCTTCC CTATCTAGTT  660
AAGAGGGCCG AAAAGCTCGG GATAAAGCTA CCCCTGGGAA GGGACGGTAG TGAGCCAAAG  720
ATGCAGAGGC TTGGGGATAT GACAGCGGTG GAGATAAAGG GAAGGATACA CTTTGACCTC  780
TACCACGTGA TTAGGAGAAC GATAAACCTC CCAACATACA CCCTCGAGGC AGTTTATGAG  840
GCAATCTTCG GAAAGCCAAA GGAGAAAGTT TACGCTCACG AGATAGCTGA GGCCTGGGAG  900
ACTGGAAAGG GACTGGAGAG AGTTGCAAAG TATTCAATGG AGGATGCAAA GGTAACGTAC  960
GAGCTCGGTA GGGAGTTCTT CCCAATGGAG GCCCAGCTTT CAAGGTTAGT CGGCCAGCCC 1020
CTGTGGGATG TTTCTAGGTC TTCAACTGGC AACTTGGTGG AGTGGTACCT CCTCAGGAAG 1080
GCCTACGAGA GGAATGAATT GGCTCCAAAC AAGCCGGATG AGAGGGAGTA CGAGAGAAGG 1140
CTAAGGGAGA GCTACGCTGG GGGATACGTT AAGGAGCCGG AGAAAGGGCT CTGGGAGGGG 1200
TTAGTTTCCC TAGATTTCAG GAGCCTGTAC CCCTCGATAA TAATCACCCA TAACGTCTCA 1260
CCGGATACGC TGAACAGGGA AGGGTGTAGG GAATACGATG TCGCCCCAGA GGTTGGGCAC 1320
AAGTTCTGCA AGGACTTCCC GGGGTTTATC CCCAGCCTGC TCAAGAGGTT ATTGGATGAA 1380
```

FIG. 8P-2

```
AGGCAAGAAA TAAAAAGGAA GATGAAAGCT TCTAAAGACC CAATCGAGAA GAAGATGCTT  1440
GATTACAGGC AACGGGCAAT CAAAATCCTG GCAAACAGCT ATTATGGGTA TTATGGGTAC  1500
GCAAAAGCCC GTTGGTACTG TAAGGAGTGC GCAGAGAGCG TTACGGCCTG GGGGAGGGAA  1560
TATATAGAGT TCGTAAGGAA GGAACTGGAG GAAAAGTTCG GGTTCAAAGT CTTATACATA  1620
GACACAGATG GACTCTACGC CACAATTCCT GGGGCAAAAC CCGAGGAGAT AAAGAAGAAA  1680
GCCCTAGAGT TCGTAGATTA TATAAACGCC AAGCTCCCAG GGCTGTTGGA GCTTGAGTAC  1740
GAGGGCTTCT ACGTGAGAGG GTTCTTCGTG ACGAAGAAGA AGTATGCGTT GATAGATGAG  1800
GAAGGGAAGA TAATCACTAG GGGGCTTGAA ATAGTCAGGA GGGACTGGAG CGAAATAGCC  1860
AAAGAAACCC AAGCAAAAGT CCTAGAGGCT ATCCTAAAGC ATGGCAACGT TGAGGAGGCA  1920
GTAAAGATAG TTAAGGAGGT AACTGAAAAG CTGAGCAAGT ACGAAATACC TCCAGAAAAG  1980
CTAGTTATTT ACGAGCAGAT CACGAGGCCC CTTCACGAGT ACAAGGCTAT AGGTCCGCAC  2040
GTTGCCGTGG CAAAAAGGTT AGCCGCTAGA GGAGTAAAGG TGAGGCCTGG CATGGTGATA  2100
GGGTACATAG TGCTGAGGGG AGACGGGCCA ATAAGCAAGA GGGCTATCCT TGCAGAGGAG  2160
TTCGATCTCA GGAAGCATAA GTATGACGCT GAGTATTACA TAGAAAATCA GGTTTTACCT  2220
GCCGTTCTTA GAATATTAGA GGCCTTTGGG TACAGGAAAG AAGACCTCAG GTGGCAGAAG  2280
ACTAAACAGA CAGGTCTTAC GGCATGGCTT AACATCAAGA AGAAG //                2328

//ATG ATG GGA GAA TTA CCA ATT GCC CCA GTT GAC AGA CTT ATA AGA AAG GCT GGT      54
   GCT CAG AGA GTT AGC GAG CAA GCA GCT AAG GTA CTT GCA GAG CAC CTT GAG GAA    108
   AAA GCT ATT GAG ATC GCA AAA AAG GCA GTA GAT CTT GCA AAG CAC GCA GGT AGA    162
   AAG ACC GTT AAG GTC GAA GAC ATT AAG CTC GCA ATT AAG AGC TGA
```

| |
|---|
| FIG. 8Q-1 |
| FIG. 8Q-2 |
| FIG. 8Q-3 |

(HMflike) - Deep Vent DNA polymerase fusion protein

Nucleotide sequence (SEQ ID NO: 63) // Nucleotide sequence (SEQ ID NO: 37)
Nucleotide sequence (SEQ ID NO: 63) // Nucleotide sequence (SEQ ID NO: 38)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
//ATG ATG GGA GAA TTA CCA ATT GCC CCA GTT GAC AGA CTT ATA AGA AAG GCT GGT    54
  GCT CAG AGA GTT AGC GAG CAA GCA GCT AAG GTA CTT GCA GAG CAC CTT GAG GAA   108
  AAA GCT ATT GAG ATC GCA AAA AAG GCA GTA GAT CTT GCA AAG CAC GCA GGT AGA   162
  AAG ACC GTT AAG GTC GAA GAC ATT AAG CTC GCA ATT AAG AGC TGA
```

FIG. 8Q-1

//ATGATACTTG ACGCTGACTA CATCACCGAG GATGGGAAGC CGATTATAAG GATTTTCAAG 60

AAAGAAAACG GCGAGTTTAA GGTTGAGTAC GACAGAAACT TTAGACCTTA CATTTACGCT 120

CTCCTCAAAG ATGACTCGCA GATTGATGAG GTTAGGAAGA TAACCGCCGA GAGGCATGGG 180

AAGATAGTGA GAATTATAGA TGCCGAAAAG GTAAGGAAGA AGTTCCTGGG GAGGCCGATT 240

GAGGTATGGA GGCTGTACTT TGAACACCCT CAGGACXXXC CCGCAATAAG GGATAAGATA 300

AGAGAGCATT CCGCAGTTAT TGACATCTTT GAGTACGACA TTCCGTTCGC GAAGAGGTAC 360

CTAATAGACA AAGGCCTAAT TCCAATGGAA GGCGATGAAG AGCTCAAGTT GCTCGCATTT 420

GACATAGAAA CCCTCTATCA CGAAGGGGAG GAGTTCGCGA AGGGGCCCAT TATAATGATA 480

AGCTATGCTG ATGAGGAAGA AGCCAAAGTC ATAACGTGGA AAAAGATCGA TCTCCCGTAC 540

GTCGAGGTAG TTTCCAGCGA GAGGGAGATG ATAAAGCGGT TCCTCAAGGT GATAAGGGAG 600

AAAGATCCCG ATGTTATAAT TACCTACAAC GGCGATTCTT TCGACCTTCC CTATCTAGTT 660

AAGAGGGCCG AAAAGCTCGG GATAAAGCTA CCCCTGGGAA GGGACGGTAG TGAGCCAAAG 720

ATGCAGAGGC TTGGGGATAT GACAGCGGTG GAGATAAAGG GAAGGATACA CTTTGACCTC 780

TACCACGTGA TTAGGAGAAC GATAAACCTC CCAACATACA CCCTCGAGGC AGTTTATGAG 840

GCAATCTTCG GAAAGCCAAA GGAGAAAGTT TACGCTCACG AGATAGCTGA GGCCTGGGAG 900

ACTGGAAAGG GACTGGAGAG AGTTGCAAAG TATTCAATGG AGGATGCAAA GGTAACGTAC 960

GAGCTCGGTA GGGAGTTCTT CCCAATGGAG GCCCAGCTTT CAAGGTTAGT CGGCCAGCCC 1020

CTGTGGGATG TTTCTAGGTC TTCAACTGGC AACTTGGTGG AGTGGTACCT CCTCAGGAAG 1080

FIG. 8Q-2

```
GCCTACGAGA GGAATGAATT GGCTCCAAAC AAGCCGGATG AGAGGGAGTA CGAGAGAAGG  1140
CTAAGGGAGA GCTACGCTGG GGGATACGTT AAGGAGCCGG AGAAAGGGCT CTGGGAGGGG  1200
TTAGTTTCCC TAGATTTCAG GAGCCTGTAC CCCTCGATAA TAATCACCCA TAACGTCTCA  1260
CCGGATACGC TGAACAGGGA AGGGTGTAGG GAATACGATG TCGCCCCAGA GGTTGGGCAC  1320
AAGTTCTGCA AGGACTTCCC GGGGTTTATC CCCAGCCTGC TCAAGAGGTT ATTGGATGAA  1380
AGGCAAGAAA TAAAAAGGAA GATGAAAGCT TCTAAAGACC CAATCGAGAA GAAGATGCTT  1440
GATTACAGGC AACGGGCAAT CAAAATCCTG GCAAACAGCT ATTATGGGTA TTATGGGTAC  1500
GCAAAAGCCC GTTGGTACTG TAAGGAGTGC GCAGAGAGCG TTACGGCCTG GGGGAGGGAA  1560
TATATAGAGT TCGTAAGGAA GGAACTGGAG GAAAAGTTCG GGTTCAAAGT CTTATACATA  1620
GACACAGATG GACTCTACGC CACAATTCCT GGGGCAAAAC CCGAGGAGAT AAAGAAGAAA  1680
GCCCTAGAGT TCGTAGATTA TATAAACGCC AAGCTCCCAG GGCTGTTGGA GCTTGAGTAC  1740
GAGGGCTTCT ACGTGAGAGG GTTCTTCGTG ACGAAGAAGA AGTATGCGTT GATAGATGAG  1800
GAAGGGAAGA TAATCACTAG GGGGCTTGAA ATAGTCAGGA GGGACTGGAG CGAAATAGCC  1860
AAAGAAACCC AAGCAAAAGT CCTAGAGGCT ATCCTAAAGC ATGGCAACGT TGAGGAGGCA  1920
GTAAAGATAG TTAAGGAGGT AACTGAAAAG CTGAGCAAGT ACGAAATACC TCCAGAAAAG  1980
CTAGTTATTT ACGAGCAGAT CACGAGGCCC CTTCACGAGT ACAAGGCTAT AGGTCCGCAC  2040
GTTGCCGTGG CAAAAAGGTT AGCCGCTAGA GGAGTAAAGG TGAGGCCTGG CATGGTGATA  2100
GGGTACATAG TGCTGAGGGG AGACGGGCCA ATAAGCAAGA GGGCTATCCT TGCAGAGGAG  2160
TTCGATCTCA GGAAGCATAA GTATGACGCT GAGTATTACA TAGAAAATCA GGTTTTACCT  2220
GCCGTTCTTA GAATATTAGA GGCCTTTGGG TACAGGAAAG AAGACCTCAG GTGGCAGAAG  2280
ACTAAACAGA CAGGTCTTAC GGCATGGCTT AACATCAAGA AGAAG TAA              2328
```

| FIG. 8R-1 |
| --- |
| FIG. 8R-2 |

JDF-3 - (HMf-like) fusion protein

Nucleotide sequence (SEQ ID NO: 39) // Nucleotide sequence (SEQ ID NO: 63)
Nucleotide sequence (SEQ ID NO: 40) // Nucleotide sequence (SEQ ID NO: 63)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

ATGATCCTTGACGTTGATTACATCACCGAGAATGGAAAGCCCGTCATCAGGGTCTTCAAGAAGGAGAACGGCGAGTTCAGGATTGAATACGACCGCGAGTTCGAGCCCTACTTCT
ACGCGCTCCTCAGGGACGACTCTGCCATCGAAGAAATCAAAAAGATAACCGCGGAGAGGCACGGCAGGGTCGTTAAGGTTAAGCGCGCGGAGAAGGTGAAGAAAAAGTTCCTCGG
CAGGTCTGTGGAGGTCTGGGTCCTCTACTTCACGCACCCGCAGGACXXXCCGGCAATCCGCGACAAAATAAGGAAGCACCCCGCGGTCATCGACATCTACGAGTACGACATACCC
TTCGCCAAGCGCTACCTCATAGACAAGGGCCTAATCCCGATGGAAGGTGAGGAAGAGCTTAAACTCATGTCCTTCGACATCGAGACGCTCTACCACGAGGGAGAAGAGTTTGGAA

FIG. 8R-1

CCGGGCCGATTCTGATGATAAGCTACGCCGATGAAAGCGAGGCGCGCGTGATAACCTGGAAGAAGATCGACCTTCCTTACGTTGAGGTTGTCTCCACCGAGAAGGAGATGATTAA
GCGCTTCTTGAGGGTCGTTAAGGAGAAGGACCCGGACGTGCTGATAACATACAACGGCGACAACTTCGACTTCGCCTACCTGAAAAAGCGCTGTGAGAAGCTTGGCGTGAGCTTT
ACCCTCGGGAGGGACGGGAGCGAGCCGAAGATACAGCGCATGGGGGACAGGTTTGCGGTCGAGGTGAAGGGCAGGGTACACTTCGACCTTTATCCAGTCATAAGGCGCACCATAA
ACCTCCCGACCTACACCCTTGAGGCTGTATACGAGGCGGTTTTCGGCAAGCCCAAGGAGAAGGTCTACGCCGAGGAGATAGCCACCGCCTGGGAGACCGGCGAGGGGCTTGAGAG
GGTCGCGCGCTACTCGATGGAGGACGCGAGGGTTACCTACGAGCTTGGCAGGGAGTTCTTCCCGATGGAGGCCCAGCTTTCCAGGCTCATCGGCCAAGGCCTCTGGGACGTTTCC
CGCTCCAGCACCGGCAACCTCGTCGAGTGGTTCCTCCTAAGGAAGGCCTACGAGAGGAACGAACTCGCTCCCAACAAGCCCGACGAGAGGGAGCTGGCGAGGAGAAGGGGGGCT
ACgcCGGTGGCTACGTCAAGGAGCCGGAGCGGGGACTGTGGGACAATATCGTGTATCTAGACTTTCGTAGTCTCTACCCTTCAATCATAATCACCCACAACGTCTCGCCAGATAC
GCTCAACCGCGAGGGGTGTAGGAGCTACGACGTTGCCCCCGAGGTCGGTCACAAGTTCTGCAAGGACTTCCCCGGCTTCATTCCGAGCCTGCTCGGAAACCTGCTGGAGGAAAGG
CAGAAGATAAAGAGGAAGATGAAGGCAACTCTCGACCCGCTGGAGAAGAATCTCCTCGATTACAGGCAACGCGCCATCAAGATTCTCGCCAACAGCTACTACGGCTACTACGGCT
ATGCCAGGGCAAGATGGTACTGCAGGGAGTGCGCCGAGAGCGTTACGGCATGGGGAAGGGAGTACATCGAAATGGTCATCAGAGAGCTTGAGGAAAAGTTCGGTTTTAAAGTCCT
CTATGCAGACACAGACGGTCTCCATGCCACCATTCCTGGAGCGGACGCTGAAACAGTCAAGAAAAAGGCAATGGAGTTCTTAAACTATATCAATCCCAAACTGCCCGGCCTTCTC
GAACTCGAATACGAGGGCTTCTACGTCAGGGGCTTCTTCGTCACGAAGAAAAAGTACGCGGTCATCGACGAGGAGGGCAAGATAACCACGCGCGGGCTTGAGATAGTCAGGCGCG
ACTGGAGCGAGATAGCGAAGGAGACGCAGGCGAGGGTTTTGGAGGCGATACTCAGGCACGGTGACGTTGAAGAGGCCGTCAGAATTGTCAGGGAAGTCACCGAAAAGCTGAGCAA
GTACGAGGTTCCGCCGGAGAAGCTGGTTATCCACGAGCAGATAACGCGCGAGCTCAAGGACTACAAGGCCACCGGCCCGCACGTAGCCATAGCGAAgcGTTTGGCCGCCAGAGGT
GTTAAAATCCGGCCCGGAACTGTGATAAGCTACATCGTTCTGAAGGGCTCCGGAAGGATAGGCGACAGGGCGATTCCCTTCGACGAGTTCGACCCGACGAAGCACAAGTACGATG
CGGACTACTACATCGAGAACCAGGTTCTGCCGGCAGTTGAGAGAATCCTCAGGGCCTTCGGCTACCGCAAGGAAGACCTGCGCTACCAGAAGACGAGGCAGGTCGGGCTTGGCGC
GTGGCTGAAGCCGAAGGGGAAGAAGAAG//

//ATG ATG GGA GAA TTA CCA ATT GCC CCA GTT GAC AGA CTT ATA AGA AAG GCT GGT 54
GCT CAG AGA GTT AGC GAG CAA GCA GCT AAG GTA CTT GCA GAG CAC CTT GAG GAA 108
AAA GCT ATT GAG ATC GCA AAA AAG GCA GTA GAT CTT GCA AAG CAC GCA GGT AGA 162
AAG ACC GTT AAG GTC GAA GAC ATT AAG CTC GCA ATT AAG AGC TGA

| |
|---|
| FIG. 8S-1 |
| FIG. 8S-2 |

<u>(HMf-like) - JDF-3 fusion protein</u>

Nucleotide sequence (SEQ ID NO: 63) // Nucleotide sequence (SEQ ID NO: 39)
Nucleotide sequence (SEQ ID NO: 63) // Nucleotide sequence (SEQ ID NO: 40)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
//ATG ATG GGA GAA TTA CCA ATT GCC CCA GTT GAC AGA CTT ATA AGA AAG GCT GGT     54
   GCT CAG AGA GTT AGC GAG CAA GCA GCT AAG GTA CTT GCA GAG CAC CTT GAG GAA   108
   AAA GCT ATT GAG ATC GCA AAA AAG GCA GTA GAT CTT GCA AAG CAC GCA GGT AGA   162
   AAG ACC GTT AAG GTC GAA GAC ATT AAG CTC GCA ATT AAG AGC //
```

FIG. 8S-1

//ATGATCCTTGACGTTGATTACATCACCGAGAATGGAAAGCCCGTCATCAGGGTCTTCAAGAAGGAGAACGGCGAGTTCAGGATTGAATACGACCGCGAGTTCGAG
CCCTACTTCTACGCGCTCCTCAGGGACGACTCTGCCATCGAAGAAATCAAAAAGATAACCGCGGAGAGGCACGGCAGGGTCGTTAAGGTTAAGCGCGCGGAGAAGGT
GAAGAAAAAGTTCCTCGGCAGGTCTGTGGAGGTCTGGGTCCTCTACTTCACGCACCCGCAGGACXXXCCGGCAATCCGCGACAAAATAAGGAAGCACCCCGCGGTCA
TCGACATCTACGAGTACGACATACCCTTCGCCAAGCGCTACCTCATAGACAAGGGCCTAATCCCGATGGAAGGTGAGGAAGAGCTTAAACTCATGTCCTTCGACATC
GAGACGCTCTACCACGAGGGAGAAGAGTTTGGAACCGGGCCGATTCTGATGATAAGCTACGCCGATGAAAGCGAGGCGCGCGTGATAACCTGGAAGAAGATCGACCT
TCCTTACGTTGAGGTTGTCTCCACCGAGAAGGAGATGATTAAGCGCTTCTTGAGGGTCGTTAAGGAGAAGGACCCGGACGTGCTGATAACATACAACGGCGACAACT
TCGACTTCGCCTACCTGAAAAAGCGCTGTGAGAAGCTTGGCGTGAGCTTTACCCTCGGGAGGGACGGGAGCGAGCCGAAGATACAGCGCATGGGGGACAGGTTTGCG
GTCGAGGTGAAGGGCAGGGTACACTTCGACCTTTATCCAGTCATAAGGCGCACCATAAACCTCCCGACCTACACCCTTGAGGCTGTATACGAGGCGGTTTTCGGCAA
GCCCAAGGAGAAGGTCTACGCCGAGGAGATAGCCACCGCCTGGGAGACCGGCGAGGGGCTTGAGAGGGTCGCGCGCTACTCGATGGAGGACGCGAGGGTTACCTACG
AGCTTGGCAGGGAGTTCTTCCCGATGGAGGCCCAGCTTTCCAGGCTCATCGGCCAAGGCCTCTGGGACGTTTCCCGCTCCAGCACCGGCAACCTCGTCGAGTGGTTC
CTCCTAAGGAAGGCCTACGAGAGGAACGAACTCGCTCCCAACAAGCCCGACGAGAGGGAGCTGGCGAGGAGAAGGGGGGGCTACgcCGGTGGCTACGTCAAGGAGCC
GGAGCGGGGACTGTGGGACAATATCGTGTATCTAGACTTTCGTAGTCTCTACCCTTCAATCATAATCACCCACAACGTCTCGCCAGATACGCTCAACCGCGAGGGGT
GTAGGAGCTACGACGTTGCCCCCGAGGTCGGTCACAAGTTCTGCAAGGACTTCCCCGGCTTCATTCCGAGCCTGCTCGGAAACCTGCTGGAGGAAAGGCAGAAGATA
AAGAGGAAGATGAAGGCAACTCTCGACCCGCTGGAGAAGAATCTCCTCGATTACAGGCAACGCGCCATCAAGATTCTCGCCAACAGCTACTACGGCTACTACGGCTA
TGCCAGGGCAAGATGGTACTGCAGGGAGTGCGCCGAGAGCGTTACGGCATGGGGAAGGGAGTACATCGAAATGGTCATCAGAGAGCTTGAGGAAAAGTTCGGTTTTA
AAGTCCTCTATGCAGACACAGACGGTCTCCATGCCACCATTCCTGGAGCGGACGCTGAAACAGTCAAGAAAAAGGCAATGGAGTTCTTAAACTATATCAATCCCAAA
CTGCCCGGCCTTCTCGAACTCGAATACGAGGGCTTCTACGTCAGGGGCTTCTTCGTCACGAAGAAAAAGTACGCGGTCATCGACGAGGAGGGCAAGATAACCACGCG
CGGGCTTGAGATAGTCAGGCGCGACTGGAGCGAGATAGCGAAGGAGACGCAGGCGAGGGTTTTGGAGGCGATACTCAGGCACGGTGACGTTGAAGAGGCCGTCAGAA
TTGTCAGGGAAGTCACCGAAAAGCTGAGCAAGTACGAGGTTCCGCCGGAGAAGCTGGTTATCCACGAGCAGATAACGCGCGAGCTCAAGGACTACAAGGCCACCGGC
CCGCACGTAGCCATAGCGAAgcGTTTGGCCGCCAGAGGTGTTAAAATCCGGCCCGGAACTGTGATAAGCTACATCGTTCTGAAGGGCTCCGGAAGGATAGGCGACAG
GGCGATTCCCTTCGACGAGTTCGACCCGACGAAGCACAAGTACGATGCGGACTACTACATCGAGAACCAGGTTCTGCCGGCAGTTGAGAGAATCCTCAGGGCCTTCG
GCTACCGCAAGGAAGACCTGCGCTACCAGAAGACGAGGCAGGTCGGGCTTGGCGCGTGGCTGA

| |
|---|
| FIG. 8T-1 |
| FIG. 8T-2 |
| FIG. 8T-3 |

Pyrococcus furiosus DSM 3638, Archeael hostone (HMf-1) section 85 of 173 of the complete genome.
ACCESSION No: AE010210 REGION: complement (8333..9082)
/product="pcna sliding clamp (proliferating-cell nuclear antigen)"

Nucleotide sequence (SEQ ID NO: 67)
Amino acid sequence (SEQ ID NO: 68)

```
 M   P   F   E   I   V   F   E   G   A   K   E   F   A   Q   L   I   D     18
ATG CCA TTT GAA ATC GTA TTT GAA GGT GCA AAA GAG TTT GCC CAA CTT ATA GAC    54

 T   A   S   K   L   I   D   E   A   A   F   K   V   T   E   D   G   I     36
ACC GCA AGT AAG TTA ATA GAT GAG GCC GCG TTT AAA GTT ACA GAA GAT GGG ATA   108
```

FIG. 8T-1

```
 S   M   R   A   M   D   P   S   R   V   V   L   I   D   L   N   L   P      54
AGC ATG AGG GCC ATG GAT CCA AGT AGA GTT GTC CTG ATT GAC CTA AAT CTC CCG    162

 S   S   I   F   S   K   Y   E   V   V   E   P   E   T   I   G   V   N      72
TCA AGC ATA TTT AGC AAA TAT GAA GTT GTT GAA CCA GAA ACA ATT GGA GTT AAC    216

 M   D   H   L   K   K   I   L   K   R   G   K   A   K   D   T   L   I      90
ATG GAC CAC CTA AAG AAG ATC CTA AAG AGA GGT AAA GCA AAG GAC ACC TTA ATA    270

 L   K   K   G   E   E   N   F   L   E   I   T   I   Q   G   T   A   T     108
CTC AAG AAA GGA GAG GAA AAC TTC TTA GAG ATA ACA ATT CAA GGA ACT GCA ACA    324

 R   T   F   R   V   P   L   I   D   V   E   E   M   E   V   D   L   P     126
AGA ACA TTT AGA GTT CCC CTA ATA GAT GTA GAA GAG ATG GAA GTT GAC CTC CCA    378

 E   L   P   F   T   A   K   V   V   V   L   G   E   V   L   K   D   A     144
GAA CTT CCA TTC ACT GCA AAG GTT GTA GTT CTT GGA GAA GTC CTA AAA GAT GCT    432
```

FIG. 8T-2

```
 V   K   D   A   S   L   V   S   D   S   I   K   F   I   A   R   E   N    162
GTT AAA GAT GCC TCT CTA GTG AGT GAC AGC ATA AAA TTT ATT GCC AGG GAA AAT   486

 E   F   I   M   K   A   E   G   E   T   Q   E   V   E   I   K   L   T    180
GAA TTT ATA ATG AAG GCA GAG GGA GAA ACC CAG GAA GTT GAG ATA AAG CTA ACT   540

 L   E   D   E   G   L   L   D   I   E   V   Q   E   E   T   K   S   A    198
CTT GAA GAT GAG GGA TTA TTG GAC ATC GAG GTT CAA GAG GAG ACA AAG AGC GCA   594

 Y   G   V   S   Y   L   S   D   M   V   K   G   L   G   K   A   D   E    216
TAT GGA GTC AGC TAT CTC TCC GAC ATG GTT AAA GGA CTT GGA AAG GCC GAT GAA   648

 V   T   I   K   F   G   N   E   M   P   M   Q   M   E   Y   Y   I   R    234
GTT ACA ATA AAG TTT GGA AAT GAA ATG CCC ATG CAA ATG GAG TAT TAC ATT AGA   702

 D   E   G   R   L   T   F   L   L   A   P   R   V   E   E   *            250
GAT GAA GGA AGA CTT ACA TTC CTA CTG GCT CCA AGA GTT GAA GAG TGA           750
```

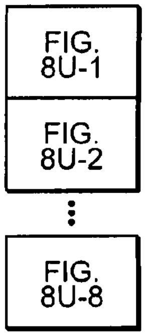

(PCNA)-Taq DNA polymerase fusion protein

Nucleotide sequence (SEQ ID NO: 67) // Nucleotide sequence (SEQ ID NO: 65)
Amino acid sequence (SEQ ID NO: 68) // Amino acid sequence (SEQ ID NO: 66)

```
 M   P   F   E   I   V   F   E   G   A   K   E   F   A   Q   L   I   D     18
ATG CCA TTT GAA ATC GTA TTT GAA GGT GCA AAA GAG TTT GCC CAA CTT ATA GAC    54

 T   A   S   K   L   I   D   E   A   A   F   K   V   T   E   D   G   I     36
ACC GCA AGT AAG TTA ATA GAT GAG GCC GCG TTT AAA GTT ACA GAA GAT GGG ATA   108

 S   M   R   A   M   D   P   S   R   V   V   L   I   D   L   N   L   P     54
AGC ATG AGG GCC ATG GAT CCA AGT AGA GTT GTC CTG ATT GAC CTA AAT CTC CCG   162

 S   S   I   F   S   K   Y   E   V   V   E   P   E   T   I   G   V   N     72
TCA AGC ATA TTT AGC AAA TAT GAA GTT GTT GAA CCA GAA ACA ATT GGA GTT AAC   216

 M   D   H   L   K   K   I   L   K   R   G   K   A   K   D   T   L   I     90
ATG GAC CAC CTA AAG AAG ATC CTA AAG AGA GGT AAA GCA AAG GAC ACC TTA ATA   270

 L   K   K   G   E   E   N   F   L   E   I   T   I   Q   G   T   A   T    108
CTC AAG AAA GGA GAG GAA AAC TTC TTA GAG ATA ACA ATT CAA GGA ACT GCA ACA   324
```

FIG. 8U-1

R T F R V P L I D V E E M E V D L P 126
AGA ACA TTT AGA GTT CCC CTA ATA GAT GTA GAA GAG ATG GAA GTT GAC CTC CCA 378

E L P F T A K V V V L G E V L K D A 144
GAA CTT CCA TTC ACT GCA AAG GTT GTA GTT CTT GGA GAA GTC CTA AAA GAT GCT 432

V K D A S L V S D S I K F I A R E N 162
GTT AAA GAT GCC TCT CTA GTG AGT GAC AGC ATA AAA TTT ATT GCC AGG GAA AAT 486

E F I M K A E G E T Q E V E I K L T 180
GAA TTT ATA ATG AAG GCA GAG GGA GAA ACC CAG GAA GTT GAG ATA AAG CTA ACT 540

L E D E G L L D I E V Q E E T K S A 198
CTT GAA GAT GAG GGA TTA TTG GAC ATC GAG GTT CAA GAG GAG ACA AAG AGC GCA 594

Y G V S Y L S D M V K G L G K A D E 216
TAT GGA GTC AGC TAT CTC TCC GAC ATG GTT AAA GGA CTT GGA AAG GCC GAT GAA 648

V T I K F G N E M P M Q M E Y Y I R 234
GTT ACA ATA AAG TTT GGA AAT GAA ATG CCC ATG CAA ATG GAG TAT TAC ATT AGA 702

D E G R L T F L L A P R V E E 250
GAT GAA GGA AGA CTT ACA TTC CTA CTG GCT CCA AGA GTT GAA GAG

FIG. 8U-2

```
    G   G   G
// GGC GGC GGT

 V   T   S   G   M   L   P   L   F   E   P   K   G   R   V   L   L   V
GTC ACT AGT GGG ATG CTG CCC CTC TTT GAG CCC AAG GGC CGG GTC CTC CTG GTG

 D   G   H   H   L   A   Y   R   T   F   H   A   L   K   G   L   T   T
GAC GGC CAC CAC CTG GCC TAC CGC ACC TTC CAC GCC CTG AAG GGC CTC ACC ACC

 S   R   G   E   P   V   Q   A   V   Y   G   F   A   K   S   L   L   K
AGC CGG GGG GAG CCG GTG CAG GCG GTC TAC GGC TTC GCC AAG AGC CTC CTC AAG

 A   L   K   E   D   G   D   A   V   I   V   V   F   D   A   K   A   P
GCC CTC AAG GAG GAC GGG GAC GCG GTG ATC GTG GTC TTT GAC GCC AAG GCC CCC

 S   F   R   H   E   A   Y   G   G   Y   K   A   G   R   A   P   T   P
TCC TTC CGC CAC GAG GCC TAC GGG GGG TAC AAG GCG GGC CGG GCC CCC ACG CCA

 E   D   F   P   R   Q   L   A   L   I   K   E   L   V   D   L   L   G
GAG GAC TTT CCC CGG CAA CTC GCC CTC ATC AAG GAG CTG GTG GAC CTC CTG GGG

 L   A   R   L   E   V   P   G   Y   E   A   D   D   V   L   A   S   L
CTG GCG CGC CTC GAG GTC CCG GGC TAC GAG GCG GAC GAC GTC CTG GCC AGC CTG
```

FIG. 8U-3

```
 A   K   K   A   E   K   E   G   Y   E   V   R   I   L   T   A   D   K
GCC AAG AAG GCG GAA AAG GAG GGC TAC GAG GTC CGC ATC CTC ACC GCC GAC AAA

 D   L   Y   Q   L   L   S   D   R   I   H   V   L   H   P   E   G   Y
GAC CTT TAC CAG CTC CTT TCC GAC CGC ATC CAC GTC CTC CAC CCC GAG GGG TAC

 L   I   T   P   A   W   L   W   E   K   Y   G   L   R   P   D   Q   W
CTC ATC ACC CCG GCC TGG CTT TGG GAA AAG TAC GGC CTG AGG CCC GAC CAG TGG

 A   D   Y   R   A   L   T   G   D   E   S   D   N   L   P   G   V   K
GCC GAC TAC CGG GCC CTG ACC GGG GAC GAG TCC GAC AAC CTT CCC GGG GTC AAG

 G   I   G   E   K   T   A   R   K   L   L   E   E   W   G   S   L   E
GGC ATC GGG GAG AAG ACG GCG AGG AAG CTT CTG GAG GAG TGG GGG AGC CTG GAA

 A   L   L   K   N   L   D   R   L   K   P   A   I   R   E   K   I   L
GCC CTC CTC AAG AAC CTG GAC CGG CTG AAG CCC GCC ATC CGG GAG AAG ATC CTG

 A   H   M   D   D   L   K   L   S   W   D   L   A   K   V   R   T   D
GCC CAC ATG GAC GAT CTG AAG CTC TCC TGG GAC CTG GCC AAG GTG CGC ACC GAC

 L   P   L   E   V   D   F   A   K   R   R   E   P   D   R   E   R   L
CTG CCC CTG GAG GTG GAC TTC GCC AAA AGG CGG GAG CCC GAC CGG GAG AGG CTT
```

FIG. 8U-4

```
R   A   F   L   E   R   L   E   F   G   S   L   L   H   E   F   G   L
AGG GCC TTT CTG GAG AGG CTT GAG TTT GGC AGC CTC CTC CAC GAG TTC GGC CTT

L   E   S   P   K   A   L   E   E   A   P   W   P   P   P   E   G   A
CTG GAA AGC CCC AAG GCC CTG GAG GAG GCC CCC TGG CCC CCG CCG GAA GGG GCC

F   V   G   F   V   L   S   R   K   E   P   M   W   A   D   L   L   A
TTC GTG GGC TTT GTG CTT TCC CGC AAG GAG CCC ATG TGG GCC GAT CTT CTG GCC

L   A   A   A   R   G   G   R   V   H   R   A   P   E   P   Y   K   A
CTG GCC GCC GCC AGG GGG GGC CGG GTC CAC CGG GCC CCC GAG CCT TAT AAA GCC

L   R   D   L   K   E   A   R   G   L   L   A   K   D   L   S   V   L
CTC AGG GAC CTG AAG GAG GCG CGG GGG CTT CTC GCC AAA GAC CTG AGC GTT CTG

A   L   R   E   G   L   G   L   P   P   G   D   D   P   M   L   L   A
GCC CTG AGG GAA GGC CTT GGC CTC CCG CCC GGC GAC GAC CCC ATG CTC CTC GCC

Y   L   L   D   P   S   N   T   T   P   E   G   V   A   R   R   Y   G
TAC CTC CTG GAC CCT TCC AAC ACC ACC CCC GAG GGG GTG GCC CGG CGC TAC GGC

G   E   W   T   E   E   A   G   E   R   A   A   L   S   E   R   L   F
GGG GAG TGG ACG GAG GAG GCG GGG GAG CGG GCC GCC CTT TCC GAG AGG CTC TTC
```

FIG. 8U-5

```
 A   N   L   W   G   R   L   E   G   E   E   R   L   L   W   L   Y   R
GCC AAC CTG TGG GGG AGG CTT GAG GGG GAG GAG AGG CTC CTT TGG CTT TAC CGG

 E   V   E   R   P   L   S   A   V   L   A   H   M   E   A   T   G   V
GAG GTG GAG AGG CCC CTT TCC GCT GTC CTG GCC CAC ATG GAG GCC ACG GGG GTG

 R   L   D   V   A   Y   L   R   A   L   S   L   E   V   A   E   E   I
CGC CTG GAC GTG GCC TAT CTC AGG GCC TTG TCC CTG GAG GTG GCC GAG GAG ATC

 A   R   L   E   A   E   V   F   R   L   A   G   H   P   F   N   L   N
GCC CGC CTC GAG GCC GAG GTC TTC CGC CTG GCC GGC CAC CCC TTC AAC CTC AAC

 S   R   D   Q   L   E   R   V   L   F   D   E   L   G   L   P   A   I
TCC CGG GAC CAG CTG GAA AGG GTC CTC TTT GAC GAG CTA GGG CTT CCC GCC ATC

 G   K   T   E   K   T   G   K   R   S   T   S   A   A   V   L   E   A
GGC AAG ACG GAG AAG ACC GGC AAG CGC TCC ACC AGC GCC GCC GTC CTG GAG GCC

 L   R   E   A   H   P   I   V   E   K   I   L   Q   Y   R   E   L   T
CTC CGC GAG GCC CAC CCC ATC GTG GAG AAG ATC CTG CAG TAC CGG GAG CTC ACC

 K   L   K   S   T   Y   I   D   P   L   P   D   L   I   H   P   R   T
AAG CTG AAG AGC ACC TAC ATT GAC CCC TTG CCG GAC CTC ATC CAC CCC AGG ACG
```

FIG. 8U-6

```
 G   R   L   H   T   R   F   N   Q   T   A   T   A   T   G   R   L   S
GGC CGC CTC CAC ACC CGC TTC AAC CAG ACG GCC ACG GCC ACG GGC AGG CTA AGT

 S   S   D   P   N   L   Q   N   I   P   V   R   T   P   L   G   Q   R
AGC TCC GAT CCC AAC CTC CAG AAC ATC CCC GTC CGC ACC CCG CTT GGG CAG AGG

 I   R   R   A   F   I   A   E   E   G   W   L   L   V   A   L   D   Y
ATC CGC CGG GCC TTC ATC GCC GAG GAG GGG TGG CTA TTG GTG GCC CTG GAC TAT

 S   Q   I   E   L   R   V   L   A   H   L   S   G   D   E   N   L   I
AGC CAG ATA GAG CTC AGG GTG CTG GCC CAC CTC TCC GGC GAC GAG AAC CTG ATC

 R   V   F   Q   E   G   R   D   I   H   T   E   T   A   S   W   M   F
CGG GTC TTC CAG GAG GGG CGG GAC ATC CAC ACG GAG ACC GCC AGC TGG ATG TTC

 G   V   P   R   E   A   V   D   P   L   M   R   R   A   A   K   T   I
GGC GTC CCC CGG GAG GCC GTG GAC CCC CTG ATG CGC CGG GCG GCC AAG ACC ATC

 N   F   G   V   L   Y   G   M   S   A   H   R   L   S   Q   E   L   A
AAC TTC GGG GTC CTC TAC GGC ATG TCG GCC CAC CGC CTC TCC CAG GAG CTA GCC

 I   P   Y   E   E   A   Q   A   F   I   E   R   Y   F   Q   S   F   P
ATC CCT TAC GAG GAG GCC CAG GCC TTC ATT GAG CGC TAC TTT CAG AGC TTC CCC
```

FIG. 8U-7

```
 K   V   R   A   W   I   E   K   T   L   E   E   G   R   R   R   G   Y
AAG GTG CGG GCC TGG ATT GAG AAG ACC CTG GAG GAG GGC AGG AGG CGG GGG TAC

 V   E   T   L   F   G   R   R   R   Y   V   P   D   L   E   A   R   V
GTG GAG ACC CTC TTC GGC CGC CGC CGC TAC GTG CCA GAC CTA GAG GCC CGG GTG

 K   S   V   R   E   A   A   E   R   M   A   F   N   M   P   V   Q   G
AAG AGC GTG CGG GAG GCG GCC GAG CGC ATG GCC TTC AAC ATG CCC GTC CAG GGC

 T   A   A   D   L   M   K   L   A   M   V   K   L   F   P   R   L   E
ACC GCC GCC GAC CTC ATG AAG CTG GCT ATG GTG AAG CTC TTC CCC AGG CTG GAG

 E   M   G   A   R   M   L   L   Q   V   H   D   E   L   V   L   E   A
GAA ATG GGG GCC AGG ATG CTC CTT CAG GTC CAC GAC GAG CTG GTC CTC GAG GCC

 P   K   E   R   A   E   A   V   A   R   L   A   K   E   V   M   E   G
CCA AAA GAG AGG GCG GAG GCC GTG GCC CGG CTG GCC AAG GAG GTC ATG GAG GGG

 V   Y   P   L   A   V   P   L   E   V   E   V   G   I   G   E   D   W
GTG TAT CCC CTG GCC GTG CCC CTG GAG GTG GAG GTG GGG ATA GGG GAG GAC TGG

 L   S   A   K   E   G   I   D   G   R   G   G   G   G   H   H   H   H
CTC TCC GCC AAG GAG GGC ATT GAT GGC CGC GGC GGA GGC GGG CAT CAT CAT CAT

 H   H   *
CAT CAT TAA
```

FIG. 8U-8

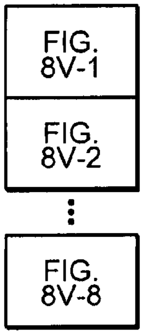

FIG. 8V

Taq DNA polymerase- (PCNA) fusion protein

Nucleotide sequence (SEQ ID NO: 65) //Nucleotide sequence (SEQ ID NO: 67)
Amino acid sequence (SEQ ID NO: 66) /Amino acid sequence (SEQ ID NO: 68)

```
    G   G   G
//  GGC GGC GGT

V   T   S   G   M   L   P   L   F   E   P   K   G   R   V   L   L   V
GTC ACT AGT GGG ATG CTG CCC CTC TTT GAG CCC AAG GGC CGG GTC CTC CTG GTG

D   G   H   H   L   A   Y   R   T   F   H   A   L   K   G   L   T   T
GAC GGC CAC CAC CTG GCC TAC CGC ACC TTC CAC GCC CTG AAG GGC CTC ACC ACC

S   R   G   E   P   V   Q   A   V   Y   G   F   A   K   S   L   L   K
AGC CGG GGG GAG CCG GTG CAG GCG GTC TAC GGC TTC GCC AAG AGC CTC CTC AAG

A   L   K   E   D   G   D   A   V   I   V   V   F   D   A   K   A   P
GCC CTC AAG GAG GAC GGG GAC GCG GTG ATC GTG GTC TTT GAC GCC AAG GCC CCC

S   F   R   H   E   A   Y   G   G   Y   K   A   G   R   A   P   T   P
TCC TTC CGC CAC GAG GCC TAC GGG GGG TAC AAG GCG GGC CGG GCC CCC ACG CCA
```

FIG. 8V-1

```
 E   D   F   P   R   Q   L   A   L   I   K   E   L   V   D   L   L   G
GAG GAC TTT CCC CGG CAA CTC GCC CTC ATC AAG GAG CTG GTG GAC CTC CTG GGG

 L   A   R   L   E   V   P   G   Y   E   A   D   D   V   L   A   S   L
CTG GCG CGC CTC GAG GTC CCG GGC TAC GAG GCG GAC GAC GTC CTG GCC AGC CTG

 A   K   K   A   E   K   E   G   Y   E   V   R   I   L   T   A   D   K
GCC AAG AAG GCG GAA AAG GAG GGC TAC GAG GTC CGC ATC CTC ACC GCC GAC AAA

 D   L   Y   Q   L   L   S   D   R   I   H   V   L   H   P   E   G   Y
GAC CTT TAC CAG CTC CTT TCC GAC CGC ATC CAC GTC CTC CAC CCC GAG GGG TAC

 L   I   T   P   A   W   L   W   E   K   Y   G   L   R   P   D   Q   W
CTC ATC ACC CCG GCC TGG CTT TGG GAA AAG TAC GGC CTG AGG CCC GAC CAG TGG

 A   D   Y   R   A   L   T   G   D   E   S   D   N   L   P   G   V   K
GCC GAC TAC CGG GCC CTG ACC GGG GAC GAG TCC GAC AAC CTT CCC GGG GTC AAG

 G   I   G   E   K   T   A   R   K   L   L   E   E   W   G   S   L   E
GGC ATC GGG GAG AAG ACG GCG AGG AAG CTT CTG GAG GAG TGG GGG AGC CTG GAA

 A   L   L   K   N   L   D   R   L   K   P   A   I   R   E   K   I   L
GCC CTC CTC AAG AAC CTG GAC CGG CTG AAG CCC GCC ATC CGG GAG AAG ATC CTG
```

FIG. 8V-2

```
 A   H   M   D   D   L   K   L   S   W   D   L   A   K   V   R   T   D
GCC CAC ATG GAC GAT CTG AAG CTC TCC TGG GAC CTG GCC AAG GTG CGC ACC GAC

 L   P   L   E   V   D   F   A   K   R   R   E   P   D   R   E   R   L
CTG CCC CTG GAG GTG GAC TTC GCC AAA AGG CGG GAG CCC GAC CGG GAG AGG CTT

 R   A   F   L   E   R   L   E   F   G   S   L   L   H   E   F   G   L
AGG GCC TTT CTG GAG AGG CTT GAG TTT GGC AGC CTC CTC CAC GAG TTC GGC CTT

 L   E   S   P   K   A   L   E   E   A   P   W   P   P   P   E   G   A
CTG GAA AGC CCC AAG GCC CTG GAG GAG GCC CCC TGG CCC CCG CCG GAA GGG GCC

 F   V   G   F   V   L   S   R   K   E   P   M   W   A   D   L   L   A
TTC GTG GGC TTT GTG CTT TCC CGC AAG GAG CCC ATG TGG GCC GAT CTT CTG GCC

 L   A   A   A   R   G   G   R   V   H   R   A   P   E   P   Y   K   A
CTG GCC GCC GCC AGG GGG GGC CGG GTC CAC CGG GCC CCC GAG CCT TAT AAA GCC

 L   R   D   L   K   E   A   R   G   L   L   A   K   D   L   S   V   L
CTC AGG GAC CTG AAG GAG GCG CGG GGG CTT CTC GCC AAA GAC CTG AGC GTT CTG

 A   L   R   E   G   L   G   L   P   P   G   D   D   P   M   L   L   A
GCC CTG AGG GAA GGC CTT GGC CTC CCG CCC GGC GAC GAC CCC ATG CTC CTC GCC
```

FIG. 8V-3

```
 Y   L   L   D   P   S   N   T   T   P   E   G   V   A   R   R   Y   G
TAC CTC CTG GAC CCT TCC AAC ACC ACC CCC GAG GGG GTG GCC CGG CGC TAC GGC

 G   E   W   T   E   E   A   G   E   R   A   A   L   S   E   R   L   F
GGG GAG TGG ACG GAG GAG GCG GGG GAG CGG GCC GCC CTT TCC GAG AGG CTC TTC

 A   N   L   W   G   R   L   E   G   E   E   R   L   L   W   L   Y   R
GCC AAC CTG TGG GGG AGG CTT GAG GGG GAG GAG AGG CTC CTT TGG CTT TAC CGG

 E   V   E   R   P   L   S   A   V   L   A   H   M   E   A   T   G   V
GAG GTG GAG AGG CCC CTT TCC GCT GTC CTG GCC CAC ATG GAG GCC ACG GGG GTG

 R   L   D   V   A   Y   L   R   A   L   S   L   E   V   A   E   E   I
CGC CTG GAC GTG GCC TAT CTC AGG GCC TTG TCC CTG GAG GTG GCC GAG GAG ATC

 A   R   L   E   A   E   V   F   R   L   A   G   H   P   F   N   L   N
GCC CGC CTC GAG GCC GAG GTC TTC CGC CTG GCC GGC CAC CCC TTC AAC CTC AAC

 S   R   D   Q   L   E   R   V   L   F   D   E   L   G   L   P   A   I
TCC CGG GAC CAG CTG GAA AGG GTC CTC TTT GAC GAG CTA GGG CTT CCC GCC ATC

 G   K   T   E   K   T   G   K   R   S   T   S   A   A   V   L   E   A
GGC AAG ACG GAG AAG ACC GGC AAG CGC TCC ACC AGC GCC GCC GTC CTG GAG GCC
```

FIG. 8V-4

```
 L   R   E   A   H   P   I   V   E   K   I   L   Q   Y   R   E   L   T
CTC CGC GAG GCC CAC CCC ATC GTG GAG AAG ATC CTG CAG TAC CGG GAG CTC ACC

 K   L   K   S   T   Y   I   D   P   L   P   D   L   I   H   P   R   T
AAG CTG AAG AGC ACC TAC ATT GAC CCC TTG CCG GAC CTC ATC CAC CCC AGG ACG

 G   R   L   H   T   R   F   N   Q   T   A   T   A   T   G   R   L   S
GGC CGC CTC CAC ACC CGC TTC AAC CAG ACG GCC ACG GCC ACG GGC AGG CTA AGT

 S   S   D   P   N   L   Q   N   I   P   V   R   T   P   L   G   Q   R
AGC TCC GAT CCC AAC CTC CAG AAC ATC CCC GTC CGC ACC CCG CTT GGG CAG AGG

 I   R   R   A   F   I   A   E   E   G   W   L   L   V   A   L   D   Y
ATC CGC CGG GCC TTC ATC GCC GAG GAG GGG TGG CTA TTG GTG GCC CTG GAC TAT

 S   Q   I   E   L   R   V   L   A   H   L   S   G   D   E   N   L   I
AGC CAG ATA GAG CTC AGG GTG CTG GCC CAC CTC TCC GGC GAC GAG AAC CTG ATC

 R   V   F   Q   E   G   R   D   I   H   T   E   T   A   S   W   M   F
CGG GTC TTC CAG GAG GGG CGG GAC ATC CAC ACG GAG ACC GCC AGC TGG ATG TTC

 G   V   P   R   E   A   V   D   P   L   M   R   R   A   A   K   T   I
GGC GTC CCC CGG GAG GCC GTG GAC CCC CTG ATG CGC CGG GCG GCC AAG ACC ATC
```

FIG. 8V-5

```
 N   F   G   V   L   Y   G   M   S   A   H   R   L   S   Q   E   L   A
AAC TTC GGG GTC CTC TAC GGC ATG TCG GCC CAC CGC CTC TCC CAG GAG CTA GCC

 I   P   Y   E   E   A   Q   A   F   I   E   R   Y   F   Q   S   F   P
ATC CCT TAC GAG GAG GCC CAG GCC TTC ATT GAG CGC TAC TTT CAG AGC TTC CCC

 K   V   R   A   W   I   E   K   T   L   E   E   G   R   R   R   G   Y
AAG GTG CGG GCC TGG ATT GAG AAG ACC CTG GAG GAG GGC AGG AGG CGG GGG TAC

 V   E   T   L   F   G   R   R   R   Y   V   P   D   L   E   A   R   V
GTG GAG ACC CTC TTC GGC CGC CGC CGC TAC GTG CCA GAC CTA GAG GCC CGG GTG

 K   S   V   R   E   A   A   E   R   M   A   F   N   M   P   V   Q   G
AAG AGC GTG CGG GAG GCG GCC GAG CGC ATG GCC TTC AAC ATG CCC GTC CAG GGC

 T   A   A   D   L   M   K   L   A   M   V   K   L   F   P   R   L   E
ACC GCC GCC GAC CTC ATG AAG CTG GCT ATG GTG AAG CTC TTC CCC AGG CTG GAG

 E   M   G   A   R   M   L   L   Q   V   H   D   E   L   V   L   E   A
GAA ATG GGG GCC AGG ATG CTC CTT CAG GTC CAC GAC GAG CTG GTC CTC GAG GCC

 P   K   E   R   A   E   A   V   A   R   L   A   K   E   V   M   E   G
CCA AAA GAG AGG GCG GAG GCC GTG GCC CGG CTG GCC AAG GAG GTC ATG GAG GGG
```

FIG. 8V-6

```
 V   Y   P   L   A   V   P   L   E   V   E   V   G   I   G   E   D   W
GTG TAT CCC CTG GCC GTG CCC CTG GAG GTG GAG GTG GGG ATA GGG GAG GAC TGG

 L   S   A   K   E   G   I   D   G   R   G   G   G   G   H   H   H   H
CTC TCC GCC AAG GAG GGC ATT GAT GGC CGC GGC GGA GGC GGG CAT CAT CAT CAT

 H   H   //
CAT CAT  //

 M   P   F   E   I   V   F   E   G   A   K   E   F   A   Q   L   I   D      18
ATG CCA TTT GAA ATC GTA TTT GAA GGT GCA AAA GAG TTT GCC CAA CTT ATA GAC     54

 T   A   S   K   L   I   D   E   A   A   F   K   V   T   E   D   G   I      36
ACC GCA AGT AAG TTA ATA GAT GAG GCC GCG TTT AAA GTT ACA GAA GAT GGG ATA    108

 S   M   R   A   M   D   P   S   R   V   V   L   I   D   L   N   L   P      54
AGC ATG AGG GCC ATG GAT CCA AGT AGA GTT GTC CTG ATT GAC CTA AAT CTC CCG    162

 S   S   I   F   S   K   Y   E   V   V   E   P   E   T   I   G   V   N      72
TCA AGC ATA TTT AGC AAA TAT GAA GTT GTT GAA CCA GAA ACA ATT GGA GTT AAC    216

 M   D   H   L   K   K   I   L   K   R   G   K   A   K   D   T   L   I      90
ATG GAC CAC CTA AAG AAG ATC CTA AAG AGA GGT AAA GCA AAG GAC ACC TTA ATA    270
```

FIG. 8V-7

```
 L   K   K   G   E   E   N   F   L   E   I   T   I   Q   G   T   A   T     108
CTC AAG AAA GGA GAG GAA AAC TTC TTA GAG ATA ACA ATT CAA GGA ACT GCA ACA    324

 R   T   F   R   V   P   L   I   D   V   E   E   M   E   V   D   L   P     126
AGA ACA TTT AGA GTT CCC CTA ATA GAT GTA GAA GAG ATG GAA GTT GAC CTC CCA    378

 E   L   P   F   T   A   K   V   V   V   L   G   E   V   L   K   D   A     144
GAA CTT CCA TTC ACT GCA AAG GTT GTA GTT CTT GGA GAA GTC CTA AAA GAT GCT    432

 V   K   D   A   S   L   V   S   D   S   I   K   F   I   A   R   E   N     162
GTT AAA GAT GCC TCT CTA GTG AGT GAC AGC ATA AAA TTT ATT GCC AGG GAA AAT    486

 E   F   I   M   K   A   E   G   E   T   Q   E   V   E   I   K   L   T     180
GAA TTT ATA ATG AAG GCA GAG GGA GAA ACC CAG GAA GTT GAG ATA AAG CTA ACT    540

 L   E   D   E   G   L   L   D   I   E   V   Q   E   E   T   K   S   A     198
CTT GAA GAT GAG GGA TTA TTG GAC ATC GAG GTT CAA GAG GAG ACA AAG AGC GCA    594

 Y   G   V   S   Y   L   S   D   M   V   K   G   L   G   K   A   D   E     216
TAT GGA GTC AGC TAT CTC TCC GAC ATG GTT AAA GGA CTT GGA AAG GCC GAT GAA    648

 V   T   I   K   F   G   N   E   M   P   M   Q   M   E   Y   Y   I   R     234
GTT ACA ATA AAG TTT GGA AAT GAA ATG CCC ATG CAA ATG GAG TAT TAC ATT AGA    702

 D   E   G   R   L   T   F   L   L   A   P   R   V   E   E   *             250
GAT GAA GGA AGA CTT ACA TTC CTA CTG GCT CCA AGA GTT GAA GAG TGA
```

Pfu DNA Polymerase (WT) -(PCNA) fusion protein

Nucleotide sequence (SEQ ID NO: 61) // Nucleotide sequence (SEQ ID NO: 67)

//
ccctggtcct gggtccacat atatgttctt actcgccttt atgaagaatc ccccagtcgc tctaacctgg gttatagtga caaatcttcc tccaccaccg cccaagaagg ttatttctat caactctaca cctcccctat tttctctctt atgagatttt taagtatagt tatagagaag gttttatact ccaaactgag ttagtagata tgtggggagc ataatgattt tagatgtgga ttacataact gaagaaggaa aacctgttat taggctattc aaaaaagaga acggaaaatt taagatagag catgatagaa cttttagacc atacatttac gctcttctca gggatgattc aaagattgaa gaagttaaga aaataacggg ggaaaggcat ggaaagattg tgagaattgt

FIG. 8W-1

```
tgatgtagag aaggttgaga aaaagtttct cggcaagcct attaccgtgt ggaaacttta
tttggaacat ccccaagatg ttcccactat tagagaaaaa gttagagaac atccagcagt
tgtggacatc ttcgaatacg atattccatt tgcaaagaga tacctcatcg acaaaggcct
aataccaatg gagggggaag aagagctaaa gattcttgcc ttcgatatag aaaccctcta
tcacgaagga gaagagtttg gaaaaggccc aattataatg attagttatg cagatgaaaa
tgaagcaaag gtgattactt ggaaaaacat agatcttcca tacgttgagg ttgtatcaag
cgagagagag atgataaaga gatttctcag gattatcagg gagaaggatc ctgacattat
agttacttat aatggagact cattcgactt cccatattta gcgaaaaggg cagaaaaact
tgggattaaa ttaaccattg gaagagatgg aagcgagccc aagatgcaga gaataggcga
tatgacggct gtagaagtca agggaagaat acatttcgac ttgtatcatg taataacaag
gacaataaat ctcccaacat acacactaga ggctgtatat gaagcaattt ttggaaagcc
aaaggagaag gtatacgccg acgagatagc aaaagcctgg gaaagtggag agaaccttga
```

FIG. 8W-2 gagagttgcc aaatactcga tggaagatgc aaaggcaact tatgaactcg ggaaagaatt ccttccaatg gaaattcagc tttcaagatt agttggacaa cctttatggg atgtttcaag gtcaagcaca gggaaccttg tagagtggtt cttacttagg aaagcctacg aaagaaacga agtagctcca aacaagccaa gtgaagagga gtatcaaaga aggctcaggg agagctacac aggtggattc gttaaagagc cagaaaaggg gttgtgggaa aacatagtat acctagattt tagagcccta tatccctcga ttataattac ccacaatgtt tctcccgata ctctaaatct tgagggatgc aagaactatg atatcgctcc tcaagtaggc cacaagttct gcaaggacat ccctggtttt ataccaagtc tcttgggaca tttgttagag gaaagacaaa agattaagac aaaaatgaag gaaactcaag atcctataga aaaaatactc cttgactata gacaaaaagc gataaaactc ttagcaaatt ctttctacgg atattatggc tatgcaaaag caagatggta ctgtaaggag tgtgctgaga gcgttactgc ctggggaaga aagtacatcg agttagtatg gaaggagctc gaagaaaagt ttggatttaa agtcctctac attgacactg atggtctcta

FIG. 8W-3 tgcaactatc ccaggaggag aaagtgagga aataaagaaa aaggctctag aatttgtaaa
atacataaat tcaaagctcc ctggactgct agagcttgaa tatgaagggt tttataagag
gggattcttc gttacgaaga agaggtatgc agtaatagat gaagaaggaa aagtcattac
tcgtggttta gagatagtta ggagagattg gagtgaaatt gcaaaagaaa ctcaagctag
agttttggag acaatactaa aacacggaga tgttgaagaa gctgtgagaa tagtaaaaga
agtaatacaa aagcttgcca attatgaaat tccaccagag aagctcgcaa tatatgagca
gataacaaga ccattacatg agtataaggc gataggtcct cacgtagctg ttgcaaagaa
actagctgct aaaggagtta aaataaagcc aggaatggta attggataca tagtacttag
aggcgatggt ccaattagca atagggcaat tctagctgag gaatacgatc ccaaaaagca
caagtatgac gcagaatatt acattgagaa ccaggttctt ccagcggtac ttaggatatt
ggagggattt ggatacagaa aggaagacct cagataccaa aagacaagac aagtcggcct
aacttcctgg cttaacatta aaaaatccta gaaaagcgat agatatcaac ttttattctt

FIG. 8W-4 tctaaccttt ttctatgaaa gaagaactga gcaggaatta ccagttcttc cgttatttta tgggtaatta aaaacccatg ctcttgggag aatcttcgaa taaaatccct aacttcaggc tttgctaagt gaatagaata aacaacatca ctcacttcaa acgccttcgt tagaaatggt ctatctgcat gcttctctgg ctcggaanng gaggattcat aacaacagta tcaacattct cagagaattg agaaacatca gaaactttga cttctacaac atttctaact ttgcaactct tcaagatttt ctaaaagaat tttaacggcc tcctcgtcaa tttcgacgac gtagatcttt tttgctccaa gcagagccgc tccaatggat aacacccctg ttcccgcacc caagtccgct acaatttttt ccttgtatct cctaatgtat aagcaagcca aaggagagta gatgctacct ttccgggagt tttgtattgc tctagccaag gtttgggatt tttgaatcct ttaactctgg aaagtataat ttcaagctcc ttcttcttca tgacagatga aaaattgttt tgtctctttt taacttttac agaaataact gtctcaaatt atgacaactc ttgacatttt tacttcatta ccagggtaat gtttttaagt atgaaatttt tctttcatag aggaggnnnn nngtcctctc

FIG. 8W-5

```
ctcgatttcc ttggttgtgc tccatatgat aagcttccaa agtgggtgtt cagactttta

gacactcaaa taccagacga caatggtgtg ctcactcaag ccccatatgg gttgagaaaa

gtagaagcgg cactactcag atgcttcccc aggaatgagg ttgttgtagc tcntcccnga

aagattgaga tgttcttgg  //

ATG CCA TTT GAA ATC GTA TTT GAA GGT GCA AAA GAG TTT GCC CAA CTT ATA GAC    54
ACC GCA AGT AAG TTA ATA GAT GAG GCC GCG TTT AAA GTT ACA GAA GAT GGG ATA   108
AGC ATG AGG GCC ATG GAT CCA AGT AGA GTT GTC CTG ATT GAC CTA AAT CTC CCG   162
TCA AGC ATA TTT AGC AAA TAT GAA GTT GTT GAA CCA GAA ACA ATT GGA GTT AAC   216
ATG GAC CAC CTA AAG AAG ATC CTA AAG AGA GGT AAA GCA AAG GAC ACC TTA ATA   270
CTC AAG AAA GGA GAG GAA AAC TTC TTA GAG ATA ACA ATT CAA GGA ACT GCA ACA   324
AGA ACA TTT AGA GTT CCC CTA ATA GAT GTA GAA GAG ATG GAA GTT GAC CTC CCA   378
GAA CTT CCA TTC ACT GCA AAG GTT GTA GTT CTT GGA GAA GTC CTA AAA GAT GCT   432
GTT AAA GAT GCC TCT CTA GTG AGT GAC AGC ATA AAA TTT ATT GCC AGG GAA AAT   486
GAA TTT ATA ATG AAG GCA GAG GGA GAA ACC CAG GAA GTT GAG ATA AAG CTA ACT   540
CTT GAA GAT GAG GGA TTA TTG GAC ATC GAG GTT CAA GAG GAG ACA AAG AGC GCA   594
TAT GGA GTC AGC TAT CTC TCC GAC ATG GTT AAA GGA CTT GGA AAG GCC GAT GAA   648
GTT ACA ATA AAG TTT GGA AAT GAA ATG CCC ATG CAA ATG GAG TAT TAC ATT AGA   702
GAT GAA GGA AGA CTT ACA TTC CTA CTG GCT CCA AGA GTT GAA GAG TGA
```

(PCNA) - Pfu DNA Polymerase (WT) fusion protein

Nucleotide sequence (SEQ ID NO: 67) // Nucleotide sequence (SEQ ID NO: 61)

```
ATG CCA TTT GAA ATC GTA TTT GAA GGT GCA AAA GAG TTT GCC CAA CTT ATA GAC    54
ACC GCA AGT AAG TTA ATA GAT GAG GCC GCG TTT AAA GTT ACA GAA GAT GGG ATA   108
AGC ATG AGG GCC ATG GAT CCA AGT AGA GTT GTC CTG ATT GAC CTA AAT CTC CCG   162
TCA AGC ATA TTT AGC AAA TAT GAA GTT GTT GAA CCA GAA ACA ATT GGA GTT AAC   216
ATG GAC CAC CTA AAG AAG ATC CTA AAG AGA GGT AAA GCA AAG GAC ACC TTA ATA   270
CTC AAG AAA GGA GAG GAA AAC TTC TTA GAG ATA ACA ATT CAA GGA ACT GCA ACA   324
AGA ACA TTT AGA GTT CCC CTA ATA GAT GTA GAA GAG ATG GAA GTT GAC CTC CCA   378
GAA CTT CCA TTC ACT GCA AAG GTT GTA GTT CTT GGA GAA GTC CTA AAA GAT GCT   432
GTT AAA GAT GCC TCT CTA GTG AGT GAC AGC ATA AAA TTT ATT GCC AGG GAA AAT   486
GAA TTT ATA ATG AAG GCA GAG GGA GAA ACC CAG GAA GTT GAG ATA AAG CTA ACT   540
CTT GAA GAT GAG GGA TTA TTG GAC ATC GAG GTT CAA GAG GAG ACA AAG AGC GCA   594
TAT GGA GTC AGC TAT CTC TCC GAC ATG GTT AAA GGA CTT GGA AAG GCC GAT GAA   648
GTT ACA ATA AAG TTT GGA AAT GAA ATG CCC ATG CAA ATG GAG TAT TAC ATT AGA   702
GAT GAA GGA AGA CTT ACA TTC CTA CTG GCT CCA AGA GTT GAA GAG
//
```

FIG. 8X-1 ccctggtcct gggtccacat atatgttctt actcgccttt atgaagaatc ccccagtcgc tctaacctgg gttatagtga caaatcttcc tccaccaccg cccaagaagg ttatttctat caactctaca cctcccctat tttctctctt atgagatttt taagtatagt tatagagaag gttttatact ccaaactgag ttagtagata tgtggggagc ataatgattt tagatgtgga ttacataact gaagaaggaa aacctgttat taggctattc aaaaaagaga acggaaaatt taagatagag catgatagaa cttttagacc atacatttac gctcttctca gggatgattc aaagattgaa gaagttaaga aaataacggg ggaaaggcat ggaaagattg tgagaattgt tgatgtagag aaggttgaga aaaagtttct cggcaagcct attaccgtgt ggaaacttta tttggaacat ccccaagatg ttcccactat tagagaaaaa gttagagaac atccagcagt tgtggacatc ttcgaatacg atattccatt tgcaaagaga tacctcatcg acaaaggcct aataccaatg gagggggaag aagagctaaa gattcttgcc ttcgatatag aaaccctcta

FIG. 8X-2 tcacgaagga gaagagtttg gaaaaggccc aattataatg attagttatg cagatgaaaa
tgaagcaaag gtgattactt ggaaaaacat agatcttcca tacgttgagg ttgtatcaag
cgagagagag atgataaaga gatttctcag gattatcagg gagaaggatc ctgacattat
agttacttat aatggagact cattcgactt cccatattta gcgaaaaggg cagaaaaact
tgggattaaa ttaaccattg gaagagatgg aagcgagccc aagatgcaga gaataggcga
tatgacggct gtagaagtca agggaagaat acatttcgac ttgtatcatg taataacaag
gacaataaat ctcccaacat acacactaga ggctgtatat gaagcaattt ttggaaagcc
aaaggagaag gtatacgccg acgagatagc aaaagcctgg gaaagtggag agaaccttga
gagagttgcc aaatactcga tggaagatgc aaaggcaact tatgaactcg ggaaagaatt
ccttccaatg gaaattcagc tttcaagatt agttggacaa cctttatggg atgtttcaag
gtcaagcaca gggaaccttg tagagtggtt cttacttagg aaagcctacg aaagaaacga
agtagctcca aacaagccaa gtgaagagga gtatcaaaga aggctcaggg agagctacac

FIG. 8X-3 aggtggattc gttaaagagc cagaaaaggg gttgtgggaa aacatagtat acctagattt tagagcccta tatccctcga ttataattac ccacaatgtt tctcccgata ctctaaatct tgagggatgc aagaactatg atatcgctcc tcaagtaggc cacaagttct gcaaggacat ccctggtttt ataccaagtc tcttgggaca tttgttagag gaaagacaaa agattaagac aaaaatgaag gaaactcaag atcctataga aaaaatactc cttgactata gacaaaaagc gataaaactc ttagcaaatt ctttctacgg atattatggc tatgcaaaag caagatggta ctgtaaggag tgtgctgaga gcgttactgc ctggggaaga aagtacatcg agttagtatg gaaggagctc gaagaaaagt ttggatttaa agtcctctac attgacactg atggtctcta tgcaactatc ccaggaggag aaagtgagga aataaagaaa aaggctctag aatttgtaaa atacataaat tcaaagctcc ctggactgct agagcttgaa tatgaagggt tttataagag gggattcttc gttacgaaga agaggtatgc agtaatagat gaagaaggaa aagtcattac tcgtggttta gagatagtta ggagagattg gagtgaaatt gcaaaagaaa ctcaagctag

FIG. 8X-4 agttttggag acaatactaa aacacggaga tgttgaagaa gctgtgagaa tagtaaaaga agtaatacaa aagcttgcca attatgaaat tccaccagag aagctcgcaa tatatgagca gataacaaga ccattacatg agtataaggc gataggtcct cacgtagctg ttgcaaagaa actagctgct aaaggagtta aaataaagcc aggaatggta attggataca tagtacttag aggcgatggt ccaattagca atagggcaat tctagctgag gaatacgatc ccaaaaagca caagtatgac gcagaatatt acattgagaa ccaggttctt ccagcggtac ttaggatatt ggagggattt ggatacagaa aggaagacct cagataccaa aagacaagac aagtcggcct aacttcctgg cttaacatta aaaaatccta gaaaagcgat agatatcaac ttttattctt tctaaccttt ttctatgaaa gaagaactga gcaggaatta ccagttcttc cgttatttta tgggtaatta aaaacccatg ctcttgggag aatcttcgaa taaaatccct aacttcaggc tttgctaagt gaatagaata aacaacatca ctcacttcaa acgccttcgt tagaaatggt ctatctgcat gcttctctgg ctcggaanng gaggattcat aacaacagta tcaacattct

FIG. 8X-5 cagagaattg agaaacatca gaaactttga cttctacaac atttctaact ttgcaactct tcaagatttt ctaaaagaat tttaacggcc tcctcgtcaa tttcgacgac gtagatcttt tttgctccaa gcagagccgc tccaatggat aacacccctg ttcccgcacc caagtccgct acaatttttt ccttgtatct cctaatgtat aagcaagcca aaggagagta gatgctacct ttccgggagt tttgtattgc tctagccaag gtttgggatt tttgaatcct ttaactctgg aaagtataat ttcaagctcc ttcttcttca tgacagatga aaaattgttt tgtctctttt taacttttac agaaataact gtctcaaatt atgacaactc ttgacatttt tacttcatta ccagggtaat gtttttaagt atgaaatttt tctttcatag aggaggnnnn nngtcctctc ctcgatttcc ttggttgtgc tccatatgat aagcttccaa agtgggtgtt cagactttta gacactcaaa taccagacga caatggtgtg ctcactcaag ccccatatgg gttgagaaaa gtagaagcgg cactactcag atgcttcccc aggaatgagg ttgttgtagc tcntcccnga aagattgaga tgttcttgg // TGA

| |
|---|
| FIG. 8Y-1 |
| FIG. 8Y-2 |
| FIG. 8Y-3 |

(PCNA) - PFU DNA POLYMERASE (V93 R OR E) fusion protein

Nucleotide sequence (SEQ ID NO: 67) // Nucleotide sequence (SEQ ID NO: 27)
Nucleotide sequence (SEQ ID NO: 67) //Nucleotide sequence (SEQ ID NO: 28)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

FIG. 8Y-1

ATG CCA TTT GAA ATC GTA TTT GAA GGT GCA AAA GAG TTT GCC CAA CTT ATA GAC 54
ACC GCA AGT AAG TTA ATA GAT GAG GCC GCG TTT AAA GTT ACA GAA GAT GGG ATA 108
AGC ATG AGG GCC ATG GAT CCA AGT AGA GTT GTC CTG ATT GAC CTA AAT CTC CCG 162
TCA AGC ATA TTT AGC AAA TAT GAA GTT GTT GAA CCA GAA ACA ATT GGA GTT AAC 216
ATG GAC CAC CTA AAG AAG ATC CTA AAG AGA GGT AAA GCA AAG GAC ACC TTA ATA 270
CTC AAG AAA GGA GAG GAA AAC TTC TTA GAG ATA ACA ATT CAA GGA ACT GCA ACA 324
AGA ACA TTT AGA GTT CCC CTA ATA GAT GTA GAA GAG ATG GAA GTT GAC CTC CCA 378
GAA CTT CCA TTC ACT GCA AAG GTT GTA GTT CTT GGA GAA GTC CTA AAA GAT GCT 432
GTT AAA GAT GCC TCT CTA GTG AGT GAC AGC ATA AAA TTT ATT GCC AGG GAA AAT 486
GAA TTT ATA ATG AAG GCA GAG GGA GAA ACC CAG GAA GTT GAG ATA AAG CTA ACT 540
CTT GAA GAT GAG GGA TTA TTG GAC ATC GAG GTT CAA GAG GAG ACA AAG AGC GCA 594
TAT GGA GTC AGC TAT CTC TCC GAC ATG GTT AAA GGA CTT GGA AAG GCC GAT GAA 648
GTT ACA ATA AAG TTT GGA AAT GAA ATG CCC ATG CAA ATG GAG TAT TAC ATT AGA 702
GAT GAA GGA AGA CTT ACA TTC CTA CTG GCT CCA AGA GTT GAA GAG //

//ATGATTTTAG ATGTGGATTA CATAACTGAA GAAGGAAAAC CTGTTATTAG GCTATTCAAA 60
AAAGAGAACG GAAAATTTAA GATAGAGCAT
GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC
CAAGATXXXC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GATATAGAAA CCCTCTATCA CGAAGGAGAA
GAGTTTGGAA AAGGCCCAAT TATAATGATT 480
AGTTATGCAG ATGAAAATGA AGCAAAGGTG ATTACTTGGA AAAACATAGA TCTTCCATAC 540

FIG. 8Y-2

GTTGAGGTTG TATCAAGCGA GAGAGAGATG ATAAAGAGAT TTCTCAGGAT TATCAGGGAG 600
AAGGATCCTG ACATTATAGT TACTTATAAT
GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC
CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA
ATTCAGCTTT CAAGATTAGT TGGACAACCT 1020
TTATGGGATG TTTCAAGGTC AAGCACAGGG AACCTTGTAG AGTGGTTCTT ACTTAGGAAA
1080 GCCTACGAAA GAAACGAAGT AGCTCCAAAC AAGCCAAGTG AAGAGGAGTA TCAAAGAAGG 1140 CTCAGGGAGA GCTACACAGG
TGGATTCGTT AAAGAGCCAG AAAAGGGGTT GTGGGAAAAC 1200
ATAGTATACC TAGATTTTAG AGCCCTATAT CCCTCGATTA TAATTACCCA
CAATGTTTCT 1260 CCCGATACTC TAAATCTTGA GGGATGCAAG AACTATGATA TCGCTCCTCA AGTAGGCCAC 1320 AAGTTCTGCA
AGGACATCCC TGGTTTTATA CCAAGTCTCT TGGGACATTT GTTAGAGGAA 1380
AGACAAAAGA TTAAGACAAA AATGAAGGAA ACTCAAGATC
CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA
GAAAAGTTTG GATTTAAAGT CCTCTACATT 1620
GACACTGATG GTCTCTATGC AACTATCCCA GGAGGAGAAA GTGAGGAAAT AAAGAAAAAG
1680 GCTCTAGAAT TTGTAAAATA CATAAATTCA AAGCTCCCTG GACTGCTAGA GCTTGAATAT 1740 GAAGGGTTTT ATAAGAGGGG
ATTCTTCGTT ACGAAGAAGA GGTATGCAGT AATAGATGAA 1800
GAAGGAAAAG TCATTACTCG TGGTTTAGAG ATAGTTAGGA GAGATTGGAG
TGAAATTGCA 1860 AAAGAAACTC AAGCTAGAGT TTTGGAGACA ATACTAAAAC ACGGAGATGT TGAAGAAGCT 1920 GTGAGAATAG
TAAAAGAAGT AATACAAAAG CTTGCCAATT ATGAAATTCC ACCAGAGAAG 1980
CTCGCAATAT ATGAGCAGAT AACAAGACCA TTACATGAGT
ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA
GAATATTACA TGGAGAACCA GGTTCTTCCA 2220
GCGGTACTTA GGATATTGGA GGGATTTGGA TACAGAAAGG AAGACCTCAG ATACCAAAAG
2280 ACAAGACAAG TCGGCCTAAC TTCCTGGCTT AACATTAAAA AATCC // 2328
// TGA

| |
|---|
| FIG. 8Z-1 |
| FIG. 8Z-2 |
| FIG. 8Z-3 |

PFU DNA POLYMERASE (V93 R OR E)-(PCNA) fusion protein

Nucleotide sequence (SEQ ID NO: 27) // Nucleotide sequence (SEQ ID NO: 67)
Nucleotide sequence (SEQ ID NO: 28) // Nucleotide sequence (SEQ ID NO: 67)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATTTTAG ATGTGGATTA CATAACTGAA GAAGGAAAAC CTGTTATTAG GCTATTCAAA 60
AAAGAGAACG GAAAATTTAA GATAGAGCAT
GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC
CAAGATXXXC CCACTATTAG AGAAAAAGTT 300
AGAGAACATC CAGCAGTTGT GGACATCTTC GAATACGATA TTCCATTTGC AAAGAGATAC 360
```

FIG. 8Z-1

CTCATCGACA AAGGCCTAAT ACCAATGGAG GGGGAAGAAG AGCTAAAGAT TCTTGCCTTC 420
GATATAGAAA CCCTCTATCA CGAAGGAGAA
GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT
GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC
CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA
ATTCAGCTTT CAAGATTAGT TGGACAACCT 1020
TTATGGGATG TTTCAAGGTC AAGCACAGGG AACCTTGTAG AGTGGTTCTT ACTTAGGAAA
1080 GCCTACGAAA GAAACGAAGT AGCTCCAAAC AAGCCAAGTG AAGAGGAGTA TCAAAGAAGG 1140 CTCAGGGAGA GCTACACAGG
TGGATTCGTT AAAGAGCCAG AAAAGGGGTT GTGGGAAAAC 1200
ATAGTATACC TAGATTTTAG AGCCCTATAT CCCTCGATTA TAATTACCCA
CAATGTTTCT 1260 CCCGATACTC TAAATCTTGA GGGATGCAAG AACTATGATA TCGCTCCTCA AGTAGGCCAC 1320 AAGTTCTGCA
AGGACATCCC TGGTTTTATA CCAAGTCTCT TGGGACATTT GTTAGAGGAA 1380
AGACAAAAGA TTAAGACAAA AATGAAGGAA ACTCAAGATC
CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA
GAAAAGTTTG GATTTAAAGT CCTCTACATT 1620
GACACTGATG GTCTCTATGC AACTATCCCA GGAGGAGAAA GTGAGGAAAT AAAGAAAAAG
1680 GCTCTAGAAT TTGTAAAATA CATAAATTCA AAGCTCCCTG GACTGCTAGA GCTTGAATAT 1740 GAAGGGTTTT ATAAGAGGGG
ATTCTTCGTT ACGAAGAAGA GGTATGCAGT AATAGATGAA 1800
GAAGGAAAAG TCATTACTCG TGGTTTAGAG ATAGTTAGGA GAGATTGGAG
TGAAATTGCA 1860 AAAGAAACTC AAGCTAGAGT TTTGGAGACA ATACTAAAAC ACGGAGATGT TGAAGAAGCT 1920 GTGAGAATAG
TAAAAGAAGT AATACAAAAG CTTGCCAATT ATGAAATTCC ACCAGAGAAG 1980
CTCGCAATAT ATGAGCAGAT AACAAGACCA TTACATGAGT

FIG. 8Z-2

```
ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA
GAATATTACA TGGAGAACCA GGTTCTTCCA 2220
GCGGTACTTA GGATATTGGA GGGATTTGGA TACAGAAAGG AAGACCTCAG ATACCAAAAG
2280 ACAAGACAAG TCGGCCTAAC TTCCTGGCTT AACATTAAAA AATCC                2328
   ATG CCA TTT GAA ATC GTA TTT GAA GGT GCA AAA GAG TTT GCC CAA CTT ATA GAC    54
   ACC GCA AGT AAG TTA ATA GAT GAG GCC GCG TTT AAA GTT ACA GAA GAT GGG ATA   108
   AGC ATG AGG GCC ATG GAT CCA AGT AGA GTT GTC CTG ATT GAC CTA AAT CTC CCG   162
   TCA AGC ATA TTT AGC AAA TAT GAA GTT GTT GAA CCA GAA ACA ATT GGA GTT AAC   216
   ATG GAC CAC CTA AAG AAG ATC CTA AAG AGA GGT AAA GCA AAG GAC ACC TTA ATA   270
   CTC AAG AAA GGA GAG GAA AAC TTC TTA GAG ATA ACA ATT CAA GGA ACT GCA ACA   324
   AGA ACA TTT AGA GTT CCC CTA ATA GAT GTA GAA GAG ATG GAA GTT GAC CTC CCA   378
   GAA CTT CCA TTC ACT GCA AAG GTT GTA GTT CTT GGA GAA GTC CTA AAA GAT GCT   432
   GTT AAA GAT GCC TCT CTA GTG AGT GAC AGC ATA AAA TTT ATT GCC AGG GAA AAT   486
   GAA TTT ATA ATG AAG GCA GAG GGA GAA ACC CAG GAA GTT GAG ATA AAG CTA ACT   540
   CTT GAA GAT GAG GGA TTA TTG GAC ATC GAG GTT CAA GAG GAG ACA AAG AGC GCA   594
   TAT GGA GTC AGC TAT CTC TCC GAC ATG GTT AAA GGA CTT GGA AAG GCC GAT GAA   648
   GTT ACA ATA AAG TTT GGA AAT GAA ATG CCC ATG CAA ATG GAG TAT TAC ATT AGA   702
   GAT GAA GGA AGA CTT ACA TTC CTA CTG GCT CCA AGA GTT GAA GAG TGA
```

| |
|---|
| FIG. 8AA-1 |
| FIG. 8AA-2 |
| FIG. 8AA-3 |

PFU DNA POLYMERASE (G387P/V93R OR E)-(PCNA) fusion protein

Nucleotide sequence (SEQ ID NO: 29) // Nucleotide sequence (SEQ ID NO: 67)
Nucleotide sequence (SEQ ID NO: 30) // Nucleotide sequence (SEQ ID NO: 67)

G387P Mutant (CCN is the codon for Proline where N = C, G, A, or T)
V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

ATGATTTTAG ATGTGGATTA CATAACTGAA GAAGGAAAAC CTGTTATTAG GCTATTCAAA 60
AAAGAGAACG GAAAATTTAA GATAGAGCAT
GATAGAACTT TTAGACCATA CATTTACGCT 120
CTTCTCAGGG ATGATTCAAA GATTGAAGAA GTTAAGAAAA TAACGGGGGA AAGGCATGGA 180

FIG. 8AA-1

AAGATTGTGA GAATTGTTGA TGTAGAGAAG GTTGAGAAAA AGTTTCTCGG CAAGCCTATT 240
ACCGTGTGGA AACTTTATTT GGAACATCCC
CAAGATXXXC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GATATAGAAA CCCTCTATCA CGAAGGAGAA
GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT
GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC
CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA
ATTCAGCTTT CAAGATTAGT TGGACAACCT 1020
TTATGGGATG TTTCAAGGTC AAGCACAGGG AACCTTGTAG AGTGGTTCTT ACTTAGGAAA
1080 GCCTACGAAA GAAACGAAGT AGCTCCAAAC AAGCCAAGTG AAGAGGAGTA TCAAAGAAGG 1140 CTCAGGGAGA GCTACACACC
NGGATTCGTT AAAGAGCCAG AAAAGGGGTT GTGGGAAAAC 1200
ATAGTATACC TAGATTTTAG AGCCCTATAT CCCTCGATTA TAATTACCCA
CAATGTTTCT 1260 CCCGATACTC TAAATCTTGA GGGATGCAAG AACTATGATA TCGCTCCTCA AGTAGGCCAC 1320 AAGTTCTGCA
AGGACATCCC TGGTTTTATA CCAAGTCTCT TGGGACATTT GTTAGAGGAA 1380
AGACAAAAGA TTAAGACAAA AATGAAGGAA ACTCAAGATC
CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA
GAAAAGTTTG GATTTAAAGT CCTCTACATT 1620
GACACTGATG GTCTCTATGC AACTATCCCA GGAGGAGAAA GTGAGGAAAT AAAGAAAAAG
1680 GCTCTAGAAT TTGTAAAATA CATAAATTCA AAGCTCCCTG GACTGCTAGA GCTTGAATAT 1740 GAAGGGTTTT ATAAGAGGGG
ATTCTTCGTT ACGAAGAAGA GGTATGCAGT AATAGATGAA 1800
GAAGGAAAAG TCATTACTCG TGGTTTAGAG ATAGTTAGGA GAGATTGGAG
TGAAATTGCA 1860 AAAGAAACTC AAGCTAGAGT TTTGGAGACA ATACTAAAAC ACGGAGATGT TGAAGAAGCT 1920 GTGAGAATAG
TAAAAGAAGT AATACAAAAG CTTGCCAATT ATGAAATTCC ACCAGAGAAG 1980
CTCGCAATAT ATGAGCAGAT AACAAGACCA TTACATGAGT
ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA

FIG. 8AA-2

GAATATTACA TGGAGAACCA GGTTCTTCCA 2220
GCGGTACTTA GGATATTGGA GGGATTTGGA TACAGAAAGG AAGACCTCAG ATACCAAAAG
2280 ACAAGACAAG TCGGCCTAAC TTCCTGGCTT AACATTAAAA AATCC // 2328

// ATG CCA TTT GAA ATC GTA TTT GAA GGT GCA AAA GAG TTT GCC CAA CTT ATA GAC 54
ACC GCA AGT AAG TTA ATA GAT GAG GCC GCG TTT AAA GTT ACA GAA GAT GGG ATA 108
AGC ATG AGG GCC ATG GAT CCA AGT AGA GTT GTC CTG ATT GAC CTA AAT CTC CCG 162
TCA AGC ATA TTT AGC AAA TAT GAA GTT GTT GAA CCA GAA ACA ATT GGA GTT AAC 216
ATG GAC CAC CTA AAG AAG ATC CTA AAG AGA GGT AAA GCA AAG GAC ACC TTA ATA 270
CTC AAG AAA GGA GAG GAA AAC TTC TTA GAG ATA ACA ATT CAA GGA ACT GCA ACA 324
AGA ACA TTT AGA GTT CCC CTA ATA GAT GTA GAA GAG ATG GAA GTT GAC CTC CCA 378
GAA CTT CCA TTC ACT GCA AAG GTT GTA GTT CTT GGA GAA GTC CTA AAA GAT GCT 432
GTT AAA GAT GCC TCT CTA GTG AGT GAC AGC ATA AAA TTT ATT GCC AGG GAA AAT 486
GAA TTT ATA ATG AAG GCA GAG GGA GAA ACC CAG GAA GTT GAG ATA AAG CTA ACT 540
CTT GAA GAT GAG GGA TTA TTG GAC ATC GAG GTT CAA GAG GAG ACA AAG AGC GCA 594
TAT GGA GTC AGC TAT CTC TCC GAC ATG GTT AAA GGA CTT GGA AAG GCC GAT GAA 648
GTT ACA ATA AAG TTT GGA AAT GAA ATG CCC ATG CAA ATG GAG TAT TAC ATT AGA 702
GAT GAA GGA AGA CTT ACA TTC CTA CTG GCT CCA AGA GTT GAA GAG TGA

| |
|---|
| FIG. 8BB-1 |
| FIG. 8BB-2 |
| FIG. 8BB-3 |

(PCNA) - PFU DNA POLYMERASE (G387P/V93R OR E) fusion protein

Nucleotide sequence (SEQ ID NO: 67) // Nucleotide sequence (SEQ ID NO: 29)
Nucleotide sequence (SEQ ID NO: 67) // Nucleotide sequence (SEQ ID NO: 30)

G387P Mutant (CCN is the codon for Proline where N = C, G, A, or T)
V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

FIG. 8BB-1

```
ATG CCA TTT GAA ATC GTA TTT GAA GGT GCA AAA GAG TTT GCC CAA CTT ATA GAC     54
ACC GCA AGT AAG TTA ATA GAT GAG GCC GCG TTT AAA GTT ACA GAA GAT GGG ATA    108
AGC ATG AGG GCC ATG GAT CCA AGT AGA GTT GTC CTG ATT GAC CTA AAT CTC CCG    162
TCA AGC ATA TTT AGC AAA TAT GAA GTT GTT GAA CCA GAA ACA ATT GGA GTT AAC    216
ATG GAC CAC CTA AAG AAG ATC CTA AAG AGA GGT AAA GCA AAG GAC ACC TTA ATA    270
CTC AAG AAA GGA GAG GAA AAC TTC TTA GAG ATA ACA ATT CAA GGA ACT GCA ACA    324
AGA ACA TTT AGA GTT CCC CTA ATA GAT GTA GAA GAG ATG GAA GTT GAC CTC CCA    378
GAA CTT CCA TTC ACT GCA AAG GTT GTA GTT CTT GGA GAA GTC CTA AAA GAT GCT    432
GTT AAA GAT GCC TCT CTA GTG AGT GAC AGC ATA AAA TTT ATT GCC AGG GAA AAT    486
GAA TTT ATA ATG AAG GCA GAG GGA GAA ACC CAG GAA GTT GAG ATA AAG CTA ACT    540
CTT GAA GAT GAG GGA TTA TTG GAC ATC GAG GTT CAA GAG GAG ACA AAG AGC GCA    594
TAT GGA GTC AGC TAT CTC TCC GAC ATG GTT AAA GGA CTT GGA AAG GCC GAT GAA    648
GTT ACA ATA AAG TTT GGA AAT GAA ATG CCC ATG CAA ATG GAG TAT TAC ATT AGA    702
GAT GAA GGA AGA CTT ACA TTC CTA CTG GCT CCA AGA GTT GAA GAG //

//ATGATTTTAG ATGTGGATTA CATAACTGAA GAAGGAAAAC CTGTTATTAG GCTATTCAAA 60
AAAGAGAACG GAAAATTTAA GATAGAGCAT
GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC
CAAGATXXXC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GATATAGAAA CCCTCTATCA CGAAGGAGAA
```

FIG. 8BB-2

GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT
GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC
CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA
ATTCAGCTTT CAAGATTAGT TGGACAACCT 1020
TTATGGGATG TTTCAAGGTC AAGCACAGGG AACCTTGTAG AGTGGTTCTT ACTTAGGAAA
1080 GCCTACGAAA GAAACGAAGT AGCTCCAAAC AAGCCAAGTG AAGAGGAGTA TCAAAGAAGG 1140 CTCAGGGAGA GCTACACACC
NGGATTCGTT AAAGAGCCAG AAAAGGGGTT GTGGGAAAAC 1200
ATAGTATACC TAGATTTTAG AGCCCTATAT CCCTCGATTA TAATTACCCA
CAATGTTTCT 1260 CCCGATACTC TAAATCTTGA GGGATGCAAG AACTATGATA TCGCTCCTCA AGTAGGCCAC 1320 AAGTTCTGCA
AGGACATCCC TGGTTTTATA CCAAGTCTCT TGGGACATTT GTTAGAGGAA 1380
AGACAAAAGA TTAAGACAAA AATGAAGGAA ACTCAAGATC
CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA
GAAAAGTTTG GATTTAAAGT CCTCTACATT 1620
GACACTGATG GTCTCTATGC AACTATCCCA GGAGGAGAAA GTGAGGAAAT AAAGAAAAAG
1680 GCTCTAGAAT TTGTAAAATA CATAAATTCA AAGCTCCCTG GACTGCTAGA GCTTGAATAT 1740 GAAGGGTTTT ATAAGAGGGG
ATTCTTCGTT ACGAAGAAGA GGTATGCAGT AATAGATGAA 1800
GAAGGAAAAG TCATTACTCG TGGTTTAGAG ATAGTTAGGA GAGATTGGAG
TGAAATTGCA 1860 AAAGAAACTC AAGCTAGAGT TTTGGAGACA ATACTAAAAC ACGGAGATGT TGAAGAAGCT 1920 GTGAGAATAG
TAAAAGAAGT AATACAAAAG CTTGCCAATT ATGAAATTCC ACCAGAGAAG 1980
CTCGCAATAT ATGAGCAGAT AACAAGACCA TTACATGAGT
ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA
GAATATTACA TGGAGAACCA GGTTCTTCCA 2220
GCGGTACTTA GGATATTGGA GGGATTTGGA TACAGAAAGG AAGACCTCAG ATACCAAAAG
2280 ACAAGACAAG TCGGCCTAAC TTCCTGGCTT AACATTAAAA AATCC //TAG 2328

| |
|---|
| FIG. 8CC-1 |
| FIG. 8CC-2 |
| FIG. 8CC-3 |

(PCNA)-PFU DNA POLYMERASE(D141A/E143A/V93R OR E) fusion protein

Nucleotide sequence (SEQ ID NO: 67) // Nucleotide sequence (SEQ ID NO: 31)
Nucleotide sequence (SEQ ID NO: 67) // Nucleotide sequence (SEQ ID NO: 32)

D141A/E143A Mutant (GCN is the codon for alanine where N = C, G, A, or T)
V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

FIG. 8CC-1

ATG CCA TTT GAA ATC GTA TTT GAA GGT GCA AAA GAG TTT GCC CAA CTT ATA GAC 54
ACC GCA AGT AAG TTA ATA GAT GAG GCC GCG TTT AAA GTT ACA GAA GAT GGG ATA 108
AGC ATG AGG GCC ATG GAT CCA AGT AGA GTT GTC CTG ATT GAC CTA AAT CTC CCG 162
TCA AGC ATA TTT AGC AAA TAT GAA GTT GTT GAA CCA GAA ACA ATT GGA GTT AAC 216
ATG GAC CAC CTA AAG AAG ATC CTA AAG AGA GGT AAA GCA AAG GAC ACC TTA ATA 270
CTC AAG AAA GGA GAG GAA AAC TTC TTA GAG ATA ACA ATT CAA GGA ACT GCA ACA 324
AGA ACA TTT AGA GTT CCC CTA ATA GAT GTA GAA GAG ATG GAA GTT GAC CTC CCA 378
GAA CTT CCA TTC ACT GCA AAG GTT GTA GTT CTT GGA GAA GTC CTA AAA GAT GCT 432
GTT AAA GAT GCC TCT CTA GTG AGT GAC AGC ATA AAA TTT ATT GCC AGG GAA AAT 486
GAA TTT ATA ATG AAG GCA GAG GGA GAA ACC CAG GAA GTT GAG ATA AAG CTA ACT 540
CTT GAA GAT GAG GGA TTA TTG GAC ATC GAG GTT CAA GAG GAG ACA AAG AGC GCA 594
TAT GGA GTC AGC TAT CTC TCC GAC ATG GTT AAA GGA CTT GGA AAG GCC GAT GAA 648
GTT ACA ATA AAG TTT GGA AAT GAA ATG CCC ATG CAA ATG GAG TAT TAC ATT AGA 702
GAT GAA GGA AGA CTT ACA TTC CTA CTG GCT CCA AGA GTT GAA GAG //

//ATGATTTTAG ATGTGGATTA CATAACTGAA GAAGGAAAAC CTGTTATTAG GCTATTCAAA 60
AAAGAGAACG GAAAATTTAA GATAGAGCAT
GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC
CAAGATXXXC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GCNATAGCNA CCCTCTATCA CGAAGGAGAA
GAGTTTGGAA AAGGCCCAAT TATAATGATT 480
AGTTATGCAG ATGAAAATGA AGCAAAGGTG ATTACTTGGA AAAACATAGA TCTTCCATAC 540

FIG. 8CC-2

GTTGAGGTTG TATCAAGCGA GAGAGAGATG ATAAAGAGAT TTCTCAGGAT TATCAGGGAG 600
AAGGATCCTG ACATTATAGT TACTTATAAT
GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC
CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA
ATTCAGCTTT CAAGATTAGT TGGACAACCT 1020
TTATGGGATG TTTCAAGGTC AAGCACAGGG AACCTTGTAG AGTGGTTCTT ACTTAGGAAA
1080 GCCTACGAAA GAAACGAAGT AGCTCCAAAC AAGCCAAGTG AAGAGGAGTA TCAAAGAAGG 1140 CTCAGGGAGA GCTACACA GTT
GGATTCGTT AAAGAGCCAG AAAAGGGGTT GTGGGAAAAC 1200
ATAGTATACC TAGATTTTAG AGCCCTATAT CCCTCGATTA TAATTACCCA
CAATGTTTCT 1260 CCCGATACTC TAAATCTTGA GGGATGCAAG AACTATGATA TCGCTCCTCA AGTAGGCCAC 1320 AAGTTCTGCA
AGGACATCCC TGGTTTTATA CCAAGTCTCT TGGGACATTT GTTAGAGGAA 1380
AGACAAAAGA TTAAGACAAA AATGAAGGAA ACTCAAGATC
CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA
GAAAAGTTTG GATTTAAAGT CCTCTACATT 1620
GACACTGATG GTCTCTATGC AACTATCCCA GGAGGAGAAA GTGAGGAAAT AAAGAAAAAG
1680 GCTCTAGAAT TTGTAAAATA CATAAATTCA AAGCTCCCTG GACTGCTAGA GCTTGAATAT 1740 GAAGGGTTTT ATAAGAGGGG
ATTCTTCGTT ACGAAGAAGA GGTATGCAGT AATAGATGAA 1800
GAAGGAAAAG TCATTACTCG TGGTTTAGAG ATAGTTAGGA GAGATTGGAG
TGAAATTGCA 1860 AAAGAAACTC AAGCTAGAGT TTTGGAGACA ATACTAAAAC ACGGAGATGT TGAAGAAGCT 1920 GTGAGAATAG
TAAAAGAAGT AATACAAAAG CTTGCCAATT ATGAAATTCC ACCAGAGAAG 1980
CTCGCAATAT ATGAGCAGAT AACAAGACCA TTACATGAGT
ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA
GAATATTACA TGGAGAACCA GGTTCTTCCA 2220
GCGGTACTTA GGATATTGGA GGGATTTGGA TACAGAAAGG AAGACCTCAG ATACCAAAAG
2280 ACAAGACAAG TCGGCCTAAC TTCCTGGCTT AACATTAAAA AATCC // 2328

TGA

FIG. 8CC-3

| FIG. 8DD-1 |
| --- |
| FIG. 8DD-2 |
| FIG. 8DD-3 |

FIG. 8DD

<u>PFU DNA POLYMERASE(D141A/E143A/V93R OR E) - (PCNA) fusion protein</u>

Nucleotide sequence (SEQ ID NO: 31) // Nucleotide sequence (SEQ ID NO: 67)
Nucleotide sequence (SEQ ID NO: 32) // Nucleotide sequence (SEQ ID NO: 67)

D141A/E143A Mutant (GCN is the codon for alanine where N = C, G, A, or T)
V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

FIG. 8DD-1

ATGATTTTAG ATGTGGATTA CATAACTGAA GAAGGAAAAC CTGTTATTAG GCTATTCAAA 60
AAAGAGAACG GAAAATTTAA GATAGAGCAT
GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC
CAAGATXXXC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GCNATAGCNA CCCTCTATCA CGAAGGAGAA
GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT
GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC
CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA
ATTCAGCTTT CAAGATTAGT TGGACAACCT 1020
TTATGGGATG TTTCAAGGTC AAGCACAGGG AACCTTGTAG AGTGGTTCTT ACTTAGGAAA
1080 GCCTACGAAA GAAACGAAGT AGCTCCAAAC AAGCCAAGTG AAGAGGAGTA TCAAAGAAGG 1140 CTCAGGGAGA GCTACACA GTT
GGATTCGTT AAAGAGCCAG AAAAGGGGTT GTGGGAAAAC 1200
ATAGTATACC TAGATTTTAG AGCCCTATAT CCCTCGATTA TAATTACCCA
CAATGTTTCT 1260 CCCGATACTC TAAATCTTGA GGGATGCAAG AACTATGATA TCGCTCCTCA AGTAGGCCAC 1320 AAGTTCTGCA
AGGACATCCC TGGTTTTATA CCAAGTCTCT TGGGACATTT GTTAGAGGAA 1380
AGACAAAAGA TTAAGACAAA AATGAAGGAA ACTCAAGATC
CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA
GAAAAGTTTG GATTTAAAGT CCTCTACATT 1620
GACACTGATG GTCTCTATGC AACTATCCCA GGAGGAGAAA GTGAGGAAAT AAAGAAAAAG
1680 GCTCTAGAAT TTGTAAAATA CATAAATTCA AAGCTCCCTG GACTGCTAGA GCTTGAATAT 1740 GAAGGGTTTT ATAAGAGGGG

FIG. 8DD-2

ATTCTTCGTT ACGAAGAAGA GGTATGCAGT AATAGATGAA 1800
GAAGGAAAAG TCATTACTCG TGGTTTAGAG ATAGTTAGGA GAGATTGGAG
TGAAATTGCA 1860 AAAGAAACTC AAGCTAGAGT TTTGGAGACA ATACTAAAAC ACGGAGATGT TGAAGAAGCT 1920 GTGAGAATAG
TAAAAGAAGT AATACAAAAG CTTGCCAATT ATGAAATTCC ACCAGAGAAG 1980
CTCGCAATAT ATGAGCAGAT AACAAGACCA TTACATGAGT
ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA
GAATATTACA TGGAGAACCA GGTTCTTCCA 2220
GCGGTACTTA GGATATTGGA GGGATTTGGA TACAGAAAGG AAGACCTCAG ATACCAAAAG
2280 ACAAGACAAG TCGGCCTAAC TTCCTGGCTT AACATTAAAA AATCC // 2328

// ATG CCA TTT GAA ATC GTA TTT GAA GGT GCA AAA GAG TTT GCC CAA CTT ATA GAC 54
ACC GCA AGT AAG TTA ATA GAT GAG GCC GCG TTT AAA GTT ACA GAA GAT GGG ATA 108
AGC ATG AGG GCC ATG GAT CCA AGT AGA GTT GTC CTG ATT GAC CTA AAT CTC CCG 162
TCA AGC ATA TTT AGC AAA TAT GAA GTT GTT GAA CCA GAA ACA ATT GGA GTT AAC 216
ATG GAC CAC CTA AAG AAG ATC CTA AAG AGA GGT AAA GCA AAG GAC ACC TTA ATA 270
CTC AAG AAA GGA GAG GAA AAC TTC TTA GAG ATA ACA ATT CAA GGA ACT GCA ACA 324
AGA ACA TTT AGA GTT CCC CTA ATA GAT GTA GAA GAG ATG GAA GTT GAC CTC CCA 378
GAA CTT CCA TTC ACT GCA AAG GTT GTA GTT CTT GGA GAA GTC CTA AAA GAT GCT 432
GTT AAA GAT GCC TCT CTA GTG AGT GAC AGC ATA AAA TTT ATT GCC AGG GAA AAT 486
GAA TTT ATA ATG AAG GCA GAG GGA GAA ACC CAG GAA GTT GAG ATA AAG CTA ACT 540
CTT GAA GAT GAG GGA TTA TTG GAC ATC GAG GTT CAA GAG GAG ACA AAG AGC GCA 594
TAT GGA GTC AGC TAT CTC TCC GAC ATG GTT AAA GGA CTT GGA AAG GCC GAT GAA 648
GTT ACA ATA AAG TTT GGA AAT GAA ATG CCC ATG CAA ATG GAG TAT TAC ATT AGA 702
GAT GAA GGA AGA CTT ACA TTC CTA CTG GCT CCA AGA GTT GAA GAG TGA

| |
|---|
| FIG. 8EE-1 |
| FIG. 8EE-2 |
| FIG. 8EE-3 |

KOD DNA POLYMERASE - (PCNA) fusion protein

Nucleotide sequence (SEQ ID NO: 33) // Nucleotide sequence (SEQ ID NO: 67)
Nucleotide sequence (SEQ ID NO: 34) // Nucleotide sequence (SEQ ID NO: 67)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATCCTCG ACACTGACTA CATAACCGAG GATGGAAAGC CTGTCATAAG AATTTTCAAG 60
AAGGAAAACG GCGAGTTTAA GATTGAGTAC GACCGGACTT TTGAACCCTA CTTCTACGCC 120
CTCCTGAAGG ACGATTCTGC CATTGAGGAA GTCAAGAAGA TAACCGCCGA GAGGCACGGG 180
ACGGTTGTAA CGGTTAAGCG GGTTGAAAAG GTTCAGAAGA AGTTCCTCGG GAGACCAGTT 240
GAGGTCTGGA AACTCTACTT TACTCATCCG CAGGACXXXC CAGCGATAAG GGACAAGATA 300
CGAGAGCATC CAGCAGTTAT TGACATCTAC GAGTACGACA TACCCTTCGC CAAGCGCTAC 360
CTCATAGACA AGGGATTAGT GCCAATGGAA GGCGACGAGG AGCTGAAAAT GCTCGCCTTC 420
```

FIG. 8EE-1

```
GACATTGAAA CTCTCTACCA TGAGGGCGAG GAGTTCGCCG AGGGGCCAAT CCTTATGATA 480
AGCTACGCCG ACGAGGAAGG GGCCAGGGTG ATAACTTGGA AGAACGTGGA TCTCCCCTAC 540
GTTGACGTCG TCTCGACGGA GAGGGAGATG ATAAAGCGCT TCCTCCGTGT TGTGAAGGAG 600
AAAGACCCGG ACGTTCTCAT AACCTACAAC GGCGACAACT TCGACTTCGC CTATCTGAAA 660
AAGCGCTGTG AAAAGCTCGG AATAAACTTC GCCCTCGGAA GGGATGGAAG CGAGCCGAAG 720
ATTCAGAGGA TGGGCGACAG GTTTGCCGTC GAAGTGAAGG GACGGATACA CTTCGATCTC 780
TATCCTGTGA TAAGACGGAC GATAAACCTG CCCACATACA CGCTTGAGGC CGTTTATGAA 840
GCCGTCTTCG GTCAGCCGAA GGAGAAGGTT TACGCTGAGG AAATAACCAC AGCCTGGGAA 900
ACCGGCGAGA ACCTTGAGAG AGTCGCCCGC TACTCGATGG AAGATGCGAA GGTCACATAC 960
GAGCTTGGGA AGGAGTTCCT TCCGATGGAG GCCCAGCTTT CTCGCTTAAT CGGCCAGTCC 1020
CTCTGGGACG TCTCCCGCTC CAGCACTGGC AACCTCGTTG AGTGGTTCCT CCTCAGGAAG 1080
GCCTATGAGA GGAATGAGCT GGCCCCGAAC AAGCCCGATG AAAAGGAGCT GGCCAGAAGA 1140
CGGCAGAGCT ATGAAGGAGG CTATGTAAAA GAGCCCGAGA GAGGGTTGTG GGAGAACATA 1200
GTGTACCTAG ATTTTAGATC CCTGTACCCC TCAATCATCA TCACCCACAA CGTCTCGCCG 1260
GATACGCTCA ACAGAGAAGG ATGCAAGGAA TATGACGTTG CCCCACAGGT CGGCCACCGC 1320
TTCTGCAAGG ACTTCCCAGG ATTTATCCCG AGCCTGCTTG GAGACCTCCT AGAGGAGAGG 1380
CAGAAGATAA AGAAGAAGAT GAAGGCCACG ATTGACCCGA TCGAGAGGAA GCTCCTCGAT 1440
TACAGGCAGA GGGCCATCAA GATCCTGGCA AACAGCTACT ACGGTTACTA CGGCTATGCA 1500
AGGGCGCGCT GGTACTGCAA GGAGTGTGCA GAGAGCGTAA CGGCCTGGGG AAGGGAGTAC 1560
ATAACGATGA CCATCAAGGA GATAGAGGAA AAGTACGGCT TTAAGGTAAT CTACAGCGAC 1620
ACCGACGGAT TTTTTGCCAC AATACCTGGA GCCGATGCTG AAACCGTCAA AAAGAAGGCT 1680
ATGGAGTTCC TCAAGTATAT CAACGCCAAA CTTCCGGGCG CGCTTGAGCT CGAGTACGAG 1740
GGCTTCTACA AACGCGGCTT CTTCGTCACG AAGAAGAAGT ATGCGGTGAT AGACGAGGAA 1800
```

FIG. 8EE-2

```
GGCAAGATAA CAACGCGCGG ACTTGAGATT GTGAGGCGTG ACTGGAGCGA GATAGCGAAA 1860
GAGACGCAGG CGAGGGTTCT TGAAGCTTTG CTAAAGGACG GTGACGTCGA GAAGGCCGTG 1920
AGGATAGTCA AAGAAGTTAC CGAAAAGCTG AGCAAGTACG AGGTTCCGCC GGAGAAGCTG 1980
GTGATCCACG AGCAGATAAC GAGGGATTTA AAGGACTACA AGGCAACCGG TCCCCACGTT 2040
GCCGTTGCCA AGAGGTTGGC CGCGAGAGGA GTCAAAATAC GCCCTGGAAC GGTGATAAGC 2100
TACATCGTGC TCAAGGGCTC TGGGAGGATA GGCGACAGGG CGATACCGTT CGACGAGTTC 2160
GACCCGACGA AGCACAAGTA CGACGCCGAG TACTACATTG AGAACCAGGT TCTCCCAGCC 2220
GTTGAGAGAA TTCTGAGAGC CTTCGGTTAC CGCAAGGAAG ACCTGCGCTA CCAGAAGACG 2280
AGACAGGTTG GTTTGAGTGC TTGGCTGAAG CCGAAGGGAA CT  2325
    ATG CCA TTT GAA ATC GTA TTT GAA GGT GCA AAA GAG TTT GCC CAA CTT ATA GAC    54
    ACC GCA AGT AAG TTA ATA GAT GAG GCC GCG TTT AAA GTT ACA GAA GAT GGG ATA   108
    AGC ATG AGG GCC ATG GAT CCA AGT AGA GTT GTC CTG ATT GAC CTA AAT CTC CCG   162
    TCA AGC ATA TTT AGC AAA TAT GAA GTT GTT GAA CCA GAA ACA ATT GGA GTT AAC   216
    ATG GAC CAC CTA AAG AAG ATC CTA AAG AGA GGT AAA GCA AAG GAC ACC TTA ATA   270
    CTC AAG AAA GGA GAG GAA AAC TTC TTA GAG ATA ACA ATT CAA GGA ACT GCA ACA   324
    AGA ACA TTT AGA GTT CCC CTA ATA GAT GTA GAA GAG ATG GAA GTT GAC CTC CCA   378
    GAA CTT CCA TTC ACT GCA AAG GTT GTA GTT CTT GGA GAA GTC CTA AAA GAT GCT   432
    GTT AAA GAT GCC TCT CTA GTG AGT GAC AGC ATA AAA TTT ATT GCC AGG GAA AAT   486
    GAA TTT ATA ATG AAG GCA GAG GGA GAA ACC CAG GAA GTT GAG ATA AAG CTA ACT   540
    CTT GAA GAT GAG GGA TTA TTG GAC ATC GAG GTT CAA GAG GAG ACA AAG AGC GCA   594
    TAT GGA GTC AGC TAT CTC TCC GAC ATG GTT AAA GGA CTT GGA AAG GCC GAT GAA   648
    GTT ACA ATA AAG TTT GGA AAT GAA ATG CCC ATG CAA ATG GAG TAT TAC ATT AGA   702
    GAT GAA GGA AGA CTT ACA TTC CTA CTG GCT CCA AGA GTT GAA GAG TGA
```

| |
|---|
| FIG. 8FF-1 |
| FIG. 8FF-2 |
| FIG. 8FF-3 |

(PCNA) - KOD DNA POLYMERASE fusion protein

Nucleotide sequence (SEQ ID NO: 67) // Nucleotide sequence (SEQ ID NO: 33)
Nucleotide sequence (SEQ ID NO: 67) // Nucleotide sequence (SEQ ID NO: 34)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATG CCA TTT GAA ATC GTA TTT GAA GGT GCA AAA GAG TTT GCC CAA CTT ATA GAC    54
ACC GCA AGT AAG TTA ATA GAT GAG GCC GCG TTT AAA GTT ACA GAA GAT GGG ATA   108
AGC ATG AGG GCC ATG GAT CCA AGT AGA GTT GTC CTG ATT GAC CTA AAT CTC CCG   162
TCA AGC ATA TTT AGC AAA TAT GAA GTT GTT GAA CCA GAA ACA ATT GGA GTT AAC   216
ATG GAC CAC CTA AAG AAG ATC CTA AAG AGA GGT AAA GCA AAG GAC ACC TTA ATA   270
CTC AAG AAA GGA GAG GAA AAC TTC TTA GAG ATA ACA ATT CAA GGA ACT GCA ACA   324
AGA ACA TTT AGA GTT CCC CTA ATA GAT GTA GAA GAG ATG GAA GTT GAC CTC CCA   378
GAA CTT CCA TTC ACT GCA AAG GTT GTA GTT CTT GGA GAA GTC CTA AAA GAT GCT   432
```

FIG. 8FF-1

```
GTT AAA GAT GCC TCT CTA GTG AGT GAC AGC ATA AAA TTT ATT GCC AGG GAA AAT     486
GAA TTT ATA ATG AAG GCA GAG GGA GAA ACC CAG GAA GTT GAG ATA AAG CTA ACT     540
CTT GAA GAT GAG GGA TTA TTG GAC ATC GAG GTT CAA GAG GAG ACA AAG AGC GCA     594
TAT GGA GTC AGC TAT CTC TCC GAC ATG GTT AAA GGA CTT GGA AAG GCC GAT GAA     648
GTT ACA ATA AAG TTT GGA AAT GAA ATG CCC ATG CAA ATG GAG TAT TAC ATT AGA     702
GAT GAA GGA AGA CTT ACA TTC CTA CTG GCT CCA AGA GTT GAA GAG //

//ATGATCCTCG ACACTGACTA CATAACCGAG GATGGAAAGC CTGTCATAAG AATTTTCAAG 60
AAGGAAAACG GCGAGTTTAA GATTGAGTAC GACCGGACTT TTGAACCCTA CTTCTACGCC 120
CTCCTGAAGG ACGATTCTGC CATTGAGGAA GTCAAGAAGA TAACCGCCGA GAGGCACGGG 180
ACGGTTGTAA CGGTTAAGCG GGTTGAAAAG GTTCAGAAGA AGTTCCTCGG GAGACCAGTT 240
GAGGTCTGGA AACTCTACTT TACTCATCCG CAGGACXXXC CAGCGATAAG GGACAAGATA 300
CGAGAGCATC CAGCAGTTAT TGACATCTAC GAGTACGACA TACCCTTCGC CAAGCGCTAC 360
CTCATAGACA AGGGATTAGT GCCAATGGAA GGCGACGAGG AGCTGAAAAT GCTCGCCTTC 420
GACATTGAAA CTCTCTACCA TGAGGGCGAG GAGTTCGCCG AGGGGCCAAT CCTTATGATA 480
AGCTACGCCG ACGAGGAAGG GGCCAGGGTG ATAACTTGGA AGAACGTGGA TCTCCCCTAC 540
GTTGACGTCG TCTCGACGGA GAGGGAGATG ATAAAGCGCT TCCTCCGTGT TGTGAAGGAG 600
AAAGACCCGG ACGTTCTCAT AACCTACAAC GGCGACAACT TCGACTTCGC CTATCTGAAA 660
AAGCGCTGTG AAAAGCTCGG AATAAACTTC GCCCTCGGAA GGGATGGAAG CGAGCCGAAG 720
ATTCAGAGGA TGGGCGACAG GTTTGCCGTC GAAGTGAAGG GACGGATACA CTTCGATCTC 780
TATCCTGTGA TAAGACGGAC GATAAACCTG CCCACATACA CGCTTGAGGC CGTTTATGAA 840
GCCGTCTTCG GTCAGCCGAA GGAGAAGGTT TACGCTGAGG AAATAACCAC AGCCTGGGAA 900
ACCGGCGAGA ACCTTGAGAG AGTCGCCCGC TACTCGATGG AAGATGCGAA GGTCACATAC 960
```

FIG. 8FF-2

```
GAGCTTGGGA AGGAGTTCCT TCCGATGGAG GCCCAGCTTT CTCGCTTAAT CGGCCAGTCC 1020
CTCTGGGACG TCTCCCGCTC CAGCACTGGC AACCTCGTTG AGTGGTTCCT CCTCAGGAAG 1080
GCCTATGAGA GGAATGAGCT GGCCCCGAAC AAGCCCGATG AAAAGGAGCT GGCCAGAAGA 1140
CGGCAGAGCT ATGAAGGAGG CTATGTAAAA GAGCCCGAGA GAGGGTTGTG GGAGAACATA 1200
GTGTACCTAG ATTTTAGATC CCTGTACCCC TCAATCATCA TCACCCACAA CGTCTCGCCG 1260
GATACGCTCA ACAGAGAAGG ATGCAAGGAA TATGACGTTG CCCCACAGGT CGGCCACCGC 1320
TTCTGCAAGG ACTTCCCAGG ATTTATCCCG AGCCTGCTTG GAGACCTCCT AGAGGAGAGG 1380
CAGAAGATAA AGAAGAAGAT GAAGGCCACG ATTGACCCGA TCGAGAGGAA GCTCCTCGAT 1440
TACAGGCAGA GGGCCATCAA GATCCTGGCA AACAGCTACT ACGGTTACTA CGGCTATGCA 1500
AGGGCGCGCT GGTACTGCAA GGAGTGTGCA GAGAGCGTAA CGGCCTGGGG AAGGGAGTAC 1560
ATAACGATGA CCATCAAGGA GATAGAGGAA AAGTACGGCT TTAAGGTAAT CTACAGCGAC 1620
ACCGACGGAT TTTTTGCCAC AATACCTGGA GCCGATGCTG AAACCGTCAA AAAGAAGGCT 1680
ATGGAGTTCC TCAAGTATAT CAACGCCAAA CTTCCGGGCG CGCTTGAGCT CGAGTACGAG 1740
GGCTTCTACA AACGCGGCTT CTTCGTCACG AAGAAGAAGT ATGCGGTGAT AGACGAGGAA 1800
GGCAAGATAA CAACGCGCGG ACTTGAGATT GTGAGGCGTG ACTGGAGCGA GATAGCGAAA 1860
GAGACGCAGG CGAGGGTTCT TGAAGCTTTG CTAAAGGACG GTGACGTCGA GAAGGCCGTG 1920
AGGATAGTCA AAGAAGTTAC CGAAAAGCTG AGCAAGTACG AGGTTCCGCC GGAGAAGCTG 1980
GTGATCCACG AGCAGATAAC GAGGGATTTA AAGGACTACA AGGCAACCGG TCCCCACGTT 2040
GCCGTTGCCA AGAGGTTGGC CGCGAGAGGA GTCAAAATAC GCCCTGGAAC GGTGATAAGC 2100
TACATCGTGC TCAAGGGCTC TGGGAGGATA GGCGACAGGG CGATACCGTT CGACGAGTTC 2160
GACCCGACGA AGCACAAGTA CGACGCCGAG TACTACATTG AGAACCAGGT TCTCCCAGCC 2220
GTTGAGAGAA TTCTGAGAGC CTTCGGTTAC CGCAAGGAAG ACCTGCGCTA CCAGAAGACG 2280
AGACAGGTTG GTTTGAGTGC TTGGCTGAAG CCGAAGGGAA CT //TAG 2325
```

| |
|---|
| FIG. 8GG-1 |
| FIG. 8GG-2 |
| FIG. 8GG-3 |

(PCNA)-Vent DNA POLYMERASE FUSION PROTEIN

Nucleotide sequence (SEQ ID NO: 67) // Nucleotide sequence (SEQ ID NO: 35)
Nucleotide sequence (SEQ ID NO: 67) // Nucleotide sequence (SEQ ID NO: 36)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATG CCA TTT GAA ATC GTA TTT GAA GGT GCA AAA GAG TTT GCC CAA CTT ATA GAC     54
   ACC GCA AGT AAG TTA ATA GAT GAG GCC GCG TTT AAA GTT ACA GAA GAT GGG ATA   108
   AGC ATG AGG GCC ATG GAT CCA AGT AGA GTT GTC CTG ATT GAC CTA AAT CTC CCG   162
   TCA AGC ATA TTT AGC AAA TAT GAA GTT GTT GAA CCA GAA ACA ATT GGA GTT AAC   216
   ATG GAC CAC CTA AAG AAG ATC CTA AAG AGA GGT AAA GCA AAG GAC ACC TTA ATA   270
   CTC AAG AAA GGA GAG GAA AAC TTC TTA GAG ATA ACA ATT CAA GGA ACT GCA ACA   324
   AGA ACA TTT AGA GTT CCC CTA ATA GAT GTA GAA GAG ATG GAA GTT GAC CTC CCA   378
   GAA CTT CCA TTC ACT GCA AAG GTT GTA GTT CTT GGA GAA GTC CTA AAA GAT GCT   432
```

FIG. 8GG-1

```
GTT AAA GAT GCC TCT CTA GTG AGT GAC AGC ATA AAA TTT ATT GCC AGG GAA AAT    486
GAA TTT ATA ATG AAG GCA GAG GGA GAA ACC CAG GAA GTT GAG ATA AAG CTA ACT    540
CTT GAA GAT GAG GGA TTA TTG GAC ATC GAG GTT CAA GAG GAG ACA AAG AGC GCA    594
TAT GGA GTC AGC TAT CTC TCC GAC ATG GTT AAA GGA CTT GGA AAG GCC GAT GAA    648
GTT ACA ATA AAG TTT GGA AAT GAA ATG CCC ATG CAA ATG GAG TAT TAC ATT AGA    702
GAT GAA GGA AGA CTT ACA TTC CTA CTG GCT CCA AGA GTT GAA GAG //

ATGATACTGG ACACTGATTA CATAACAAAA GATGGCAAGC CTATAATCCG AATTTTTAAG 60
AAAGAGAACG GGGAGTTTAA AATAGAACTT GACCCTCATT TTCAGCCCTA TATATATGCT 120
CTTCTCAAAG ATGACTCCGC TATTGAGGAG ATAAAGGCAA TAAAGGGCGA GAGACATGGA 180
AAAACTGTGA GAGTGCTCGA TGCAGTGAAA GTCAGGAAAA AATTTTTGGG AAGGGAAGTT 240
GAAGTCTGGA AGCTCATTTT CGAGCATCCC CAAGACXXXC CAGCTATGCG GGGCAAAATA 300
AGGGAACATC CAGCTGTGGT TGACATTTAC GAATATGACA TACCCTTTGC CAAGCGTTAT 360
CTCATAGACA AGGGCTTGAT TCCCATGGAG GGAGACGAGG AGCTTAAGCT CCTTGCCTTT 420
GATATTGAAA CGTTTTATCA TGAGGGAGAT GAATTTGGAA AGGGCGAGAT AATAATGATT 480
AGTTATGCCG ATGAAGAAGA GGCCAGAGTA ATCACATGGA AAAATATCGA TTTGCCGTAT 540
GTCGATGTTG TGTCCAATGA AAGAGAAATG ATAAAGCGTT TTGTTCAAGT TGTTAAAGAA 600
AAAGACCCCG ATGTGATAAT AACTTACAAT GGGGACAATT TTGATTTGCC GTATCTCATA 660
AAACGGGCAG AAAAGCTGGG AGTTCGGCTT GTCTTAGGAA GGGACAAAGA ACATCCCGAA 720
CCCAAGATTC AGAGGATGGG TGATAGTTTT GCTGTGGAAA TCAAGGGTAG AATCCACTTT 780
GATCTTTTCC CAGTTGTGCG AAGGACGATA AACCTCCCAA CGTATACGCT TGAGGCAGTT 840
TATGAAGCAG TTTTAGGAAA AACCAAAAGC AAATTAGGAG CAGAGGAAAT TGCCGCTATA 900
TGGGAAACAG AAGAAAGCAT GAAAAAACTA GCCCAGTACT CAATGGAAGA TGCTAGGGCA 960
```

FIG. 8GG-2

```
ACGTATGAGC TCGGGAAGGA ATTCTTCCCC ATGGAAGCTG AGCTGGCAAA GCTGATAGGT 1020
CAAAGTGTAT GGGACGTCTC GAGATCAAGC ACCGGCAACC TCGTGGAGTG GTATCTTTTA 1080
AGGGTGGCAT ACGCGAGGAA TGAACTTGCA CCGAACAAAC CTGATGAGGA AGAGTATAAA 1140
CGGCGCTTAA GAACAACTTA CCTGGGAGGA TATGTAAAAG AGCCAGAAAA AGGTTTGTGG 1200
GAAAATATCA TTTATTTGGA TTTCCGCAGT CTGTACCCTT CAATAATAGT TACTCACAAC 1260
GTATCCCCAG ATACCCTTGA AAAAGAGGGC TGTAAGAATT ACGATGTTGC TCCGATAGTA 1320
GGATATAGGT TCTGCAAGGA CTTTCCGGGC TTTATTCCCT CCATACTCGG GGACTTAATT 1380
GCAATGAGGC AAGATATAAA GAAGAAAATG AAATCCACAA TTGACCCGAT CGAAAAGAAA 1440
ATGCTCGATT ATAGGCAAAG GGCTATTAAA TTGCTTGCAA ACAGCTATTA CGGCTATATG 1500
GGGTATCCTA AGGCAAGATG GTACTCGAAG GAATGTGCTG AAAGCGTTAC CGCATGGGGG 1560
AGACACTACA TAGAGATGAC GATAAGAGAA ATAGAGGAAA AGTTCGGCTT TAAGGTTCTT 1620
TATGCGGACA CTGACGGCTT TTATGCCACA ATACCCGGGG AAAAGCCTGA ACTCATTAAA 1680
AAGAAAGCCA AGGAATTCCT AAACTACATA AACTCCAAAC TTCCAGGTCT GCTTGAGCTT 1740
GAGTATGAGG GCTTTTACTT GAGAGGATTC TTTGTTACAA AAAAGCGCTA TGCAGTCATA 1800
GATGAAGAGG GCAGGATAAC AACAAGGGGC TTGGAAGTAG TAAGGAGAGA TTGGAGTGAG 1860
ATAGCTAAGG AGACTCAGGC AAAGGTTTTA GAGGCTATAC TTAAAGAGGG AAGTGTTGAA 1920
AAAGCTGTAG AAGTTGTTAG AGATGTTGTA GAGAAAATAG CAAAATACAG GGTTCCACTT 1980
GAAAAGCTTG TTATCCATGA GCAGATTACC AGGGATTTAA AGGACTACAA AGCCATTGGC 2040
CCTCATGTCG CGATAGCAAA AAGACTTGCC GCAAGAGGGA TAAAAGTGAA ACCGGGCACA 2100
ATAATAAGCT ATATCGTTCT CAAAGGGAGC GGAAAGATAA GCGATAGGGT AATTTTACTT 2160
ACAGAATACG ATCCTAGAAA ACACAAGTAC GATCCGGACT ACTACATAGA AAACCAAGTT 2220
TTGCCGGCAG TACTTAGGAT ACTCGAAGCG TTTGGATACA GAAAGGAGGA TTTAAGGTAT 2280
CAAAGCTCAA AACAAACCGG CTTAGATGCA TGGCTCAAGA GGTAG 2325
```

| FIG. 8HH-1 |
|---|
| FIG. 8HH-2 |
| FIG. 8HH-3 |

Vent DNA POLYMERASE - (PCNA) FUSION PROTEIN

Nucleotide sequence (SEQ ID NO: 35) // Nucleotide sequence (SEQ ID NO: 67)
Nucleotide sequence (SEQ ID NO: 36) // Nucleotide sequence (SEQ ID NO: 67)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATACTGG ACACTGATTA CATAACAAAA GATGGCAAGC CTATAATCCG AATTTTTAAG 60
AAAGAGAACG GGGAGTTTAA AATAGAACTT GACCCTCATT TTCAGCCCTA TATATATGCT 120
CTTCTCAAAG ATGACTCCGC TATTGAGGAG ATAAAGGCAA TAAAGGGCGA GAGACATGGA 180
AAAACTGTGA GAGTGCTCGA TGCAGTGAAA GTCAGGAAAA AATTTTTGGG AAGGGAAGTT 240
GAAGTCTGGA AGCTCATTTT CGAGCATCCC CAAGACXXXC CAGCTATGCG GGGCAAAATA 300
AGGGAACATC CAGCTGTGGT TGACATTTAC GAATATGACA TACCCTTTGC CAAGCGTTAT 360
CTCATAGACA AGGGCTTGAT TCCCATGGAG GGAGACGAGG AGCTTAAGCT CCTTGCCTTT 420
GATATTGAAA CGTTTTATCA TGAGGGAGAT GAATTTGGAA AGGGCGAGAT AATAATGATT 480
```

FIG. 8HH-1

```
AGTTATGCCG ATGAAGAAGA GGCCAGAGTA ATCACATGGA AAAATATCGA TTTGCCGTAT 540
GTCGATGTTG TGTCCAATGA AAGAGAAATG ATAAAGCGTT TTGTTCAAGT TGTTAAAGAA 600
AAAGACCCCG ATGTGATAAT AACTTACAAT GGGGACAATT TTGATTTGCC GTATCTCATA 660
AAACGGGCAG AAAAGCTGGG AGTTCGGCTT GTCTTAGGAA GGGACAAAGA ACATCCCGAA 720
CCCAAGATTC AGAGGATGGG TGATAGTTTT GCTGTGGAAA TCAAGGGTAG AATCCACTTT 780
GATCTTTTCC CAGTTGTGCG AAGGACGATA AACCTCCCAA CGTATACGCT TGAGGCAGTT 840
TATGAAGCAG TTTTAGGAAA AACCAAAAGC AAATTAGGAG CAGAGGAAAT TGCCGCTATA 900
TGGGAAACAG AAGAAAGCAT GAAAAAACTA GCCCAGTACT CAATGGAAGA TGCTAGGGCA 960
ACGTATGAGC TCGGGAAGGA ATTCTTCCCC ATGGAAGCTG AGCTGGCAAA GCTGATAGGT 1020
CAAAGTGTAT GGGACGTCTC GAGATCAAGC ACCGGCAACC TCGTGGAGTG GTATCTTTTA 1080
AGGGTGGCAT ACGCGAGGAA TGAACTTGCA CCGAACAAAC CTGATGAGGA AGAGTATAAA 1140
CGGCGCTTAA GAACAACTTA CCTGGGAGGA TATGTAAAAG AGCCAGAAAA AGGTTTGTGG 1200
GAAAATATCA TTTATTTGGA TTTCCGCAGT CTGTACCCTT CAATAATAGT TACTCACAAC 1260
GTATCCCCAG ATACCCTTGA AAAAGAGGGC TGTAAGAATT ACGATGTTGC TCCGATAGTA 1320
GGATATAGGT TCTGCAAGGA CTTTCCGGGC TTTATTCCCT CCATACTCGG GGACTTAATT 1380
GCAATGAGGC AAGATATAAA GAAGAAAATG AAATCCACAA TTGACCCGAT CGAAAAGAAA 1440
ATGCTCGATT ATAGGCAAAG GGCTATTAAA TTGCTTGCAA ACAGCTATTA CGGCTATATG 1500
GGGTATCCTA AGGCAAGATG GTACTCGAAG GAATGTGCTG AAAGCGTTAC CGCATGGGGG 1560
AGACACTACA TAGAGATGAC GATAAGAGAA ATAGAGGAAA AGTTCGGCTT TAAGGTTCTT 1620
TATGCGGACA CTGACGGCTT TTATGCCACA ATACCCGGGG AAAAGCCTGA ACTCATTAAA 1680
AAGAAAGCCA AGGAATTCCT AAACTACATA AACTCCAAAC TTCCAGGTCT GCTTGAGCTT 1740
GAGTATGAGG GCTTTTACTT GAGAGGATTC TTTGTTACAA AAAAGCGCTA TGCAGTCATA 1800
GATGAAGAGG GCAGGATAAC AACAAGGGGC TTGGAAGTAG TAAGGAGAGA TTGGAGTGAG 1860
```

FIG. 8HH-2

ATAGCTAAGG AGACTCAGGC AAAGGTTTTA GAGGCTATAC TTAAAGAGGG AAGTGTTGAA 1920
AAAGCTGTAG AAGTTGTTAG AGATGTTGTA GAGAAAATAG CAAAATACAG GGTTCCACTT 1980
GAAAAGCTTG TTATCCATGA GCAGATTACC AGGGATTTAA AGGACTACAA AGCCATTGGC 2040
CCTCATGTCG CGATAGCAAA AAGACTTGCC GCAAGAGGGA TAAAAGTGAA ACCGGGCACA 2100
ATAATAAGCT ATATCGTTCT CAAAGGGAGC GGAAAGATAA GCGATAGGGT AATTTTACTT 2160
ACAGAATACG ATCCTAGAAA ACACAAGTAC GATCCGGACT ACTACATAGA AAACCAAGTT 2220
TTGCCGGCAG TACTTAGGAT ACTCGAAGCG TTTGGATACA GAAAGGAGGA TTTAAGGTAT 2280
CAAAGCTCAA AACAAACCGG CTTAGATGCA TGGCTCAAGA GG 2325 //

ATG CCA TTT GAA ATC GTA TTT GAA GGT GCA AAA GAG TTT GCC CAA CTT ATA GAC 54
ACC GCA AGT AAG TTA ATA GAT GAG GCC GCG TTT AAA GTT ACA GAA GAT GGG ATA 108
AGC ATG AGG GCC ATG GAT CCA AGT AGA GTT GTC CTG ATT GAC CTA AAT CTC CCG 162
TCA AGC ATA TTT AGC AAA TAT GAA GTT GTT GAA CCA GAA ACA ATT GGA GTT AAC 216
ATG GAC CAC CTA AAG AAG ATC CTA AAG AGA GGT AAA GCA AAG GAC ACC TTA ATA 270
CTC AAG AAA GGA GAG GAA AAC TTC TTA GAG ATA ACA ATT CAA GGA ACT GCA ACA 324
AGA ACA TTT AGA GTT CCC CTA ATA GAT GTA GAA GAG ATG GAA GTT GAC CTC CCA 378
GAA CTT CCA TTC ACT GCA AAG GTT GTA GTT CTT GGA GAA GTC CTA AAA GAT GCT 432
GTT AAA GAT GCC TCT CTA GTG AGT GAC AGC ATA AAA TTT ATT GCC AGG GAA AAT 486
GAA TTT ATA ATG AAG GCA GAG GGA GAA ACC CAG GAA GTT GAG ATA AAG CTA ACT 540
CTT GAA GAT GAG GGA TTA TTG GAC ATC GAG GTT CAA GAG GAG ACA AAG AGC GCA 594
TAT GGA GTC AGC TAT CTC TCC GAC ATG GTT AAA GGA CTT GGA AAG GCC GAT GAA 648
GTT ACA ATA AAG TTT GGA AAT GAA ATG CCC ATG CAA ATG GAG TAT TAC ATT AGA 702
GAT GAA GGA AGA CTT ACA TTC CTA CTG GCT CCA AGA GTT GAA GAG TGA

| FIG. 8II-1 |
| --- |
| FIG. 8II-2 |
| FIG. 8II-3 |

<u>Deep Vent- (PCNA) DNA polymerase fusion protein</u>

Nucleotide sequence (SEQ ID NO: 37) // Nucleotide sequence (SEQ ID NO: 67)
Nucleotide sequence (SEQ ID NO: 38) // Nucleotide sequence (SEQ ID NO: 67)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATACTTG ACGCTGACTA CATCACCGAG GATGGGAAGC CGATTATAAG GATTTTCAAG    60
AAAGAAAACG GCGAGTTTAA GGTTGAGTAC GACAGAAACT TTAGACCTTA CATTTACGCT   120
CTCCTCAAAG ATGACTCGCA GATTGATGAG GTTAGGAAGA TAACCGCCGA GAGGCATGGG   180
AAGATAGTGA GAATTATAGA TGCCGAAAAG GTAAGGAAGA AGTTCCTGGG GAGGCCGATT   240
GAGGTATGGA GGCTGTACTT TGAACACCCT CAGGACXXXC CCGCAATAAG GGATAAGATA   300
AGAGAGCATT CCGCAGTTAT TGACATCTTT GAGTACGACA TTCCGTTCGC GAAGAGGTAC   360
CTAATAGACA AAGGCCTAAT TCCAATGGAA GGCGATGAAG AGCTCAAGTT GCTCGCATTT   420
GACATAGAAA CCCTCTATCA CGAAGGGGAG GAGTTCGCGA AGGGGCCCAT TATAATGATA   480
```

FIG. 8II-1

```
AGCTATGCTG ATGAGGAAGA AGCCAAAGTC ATAACGTGGA AAAAGATCGA TCTCCCGTAC   540
GTCGAGGTAG TTTCCAGCGA GAGGGAGATG ATAAAGCGGT TCCTCAAGGT GATAAGGGAG   600
AAAGATCCCG ATGTTATAAT TACCTACAAC GGCGATTCTT TCGACCTTCC CTATCTAGTT   660
AAGAGGGCCG AAAAGCTCGG GATAAAGCTA CCCCTGGGAA GGGACGGTAG TGAGCCAAAG   720
ATGCAGAGGC TTGGGGATAT GACAGCGGTG GAGATAAAGG GAAGGATACA CTTTGACCTC   780
TACCACGTGA TTAGGAGAAC GATAAACCTC CCAACATACA CCCTCGAGGC AGTTTATGAG   840
GCAATCTTCG GAAAGCCAAA GGAGAAAGTT TACGCTCACG AGATAGCTGA GGCCTGGGAG   900
ACTGGAAAGG GACTGGAGAG AGTTGCAAAG TATTCAATGG AGGATGCAAA GGTAACGTAC   960
GAGCTCGGTA GGGAGTTCTT CCCAATGGAG GCCCAGCTTT CAAGGTTAGT CGGCCAGCCC  1020
CTGTGGGATG TTTCTAGGTC TTCAACTGGC AACTTGGTGG AGTGGTACCT CCTCAGGAAG  1080
GCCTACGAGA GGAATGAATT GGCTCCAAAC AAGCCGGATG AGAGGGAGTA CGAGAGAAGG  1140
CTAAGGGAGA GCTACGCTGG GGGATACGTT AAGGAGCCGG AGAAAGGGCT CTGGGAGGGG  1200
TTAGTTTCCC TAGATTTCAG GAGCCTGTAC CCCTCGATAA TAATCACCCA TAACGTCTCA  1260
CCGGATACGC TGAACAGGGA AGGGTGTAGG GAATACGATG TCGCCCCAGA GGTTGGGCAC  1320
AAGTTCTGCA AGGACTTCCC GGGGTTTATC CCCAGCCTGC TCAAGAGGTT ATTGGATGAA  1380
AGGCAAGAAA TAAAAAGGAA GATGAAAGCT TCTAAAGACC CAATCGAGAA GAAGATGCTT  1440
GATTACAGGC AACGGGCAAT CAAAATCCTG GCAAACAGCT ATTATGGGTA TTATGGGTAC  1500
GCAAAAGCCC GTTGGTACTG TAAGGAGTGC GCAGAGAGCG TTACGGCCTG GGGGAGGGAA  1560
TATATAGAGT TCGTAAGGAA GGAACTGGAG GAAAAGTTCG GGTTCAAAGT CTTATACATA  1620
GACACAGATG GACTCTACGC CACAATTCCT GGGGCAAAAC CCGAGGAGAT AAAGAAGAAA  1680
GCCCTAGAGT TCGTAGATTA TATAAACGCC AAGCTCCCAG GGCTGTTGGA GCTTGAGTAC  1740
GAGGGCTTCT ACGTGAGAGG GTTCTTCGTG ACGAAGAAGA AGTATGCGTT GATAGATGAG  1800
GAAGGGAAGA TAATCACTAG GGGGCTTGAA ATAGTCAGGA GGGACTGGAG CGAAATAGCC  1860
```

FIG. 8II-2

```
AAAGAAACCC AAGCAAAAGT CCTAGAGGCT ATCCTAAAGC ATGGCAACGT TGAGGAGGCA  1920
GTAAAGATAG TTAAGGAGGT AACTGAAAAG CTGAGCAAGT ACGAAATACC TCCAGAAAAG  1980
CTAGTTATTT ACGAGCAGAT CACGAGGCCC CTTCACGAGT ACAAGGCTAT AGGTCCGCAC  2040
GTTGCCGTGG CAAAAAGGTT AGCCGCTAGA GGAGTAAAGG TGAGGCCTGG CATGGTGATA  2100
GGGTACATAG TGCTGAGGGG AGACGGGCCA ATAAGCAAGA GGGCTATCCT TGCAGAGGAG  2160
TTCGATCTCA GGAAGCATAA GTATGACGCT GAGTATTACA TAGAAAATCA GGTTTTACCT  2220
GCCGTTCTTA GAATATTAGA GGCCTTTGGG TACAGGAAAG AAGACCTCAG GTGGCAGAAG  2280
ACTAAACAGA CAGGTCTTAC GGCATGGCTT AACATCAAGA AGAAG //             2328

// ATG CCA TTT GAA ATC GTA TTT GAA GGT GCA AAA GAG TTT GCC CAA CTT ATA GAC   54
   ACC GCA AGT AAG TTA ATA GAT GAG GCC GCG TTT AAA GTT ACA GAA GAT GGG ATA  108
   AGC ATG AGG GCC ATG GAT CCA AGT AGA GTT GTC CTG ATT GAC CTA AAT CTC CCG  162
   TCA AGC ATA TTT AGC AAA TAT GAA GTT GTT GAA CCA GAA ACA ATT GGA GTT AAC  216
   ATG GAC CAC CTA AAG AAG ATC CTA AAG AGA GGT AAA GCA AAG GAC ACC TTA ATA  270
   CTC AAG AAA GGA GAG GAA AAC TTC TTA GAG ATA ACA ATT CAA GGA ACT GCA ACA  324
   AGA ACA TTT AGA GTT CCC CTA ATA GAT GTA GAA GAG ATG GAA GTT GAC CTC CCA  378
   GAA CTT CCA TTC ACT GCA AAG GTT GTA GTT CTT GGA GAA GTC CTA AAA GAT GCT  432
   GTT AAA GAT GCC TCT CTA GTG AGT GAC AGC ATA AAA TTT ATT GCC AGG GAA AAT  486
   GAA TTT ATA ATG AAG GCA GAG GGA GAA ACC CAG GAA GTT GAG ATA AAG CTA ACT  540
   CTT GAA GAT GAG GGA TTA TTG GAC ATC GAG GTT CAA GAG GAG ACA AAG AGC GCA  594
   TAT GGA GTC AGC TAT CTC TCC GAC ATG GTT AAA GGA CTT GGA AAG GCC GAT GAA  648
   GTT ACA ATA AAG TTT GGA AAT GAA ATG CCC ATG CAA ATG GAG TAT TAC ATT AGA  702
   GAT GAA GGA AGA CTT ACA TTC CTA CTG GCT CCA AGA GTT GAA GAG TGA
```

| |
|---|
| FIG. 8JJ-1 |
| FIG. 8JJ-2 |
| FIG. 8JJ-3 |

(PCNA) - Deep Vent DNA polymerase fusion protein

Nucleotide sequence (SEQ ID NO: 67) // Nucleotide sequence (SEQ ID NO: 37)
Nucleotide sequence (SEQ ID NO: 67) // Nucleotide sequence (SEQ ID NO: 38)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATG CCA TTT GAA ATC GTA TTT GAA GGT GCA AAA GAG TTT GCC CAA CTT ATA GAC     54
  ACC GCA AGT AAG TTA ATA GAT GAG GCC GCG TTT AAA GTT ACA GAA GAT GGG ATA   108
  AGC ATG AGG GCC ATG GAT CCA AGT AGA GTT GTC CTG ATT GAC CTA AAT CTC CCG   162
  TCA AGC ATA TTT AGC AAA TAT GAA GTT GTT GAA CCA GAA ACA ATT GGA GTT AAC   216
  ATG GAC CAC CTA AAG AAG ATC CTA AAG AGA GGT AAA GCA AAG GAC ACC TTA ATA   270
  CTC AAG AAA GGA GAG GAA AAC TTC TTA GAG ATA ACA ATT CAA GGA ACT GCA ACA   324
  AGA ACA TTT AGA GTT CCC CTA ATA GAT GTA GAA GAG ATG GAA GTT GAC CTC CCA   378
  GAA CTT CCA TTC ACT GCA AAG GTT GTA GTT CTT GGA GAA GTC CTA AAA GAT GCT   432
  GTT AAA GAT GCC TCT CTA GTG AGT GAC AGC ATA AAA TTT ATT GCC AGG GAA AAT   486
  GAA TTT ATA ATG AAG GCA GAG GGA GAA ACC CAG GAA GTT GAG ATA AAG CTA ACT   540
```

FIG. 8JJ-1

```
CTT GAA GAT GAG GGA TTA TTG GAC ATC GAG GTT CAA GAG GAG ACA AAG AGC GCA    594
TAT GGA GTC AGC TAT CTC TCC GAC ATG GTT AAA GGA CTT GGA AAG GCC GAT GAA    648
GTT ACA ATA AAG TTT GGA AAT GAA ATG CCC ATG CAA ATG GAG TAT TAC ATT AGA    702
GAT GAA GGA AGA CTT ACA TTC CTA CTG GCT CCA AGA GTT GAA GAG //
```

```
//ATGATACTTG ACGCTGACTA CATCACCGAG GATGGGAAGC CGATTATAAG GATTTTCAAG    60
AAAGAAAACG GCGAGTTTAA GGTTGAGTAC GACAGAAACT TTAGACCTTA CATTTACGCT   120
CTCCTCAAAG ATGACTCGCA GATTGATGAG GTTAGGAAGA TAACCGCCGA GAGGCATGGG   180
AAGATAGTGA GAATTATAGA TGCCGAAAAG GTAAGGAAGA AGTTCCTGGG GAGGCCGATT   240
GAGGTATGGA GGCTGTACTT TGAACACCCT CAGGACXXXC CCGCAATAAG GGATAAGATA   300
AGAGAGCATT CCGCAGTTAT TGACATCTTT GAGTACGACA TTCCGTTCGC GAAGAGGTAC   360
CTAATAGACA AAGGCCTAAT TCCAATGGAA GGCGATGAAG AGCTCAAGTT GCTCGCATTT   420
GACATAGAAA CCCTCTATCA CGAAGGGGAG GAGTTCGCGA AGGGGCCCAT TATAATGATA   480
AGCTATGCTG ATGAGGAAGA AGCCAAAGTC ATAACGTGGA AAAAGATCGA TCTCCCGTAC   540
GTCGAGGTAG TTTCCAGCGA GAGGGAGATG ATAAAGCGGT TCCTCAAGGT GATAAGGGAG   600
AAAGATCCCG ATGTTATAAT TACCTACAAC GGCGATTCTT TCGACCTTCC CTATCTAGTT   660
AAGAGGGCCG AAAAGCTCGG GATAAAGCTA CCCCTGGGAA GGGACGGTAG TGAGCCAAAG   720
ATGCAGAGGC TTGGGGATAT GACAGCGGTG GAGATAAAGG GAAGGATACA CTTTGACCTC   780
TACCACGTGA TTAGGAGAAC GATAAACCTC CCAACATACA CCCTCGAGGC AGTTTATGAG   840
GCAATCTTCG GAAAGCCAAA GGAGAAAGTT TACGCTCACG AGATAGCTGA GGCCTGGGAG   900
ACTGGAAAGG GACTGGAGAG AGTTGCAAAG TATTCAATGG AGGATGCAAA GGTAACGTAC   960
```

FIG. 8JJ-2

```
GAGCTCGGTA GGGAGTTCTT CCCAATGGAG GCCCAGCTTT CAAGGTTAGT CGGCCAGCCC  1020
CTGTGGGATG TTTCTAGGTC TTCAACTGGC AACTTGGTGG AGTGGTACCT CCTCAGGAAG  1080
GCCTACGAGA GGAATGAATT GGCTCCAAAC AAGCCGGATG AGAGGGAGTA CGAGAGAAGG  1140
CTAAGGGAGA GCTACGCTGG GGGATACGTT AAGGAGCCGG AGAAAGGGCT CTGGGAGGGG  1200
TTAGTTTCCC TAGATTTCAG GAGCCTGTAC CCCTCGATAA TAATCACCCA TAACGTCTCA  1260
CCGGATACGC TGAACAGGGA AGGGTGTAGG GAATACGATG TCGCCCCAGA GGTTGGGCAC  1320
AAGTTCTGCA AGGACTTCCC GGGGTTTATC CCCAGCCTGC TCAAGAGGTT ATTGGATGAA  1380
AGGCAAGAAA TAAAAAGGAA GATGAAAGCT TCTAAAGACC CAATCGAGAA GAAGATGCTT  1440
GATTACAGGC AACGGGCAAT CAAAATCCTG GCAAACAGCT ATTATGGGTA TTATGGGTAC  1500
GCAAAAGCCC GTTGGTACTG TAAGGAGTGC GCAGAGAGCG TTACGGCCTG GGGGAGGGAA  1560
TATATAGAGT TCGTAAGGAA GGAACTGGAG GAAAAGTTCG GGTTCAAAGT CTTATACATA  1620
GACACAGATG GACTCTACGC CACAATTCCT GGGGCAAAAC CCGAGGAGAT AAAGAAGAAA  1680
GCCCTAGAGT TCGTAGATTA TATAAACGCC AAGCTCCCAG GGCTGTTGGA GCTTGAGTAC  1740
GAGGGCTTCT ACGTGAGAGG GTTCTTCGTG ACGAAGAAGA AGTATGCGTT GATAGATGAG  1800
GAAGGGAAGA TAATCACTAG GGGGCTTGAA ATAGTCAGGA GGGACTGGAG CGAAATAGCC  1860
AAAGAAACCC AAGCAAAAGT CCTAGAGGCT ATCCTAAAGC ATGGCAACGT TGAGGAGGCA  1920
GTAAAGATAG TTAAGGAGGT AACTGAAAAG CTGAGCAAGT ACGAAATACC TCCAGAAAAG  1980
CTAGTTATTT ACGAGCAGAT CACGAGGCCC CTTCACGAGT ACAAGGCTAT AGGTCCGCAC  2040
GTTGCCGTGG CAAAAAGGTT AGCCGCTAGA GGAGTAAAGG TGAGGCCTGG CATGGTGATA  2100
GGGTACATAG TGCTGAGGGG AGACGGGCCA ATAAGCAAGA GGGCTATCCT TGCAGAGGAG  2160
TTCGATCTCA GGAAGCATAA GTATGACGCT GAGTATTACA TAGAAAATCA GGTTTTACCT  2220
GCCGTTCTTA GAATATTAGA GGCCTTTGGG TACAGGAAAG AAGACCTCAG GTGGCAGAAG  2280
ACTAAACAGA CAGGTCTTAC GGCATGGCTT AACATCAAGA AGAAG TAA              2328
```

| FIG. 8KK-1 |
|---|
| FIG. 8KK-2 |

JDF-3 - (PCNA) fusion protein

Nucleotide sequence (SEQ ID NO: 39) // Nucleotide sequence (SEQ ID NO: 67)
Nucleotide sequence (SEQ ID NO: 40) // Nucleotide sequence (SEQ ID NO: 67)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

ATGATCCTTGACGTTGATTACATCACCGAGAATGGAAAGCCCGTCATCAGGGTCTTCAAGAAGGAGAACGGCGAGTTCAGGATTGAATACGACCGCGAGTTCGAGCCCTACTTCT
ACGCGCTCCTCAGGGACGACTCTGCCATCGAAGAAATCAAAAAGATAACCGCGGAGAGGCACGGCAGGGTCGTTAAGGTTAAGCGCGCGGAGAAGGTGAAGAAAAAGTTCCTCGG
CAGGTCTGTGGAGGTCTGGGTCCTCTACTTCACGCACCCGCAGGACXXXCCGGCAATCCGCGACAAAATAAGGAAGCACCCCGCGGTCATCGACATCTACGAGTACGACATACCC
TTCGCCAAGCGCTACCTCATAGACAAGGGCCTAATCCCGATGGAAGGTGAGGAAGAGCTTAAACTCATGTCCTTCGACATCGAGACGCTCTACCACGAGGGAGAAGAGTTTGGAA
CCGGGCCGATTCTGATGATAAGCTACGCCGATGAAAGCGAGGCGCGCGTGATAACCTGGAAGAAGATCGACCTTCCTTACGTTGAGGTTGTCTCCACCGAGAAGGAGATGATTAA
GCGCTTCTTGAGGGTCGTTAAGGAGAAGGACCCGGACGTGCTGATAACATACAACGGCGACAACTTCGACTTCGCCTACCTGAAAAAGCGCTGTGAGAAGCTTGGCGTGAGCTTT
ACCCTCGGGAGGGACGGGAGCGAGCCGAAGATACAGCGCATGGGGGACAGGTTTGCGGTCGAGGTGAAGGGCAGGGTACACTTCGACCTTTATCCAGTCATAAGGCGCACCATAA
ACCTCCCGACCTACACCCTTGAGGCTGTATACGAGGCGGTTTTCGGCAAGCCCAAGGAGAAGGTCTACGCCGAGGAGATAGCCACCGCCTGGGAGACCGGCGAGGGGCTTGAGAG
GGTCGCGCGCTACTCGATGGAGGACGCGAGGGTTACCTACGAGCTTGGCAGGGAGTTCTTCCCGATGGAGGCCCAGCTTTCCAGGCTCATCGGCCAAGGCCTCTGGGACGTTTCC
CGCTCCAGCACCGGCAACCTCGTCGAGTGGTTCCTCCTAAGGAAGGCCTACGAGAGGAACGAACTCGCTCCCAACAAGCCCGACGAGAGGGAGCTGGCGAGGAGAAGGGGGGCT
ACgcCGGTGGCTACGTCAAGGAGCCGGAGCGGGGACTGTGGGACAATATCGTGTATCTAGACTTTCGTAGTCTCTACCCTTCAATCATAATCACCCACAACGTCTCGCCAGATAC
GCTCAACCGCGAGGGGTGTAGGAGCTACGACGTTGCCCCCGAGGTCGGTCACAAGTTCTGCAAGGACTTCCCCGGCTTCATTCCGAGCCTGCTCGGAAACCTGCTGGAGGAAAGG
CAGAAGATAAAGAGGAAGATGAAGGCAACTCTCGACCCGCTGGAGAAGAATCTCCTCGATTACAGGCAACGCGCCATCAAGATTCTCGCCAACAGCTACTACGGCTACTACGGCT

FIG. 8KK-1

ATGCCAGGGCAAGATGGTACTGCAGGGAGTGCGCCGAGAGCGTTACGGCATGGGGAAGGGAGTACATCGAAATGGTCATCAGAGAGCTTGAGGAAAAGTTCGGTTTTAAAGTCCT
CTATGCAGACACAGACGGTCTCCATGCCACCATTCCTGGAGCGGACGCTGAAACAGTCAAGAAAAAGGCAATGGAGTTCTTAAACTATATCAATCCCAAACTGCCCGGCCTTCTC
GAACTCGAATACGAGGGCTTCTACGTCAGGGGCTTCTTCGTCACGAAGAAAAAGTACGCGGTCATCGACGAGGAGGGCAAGATAACCACGCGCGGGCTTGAGATAGTCAGGCGCG
ACTGGAGCGAGATAGCGAAGGAGACGCAGGCGAGGGTTTTGGAGGCGATACTCAGGCACGGTGACGTTGAAGAGGCCGTCAGAATTGTCAGGGAAGTCACCGAAAAGCTGAGCAA
GTACGAGGTTCCGCCGGAGAAGCTGGTTATCCACGAGCAGATAACGCGCGAGCTCAAGGACTACAAGGCCACCGGCCCGCACGTAGCCATAGCGAAgcGTTTGGCCGCCAGAGGT
GTTAAAATCCGGCCCGGAACTGTGATAAGCTACATCGTTCTGAAGGGCTCCGGAAGGATAGGCGACAGGGCGATTCCCTTCGACGAGTTCGACCCGACGAAGCACAAGTACGATG
CGGACTACTACATCGAGAACCAGGTTCTGCCGGCAGTTGAGAGAATCCTCAGGGCCTTCGGCTACCGCAAGGAAGACCTGCGCTACCAGAAGACGAGGCAGGTCGGGCTTGGCGC
GTGGCTGAAGCCGAAGGGGAAGAAGAAG//

ATG CCA TTT GAA ATC GTA TTT GAA GGT GCA AAA GAG TTT GCC CAA CTT ATA GAC 54
ACC GCA AGT AAG TTA ATA GAT GAG GCC GCG TTT AAA GTT ACA GAA GAT GGG ATA 108
AGC ATG AGG GCC ATG GAT CCA AGT AGA GTT GTC CTG ATT GAC CTA AAT CTC CCG 162
TCA AGC ATA TTT AGC AAA TAT GAA GTT GTT GAA CCA GAA ACA ATT GGA GTT AAC 216
ATG GAC CAC CTA AAG AAG ATC CTA AAG AGA GGT AAA GCA AAG GAC ACC TTA ATA 270
CTC AAG AAA GGA GAG GAA AAC TTC TTA GAG ATA ACA ATT CAA GGA ACT GCA ACA 324
AGA ACA TTT AGA GTT CCC CTA ATA GAT GTA GAA GAG ATG GAA GTT GAC CTC CCA 378
GAA CTT CCA TTC ACT GCA AAG GTT GTA GTT CTT GGA GAA GTC CTA AAA GAT GCT 432
GTT AAA GAT GCC TCT CTA GTG AGT GAC AGC ATA AAA TTT ATT GCC AGG GAA AAT 486
GAA TTT ATA ATG AAG GCA GAG GGA GAA ACC CAG GAA GTT GAG ATA AAG CTA ACT 540
CTT GAA GAT GAG GGA TTA TTG GAC ATC GAG GTT CAA GAG GAG ACA AAG AGC GCA 594
TAT GGA GTC AGC TAT CTC TCC GAC ATG GTT AAA GGA CTT GGA AAG GCC GAT GAA 648
GTT ACA ATA AAG TTT GGA AAT GAA ATG CCC ATG CAA ATG GAG TAT TAC ATT AGA 702
GAT GAA GGA AGA CTT ACA TTC CTA CTG GCT CCA AGA GTT GAA GAG TGA

| |
|---|
| FIG. 8LL-1 |
| FIG. 8LL-2 |

(PCNA) - JDF-3 fusion protein

Nucleotide sequence (SEQ ID NO: 67) // Nucleotide sequence (SEQ ID NO: 39)
Nucleotide sequence (SEQ ID NO: 67) // Nucleotide sequence (SEQ ID NO: 40)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATG CCA TTT GAA ATC GTA TTT GAA GGT GCA AAA GAG TTT GCC CAA CTT ATA GAC    54
ACC GCA AGT AAG TTA ATA GAT GAG GCC GCG TTT AAA GTT ACA GAA GAT GGG ATA   108
AGC ATG AGG GCC ATG GAT CCA AGT AGA GTT GTC CTG ATT GAC CTA AAT CTC CCG   162
TCA AGC ATA TTT AGC AAA TAT GAA GTT GTT GAA CCA GAA ACA ATT GGA GTT AAC   216
ATG GAC CAC CTA AAG AAG ATC CTA AAG AGA GGT AAA GCA AAG GAC ACC TTA ATA   270
CTC AAG AAA GGA GAG GAA AAC TTC TTA GAG ATA ACA ATT CAA GGA ACT GCA ACA   324
AGA ACA TTT AGA GTT CCC CTA ATA GAT GTA GAA GAG ATG GAA GTT GAC CTC CCA   378
GAA CTT CCA TTC ACT GCA AAG GTT GTA GTT CTT GGA GAA GTC CTA AAA GAT GCT   432
GTT AAA GAT GCC TCT CTA GTG AGT GAC AGC ATA AAA TTT ATT GCC AGG GAA AAT   486
GAA TTT ATA ATG AAG GCA GAG GGA GAA ACC CAG GAA GTT GAG ATA AAG CTA ACT   540
CTT GAA GAT GAG GGA TTA TTG GAC ATC GAG GTT CAA GAG GAG ACA AAG AGC GCA   594
TAT GGA GTC AGC TAT CTC TCC GAC ATG GTT AAA GGA CTT GGA AAG GCC GAT GAA   648
GTT ACA ATA AAG TTT GGA AAT GAA ATG CCC ATG CAA ATG GAG TAT TAC ATT AGA   702
GAT GAA GGA AGA CTT ACA TTC CTA CTG GCT CCA AGA GTT GAA GAG //
```

FIG. 8LL-1

//ATGATCCTTGACGTTGATTACATCACCGAGAATGGAAAGCCCGTCATCAGGGTCTTCAAGAAGGAGAACGGCGAGTTCAGGATTGAATACGACCGCGAGTTCGAG
CCCTACTTCTACGCGCTCCTCAGGGACGACTCTGCCATCGAAGAAATCAAAAAGATAACCGCGGAGAGGCACGGCAGGGTCGTTAAGGTTAAGCGCGCGGAGAAGGT
GAAGAAAAAGTTCCTCGGCAGGTCTGTGGAGGTCTGGGTCCTCTACTTCACGCACCCGCAGGACXXXCCGGCAATCCGCGACAAAATAAGGAAGCACCCCGCGGTCA
TCGACATCTACGAGTACGACATACCCTTCGCCAAGCGCTACCTCATAGACAAGGGCCTAATCCCGATGGAAGGTGAGGAAGAGCTTAAACTCATGTCCTTCGACATC
GAGACGCTCTACCACGAGGGAGAAGAGTTTGGAACCGGGCCGATTCTGATGATAAGCTACGCCGATGAAAGCGAGGCGCGCGTGATAACCTGGAAGAAGATCGACCT
TCCTTACGTTGAGGTTGTCTCCACCGAGAAGGAGATGATTAAGCGCTTCTTGAGGGTCGTTAAGGAGAAGGACCCGGACGTGCTGATAACATACAACGGCGACAACT
TCGACTTCGCCTACCTGAAAAAGCGCTGTGAGAAGCTTGGCGTGAGCTTTACCCTCGGGAGGGACGGAGCGAGCCGAAGATACAGCGCATGGGGGACAGGTTTGCG
GTCGAGGTGAAGGGCAGGGTACACTTCGACCTTTATCCAGTCATAAGGCGCACCATAAACCTCCCGACCTACACCCTTGAGGCTGTATACGAGGCGGTTTTCGGCAA
GCCCAAGGAGAAGGTCTACGCCGAGGAGATAGCCACCGCCTGGGAGACCGGCGAGGGGCTTGAGAGGGTCGCGCGCTACTCGATGGAGGACGCGAGGGTTACCTACG
AGCTTGGCAGGGAGTTCTTCCCGATGGAGGCCCAGCTTTCCAGGCTCATCGGCCAAGGCCTCTGGGACGTTTCCCGCTCCAGCACCGGCAACCTCGTCGAGTGGTTC
CTCCTAAGGAAGGCCTACGAGAGGAACGAACTCGCTCCCAACAAGCCCGACGAGAGGGAGCTGGCGAGGAGAAGGGGGGGCTACgcCGGTGGCTACGTCAAGGAGCC
GGAGCGGGGACTGTGGGACAATATCGTGTATCTAGACTTTCGTAGTCTCTACCCTTCAATCATAATCACCCACAACGTCTCGCCAGATACGCTCAACCGCGAGGGGT
GTAGGAGCTACGACGTTGCCCCCGAGGTCGGTCACAAGTTCTGCAAGGACTTCCCCGGCTTCATTCCGAGCCTGCTCGGAAACCTGCTGGAGGAAAGGCAGAAGATA
AAGAGGAAGATGAAGGCAACTCTCGACCCGCTGGAGAAGAATCTCCTCGATTACAGGCAACGCGCCATCAAGATTCTCGCCAACAGCTACTACGGCTACTACGGCTA
TGCCAGGGCAAGATGGTACTGCAGGGAGTGCGCCGAGAGCGTTACGGCATGGGGAAGGGAGTACATCGAAATGGTCATCAGAGAGCTTGAGGAAAAGTTCGGTTTTA
AAGTCCTCTATGCAGACACAGACGGTCTCCATGCCACCATTCCTGGAGCGGACGCTGAAACAGTCAAGAAAAAGGCAATGGAGTTCTTAAACTATATCAATCCCAAA
CTGCCCGGCCTTCTCGAACTCGAATACGAGGGCTTCTACGTCAGGGGCTTCTTCGTCACGAAGAAAAAGTACGCGGTCATCGACGAGGAGGGCAAGATAACCACGCG
CGGGCTTGAGATAGTCAGGCGCGACTGGAGCGAGATAGCGAAGGAGACGCAGGCGAGGGTTTTGGAGGCGATACTCAGGCACGGTGACGTTGAAGAGGCCGTCAGAA
TTGTCAGGGAAGTCACCGAAAAGCTGAGCAAGTACGAGGTTCCGCCGGAGAAGCTGGTTATCCACGAGCAGATAACGCGCGAGCTCAAGGACTACAAGGCCACCGGC
CCGCACGTAGCCATAGCGAAgcGTTTGGCCGCCAGAGGTGTTAAAATCCGGCCCGGAACTGTGATAAGCTACATCGTTCTGAAGGGCTCCGGAAGGATAGGCGACAG
GGCGATTCCCTTCGACGAGTTCGACCCGACGAAGCACAAGTACGATGCGGACTACTACATCGAGAACCAGGTTCTGCCGGCAGTTGAGAGAATCCTCAGGGCCTTCG
GCTACCGCAAGGAAGACCTGCGCTACCAGAAGACGAGGCAGGTCGGGCTTGGCGCGTGGCTGA

FIG. 8LL-2

Sac7d gene (ACCESSION No: M87569)

Nucleotide sequence (SEQ ID NO: 69)
Amino acid sequence (SEQ ID NO: 70)

```
 M   V   K   V   K   F   K   Y   K   G   E   E   K   E   V   D   T   S     18
ATG GTG AAG GTA AAG TTC AAG TAT AAG GGT GAA GAG AAA GAA GTA GAC ACT TCA    54

 K   I   K   K   V   W   R   V   G   K   M   V   S   F   T   Y   D   D     36
AAG ATA AAG AAG GTT TGG AGA GTA GGC AAA ATG GTG TCC TTT ACC TAT GAC GAC   108

 N   G   K   T   G   R   G   A   V   S   E   K   D   A   P   K   E   L     54
AAT GGT AAG ACA GGT AGA GGA GCT GTA AGC GAG AAA GAT GCT CCA AAA GAA TTA   162

 L   D   M   L   A   R   A   E   R   E   K   K   *                         67
TTA GAC ATG TTA GCA AGA GCA GAA AGA GAG AAG AAA TAA                       201
```

FIG. 8MM

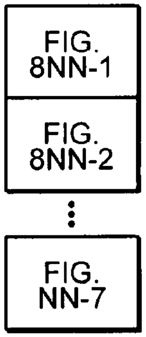

FIG. 8NN

Sac7d-Taq DNA polymerase fusion protein

Nucleotide sequence (SEQ ID NO: 69) // Nucleotide sequence (SEQ ID NO: 65)
Amino acid sequence (SEQ ID NO: 70) // Amino acid sequence (SEQ ID NO: 66)

```
 M   V   K   V   K   F   K   Y   K   G   E   E   K   E   V   D   T   S
ATG GTG AAG GTA AAG TTC AAG TAT AAG GGT GAA GAG AAA GAA GTA GAC ACT TCA

 K   I   K   K   V   W   R   V   G   K   M   V   S   F   T   Y   D   D
AAG ATA AAG AAG GTT TGG AGA GTA GGC AAA ATG GTG TCC TTT ACC TAT GAC GAC

 N   G   K   T   G   R   G   A   V   S   E   K   D   A   P   K   E   L
AAT GGT AAG ACA GGT AGA GGA GCT GTA AGC GAG AAA GAT GCT CCA AAA GAA TTA

 L   D   M   L   A   R   A   E   R   E   K   K  //
TTA GAC ATG TTA GCA AGA GCA GAA AGA GAG AAG AAA //

    G   G   G
// GGC GGC GGT

 V   T   S   G   M   L   P   L   F   E   P   K   G   R   V   L   L   V
GTC ACT AGT GGG ATG CTG CCC CTC TTT GAG CCC AAG GGC CGG GTC CTC CTG GTG
```

FIG. 8NN-1

```
 D   G   H   H   L   A   Y   R   T   F   H   A   L   K   G   L   T   T
GAC GGC CAC CAC CTG GCC TAC CGC ACC TTC CAC GCC CTG AAG GGC CTC ACC ACC

 S   R   G   E   P   V   Q   A   V   Y   G   F   A   K   S   L   L   K
AGC CGG GGG GAG CCG GTG CAG GCG GTC TAC GGC TTC GCC AAG AGC CTC CTC AAG

 A   L   K   E   D   G   D   A   V   I   V   V   F   D   A   K   A   P
GCC CTC AAG GAG GAC GGG GAC GCG GTG ATC GTG GTC TTT GAC GCC AAG GCC CCC

 S   F   R   H   E   A   Y   G   G   Y   K   A   G   R   A   P   T   P
TCC TTC CGC CAC GAG GCC TAC GGG GGG TAC AAG GCG GGC CGG GCC CCC ACG CCA

 E   D   F   P   R   Q   L   A   L   I   K   E   L   V   D   L   L   G
GAG GAC TTT CCC CGG CAA CTC GCC CTC ATC AAG GAG CTG GTG GAC CTC CTG GGG

 L   A   R   L   E   V   P   G   Y   E   A   D   D   V   L   A   S   L
CTG GCG CGC CTC GAG GTC CCG GGC TAC GAG GCG GAC GAC GTC CTG GCC AGC CTG

 A   K   K   A   E   K   E   G   Y   E   V   R   I   L   T   A   D   K
GCC AAG AAG GCG GAA AAG GAG GGC TAC GAG GTC CGC ATC CTC ACC GCC GAC AAA

 D   L   Y   Q   L   L   S   D   R   I   H   V   L   H   P   E   G   Y
GAC CTT TAC CAG CTC CTT TCC GAC CGC ATC CAC GTC CTC CAC CCC GAG GGG TAC
```

FIG. 8NN-2

```
 L   I   T   P   A   W   L   W   E   K   Y   G   L   R   P   D   Q   W
CTC ATC ACC CCG GCC TGG CTT TGG GAA AAG TAC GGC CTG AGG CCC GAC CAG TGG

 A   D   Y   R   A   L   T   G   D   E   S   D   N   L   P   G   V   K
GCC GAC TAC CGG GCC CTG ACC GGG GAC GAG TCC GAC AAC CTT CCC GGG GTC AAG

 G   I   G   E   K   T   A   R   K   L   L   E   E   W   G   S   L   E
GGC ATC GGG GAG AAG ACG GCG AGG AAG CTT CTG GAG GAG TGG GGG AGC CTG GAA

 A   L   L   K   N   L   D   R   L   K   P   A   I   R   E   K   I   L
GCC CTC CTC AAG AAC CTG GAC CGG CTG AAG CCC GCC ATC CGG GAG AAG ATC CTG

 A   H   M   D   D   L   K   L   S   W   D   L   A   K   V   R   T   D
GCC CAC ATG GAC GAT CTG AAG CTC TCC TGG GAC CTG GCC AAG GTG CGC ACC GAC

 L   P   L   E   V   D   F   A   K   R   R   E   P   D   R   E   R   L
CTG CCC CTG GAG GTG GAC TTC GCC AAA AGG CGG GAG CCC GAC CGG GAG AGG CTT

 R   A   F   L   E   R   L   E   F   G   S   L   L   H   E   F   G   L
AGG GCC TTT CTG GAG AGG CTT GAG TTT GGC AGC CTC CTC CAC GAG TTC GGC CTT

 L   E   S   P   K   A   L   E   E   A   P   W   P   P   P   E   G   A
CTG GAA AGC CCC AAG GCC CTG GAG GAG GCC CCC TGG CCC CCG CCG GAA GGG GCC
```

FIG. 8NN-3

```
 F   V   G   F   V   L   S   R   K   E   P   M   W   A   D   L   L   A
TTC GTG GGC TTT GTG CTT TCC CGC AAG GAG CCC ATG TGG GCC GAT CTT CTG GCC

 L   A   A   A   R   G   G   R   V   H   R   A   P   E   P   Y   K   A
CTG GCC GCC GCC AGG GGG GGC CGG GTC CAC CGG GCC CCC GAG CCT TAT AAA GCC

 L   R   D   L   K   E   A   R   G   L   L   A   K   D   L   S   V   L
CTC AGG GAC CTG AAG GAG GCG CGG GGG CTT CTC GCC AAA GAC CTG AGC GTT CTG

 A   L   R   E   G   L   G   L   P   P   G   D   D   P   M   L   L   A
GCC CTG AGG GAA GGC CTT GGC CTC CCG CCC GGC GAC GAC CCC ATG CTC CTC GCC

 Y   L   L   D   P   S   N   T   T   P   E   G   V   A   R   R   Y   G
TAC CTC CTG GAC CCT TCC AAC ACC ACC CCC GAG GGG GTG GCC CGG CGC TAC GGC

 G   E   W   T   E   E   A   G   E   R   A   A   L   S   E   R   L   F
GGG GAG TGG ACG GAG GAG GCG GGG GAG CGG GCC GCC CTT TCC GAG AGG CTC TTC

 A   N   L   W   G   R   L   E   G   E   E   R   L   L   W   L   Y   R
GCC AAC CTG TGG GGG AGG CTT GAG GGG GAG GAG AGG CTC CTT TGG CTT TAC CGG

 E   V   E   R   P   L   S   A   V   L   A   H   M   E   A   T   G   V
GAG GTG GAG AGG CCC CTT TCC GCT GTC CTG GCC CAC ATG GAG GCC ACG GGG GTG
```

FIG. 8NN-4

```
 R   L   D   V   A   Y   L   R   A   L   S   L   E   V   A   E   E   I
CGC CTG GAC GTG GCC TAT CTC AGG GCC TTG TCC CTG GAG GTG GCC GAG GAG ATC

 A   R   L   E   A   E   V   F   R   L   A   G   H   P   F   N   L   N
GCC CGC CTC GAG GCC GAG GTC TTC CGC CTG GCC GGC CAC CCC TTC AAC CTC AAC

 S   R   D   Q   L   E   R   V   L   F   D   E   L   G   L   P   A   I
TCC CGG GAC CAG CTG GAA AGG GTC CTC TTT GAC GAG CTA GGG CTT CCC GCC ATC

 G   K   T   E   K   T   G   K   R   S   T   S   A   A   V   L   E   A
GGC AAG ACG GAG AAG ACC GGC AAG CGC TCC ACC AGC GCC GCC GTC CTG GAG GCC

 L   R   E   A   H   P   I   V   E   K   I   L   Q   Y   R   E   L   T
CTC CGC GAG GCC CAC CCC ATC GTG GAG AAG ATC CTG CAG TAC CGG GAG CTC ACC

 K   L   K   S   T   Y   I   D   P   L   P   D   L   I   H   P   R   T
AAG CTG AAG AGC ACC TAC ATT GAC CCC TTG CCG GAC CTC ATC CAC CCC AGG ACG

 G   R   L   H   T   R   F   N   Q   T   A   T   A   T   G   R   L   S
GGC CGC CTC CAC ACC CGC TTC AAC CAG ACG GCC ACG GCC ACG GGC AGG CTA AGT

 S   S   D   P   N   L   Q   N   I   P   V   R   T   P   L   G   Q   R
AGC TCC GAT CCC AAC CTC CAG AAC ATC CCC GTC CGC ACC CCG CTT GGG CAG AGG
```

FIG. 8NN-5

```
 I   R   R   A   F   I   A   E   E   G   W   L   L   V   A   L   D   Y
ATC CGC CGG GCC TTC ATC GCC GAG GAG GGG TGG CTA TTG GTG GCC CTG GAC TAT

 S   Q   I   E   L   R   V   L   A   H   L   S   G   D   E   N   L   I
AGC CAG ATA GAG CTC AGG GTG CTG GCC CAC CTC TCC GGC GAC GAG AAC CTG ATC

 R   V   F   Q   E   G   R   D   I   H   T   E   T   A   S   W   M   F
CGG GTC TTC CAG GAG GGG CGG GAC ATC CAC ACG GAG ACC GCC AGC TGG ATG TTC

 G   V   P   R   E   A   V   D   P   L   M   R   R   A   A   K   T   I
GGC GTC CCC CGG GAG GCC GTG GAC CCC CTG ATG CGC CGG GCG GCC AAG ACC ATC

 N   F   G   V   L   Y   G   M   S   A   H   R   L   S   Q   E   L   A
AAC TTC GGG GTC CTC TAC GGC ATG TCG GCC CAC CGC CTC TCC CAG GAG CTA GCC

 I   P   Y   E   E   A   Q   A   F   I   E   R   Y   F   Q   S   F   P
ATC CCT TAC GAG GAG GCC CAG GCC TTC ATT GAG CGC TAC TTT CAG AGC TTC CCC

 K   V   R   A   W   I   E   K   T   L   E   E   G   R   R   R   G   Y
AAG GTG CGG GCC TGG ATT GAG AAG ACC CTG GAG GAG GGC AGG AGG CGG GGG TAC

 V   E   T   L   F   G   R   R   R   Y   V   P   D   L   E   A   R   V
GTG GAG ACC CTC TTC GGC CGC CGC CGC TAC GTG CCA GAC CTA GAG GCC CGG GTG
```

FIG. 8NN-6

```
 K   S   V   R   E   A   A   E   R   M   A   F   N   M   P   V   Q   G
AAG AGC GTG CGG GAG GCG GCC GAG CGC ATG GCC TTC AAC ATG CCC GTC CAG GGC

 T   A   A   D   L   M   K   L   A   M   V   K   L   F   P   R   L   E
ACC GCC GCC GAC CTC ATG AAG CTG GCT ATG GTG AAG CTC TTC CCC AGG CTG GAG

 E   M   G   A   R   M   L   L   Q   V   H   D   E   L   V   L   E   A
GAA ATG GGG GCC AGG ATG CTC CTT CAG GTC CAC GAC GAG CTG GTC CTC GAG GCC

 P   K   E   R   A   E   A   V   A   R   L   A   K   E   V   M   E   G
CCA AAA GAG AGG GCG GAG GCC GTG GCC CGG CTG GCC AAG GAG GTC ATG GAG GGG

 V   Y   P   L   A   V   P   L   E   V   E   V   G   I   G   E   D   W
GTG TAT CCC CTG GCC GTG CCC CTG GAG GTG GAG GTG GGG ATA GGG GAG GAC TGG

 L   S   A   K   E   G   I   D   G   R   G   G   G   G   H   H   H   H
CTC TCC GCC AAG GAG GGC ATT GAT GGC CGC GGC GGA GGC GGG CAT CAT CAT CAT

 H   H   *
CAT CAT TAA
```

FIG. 8NN-7

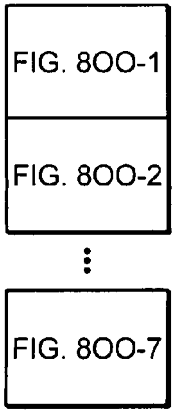

FIG. 8OO

Taq DNA polymerase- Sac7d fusion protein

Nucleotide sequence (SEQ ID NO: 65) //Nucleotide sequence (SEQ ID NO: 69)
Amino acid sequence (SEQ ID NO: 66) /Amino acid sequence (SEQ ID NO: 70)

```
    G   G   G
// GGC GGC GGT

 V   T   S   G   M   L   P   L   F   E   P   K   G   R   V   L   L   V
GTC ACT AGT GGG ATG CTG CCC CTC TTT GAG CCC AAG GGC CGG GTC CTC CTG GTG

 D   G   H   H   L   A   Y   R   T   F   H   A   L   K   G   L   T   T
GAC GGC CAC CAC CTG GCC TAC CGC ACC TTC CAC GCC CTG AAG GGC CTC ACC ACC

 S   R   G   E   P   V   Q   A   V   Y   G   F   A   K   S   L   L   K
AGC CGG GGG GAG CCG GTG CAG GCG GTC TAC GGC TTC GCC AAG AGC CTC CTC AAG

 A   L   K   E   D   G   D   A   V   I   V   V   F   D   A   K   A   P
GCC CTC AAG GAG GAC GGG GAC GCG GTG ATC GTG GTC TTT GAC GCC AAG GCC CCC
```

FIG. 8OO-1

```
 S   F   R   H   E   A   Y   G   G   Y   K   A   G   R   A   P   T   P
TCC TTC CGC CAC GAG GCC TAC GGG GGG TAC AAG GCG GGC CGG GCC CCC ACG CCA

 E   D   F   P   R   Q   L   A   L   I   K   E   L   V   D   L   L   G
GAG GAC TTT CCC CGG CAA CTC GCC CTC ATC AAG GAG CTG GTG GAC CTC CTG GGG

 L   A   R   L   E   V   P   G   Y   E   A   D   D   V   L   A   S   L
CTG GCG CGC CTC GAG GTC CCG GGC TAC GAG GCG GAC GAC GTC CTG GCC AGC CTG

 A   K   K   A   E   K   E   G   Y   E   V   R   I   L   T   A   D   K
GCC AAG AAG GCG GAA AAG GAG GGC TAC GAG GTC CGC ATC CTC ACC GCC GAC AAA

 D   L   Y   Q   L   L   S   D   R   I   H   V   L   H   P   E   G   Y
GAC CTT TAC CAG CTC CTT TCC GAC CGC ATC CAC GTC CTC CAC CCC GAG GGG TAC

 L   I   T   P   A   W   L   W   E   K   Y   G   L   R   P   D   Q   W
CTC ATC ACC CCG GCC TGG CTT TGG GAA AAG TAC GGC CTG AGG CCC GAC CAG TGG

 A   D   Y   R   A   L   T   G   D   E   S   D   N   L   P   G   V   K
GCC GAC TAC CGG GCC CTG ACC GGG GAC GAG TCC GAC AAC CTT CCC GGG GTC AAG

 G   I   G   E   K   T   A   R   K   L   L   E   E   W   G   S   L   E
GGC ATC GGG GAG AAG ACG GCG AGG AAG CTT CTG GAG GAG TGG GGG AGC CTG GAA
```

FIG. 8OO-2

```
 A   L   L   K   N   L   D   R   L   K   P   A   I   R   E   K   I   L
GCC CTC CTC AAG AAC CTG GAC CGG CTG AAG CCC GCC ATC CGG GAG AAG ATC CTG

 A   H   M   D   D   L   K   L   S   W   D   L   A   K   V   R   T   D
GCC CAC ATG GAC GAT CTG AAG CTC TCC TGG GAC CTG GCC AAG GTG CGC ACC GAC

 L   P   L   E   V   D   F   A   K   R   R   E   P   D   R   E   R   L
CTG CCC CTG GAG GTG GAC TTC GCC AAA AGG CGG GAG CCC GAC CGG GAG AGG CTT

 R   A   F   L   E   R   L   E   F   G   S   L   L   H   E   F   G   L
AGG GCC TTT CTG GAG AGG CTT GAG TTT GGC AGC CTC CTC CAC GAG TTC GGC CTT

 L   E   S   P   K   A   L   E   E   A   P   W   P   P   P   E   G   A
CTG GAA AGC CCC AAG GCC CTG GAG GAG GCC CCC TGG CCC CCG CCG GAA GGG GCC

 F   V   G   F   V   L   S   R   K   E   P   M   W   A   D   L   L   A
TTC GTG GGC TTT GTG CTT TCC CGC AAG GAG CCC ATG TGG GCC GAT CTT CTG GCC

 L   A   A   A   R   G   G   R   V   H   R   A   P   E   P   Y   K   A
CTG GCC GCC GCC AGG GGG GGC CGG GTC CAC CGG GCC CCC GAG CCT TAT AAA GCC

 L   R   D   L   K   E   A   R   G   L   L   A   K   D   L   S   V   L
CTC AGG GAC CTG AAG GAG GCG CGG GGG CTT CTC GCC AAA GAC CTG AGC GTT CTG
```

FIG. 8OO-3

```
 A   L   R   E   G   L   G   L   P   P   G   D   D   P   M   L   L   A
GCC CTG AGG GAA GGC CTT GGC CTC CCG CCC GGC GAC GAC CCC ATG CTC CTC GCC

 Y   L   L   D   P   S   N   T   T   P   E   G   V   A   R   R   Y   G
TAC CTC CTG GAC CCT TCC AAC ACC ACC CCC GAG GGG GTG GCC CGG CGC TAC GGC

 G   E   W   T   E   E   A   G   E   R   A   A   L   S   E   R   L   F
GGG GAG TGG ACG GAG GAG GCG GGG GAG CGG GCC GCC CTT TCC GAG AGG CTC TTC

 A   N   L   W   G   R   L   E   G   E   E   R   L   L   W   L   Y   R
GCC AAC CTG TGG GGG AGG CTT GAG GGG GAG GAG AGG CTC CTT TGG CTT TAC CGG

 E   V   E   R   P   L   S   A   V   L   A   H   M   E   A   T   G   V
GAG GTG GAG AGG CCC CTT TCC GCT GTC CTG GCC CAC ATG GAG GCC ACG GGG GTG

 R   L   D   V   A   Y   L   R   A   L   S   L   E   V   A   E   E   I
CGC CTG GAC GTG GCC TAT CTC AGG GCC TTG TCC CTG GAG GTG GCC GAG GAG ATC

 A   R   L   E   A   E   V   F   R   L   A   G   H   P   F   N   L   N
GCC CGC CTC GAG GCC GAG GTC TTC CGC CTG GCC GGC CAC CCC TTC AAC CTC AAC

 S   R   D   Q   L   E   R   V   L   F   D   E   L   G   L   P   A   I
TCC CGG GAC CAG CTG GAA AGG GTC CTC TTT GAC GAG CTA GGG CTT CCC GCC ATC
```

FIG. 8OO-4

```
 G   K   T   E   K   T   G   K   R   S   T   S   A   A   V   L   E   A
GGC AAG ACG GAG AAG ACC GGC AAG CGC TCC ACC AGC GCC GCC GTC CTG GAG GCC

 L   R   E   A   H   P   I   V   E   K   I   L   Q   Y   R   E   L   T
CTC CGC GAG GCC CAC CCC ATC GTG GAG AAG ATC CTG CAG TAC CGG GAG CTC ACC

 K   L   K   S   T   Y   I   D   P   L   P   D   L   I   H   P   R   T
AAG CTG AAG AGC ACC TAC ATT GAC CCC TTG CCG GAC CTC ATC CAC CCC AGG ACG

 G   R   L   H   T   R   F   N   Q   T   A   T   A   T   G   R   L   S
GGC CGC CTC CAC ACC CGC TTC AAC CAG ACG GCC ACG GCC ACG GGC AGG CTA AGT

 S   S   D   P   N   L   Q   N   I   P   V   R   T   P   L   G   Q   R
AGC TCC GAT CCC AAC CTC CAG AAC ATC CCC GTC CGC ACC CCG CTT GGG CAG AGG

 I   R   R   A   F   I   A   E   E   G   W   L   L   V   A   L   D   Y
ATC CGC CGG GCC TTC ATC GCC GAG GAG GGG TGG CTA TTG GTG GCC CTG GAC TAT

 S   Q   I   E   L   R   V   L   A   H   L   S   G   D   E   N   L   I
AGC CAG ATA GAG CTC AGG GTG CTG GCC CAC CTC TCC GGC GAC GAG AAC CTG ATC

 R   V   F   Q   E   G   R   D   I   H   T   E   T   A   S   W   M   F
CGG GTC TTC CAG GAG GGG CGG GAC ATC CAC ACG GAG ACC GCC AGC TGG ATG TTC
```

FIG. 8OO-5

```
 G   V   P   R   E   A   V   D   P   L   M   R   R   A   A   K   T   I
GGC GTC CCC CGG GAG GCC GTG GAC CCC CTG ATG CGC CGG GCG GCC AAG ACC ATC

 N   F   G   V   L   Y   G   M   S   A   H   R   L   S   Q   E   L   A
AAC TTC GGG GTC CTC TAC GGC ATG TCG GCC CAC CGC CTC TCC CAG GAG CTA GCC

 I   P   Y   E   E   A   Q   A   F   I   E   R   Y   F   Q   S   F   P
ATC CCT TAC GAG GAG GCC CAG GCC TTC ATT GAG CGC TAC TTT CAG AGC TTC CCC

 K   V   R   A   W   I   E   K   T   L   E   E   G   R   R   R   G   Y
AAG GTG CGG GCC TGG ATT GAG AAG ACC CTG GAG GAG GGC AGG AGG CGG GGG TAC

 V   E   T   L   F   G   R   R   R   Y   V   P   D   L   E   A   R   V
GTG GAG ACC CTC TTC GGC CGC CGC CGC TAC GTG CCA GAC CTA GAG GCC CGG GTG

 K   S   V   R   E   A   A   E   R   M   A   F   N   M   P   V   Q   G
AAG AGC GTG CGG GAG GCG GCC GAG CGC ATG GCC TTC AAC ATG CCC GTC CAG GGC

 T   A   A   D   L   M   K   L   A   M   V   K   L   F   P   R   L   E
ACC GCC GCC GAC CTC ATG AAG CTG GCT ATG GTG AAG CTC TTC CCC AGG CTG GAG

 E   M   G   A   R   M   L   L   Q   V   H   D   E   L   V   L   E   A
GAA ATG GGG GCC AGG ATG CTC CTT CAG GTC CAC GAC GAG CTG GTC CTC GAG GCC
```

FIG. 8OO-6

```
 P   K   E   R   A   E   A   V   A   R   L   A   K   E   V   M   E   G
CCA AAA GAG AGG GCG GAG GCC GTG GCC CGG CTG GCC AAG GAG GTC ATG GAG GGG

 V   Y   P   L   A   V   P   L   E   V   E   V   G   I   G   E   D   W
GTG TAT CCC CTG GCC GTG CCC CTG GAG GTG GAG GTG GGG ATA GGG GAG GAC TGG

 L   S   A   K   E   G   I   D   G   R   G   G   G   G   H   H   H   H
CTC TCC GCC AAG GAG GGC ATT GAT GGC CGC GGC GGA GGC GGG CAT CAT CAT CAT

 H   H  //
CAT CAT //

 M   V   K   V   K   F   K   Y   K   G   E   E   K   E   V   D   T   S
ATG GTG AAG GTA AAG TTC AAG TAT AAG GGT GAA GAG AAA GAA GTA GAC ACT TCA

 K   I   K   K   V   W   R   V   G   K   M   V   S   F   T   Y   D   D
AAG ATA AAG AAG GTT TGG AGA GTA GGC AAA ATG GTG TCC TTT ACC TAT GAC GAC

 N   G   K   T   G   R   G   A   V   S   E   K   D   A   P   K   E   L
AAT GGT AAG ACA GGT AGA GGA GCT GTA AGC GAG AAA GAT GCT CCA AAA GAA TTA

 L   D   M   L   A   R   A   E   R   E   K   K  //   *
TTA GAC ATG TTA GCA AGA GCA GAA AGA GAG AAG AAA //  TAG
```

FIG. 8OO-7

Pfu DNA Polymerase (WT) -Sac7d fusion protein

Nucleotide sequence (SEQ ID NO: 61) // Nucleotide sequence (SEQ ID NO: 69)

//
```
ccctggtcct gggtccacat atatgttctt actcgccttt atgaagaatc ccccagtcgc
tctaacctgg gttatagtga caaatcttcc tccaccaccg cccaagaagg ttatttctat
caactctaca cctcccctat tttctctctt atgagatttt taagtatagt tatagagaag
gttttatact ccaaactgag ttagtagata tgtggggagc ataatgattt tagatgtgga
ttacataact gaagaaggaa aacctgttat taggctattc aaaaaagaga acggaaaatt
taagatagag catgatagaa cttttagacc atacatttac gctcttctca gggatgattc
aaagattgaa gaagttaaga aaataacggg ggaaaggcat ggaaagattg tgagaattgt
tgatgtagag aaggttgaga aaaagtttct cggcaagcct attaccgtgt ggaaacttta
tttggaacat ccccaagatg ttcccactat tagagaaaaa gttagagaac atccagcagt
```

FIG. 8PP-1 tgtggacatc ttcgaatacg atattccatt tgcaaagaga tacctcatcg acaaaggcct
aataccaatg gagggggaag aagagctaaa gattcttgcc ttcgatatag aaaccctcta
tcacgaagga gaagagtttg gaaaaggccc aattataatg attagttatg cagatgaaaa
tgaagcaaag gtgattactt ggaaaaacat agatcttcca tacgttgagg ttgtatcaag
cgagagagag atgataaaga gatttctcag gattatcagg gagaaggatc ctgacattat
agttacttat aatggagact cattcgactt cccatattta gcgaaaaggg cagaaaaact
tgggattaaa ttaaccattg gaagagatgg aagcgagccc aagatgcaga gaataggcga
tatgacggct gtagaagtca agggaagaat acatttcgac ttgtatcatg taataacaag
gacaataaat ctcccaacat acacactaga ggctgtatat gaagcaattt ttggaaagcc
aaaggagaag gtatacgccg acgagatagc aaaagcctgg gaaagtggag agaaccttga
gagagttgcc aaatactcga tggaagatgc aaaggcaact tatgaactcg ggaaagaatt
ccttccaatg gaaattcagc tttcaagatt agttggacaa cctttatggg atgtttcaag
gtcaagcaca gggaaccttg tagagtggtt cttacttagg aaagcctacg aaagaaacga
agtagctcca aacaagccaa gtgaagagga gtatcaaaga aggctcaggg agagctacac

FIG. 8PP-2 aggtggattc gttaaagagc cagaaaaggg gttgtgggaa aacatagtat acctagattt tagagcccta tatccctcga ttataattac ccacaatgtt tctcccgata ctctaaatct tgagggatgc aagaactatg atatcgctcc tcaagtaggc cacaagttct gcaaggacat ccctggtttt ataccaagtc tcttgggaca tttgttagag gaaagacaaa agattaagac aaaaatgaag gaaactcaag atcctataga aaaaatactc cttgactata gacaaaaagc gataaaactc ttagcaaatt ctttctacgg atattatggc tatgcaaaag caagatggta ctgtaaggag tgtgctgaga gcgttactgc ctggggaaga aagtacatcg agttagtatg gaaggagctc gaagaaaagt ttggatttaa agtcctctac attgacactg atggtctcta tgcaactatc ccaggaggag aaagtgagga aataaagaaa aaggctctag aatttgtaaa atacataaat tcaaagctcc ctggactgct agagcttgaa tatgaagggt tttataagag gggattcttc gttacgaaga agaggtatgc agtaatagat gaagaaggaa aagtcattac tcgtggttta gagatagtta ggagagattg gagtgaaatt gcaaaagaaa ctcaagctag agttttggag acaatactaa aacacggaga tgttgaagaa gctgtgagaa tagtaaaaga

FIG. 8PP-3 agtaatacaa aagcttgcca attatgaaat tccaccagag aagctcgcaa tatatgagca gataacaaga ccattacatg agtataaggc gataggtcct cacgtagctg ttgcaaagaa actagctgct aaaggagtta aaataaagcc aggaatggta attggataca tagtacttag aggcgatggt ccaattagca atagggcaat tctagctgag gaatacgatc ccaaaaagca caagtatgac gcagaatatt acattgagaa ccaggttctt ccagcggtac ttaggatatt ggagggattt ggatacagaa aggaagacct cagataccaa aagacaagac aagtcggcct aacttcctgg cttaacatta aaaaatccta gaaaagcgat agatatcaac ttttattctt tctaaccttt ttctatgaaa gaagaactga gcaggaatta ccagttcttc cgttatttta tgggtaatta aaaacccatg ctcttgggag aatcttcgaa taaaatccct aacttcaggc tttgctaagt gaatagaata aacaacatca ctcacttcaa acgccttcgt tagaaatggt ctatctgcat gcttctctgg ctcggaanng gaggattcat aacaacagta tcaacattct cagagaattg agaaacatca gaaactttga cttctacaac atttctaact ttgcaactct tcaagatttt ctaaaagaat tttaacggcc tcctcgtcaa tttcgacgac gtagatcttt

FIG. 8PP-4 tttgctccaa gcagagccgc tccaatggat aacacccctg ttcccgcacc caagtccgct acaatttttt ccttgtatct cctaatgtat aagcaagcca aaggagagta gatgctacct ttccgggagt tttgtattgc tctagccaag gtttgggatt tttgaatcct ttaactctgg aaagtataat ttcaagctcc ttcttcttca tgacagatga aaaattgttt tgtctctttt taacttttac agaaataact gtctcaaatt atgacaactc ttgacatttt tacttcatta ccagggtaat gtttttaagt atgaaatttt tctttcatag aggaggnnnn nngtcctctc ctcgatttcc ttggttgtgc tccatatgat aagcttccaa agtgggtgtt cagactttta gacactcaaa taccagacga caatggtgtg ctcactcaag ccccatatgg gttgagaaaa gtagaagcgg cactactcag atgcttcccc aggaatgagg ttgttgtagc tcntcccnga aagattgaga tgttcttgg //

// ATG GTG AAG GTA AAG TTC AAG TAT AAG GGT GAA GAG AAA GAA GTA GAC ACT TCA
AAG ATA AAG AAG GTT TGG AGA GTA GGC AAA ATG GTG TCC TTT ACC TAT GAC GAC
AAT GGT AAG ACA GGT AGA GGA GCT GTA AGC GAG AAA GAT GCT CCA AAA GAA TTA
TTA GAC ATG TTA GCA AGA GCA GAA AGA GAG AAG AAA //TGA

| FIG. 8QQ-1 |
| --- |
| FIG. 8QQ-2 |
| ⋮ |
| FIG. 8QQ-6 |

Sac7d - Pfu DNA Polymerase (WT) fusion protein

Nucleotide sequence (SEQ ID NO: 69) // Nucleotide sequence (SEQ ID NO: 61)

```
// ATG GTG AAG GTA AAG TTC AAG TAT AAG GGT GAA GAG AAA GAA GTA GAC ACT TCA
   AAG ATA AAG AAG GTT TGG AGA GTA GGC AAA ATG GTG TCC TTT ACC TAT GAC GAC
   AAT GGT AAG ACA GGT AGA GGA GCT GTA AGC GAG AAA GAT GCT CCA AAA GAA TTA
   TTA GAC ATG TTA GCA AGA GCA GAA AGA GAG AAG AAA //
//
ccctggtcct gggtccacat atatgttctt actcgccttt atgaagaatc ccccagtcgc

tctaacctgg gttatagtga caaatcttcc tccaccaccg cccaagaagg ttatttctat

caactctaca cctcccctat tttctctctt atgagatttt taagtatagt tatagagaag
```

FIG. 8QQ-1 gttttatact ccaaactgag ttagtagata tgtggggagc ataatgattt tagatgtgga ttacataact gaagaaggaa aacctgttat taggctattc aaaaaagaga acggaaaatt taagatagag catgatagaa cttttagacc atacatttac gctcttctca gggatgattc aaagattgaa gaagttaaga aaataacggg ggaaaggcat ggaaagattg tgagaattgt tgatgtagag aaggttgaga aaaagtttct cggcaagcct attaccgtgt ggaaacttta tttggaacat ccccaagatg ttcccactat tagagaaaaa gttagagaac atccagcagt tgtggacatc ttcgaatacg atattccatt tgcaaagaga tacctcatcg acaaaggcct aataccaatg gagggggaag aagagctaaa gattcttgcc ttcgatatag aaaccctcta tcacgaagga gaagagtttg gaaaaggccc aattataatg attagttatg cagatgaaaa tgaagcaaag gtgattactt ggaaaaacat agatcttcca tacgttgagg ttgtatcaag

FIG. 8QQ-2 cgagagagag atgataaaga gatttctcag gattatcagg gagaaggatc ctgacattat agttacttat aatggagact cattcgactt cccatattta gcgaaaaggg cagaaaaact tgggattaaa ttaaccattg gaagagatgg aagcgagccc aagatgcaga gaataggcga tatgacggct gtagaagtca agggaagaat acatttcgac ttgtatcatg taataacaag gacaataaat ctcccaacat acacactaga ggctgtatat gaagcaattt ttggaaagcc aaaggagaag gtatacgccg acgagatagc aaaagcctgg gaaagtggag agaaccttga gagagttgcc aaatactcga tggaagatgc aaaggcaact tatgaactcg ggaaagaatt ccttccaatg gaaattcagc tttcaagatt agttggacaa cctttatggg atgtttcaag gtcaagcaca gggaaccttg tagagtggtt cttacttagg aaagcctacg aaagaaacga agtagctcca aacaagccaa gtgaagagga gtatcaaaga aggctcaggg agagctacac aggtggattc gttaaagagc cagaaaaggg gttgtgggaa aacatagtat acctagattt tagagcccta tatccctcga ttataattac ccacaatgtt tctcccgata ctctaaatct

FIG. 8QQ-3 tgagggatgc aagaactatg atatcgctcc tcaagtaggc cacaagttct gcaaggacat ccctggtttt ataccaagtc tcttgggaca tttgttagag gaaagacaaa agattaagac aaaaatgaag gaaactcaag atcctataga aaaaatactc cttgactata gacaaaaagc gataaaactc ttagcaaatt ctttctacgg atattatggc tatgcaaaag caagatggta ctgtaaggag tgtgctgaga gcgttactgc ctggggaaga aagtacatcg agttagtatg gaaggagctc gaagaaaagt ttggatttaa agtcctctac attgacactg atggtctcta tgcaactatc ccaggaggag aaagtgagga aataaagaaa aaggctctag aatttgtaaa atacataaat tcaaagctcc ctggactgct agagcttgaa tatgaagggt tttataagag gggattcttc gttacgaaga agaggtatgc agtaatagat gaagaaggaa aagtcattac tcgtggttta gagatagtta ggagagattg gagtgaaatt gcaaaagaaa ctcaagctag agttttggag acaatactaa aacacggaga tgttgaagaa gctgtgagaa tagtaaaaga agtaatacaa aagcttgcca attatgaaat tccaccagag aagctcgcaa tatatgagca

FIG. 8QQ-4 gataacaaga ccattacatg agtataaggc gataggtcct cacgtagctg ttgcaaagaa actagctgct aaaggagtta aaataaagcc aggaatggta attggataca tagtacttag aggcgatggt ccaattagca atagggcaat tctagctgag gaatacgatc ccaaaaagca caagtatgac gcagaatatt acattgagaa ccaggttctt ccagcggtac ttaggatatt ggagggattt ggatacagaa aggaagacct cagataccaa aagacaagac aagtcggcct aacttcctgg cttaacatta aaaaatccta gaaaagcgat agatatcaac ttttattctt tctaaccttt ttctatgaaa gaagaactga gcaggaatta ccagttcttc cgttatttta tgggtaatta aaaacccatg ctcttgggag aatcttcgaa taaaatccct aacttcaggc tttgctaagt gaatagaata aacaacatca ctcacttcaa acgccttcgt tagaaatggt ctatctgcat gcttctctgg ctcggaanng gaggattcat aacaacagta tcaacattct cagagaattg agaaacatca gaaactttga cttctacaac atttctaact ttgcaactct tcaagatttt ctaaaagaat tttaacggcc tcctcgtcaa tttcgacgac gtagatcttt

FIG. 8QQ-5 tttgctccaa gcagagccgc tccaatggat aacacccctg ttcccgcacc caagtccgct acaatttttt ccttgtatct cctaatgtat aagcaagcca aaggagagta gatgctacct ttccgggagt tttgtattgc tctagccaag gtttgggatt tttgaatcct ttaactctgg aaagtataat ttcaagctcc ttcttcttca tgacagatga aaaattgttt tgtctctttt taacttttac agaaataact gtctcaaatt atgacaactc ttgacatttt tacttcatta ccagggtaat gtttttaagt atgaaatttt tctttcatag aggaggnnnn nngtcctctc ctcgatttcc ttggttgtgc tccatatgat aagcttccaa agtgggtgtt cagactttta gacactcaaa taccagacga caatggtgtg ctcactcaag ccccatatgg gttgagaaaa gtagaagcgg cactactcag atgcttcccc aggaatgagg ttgttgtagc tcntcccnga aagattgaga tgttcttgg // TGA

| FIG. 8RR-1 |
| --- |
| FIG. 8RR-2 |

Sac7d - PFU DNA POLYMERASE (V93 R OR E) fusion protein

Nucleotide sequence (SEQ ID NO: 69) // Nucleotide sequence (SEQ ID NO: 27)
Nucleotide sequence (SEQ ID NO: 69) //Nucleotide sequence (SEQ ID NO: 28)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

ATG GTG AAG GTA AAG TTC AAG TAT AAG GGT GAA GAG AAA GAA GTA GAC ACT TCA
AAG ATA AAG AAG GTT TGG AGA GTA GGC AAA ATG GTG TCC TTT ACC TAT GAC GAC
AAT GGT AAG ACA GGT AGA GGA GCT GTA AGC GAG AAA GAT GCT CCA AAA GAA TTA
TTA GAC ATG TTA GCA AGA GCA GAA AGA GAG AAG AAA //

//ATGATTTTAG ATGTGGATTA CATAACTGAA GAAGGAAAAC CTGTTATTAG GCTATTCAAA 60
AAAGAGAACG GAAAATTTAA GATAGAGCAT
GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC
CAAGAT<u>XXX</u>C CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GATATAGAAA CCCTCTATCA CGAAGGAGAA

FIG. 8RR-1

GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT
GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC
CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA
ATTCAGCTTT CAAGATTAGT TGGACAACCT 1020
TTATGGGATG TTTCAAGGTC AAGCACAGGG AACCTTGTAG AGTGGTTCTT ACTTAGGAAA
1080 GCCTACGAAA GAAACGAAGT AGCTCCAAAC AAGCCAAGTG AAGAGGAGTA TCAAAGAAGG 1140 CTCAGGGAGA GCTACACAGG
TGGATTCGTT AAAGAGCCAG AAAAGGGGTT GTGGGAAAAC 1200
ATAGTATACC TAGATTTTAG AGCCCTATAT CCCTCGATTA TAATTACCCA
CAATGTTTCT 1260 CCCGATACTC TAAATCTTGA GGGATGCAAG AACTATGATA TCGCTCCTCA AGTAGGCCAC 1320 AAGTTCTGCA
AGGACATCCC TGGTTTTATA CCAAGTCTCT TGGGACATTT GTTAGAGGAA 1380
AGACAAAAGA TTAAGACAAA AATGAAGGAA ACTCAAGATC
CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA
GAAAAGTTTG GATTTAAAGT CCTCTACATT 1620
GACACTGATG GTCTCTATGC AACTATCCCA GGAGGAGAAA GTGAGGAAAT AAAGAAAAAG
1680 GCTCTAGAAT TTGTAAAATA CATAAATTCA AAGCTCCCTG GACTGCTAGA GCTTGAATAT 1740 GAAGGGTTTT ATAAGAGGGG
ATTCTTCGTT ACGAAGAAGA GGTATGCAGT AATAGATGAA 1800
GAAGGAAAAG TCATTACTCG TGGTTTAGAG ATAGTTAGGA GAGATTGGAG
TGAAATTGCA 1860 AAAGAAACTC AAGCTAGAGT TTTGGAGACA ATACTAAAAC ACGGAGATGT TGAAGAAGCT 1920 GTGAGAATAG
TAAAAGAAGT AATACAAAAG CTTGCCAATT ATGAAATTCC ACCAGAGAAG 1980
CTCGCAATAT ATGAGCAGAT AACAAGACCA TTACATGAGT
ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA
GAATATTACA TGGAGAACCA GGTTCTTCCA 2220
GCGGTACTTA GGATATTGGA GGGATTTGGA TACAGAAAGG AAGACCTCAG ATACCAAAAG
2280 ACAAGACAAG TCGGCCTAAC TTCCTGGCTT AACATTAAAA AATCC // 2328
// TGA

| FIG. 8SS-1 |
| --- |
| FIG. 8SS-2 |

PFU DNA POLYMERASE (V93 R OR E) -Sac7d fusion protein

Nucleotide sequence (SEQ ID NO: 27) // Nucleotide sequence (SEQ ID NO: 69)
Nucleotide sequence (SEQ ID NO: 28) // Nucleotide sequence (SEQ ID NO: 69)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATTTTAG ATGTGGATTA CATAACTGAA GAAGGAAAAC CTGTTATTAG GCTATTCAAA 60
AAAGAGAACG GAAAATTTAA GATAGAGCAT
GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC
CAAGATXXXC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GATATAGAAA CCCTCTATCA CGAAGGAGAA
GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT
GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC
```

FIG. 8SS-1

```
CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA
ATTCAGCTTT CAAGATTAGT TGGACAACCT 1020
TTATGGGATG TTTCAAGGTC AAGCACAGGG AACCTTGTAG AGTGGTTCTT ACTTAGGAAA
1080 GCCTACGAAA GAAACGAAGT AGCTCCAAAC AAGCCAAGTG AAGAGGAGTA TCAAAGAAGG 1140 CTCAGGGAGA GCTACACAGG
TGGATTCGTT AAAGAGCCAG AAAAGGGGTT GTGGGAAAAC 1200
ATAGTATACC TAGATTTTAG AGCCCTATAT CCCTCGATTA TAATTACCCA
CAATGTTTCT 1260 CCCGATACTC TAAATCTTGA GGGATGCAAG AACTATGATA TCGCTCCTCA AGTAGGCCAC 1320 AAGTTCTGCA
AGGACATCCC TGGTTTTATA CCAAGTCTCT TGGGACATTT GTTAGAGGAA 1380
AGACAAAAGA TTAAGACAAA AATGAAGGAA ACTCAAGATC
CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA
GAAAAGTTTG GATTTAAAGT CCTCTACATT 1620
GACACTGATG GTCTCTATGC AACTATCCCA GGAGGAGAAA GTGAGGAAAT AAAGAAAAAG
1680 GCTCTAGAAT TTGTAAAATA CATAAATTCA AAGCTCCCTG GACTGCTAGA GCTTGAATAT 1740 GAAGGGTTTT ATAAGAGGGG
ATTCTTCGTT ACGAAGAAGA GGTATGCAGT AATAGATGAA 1800
GAAGGAAAAG TCATTACTCG TGGTTTAGAG ATAGTTAGGA GAGATTGGAG
TGAAATTGCA 1860 AAAGAAACTC AAGCTAGAGT TTTGGAGACA ATACTAAAAC ACGGAGATGT TGAAGAAGCT 1920 GTGAGAATAG
TAAAAGAAGT AATACAAAAG CTTGCCAATT ATGAAATTCC ACCAGAGAAG 1980
CTCGCAATAT ATGAGCAGAT AACAAGACCA TTACATGAGT
ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA
GAATATTACA TGGAGAACCA GGTTCTTCCA 2220
GCGGTACTTA GGATATTGGA GGGATTTGGA TACAGAAAGG AAGACCTCAG ATACCAAAAG
2280 ACAAGACAAG TCGGCCTAAC TTCCTGGCTT AACATTAAAA AATCC //          2328
// ATG GTG AAG GTA AAG TTC AAG TAT AAG GGT GAA GAG AAA GAA GTA GAC ACT TCA
   AAG ATA AAG AAG GTT TGG AGA GTA GGC AAA ATG GTG TCC TTT ACC TAT GAC GAC
   AAT GGT AAG ACA GGT AGA GGA GCT GTA AGC GAG AAA GAT GCT CCA AAA GAA TTA
   TTA GAC ATG TTA GCA AGA GCA GAA AGA GAG AAG AAA //  TGA
```

| FIG. 8TT-1 |
|---|
| FIG. 8TT-2 |

PFU DNA POLYMERASE (G387P/V93R OR E) -Sac7d fusion protein

Nucleotide sequence (SEQ ID NO: 29) // Nucleotide sequence (SEQ ID NO: 69)
Nucleotide sequence (SEQ ID NO: 30) // Nucleotide sequence (SEQ ID NO: 69)

G387P Mutant (CCN is the codon for Proline where N = C, G, A, or T)
V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATTTTAG ATGTGGATTA CATAACTGAA GAAGGAAAAC CTGTTATTAG GCTATTCAAA 60
AAAGAGAACG GAAAATTTAA GATAGAGCAT
GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC
CAAGATXXXC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GATATAGAAA CCCTCTATCA CGAAGGAGAA
GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT
GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC
CCAACATACA CACTAGAGGC TGTATATGAA 840
GCAATTTTTG GAAAGCCAAA GGAGAAGGTA TACGCCGACG AGATAGCAAA AGCCTGGGAA 900
```

FIG. 8TT-1

AGTGGAGAGA ACCTTGAGAG AGTTGCCAAA TACTCGATGG AAGATGCAAA GGCAACTTAT 960
GAACTCGGGA AAGAATTCCT TCCAATGGAA
ATTCAGCTTT CAAGATTAGT TGGACAACCT 1020
TTATGGGATG TTTCAAGGTC AAGCACAGGG AACCTTGTAG AGTGGTTCTT ACTTAGGAAA
1080 GCCTACGAAA GAAACGAAGT AGCTCCAAAC AAGCCAAGTG AAGAGGAGTA TCAAAGAAGG 1140 CTCAGGGAGA GCTACACACC
NGGATTCGTT AAAGAGCCAG AAAAGGGGTT GTGGGAAAAC 1200
ATAGTATACC TAGATTTTAG AGCCCTATAT CCCTCGATTA TAATTACCCA
CAATGTTTCT 1260 CCCGATACTC TAAATCTTGA GGGATGCAAG AACTATGATA TCGCTCCTCA AGTAGGCCAC 1320 AAGTTCTGCA
AGGACATCCC TGGTTTTATA CCAAGTCTCT TGGGACATTT GTTAGAGGAA 1380
AGACAAAAGA TTAAGACAAA AATGAAGGAA ACTCAAGATC
CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA
GAAAAGTTTG GATTTAAAGT CCTCTACATT 1620
GACACTGATG GTCTCTATGC AACTATCCCA GGAGGAGAAA GTGAGGAAAT AAAGAAAAAG
1680 GCTCTAGAAT TTGTAAAATA CATAAATTCA AAGCTCCCTG GACTGCTAGA GCTTGAATAT 1740 GAAGGGTTTT ATAAGAGGGG
ATTCTTCGTT ACGAAGAAGA GGTATGCAGT AATAGATGAA 1800
GAAGGAAAAG TCATTACTCG TGGTTTAGAG ATAGTTAGGA GAGATTGGAG
TGAAATTGCA 1860 AAAGAAACTC AAGCTAGAGT TTTGGAGACA ATACTAAAAC ACGGAGATGT TGAAGAAGCT 1920 GTGAGAATAG
TAAAAGAAGT AATACAAAAG CTTGCCAATT ATGAAATTCC ACCAGAGAAG 1980
CTCGCAATAT ATGAGCAGAT AACAAGACCA TTACATGAGT
ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA
GAATATTACA TGGAGAACCA GGTTCTTCCA 2220
GCGGTACTTA GGATATTGGA GGGATTTGGA TACAGAAAGG AAGACCTCAG ATACCAAAAG
2280 ACAAGACAAG TCGGCCTAAC TTCCTGGCTT AACATTAAAA AATCC // 2328

// ATG GTG AAG GTA AAG TTC AAG TAT AAG GGT GAA GAG AAA GAA GTA GAC ACT TCA
AAG ATA AAG AAG GTT TGG AGA GTA GGC AAA ATG GTG TCC TTT ACC TAT GAC GAC
AAT GGT AAG ACA GGT AGA GGA GCT GTA AGC GAG AAA GAT GCT CCA AAA GAA TTA
TTA GAC ATG TTA GCA AGA GCA GAA AGA GAG AAG AAA // TGA

| |
|---|
| FIG. 8UU-1 |
| FIG. 8UU-2 |

PFU DNA POLYMERASE (G387P/V93R OR E)-Sac7d fusion protein

Nucleotide sequence (SEQ ID NO: 29) // Nucleotide sequence (SEQ ID NO: 69)
Nucleotide sequence (SEQ ID NO: 30) // Nucleotide sequence (SEQ ID NO: 69)

G387P Mutant (CCN is the codon for Proline where N = C, G, A, or T)
V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATTTTAG ATGTGGATTA CATAACTGAA GAAGGAAAAC CTGTTATTAG GCTATTCAAA 60
AAAGAGAACG GAAAATTTAA GATAGAGCAT
GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC
CAAGATXXXC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GATATAGAAA CCCTCTATCA CGAAGGAGAA
GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT
GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC
CCAACATACA CACTAGAGGC TGTATATGAA 840
GCAATTTTTG GAAAGCCAAA GGAGAAGGTA TACGCCGACG AGATAGCAAA AGCCTGGGAA 900
```

FIG. 8UU-1

AGTGGAGAGA ACCTTGAGAG AGTTGCCAAA TACTCGATGG AAGATGCAAA GGCAACTTAT 960
GAACTCGGGA AAGAATTCCT TCCAATGGAA
ATTCAGCTTT CAAGATTAGT TGGACAACCT 1020
TTATGGGATG TTTCAAGGTC AAGCACAGGG AACCTTGTAG AGTGGTTCTT ACTTAGGAAA
1080 GCCTACGAAA GAAACGAAGT AGCTCCAAAC AAGCCAAGTG AAGAGGAGTA TCAAAGAAGG 1140 CTCAGGGAGA GCTACACAGTTGGATTCGTT
AAAGAGCCAG AAAAGGGGTT GTGGGAAAAC 1200
ATAGTATACC TAGATTTTAG AGCCCTATAT CCCTCGATTA TAATTACCCA CAATGTTTCT
1260 CCCGATACTC TAAATCTTGA GGGATGCAAG AACTATGATA TCGCTCCTCA AGTAGGCCAC 1320 AAGTTCTGCA AGGACATCCC
TGGTTTTATA CCAAGTCTCT TGGGACATTT GTTAGAGGAA 1380
AGACAAAAGA TTAAGACAAA AATGAAGGAA ACTCAAGATC CTATAGAAAA
AATACTCCTT 1440 GACTATAGAC AAAAAGCGAT AAAACTCTTA GCAAATTCTT TCTACGGATA TTATGGCTAT 1500 GCAAAAGCAA
GATGGTACTG TAAGGAGTGT GCTGAGAGCG TTACTGCCTG GGGAAGAAAG 1560
TACATCGAGT TAGTATGGAA GGAGCTCGAA GAAAAGTTTG
GATTTAAAGT CCTCTACATT 1620
GACACTGATG GTCTCTATGC AACTATCCCA GGAGGAGAAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT
ACGAAGAAGA GGTATGCAGT AATAGATGAA 1800
GAAGGAAAAG TCATTACTCG TGGTTTAGAG ATAGTTAGGA GAGATTGGAG TGAAATTGCA
1860 AAAGAAACTC AAGCTAGAGT TTTGGAGACA ATACTAAAAC ACGGAGATGT TGAAGAAGCT 1920 GTGAGAATAG TAAAAGAAGT
AATACAAAAG CTTGCCAATT ATGAAATTCC ACCAGAGAAG 1980
CTCGCAATAT ATGAGCAGAT AACAAGACCA TTACATGAGT ATAAGGCGAT
AGGTCCTCAC 2040 GTAGCTGTTG CAAAGAAACT AGCTGCTAAA GGAGTTAAAA TAAAGCCAGG AATGGTAATT 2100 GGATACATAG
TACTTAGAGG CGATGGTCCA ATTAGCAATA GGGCAATTCT AGCTGAGGAA 2160
TACGATCCCA AAAAGCACAA GTATGACGCA GAATATTACA
TGGAGAACCA GGTTCTTCCA 2220
GCGGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCC // 2328

// ATG GTG AAG GTA AAG TTC AAG TAT AAG GGT GAA GAG AAA GAA GTA GAC ACT TCA
AAG ATA AAG AAG GTT TGG AGA GTA GGC AAA ATG GTG TCC TTT ACC TAT GAC GAC
AAT GGT AAG ACA GGT AGA GGA GCT GTA AGC GAG AAA GAT GCT CCA AAA GAA TTA
TTA GAC ATG TTA GCA AGA GCA GAA AGA GAG AAG AAA // TGA

| FIG. 8VV-1 |
|---|
| FIG. 8VV-2 |

SAC7D-PFU DNA POLYMERASE (D141A/E143A/V93R OR E) fusion protein

Nucleotide sequence (SEQ ID NO: 69) // Nucleotide sequence (SEQ ID NO: 31)
Nucleotide sequence (SEQ ID NO: 69) // Nucleotide sequence (SEQ ID NO: 32)

D141A/E143A Mutant (GCN is the codon for alanine where N = C, G, A, or T)
V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
// ATG GTG AAG GTA AAG TTC AAG TAT AAG GGT GAA GAG AAA GAA GTA GAC ACT TCA
   AAG ATA AAG AAG GTT TGG AGA GTA GGC AAA ATG GTG TCC TTT ACC TAT GAC GAC
   AAT GGT AAG ACA GGT AGA GGA GCT GTA AGC GAG AAA GAT GCT CCA AAA GAA TTA
   TTA GAC ATG TTA GCA AGA GCA GAA AGA GAG AAG AAA //

//ATGATTTTAG ATGTGGATTA CATAACTGAA GAAGGAAAAC CTGTTATTAG GCTATTCAAA 60
AAAGAGAACG GAAAATTTAA GATAGAGCAT
GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC
CAAGATXXXC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GCNATAGCNA CCCTCTATCA CGAAGGAGAA
GAGTTTGGAA AAGGCCCAAT TATAATGATT 480
AGTTATGCAG ATGAAAATGA AGCAAAGGTG ATTACTTGGA AAAACATAGA TCTTCCATAC 540
```

FIG. 8VV-1

GTTGAGGTTG TATCAAGCGA GAGAGAGATG ATAAAGAGAT TTCTCAGGAT TATCAGGGAG 600
AAGGATCCTG ACATTATAGT TACTTATAAT
GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC
CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA
ATTCAGCTTT CAAGATTAGT TGGACAACCT 1020
TTATGGGATG TTTCAAGGTC AAGCACAGGG AACCTTGTAG AGTGGTTCTT ACTTAGGAAA
1080 GCCTACGAAA GAAACGAAGT AGCTCCAAAC AAGCCAAGTG AAGAGGAGTA TCAAAGAAGG 1140 CTCAGGGAGA GCTACACAGTTGGATTCGTT
AAAGAGCCAG AAAAGGGGTT GTGGGAAAAC 1200
ATAGTATACC TAGATTTTAG AGCCCTATAT CCCTCGATTA TAATTACCCA CAATGTTTCT
1260 CCCGATACTC TAAATCTTGA GGGATGCAAG AACTATGATA TCGCTCCTCA AGTAGGCCAC 1320 AAGTTCTGCA AGGACATCCC
TGGTTTTATA CCAAGTCTCT TGGGACATTT GTTAGAGGAA 1380
AGACAAAAGA TTAAGACAAA AATGAAGGAA ACTCAAGATC CTATAGAAAA
AATACTCCTT 1440 GACTATAGAC AAAAAGCGAT AAAACTCTTA GCAAATTCTT TCTACGGATA TTATGGCTAT 1500 GCAAAAGCAA
GATGGTACTG TAAGGAGTGT GCTGAGAGCG TTACTGCCTG GGGAAGAAAG 1560
TACATCGAGT TAGTATGGAA GGAGCTCGAA GAAAAGTTTG
GATTTAAAGT CCTCTACATT 1620
GACACTGATG GTCTCTATGC AACTATCCCA GGAGGAGAAA GTGAGGAAAT AAAGAAAAAG 1680
GCTCTAGAAT TTGTAAAATA CATAAATTCA AAGCTCCCTG GACTGCTAGA GCTTGAATAT 1740
GAAGGGTTTT ATAAGAGGGG ATTCTTCGTT
ACGAAGAAGA GGTATGCAGT AATAGATGAA 1800
GAAGGAAAAG TCATTACTCG TGGTTTAGAG ATAGTTAGGA GAGATTGGAG TGAAATTGCA
1860 AAAGAAACTC AAGCTAGAGT TTTGGAGACA ATACTAAAAC ACGGAGATGT TGAAGAAGCT 1920 GTGAGAATAG TAAAAGAAGT
AATACAAAAG CTTGCCAATT ATGAAATTCC ACCAGAGAAG 1980
CTCGCAATAT ATGAGCAGAT AACAAGACCA TTACATGAGT ATAAGGCGAT
AGGTCCTCAC 2040 GTAGCTGTTG CAAAGAAACT AGCTGCTAAA GGAGTTAAAA TAAAGCCAGG AATGGTAATT 2100 GGATACATAG
TACTTAGAGG CGATGGTCCA ATTAGCAATA GGGCAATTCT AGCTGAGGAA 2160
TACGATCCCA AAAAGCACAA GTATGACGCA GAATATTACA
TGGAGAACCA GGTTCTTCCA 2220
GCGGTACTTA GGATATTGGA GGGATTTGGA TACAGAAAGG AAGACCTCAG ATACCAAAAG 2280
ACAAGACAAG TCGGCCTAAC TTCCTGGCTT AACATTAAAA AATCC // 2328

TGA

| FIG. 8WW-1 |
|---|
| FIG. 8WW-2 |
| FIG. 8WW-3 |

KOD DNA POLYMERASE - Sac7d fusion protein

Nucleotide sequence (SEQ ID NO: 33) // Nucleotide sequence (SEQ ID NO: 69)
Nucleotide sequence (SEQ ID NO: 34) // Nucleotide sequence (SEQ ID NO: 69)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATCCTCG ACACTGACTA CATAACCGAG GATGGAAAGC CTGTCATAAG AATTTTCAAG 60
AAGGAAAACG GCGAGTTTAA GATTGAGTAC GACCGGACTT TTGAACCCTA CTTCTACGCC 120
CTCCTGAAGG ACGATTCTGC CATTGAGGAA GTCAAGAAGA TAACCGCCGA GAGGCACGGG 180
ACGGTTGTAA CGGTTAAGCG GGTTGAAAAG GTTCAGAAGA AGTTCCTCGG GAGACCAGTT 240
GAGGTCTGGA AACTCTACTT TACTCATCCG CAGGACXXXC CAGCGATAAG GGACAAGATA 300
```

FIG. 8WW-1

```
CGAGAGCATC CAGCAGTTAT TGACATCTAC GAGTACGACA TACCCTTCGC CAAGCGCTAC 360
CTCATAGACA AGGGATTAGT GCCAATGGAA GGCGACGAGG AGCTGAAAAT GCTCGCCTTC 420
GACATTGAAA CTCTCTACCA TGAGGGCGAG GAGTTCGCCG AGGGGCCAAT CCTTATGATA 480
AGCTACGCCG ACGAGGAAGG GGCCAGGGTG ATAACTTGGA AGAACGTGGA TCTCCCCTAC 540
GTTGACGTCG TCTCGACGGA GAGGGAGATG ATAAAGCGCT TCCTCCGTGT TGTGAAGGAG 600
AAAGACCCGG ACGTTCTCAT AACCTACAAC GGCGACAACT TCGACTTCGC CTATCTGAAA 660
AAGCGCTGTG AAAAGCTCGG AATAAACTTC GCCCTCGGAA GGGATGGAAG CGAGCCGAAG 720
ATTCAGAGGA TGGGCGACAG GTTTGCCGTC GAAGTGAAGG GACGGATACA CTTCGATCTC 780
TATCCTGTGA TAAGACGGAC GATAAACCTG CCCACATACA CGCTTGAGGC CGTTTATGAA 840
GCCGTCTTCG GTCAGCCGAA GGAGAAGGTT TACGCTGAGG AAATAACCAC AGCCTGGGAA 900
ACCGGCGAGA ACCTTGAGAG AGTCGCCCGC TACTCGATGG AAGATGCGAA GGTCACATAC 960
GAGCTTGGGA AGGAGTTCCT TCCGATGGAG GCCCAGCTTT CTCGCTTAAT CGGCCAGTCC 1020
CTCTGGGACG TCTCCCGCTC CAGCACTGGC AACCTCGTTG AGTGGTTCCT CCTCAGGAAG 1080
GCCTATGAGA GGAATGAGCT GGCCCCGAAC AAGCCCGATG AAAAGGAGCT GGCCAGAAGA 1140
CGGCAGAGCT ATGAAGGAGG CTATGTAAAA GAGCCCGAGA GAGGGTTGTG GGAGAACATA 1200
GTGTACCTAG ATTTTAGATC CCTGTACCCC TCAATCATCA TCACCCACAA CGTCTCGCCG 1260
GATACGCTCA ACAGAGAAGG ATGCAAGGAA TATGACGTTG CCCCACAGGT CGGCCACCGC 1320
TTCTGCAAGG ACTTCCCAGG ATTTATCCCG AGCCTGCTTG GAGACCTCCT AGAGGAGAGG 1380
CAGAAGATAA AGAAGAAGAT GAAGGCCACG ATTGACCCGA TCGAGAGGAA GCTCCTCGAT 1440
```

FIG. 8WW-2

```
TACAGGCAGA GGGCCATCAA GATCCTGGCA AACAGCTACT ACGGTTACTA CGGCTATGCA 1500
AGGGCGCGCT GGTACTGCAA GGAGTGTGCA GAGAGCGTAA CGGCCTGGGG AAGGGAGTAC 1560
ATAACGATGA CCATCAAGGA GATAGAGGAA AAGTACGGCT TTAAGGTAAT CTACAGCGAC 1620
ACCGACGGAT TTTTTGCCAC AATACCTGGA GCCGATGCTG AAACCGTCAA AAAGAAGGCT 1680
ATGGAGTTCC TCAAGTATAT CAACGCCAAA CTTCCGGGCG CGCTTGAGCT CGAGTACGAG 1740
GGCTTCTACA AACGCGGCTT CTTCGTCACG AAGAAGAAGT ATGCGGTGAT AGACGAGGAA 1800
GGCAAGATAA CAACGCGCGG ACTTGAGATT GTGAGGCGTG ACTGGAGCGA GATAGCGAAA 1860
GAGACGCAGG CGAGGGTTCT TGAAGCTTTG CTAAAGGACG GTGACGTCGA GAAGGCCGTG 1920
AGGATAGTCA AAGAAGTTAC CGAAAAGCTG AGCAAGTACG AGGTTCCGCC GGAGAAGCTG 1980
GTGATCCACG AGCAGATAAC GAGGGATTTA AAGGACTACA AGGCAACCGG TCCCCACGTT 2040
GCCGTTGCCA AGAGGTTGGC CGCGAGAGGA GTCAAAATAC GCCCTGGAAC GGTGATAAGC 2100
TACATCGTGC TCAAGGGCTC TGGGAGGATA GGCGACAGGG CGATACCGTT CGACGAGTTC 2160
GACCCGACGA AGCACAAGTA CGACGCCGAG TACTACATTG AGAACCAGGT TCTCCCAGCC 2220
GTTGAGAGAA TTCTGAGAGC CTTCGGTTAC CGCAAGGAAG ACCTGCGCTA CCAGAAGACG 2280
AGACAGGTTG GTTTGAGTGC TTGGCTGAAG CCGAAGGGAA CT  2325
// ATG GTG AAG GTA AAG TTC AAG TAT AAG GGT GAA GAG AAA GAA GTA GAC ACT TCA
   AAG ATA AAG AAG GTT TGG AGA GTA GGC AAA ATG GTG TCC TTT ACC TAT GAC GAC
   AAT GGT AAG ACA GGT AGA GGA GCT GTA AGC GAG AAA GAT GCT CCA AAA GAA TTA
   TTA GAC ATG TTA GCA AGA GCA GAA AGA GAG AAG AAA //  TGA
```

| |
|---|
| FIG. 8XX-1 |
| FIG. 8XX-2 |
| FIG. 8XX-3 |

Sac7d - KOD DNA POLYMERASE fusion protein

Nucleotide sequence (SEQ ID NO: 69) // Nucleotide sequence (SEQ ID NO: 33)
Nucleotide sequence (SEQ ID NO: 69) // Nucleotide sequence (SEQ ID NO: 34)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

// ATG GTG AAG GTA AAG TTC AAG TAT AAG GGT GAA GAG AAA GAA GTA GAC ACT TCA
AAG ATA AAG AAG GTT TGG AGA GTA GGC AAA ATG GTG TCC TTT ACC TAT GAC GAC
AAT GGT AAG ACA GGT AGA GGA GCT GTA AGC GAG AAA GAT GCT CCA AAA GAA TTA
TTA GAC ATG TTA GCA AGA GCA GAA AGA GAG AAG AAA //

FIG. 8XX-1

```
//ATGATCCTCG ACACTGACTA CATAACCGAG GATGGAAAGC CTGTCATAAG AATTTTCAAG 60
AAGGAAAACG GCGAGTTTAA GATTGAGTAC GACCGGACTT TTGAACCCTA CTTCTACGCC 120
CTCCTGAAGG ACGATTCTGC CATTGAGGAA GTCAAGAAGA TAACCGCCGA GAGGCACGGG 180
ACGGTTGTAA CGGTTAAGCG GGTTGAAAAG GTTCAGAAGA AGTTCCTCGG GAGACCAGTT 240
GAGGTCTGGA AACTCTACTT TACTCATCCG CAGGACXXXC CAGCGATAAG GGACAAGATA 300
CGAGAGCATC CAGCAGTTAT TGACATCTAC GAGTACGACA TACCCTTCGC CAAGCGCTAC 360
CTCATAGACA AGGGATTAGT GCCAATGGAA GGCGACGAGG AGCTGAAAAT GCTCGCCTTC 420
GACATTGAAA CTCTCTACCA TGAGGGCGAG GAGTTCGCCG AGGGGCCAAT CCTTATGATA 480
AGCTACGCCG ACGAGGAAGG GGCCAGGGTG ATAACTTGGA AGAACGTGGA TCTCCCCTAC 540
GTTGACGTCG TCTCGACGGA GAGGGAGATG ATAAAGCGCT TCCTCCGTGT TGTGAAGGAG 600
AAAGACCCGG ACGTTCTCAT AACCTACAAC GGCGACAACT TCGACTTCGC CTATCTGAAA 660
AAGCGCTGTG AAAAGCTCGG AATAAACTTC GCCCTCGGAA GGGATGGAAG CGAGCCGAAG 720
ATTCAGAGGA TGGGCGACAG GTTTGCCGTC GAAGTGAAGG GACGGATACA CTTCGATCTC 780
TATCCTGTGA TAAGACGGAC GATAAACCTG CCCACATACA CGCTTGAGGC CGTTTATGAA 840
GCCGTCTTCG GTCAGCCGAA GGAGAAGGTT TACGCTGAGG AAATAACCAC AGCCTGGGAA 900
ACCGGCGAGA ACCTTGAGAG AGTCGCCCGC TACTCGATGG AAGATGCGAA GGTCACATAC 960
GAGCTTGGGA AGGAGTTCCT TCCGATGGAG GCCCAGCTTT CTCGCTTAAT CGGCCAGTCC 1020
CTCTGGGACG TCTCCCGCTC CAGCACTGGC AACCTCGTTG AGTGGTTCCT CCTCAGGAAG 1080
```

FIG. 8XX-2

```
GCCTATGAGA GGAATGAGCT GGCCCCGAAC AAGCCCGATG AAAAGGAGCT GGCCAGAAGA 1140
CGGCAGAGCT ATGAAGGAGG CTATGTAAAA GAGCCCGAGA GAGGGTTGTG GGAGAACATA 1200
GTGTACCTAG ATTTTAGATC CCTGTACCCC TCAATCATCA TCACCCACAA CGTCTCGCCG 1260
GATACGCTCA ACAGAGAAGG ATGCAAGGAA TATGACGTTG CCCCACAGGT CGGCCACCGC 1320
TTCTGCAAGG ACTTCCCAGG ATTTATCCCG AGCCTGCTTG GAGACCTCCT AGAGGAGAGG 1380
CAGAAGATAA AGAAGAAGAT GAAGGCCACG ATTGACCCGA TCGAGAGGAA GCTCCTCGAT 1440
TACAGGCAGA GGGCCATCAA GATCCTGGCA AACAGCTACT ACGGTTACTA CGGCTATGCA 1500
AGGGCGCGCT GGTACTGCAA GGAGTGTGCA GAGAGCGTAA CGGCCTGGGG AAGGGAGTAC 1560
ATAACGATGA CCATCAAGGA GATAGAGGAA AAGTACGGCT TTAAGGTAAT CTACAGCGAC 1620
ACCGACGGAT TTTTTGCCAC AATACCTGGA GCCGATGCTG AAACCGTCAA AAAGAAGGCT 1680
ATGGAGTTCC TCAAGTATAT CAACGCCAAA CTTCCGGGCG CGCTTGAGCT CGAGTACGAG 1740
GGCTTCTACA AACGCGGCTT CTTCGTCACG AAGAAGAAGT ATGCGGTGAT AGACGAGGAA 1800
GGCAAGATAA CAACGCGCGG ACTTGAGATT GTGAGGCGTG ACTGGAGCGA GATAGCGAAA 1860
GAGACGCAGG CGAGGGTTCT TGAAGCTTTG CTAAAGGACG GTGACGTCGA GAAGGCCGTG 1920
AGGATAGTCA AAGAAGTTAC CGAAAAGCTG AGCAAGTACG AGGTTCCGCC GGAGAAGCTG 1980
GTGATCCACG AGCAGATAAC GAGGGATTTA AAGGACTACA AGGCAACCGG TCCCCACGTT 2040
GCCGTTGCCA AGAGGTTGGC CGCGAGAGGA GTCAAAATAC GCCCTGGAAC GGTGATAAGC 2100
TACATCGTGC TCAAGGGCTC TGGGAGGATA GGCGACAGGG CGATACCGTT CGACGAGTTC 2160
GACCCGACGA AGCACAAGTA CGACGCCGAG TACTACATTG AGAACCAGGT TCTCCCAGCC 2220
GTTGAGAGAA TTCTGAGAGC CTTCGGTTAC CGCAAGGAAG ACCTGCGCTA CCAGAAGACG 2280
AGACAGGTTG GTTTGAGTGC TTGGCTGAAG CCGAAGGGAA CT //TAG 2325
```

| FIG. 8YY-1 |
| --- |
| FIG. 8YY-2 |
| FIG. 8YY-3 |

Sac7d-Vent DNA POLYMERASE FUSION PROTEIN

Nucleotide sequence (SEQ ID NO: 69) // Nucleotide sequence (SEQ ID NO: 35)
Nucleotide sequence (SEQ ID NO: 69) // Nucleotide sequence (SEQ ID NO: 36)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
// ATG GTG AAG GTA AAG TTC AAG TAT AAG GGT GAA GAG AAA GAA GTA GAC ACT TCA
 AAG ATA AAG AAG GTT TGG AGA GTA GGC AAA ATG GTG TCC TTT ACC TAT GAC GAC
 AAT GGT AAG ACA GGT AGA GGA GCT GTA AGC GAG AAA GAT GCT CCA AAA GAA TTA
 TTA GAC ATG TTA GCA AGA GCA GAA AGA GAG AAG AAA //
```

FIG. YY-1

ATGATACTGG ACACTGATTA CATAACAAAA GATGGCAAGC CTATAATCCG AATTTTTAAG 60
AAAGAGAACG GGGAGTTTAA AATAGAACTT GACCCTCATT TTCAGCCCTA TATATATGCT 120
CTTCTCAAAG ATGACTCCGC TATTGAGGAG ATAAAGGCAA TAAAGGGCGA GAGACATGGA 180
AAAACTGTGA GAGTGCTCGA TGCAGTGAAA GTCAGGAAAA AATTTTTGGG AAGGGAAGTT 240
GAAGTCTGGA AGCTCATTTT CGAGCATCCC CAAGACXXXC CAGCTATGCG GGGCAAAATA 300
AGGGAACATC CAGCTGTGGT TGACATTTAC GAATATGACA TACCCTTTGC CAAGCGTTAT 360
CTCATAGACA AGGGCTTGAT TCCCATGGAG GGAGACGAGG AGCTTAAGCT CCTTGCCTTT 420
GATATTGAAA CGTTTTATCA TGAGGGAGAT GAATTTGGAA AGGGCGAGAT AATAATGATT 480
AGTTATGCCG ATGAAGAAGA GGCCAGAGTA ATCACATGGA AAAATATCGA TTTGCCGTAT 540
GTCGATGTTG TGTCCAATGA AAGAGAAATG ATAAAGCGTT TTGTTCAAGT TGTTAAAGAA 600
AAAGACCCCG ATGTGATAAT AACTTACAAT GGGGACAATT TTGATTTGCC GTATCTCATA 660
AAACGGGCAG AAAAGCTGGG AGTTCGGCTT GTCTTAGGAA GGGACAAAGA ACATCCCGAA 720
CCCAAGATTC AGAGGATGGG TGATAGTTTT GCTGTGGAAA TCAAGGGTAG AATCCACTTT 780
GATCTTTTCC CAGTTGTGCG AAGGACGATA AACCTCCCAA CGTATACGCT TGAGGCAGTT 840
TATGAAGCAG TTTTAGGAAA AACCAAAAGC AAATTAGGAG CAGAGGAAAT TGCCGCTATA 900
TGGGAAACAG AAGAAAGCAT GAAAAAACTA GCCCAGTACT CAATGGAAGA TGCTAGGGCA 960
ACGTATGAGC TCGGGAAGGA ATTCTTCCCC ATGGAAGCTG AGCTGGCAAA GCTGATAGGT 1020
CAAAGTGTAT GGGACGTCTC GAGATCAAGC ACCGGCAACC TCGTGGAGTG GTATCTTTTA 1080
AGGGTGGCAT ACGCGAGGAA TGAACTTGCA CCGAACAAAC CTGATGAGGA AGAGTATAAA 1140
CGGCGCTTAA GAACAACTTA CCTGGGAGGA TATGTAAAAG AGCCAGAAAA AGGTTTGTGG 1200

FIG. YY-2

```
GAAAATATCA TTTATTTGGA TTTCCGCAGT CTGTACCCTT CAATAATAGT TACTCACAAC 1260
GTATCCCCAG ATACCCTTGA AAAAGAGGGC TGTAAGAATT ACGATGTTGC TCCGATAGTA 1320
GGATATAGGT TCTGCAAGGA CTTTCCGGGC TTTATTCCCT CCATACTCGG GGACTTAATT 1380
GCAATGAGGC AAGATATAAA GAAGAAAATG AAATCCACAA TTGACCCGAT CGAAAAGAAA 1440
ATGCTCGATT ATAGGCAAAG GGCTATTAAA TTGCTTGCAA ACAGCTATTA CGGCTATATG 1500
GGGTATCCTA AGGCAAGATG GTACTCGAAG GAATGTGCTG AAAGCGTTAC CGCATGGGGG 1560
AGACACTACA TAGAGATGAC GATAAGAGAA ATAGAGGAAA AGTTCGGCTT TAAGGTTCTT 1620
TATGCGGACA CTGACGGCTT TTATGCCACA ATACCCGGGG AAAAGCCTGA ACTCATTAAA 1680
AAGAAAGCCA AGGAATTCCT AAACTACATA AACTCCAAAC TTCCAGGTCT GCTTGAGCTT 1740
GAGTATGAGG GCTTTTACTT GAGAGGATTC TTTGTTACAA AAAAGCGCTA TGCAGTCATA 1800
GATGAAGAGG GCAGGATAAC AACAAGGGGC TTGGAAGTAG TAAGGAGAGA TTGGAGTGAG 1860
ATAGCTAAGG AGACTCAGGC AAAGGTTTTA GAGGCTATAC TTAAAGAGGG AAGTGTTGAA 1920
AAAGCTGTAG AAGTTGTTAG AGATGTTGTA GAGAAAATAG CAAAATACAG GGTTCCACTT 1980
GAAAAGCTTG TTATCCATGA GCAGATTACC AGGGATTTAA AGGACTACAA AGCCATTGGC 2040
CCTCATGTCG CGATAGCAAA AAGACTTGCC GCAAGAGGGA TAAAAGTGAA ACCGGGCACA 2100
ATAATAAGCT ATATCGTTCT CAAAGGGAGC GGAAAGATAA GCGATAGGGT AATTTTACTT 2160
ACAGAATACG ATCCTAGAAA ACACAAGTAC GATCCGGACT ACTACATAGA AAACCAAGTT 2220
TTGCCGGCAG TACTTAGGAT ACTCGAAGCG TTTGGATACA GAAAGGAGGA TTTAAGGTAT 2280
CAAAGCTCAA AACAAACCGG CTTAGATGCA TGGCTCAAGA GGTAG 2325
```

FIG. YY-3

| |
|---|
| FIG. 8ZZ-1 |
| FIG. 8ZZ-2 |
| FIG. 8ZZ-3 |

FIG. 8ZZ

Vent DNA POLYMERASE - Sac7d FUSION PROTEIN

Nucleotide sequence (SEQ ID NO: 35) // Nucleotide sequence (SEQ ID NO: 69)
Nucleotide sequence (SEQ ID NO: 36) // Nucleotide sequence (SEQ ID NO: 69)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATACTGG ACACTGATTA CATAACAAAA GATGGCAAGC CTATAATCCG AATTTTTAAG 60
AAAGAGAACG GGGAGTTTAA AATAGAACTT GACCCTCATT TTCAGCCCTA TATATATGCT 120
CTTCTCAAAG ATGACTCCGC TATTGAGGAG ATAAAGGCAA TAAAGGGCGA GAGACATGGA 180
AAAACTGTGA GAGTGCTCGA TGCAGTGAAA GTCAGGAAAA AATTTTTGGG AAGGGAAGTT 240
GAAGTCTGGA AGCTCATTTT CGAGCATCCC CAAGACXXXC CAGCTATGCG GGGCAAAATA 300
AGGGAACATC CAGCTGTGGT TGACATTTAC GAATATGACA TACCCTTTGC CAAGCGTTAT 360
CTCATAGACA AGGGCTTGAT TCCCATGGAG GGAGACGAGG AGCTTAAGCT CCTTGCCTTT 420
GATATTGAAA CGTTTTATCA TGAGGGAGAT GAATTTGGAA AGGGCGAGAT AATAATGATT 480
AGTTATGCCG ATGAAGAAGA GGCCAGAGTA ATCACATGGA AAAATATCGA TTTGCCGTAT 540
```

FIG. 8ZZ-1

```
GTCGATGTTG TGTCCAATGA AAGAGAAATG ATAAAGCGTT TTGTTCAAGT TGTTAAAGAA 600
AAAGACCCCG ATGTGATAAT AACTTACAAT GGGGACAATT TTGATTTGCC GTATCTCATA 660
AAACGGGCAG AAAAGCTGGG AGTTCGGCTT GTCTTAGGAA GGGACAAAGA ACATCCCGAA 720
CCCAAGATTC AGAGGATGGG TGATAGTTTT GCTGTGGAAA TCAAGGGTAG AATCCACTTT 780
GATCTTTTCC CAGTTGTGCG AAGGACGATA AACCTCCCAA CGTATACGCT TGAGGCAGTT 840
TATGAAGCAG TTTTAGGAAA AACCAAAAGC AAATTAGGAG CAGAGGAAAT TGCCGCTATA 900
TGGGAAACAG AAGAAAGCAT GAAAAAACTA GCCCAGTACT CAATGGAAGA TGCTAGGGCA 960
ACGTATGAGC TCGGGAAGGA ATTCTTCCCC ATGGAAGCTG AGCTGGCAAA GCTGATAGGT 1020
CAAAGTGTAT GGGACGTCTC GAGATCAAGC ACCGGCAACC TCGTGGAGTG GTATCTTTTA 1080
AGGGTGGCAT ACGCGAGGAA TGAACTTGCA CCGAACAAAC CTGATGAGGA AGAGTATAAA 1140
CGGCGCTTAA GAACAACTTA CCTGGGAGGA TATGTAAAAG AGCCAGAAAA AGGTTTGTGG 1200
GAAAATATCA TTTATTTGGA TTTCCGCAGT CTGTACCCTT CAATAATAGT TACTCACAAC 1260
GTATCCCCAG ATACCCTTGA AAAAGAGGGC TGTAAGAATT ACGATGTTGC TCCGATAGTA 1320
GGATATAGGT TCTGCAAGGA CTTTCCGGGC TTTATTCCCT CCATACTCGG GGACTTAATT 1380
GCAATGAGGC AAGATATAAA GAAGAAAATG AAATCCACAA TTGACCCGAT CGAAAAGAAA 1440
ATGCTCGATT ATAGGCAAAG GGCTATTAAA TTGCTTGCAA ACAGCTATTA CGGCTATATG 1500
GGGTATCCTA AGGCAAGATG GTACTCGAAG GAATGTGCTG AAAGCGTTAC CGCATGGGGG 1560
AGACACTACA TAGAGATGAC GATAAGAGAA ATAGAGGAAA AGTTCGGCTT TAAGGTTCTT 1620
TATGCGGACA CTGACGGCTT TTATGCCACA ATACCCGGGG AAAAGCCTGA ACTCATTAAA 1680
```

FIG. 8ZZ-2

```
AAGAAAGCCA AGGAATTCCT AAACTACATA AACTCCAAAC TTCCAGGTCT GCTTGAGCTT 1740
GAGTATGAGG GCTTTTACTT GAGAGGATTC TTTGTTACAA AAAAGCGCTA TGCAGTCATA 1800
GATGAAGAGG GCAGGATAAC AACAAGGGGC TTGGAAGTAG TAAGGAGAGA TTGGAGTGAG 1860
ATAGCTAAGG AGACTCAGGC AAAGGTTTTA GAGGCTATAC TTAAAGAGGG AAGTGTTGAA 1920
AAAGCTGTAG AAGTTGTTAG AGATGTTGTA GAGAAAATAG CAAAATACAG GGTTCCACTT 1980
GAAAAGCTTG TTATCCATGA GCAGATTACC AGGGATTTAA AGGACTACAA AGCCATTGGC 2040
CCTCATGTCG CGATAGCAAA AAGACTTGCC GCAAGAGGGA TAAAAGTGAA ACCGGGCACA 2100
ATAATAAGCT ATATCGTTCT CAAAGGGAGC GGAAAGATAA GCGATAGGGT AATTTTACTT 2160
ACAGAATACG ATCCTAGAAA ACACAAGTAC GATCCGGACT ACTACATAGA AAACCAAGTT 2220
TTGCCGGCAG TACTTAGGAT ACTCGAAGCG TTTGGATACA GAAAGGAGGA TTTAAGGTAT 2280
CAAAGCTCAA AACAAACCGG CTTAGATGCA TGGCTCAAGA GG 2325 //

// ATG GTG AAG GTA AAG TTC AAG TAT AAG GGT GAA GAG AAA GAA GTA GAC ACT TCA
   AAG ATA AAG AAG GTT TGG AGA GTA GGC AAA ATG GTG TCC TTT ACC TAT GAC GAC
   AAT GGT AAG ACA GGT AGA GGA GCT GTA AGC GAG AAA GAT GCT CCA AAA GAA TTA
   TTA GAC ATG TTA GCA AGA GCA GAA AGA GAG AAG AAA //  TGA
```

| |
|---|
| FIG. 8AAA-1 |
| FIG. 8AAA-2 |
| FIG. 8AAA-3 |

<u>Deep Vent- Sac7d DNA polymerase fusion protein</u>

Nucleotide sequence (SEQ ID NO: 37) // Nucleotide sequence (SEQ ID NO: 69)
Nucleotide sequence (SEQ ID NO: 38) // Nucleotide sequence (SEQ ID NO: 69)

```
V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)
ATGATACTTG ACGCTGACTA CATCACCGAG GATGGGAAGC CGATTATAAG GATTTTCAAG    60
AAAGAAAACG GCGAGTTTAA GGTTGAGTAC GACAGAAACT TTAGACCTTA CATTTACGCT   120
CTCCTCAAAG ATGACTCGCA GATTGATGAG GTTAGGAAGA TAACCGCCGA GAGGCATGGG   180
AAGATAGTGA GAATTATAGA TGCCGAAAAG GTAAGGAAGA AGTTCCTGGG GAGGCCGATT   240
GAGGTATGGA GGCTGTACTT TGAACACCCT CAGGACXXXC CCGCAATAAG GGATAAGATA   300
AGAGAGCATT CCGCAGTTAT TGACATCTTT GAGTACGACA TTCCGTTCGC GAAGAGGTAC   360
CTAATAGACA AAGGCCTAAT TCCAATGGAA GGCGATGAAG AGCTCAAGTT GCTCGCATTT   420
GACATAGAAA CCCTCTATCA CGAAGGGGAG GAGTTCGCGA AGGGGCCCAT TATAATGATA   480
```

FIG. 8AAA-1

```
AGCTATGCTG ATGAGGAAGA AGCCAAAGTC ATAACGTGGA AAAAGATCGA TCTCCCGTAC   540
GTCGAGGTAG TTTCCAGCGA GAGGGAGATG ATAAAGCGGT TCCTCAAGGT GATAAGGGAG   600
AAAGATCCCG ATGTTATAAT TACCTACAAC GGCGATTCTT TCGACCTTCC CTATCTAGTT   660
AAGAGGGCCG AAAAGCTCGG GATAAAGCTA CCCCTGGGAA GGGACGGTAG TGAGCCAAAG   720
ATGCAGAGGC TTGGGGATAT GACAGCGGTG GAGATAAAGG GAAGGATACA CTTTGACCTC   780
TACCACGTGA TTAGGAGAAC GATAAACCTC CCAACATACA CCCTCGAGGC AGTTTATGAG   840
GCAATCTTCG GAAAGCCAAA GGAGAAAGTT TACGCTCACG AGATAGCTGA GGCCTGGGAG   900
ACTGGAAAGG GACTGGAGAG AGTTGCAAAG TATTCAATGG AGGATGCAAA GGTAACGTAC   960
GAGCTCGGTA GGGAGTTCTT CCCAATGGAG GCCCAGCTTT CAAGGTTAGT CGGCCAGCCC  1020
CTGTGGGATG TTTCTAGGTC TTCAACTGGC AACTTGGTGG AGTGGTACCT CCTCAGGAAG  1080
GCCTACGAGA GGAATGAATT GGCTCCAAAC AAGCCGGATG AGAGGGAGTA CGAGAGAAGG  1140
CTAAGGGAGA GCTACGCTGG GGGATACGTT AAGGAGCCGG AGAAAGGGCT CTGGGAGGGG  1200
TTAGTTTCCC TAGATTTCAG GAGCCTGTAC CCCTCGATAA TAATCACCCA TAACGTCTCA  1260
CCGGATACGC TGAACAGGGA AGGGTGTAGG GAATACGATG TCGCCCCAGA GGTTGGGCAC  1320
AAGTTCTGCA AGGACTTCCC GGGGTTTATC CCCAGCCTGC TCAAGAGGTT ATTGGATGAA  1380
AGGCAAGAAA TAAAAAGGAA GATGAAAGCT TCTAAAGACC CAATCGAGAA GAAGATGCTT  1440
GATTACAGGC AACGGGCAAT CAAAATCCTG GCAAACAGCT ATTATGGGTA TTATGGGTAC  1500
GCAAAAGCCC GTTGGTACTG TAAGGAGTGC GCAGAGAGCG TTACGGCCTG GGGGAGGGAA  1560
```

FIG. 8AAA-2

```
TATATAGAGT TCGTAAGGAA GGAACTGGAG GAAAAGTTCG GGTTCAAAGT CTTATACATA  1620
GACACAGATG GACTCTACGC CACAATTCCT GGGGCAAAAC CCGAGGAGAT AAAGAAGAAA  1680
GCCCTAGAGT TCGTAGATTA TATAAACGCC AAGCTCCCAG GGCTGTTGGA GCTTGAGTAC  1740
GAGGGCTTCT ACGTGAGAGG GTTCTTCGTG ACGAAGAAGA AGTATGCGTT GATAGATGAG  1800
GAAGGGAAGA TAATCACTAG GGGGCTTGAA ATAGTCAGGA GGGACTGGAG CGAAATAGCC  1860
AAAGAAACCC AAGCAAAAGT CCTAGAGGCT ATCCTAAAGC ATGGCAACGT TGAGGAGGCA  1920
GTAAAGATAG TTAAGGAGGT AACTGAAAAG CTGAGCAAGT ACGAAATACC TCCAGAAAAG  1980
CTAGTTATTT ACGAGCAGAT CACGAGGCCC CTTCACGAGT ACAAGGCTAT AGGTCCGCAC  2040
GTTGCCGTGG CAAAAAGGTT AGCCGCTAGA GGAGTAAAGG TGAGGCCTGG CATGGTGATA  2100
GGGTACATAG TGCTGAGGGG AGACGGGCCA ATAAGCAAGA GGGCTATCCT TGCAGAGGAG  2160
TTCGATCTCA GGAAGCATAA GTATGACGCT GAGTATTACA TAGAAAATCA GGTTTTACCT  2220
GCCGTTCTTA GAATATTAGA GGCCTTTGGG TACAGGAAAG AAGACCTCAG GTGGCAGAAG  2280
ACTAAACAGA CAGGTCTTAC GGCATGGCTT AACATCAAGA AGAAG //               2328

// ATG GTG AAG GTA AAG TTC AAG TAT AAG GGT GAA GAG AAA GAA GTA GAC ACT TCA
   AAG ATA AAG AAG GTT TGG AGA GTA GGC AAA ATG GTG TCC TTT ACC TAT GAC GAC
   AAT GGT AAG ACA GGT AGA GGA GCT GTA AGC GAG AAA GAT GCT CCA AAA GAA TTA
   TTA GAC ATG TTA GCA AGA GCA GAA AGA GAG AAG AAA //  TGA
```

| |
|---|
| FIG. 8BBB-1 |
| FIG. 8BBB-2 |
| FIG. 8BBB-3 |

Sac7d - Deep Vent DNA polymerase fusion protein

Nucleotide sequence (SEQ ID NO: 69) // Nucleotide sequence (SEQ ID NO: 37)
Nucleotide sequence (SEQ ID NO: 69) // Nucleotide sequence (SEQ ID NO: 38)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
// ATG GTG AAG GTA AAG TTC AAG TAT AAG GGT GAA GAG AAA GAA GTA GAC ACT TCA
 AAG ATA AAG AAG GTT TGG AGA GTA GGC AAA ATG GTG TCC TTT ACC TAT GAC GAC
 AAT GGT AAG ACA GGT AGA GGA GCT GTA AGC GAG AAA GAT GCT CCA AAA GAA TTA
 TTA GAC ATG TTA GCA AGA GCA GAA AGA GAG AAG AAA //

//ATGATACTTG ACGCTGACTA CATCACCGAG GATGGGAAGC CGATTATAAG GATTTTCAAG    60
AAAGAAAACG GCGAGTTTAA GGTTGAGTAC GACAGAAACT TTAGACCTTA CATTTACGCT   120
CTCCTCAAAG ATGACTCGCA GATTGATGAG GTTAGGAAGA TAACCGCCGA GAGGCATGGG   180
```

FIG. 8BBB-1

```
AAGATAGTGA GAATTATAGA TGCCGAAAAG GTAAGGAAGA AGTTCCTGGG GAGGCCGATT   240
GAGGTATGGA GGCTGTACTT TGAACACCCT CAGGACXXXC CCGCAATAAG GGATAAGATA   300
AGAGAGCATT CCGCAGTTAT TGACATCTTT GAGTACGACA TTCCGTTCGC GAAGAGGTAC   360
CTAATAGACA AAGGCCTAAT TCCAATGGAA GGCGATGAAG AGCTCAAGTT GCTCGCATTT   420
GACATAGAAA CCCTCTATCA CGAAGGGGAG GAGTTCGCGA AGGGGCCCAT TATAATGATA   480
AGCTATGCTG ATGAGGAAGA AGCCAAAGTC ATAACGTGGA AAAAGATCGA TCTCCCGTAC   540
GTCGAGGTAG TTTCCAGCGA GAGGGAGATG ATAAAGCGGT TCCTCAAGGT GATAAGGGAG   600
AAAGATCCCG ATGTTATAAT TACCTACAAC GGCGATTCTT TCGACCTTCC CTATCTAGTT   660
AAGAGGGCCG AAAAGCTCGG GATAAAGCTA CCCCTGGGAA GGGACGGTAG TGAGCCAAAG   720
ATGCAGAGGC TTGGGGATAT GACAGCGGTG GAGATAAAGG GAAGGATACA CTTTGACCTC   780
TACCACGTGA TTAGGAGAAC GATAAACCTC CCAACATACA CCCTCGAGGC AGTTTATGAG   840
GCAATCTTCG GAAAGCCAAA GGAGAAAGTT TACGCTCACG AGATAGCTGA GGCCTGGGAG   900
ACTGGAAAGG GACTGGAGAG AGTTGCAAAG TATTCAATGG AGGATGCAAA GGTAACGTAC   960
GAGCTCGGTA GGGAGTTCTT CCCAATGGAG GCCCAGCTTT CAAGGTTAGT CGGCCAGCCC  1020
CTGTGGGATG TTTCTAGGTC TTCAACTGGC AACTTGGTGG AGTGGTACCT CCTCAGGAAG  1080
GCCTACGAGA GGAATGAATT GGCTCCAAAC AAGCCGGATG AGAGGGAGTA CGAGAGAAGG  1140
CTAAGGGAGA GCTACGCTGG GGGATACGTT AAGGAGCCGG AGAAAGGGCT CTGGGAGGGG  1200
TTAGTTTCCC TAGATTTCAG GAGCCTGTAC CCCTCGATAA TAATCACCCA TAACGTCTCA  1260
```

FIG. 8BBB-2

```
CCGGATACGC TGAACAGGGA AGGGTGTAGG GAATACGATG TCGCCCCAGA GGTTGGGCAC 1320
AAGTTCTGCA AGGACTTCCC GGGGTTTATC CCCAGCCTGC TCAAGAGGTT ATTGGATGAA 1380
AGGCAAGAAA TAAAAAGGAA GATGAAAGCT TCTAAAGACC CAATCGAGAA GAAGATGCTT 1440
GATTACAGGC AACGGGCAAT CAAAATCCTG GCAAACAGCT ATTATGGGTA TTATGGGTAC 1500
GCAAAAGCCC GTTGGTACTG TAAGGAGTGC GCAGAGAGCG TTACGGCCTG GGGGAGGGAA 1560
TATATAGAGT TCGTAAGGAA GGAACTGGAG GAAAAGTTCG GGTTCAAAGT CTTATACATA 1620
GACACAGATG GACTCTACGC CACAATTCCT GGGGCAAAAC CCGAGGAGAT AAAGAAGAAA 1680
GCCCTAGAGT TCGTAGATTA TATAAACGCC AAGCTCCCAG GGCTGTTGGA GCTTGAGTAC 1740
GAGGGCTTCT ACGTGAGAGG GTTCTTCGTG ACGAAGAAGA AGTATGCGTT GATAGATGAG 1800
GAAGGGAAGA TAATCACTAG GGGGCTTGAA ATAGTCAGGA GGGACTGGAG CGAAATAGCC 1860
AAAGAAACCC AAGCAAAAGT CCTAGAGGCT ATCCTAAAGC ATGGCAACGT TGAGGAGGCA 1920
GTAAAGATAG TTAAGGAGGT AACTGAAAAG CTGAGCAAGT ACGAAATACC TCCAGAAAAG 1980
CTAGTTATTT ACGAGCAGAT CACGAGGCCC CTTCACGAGT ACAAGGCTAT AGGTCCGCAC 2040
GTTGCCGTGG CAAAAAGGTT AGCCGCTAGA GGAGTAAAGG TGAGGCCTGG CATGGTGATA 2100
GGGTACATAG TGCTGAGGGG AGACGGGCCA ATAAGCAAGA GGGCTATCCT TGCAGAGGAG 2160
TTCGATCTCA GGAAGCATAA GTATGACGCT GAGTATTACA TAGAAAATCA GGTTTTACCT 2220
GCCGTTCTTA GAATATTAGA GGCCTTTGGG TACAGGAAAG AAGACCTCAG GTGGCAGAAG 2280
ACTAAACAGA CAGGTCTTAC GGCATGGCTT AACATCAAGA AGAAG TAA            2328
```

FIG. 8BBB-3

| FIG. 8CCC-1 |
|---|
| FIG. 8CCC-2 |

FIG. 8CCC

JDF-3 - Sac7d fusion protein

Nucleotide sequence (SEQ ID NO: 39) // Nucleotide sequence (SEQ ID NO: 69)
Nucleotide sequence (SEQ ID NO: 40) // Nucleotide sequence (SEQ ID NO: 69)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

ATGATCCTTGACGTTGATTACATCACCGAGAATGGAAAGCCCGTCATCAGGGTCTTCAAGAAGGAGAACGGCGAGTTCAGGATTGAATACGACCGCGAGTTCGAGCCCTACTTCT
ACGCGCTCCTCAGGGACGACTCTGCCATCGAAGAAATCAAAAAGATAACCGCGGAGAGGCACGGCAGGGTCGTTAAGGTTAAGCGCGCGGAGAAGGTGAAGAAAAAGTTCCTCGG
CAGGTCTGTGGAGGTCTGGGTCCTCTACTTCACGCACCCGCAGGACXXXCCGGCAATCCGCGACAAAATAAGGAAGCACCCCGCGGTCATCGACATCTACGAGTACGACATACCC
TTCGCCAAGCGCTACCTCATAGACAAGGGCCTAATCCCGATGGAAGGTGAGGAAGAGCTTAAACTCATGTCCTTCGACATCGAGACGCTCTACCACGAGGGAGAAGAGTTTGGAA
CCGGGCCGATTCTGATGATAAGCTACGCCGATGAAAGCGAGGCGCGCGTGATAACCTGGAAGAAGATCGACCTTCCTTACGTTGAGGTTGTCTCCACCGAGAAGGAGATGATTAA
GCGCTTCTTGAGGGTCGTTAAGGAGAAGGACCCGGACGTGCTGATAACATACAACGGCGACAACTTCGACTTCGCCTACCTGAAAAAGCGCTGTGAGAAGCTTGGCGTGAGCTTT
ACCCTCGGGAGGGACGGGAGCGAGCCGAAGATACAGCGCATGGGGGACAGGTTTGCGGTCGAGGTGAAGGGCAGGGTACACTTCGACCTTTATCCAGTCATAAGGCGCACCATAA
ACCTCCCGACCTACACCCTTGAGGCTGTATACGAGGCGGTTTTCGGCAAGCCCAAGGAGAAGGTCTACGCCGAGGAGATAGCCACCGCCTGGGAGACCGGCGAGGGGCTTGAGAG
GGTCGCGCGCTACTCGATGGAGGACGCGAGGGTTACCTACGAGCTTGGCAGGGAGTTCTTCCCGATGGAGGCCCAGCTTTCCAGGCTCATCGGCCAAGGCCTCTGGGACGTTTCC

FIG. 8CCC-1

CGCTCCAGCACCGGCAACCTCGTCGAGTGGTTCCTCCTAAGGAAGGCCTACGAGAGGAACGAACTCGCTCCCAACAAGCCCGACGAGAGGGAGCTGGCGAGGAGAAGGGGGGCT
ACgcCGGTGGCTACGTCAAGGAGCCGGAGCGGGGACTGTGGACAATATCGTGTATCTAGACTTTCGTAGTCTCTACCCTTCAATCATAATCACCCACAACGTCTCGCCAGATAC
GCTCAACCGCGAGGGGTGTAGGAGCTACGACGTTGCCCCCGAGGTCGGTCACAAGTTCTGCAAGGACTTCCCCGGCTTCATTCCGAGCCTGCTCGGAAACCTGCTGGAGGAAAGG
CAGAAGATAAAGAGGAAGATGAAGGCAACTCTCGACCCGCTGGAGAAGAATCTCCTCGATTACAGGCAACGCGCCATCAAGATTCTCGCCAACAGCTACTACGGCTACTACGGCT
ATGCCAGGGCAAGATGGTACTGCAGGGAGTGCGCCGAGAGCGTTACGGCATGGGGAAGGGAGTACATCGAAATGGTCATCAGAGAGCTTGAGGAAAAGTTCGGTTTTAAAGTCCT
CTATGCAGACACAGACGGTCTCCATGCCACCATTCCTGGAGCGGACGCTGAAACAGTCAAGAAAAAGGCAATGGAGTTCTTAAACTATATCAATCCCAAACTGCCCGGCCTTCTC
GAACTCGAATACGAGGGCTTCTACGTCAGGGGCTTCTTCGTCACGAAGAAAAAGTACGCGGTCATCGACGAGGAGGGCAAGATAACCACGCGCGGGCTTGAGATAGTCAGGCGCG
ACTGGAGCGAGATAGCGAAGGAGACGCAGGCGAGGGTTTTGGAGGCGATACTCAGGCACGGTGACGTTGAAGAGGCCGTCAGAATTGTCAGGGAAGTCACCGAAAAGCTGAGCAA
GTACGAGGTTCCGCCGGAGAAGCTGGTTATCCACGAGCAGATAACGCGCGAGCTCAAGGACTACAAGGCCACCGGCCCGCACGTAGCCATAGCGAAgcGTTTGGCCGCCAGAGGT
GTTAAAATCCGGCCCGGAACTGTGATAAGCTACATCGTTCTGAAGGGCTCCGGAAGGATAGGCGACAGGGCGATTCCCTTCGACGAGTTCGACCCGACGAAGCACAAGTACGATG
CGGACTACTACATCGAGAACCAGGTTCTGCCGGCAGTTGAGAGAATCCTCAGGGCCTTCGGCTACCGCAAGGAAGACCTGCGCTACCAGAAGACGAGGCAGGTCGGGCTTGGCGC
GTGGCTGAAGCCGAAGGGGAAGAAGAAG//

//ATG GTG AAG GTA AAG TTC AAG TAT AAG GGT GAA GAG AAA GAA GTA GAC ACT TCA
AAG ATA AAG AAG GTT TGG AGA GTA GGC AAA ATG GTG TCC TTT ACC TAT GAC GAC
AAT GGT AAG ACA GGT AGA GGA GCT GTA AGC GAG AAA GAT GCT CCA AAA GAA TTA
TTA GAC ATG TTA GCA AGA GCA GAA AGA GAG AAG AAA // TAG

FIG. 8CCC-2

| FIG. 8DDD-1 |
| --- |
| FIG. 8DDD-2 |

FIG. 8DDD

<u>Sac7d - JDF-3 fusion protein</u>

Nucleotide sequence (SEQ ID NO: 69) // Nucleotide sequence (SEQ ID NO: 39)
Nucleotide sequence (SEQ ID NO: 69) // Nucleotide sequence (SEQ ID NO: 40)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

//ATG GTG AAG GTA AAG TTC AAG TAT AAG GGT GAA GAG AAA GAA GTA GAC ACT TCA
AAG ATA AAG AAG GTT TGG AGA GTA GGC AAA ATG GTG TCC TTT ACC TAT GAC GAC
AAT GGT AAG ACA GGT AGA GGA GCT GTA AGC GAG AAA GAT GCT CCA AAA GAA TTA
TTA GAC ATG TTA GCA AGA GCA GAA AGA GAG AAG AAA //

//ATGATCCTTGACGTTGATTACATCACCGAGAATGGAAAGCCCGTCATCAGGGTCTTCAAGAAGGAGAACGGCGAGTTCAGGATTGAATACGACCGCGAGTTCGAGCCCTACTT
CTACGCGCTCCTCAGGGACGACTCTGCCATCGAAGAAATCAAAAAGATAACCGCGGAGAGGCACGGCAGGGTCGTTAAGGTTAAGCGCGCGGAGAAGGTGAAGAAAAAGTTCCTC
GGCAGGTCTGTGGAGGTCTGGGTCCTCTACTTCACGCACCCGCAGGAC<u>XXX</u>CCGGCAATCCGCGACAAAATAAGGAAGCACCCCGCGGTCATCGACATCTACGAGTACGACATAC

FIG. 8DDD-1

CCTTCGCCAAGCGCTACCTCATAGACAAGGGCCTAATCCCGATGGAAGGTGAGGAAGAGCTTAAACTCATGTCCTTCGACATCGAGACGCTCTACCACGAGGGAGAAGAGTTTGG
AACCGGGCCGATTCTGATGATAAGCTACGCCGATGAAAGCGAGGCGCGCGTGATAACCTGGAAGAAGATCGACCTTCCTTACGTTGAGGTTGTCTCCACCGAGAAGGAGATGATT
AAGCGCTTCTTGAGGGTCGTTAAGGAGAAGGACCCGGACGTGCTGATAACATACAACGGCGACAACTTCGACTTCGCCTACCTGAAAAAGCGCTGTGAGAAGCTTGGCGTGAGCT
TTACCCTCGGGAGGGACGGGAGCGAGCCGAAGATACAGCGCATGGGGGACAGGTTTGCGGTCGAGGTGAAGGGCAGGGTACACTTCGACCTTTATCCAGTCATAAGGCGCACCAT
AAACCTCCCGACCTACACCCTTGAGGCTGTATACGAGGCGGTTTTCGGCAAGCCCAAGGAGAAGGTCTACGCCGAGGAGATAGCCACCGCCTGGGAGACCGGCGAGGGGCTTGAG
AGGGTCGCGCGCTACTCGATGGAGGACGCGAGGGTTACCTACGAGCTTGGCAGGGAGTTCTTCCCGATGGAGGCCCAGCTTTCCAGGCTCATCGGCCAAGGCCTCTGGGACGTTT
CCCGCTCCAGCACCGGCAACCTCGTCGAGTGGTTCCTCCTAAGGAAGGCCTACGAGAGGAACGAACTCGCTCCCAACAAGCCCGACGAGAGGGAGCTGGCGAGGAGAAGGGGGGG
CTACgcCGGTGGCTACGTCAAGGAGCCGGAGCGGGGACTGTGGGACAATATCGTGTATCTAGACTTTCGTAGTCTCTACCCTTCAATCATAATCACCCACAACGTCTCGCCAGAT
ACGCTCAACCGCGAGGGGTGTAGGAGCTACGACGTTGCCCCCGAGGTCGGTCACAAGTTCTGCAAGGACTTCCCCGGCTTCATTCCGAGCCTGCTCGGAAACCTGCTGGAGGAAA
GGCAGAAGATAAAGAGGAAGATGAAGGCAACTCTCGACCCGCTGGAGAAGAATCTCCTCGATTACAGGCAACGCGCCATCAAGATTCTCGCCAACAGCTACTACGGCTACTACGG
CTATGCCAGGGCAAGATGGTACTGCAGGGAGTGCGCCGAGAGCGTTACGGCATGGGGAAGGGAGTACATCGAAATGGTCATCAGAGAGCTTGAGGAAAAGTTCGGTTTTAAAGTC
CTCTATGCAGACACAGACGGTCTCCATGCCACCATTCCTGGAGCGGACGCTGAAACAGTCAAGAAAAAGGCAATGGAGTTCTTAAACTATATCAATCCCAAACTGCCCGGCCTTC
TCGAACTCGAATACGAGGGCTTCTACGTCAGGGGCTTCTTCGTCACGAAGAAAAAGTACGCGGTCATCGACGAGGAGGGCAAGATAACCACGCGCGGGCTTGAGATAGTCAGGCG
CGACTGGAGCGAGATAGCGAAGGAGACGCAGGCGAGGGTTTTGGAGGCGATACTCAGGCACGGTGACGTTGAAGAGGCCGTCAGAATTGTCAGGGAAGTCACCGAAAAGCTGAGC
AAGTACGAGGTTCCGCCGGAGAAGCTGGTTATCCACGAGCAGATAACGCGCGAGCTCAAGGACTACAAGGCCACCGGCCCGCACGTAGCCATAGCGAAgcGTTTGGCCGCCAGAG
GTGTTAAAATCCGGCCCGGAACTGTGATAAGCTACATCGTTCTGAAGGGCTCCGGAAGGATAGGCGACAGGGCGATTCCCTTCGACGAGTTCGACCCGACGAAGCACAAGTACGA
TGCGGACTACTACATCGAGAACCAGGTTCTGCCGGCAGTTGAGAGAATCCTCAGGGCCTTCGGCTACCGCAAGGAAGACCTGCGCTACCAGAAGACGAGGCAGGTCGGGCTTGGC
GCGTGGCTGAAGCCGAAGGGGAAGAAGAAGTGA

FIG. 8DDD-2

Synthetic Sso7d gene:

Nucleotide sequence (SEQ ID NO: 71)
Amino acid sequence (SEQ ID NO: 72)

```
 A   T   V   K   F   K   Y   K   G   E   E   K   E   V   D   I   S   K
GCA ACC GTA AAG TTC AAG TAC AAA GGC GAA GAA AAA GAG GTA GAC ATC TCC AAG

 I   K   K   V   W   R   V   G   K   M   I   S   F   T   Y   D   E   G
ATC AAG AAA GTA TGG CGT GTG GGC AAG ATG ATC TCC TTC ACC TAC GAC GAG GGC

 G   G   K   T   G   R   G   A   V   S   E   K   D   A   P   K   E   L
GGT GGC AAG ACC GGC CGT GGT GCG GTA AGC GAA AAG GAC GCG CCG AAG GAG CTG

 L   Q   M   L   E   K   Q   K   K
CTG CAG ATG CTG GAG AAG CAG AAA AAG
```

FIG. 8EEE

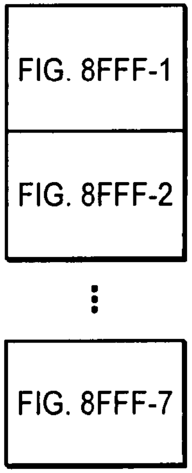

FIG. 8FFF

Sso7d-Taq DNA polymerase fusion protein

Nucleotide sequence (SEQ ID NO: 71) // Nucleotide sequence (SEQ ID NO: 65)
Amino acid sequence (SEQ ID NO: 72) // Amino acid sequence (SEQ ID NO: 66)

```
 // A   T   V   K   F   K   Y   K   G   E   E   K   E   V   D   I   S   K
// GCA ACC GTA AAG TTC AAG TAC AAA GGC GAA GAA AAA GAG GTA GAC ATC TCC AAG

  I   K   K   V   W   R   V   G   K   M   I   S   F   T   Y   D   E   G
 ATC AAG AAA GTA TGG CGT GTG GGC AAG ATG ATC TCC TTC ACC TAC GAC GAG GGC

  G   G   K   T   G   R   G   A   V   S   E   K   D   A   P   K   E   L
 GGT GGC AAG ACC GGC CGT GGT GCG GTA AGC GAA AAG GAC GCG CCG AAG GAG CTG

  L   Q   M   L   E   K   Q   K   K      //     G   G   G
 CTG CAG ATG CTG GAG AAG CAG AAA AAG    //     GGC GGC GGT
```

FIG. 8FFF-1

```
 V   T   S   G   M   L   P   L   F   E   P   K   G   R   V   L   L   V
GTC ACT AGT GGG ATG CTG CCC CTC TTT GAG CCC AAG GGC CGG GTC CTC CTG GTG

 D   G   H   H   L   A   Y   R   T   F   H   A   L   K   G   L   T   T
GAC GGC CAC CAC CTG GCC TAC CGC ACC TTC CAC GCC CTG AAG GGC CTC ACC ACC

 S   R   G   E   P   V   Q   A   V   Y   G   F   A   K   S   L   L   K
AGC CGG GGG GAG CCG GTG CAG GCG GTC TAC GGC TTC GCC AAG AGC CTC CTC AAG

 A   L   K   E   D   G   D   A   V   I   V   V   F   D   A   K   A   P
GCC CTC AAG GAG GAC GGG GAC GCG GTG ATC GTG GTC TTT GAC GCC AAG GCC CCC

 S   F   R   H   E   A   Y   G   G   Y   K   A   G   R   A   P   T   P
TCC TTC CGC CAC GAG GCC TAC GGG GGG TAC AAG GCG GGC CGG GCC CCC ACG CCA

 E   D   F   P   R   Q   L   A   L   I   K   E   L   V   D   L   L   G
GAG GAC TTT CCC CGG CAA CTC GCC CTC ATC AAG GAG CTG GTG GAC CTC CTG GGG

 L   A   R   L   E   V   P   G   Y   E   A   D   D   V   L   A   S   L
CTG GCG CGC CTC GAG GTC CCG GGC TAC GAG GCG GAC GAC GTC CTG GCC AGC CTG

 A   K   K   A   E   K   E   G   Y   E   V   R   I   L   T   A   D   K
GCC AAG AAG GCG GAA AAG GAG GGC TAC GAG GTC CGC ATC CTC ACC GCC GAC AAA
```

FIG. 8FFF-2

```
 D   L   Y   Q   L   L   S   D   R   I   H   V   L   H   P   E   G   Y
GAC CTT TAC CAG CTC CTT TCC GAC CGC ATC CAC GTC CTC CAC CCC GAG GGG TAC

 L   I   T   P   A   W   L   W   E   K   Y   G   L   R   P   D   Q   W
CTC ATC ACC CCG GCC TGG CTT TGG GAA AAG TAC GGC CTG AGG CCC GAC CAG TGG

 A   D   Y   R   A   L   T   G   D   E   S   D   N   L   P   G   V   K
GCC GAC TAC CGG GCC CTG ACC GGG GAC GAG TCC GAC AAC CTT CCC GGG GTC AAG

 G   I   G   E   K   T   A   R   K   L   L   E   E   W   G   S   L   E
GGC ATC GGG GAG AAG ACG GCG AGG AAG CTT CTG GAG GAG TGG GGG AGC CTG GAA

 A   L   L   K   N   L   D   R   L   K   P   A   I   R   E   K   I   L
GCC CTC CTC AAG AAC CTG GAC CGG CTG AAG CCC GCC ATC CGG GAG AAG ATC CTG

 A   H   M   D   D   L   K   L   S   W   D   L   A   K   V   R   T   D
GCC CAC ATG GAC GAT CTG AAG CTC TCC TGG GAC CTG GCC AAG GTG CGC ACC GAC

 L   P   L   E   V   D   F   A   K   R   R   E   P   D   R   E   R   L
CTG CCC CTG GAG GTG GAC TTC GCC AAA AGG CGG GAG CCC GAC CGG GAG AGG CTT

 R   A   F   L   E   R   L   E   F   G   S   L   L   H   E   F   G   L
AGG GCC TTT CTG GAG AGG CTT GAG TTT GGC AGC CTC CTC CAC GAG TTC GGC CTT
```

FIG. 8FFF-3

```
 L   E   S   P   K   A   L   E   E   A   P   W   P   P   P   E   G   A
CTG GAA AGC CCC AAG GCC CTG GAG GAG GCC CCC TGG CCC CCG CCG GAA GGG GCC

 F   V   G   F   V   L   S   R   K   E   P   M   W   A   D   L   L   A
TTC GTG GGC TTT GTG CTT TCC CGC AAG GAG CCC ATG TGG GCC GAT CTT CTG GCC

 L   A   A   A   R   G   G   R   V   H   R   A   P   E   P   Y   K   A
CTG GCC GCC GCC AGG GGG GGC CGG GTC CAC CGG GCC CCC GAG CCT TAT AAA GCC

 L   R   D   L   K   E   A   R   G   L   L   A   K   D   L   S   V   L
CTC AGG GAC CTG AAG GAG GCG CGG GGG CTT CTC GCC AAA GAC CTG AGC GTT CTG

 A   L   R   E   G   L   G   L   P   P   G   D   D   P   M   L   L   A
GCC CTG AGG GAA GGC CTT GGC CTC CCG CCC GGC GAC GAC CCC ATG CTC CTC GCC

 Y   L   L   D   P   S   N   T   T   P   E   G   V   A   R   R   Y   G
TAC CTC CTG GAC CCT TCC AAC ACC ACC CCC GAG GGG GTG GCC CGG CGC TAC GGC

 G   E   W   T   E   E   A   G   E   R   A   A   L   S   E   R   L   F
GGG GAG TGG ACG GAG GAG GCG GGG GAG CGG GCC GCC CTT TCC GAG AGG CTC TTC

 A   N   L   W   G   R   L   E   G   E   E   R   L   L   W   L   Y   R
GCC AAC CTG TGG GGG AGG CTT GAG GGG GAG GAG AGG CTC CTT TGG CTT TAC CGG
```

FIG. 8FFF-4

```
 E   V   E   R   P   L   S   A   V   L   A   H   M   E   A   T   G   V
GAG GTG GAG AGG CCC CTT TCC GCT GTC CTG GCC CAC ATG GAG GCC ACG GGG GTG

 R   L   D   V   A   Y   L   R   A   L   S   L   E   V   A   E   E   I
CGC CTG GAC GTG GCC TAT CTC AGG GCC TTG TCC CTG GAG GTG GCC GAG GAG ATC

 A   R   L   E   A   E   V   F   R   L   A   G   H   P   F   N   L   N
GCC CGC CTC GAG GCC GAG GTC TTC CGC CTG GCC GGC CAC CCC TTC AAC CTC AAC

 S   R   D   Q   L   E   R   V   L   F   D   E   L   G   L   P   A   I
TCC CGG GAC CAG CTG GAA AGG GTC CTC TTT GAC GAG CTA GGG CTT CCC GCC ATC

 G   K   T   E   K   T   G   K   R   S   T   S   A   A   V   L   E   A
GGC AAG ACG GAG AAG ACC GGC AAG CGC TCC ACC AGC GCC GCC GTC CTG GAG GCC

 L   R   E   A   H   P   I   V   E   K   I   L   Q   Y   R   E   L   T
CTC CGC GAG GCC CAC CCC ATC GTG GAG AAG ATC CTG CAG TAC CGG GAG CTC ACC

 K   L   K   S   T   Y   I   D   P   L   P   D   L   I   H   P   R   T
AAG CTG AAG AGC ACC TAC ATT GAC CCC TTG CCG GAC CTC ATC CAC CCC AGG ACG

 G   R   L   H   T   R   F   N   Q   T   A   T   A   T   G   R   L   S
GGC CGC CTC CAC ACC CGC TTC AAC CAG ACG GCC ACG GCC ACG GGC AGG CTA AGT
```

FIG. 8FFF-5

```
 S   S   D   P   N   L   Q   N   I   P   V   R   T   P   L   G   Q   R
AGC TCC GAT CCC AAC CTC CAG AAC ATC CCC GTC CGC ACC CCG CTT GGG CAG AGG

 I   R   R   A   F   I   A   E   E   G   W   L   L   V   A   L   D   Y
ATC CGC CGG GCC TTC ATC GCC GAG GAG GGG TGG CTA TTG GTG GCC CTG GAC TAT

 S   Q   I   E   L   R   V   L   A   H   L   S   G   D   E   N   L   I
AGC CAG ATA GAG CTC AGG GTG CTG GCC CAC CTC TCC GGC GAC GAG AAC CTG ATC

 R   V   F   Q   E   G   R   D   I   H   T   E   T   A   S   W   M   F
CGG GTC TTC CAG GAG GGG CGG GAC ATC CAC ACG GAG ACC GCC AGC TGG ATG TTC

 G   V   P   R   E   A   V   D   P   L   M   R   R   A   A   K   T   I
GGC GTC CCC CGG GAG GCC GTG GAC CCC CTG ATG CGC CGG GCG GCC AAG ACC ATC

 N   F   G   V   L   Y   G   M   S   A   H   R   L   S   Q   E   L   A
AAC TTC GGG GTC CTC TAC GGC ATG TCG GCC CAC CGC CTC TCC CAG GAG CTA GCC

 I   P   Y   E   E   A   Q   A   F   I   E   R   Y   F   Q   S   F   P
ATC CCT TAC GAG GAG GCC CAG GCC TTC ATT GAG CGC TAC TTT CAG AGC TTC CCC

 K   V   R   A   W   I   E   K   T   L   E   E   G   R   R   R   G   Y
AAG GTG CGG GCC TGG ATT GAG AAG ACC CTG GAG GAG GGC AGG AGG CGG GGG TAC
```

FIG. 8FFF-6

```
 V   E   T   L   F   G   R   R   R   Y   V   P   D   L   E   A   R   V
GTG GAG ACC CTC TTC GGC CGC CGC CGC TAC GTG CCA GAC CTA GAG GCC CGG GTG

 K   S   V   R   E   A   A   E   R   M   A   F   N   M   P   V   Q   G
AAG AGC GTG CGG GAG GCG GCC GAG CGC ATG GCC TTC AAC ATG CCC GTC CAG GGC

 T   A   A   D   L   M   K   L   A   M   V   K   L   F   P   R   L   E
ACC GCC GCC GAC CTC ATG AAG CTG GCT ATG GTG AAG CTC TTC CCC AGG CTG GAG

 E   M   G   A   R   M   L   L   Q   V   H   D   E   L   V   L   E   A
GAA ATG GGG GCC AGG ATG CTC CTT CAG GTC CAC GAC GAG CTG GTC CTC GAG GCC

 P   K   E   R   A   E   A   V   A   R   L   A   K   E   V   M   E   G
CCA AAA GAG AGG GCG GAG GCC GTG GCC CGG CTG GCC AAG GAG GTC ATG GAG GGG

 V   Y   P   L   A   V   P   L   E   V   E   V   G   I   G   E   D   W
GTG TAT CCC CTG GCC GTG CCC CTG GAG GTG GAG GTG GGG ATA GGG GAG GAC TGG

 L   S   A   K   E   G   I   D   G   R   G   G   G   G   H   H   H   H
CTC TCC GCC AAG GAG GGC ATT GAT GGC CGC GGC GGA GGC GGG CAT CAT CAT CAT

 H   H   *
CAT CAT TAA
```

FIG. 8FFF-7

Pfu DNA Polymerase (WT) -Sso7d fusion protein

Nucleotide sequence (SEQ ID NO: 61) // Nucleotide sequence (SEQ ID NO: 71)

//
ccctggtcct gggtccacat atatgttctt actcgccttt atgaagaatc ccccagtcgc tctaacctgg gttatagtga caaatcttcc tccaccaccg cccaagaagg ttatttctat caactctaca cctcccctat tttctctctt atgagatttt taagtatagt tatagagaag gttttatact ccaaactgag ttagtagata tgtggggagc ataatgattt tagatgtgga

FIG. 8GGG-1

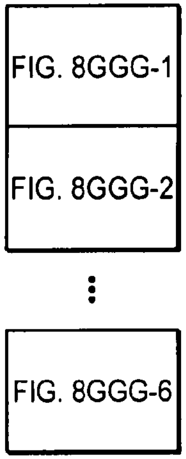

FIG. 8GGG ttacataact gaagaaggaa aacctgttat taggctattc aaaaaagaga acggaaaatt taagatagag catgatagaa cttttagacc atacatttac gctcttctca gggatgattc aaagattgaa gaagttaaga aaataacggg ggaaaggcat ggaaagattg tgagaattgt tgatgtagag aaggttgaga aaaagtttct cggcaagcct attaccgtgt ggaaacttta tttggaacat ccccaagatg ttcccactat tagagaaaaa gttagagaac atccagcagt tgtggacatc ttcgaatacg atattccatt tgcaaagaga tacctcatcg acaaaggcct aataccaatg gaggggggaag aagagctaaa gattcttgcc ttcgatatag aaaccctcta tcacgaagga gaagagtttg gaaaaggccc aattataatg attagttatg cagatgaaaa tgaagcaaag gtgattactt ggaaaaacat agatcttcca tacgttgagg ttgtatcaag cgagagagag atgataaaga gatttctcag gattatcagg gagaaggatc ctgacattat agttacttat aatggagact cattcgactt cccatattta gcgaaaaggg cagaaaaact

FIG. 8GGG-2 tgggattaaa ttaaccattg gaagagatgg aagcgagccc aagatgcaga gaataggcga tatgacggct gtagaagtca agggaagaat acatttcgac ttgtatcatg taataacaag gacaataaat ctcccaacat acacactaga ggctgtatat gaagcaattt ttggaaagcc aaaggagaag gtatacgccg acgagatagc aaaagcctgg gaaagtggag agaaccttga gagagttgcc aaatactcga tggaagatgc aaaggcaact tatgaactcg ggaaagaatt ccttccaatg gaaattcagc tttcaagatt agttggacaa cctttatggg atgtttcaag gtcaagcaca gggaaccttg tagagtggtt cttacttagg aaagcctacg aaagaaacga agtagctcca aacaagccaa gtgaagagga gtatcaaaga aggctcaggg agagctacac aggtggattc gttaaagagc cagaaaaggg gttgtgggaa aacatagtat acctagattt tagagcccta tatccctcga ttataattac ccacaatgtt tctcccgata ctctaaatct tgagggatgc aagaactatg atatcgctcc tcaagtaggc cacaagttct gcaaggacat ccctggtttt ataccaagtc tcttgggaca tttgttagag gaaagacaaa agattaagac

FIG. 8GGG-3 aaaaatgaag gaaactcaag atcctataga aaaaatactc cttgactata gacaaaaagc gataaaactc ttagcaaatt ctttctacgg atattatggc tatgcaaaag caagatggta ctgtaaggag tgtgctgaga gcgttactgc ctggggaaga aagtacatcg agttagtatg gaaggagctc gaagaaaagt ttggatttaa agtcctctac attgacactg atggtctcta tgcaactatc ccaggaggag aaagtgagga aataaagaaa aaggctctag aatttgtaaa atacataaat tcaaagctcc ctggactgct agagcttgaa tatgaagggt tttataagag gggattcttc gttacgaaga agaggtatgc agtaatagat gaagaaggaa aagtcattac tcgtggttta gagatagtta ggagagattg gagtgaaatt gcaaaagaaa ctcaagctag agttttggag acaatactaa aacacggaga tgttgaagaa gctgtgagaa tagtaaaaga agtaatacaa aagcttgcca attatgaaat tccaccagag aagctcgcaa tatatgagca gataacaaga ccattacatg agtataaggc gataggtcct cacgtagctg ttgcaaagaa actagctgct aaaggagtta aaataaagcc aggaatggta attggataca tagtacttag

FIG. 8GGG-4 aggcgatggt ccaattagca atagggcaat tctagctgag gaatacgatc ccaaaaagca caagtatgac gcagaatatt acattgagaa ccaggttctt ccagcggtac ttaggatatt ggagggattt ggatacagaa aggaagacct cagataccaa aagacaagac aagtcggcct aacttcctgg cttaacatta aaaaatccta gaaaagcgat agatatcaac ttttattctt tctaaccttt ttctatgaaa gaagaactga gcaggaatta ccagttcttc cgttatttta tgggtaatta aaaacccatg ctcttgggag aatcttcgaa taaaatccct aacttcaggc tttgctaagt gaatagaata aacaacatca ctcacttcaa acgccttcgt tagaaatggt ctatctgcat gcttctctgg ctcggaanng gaggattcat aacaacagta tcaacattct cagagaattg agaaacatca gaaactttga cttctacaac atttctaact ttgcaactct tcaagatttt ctaaaagaat tttaacggcc tcctcgtcaa tttcgacgac gtagatcttt tttgctccaa gcagagccgc tccaatggat aacacccctg ttcccgcacc caagtccgct acaatttttt ccttgtatct cctaatgtat aagcaagcca aaggagagta gatgctacct

FIG. 8GGG-5 ttccgggagt tttgtattgc tctagccaag gtttgggatt tttgaatcct ttaactctgg aaagtataat ttcaagctcc ttcttcttca tgacagatga aaaattgttt tgtctctttt taacttttac agaaataact gtctcaaatt atgacaactc ttgacatttt tacttcatta ccagggtaat gtttttaagt atgaaatttt tctttcatag aggaggnnnn nngtcctctc ctcgatttcc ttggttgtgc tccatatgat aagcttccaa agtgggtgtt cagactttta gacactcaaa taccagacga caatggtgtg ctcactcaag ccccatatgg gttgagaaaa gtagaagcgg cactactcag atgcttcccc aggaatgagg ttgttgtagc tcntcccnga aagattgaga tgttcttgg //

// GCA ACC GTA AAG TTC AAG TAC AAA GGC GAA GAA AAA GAG GTA GAC ATC TCC AAG

ATC AAG AAA GTA TGG CGT GTG GGC AAG ATG ATC TCC TTC ACC TAC GAC GAG GGC

GGT GGC AAG ACC GGC CGT GGT GCG GTA AGC GAA AAG GAC GCG CCG AAG GAG CTG

CTG CAG ATG CTG GAG AAG CAG AAA AAG // TGA

PFU DNA POLYMERASE (V93 R OR E) -Sso7d fusion protein

Nucleotide sequence (SEQ ID NO: 27) // Nucleotide sequence (SEQ ID NO: 71)
Nucleotide sequence (SEQ ID NO: 28) // Nucleotide sequence (SEQ ID NO: 71)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATTTTAG ATGTGGATTA CATAACTGAA GAAGGAAAAC CTGTTATTAG GCTATTCAAA 60
AAAGAGAACG GAAAATTTAA GATAGAGCAT
GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC
CAAGATXXXC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GATATAGAAA CCCTCTATCA CGAAGGAGAA
GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT
GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC
CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA
```

FIG. 8HHH-1

ATTCAGCTTT CAAGATTAGT TGGACAACCT 1020
TTATGGGATG TTTCAAGGTC AAGCACAGGG AACCTTGTAG AGTGGTTCTT ACTTAGGAAA
1080 GCCTACGAAA GAAACGAAGT AGCTCCAAAC AAGCCAAGTG AAGAGGAGTA TCAAAGAAGG 1140 CTCAGGGAGA GCTACACAGG
TGGATTCGTT AAAGAGCCAG AAAAGGGGTT GTGGGAAAAC 1200
ATAGTATACC TAGATTTTAG AGCCCTATAT CCCTCGATTA TAATTACCCA
CAATGTTTCT 1260 CCCGATACTC TAAATCTTGA GGGATGCAAG AACTATGATA TCGCTCCTCA AGTAGGCCAC 1320 AAGTTCTGCA
AGGACATCCC TGGTTTTATA CCAAGTCTCT TGGGACATTT GTTAGAGGAA 1380
AGACAAAAGA TTAAGACAAA AATGAAGGAA ACTCAAGATC
CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA
GAAAAGTTTG GATTTAAAGT CCTCTACATT 1620
GACACTGATG GTCTCTATGC AACTATCCCA GGAGGAGAAA GTGAGGAAAT AAAGAAAAAG
1680 GCTCTAGAAT TTGTAAAATA CATAAATTCA AAGCTCCCTG GACTGCTAGA GCTTGAATAT 1740 GAAGGGTTTT ATAAGAGGGG
ATTCTTCGTT ACGAAGAAGA GGTATGCAGT AATAGATGAA 1800
GAAGGAAAAG TCATTACTCG TGGTTTAGAG ATAGTTAGGA GAGATTGGAG
TGAAATTGCA 1860 AAAGAAACTC AAGCTAGAGT TTTGGAGACA ATACTAAAAC ACGGAGATGT TGAAGAAGCT 1920 GTGAGAATAG
TAAAAGAAGT AATACAAAAG CTTGCCAATT ATGAAATTCC ACCAGAGAAG 1980
CTCGCAATAT ATGAGCAGAT AACAAGACCA TTACATGAGT
ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA
GAATATTACA TGGAGAACCA GGTTCTTCCA 2220
GCGGTACTTA GGATATTGGA GGGATTTGGA TACAGAAAGG AAGACCTCAG ATACCAAAAG
2280 ACAAGACAAG TCGGCCTAAC TTCCTGGCTT AACATTAAAA AATCC 2328
// GCA ACC GTA AAG TTC AAG TAC AAA GGC GAA GAA AAA GAG GTA GAC ATC TCC AAG
ATC AAG AAA GTA TGG CGT GTG GGC AAG ATG ATC TCC TTC ACC TAC GAC GAG GGC
GGT GGC AAG ACC GGC CGT GGT GCG GTA AGC GAA AAG GAC GCG CCG AAG GAG CTG
CTG CAG ATG CTG GAG AAG CAG AAA AAG // TGA

FIG. 8HHH-2

PFU DNA POLYMERASE (G387P/V93R OR E) -Sso7d fusion protein

Nucleotide sequence (SEQ ID NO: 29) // Nucleotide sequence (SEQ ID NO: 71)
Nucleotide sequence (SEQ ID NO: 30) // Nucleotide sequence (SEQ ID NO: 71)

| FIG. 8III-1 |
| --- |
| FIG. 8III-2 |

FIG. 8III

G387P Mutant (CCN is the codon for Proline where N = C, G, A, or T)
V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATTTTAG ATGTGGATTA CATAACTGAA GAAGGAAAAC CTGTTATTAG GCTATTCAAA 60
AAAGAGAACG GAAAATTTAA GATAGAGCAT
GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC
CAAGATXXXC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GATATAGAAA CCCTCTATCA CGAAGGAGAA
GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT
GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC
CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA
```

FIG. 8III-1

ATTCAGCTTT CAAGATTAGT TGGACAACCT 1020
TTATGGGATG TTTCAAGGTC AAGCACAGGG AACCTTGTAG AGTGGTTCTT ACTTAGGAAA
1080 GCCTACGAAA GAAACGAAGT AGCTCCAAAC AAGCCAAGTG AAGAGGAGTA TCAAAGAAGG 1140 CTCAGGGAGA GCTACACACC
NGGATTCGTT AAAGAGCCAG AAAAGGGGTT GTGGGAAAAC 1200
ATAGTATACC TAGATTTTAG AGCCCTATAT CCCTCGATTA TAATTACCCA
CAATGTTTCT 1260 CCCGATACTC TAAATCTTGA GGGATGCAAG AACTATGATA TCGCTCCTCA AGTAGGCCAC 1320 AAGTTCTGCA
AGGACATCCC TGGTTTTATA CCAAGTCTCT TGGGACATTT GTTAGAGGAA 1380
AGACAAAAGA TTAAGACAAA AATGAAGGAA ACTCAAGATC
CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA
GAAAAGTTTG GATTTAAAGT CCTCTACATT 1620
GACACTGATG GTCTCTATGC AACTATCCCA GGAGGAGAAA GTGAGGAAAT AAAGAAAAAG
1680 GCTCTAGAAT TTGTAAAATA CATAAATTCA AAGCTCCCTG GACTGCTAGA GCTTGAATAT 1740 GAAGGGTTTT ATAAGAGGGG
ATTCTTCGTT ACGAAGAAGA GGTATGCAGT AATAGATGAA 1800
GAAGGAAAAG TCATTACTCG TGGTTTAGAG ATAGTTAGGA GAGATTGGAG
TGAAATTGCA 1860 AAAGAAACTC AAGCTAGAGT TTTGGAGACA ATACTAAAAC ACGGAGATGT TGAAGAAGCT 1920 GTGAGAATAG
TAAAAGAAGT AATACAAAAG CTTGCCAATT ATGAAATTCC ACCAGAGAAG 1980
CTCGCAATAT ATGAGCAGAT AACAAGACCA TTACATGAGT
ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA
GAATATTACA TGGAGAACCA GGTTCTTCCA 2220
GCGGTACTTA GGATATTGGA GGGATTTGGA TACAGAAAGG AAGACCTCAG ATACCAAAAG
2280 ACAAGACAAG TCGGCCTAAC TTCCTGGCTT AACATTAAAA AATCC // 2328

// GCA ACC GTA AAG TTC AAG TAC AAA GGC GAA GAA AAA GAG GTA GAC ATC TCC AAG
ATC AAG AAA GTA TGG CGT GTG GGC AAG ATG ATC TCC TTC ACC TAC GAC GAG GGC
GGT GGC AAG ACC GGC CGT GGT GCG GTA AGC GAA AAG GAC GCG CCG AAG GAG CTG
CTG CAG ATG CTG GAG AAG CAG AAA AAG // TGA

FIG. 8III-2

| FIG. 8JJJ-1 |
| --- |
| FIG. 8JJJ-2 |

FIG. 8JJJ

PFU DNA POLYMERASE(D141A/E143A/V93R OR E)-Sso7d fusion protein

Nucleotide sequence (SEQ ID NO: 31) // Nucleotide sequence (SEQ ID NO: 71)
Nucleotide sequence (SEQ ID NO: 32) // Nucleotide sequence (SEQ ID NO: 71)

D141A/E143A Mutant (GCN is the codon for alanine where N = C, G, A, or T)
V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATTTTAG ATGTGGATTA CATAACTGAA GAAGGAAAAC CTGTTATTAG GCTATTCAAA 60
AAAGAGAACG GAAAATTTAA GATAGAGCAT
GATAGAACTT TTAGACCATA CATTTACGCT 120
CTTCTCAGGG ATGATTCAAA GATTGAAGAA GTTAAGAAAA TAACGGGGGA AAGGCATGGA 180
AAGATTGTGA GAATTGTTGA TGTAGAGAAG GTTGAGAAAA AGTTTCTCGG CAAGCCTATT 240
ACCGTGTGGA AACTTTATTT GGAACATCCC
CAAGATXXXC CCACTATTAG AGAAAAAGTT 300
AGAGAACATC CAGCAGTTGT GGACATCTTC GAATACGATA TTCCATTTGC AAAGAGATAC 360
CTCATCGACA AAGGCCTAAT ACCAATGGAG GGGGAAGAAG AGCTAAAGAT TCTTGCCTTC 420
GCNATAGCNA CCCTCTATCA CGAAGGAGAA
GAGTTTGGAA AAGGCCCAAT TATAATGATT 480
AGTTATGCAG ATGAAAATGA AGCAAAGGTG ATTACTTGGA AAAACATAGA TCTTCCATAC 540
GTTGAGGTTG TATCAAGCGA GAGAGAGATG ATAAAGAGAT TTCTCAGGAT TATCAGGGAG 600
AAGGATCCTG ACATTATAGT TACTTATAAT
GGAGACTCAT TCGCATTCCC ATATTTAGCG 660
AAAAGGGCAG AAAAACTTGG GATTAAATTA ACCATTGGAA GAGATGGAAG CGAGCCCAAG 720
ATGCAGAGAA TAGGCGATAT GACGGCTGTA GAAGTCAAGG GAAGAATACA TTTCGACTTG 780
TATCATGTAA TAACAAGGAC AATAAATCTC
CCAACATACA CACTAGAGGC TGTATATGAA 840
GCAATTTTTG GAAAGCCAAA GGAGAAGGTA TACGCCGACG AGATAGCAAA AGCCTGGGAA 900
AGTGGAGAGA ACCTTGAGAG AGTTGCCAAA TACTCGATGG AAGATGCAAA GGCAACTTAT 960
GAACTCGGGA AAGAATTCCT TCCAATGGAA
```

FIG. 8JJJ-1

ATTCAGCTTT CAAGATTAGT TGGACAACCT 1020
TTATGGGATG TTTCAAGGTC AAGCACAGGG AACCTTGTAG AGTGGTTCTT ACTTAGGAAA
1080 GCCTACGAAA GAAACGAAGT AGCTCCAAAC AAGCCAAGTG AAGAGGAGTA TCAAAGAAGG 1140 CTCAGGGAGA GCTACACA
GTTGGATTCGTT AAAGAGCCAG AAAAGGGGTT GTGGGAAAAC 1200
ATAGTATACC TAGATTTTAG AGCCCTATAT CCCTCGATTA TAATTACCCA
CAATGTTTCT 1260 CCCGATACTC TAAATCTTGA GGGATGCAAG AACTATGATA TCGCTCCTCA AGTAGGCCAC 1320 AAGTTCTGCA
AGGACATCCC TGGTTTTATA CCAAGTCTCT TGGGACATTT GTTAGAGGAA 1380
AGACAAAAGA TTAAGACAAA AATGAAGGAA ACTCAAGATC
CTATAGAAAA AATACTCCTT 1440
GACTATAGAC AAAAAGCGAT AAAACTCTTA GCAAATTCTT TCTACGGATA TTATGGCTAT 1500
GCAAAAGCAA GATGGTACTG TAAGGAGTGT GCTGAGAGCG TTACTGCCTG GGGAAGAAAG 1560
TACATCGAGT TAGTATGGAA GGAGCTCGAA
GAAAAGTTTG GATTTAAAGT CCTCTACATT 1620
GACACTGATG GTCTCTATGC AACTATCCCA GGAGGAGAAA GTGAGGAAAT AAAGAAAAAG
1680 GCTCTAGAAT TTGTAAAATA CATAAATTCA AAGCTCCCTG GACTGCTAGA GCTTGAATAT 1740 GAAGGGTTTT ATAAGAGGGG
ATTCTTCGTT ACGAAGAAGA GGTATGCAGT AATAGATGAA 1800
GAAGGAAAAG TCATTACTCG TGGTTTAGAG ATAGTTAGGA GAGATTGGAG
TGAAATTGCA 1860 AAAGAAACTC AAGCTAGAGT TTTGGAGACA ATACTAAAAC ACGGAGATGT TGAAGAAGCT 1920 GTGAGAATAG
TAAAAGAAGT AATACAAAAG CTTGCCAATT ATGAAATTCC ACCAGAGAAG 1980
CTCGCAATAT ATGAGCAGAT AACAAGACCA TTACATGAGT
ATAAGGCGAT AGGTCCTCAC 2040
GTAGCTGTTG CAAAGAAACT AGCTGCTAAA GGAGTTAAAA TAAAGCCAGG AATGGTAATT 2100
GGATACATAG TACTTAGAGG CGATGGTCCA ATTAGCAATA GGGCAATTCT AGCTGAGGAA 2160
TACGATCCCA AAAAGCACAA GTATGACGCA
GAATATTACA TGGAGAACCA GGTTCTTCCA 2220
GCGGTACTTA GGATATTGGA GGGATTTGGA TACAGAAAGG AAGACCTCAG ATACCAAAAG
2280 ACAAGACAAG TCGGCCTAAC TTCCTGGCTT AACATTAAAA AATCC // 2328

// GCA ACC GTA AAG TTC AAG TAC AAA GGC GAA GAA AAA GAG GTA GAC ATC TCC AAG
ATC AAG AAA GTA TGG CGT GTG GGC AAG ATG ATC TCC TTC ACC TAC GAC GAG GGC
GGT GGC AAG ACC GGC CGT GGT GCG GTA AGC GAA AAG GAC GCG CCG AAG GAG CTG
CTG CAG ATG CTG GAG AAG CAG AAA AAG // TGA

KOD DNA POLYMERASE - Sso7d fusion protein

Nucleotide sequence (SEQ ID NO: 33) // Nucleotide sequence (SEQ ID NO: 71)
Nucleotide sequence (SEQ ID NO: 34) // Nucleotide sequence (SEQ ID NO: 71)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATCCTCG ACACTGACTA CATAACCGAG GATGGAAAGC CTGTCATAAG AATTTTCAAG 60
AAGGAAAACG GCGAGTTTAA GATTGAGTAC GACCGGACTT TTGAACCCTA CTTCTACGCC 120
CTCCTGAAGG ACGATTCTGC CATTGAGGAA GTCAAGAAGA TAACCGCCGA GAGGCACGGG 180
ACGGTTGTAA CGGTTAAGCG GGTTGAAAAG GTTCAGAAGA AGTTCCTCGG GAGACCAGTT 240
GAGGTCTGGA AACTCTACTT TACTCATCCG CAGGACXXXC CAGCGATAAG GGACAAGATA 300
CGAGAGCATC CAGCAGTTAT TGACATCTAC GAGTACGACA TACCCTTCGC CAAGCGCTAC 360
CTCATAGACA AGGGATTAGT GCCAATGGAA GGCGACGAGG AGCTGAAAAT GCTCGCCTTC 420
GACATTGAAA CTCTCTACCA TGAGGGCGAG GAGTTCGCCG AGGGGCCAAT CCTTATGATA 480
AGCTACGCCG ACGAGGAAGG GGCCAGGGTG ATAACTTGGA AGAACGTGGA TCTCCCCTAC 540
```

FIG. 8KKK-1

```
GTTGACGTCG TCTCGACGGA GAGGGAGATG ATAAAGCGCT TCCTCCGTGT TGTGAAGGAG 600
AAAGACCCGG ACGTTCTCAT AACCTACAAC GGCGACAACT TCGACTTCGC CTATCTGAAA 660
AAGCGCTGTG AAAAGCTCGG AATAAACTTC GCCCTCGGAA GGGATGGAAG CGAGCCGAAG 720
ATTCAGAGGA TGGGCGACAG GTTTGCCGTC GAAGTGAAGG GACGGATACA CTTCGATCTC 780
TATCCTGTGA TAAGACGGAC GATAAACCTG CCCACATACA CGCTTGAGGC CGTTTATGAA 840
GCCGTCTTCG GTCAGCCGAA GGAGAAGGTT TACGCTGAGG AAATAACCAC AGCCTGGGAA 900
ACCGGCGAGA ACCTTGAGAG AGTCGCCCGC TACTCGATGG AAGATGCGAA GGTCACATAC 960
GAGCTTGGGA AGGAGTTCCT TCCGATGGAG GCCCAGCTTT CTCGCTTAAT CGGCCAGTCC 1020
CTCTGGGACG TCTCCCGCTC CAGCACTGGC AACCTCGTTG AGTGGTTCCT CCTCAGGAAG 1080
GCCTATGAGA GGAATGAGCT GGCCCCGAAC AAGCCCGATG AAAAGGAGCT GGCCAGAAGA 1140
CGGCAGAGCT ATGAAGGAGG CTATGTAAAA GAGCCCGAGA GAGGGTTGTG GGAGAACATA 1200
GTGTACCTAG ATTTTAGATC CCTGTACCCC TCAATCATCA TCACCCACAA CGTCTCGCCG 1260
GATACGCTCA ACAGAGAAGG ATGCAAGGAA TATGACGTTG CCCCACAGGT CGGCCACCGC 1320
TTCTGCAAGG ACTTCCCAGG ATTTATCCCG AGCCTGCTTG GAGACCTCCT AGAGGAGAGG 1380
CAGAAGATAA AGAAGAAGAT GAAGGCCACG ATTGACCCGA TCGAGAGGAA GCTCCTCGAT 1440
TACAGGCAGA GGGCCATCAA GATCCTGGCA AACAGCTACT ACGGTTACTA CGGCTATGCA 1500
AGGGCGCGCT GGTACTGCAA GGAGTGTGCA GAGAGCGTAA CGGCCTGGGG AAGGGAGTAC 1560
```

FIG. 8KKK-2

```
ATAACGATGA CCATCAAGGA GATAGAGGAA AAGTACGGCT TTAAGGTAAT CTACAGCGAC 1620
ACCGACGGAT TTTTTGCCAC AATACCTGGA GCCGATGCTG AAACCGTCAA AAAGAAGGCT 1680
ATGGAGTTCC TCAAGTATAT CAACGCCAAA CTTCCGGGCG CGCTTGAGCT CGAGTACGAG 1740
GGCTTCTACA AACGCGGCTT CTTCGTCACG AAGAAGAAGT ATGCGGTGAT AGACGAGGAA 1800
GGCAAGATAA CAACGCGCGG ACTTGAGATT GTGAGGCGTG ACTGGAGCGA GATAGCGAAA 1860
GAGACGCAGG CGAGGGTTCT TGAAGCTTTG CTAAAGGACG GTGACGTCGA GAAGGCCGTG 1920
AGGATAGTCA AAGAAGTTAC CGAAAAGCTG AGCAAGTACG AGGTTCCGCC GGAGAAGCTG 1980
GTGATCCACG AGCAGATAAC GAGGGATTTA AAGGACTACA AGGCAACCGG TCCCCACGTT 2040
GCCGTTGCCA AGAGGTTGGC CGCGAGAGGA GTCAAAATAC GCCCTGGAAC GGTGATAAGC 2100
TACATCGTGC TCAAGGGCTC TGGGAGGATA GGCGACAGGG CGATACCGTT CGACGAGTTC 2160
GACCCGACGA AGCACAAGTA CGACGCCGAG TACTACATTG AGAACCAGGT TCTCCCAGCC 2220
GTTGAGAGAA TTCTGAGAGC CTTCGGTTAC CGCAAGGAAG ACCTGCGCTA CCAGAAGACG 2280
AGACAGGTTG GTTTGAGTGC TTGGCTGAAG CCGAAGGGAA CT  2325

// GCA ACC GTA AAG TTC AAG TAC AAA GGC GAA GAA AAA GAG GTA GAC ATC TCC AAG
   ATC AAG AAA GTA TGG CGT GTG GGC AAG ATG ATC TCC TTC ACC TAC GAC GAG GGC
   GGT GGC AAG ACC GGC CGT GGT GCG GTA AGC GAA AAG GAC GCG CCG AAG GAG CTG
   CTG CAG ATG CTG GAG AAG CAG AAA AAG //  TGA
```

| |
|---|
| FIG. 8LLL-1 |
| FIG. 8LLL-2 |
| FIG. 8LLL-3 |

Sso7d - KOD DNA POLYMERASE fusion protein

Nucleotide sequence (SEQ ID NO: 71) // Nucleotide sequence (SEQ ID NO: 33)
Nucleotide sequence (SEQ ID NO: 71) // Nucleotide sequence (SEQ ID NO: 34)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
//GCA ACC GTA AAG TTC AAG TAC AAA GGC GAA GAA AAA GAG GTA GAC ATC TCC AAG
  ATC AAG AAA GTA TGG CGT GTG GGC AAG ATG ATC TCC TTC ACC TAC GAC GAG GGC
  GGT GGC AAG ACC GGC CGT GGT GCG GTA AGC GAA AAG GAC GCG CCG AAG GAG CTG
  CTG CAG ATG CTG GAG AAG CAG AAA AAG   //
```

```
//ATGATCCTCG ACACTGACTA CATAACCGAG GATGGAAAGC CTGTCATAAG AATTTTCAAG 60
AAGGAAAACG GCGAGTTTAA GATTGAGTAC GACCGGACTT TTGAACCCTA CTTCTACGCC 120
CTCCTGAAGG ACGATTCTGC CATTGAGGAA GTCAAGAAGA TAACCGCCGA GAGGCACGGG 180
ACGGTTGTAA CGGTTAAGCG GGTTGAAAAG GTTCAGAAGA AGTTCCTCGG GAGACCAGTT 240
```

FIG. 8LLL-1

GAGGTCTGGA AACTCTACTT TACTCATCCG CAGGACXXXC CAGCGATAAG GGACAAGATA 300
CGAGAGCATC CAGCAGTTAT TGACATCTAC GAGTACGACA TACCCTTCGC CAAGCGCTAC 360
CTCATAGACA AGGGATTAGT GCCAATGGAA GGCGACGAGG AGCTGAAAAT GCTCGCCTTC 420
GACATTGAAA CTCTCTACCA TGAGGGCGAG GAGTTCGCCG AGGGGCCAAT CCTTATGATA 480
AGCTACGCCG ACGAGGAAGG GGCCAGGGTG ATAACTTGGA AGAACGTGGA TCTCCCCTAC 540
GTTGACGTCG TCTCGACGGA GAGGGAGATG ATAAAGCGCT TCCTCCGTGT TGTGAAGGAG 600
AAAGACCCGG ACGTTCTCAT AACCTACAAC GGCGACAACT TCGACTTCGC CTATCTGAAA 660
AAGCGCTGTG AAAAGCTCGG AATAAACTTC GCCCTCGGAA GGGATGGAAG CGAGCCGAAG 720
ATTCAGAGGA TGGGCGACAG GTTTGCCGTC GAAGTGAAGG GACGGATACA CTTCGATCTC 780
TATCCTGTGA TAAGACGGAC GATAAACCTG CCCACATACA CGCTTGAGGC CGTTTATGAA 840
GCCGTCTTCG GTCAGCCGAA GGAGAAGGTT TACGCTGAGG AAATAACCAC AGCCTGGGAA 900
ACCGGCGAGA ACCTTGAGAG AGTCGCCCGC TACTCGATGG AAGATGCGAA GGTCACATAC 960
GAGCTTGGGA AGGAGTTCCT TCCGATGGAG GCCCAGCTTT CTCGCTTAAT CGGCCAGTCC 1020
CTCTGGGACG TCTCCCGCTC CAGCACTGGC AACCTCGTTG AGTGGTTCCT CCTCAGGAAG 1080
GCCTATGAGA GGAATGAGCT GGCCCCGAAC AAGCCCGATG AAAAGGAGCT GGCCAGAAGA 1140
CGGCAGAGCT ATGAAGGAGG CTATGTAAAA GAGCCCGAGA GAGGGTTGTG GGAGAACATA 1200
GTGTACCTAG ATTTTAGATC CCTGTACCCC TCAATCATCA TCACCCACAA CGTCTCGCCG 1260
GATACGCTCA ACAGAGAAGG ATGCAAGGAA TATGACGTTG CCCCACAGGT CGGCCACCGC 1320

FIG. 8LLL-2

TTCTGCAAGG ACTTCCCAGG ATTTATCCCG AGCCTGCTTG GAGACCTCCT AGAGGAGAGG 1380
CAGAAGATAA AGAAGAAGAT GAAGGCCACG ATTGACCCGA TCGAGAGGAA GCTCCTCGAT 1440
TACAGGCAGA GGGCCATCAA GATCCTGGCA AACAGCTACT ACGGTTACTA CGGCTATGCA 1500
AGGGCGCGCT GGTACTGCAA GGAGTGTGCA GAGAGCGTAA CGGCCTGGGG AAGGGAGTAC 1560
ATAACGATGA CCATCAAGGA GATAGAGGAA AAGTACGGCT TTAAGGTAAT CTACAGCGAC 1620
ACCGACGGAT TTTTTGCCAC AATACCTGGA GCCGATGCTG AAACCGTCAA AAAGAAGGCT 1680
ATGGAGTTCC TCAAGTATAT CAACGCCAAA CTTCCGGGCG CGCTTGAGCT CGAGTACGAG 1740
GGCTTCTACA AACGCGGCTT CTTCGTCACG AAGAAGAAGT ATGCGGTGAT AGACGAGGAA 1800
GGCAAGATAA CAACGCGCGG ACTTGAGATT GTGAGGCGTG ACTGGAGCGA GATAGCGAAA 1860
GAGACGCAGG CGAGGGTTCT TGAAGCTTTG CTAAAGGACG GTGACGTCGA GAAGGCCGTG 1920
AGGATAGTCA AAGAAGTTAC CGAAAAGCTG AGCAAGTACG AGGTTCCGCC GGAGAAGCTG 1980
GTGATCCACG AGCAGATAAC GAGGGATTTA AAGGACTACA AGGCAACCGG TCCCCACGTT 2040
GCCGTTGCCA AGAGGTTGGC CGCGAGAGGA GTCAAAATAC GCCCTGGAAC GGTGATAAGC 2100
TACATCGTGC TCAAGGGCTC TGGGAGGATA GGCGACAGGG CGATACCGTT CGACGAGTTC 2160
GACCCGACGA AGCACAAGTA CGACGCCGAG TACTACATTG AGAACCAGGT TCTCCCAGCC 2220
GTTGAGAGAA TTCTGAGAGC CTTCGGTTAC CGCAAGGAAG ACCTGCGCTA CCAGAAGACG 2280
AGACAGGTTG GTTTGAGTGC TTGGCTGAAG CCGAAGGGAA CT //TAG 2325

FIG. 8LLL-3

| |
|---|
| FIG. 8MMM-1 |
| FIG. 8MMM-2 |
| FIG. 8MMM-3 |

FIG. 8MMM

Sso7d-Vent DNA POLYMERASE FUSION PROTEIN

Nucleotide sequence (SEQ ID NO: 71) // Nucleotide sequence (SEQ ID NO: 35)
Nucleotide sequence (SEQ ID NO: 71) // Nucleotide sequence (SEQ ID NO: 36)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
//GCA ACC GTA AAG TTC AAG TAC AAA GGC GAA GAA AAA GAG GTA GAC ATC TCC AAG
  ATC AAG AAA GTA TGG CGT GTG GGC AAG ATG ATC TCC TTC ACC TAC GAC GAG GGC
  GGT GGC AAG ACC GGC CGT GGT GCG GTA AGC GAA AAG GAC GCG CCG AAG GAG CTG
  CTG CAG ATG CTG GAG AAG CAG AAA AAG   //

ATGATACTGG ACACTGATTA CATAACAAAA GATGGCAAGC CTATAATCCG AATTTTTAAG 60
AAAGAGAACG GGGAGTTTAA AATAGAACTT GACCCTCATT TTCAGCCCTA TATATATGCT 120
CTTCTCAAAG ATGACTCCGC TATTGAGGAG ATAAAGGCAA TAAAGGGCGA GAGACATGGA 180
AAAACTGTGA GAGTGCTCGA TGCAGTGAAA GTCAGGAAAA AATTTTTGGG AAGGGAAGTT 240
```

FIG. 8MMM-1

```
GAAGTCTGGA AGCTCATTTT CGAGCATCCC CAAGACXXXC CAGCTATGCG GGGCAAAATA 300
AGGGAACATC CAGCTGTGGT TGACATTTAC GAATATGACA TACCCTTTGC CAAGCGTTAT 360
CTCATAGACA AGGGCTTGAT TCCCATGGAG GGAGACGAGG AGCTTAAGCT CCTTGCCTTT 420
GATATTGAAA CGTTTTATCA TGAGGGAGAT GAATTTGGAA AGGGCGAGAT AATAATGATT 480
AGTTATGCCG ATGAAGAAGA GGCCAGAGTA ATCACATGGA AAAATATCGA TTTGCCGTAT 540
GTCGATGTTG TGTCCAATGA AAGAGAAATG ATAAAGCGTT TTGTTCAAGT TGTTAAAGAA 600
AAAGACCCCG ATGTGATAAT AACTTACAAT GGGGACAATT TTGATTTGCC GTATCTCATA 660
AAACGGGCAG AAAAGCTGGG AGTTCGGCTT GTCTTAGGAA GGGACAAAGA ACATCCCGAA 720
CCCAAGATTC AGAGGATGGG TGATAGTTTT GCTGTGGAAA TCAAGGGTAG AATCCACTTT 780
GATCTTTTCC CAGTTGTGCG AAGGACGATA AACCTCCCAA CGTATACGCT TGAGGCAGTT 840
TATGAAGCAG TTTTAGGAAA AACCAAAAGC AAATTAGGAG CAGAGGAAAT TGCCGCTATA 900
TGGGAAACAG AAGAAAGCAT GAAAAAACTA GCCCAGTACT CAATGGAAGA TGCTAGGGCA 960
ACGTATGAGC TCGGGAAGGA ATTCTTCCCC ATGGAAGCTG AGCTGGCAAA GCTGATAGGT 1020
CAAAGTGTAT GGGACGTCTC GAGATCAAGC ACCGGCAACC TCGTGGAGTG GTATCTTTTA 1080
AGGGTGGCAT ACGCGAGGAA TGAACTTGCA CCGAACAAAC CTGATGAGGA AGAGTATAAA 1140
CGGCGCTTAA GAACAACTTA CCTGGGAGGA TATGTAAAAG AGCCAGAAAA AGGTTTGTGG 1200
GAAAATATCA TTTATTTGGA TTTCCGCAGT CTGTACCCTT CAATAATAGT TACTCACAAC 1260
GTATCCCCAG ATACCCTTGA AAAAGAGGGC TGTAAGAATT ACGATGTTGC TCCGATAGTA 1320
```

FIG. 8MMM-2

GGATATAGGT TCTGCAAGGA CTTTCCGGGC TTTATTCCCT CCATACTCGG GGACTTAATT 1380
GCAATGAGGC AAGATATAAA GAAGAAAATG AAATCCACAA TTGACCCGAT CGAAAAGAAA 1440
ATGCTCGATT ATAGGCAAAG GGCTATTAAA TTGCTTGCAA ACAGCTATTA CGGCTATATG 1500
GGGTATCCTA AGGCAAGATG GTACTCGAAG GAATGTGCTG AAAGCGTTAC CGCATGGGGG 1560
AGACACTACA TAGAGATGAC GATAAGAGAA ATAGAGGAAA AGTTCGGCTT TAAGGTTCTT 1620
TATGCGGACA CTGACGGCTT TTATGCCACA ATACCCGGGG AAAAGCCTGA ACTCATTAAA 1680
AAGAAAGCCA AGGAATTCCT AAACTACATA AACTCCAAAC TTCCAGGTCT GCTTGAGCTT 1740
GAGTATGAGG GCTTTTACTT GAGAGGATTC TTTGTTACAA AAAAGCGCTA TGCAGTCATA 1800
GATGAAGAGG GCAGGATAAC AACAAGGGGC TTGGAAGTAG TAAGGAGAGA TTGGAGTGAG 1860
ATAGCTAAGG AGACTCAGGC AAAGGTTTTA GAGGCTATAC TTAAAGAGGG AAGTGTTGAA 1920
AAAGCTGTAG AAGTTGTTAG AGATGTTGTA GAGAAAATAG CAAAATACAG GGTTCCACTT 1980
GAAAAGCTTG TTATCCATGA GCAGATTACC AGGGATTTAA AGGACTACAA AGCCATTGGC 2040
CCTCATGTCG CGATAGCAAA AAGACTTGCC GCAAGAGGGA TAAAAGTGAA ACCGGGCACA 2100
ATAATAAGCT ATATCGTTCT CAAAGGGAGC GGAAAGATAA GCGATAGGGT AATTTTACTT 2160
ACAGAATACG ATCCTAGAAA ACACAAGTAC GATCCGGACT ACTACATAGA AAACCAAGTT 2220
TTGCCGGCAG TACTTAGGAT ACTCGAAGCG TTTGGATACA GAAAGGAGGA TTTAAGGTAT 2280
CAAAGCTCAA AACAAACCGG CTTAGATGCA TGGCTCAAGA GGTAG 2325

| FIG. 8NNN-1 |
|---|
| FIG. 8NNN-2 |
| FIG. 8NNN-3 |

Vent DNA POLYMERASE - Sso7d FUSION PROTEIN

Nucleotide sequence (SEQ ID NO: 35) // Nucleotide sequence (SEQ ID NO: 71)
Nucleotide sequence (SEQ ID NO: 36) // Nucleotide sequence (SEQ ID NO: 71)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATACTGG ACACTGATTA CATAACAAAA GATGGCAAGC CTATAATCCG AATTTTTAAG 60
AAAGAGAACG GGGAGTTTAA AATAGAACTT GACCCTCATT TTCAGCCCTA TATATATGCT 120
CTTCTCAAAG ATGACTCCGC TATTGAGGAG ATAAAGGCAA TAAAGGGCGA GAGACATGGA 180
AAAACTGTGA GAGTGCTCGA TGCAGTGAAA GTCAGGAAAA AATTTTTGGG AAGGGAAGTT 240
GAAGTCTGGA AGCTCATTTT CGAGCATCCC CAAGACXXXC CAGCTATGCG GGGCAAAATA 300
AGGGAACATC CAGCTGTGGT TGACATTTAC GAATATGACA TACCCTTTGC CAAGCGTTAT 360
CTCATAGACA AGGGCTTGAT TCCCATGGAG GGAGACGAGG AGCTTAAGCT CCTTGCCTTT 420
GATATTGAAA CGTTTTATCA TGAGGGAGAT GAATTTGGAA AGGGCGAGAT AATAATGATT 480
AGTTATGCCG ATGAAGAAGA GGCCAGAGTA ATCACATGGA AAAATATCGA TTTGCCGTAT 540
GTCGATGTTG TGTCCAATGA AAGAGAAATG ATAAAGCGTT TTGTTCAAGT TGTTAAAGAA 600
```

FIG. 8NNN-1

```
AAAGACCCCG ATGTGATAAT AACTTACAAT GGGGACAATT TTGATTTGCC GTATCTCATA 660
AAACGGGCAG AAAAGCTGGG AGTTCGGCTT GTCTTAGGAA GGGACAAAGA ACATCCCGAA 720
CCCAAGATTC AGAGGATGGG TGATAGTTTT GCTGTGGAAA TCAAGGGTAG AATCCACTTT 780
GATCTTTTCC CAGTTGTGCG AAGGACGATA AACCTCCCAA CGTATACGCT TGAGGCAGTT 840
TATGAAGCAG TTTTAGGAAA AACCAAAAGC AAATTAGGAG CAGAGGAAAT TGCCGCTATA 900
TGGGAAACAG AAGAAAGCAT GAAAAAACTA GCCCAGTACT CAATGGAAGA TGCTAGGGCA 960
ACGTATGAGC TCGGGAAGGA ATTCTTCCCC ATGGAAGCTG AGCTGGCAAA GCTGATAGGT 1020
CAAAGTGTAT GGGACGTCTC GAGATCAAGC ACCGGCAACC TCGTGGAGTG GTATCTTTTA 1080
AGGGTGGCAT ACGCGAGGAA TGAACTTGCA CCGAACAAAC CTGATGAGGA AGAGTATAAA 1140
CGGCGCTTAA GAACAACTTA CCTGGGAGGA TATGTAAAAG AGCCAGAAAA AGGTTTGTGG 1200
GAAAATATCA TTTATTTGGA TTTCCGCAGT CTGTACCCTT CAATAATAGT TACTCACAAC 1260
GTATCCCCAG ATACCCTTGA AAAAGAGGGC TGTAAGAATT ACGATGTTGC TCCGATAGTA 1320
GGATATAGGT TCTGCAAGGA CTTTCCGGGC TTTATTCCCT CCATACTCGG GGACTTAATT 1380
GCAATGAGGC AAGATATAAA GAAGAAAATG AAATCCACAA TTGACCCGAT CGAAAAGAAA 1440
ATGCTCGATT ATAGGCAAAG GGCTATTAAA TTGCTTGCAA ACAGCTATTA CGGCTATATG 1500
GGGTATCCTA AGGCAAGATG GTACTCGAAG GAATGTGCTG AAAGCGTTAC CGCATGGGGG 1560
AGACACTACA TAGAGATGAC GATAAGAGAA ATAGAGGAAA AGTTCGGCTT TAAGGTTCTT 1620
TATGCGGACA CTGACGGCTT TTATGCCACA ATACCCGGGG AAAAGCCTGA ACTCATTAAA 1680
```

FIG. 8NNN-2

```
AAGAAAGCCA AGGAATTCCT AAACTACATA AACTCCAAAC TTCCAGGTCT GCTTGAGCTT 1740
GAGTATGAGG GCTTTTACTT GAGAGGATTC TTTGTTACAA AAAAGCGCTA TGCAGTCATA 1800
GATGAAGAGG GCAGGATAAC AACAAGGGGC TTGGAAGTAG TAAGGAGAGA TTGGAGTGAG 1860
ATAGCTAAGG AGACTCAGGC AAAGGTTTTA GAGGCTATAC TTAAAGAGGG AAGTGTTGAA 1920
AAAGCTGTAG AAGTTGTTAG AGATGTTGTA GAGAAAATAG CAAAATACAG GGTTCCACTT 1980
GAAAAGCTTG TTATCCATGA GCAGATTACC AGGGATTTAA AGGACTACAA AGCCATTGGC 2040
CCTCATGTCG CGATAGCAAA AAGACTTGCC GCAAGAGGGA TAAAAGTGAA ACCGGGCACA 2100
ATAATAAGCT ATATCGTTCT CAAAGGGAGC GGAAAGATAA GCGATAGGGT AATTTTACTT 2160
ACAGAATACG ATCCTAGAAA ACACAAGTAC GATCCGGACT ACTACATAGA AAACCAAGTT 2220
TTGCCGGCAG TACTTAGGAT ACTCGAAGCG TTTGGATACA GAAAGGAGGA TTTAAGGTAT 2280
CAAAGCTCAA AACAAACCGG CTTAGATGCA TGGCTCAAGA GG 2325 //

// GCA ACC GTA AAG TTC AAG TAC AAA GGC GAA GAA AAA GAG GTA GAC ATC TCC AAG
   ATC AAG AAA GTA TGG CGT GTG GGC AAG ATG ATC TCC TTC ACC TAC GAC GAG GGC
   GGT GGC AAG ACC GGC CGT GGT GCG GTA AGC GAA AAG GAC GCG CCG AAG GAG CTG
   CTG CAG ATG CTG GAG AAG CAG AAA AAG //  TGA
```

| |
|---|
| FIG. 8OOO-1 |
| FIG. 8OOO-2 |
| FIG. 8OOO-3 |

Deep Vent- Ssod7 DNA polymerase fusion protein

Nucleotide sequence (SEQ ID NO: 37) // Nucleotide sequence (SEQ ID NO: 71)
Nucleotide sequence (SEQ ID NO: 38) // Nucleotide sequence (SEQ ID NO: 71)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
ATGATACTTG ACGCTGACTA CATCACCGAG GATGGGAAGC CGATTATAAG GATTTTCAAG    60
AAAGAAAACG GCGAGTTTAA GGTTGAGTAC GACAGAAACT TTAGACCTTA CATTTACGCT   120
CTCCTCAAAG ATGACTCGCA GATTGATGAG GTTAGGAAGA TAACCGCCGA GAGGCATGGG   180
AAGATAGTGA GAATTATAGA TGCCGAAAAG GTAAGGAAGA AGTTCCTGGG GAGGCCGATT   240
GAGGTATGGA GGCTGTACTT TGAACACCCT CAGGACXXXC CCGCAATAAG GGATAAGATA   300
AGAGAGCATT CCGCAGTTAT TGACATCTTT GAGTACGACA TTCCGTTCGC GAAGAGGTAC   360
CTAATAGACA AAGGCCTAAT TCCAATGGAA GGCGATGAAG AGCTCAAGTT GCTCGCATTT   420
GACATAGAAA CCCTCTATCA CGAAGGGGAG GAGTTCGCGA AGGGGCCCAT TATAATGATA   480
AGCTATGCTG ATGAGGAAGA AGCCAAAGTC ATAACGTGGA AAAAGATCGA TCTCCCGTAC   540
GTCGAGGTAG TTTCCAGCGA GAGGGAGATG ATAAAGCGGT TCCTCAAGGT GATAAGGGAG   600
```

FIG. 8OOO-1

```
AAAGATCCCG ATGTTATAAT TACCTACAAC GGCGATTCTT TCGACCTTCC CTATCTAGTT   660
AAGAGGGCCG AAAAGCTCGG GATAAAGCTA CCCCTGGGAA GGGACGGTAG TGAGCCAAAG   720
ATGCAGAGGC TTGGGGATAT GACAGCGGTG GAGATAAAGG GAAGGATACA CTTTGACCTC   780
TACCACGTGA TTAGGAGAAC GATAAACCTC CCAACATACA CCCTCGAGGC AGTTTATGAG   840
GCAATCTTCG GAAAGCCAAA GGAGAAAGTT TACGCTCACG AGATAGCTGA GGCCTGGGAG   900
ACTGGAAAGG GACTGGAGAG AGTTGCAAAG TATTCAATGG AGGATGCAAA GGTAACGTAC   960
GAGCTCGGTA GGGAGTTCTT CCCAATGGAG GCCCAGCTTT CAAGGTTAGT CGGCCAGCCC  1020
CTGTGGGATG TTTCTAGGTC TTCAACTGGC AACTTGGTGG AGTGGTACCT CCTCAGGAAG  1080
GCCTACGAGA GGAATGAATT GGCTCCAAAC AAGCCGGATG AGAGGGAGTA CGAGAGAAGG  1140
CTAAGGGAGA GCTACGCTGG GGGATACGTT AAGGAGCCGG AGAAAGGGCT CTGGGAGGGG  1200
TTAGTTTCCC TAGATTTCAG GAGCCTGTAC CCCTCGATAA TAATCACCCA TAACGTCTCA  1260
CCGGATACGC TGAACAGGGA AGGGTGTAGG GAATACGATG TCGCCCCAGA GGTTGGGCAC  1320
AAGTTCTGCA AGGACTTCCC GGGGTTTATC CCCAGCCTGC TCAAGAGGTT ATTGGATGAA  1380
AGGCAAGAAA TAAAAAGGAA GATGAAAGCT TCTAAAGACC CAATCGAGAA GAAGATGCTT  1440
GATTACAGGC AACGGGCAAT CAAAATCCTG GCAAACAGCT ATTATGGGTA TTATGGGTAC  1500
GCAAAAGCCC GTTGGTACTG TAAGGAGTGC GCAGAGAGCG TTACGGCCTG GGGGAGGGAA  1560
TATATAGAGT TCGTAAGGAA GGAACTGGAG GAAAAGTTCG GGTTCAAAGT CTTATACATA  1620
GACACAGATG GACTCTACGC CACAATTCCT GGGGCAAAAC CCGAGGAGAT AAAGAAGAAA  1680
```

FIG. 8OOO-2

```
GCCCTAGAGT TCGTAGATTA TATAAACGCC AAGCTCCCAG GGCTGTTGGA GCTTGAGTAC  1740
GAGGGCTTCT ACGTGAGAGG GTTCTTCGTG ACGAAGAAGA AGTATGCGTT GATAGATGAG  1800
GAAGGGAAGA TAATCACTAG GGGGCTTGAA ATAGTCAGGA GGGACTGGAG CGAAATAGCC  1860
AAAGAAACCC AAGCAAAAGT CCTAGAGGCT ATCCTAAAGC ATGGCAACGT TGAGGAGGCA  1920
GTAAAGATAG TTAAGGAGGT AACTGAAAAG CTGAGCAAGT ACGAAATACC TCCAGAAAAG  1980
CTAGTTATTT ACGAGCAGAT CACGAGGCCC CTTCACGAGT ACAAGGCTAT AGGTCCGCAC  2040
GTTGCCGTGG CAAAAAGGTT AGCCGCTAGA GGAGTAAAGG TGAGGCCTGG CATGGTGATA  2100
GGGTACATAG TGCTGAGGGG AGACGGGCCA ATAAGCAAGA GGGCTATCCT TGCAGAGGAG  2160
TTCGATCTCA GGAAGCATAA GTATGACGCT GAGTATTACA TAGAAAATCA GGTTTTACCT  2220
GCCGTTCTTA GAATATTAGA GGCCTTTGGG TACAGGAAAG AAGACCTCAG GTGGCAGAAG  2280
ACTAAACAGA CAGGTCTTAC GGCATGGCTT AACATCAAGA AGAAG                2328

// GCA ACC GTA AAG TTC AAG TAC AAA GGC GAA GAA AAA GAG GTA GAC ATC TCC AAG
   ATC AAG AAA GTA TGG CGT GTG GGC AAG ATG ATC TCC TTC ACC TAC GAC GAG GGC
   GGT GGC AAG ACC GGC CGT GGT GCG GTA AGC GAA AAG GAC GCG CCG AAG GAG CTG
   CTG CAG ATG CTG GAG AAG CAG AAA AAG //  TGA
```

| |
|---|
| FIG. 8PPP-1 |
| FIG. 8PPP-2 |
| FIG. 8PPP-3 |

Ssod7 - Deep Vent DNA polymerase fusion protein

Nucleotide sequence (SEQ ID NO: 71) // Nucleotide sequence (SEQ ID NO: 37)
Nucleotide sequence (SEQ ID NO: 71) // Nucleotide sequence (SEQ ID NO: 38)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

```
//GCA ACC GTA AAG TTC AAG TAC AAA GGC GAA GAA AAA GAG GTA GAC ATC TCC AAG
  ATC AAG AAA GTA TGG CGT GTG GGC AAG ATG ATC TCC TTC ACC TAC GAC GAG GGC
  GGT GGC AAG ACC GGC CGT GGT GCG GTA AGC GAA AAG GAC GCG CCG AAG GAG CTG
  CTG CAG ATG CTG GAG AAG CAG AAA AAG   //

ATGATACTTG ACGCTGACTA CATCACCGAG GATGGGAAGC CGATTATAAG GATTTTCAAG    60
AAAGAAAACG GCGAGTTTAA GGTTGAGTAC GACAGAAACT TTAGACCTTA CATTTACGCT   120
CTCCTCAAAG ATGACTCGCA GATTGATGAG GTTAGGAAGA TAACCGCCGA GAGGCATGGG   180
AAGATAGTGA GAATTATAGA TGCCGAAAAG GTAAGGAAGA AGTTCCTGGG GAGGCCGATT   240
```

FIG. 8PPP-1

```
GAGGTATGGA GGCTGTACTT TGAACACCCT CAGGACXXXC CCGCAATAAG GGATAAGATA   300
AGAGAGCATT CCGCAGTTAT TGACATCTTT GAGTACGACA TTCCGTTCGC GAAGAGGTAC   360
CTAATAGACA AAGGCCTAAT TCCAATGGAA GGCGATGAAG AGCTCAAGTT GCTCGCATTT   420
GACATAGAAA CCCTCTATCA CGAAGGGGAG GAGTTCGCGA AGGGGCCCAT TATAATGATA   480
AGCTATGCTG ATGAGGAAGA AGCCAAAGTC ATAACGTGGA AAAAGATCGA TCTCCCGTAC   540
GTCGAGGTAG TTTCCAGCGA GAGGGAGATG ATAAAGCGGT TCCTCAAGGT GATAAGGGAG   600
AAAGATCCCG ATGTTATAAT TACCTACAAC GGCGATTCTT TCGACCTTCC CTATCTAGTT   660
AAGAGGGCCG AAAAGCTCGG GATAAAGCTA CCCCTGGGAA GGGACGGTAG TGAGCCAAAG   720
ATGCAGAGGC TTGGGGATAT GACAGCGGTG GAGATAAAGG GAAGGATACA CTTTGACCTC   780
TACCACGTGA TTAGGAGAAC GATAAACCTC CCAACATACA CCCTCGAGGC AGTTTATGAG   840
GCAATCTTCG GAAAGCCAAA GGAGAAAGTT TACGCTCACG AGATAGCTGA GGCCTGGGAG   900
ACTGGAAAGG GACTGGAGAG AGTTGCAAAG TATTCAATGG AGGATGCAAA GGTAACGTAC   960
GAGCTCGGTA GGGAGTTCTT CCCAATGGAG GCCCAGCTTT CAAGGTTAGT CGGCCAGCCC  1020
CTGTGGGATG TTTCTAGGTC TTCAACTGGC AACTTGGTGG AGTGGTACCT CCTCAGGAAG  1080
GCCTACGAGA GGAATGAATT GGCTCCAAAC AAGCCGGATG AGAGGGAGTA CGAGAGAAGG  1140
CTAAGGGAGA GCTACGCTGG GGGATACGTT AAGGAGCCGG AGAAAGGGCT CTGGGAGGGG  1200
TTAGTTTCCC TAGATTTCAG GAGCCTGTAC CCCTCGATAA TAATCACCCA TAACGTCTCA  1260
CCGGATACGC TGAACAGGGA AGGGTGTAGG GAATACGATG TCGCCCCAGA GGTTGGGCAC  1320
AAGTTCTGCA AGGACTTCCC GGGGTTTATC CCCAGCCTGC TCAAGAGGTT ATTGGATGAA  1380
```

FIG. 8PPP-2

```
AGGCAAGAAA TAAAAAGGAA GATGAAAGCT TCTAAAGACC CAATCGAGAA GAAGATGCTT 1440
GATTACAGGC AACGGGCAAT CAAAATCCTG GCAAACAGCT ATTATGGGTA TTATGGGTAC 1500
GCAAAAGCCC GTTGGTACTG TAAGGAGTGC GCAGAGAGCG TTACGGCCTG GGGGAGGGAA 1560
TATATAGAGT TCGTAAGGAA GGAACTGGAG GAAAAGTTCG GGTTCAAAGT CTTATACATA 1620
GACACAGATG GACTCTACGC CACAATTCCT GGGGCAAAAC CCGAGGAGAT AAAGAAGAAA 1680
GCCCTAGAGT TCGTAGATTA TATAAACGCC AAGCTCCCAG GGCTGTTGGA GCTTGAGTAC 1740
GAGGGCTTCT ACGTGAGAGG GTTCTTCGTG ACGAAGAAGA AGTATGCGTT GATAGATGAG 1800
GAAGGGAAGA TAATCACTAG GGGGCTTGAA ATAGTCAGGA GGGACTGGAG CGAAATAGCC 1860
AAAGAAACCC AAGCAAAAGT CCTAGAGGCT ATCCTAAAGC ATGGCAACGT TGAGGAGGCA 1920
GTAAAGATAG TTAAGGAGGT AACTGAAAAG CTGAGCAAGT ACGAAATACC TCCAGAAAAG 1980
CTAGTTATTT ACGAGCAGAT CACGAGGCCC CTTCACGAGT ACAAGGCTAT AGGTCCGCAC 2040
GTTGCCGTGG CAAAAAGGTT AGCCGCTAGA GGAGTAAAGG TGAGGCCTGG CATGGTGATA 2100
GGGTACATAG TGCTGAGGGG AGACGGGCCA ATAAGCAAGA GGGCTATCCT TGCAGAGGAG 2160
TTCGATCTCA GGAAGCATAA GTATGACGCT GAGTATTACA TAGAAAATCA GGTTTTACCT 2220
GCCGTTCTTA GAATATTAGA GGCCTTTGGG TACAGGAAAG AAGACCTCAG GTGGCAGAAG 2280
ACTAAACAGA CAGGTCTTAC GGCATGGCTT AACATCAAGA AGAAG TAA             2328
```

FIG. 8PPP-3

| |
|---|
| FIG. 8QQQ-1 |
| FIG. 8QQQ-2 |

FIG. 8QQQ

JDF-3 - Sso7d fusion protein

Nucleotide sequence (SEQ ID NO: 39) // Nucleotide sequence (SEQ ID NO: 71)
Nucleotide sequence (SEQ ID NO: 40) // Nucleotide sequence (SEQ ID NO: 71)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

ATGATCCTTGACGTTGATTACATCACCGAGAATGGAAAGCCCGTCATCAGGGTCTTCAAGAAGGAGAACGGCGAGTTCAGGATTGAATACGACCGCGAGTTCGAGCCCTACTTCT
ACGCGCTCCTCAGGGACGACTCTGCCATCGAAGAAATCAAAAAGATAACCGCGGAGAGGCACGGCAGGGTCGTTAAGGTTAAGCGCGCGGAGAAGGTGAAGAAAAAGTTCCTCGG
CAGGTCTGTGGAGGTCTGGGTCCTCTACTTCACGCACCCGCAGGACXXXCCGGCAATCCGCGACAAAATAAGGAAGCACCCCGCGGTCATCGACATCTACGAGTACGACATACCC
TTCGCCAAGCGCTACCTCATAGACAAGGGCCTAATCCCGATGGAAGGTGAGGAAGAGCTTAAACTCATGTCCTTCGACATCGAGACGCTCTACCACGAGGGAGAAGAGTTTGGAA
CCGGGCCGATTCTGATGATAAGCTACGCCGATGAAAGCGAGGCGCGCGTGATAACCTGGAAGAAGATCGACCTTCCTTACGTTGAGGTTGTCTCCACCGAGAAGGAGATGATTAA
GCGCTTCTTGAGGGTCGTTAAGGAGAAGGACCCGGACGTGCTGATAACATACAACGGCGACAACTTCGACTTCGCCTACCTGAAAAAGCGCTGTGAGAAGCTTGGCGTGAGCTTT
ACCCTCGGGAGGGACGGGAGCGAGCCGAAGATACAGCGCATGGGGGACAGGTTTGCGGTCGAGGTGAAGGGCAGGGTACACTTCGACCTTTATCCAGTCATAAGGCGCACCATAA
ACCTCCCGACCTACACCCTTGAGGCTGTATACGAGGCGGTTTTCGGCAAGCCCAAGGAGAAGGTCTACGCCGAGGAGATAGCCACCGCCTGGGAGACCGGCGAGGGGCTTGAGAG

FIG. 8QQQ-1

GGTCGCGCGCTACTCGATGGAGGACGCGAGGGTTACCTACGAGCTTGGCAGGGAGTTCTTCCCGATGGAGGCCCAGCTTTCCAGGCTCATCGGCCAAGGCCTCTGGGACGTTTCC
CGCTCCAGCACCGGCAACCTCGTCGAGTGGTTCCTCCTAAGGAAGGCCTACGAGAGGAACGAACTCGCTCCCAACAAGCCCGACGAGAGGGAGCTGGCGAGGAGAAGGGGGGGCT
ACgcCGGTGGCTACGTCAAGGAGCCGGAGCGGGGACTGTGGGACAATATCGTGTATCTAGACTTTCGTAGTCTCTACCCTTCAATCATAATCACCCACAACGTCTCGCCAGATAC
GCTCAACCGCGAGGGGTGTAGGAGCTACGACGTTGCCCCCGAGGTCGGTCACAAGTTCTGCAAGGACTTCCCCGGCTTCATTCCGAGCCTGCTCGGAAACCTGCTGGAGGAAAGG
CAGAAGATAAAGAGGAAGATGAAGGCAACTCTCGACCCGCTGGAGAAGAATCTCCTCGATTACAGGCAACGCGCCATCAAGATTCTCGCCAACAGCTACTACGGCTACTACGGCT
ATGCCAGGGCAAGATGGTACTGCAGGGAGTGCGCCGAGAGCGTTACGGCATGGGGAAGGGAGTACATCGAAATGGTCATCAGAGAGCTTGAGGAAAAGTTCGGTTTTAAAGTCCT
CTATGCAGACACAGACGGTCTCCATGCCACCATTCCTGGAGCGGACGCTGAAACAGTCAAGAAAAAGGCAATGGAGTTCTTAAACTATATCAATCCCAAACTGCCCGGCCTTCTC
GAACTCGAATACGAGGGCTTCTACGTCAGGGGCTTCTTCGTCACGAAGAAAAAGTACGCGGTCATCGACGAGGAGGGCAAGATAACCACGCGCGGGCTTGAGATAGTCAGGCGCG
ACTGGAGCGAGATAGCGAAGGAGACGCAGGCGAGGGTTTTGGAGGCGATACTCAGGCACGGTGACGTTGAAGAGGCCGTCAGAATTGTCAGGGAAGTCACCGAAAAGCTGAGCAA
GTACGAGGTTCCGCCGGAGAAGCTGGTTATCCACGAGCAGATAACGCGCGAGCTCAAGGACTACAAGGCCACCGGCCCGCACGTAGCCATAGCGAAgcGTTTGGCCGCCAGAGGT
GTTAAAATCCGGCCCGGAACTGTGATAAGCTACATCGTTCTGAAGGGCTCCGGAAGGATAGGCGACAGGGCGATTCCCTTCGACGAGTTCGACCCGACGAAGCACAAGTACGATG
CGGACTACTACATCGAGAACCAGGTTCTGCCGGCAGTTGAGAGAATCCTCAGGGCCTTCGGCTACCGCAAGGAAGACCTGCGCTACCAGAAGACGAGGCAGGTCGGGCTTGGCGC
GTGGCTGAAGCCGAAGGGGAAGAAGAAG//

//GCA ACC GTA AAG TTC AAG TAC AAA GGC GAA GAA AAA GAG GTA GAC ATC TCC AAG
ATC AAG AAA GTA TGG CGT GTG GGC AAG ATG ATC TCC TTC ACC TAC GAC GAG GGC
GGT GGC AAG ACC GGC CGT GGT GCG GTA AGC GAA AAG GAC GCG CCG AAG GAG CTG
CTG CAG ATG CTG GAG AAG CAG AAA AAG // TAG

FIG. 8QQQ-2

| FIG. 8RRR-1 |
|---|
| FIG. 8RRR-2 |

FIG. 8RRR

Sso7d - JDF-3 fusion protein

Nucleotide sequence (SEQ ID NO: 71) // Nucleotide sequence (SEQ ID NO: 39)
Nucleotide sequence (SEQ ID NO: 71) // Nucleotide sequence (SEQ ID NO: 40)

V93R MUTANT: XXX = AGA, AGG, CGA, CGC, CGG, CGT (ALL POSSIBLE CODONS FOR ARGININE)
V93E MUTANT: XXX = GAA, GAG (ALL CODONS FOR GLUTAMIC ACID)

//GCA ACC GTA AAG TTC AAG TAC AAA GGC GAA GAA AAA GAG GTA GAC ATC TCC AAG
ATC AAG AAA GTA TGG CGT GTG GGC AAG ATG ATC TCC TTC ACC TAC GAC GAG GGC
GGT GGC AAG ACC GGC CGT GGT GCG GTA AGC GAA AAG GAC GCG CCG AAG GAG CTG
CTG CAG ATG CTG GAG AAG CAG AAA AAG //

ATGATCCTTGACGTTGATTACATCACCGAGAATGGAAAGCCCGTCATCAGGGTCTTCAAGAAGGAGAACGGCGAGTTCAGGATTGAATACGACCGCGAGTTCGAGCCCTACTTCT
ACGCGCTCCTCAGGGACGACTCTGCCATCGAAGAAATCAAAAAGATAACCGCGGAGAGGCACGGCAGGGTCGTTAAGGTTAAGCGCGCGGAGAAGGTGAAGAAAAAGTTCCTCGG
CAGGTCTGTGGAGGTCTGGGTCCTCTACTTCACGCACCCGCAGGACXXXCCGGCAATCCGCGACAAAATAAGGAAGCACCCCGCGGTCATCGACATCTACGAGTACGACATACCC
TTCGCCAAGCGCTACCTCATAGACAAGGGCCTAATCCCGATGGAAGGTGAGGAAGAGCTTAAACTCATGTCCTTCGACATCGAGACGCTCTACCACGAGGGAGAAGAGTTTGGAA

FIG. 8RRR-1

Figure 8:
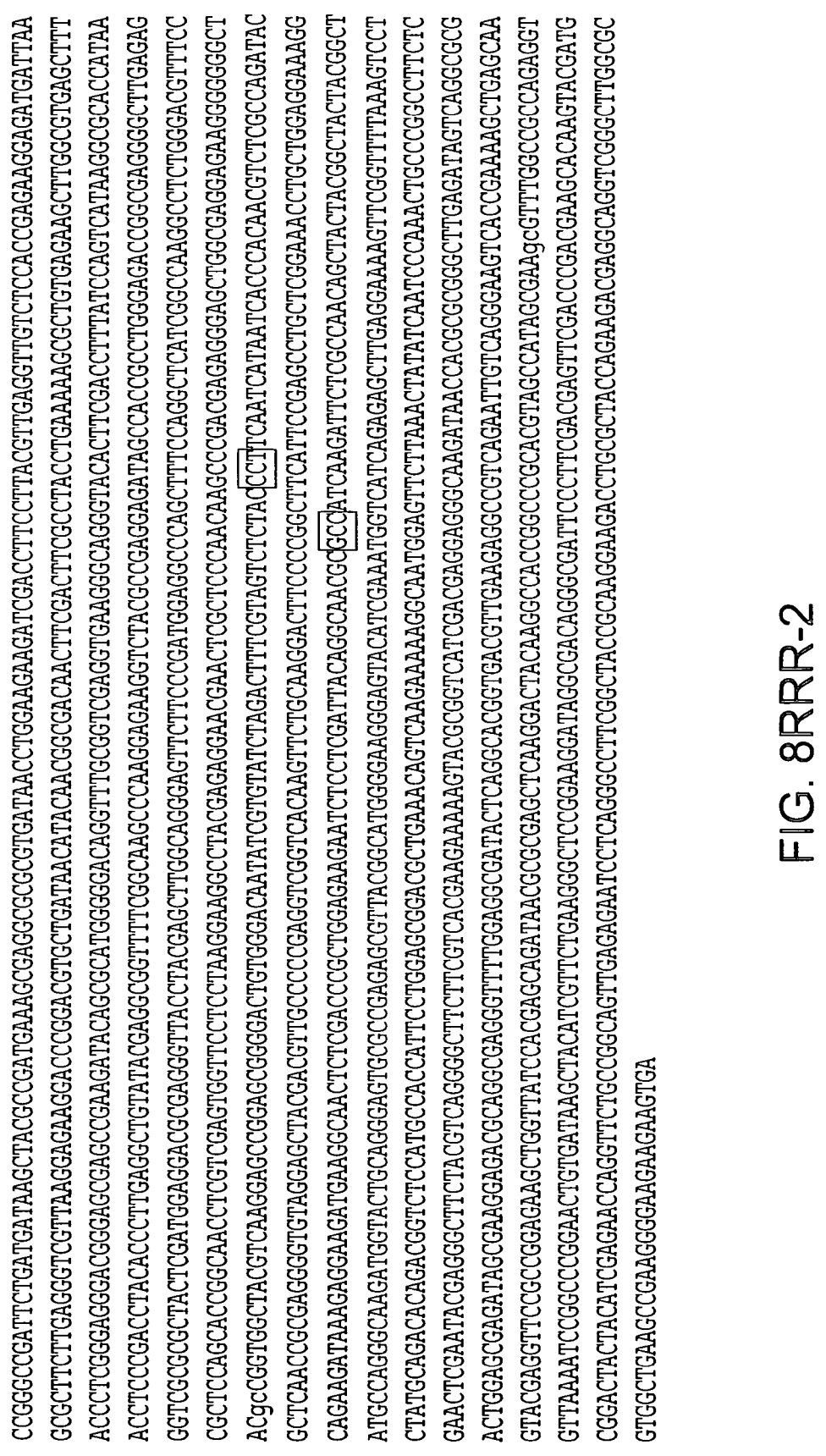

CCGGGCCGATTCTGATGATAAGCTACGCCGATGAAAGCGAGGCGCGCGTGATAACCTGGAAGAAGATCGACCTTCCTTACGTTGAGGTTGTCTCCACCGAGAAGGAGATGATTAA
GCGCTTCTTGAGGGTCGTTAAGGAGAAGGACCCGGACGTGCTGATAACATACAACGGCGACAACTTCGACTTCGCCTACCTGAAAAAGCGCTGTGAGAAGCTTGGCGTGAGCTTT
ACCCTCGGGAGGGACGGGAGCGAGCCGAAGATACAGCGCATGGGGGACAGGTTTGCGGTCGAGGTGAAGGGCAGGGTACACTTCGACCTTTATCCAGTCATAAGGCGCACCATAA
ACCTCCCGACCTACACCCTTGAGGCTGTATACGAGGCGGTTTTCGGCAAGCCCAAGGAGAAGGTCTACGCCGAGGAGATAGCCACCGCCTGGGAGACCGGCGAGGGGCTTGAGAG
GGTCGCGCGCTACTCGATGGAGGACGCGAGGGTTACCTACGAGCTTGGCAGGGAGTTCTTCCCGATGGAGGCCCAGCTTTCCAGGCTCATCGGCCAAGGCCTCTGGGACGTTTCC
CGCTCCAGCACCGGCAACCTCGTCGAGTGGTTCCTCCTAAGGAAGGCCTACGAGAGGAACGAACTCGCTCCCAACAAGCCCGACGAGAGGGAGCTGGCGAGGAGAAGGGGGGGCT
ACgcCGGTGGCTACGTCAAGGAGCCGGAGCGGGGACTGTGGGACAATATCGTGTATCTAGACTTTCGTAGTCTCTACCCTTCAATCATAATCACCCACAACGTCTCGCCAGATAC
GCTCAACCGCGAGGGGTGTAGGAGCTACGACGTTGCCCCCGAGGTCGGTCACAAGTTCTGCAAGGACTTCCCCGGCTTCATTCCGAGCCTGCTCGGAAACCTGCTGGAGGAAAGG
CAGAAGATAAAGAGGAAGATGAAGGCAACTCTCGACCCGCTGGAGAAGAATCTCCTCGATTACAGGCAACGCGCCATCAAGATTCTCGCCAACAGCTACTACGGCTACTACGGCT
ATGCCAGGGCAAGATGGTACTGCAGGGAGTGCGCCGAGAGCGTTACGGCATGGGGAAGGGAGTACATCGAAATGGTCATCAGAGAGCTTGAGGAAAAGTTCGGTTTTAAAGTCCT
CTATGCAGACACAGACGGTCTCCATGCCACCATTCCTGGAGCGGACGCTGAAACAGTCAAGAAAAAGGCAATGGAGTTCTTAAACTATATCAATCCCAAACTGCCCGGCCTTCTC
GAACTCGAATACGAGGGCTTCTACGTCAGGGGCTTCTTCGTCACGAAGAAAAAGTACGCGGTCATCGACGAGGAGGGCAAGATAACCACGCGCGGGCTTGAGATAGTCAGGCGCG
ACTGGAGCGAGATAGCGAAGGAGACGCAGGCGAGGGTTTTGGAGGCGATACTCAGGCACGGTGACGTTGAAGAGGCCGTCAGAATTGTCAGGGAAGTCACCGAAAAGCTGAGCAA
GTACGAGGTTCCGCCGGAGAAGCTGGTTATCCACGAGCAGATAACGCGCGAGCTCAAGGACTACAAGGCCACCGGCCCGCACGTAGCCATAGCGAAgcGTTTGGCCGCCAGAGGT
GTTAAAATCCGGCCCGGAACTGTGATAAGCTACATCGTTCTGAAGGGCTCCGGAAGGATAGGCGACAGGGCGATTCCCTTCGACGAGTTCGACCCGACGAAGCACAAGTACGATG
CGGACTACTACATCGAGAACCAGGTTCTGCCGGCAGTTGAGAGAATCCTCAGGGCCTTCGGCTACCGCAAGGAAGACCTGCGCTACCAGAAGACGAGGCAGGTCGGGCTTGGCGC
GTGGCTGAAGCCGAAGGGGAAGAAGAAGTGA

FIG. 8RRR-2

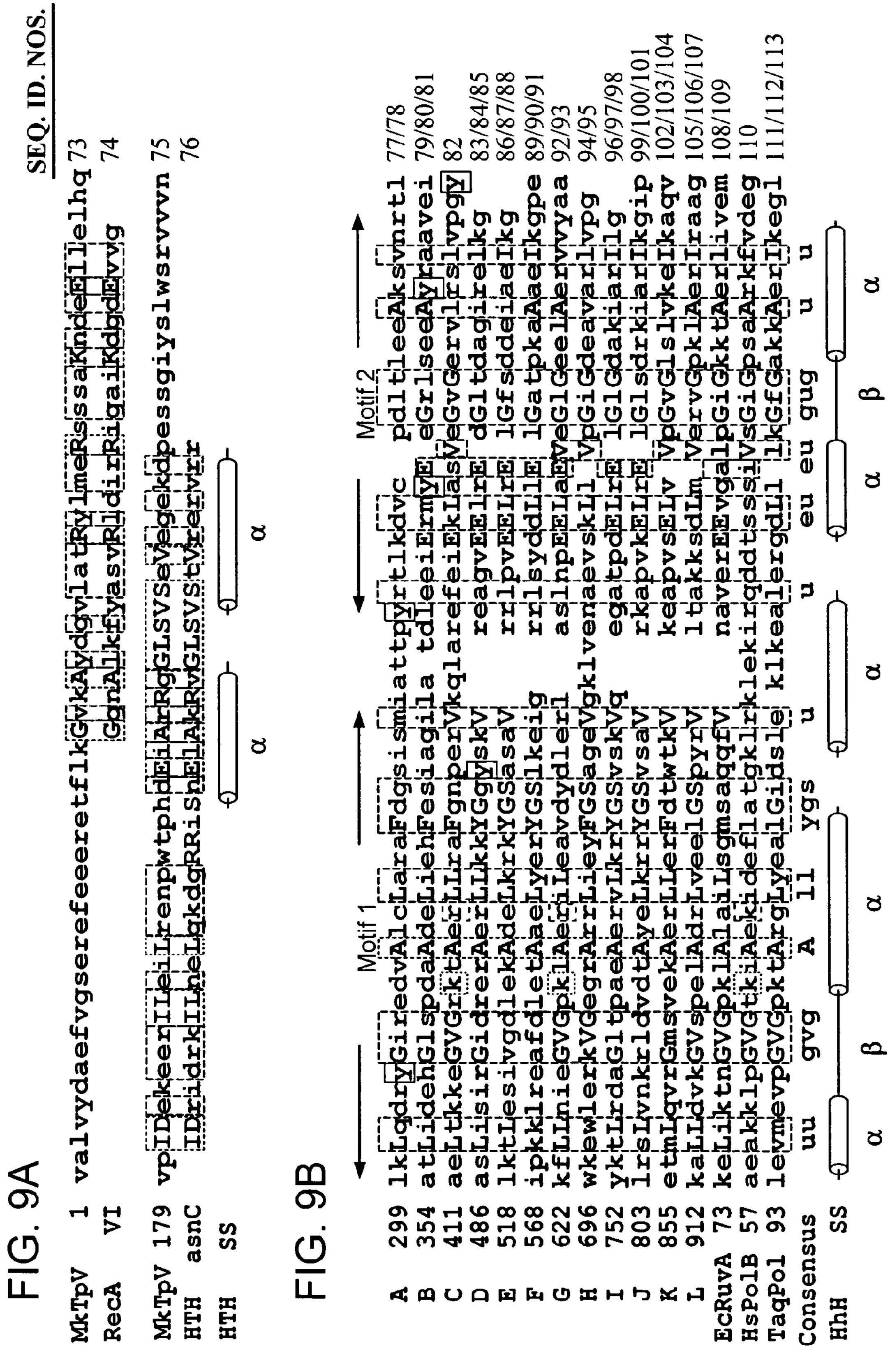

```
                                                                                       SEQ. ID. NOS.
MkTpV    1  valvydaefvgserefeeeretflkGvkAydgvlatRylmeRissaKndeFllelhq   73
RecA     VI                                GgnAlkfyasvRldirRigaikdgDEvvg  74

MkTpV  179  vpIDekeenIleiIrenpwtphdEiArRgGLSVSeVegekdpessgiylwsrvvn       75
HTH    asnC    IDrldrklIheLgkdgRRishElAkRvGLSVStVeervr                    76
HTH    SS                                  α                  α
```

```
                    Motif 1                                      Motif 2
A  299  lkLqdryGiredvAlcIaraFdgsismiattpyrtlkdvc  pdltleeAksvnrtl    77/78
B  354  atLidehGlspdaAdeLiehFesiagila tdIeeiErmyE  eGrlseeAyraavei    79/80/81
C  411  aeLtkkeGVgkrktAerlIraFgnpervkqlarefeiEklasVeGvGervlrslvpgy    82
D  486  asLisirGidreraerlIkkyGgyskV    reagvEElrE    dGltdagIrelkg    83/84/85
E  518  lktIesivgdlekAdeLkrkyGSasaV    rrlpvEELrE    lGfsddeiaeIIkg    86/87/88
F  568  ipkklIreafdletAaelyerGSlkeig   rrlsyddIlE    lGatpkaAaeIkgpe   89/90/91
G  622  kfLInieGVGpklAerlIaerchiIeavdydlerl  aslnpEELaEveGleervyaa    92/93
H  696  wkewlerkVGegrArrLieyFGSageVgklvenaevskIl  VpGiGdeavarlvpg     94/95
I  752  ykLIrdaGltpaeAervLkrlyGSvskVq   egatpdEIrE    lGlGdakiarIlg    96/97/98
J  803  lrsIvnkrldvdtAyeLkrIyGSvsaV    rkapvkELrE    lGlsdrkiarIIkgip  99/100/101
K  855  etmLqvrGmsvekAerLLerFdtwtkV    keapvsELv    VpGvGlslvkeIkaqv  102/103/104
L  912  kaLIdvkGVspelAdrLveelGSpyrV    ltakksdlm    VervGpklAerIraag  105/106/107
EcRuvA  73  keLiktnGVGpklAlaiLsgmsaqqfV   naverEEvgalpGiGkktAerllivem   108/109
HsPolB  57  aeakklpGVGtkiiAekideflatgklrklekirqddtssilVSGiGpsaArkfvdeg    110
TaqPol  93  levmevpGVGpktArglyeaIGidsle  klkealergdIl  lkGfGakkAerIkegl  111/112/113
Consensus    uu   gvg   A     ll      ygs     u        u       eu eu gug    u
HhH     SS   α    β     α                     α        α       β          α
```

DNA POLYMERASE BLENDS AND USES THEREOF

RELATED APPLICATIONS

This application is a continuation of application Ser. No. 10/324,846, filed Dec. 20, 2002. The entire teachings of the above applications are incorporated herein by reference.

FIELD OF THE INVENTION

The present invention relates to blends of chimeric and non chimeric DNA polymerases, methods for their synthesis, and methods for their use. The DNA polymerase blends disclosed herein are useful for many recombinant DNA techniques, especially nucleic acid sequencing, nucleic acid amplification by the polymerase chain reaction (PCR) or mutagenesis.

BACKGROUND

Thermostable DNA polymerases which catalyze the template-directed polymerization of deoxyribonucleoside triphosphates (dNTPs) to form DNA, are used in a variety of in vitro DNA synthesis applications, such as DNA sequencing, DNA amplification and mutagenesis. However, thermostable DNA polymerases and their associated activities (reviewed in Abramson, 1995, in PCR Strategies, (Innis et al. ed., Academic Press, Inc.)) are not always optimal for a given application (reviewed in WO0161015, hereby incorporated by reference in its entirety). Because of the diversity of properties and characteristics potentially exhibited by nucleic acid polymerases generally, practitioners in the art have sought to modify, to alter, or to recombine various features of nucleic acid polymerases in an effort to develop new and useful variants of the enzyme.

One approach has been directed to the discovery and isolation of new thermophilic nucleic acid polymerases, which may possess a unique and/or improved collection of catalytic properties. As a result, thermostable nucleic acid polymerases have been isolated from a variety of biological sources, including, but not limited to, species of the taxonomic genera, *Thermus, Thermococcus, Thermotoga, Pyrococcus*, and *Sulfolobus*.

Some of these naturally occurring thermostable DNA polymerases possess enzymatically active 3'-5'exonuclease domains, providing a natural proofreading capability and, thus, exhibiting higher fidelity than Taq DNA polymerase. However, these DNA polymerases also show slower DNA extension rates and an overall lower processivity when compared to Taq DNA polymerase, however, thus rendering these naturally occurring thermostable DNA polymerases less desirable for PCR, despite their higher fidelity.

In an effort to compensate for the deficiencies of individual thermostable polymerases, a second approach has been to develop multiple enzyme assemblages, combining, for example, Taq polymerase and a proofreading enzyme, such as Pfu polymerase or Vent DNA polymerase. These multiple-enzyme mixtures exhibit higher PCR efficiency and reduced error rates when compared to Taq polymerase alone (Barnes, PNAS USA 91:2216-2220 (1994).).

Another has been to develop new and useful variants of Taq polymerase through deletion/truncation techniques. The Stoffel fragment, for example, is a 544 amino acid C-terminal truncation of Taq DNA polymerase, possessing an enzymatically active 5' 3' polymerase domain but lacking 3'-5'exonuclease and 5'-3'exonuclease activity. Other commercially available thermostable polymerase deletions include Vent (exo-) and Deep Vent (exo-) (New England Biolabs, Beverly, Mass.). Deletion mutations serve only to remove functional domains of a nucleic acid polymerase, however, and do not add any novel features or enzymatic properties.

Polymerase mutagenesis is yet another approach that has been attempted to develop new and useful nucleic acid polymerase variants. For example, naturally occurring DNA polymerases strongly discriminate against the incorporation of nucleotide analogues. This property contributes to the fidelity of DNA replication and repair. However, the incorporation of nucleotide analogues is useful for many DNA synthesis applications, especially DNA sequencing. Hence, a DNA polymerase that lacks associated exonucleolytic activity, either 5'-nuclease activity or 3' to 5' exonuclease activity, is preferred for DNA sequencing. In order to generate thermostable DNA polymerases with reduced nucleotide discrimination, site-directed mutagenesis studies were initiated and resulted in the identification of mutant forms of a number of thermostable DNA polymerases with the requisite activities suitable for DNA sequencing (U.S. Pat. No. 5,466,591, incorporated herein by reference).

Yet another approach to modifying the property of a DNA polymerase is to generate chimeric DNA polymerases in which one or more protein domains having the requisite activity are combined with a DNA polymerase. DNA polymerase has been fused in frame to the helix-hairpin-helix DNA binding motifs from DNA topoisomerase V and shown to increase processivity, salt resistance and thermostability of the chimeric DNA polymerase as described in Pavlov et al., 2002, Proc. Natl. Acad. Sci USA, 99:13510-13515. Fusion of the thioredoxin binding domain to T7 DNA polymerase enhances the processivity of the chimeric DNA polymerase in the presence of thioredoxin as described in WO 97/29209. Fusion of the archaeal PCNA binding domain to Taq DNA polymerase results in a chimeric DNA polymerase that in the presence of PCNA has enhanced processivity and produces higher yields of PCR amplified DNA (Motz, M., et al., J. Biol. Chem. 2002 May 3; 277 (18); 16179-88). Also, fusion of the sequence non-specific DNA binding protein Sso7d or Sac7d from *Sulfolobus suafataricus* to a DNA polymerase, such as Pfu or Taq DNA polymerase, was shown to greatly increase the processivity of these DNA polymerases as disclosed in WO 01/92501 A1 which is hereby incorporated by reference in its entirety. Domain substitution of all or a portion of a DNA polymerase with the corresponding domain of a different DNA polymerase have also been described (U.S. 2002/0119461).

Despite these intense research efforts, there remains a need in the art to develop polymerases which are more suitable for nucleic acid synthesis, sequencing, and amplification.

SUMMARY OF THE INVENTION

The invention relates to a blend of two or more DNA polymerases, comprising at least one chimeric DNA polymerase and at least one non-chimeric DNA polymerase. At least one of the chimeric or non-chimeric DNA polymerase can be thermostable, an archaeal DNA polymerase, a eubacterial DNA polymerase and/or Pfu DNA polymerase.

The invention provides for blends wherein the chimeric DNA polymerase has one or more of reduced DNA polymerization activity, reduced based analog detection activity and is DNA polymerase 3'-5' exonuclease deficient.

The invention provides for blends wherein the chimeric DNA polymerase comprises a Glycine to Proline substitution at amino acid position 387 (G387P) and has reduced DNA polymerization activity. The chimeric DNA polymerase with reduced DNA polymerization activity may further comprise a mutation at position V93, wherein said mutation is a Valine to Arginine substitution, a Valine to Glutamic acid substitution, a Valine to Lysine substitution, a Valine to Aspartic acid substitution or a Valine to Asparagine substitution that confers a reduced base analog detection activity phenotype to said chimeric DNA polymerase.

The invention also provides for blends wherein the chimeric DNA polymerase comprises reduced base analog detection activity and a mutation at position V93, wherein the mutation is a Valine to Arginine substitution, a Valine to Glutamic acid substitution, a Valine to Lysine substitution, a Valine to Aspartic acid substitution or a Valine to Asparagine substitution. The chimeric DNA polymerase with reduced base analog detection activity can further comprise a Glycine to Proline substitution at amino acid position 387 (G387P) that confers a reduced DNA polymerization phenotype to said chimeric DNA polymerase. The chimeric DNA polymerase with reduced base analog detection activity may further comprise an Aspartate to alanine substitution at amino acid 141 (D141A) and a Glutamic acid to Alanine substitution at amino acid position 143 (D141A/E143A) that renders the chimeric DNA polymerase 3'-5' exonuclease deficient.

The invention also contemplates blends wherein any of the chimeric DNA polymerases described herein further comprises an Aspartate to alanine substitution at amino acid 141 (D141A) and a Glutamic acid to Alanine substitution at amino acid position 143 (D141A/E143A) that renders the chimeric DNA polymerase 3'-5' exonuclease deficient.

The invention provides for blends wherein the chimeric or non-chimeric DNA polymerase comprises a wild type, mutant or chemically modified DNA polymerase. The chimeric or non-chimeric DNA polymerase may be a proofreading polymerase, for example, Pfu, KOD, Tgo, Vent and DeepVent, or a non-proofreading polymerase, for example, Taq, Tth, exo$^-$Pfu, exo$^-$KOD, exo$^-$Tgo, exo$^-$Vent and exo$^-$DeepVent.

The non-chimeric DNA polymerase may be a mutant archaeal DNA polymerase with a reduced 3'-5' exonuclease activity, wherein said mutant archaeal DNA polymerase comprises an Aspartate to Alanine substitution at amino acid 141 (D141A) and a Glutamic acid to Alanine substitution at amino acid position 143 (D141A/E143A) that renders the mutant DNA polymerase 3'-5' exonuclease deficient.

The non-chimeric DNA polymerase may comprise a mutation selected from the group consisting of PfuV93R, PfuV93E, PfuV93D, PfuV93K, PfuV93N, PfuG387P, PfuV93R/G387P, PfuV93E/G387P, PfuV93D/G387P, PfuV93K/G387P and PfuV93N/G387P The non-chimeric DNA polymerase may be an N terminal truncation of Taq DNA polymerase that renders the mutant DNA polymerase 5'-3' exonuclease deficient.

In one embodiment, the non-chimeric DNA polymerase consists of a second blend of two or more DNA polymerases. The second blend may comprise a proofreading and a non-proofreading DNA polymerase, a non-proofreading and a non-proofreading DNA polymerase or a proofreading and a proofreading DNA polymerase. The second blend may consist of a pair of thermostable DNA polymerases selected from the group of: Pfu/Taq, Pfu/exo-Pfu, Taq/exo-Pfu or Pfu/JDF3 DNA polymerase. In one embodiment, at least one polymerase of the second blend is selected from the group consisting of Tth, Vent, DeepVent, KOD, JDF-3, exo-Vent, exo-DeepVent, exo-KOD, exo-JDF3, Tgo, exo-Tgo, PfuV93R, PfuV93E, PfuV93D, PfuV93K, PfuV93N and, PfuG387P The second blend may consist of a pair of thermostable DNA polymerases selected from the group of: Pfu/Taq, Pfu/exo-Pfu, Taq/exo-Pfu or Pfu/JDF3 DNA polymerase and further comprises a mutant selected from the group consisting of pol-Pfu (Pfu G387P), G387P/V93R, G387P/PfuV93E, G387P/PfuV93D, G387P/PfuV93K, G397P/PfuV93N, and G387P/PfuG387P pol-Pfu (Pfu G387P) DNA polymerase mutant.

The invention provides for blends wherein the chimeric DNA polymerase further comprises a polypeptide with an increase in an activity selected from the group consisting of: processivity, proofreading, fidelity, DNA binding activity, strand displacement activity, polymerase activity, nucleotide binding and recognition, efficiency, template length amplification capability, GC-rich target amplification efficiency, specificity, thermostability, intrinsic hot start capability, or salt resistance.

The chimeric DNA polymerase may further comprise a polypeptide with a reduced activity selected from the group consisting of: DNA polymerase activity at room temperature, amplification slippage on templates with tri-nucleotide repeat stretches, extension time in a PCR reaction or amplification cycles in a PCR reaction.

The chimeric DNA polymerase may comprise a protein domain selected from the group of: thioredoxin processivity factor binding domain of bacteriophage T7, archaeal PCNA binding domain, PCNA, the helix-hairpin-helix DNA binding motifs from DNA topoisomerase V or the DNA binding protein Sso7d or Sac7d from *Sulfolobus sulfataricus*.

The invention also relates to composition comprising any of the blends described herein. The compositions may further comprise a PCR enhancing factor and/or an additive.

The invention also relates to kits comprising any of the blends of the packaging materials therefor. The kits of the invention may further comprise a PCR enhancing factor and/or an additive.

The invention also relates to a chimeric DNA polymerase with reduced DNA polymerization activity, reduced base analog detection activity and/or reduced 3'-5' exonuclease activity. The chimeric DNA polymerase may comprise a thermostable DNA polymerase, an archaeal DNA polymerase, and/or Pfu DNA polymerase.

The chimeric DNA polymerase with reduced DNA polymerization activity may comprise a Glycine to Proline substitution at amino acid position 387 (G387P). The chimeric DNA polymerase with reduced DNA polymerization activity may further comprise a mutation at position V93, wherein said mutation is a Valine to Arginine substitution, a Valine to Glutamic acid substitution, a Valine to Lysine substitution, a Valine to Aspartic acid substitution or a Valine to Asparagine substitution that confers a reduced base analog detection activity phenotype to said chimeric DNA polymerase.

The chimeric DNA polymerase with reduced base analog detection activity may comprise a mutation at position V93, wherein the mutation is a Valine to Arginine substitution, a Valine to Glutamic acid substitution, a Valine to Lysine substitution, a Valine to Aspartic acid substitution or a Valine to Asparagine substitution. The chimeric DNA polymerase with reduced base analog detection activity may further comprise a Glycine to Proline substitution at amino acid position 387 (G387P) that confers a reduced DNA polymerization phenotype to said chimeric DNA polymerases.

The chimeric DNA polymerase with reduced DNA polymerization activity or reduced base analog detection activity may further comprise an Aspartate to alanine substitution at amino acid 141 (D141A) and a Glutamic acid to Alanine substitution at amino acid position 143 (D141A/E143A) that renders said chimeric DNA polymerase 3'-5' exonuclease deficient.

The invention also relates to an isolated polynucleotide comprising a nucleotide sequence encoding any of the chimeric DNA polymerases described herein.

The invention also relates to a method for DNA synthesis comprising: a) providing a blend of two or more DNA polymerases according to the invention; and contacting the enzyme with a nucleic acid template, wherein the blend permits DNA synthesis.

The invention also relates to a method for DNA synthesis comprising: (a) providing a blend of two or more DNA polymerases, according to the invention; and (b) contacting the blend with a nucleic acid template, wherein said enzyme permits DNA synthesis.

The invention also provides for a method for cloning of a DNA synthesis product comprising: (a) providing a blend of two or more DNA polymerases, according to the invention; (b) contacting the blend with a nucleic acid template, wherein the blend permits DNA synthesis to generate a synthesized DNA product; and (c) inserting the synthesized DNA product into a cloning vector.

The invention also encompasses a method for sequencing DNA comprising the steps of: a) contacting a template DNA strand with a sequencing DNA primer; b) contacting the DNA of the first step with the blend of two or more DNA polymerases of the invention with deoxyribonucleoside triphosphates, and a chain-terminating nucleotide analog, c) incubating the mixture of step (b) under conditions sufficient to synthesize a random population of DNA molecules complementary to the first DNA molecule, wherein the synthesized DNA molecules are shorter in length than the first DNA molecule and wherein the synthesized DNA molecules comprise a terminator nucleotide at their 5' termini; and d) separating the synthesized DNA molecules by size so that at least a part of the nucleotide sequence of the first DNA molecule can be determined.

The invention also provides for a method of linear or exponential PCR amplification for random or site directed mutagenesis comprising the steps of: incubating a reaction mixture comprising a nucleic acid template, at least two PCR primers, and a blend of two or more non-proofreading DNA polymerases, wherein the blend comprises a chimeric DNA polymerase and non-chimeric DNA polymerase under conditions which permit amplification of the nucleic acid template by the blend of two or more non proofreading DNA polymerases to produce a mutated amplified product.

Any of the methods of the invention can be performed in the presence of a PCR enhancing factor and/or an additive.

DEFINITIONS

As used herein, a "blend" refers to a combination of two or more DNA polymerases comprising at least one chimeric DNA polymerase and at least one non-chimeric DNA polymerase. The invention contemplates a "blend" wherein at least one of said chimeric or non-chimeric DNA polymerase is thermostable, is an archael or eubacterial DNA polymerase and/or is a Pfu DNA polymerase. The ratio of DNA polymerase enzymes in a "blend" comprising one chimeric and one non-chimeric polymerase is in the range of 1:1-1:5-5:1, or 1:1-1:10-10:1, or 1:1-1:25-25:1 or 1:1-1:100-100:1. For embodiments wherein a "blend" comprises one chimeric DNA polymerase and two non-chimeric polymerases the ratio of the first non-chimeric DNA polymerase to the second non-chimeric DNA polymerase is in the range of 1:1-1:5-5:1, or 1:1-1:10-10:1, or 1:1-1:25-25:1 or 1:1-1:100-100:1. A "blend" of the invention has a >10% increase in one or more of the following activities (using the assays described hereinbelow) as compared to the non-chimeric component of the blend for a genomic and/or plasmid template: processivity, efficiency, template length amplification capability, GC-rich target amplification efficiency, specificity, thermostability; intrinsic hot start capability, proofreading activity, fidelity, DNA binding activity, strand displacement activity, nucleotide binding and recognition, and salt resistance. A blend of the invention will also have a >10% decrease as compared to the non-chimeric blends for genomic and/or plasmid template in one or more of the following activities (assayed as described hereinbelow): amplification slippage on templates with tri-nucleotide repeat stretches or DNA polymerase activity at room temperature. In one embodiment, a "blend" of the invention has an extension time in a PCR reaction that is decreased by 5 sec, preferably 15 sec and more preferably 45 sec or more, as compared to the extension time observed in the presence of the non-chimeric component of the blend alone. In another embodiment, a "blend" of the invention has a decrease in the number of amplification cycles for PCR of 1, 1-5 or 5 or more cycles, as compared to the non-chimeric component of the blend alone. In another embodiment, fewer units (0.001, 0.01, 0.1 or 1 or more) of a "blend" of the invention are useful in an application of the invention as compared to the non-chimeric component of the blend.

A blend may also include a PCR enhancing factor and/or an additive, as described herein.

As used herein, "reduced base analog detection" refers to a DNA polymerase, with a reduced ability to recognize a base analog, for example, uracil or inosine, present in a DNA template. In this context, mutant DNA polymerase with "reduced" base analog detection activity is a DNA polymerase mutant having a base analog detection activity which is lower than that of the wild-type enzyme, i.e., having less than 10% (e.g., less than 8%, 6%, 4%, 2% or less than 1%) of the base analog detection activity of that of the wild-type enzyme. Base analog detection activity may be determined according to the assays similar to those described for the detection of DNA polymerases having a reduced uracil detection activity as described in Greagg et al. (1999) Proc. Natl. Acad. Sci. 96, 9045-9050. Alternatively, "reduced" base analog detection refers to a mutant DNA polymerase with a reduced ability to recognize a base analog, the "reduced" recognition of a base analog being evident by an increase in the amount of >10 Kb PCR of at least 10%, preferably 50%, more preferably 90%, most preferably 99% or more, as compared to a wild type DNA polymerase without a reduced base analog detection activity. The amount of a >10 Kb PCR product is measured either by spectorophotometer-absorbance assays of gel eluted >10 Kb PCR DNA product or by fluorometric analysis of >10 Kb PCR products in an ethidium bromide stained agarose electrophoresis gel using, for example, a Molecular Dynamics (MD) FluorImager™ (Amersham Biosciences, catalogue #63-0007-79).

As used herein, "reduced uracil detection" refers to a DNA polymerase with a reduced ability to recognize a uracil base present in a DNA template. In this context, mutant DNA polymerase with "reduced" uracil detection activity is a DNA polymerase mutant having a uracil detection activity which is lower than that of the wild-type enzyme, i.e., having less than 10% (e.g., less than 8%, 6%, 4%, 2% or less than 1%) of the uracil detection activity of that of the wild-type enzyme. Uracil detection activity may be determined according to the assays described in Greagg et al. (1999) Proc. Natl. Acad. Sci. 96, 9045-9050. Alternatively, "reduced" uracil detection refers to a mutant DNA polymerase with a reduced ability to recognize uracil, the "reduced" recognition of uracil being evident by an increase in the amount of >10 Kb PCR of at least 10%, preferably 50%, more preferably 90%, most preferably 99% or more, as compared to a wild type DNA polymerase without a reduced uracil detection activity. The amount of a >10 Kb PCR product is measured either by spectorophotometer-absorbance assays of gel eluted >10 Kb PCR DNA product or by fluorometric analysis of >10 Kb PCR products in an ethidium bromide stained agarose electrophoresis gel using, for example, a Molecular Dynamics (MD) FluorImager™ (Amersham Biosciences, catalogue #63-0007-79).

DNA binding and assays for detecting DNA binding are described in: PCT/US01/17492.

PCT/US01/17492 states that the activity of the sequence non-specific double-stranded nucleic acid binding domains can be assessed using a variety of assays. Suitable binding domains exhibit a marked preference for double-stranded vs. single-stranded nucleic acids.

Specificity for binding to double-stranded nucleic acids can be tested using a variety of assays well known to those skilled in the art. These include such assays as filter binding assays or gel-shift assays. For example, in a filter-binding assay the polypeptide to be assessed for binding activity to double-stranded DNA is premixed with radio-labeled DNA, either double-stranded or single-stranded, in the appropriate buffer. The mixture is filtered through a membrane (e.g., nitrocellulose) which retains the protein and the protein-DNA complex. The amount of DNA that is retained on the filter is indicative of the quantity that bound to the protein. Binding can be quantified by a competition analysis in which binding of labeled DNA is competed by the addition of increasing amounts of unlabelled DNA. A polypeptide that binds double-stranded DNA at a 10-fold or greater affinity than single-stranded DNA is defined herein as a double-stranded DNA binding protein. Alternatively, binding activity can be assessed by a gel shift assay in which radiolabeled DNA is incubated with a test polypeptide. The protein-DNA complex will migrate slower through the gel than unbound DNA, resulting in a shifted band. The amount of binding is assessed by incubation of samples with increasing amounts of double-stranded or single stranded unlabeled DNA, and quantifying the amount of radioactivity in the shifted band.

Strand displacement refers to the activity described in Hogrefe et al Methods of Enzymology (2001) 334:91-116 and Kong et al (93) J. Biol. Chem. 268:1965. Assays for measuring strand displacement activity are described in Hogrefe et al Methods of Enzymology (2001) 334:91-116 and Kong et al (93) J. Biol. Chem. 268:1965.

In Kong, 5'-$^{32}$P-end labeled 1224 primer was annealed to M13mp18 single-stranded DNA. The gap-filling oligonucleotide was simultaneously annealed downstream to the template, leaving a 79-nt gap between the oligonucleotides. Klenow and T4 DNA polymerase reactions were performed at 37° C., whereas Tli DNA polymerase reactions were incubated at 55° C., 63° C., and 72° C. Reactions were initiated by addition of DNA polymerase, and aliquots were removed as a function of time, added to a stop solution containing formamide with 0.37% EDTA (pH 7.0) and incubated on ice until all samples were collected. Subsequently samples were run on a 6% acrylamide, 6M urea sequencing gel in Tris/borate/EDTA buffer (Peacock and Dingman, 1968) and visualized by autoradiography.

DNA polymerase activity at room temperature is as described in The Methods of Enzymology (2001) 334:91-116. Assays for measuring DNA polymerase activity at room temperature are described in The Methods of Enzymology (2001) 334:91-116 and in Nielson et al (1997) Strategies 10:40-43 Newsletter articles.

As used herein, "GC—rich target amplification efficiency" refers to the amplification efficiency of DNA templates that have greater than 50% GC content and are more difficult to melt during PCR. These targets frequently form secondary structure when the temperature cycles to the annealing temperature making PCR amplification difficult. "GC-rich target amplification" is assayed by performing PCR amplification on a target with greater than 50% GC content and comparing the yield of amplicon generated on a gel (see Biotechniques 2002 April; 32(4):866, 868, 870-2, 874).

A polymerase with "intrinsic hot start capability" refers to a thermostable DNA polymerase that has very low (<25°) DNA polymerase activity at non-stringent primer annealing temperatures (≦45°). These polymerases and assays for their detection are described in Nielson et al (1997) Strategies 10:40-43.

"DNA slippage" or "amplification slippage on templates with tri-nucleotide repeat stretches" and assays for detection of this activity is as described in J Mol Biol 2001 Sep. 14; 312(2): 323-33, J Biol Chem 1999 Sep. 24; 274(39):27481-90, EMBO J 2001 May 15; 20(10):2587-95, Biochemistry 1996 Jan. 23; 35(3):1046-53.

To test the ability of different polymerases to undergo slippage, Canceill et al (*J. Biol. Chem.* 274:27481-27490, 1999) carried out primer extension reactions with radiolabeled nucleotides on a single-stranded circular plasmid DNA. This template carries two 27-bp direct repeats that flank a pair of 300-bp inverted repeats. *E. coli* pol III HE mainly generates one intermediate and two final products on this template. The intermediate, a partially replicated template, is due to the arrest of the polymerase at the hairpin formed by annealing of the two inverted repeats. One final product is a fully double-stranded molecule, termed parental, which results from synthesis through the hairpin, and therefore involves the separation of duplex DNA strands. The other is a heteroduplex molecule, composed of one recombinant and one parental DNA strand, resulting from a polymerase slippage. The recombinant strand lacks the segment flanked by the direct repeats (2 kilobases) and one of the direct repeats. The ability of the polymerase to carry out either reaction can be estimated from the proportion of these products.

To determine the slippage efficiency the reaction products were analyzed by electrophoresis on agarose gel and revealed by autoradiography.

A chimera that exhibits decreased DNA polymerase activity at room temperature preferably exhibits a shift in the activity vs. temperature profile such that reduced polymerase activity is observed at a suboptimal temperature (for example a non-specific primer annealing/extension temperature) and wild type polymerase activity was observed at stringent primer annealing/extension temperature. Such chimeras are expected to exhibit improved specificity in PCR.

The invention contemplates mutant DNA polymerases that exhibits reduced base analog detection (for example, reduced detection of a particular base analog such as uracil or inosine or reduced detection of at least two base analogs).

As used herein, "base analogs" refer to bases that have undergone a chemical modification as a result of the elevated temperatures required for PCR reactions. In a preferred embodiment, "base analog" refers to uracil that is generated by deamination of cytosine. In another preferred embodiment, "base analog" refers to inosine that is generated by deamination of adenine.

As used herein, "synthesis" refers to any in vitro method for making a new strand of polynucleotide or elongating existing polynucleotide (i.e., DNA or RNA) in a template dependent manner. Synthesis, according to the invention, includes amplification, which increases the number of copies of a polynucleotide template sequence with the use of a polymerase. Polynucleotide synthesis (e.g., amplification) results in the incorporation of nucleotides into a polynucleotide (i.e., a primer), thereby forming a new polynucleotide molecule complementary to the polynucleotide template. The formed polynucleotide molecule and its template can be used as templates to synthesize additional polynucleotide molecules.

"DNA synthesis", according to the invention, includes, but is not limited to, PCR, the labelling of polynucleotide (i.e., for probes and oligonucleotide primers), and polynucleotide sequencing.

As used herein, "polymerase" refers to an enzyme that catalyzes the polymerization of nucleotide (i.e., the polymerase activity). Generally, the enzyme will initiate synthesis at the 3'-end of the primer annealed to a polynucleotide template sequence, and will proceed toward the 5' end of the template strand. "DNA polymerase" catalyzes the polymerization of deoxynucleotides. In a preferred embodiment, the DNA polymerase according to the invention is thermostable. In another preferred embodiment, the DNA polymerase according to the invention is an archaeal DNA polymerase.

The nucleic acid polymerases used in the present invention may be mesophilic or thermophilic, and are preferably thermophilic. Preferred mesophilic DNA polymerases include T7 DNA polymerase, T5 DNA polymerase, T4 DNA polymerase, Klenow fragment DNA polymerase, DNA polymerase III and the like. Preferred thermostable DNA polymerases that may be used in the methods of the invention include Taq, Tne, Tma, Pfu, Tfl, Tth, Stoffel fragment, VENT™ and DEEPVENT™ DNA polymerases, KOD, Tgo, JDF3, and mutants, variants and derivatives thereof (U.S. Pat. No. 5,436,149; U.S. Pat. No. 4,889,818; U.S. Pat. No. 4,965,185; U.S. Pat. No. 5,079,352; U.S. Pat. No. 5,614,365; U.S. Pat. No. 5,374,553; U.S. Pat. No. 5,270,179; U.S. Pat. No. 5,047,342; U.S. Pat. No. 5,512,462; WO 92/06188; WO 92/06200; WO 96/10640; Barnes, W. M., Gene 112:29-35 (1992); Lawyer, F. C., et al., PCR Meth. Appl. 2:275-287 (1993); Flaman, J.-M, et al., Nuc. Acids Res. 22(15):3259-3260 (1994)). For amplification of long nucleic acid molecules (e.g, nucleic acid molecules longer than about 3-5 Kb in length), at least two DNA polymerases (one substantially lacking 3' exonuclease activity and the other having 3' exonuclease activity) are typically used. See U.S. Pat. No. 5,436,149; U.S. Pat. No. 5,512,462; Fames, W. M., Gene 112:29-35 (1992); and copending U.S. patent application Ser. No. 09/741,664, filed Dec. 21, 2000, the disclosures of which are incorporated herein in their entireties. Examples of DNA polymerases substantially lacking in 3' exonuclease activity include, but are not limited to, Taq, Tne(exo-), Tma(exo-), Pfu(exo-), Pwo(exo-), exo-KOD and Tth DNA polymerases, and mutants, variants and derivatives thereof.

As used herein, "archaeal" DNA polymerase refers to DNA polymerases that belong to either the Family B/pol I-type group (e.g., Pfu, KOD, Pfx, Vent, Deep Vent, Tgo, Pwo) or the pol II group (e.g., *Pyrococcus furiosus* DP1/DP2 2-subunit DNA polymerase). In one embodiment, "archaeal" DNA polymerase refers to thermostable archaeal DNA polymerases (PCR-able) and include, but are not limited to, DNA polymerases isolated from *Pyrococcus* species (*furiosus*, species GB-D, *woesii, abysii, horikoshii*), *Thermococcus* species (*kodakaraensis* KOD1, *litoralis*, species 9 degrees North-7, species JDF-3, *gorgonarius*), *Pyrodictium occultum*, and *Archaeoglobus fulgidus*. It is estimated that suitable archaea would exhibit maximal growth temperatures of >80-85° C. or optimal growth temperatures of >70-80° C. Appropriate PCR enzymes from the archaeal pol I DNA polymerase group are commercially available, including Pfu (Stratagene), KOD (Toyobo), Pfx (Life Technologies, Inc.), Vent (New England BioLabs), Deep Vent (New England BioLabs), Tgo (Roche), and Pwo (Roche). Additional archaea related to those listed above are described in the following references: Archaea: A Laboratory Manual (Robb, F. T. and Place, A. R., eds.), Cold Spring Harbor Laboratory Press, Cold Spring Harbor, N.Y., 1995

As used herein, "mutant" polymerase refers to a DNA polymerase, as defined herein, comprising one or more mutations that modulate, as defined herein, one or more activities of the DNA polymerase including, but not limited to, DNA polymerization activity, base analog detection activities, DNA polymerization activity, reverse transcriptase activity, processivity, salt resistance, DNA binding, strand displacement activity, nucleotide binding and recognition, 3'-5' or 5'-3' exonuclease activities, proofreading, fidelity, efficiency, specificity, thermostability and intrinsic hot start capability or decreased DNA polymerization at room temperature, decreased amplification slippage on templates with tri-nucleotide repeat stretches, decreased amplification cycles, decreased extension times, and a decrease in the amount of polymerase needed for the applications described herein. In one embodiment, the "mutant" polymerase of the invention refers to a DNA polymerase containing one or more mutations that reduce one or more base analog detection activities of the DNA polymerase. In one embodiment, a "mutant" refers to a polymerase that has a mutation that confers an improved polymerization rate or fidelity on the polymerase. In a preferred embodiment, the "mutant" polymerase of the invention has a reduced uracil detection activity. In a preferred embodiment, the "mutant" polymerase of the invention has a reduced inosine detection activity. In another preferred embodiment, the "mutant" polymerase of the invention has a reduced uracil and inosine detection activity. In another preferred embodiment, the "mutant" polymerase of the invention has a reduced DNA polymerization activity. Any of the "mutants" for example a mutant with reduced uracil activity, may also possess improved polymerization rate and/or fidelity, as compared to a wild-type polymerase. A "mutant" polymerase as defined herein, includes a polymerase comprising one or more amino acid substitutions, one or more amino acid insertions, a truncation or an internal deletion. A "mutant" polymerase as defined herein includes non-chimeric and chimeric polymerases as defined herein.

A "mutant" polymerase as defined herein also includes a chimeric polymerase wherein any of the single, double or triple mutant DNA polymerases described herein, any mutant DNA polymerases comprising an insertion, described herein, or any of the truncated, or deleted mutant DNA polymerases described herein, occur in combination with a polypeptide that modulates one or more activities of the DNA polymerase including, but limited to, DNA polymerization activity, base analog detection activities, DNA polymerization activity, reverse transcriptase activity, processivity, salt resistance, DNA binding, strand displacement activity, nucleotide binding and recognition, 3'-5' or 5'-3' exonuclease activities, proofreading, fidelity efficiency, specificity, thermostability and intrinsic hot start capability or decreased DNA polymerization at room temperature, decreased amplification slippage on templates with tri-nucleotide repeat stretches, decreased amplification cycles, decreased extension times, and a decrease in the amount of polymerase needed for the applications described herein, thereby forming a chimera, as defined herein. For example, a polypeptide that increases processivity and or salt resistance is described in WO 01/92501 A1 and Pavlov et al., 2002, Proc. Natl. Acad. Sci. USA, 99:13510-13515, herein incorporated by reference in their entirety.

A "chimera" as defined herein, is a fusion of a first amino acid sequence (protein) comprising a wild type or mutant DNA polymerase of the invention, joined to a second amino acid sequence defining a polypeptide that modulates one or more activities of the DNA polymerase including, but not limited to, processivity, salt-resistance, DNA binding, strand displacement activity, polymerase activity, nucleotide binding and recognition, 3'-5' or 5'-3' exonuclease activities, proofreading, fidelity and/or decreased DNA polymerization at room temperature, wherein the first and second amino acids are not found in the same relationship in nature. A "chimera" according to the invention contains two or more amino acid sequences (for example a sequence encoding a wild type or mutant DNA polymerase and a polypeptide that increases processivity and/or salt resistance) from unrelated proteins, joined to form a new functional protein. In one embodiment a "chimera" according to the invention comprises a first amino acid sequence derived from a first polymerase species (e.g. Pfu N-terminus) and a second amino acid sequence derived from a second polymerase species (e.g. KOD C-terminus. A chimera of the invention may present a foreign polypeptide which is found (albeit in a different protein) in an organism which also expresses the first protein, or it may be an "interspecies", "intergenic", etc. fusion of protein structures expressed by different kinds of organisms. The invention encompasses chimeras wherein the polypeptide that increases processivity and/or salt resistance is joined N-terminally or C-terminally to, or is inserted at any internal position of a wild-type DNA polymerase or any of the mutant DNA polymerases described herein.

"Domain" refers to a unit of a protein or protein complex, comprising a polypeptide subsequence, a complete polypeptide sequence, or a plurality of polypeptide.

"Fused" refers to linkage by covalent bonding.

As used herein, "polypeptide that increases processivity and/or salt resistance" refers to a domain that is a protein or a region of a protein or a protein complex, comprising a polypeptide sequence, or a plurality of peptide sequences wherein that region increases processivity, as defined herein, or increases salt resistance, as defined herein. A "polypeptide that increases processivity and/or salt resistance useful according to the invention includes but is not limited to any of the domains included in Pavlov et al., supra or WO 01/92501, for example Sso7d, Sac7d, HMF-like proteins, PCNA homologs, and helix-hairpin-helix domains, for example derived from Topoisomerase V.

As used herein, "joined" refers to any method known in the art for functionally connecting polypeptide domains, including without limitation recombinant fusion with or without intervening domains, intein-mediated fusion, non-covalent association, and covalent bonding, including disulfide bonding, hydrogen bonding, electrostatic bonding, and conformational bonding.

As used herein, the term "modulate" refers to an increase or decrease of 2 fold, preferably 5 fold, preferably 20 fold, preferably 100 fold, more preferably 500 fold or more in an activity of a chimeric or non-chimeric DNA polymerase of the invention comprising one or more mutations as compared to a chimeric or non-chimeric DNA polymerase of the invention that does not comprise any mutations.

As used herein, "processivity" refers to the ability of a nucleic acid modifying enzyme, for example a polymerase, to remain attached to the template or substrate and perform multiple modification reactions. "Modification reactions" include but are not limited to polymerization, and exonucleolytic cleavage. "Processivity" also refers to the ability of a nucleic acid modifying enzyme, for example a polymerase, to modify relatively long (for example 0.5-1 kb, 1-5 kb or 5 kb or more) tracts of nucleotides. "Processivity" also refers to the ability of a nucleic acid modifying enzyme, for example a DNA polymerase, to perform a sequence of polymerization steps without intervening dissociation of the enzyme from the growing DNA chains. "Processivity" can depend on the nature of the polymerase, the sequence of a DNA template, and reaction conditions, for example, salt concentration, temperature or the presence of specific proteins.

As used herein, "increased processivity" refers to an increase of 5-10%, preferably 10-50%, more preferably 50-100% or more, as compared to a wild type or mutant archael DNA polymerase that lacks a polypeptide that increases processivity and/or salt resistance as defined herein. Processivity and increased processivity can be measured according the methods defined herein and in Pavlov et al., supra and WO 01/92501 A1. A polymerase with increased processivity that is a chimera comprising a polypeptide that increases processivity, as defined herein, is described in Pavlov et al. supra and WO 01/92501 A1.

In WO 01/92501, processivity was measured by determining the number of nucleotides incorporated during a single binding event of the polymerase to a primed template.

Briefly, 40 nM of a 5' FAM-labeled primer (34 nt long) was annealed to 80 nM of circular or linearized ssM13mp18 DNA to form the primed template. The primed template was mixed with the DNA polymerase of interest at a molar ratio of approximately 4000:1 (primed DNA:DNA polymerase) in the presence of standard PCR buffer (free of $Mg^{++}$) and 200 μM of each dNTPs. $MgCl_2$ was added to a final concentration of 2 mM to initiate DNA synthesis. At various times after initiation, samples were quenched with sequencing loading dye containing 99% formamide, and analyzed on a sequencing gel. The median product length, which is defined as the product length above or below which there are equal amounts of products, was determined based on integration of all detectable product peaks. At a polymerase concentration for which the median product length change with time or polymerase concentration, the length corresponds to the processivity of the enzyme.

As used herein, "increased salt resistance" refers to a polymerase that exhibits >50% activity at a salt concentration that is know to be greater than the maximum salt concentration at which the wild-type polymerase is active. The maximum salt concentration differs for each polymerase and is known in the art, or can be experimentally determined according to methods in the art. For example, Pfu is inhibited at 30 mM (in PCR) so a Pfu enzyme with increased salt resistance would have significant activity (>50%) at salt concentrations above 30 mM. A polymerase with increased salt resistance that is a chimera comprising a polypeptide that increases salt resistance, as defined herein, is described in Pavlov et al. supra and WO 01/92501 A1.

Wang in WO 01/92501 states that the binding of a polymerase to a primed DNA template is sensitive to the ionic strength of the reaction buffer due to electrostatic interactions, which is stronger in low salt concentration and weaker in high. The presence of Sso7d in a fusion polymerase protein stabilizes the binding interaction of the polymerase to DNA template. This example demonstrates that Sso7d fusion proteins exhibit improved performance in PCR reactions containing elevated KCl concentrations.

Lambda DNA (2 pM) was used as a template in a PCR reactions with primers 57F and 732R. The concentration of KCl was varied from 10 mM to 150 mM, while all other components of the reaction buffer were unchanged. The PCR reaction was carried out using a cycling program of 94° C. for 3 min, 20 cycles of 94° C. for 30 sec, 55° C. for 30 sec, and 72° C. for 30 sec, followed by 72° C. at 10 min. Upon completion of the reaction, 5 μl of the PCR reaction was removed and mixed with 195 μl of 1:400 dilution of PicoGreen in TE to quantify the amounts of amplicon generated. The PCR reaction products were also analyzed in parallel on an agarose gel to verify that amplicons of expected length were generated.

As used herein, a DNA polymerase with a "reduced DNA polymerization activity" is a DNA polymerase mutant comprising a DNA polymerization activity which is lower than that of the wild-type enzyme, e.g., comprising less than 10% DNA (e.g., less than 8%, 6%, 4%, 2% or less than 1%) polymerization activity of that of the wild-type enzyme. Methods used to generate characterize Pfu DNA polymerases with reduced DNA polymerization activity are disclosed in the pending U.S. patent application Ser. No. 10/035,091 (Hogrefe, et al.; filed: Dec. 21, 2001); the pending U.S. patent application Ser. No. 10/079,241 (Hogrefe, et al.; filed Feb. 20, 2002); the pending U.S. patent application Ser. No. 10/208,508 (Hogrefe et al.; filed Jul. 30, 2002); and the pending U.S. patent application Ser. No. 10/227,110 (Hogrefe et al.; filed Aug. 23, 2002), the contents of which are hereby incorporated in their entirety.

US Patent publication 2003018074 teaches that known DNA polymerase mutants that selectively reduce DNA polymerization activity can be found in the art, for example, in Blanco et al., 1995 *Methods of Enzymology* 262:283-294 ((Bacteriophage Φ29); Truniger et al., 1996, EMBO J. 15:3430-3441 (Bacteriophage Φ29); Abdus Sattar et al., 1996, *Biochemistry* 35:16621-9 (Bacteriophage T4); Tuske et al., 2000, *J. Biological Chemistry* 275:23759-68 (Klenow fragment); Bohlke et al., 2000, *Nucleic Acid Research* 28:3910-3917 (*Thermococcus aggregans*); Pisani et al., 1998, *Biochemistry* 37:15005-15012 (*Sulfolobus solfataricus*); Komori et al., 2000, Protein Eng 13:41-7 (*Pyrococcus furiosus*); Shen et, al., 2001 *J. Biological Chemistry* 276: 27376-83 (*Pyrococcus horikoshi* Family D).

Site-directed mutagenesis of bacteriophage Φ29 DNA polymerase leads to the identification of mutations in the polymerase domain which reduce DNA polymerase activity, while having minimal effects on 3'-5' exonuclease activity (Blanco, L. and Salas, M. 1995, *Methods of Enzymology* 262:283-294). In one embodiment of the invention, one or more corresponding amino acids in Pfu DNA polymerases are mutated (e.g., by substitutions: D405E, Y410F, T5421), D543G, K593T, Y595S). It is understood that other amino acid side substitutions at these same sites would also selectively reduce DNA polymerase activity.

US Patent publication 20030180741 further teaches that random or site-directed mutants generated as known in the art or as described therein and expressed in bacteria may be screened for reduced polymerization by several different assays. In one method, $exo^+$ DNA polymerase proteins expressed in lytic lambda phage plaques generated by infection of host bacteria with expression vectors based on, for example, Lambda ZapII®, are transferred to a membrane support. The immobilized proteins are then assayed for polymerase activity on the membrane by immersing the membranes in a buffer containing a DNA template and the unconventional nucleotides to be monitored for incorporation.

Mutant polymerase libraries may be screened using a variation of the technique used by Sagner et al (Sagner, G., Ruger, R., and Kessler, C. (1991) *Gene* 97:119-123). For this approach, lambda phage clones are plated at a density of 10-20 plaques per square centimeter. Proteins present in the plaques are transferred to filters and moistened with polymerase screening buffer (50 mM Tris (pH 8.0), 7 mM $MgCl_2$, 3 mM ft-ME). The filters are kept between layers of plastic wrap and glass while the host cell proteins are heat-inactivated by incubation at 65° C. for 30 minutes. The heat-treated filters are then transferred to fresh plastic wrap and approximately 351 of polymerase assay cocktail are added for every square centimeter of filter. The assay cocktail consists of 1× cloned Pfu (cPfu) magnesium free buffer (1× buffer is 20 mM Tris-HCl (pII 8.8), 10 mM KCl, 10 mM $(NH_4)_2SO_4$, 100 μg/ml bovine serum albumin (BSA), and 0.1% Triton X-100; Pfu Magnesium-free buffer may be obtained from Stratagene (Catalog No. 200534)), 125 ng/ml activated calf thymus or salmon sperm DNA, 1.29 μCi/ml $\alpha$-$^{33}$P ddNTP. The filters are placed between plastic wrap and a glass plate and then incubated at 65° C. for one hour, and then at 70° C. for one hour and fifteen minutes. Filters are then washed three times in 2×SSC for five minutes per wash before rinsing twice in 100% ethanol and vacuum drying. Filters are then exposed to X-ray film (approximately 16 hours), and plaques that incorporate label are identified by aligning the filters with the original plate bearing the phage clones, Plaques identified in this way are re-plated at more dilute concentrations and assayed under similar conditions to allow the isolation of purified plaques.

In assays such as the one described above, the signal generated by the label is a direct measure of the polymerization activity of the polymerase. A plaque comprising a mutant DNA polymerase with reduced DNA polymerization activity compared to that of the wild-type enzyme can be selected.

US Patent publication 20030180741 also teaches DNA polymerase activity was measured by monitoring incorporation of radiolabelled TTP into activated calf thymus DNA. A suitable DNA polymerase reaction cocktail contains: 1×PCR reaction buffer, 200 μm each dATP, dCTP, and dGTP, 195 μM TTP, 5 μM [$^3$H]TTP (NEN #NET-221H, 20.5 Ci/mmole; partially evaporated to remove EtOH), and 250 μg/ml of activated calf thymus DNA (e.g., Pharmacia #27-4575-01). DNA polymerases (wt Pfu or Pfu mutants) were diluted in Pfu storage buffer and 1 μl of each enzyme dilution was added to aliquots of polymerase cocktail. Polymerization reactions were conducted in duplicate or triplicate for 30 minutes at 72° C. The extension reactions were quenched on ice, and then 5 μl aliquots are spotted immediately onto DE81 ion-exchange filters (2.3 cm; Whatman #13658323). Unincorporated [$^3$H] TTP was removed by 6 washes with 2×SCC (0.3M NaCl, 30 mM sodium citrate, pH 7.0), followed by a brief wash with 100% ethanol. Incorporated radioactivity is measured by scintillation counting.

Reactions that lack enzyme were set up along with sample incubations to determine "total cpms" (omit filter wash steps) and "minimum cpms" (wash filters as above). Sample cpms were subtracted by minimum cpms to determine "corrected cpms" for each DNA polymerase.

To determine percent (%) activity relative to wild type Pfu, 50-500 ng of purified Pfu mutants were assayed in a nucleotide incorporation assay, alongside will type Pfu diluted serially over the linear range of the assay (50-500 pg; 0.003-0.03 U).

As used herein, "proofreading" activity refers to 3' to 5' exonuclease activity of a DNA polymerase.

US Patent publication 20030180741 teaches that exonuclease reactions were performed (in triplicate) by adding 4 μl aliquots of diluted DNA polymerases (0.25-10 U wt Pfu; 5-200 ng) to 46 μl of reaction cocktail. Reactions were incubated for 1 hour at 72° C. Reactions lacking DNA polymerase were also set up along with sample incubations to determine "total cpms" (no TCA precipitation) and "minimum cpms" (TCA precipitation, ace below).

Exonuclease reactions are stopped by transferring the tubes to ice. Sonicated salmon sperm DNA (150 μl; 2.5 mg/ml stock) and TCA (200 μl; 10% stock) were added to all but the "total cpms" tubes. The precipitation reactions were incubated for ≧15 minutes on ice, and then spun in a microcentrifuge at 14,000 rpm for 10 minutes 200 μl of the supernatant was removed, being careful not to disturb the pellet, and transferred to scintillation fluid (Bio-Safe II™, Research Products International Corp.). The samples were thoroughly mixed by inversion and then counted in a scintillation counter.

To determine percent (%) exonuclease activity relative to wild type Pfu, equivalent amounts of Pfu and purified Pfu mutants (which fall in the linear range of the assay; ~5-200 ng Pfu) were assayed in an exonuclease assay.

A "non-proofreading" enzyme refers to a DNA polymerase that is "3' to 5' exonuclease deficient" or "3' to 5'exo-".

As used herein, "3' to 5'exonuclease deficient" or "3' to 5'exo-" refers to an enzyme that substantially lacks the ability to remove incorporated nucleotides from the 3' end of a DNA polymer. DNA polymerase exonuclease activities, such as the 3' to 5' exonuclease activity exemplified by members of the Family B polymerases, can be lost through mutation, yielding an exonuclease-deficient polymerase. As used herein, a DNA polymerase that is deficient in 3' to 5' exonuclease activity substantially lacks 3' to 5' exonuclease activity. "Substantially lacks" encompasses a complete lack of activity, for example, 0.03%, 0.05%, 0.1%, 1%, 5%, 10%, 20% or even up to 50% of the exonuclease activity relative to the parental enzyme. Methods used to generate and characterize 3'-5' exonuclease DNA polymerases including the D141A and E143A mutations as well as other mutations that reduce or eliminate 3'-5' exonuclease activity are disclosed in the pending U.S. patent application Ser. No. 09/698,341 (Sorge et al; filed Oct. 27, 2000). Additional mutations that reduce or eliminate 3' to 5' exonuclease activity are known in the art and contemplated herein.

As used herein, "fidelity" refers to the accuracy of polymerization, or the ability of the polymerase to discriminate correct from incorrect substrates, (e.g., nucleotides) when synthesizing nucleic acid molecules (e.g. RNA or DNA) which are complementary to a template. The higher the fidelity of a polymerase, the less the polymerase misincorporates nucleotides in the growing strand during nucleic acid synthesis; that is, an increase or enhancement in fidelity results in a more faithful polymerase having decreased error rate (decreased misincorporation rate).

The term "fidelity" as used herein refers to the accuracy of DNA polymerization by a template-dependent DNA polymerase. The fidelity of a DNA polymerase is measured by the error rate (the frequency of incorporating an inaccurate nucleotide, i.e., a nucleotide that is not incorporated at a template-dependent manner). The accuracy or fidelity of DNA polymerization is maintained by both the polymerase activity and the 3'-5' exonuclease activity of a DNA polymerase. The term "high fidelity" refers to an error rate of $5\times10^{-6}$ per base pair or lower. The fidelity or error rate of a DNA polymerase may be measured using assays known to the art. For example, the error rates of DNA polymerase mutants can be tested using the lacI PCR fidelity assay described in Cline, J., Braman, J. C., and Hogrefe, H. H. (96) NAR 24:3546-3551. Briefly, a 1.9 kb fragment encoding the lacIOlacZα target gene is amplified from pPRIAZ plasmid DNA using 2.5 U DNA polymerase (i.e. amount of enzyme necessary to incorporate 25 nmoles of total dNTPs in 30 min. at 72° C.) in the appropriate PCR buffer. The lacI-containing PCR products are then cloned into lambda GT10 arms, and the percentage of lacI mutants (MF, mutation frequency) is determined in a color screening assay, as described (Lundberg, K. S., Shoemaker, D. D., Adams, M. W. W., Short, J. M., Sorge, J. A., and Mathur, E. J. (1991) Gene 180:1-8). Error rates are expressed as mutation frequency per bp per duplication (MF/bp/d), where bp is the number of detectable sites in the lacI gene sequence (349) and d is the number of effective target doublings. For each DNA polymerase mutant, at least two independent PCR amplifications are performed.

A DNA polymerase having increased/enhanced/higher fidelity is defined as a polymerase having about 2 to about 10,000 fold, about 2 to about 5,000 fold, or about 2 to about 2000 fold (preferably greater than about 5 fold, more preferably greater than about 10 fold, still more preferably greater than about 50 fold, still more preferably greater than about 100 fold, still more preferably greater than about 500 fold and most preferably greater than about 1000 fold) reduction in the number of misincorporated nucleotides during synthesis of any given nucleic acid molecule of a given length. For example, a mutated polymerase may misincorporate one nucleotide in the synthesis of 1000 bases compared to an unmutated polymerase misincorporating 10 nucleotides. Such a mutant polymerase would be said to have an increase of fidelity of 10 fold.

A DNA polymerase having reduced misincorporation is defined herein as either a mutated or modified DNA polymerase that has about or less than 50%, or preferably about or less than 25%, more preferably about or less than 10% and most preferably about or less than 1% of relative misincorporation compared to the corresponding unmutated, unmodified or wild type enzyme. A DNA polymerase of lower fidelity may also initiate DNA synthesis with an incorrect nucleotide incorporation (Perrion & Loeb, 1989, J. Biol. Chem. 264:2898-2905).

The fidelity or misincorporation rate of a polymerase can be determined by sequencing or by other method known in the art (Eckert & Kunkel, Nucl. Acids Res. 3739-3744 (1990)). In one example, the sequence of a DNA molecule synthesized by the unmutated and mutated polymerase can be compared to the expected (known) sequence. In this way, the number of errors (misincorporation) can be determined for each enzyme and compared.

In WO 01/92501, Wang teaches that currently, PCR amplification of long DNA fragments requires the use of an enzyme mixture containing both a non-proofreading polymerase (e.g. Tag or DyNAzyme II) and a small amount of proofreading polymerase (e.g., Pfu or Deep Vent). In WO01/92501, Wang compared a single fusion enzyme, Pfu-Sso7d, to one of the high performance, long PCR enzymes DyNAzyme EXT (from Finnzymes) in long PCR, and demonstrated that Pfu-Sso7d outperforms DyNAzyme EXT, especially with limited extension time.

In Wang, lambda DNA (2.25 pm) was used as a PCR template. Four pairs of primers L71F (5'-CCTGCTCTGCCGCTTCACGC-3') (SEQ ID NO:114), and L71R (5'-GCACAGCGGCTGGCTGAGGA-3') (SEQ ID NO:115), L30350F (5'-CCTGCTCTGCCGCTTCACGC-3') (SEQ ID NO:114) and L35121R (5'-CACATGGTACAGCAAGCCTGGC-3') (SEQ ID NO:116), L2089F (5'-CCCGTATCTGCTGGGATACTGGC-3') (SEQ ID NO:117) and L7112R (5'-CAGCGGTGCTGACTGAATCATGG-3') (SEQ ID NO:118) and L30350F (5'-CCTGCCTGCCGCTTCACGC-3') (SEQ ID NO:119) and L40547R (5'-CCAATACCCGTTTCATCGCGGC-3') (SEQ ID NO:120) were used to amplify DNA fragments of the size of 0.9 kb, 4.8 kb, 5.0 kb and 10.2 kb, respectively. Four concentrations (10 unit/ml, 20 unit/ml, 40 unit/ml and 80 unit/ml) of Pfu-Sso7d were used, and two concentrations (20 unit/ml and 40 unit/ml) of DyNAzyme EXT were used. Each reaction contained 0.36 mM of each of the four dNTPs. The reaction buffer for the Pfu-Sso7d was as described in Example 6-1. The reaction buffer for DyNAzyme EXT contained 20 mM Tris (pH 9.0), 2 mM $MgCl_2$, 15 mM $(NH4)_2SO_4$, and 0.1% Triton X-100 (provided by Finnzymes). All reaction components were first mixed on ice, and the reactions were initiated by placing the sample plates into a thermal cycler (MJ Research) preheated to over 90° C. The PCR cycling program consists of 95° C. for 20 sec, 20 cycles of 94° C. for 10 sec and 70° C. for 1 or 1.5 min, and 1 cycle of 72° C. for 10 min.

As used herein, "mutation" refers to a change introduced into a parental or wild type DNA sequence that changes the amino acid sequence encoded by the DNA, including, but not limited to, substitutions, insertions, deletions or truncations. The consequences of a mutation include, but are not limited to, the creation of a new character, property, function, or trait not found in the protein encoded by the parental DNA, including, but not limited to, N terminal truncation, C terminal truncation or chemical modification. A "mutant" DNA polymerase as used herein, refers to a DNA polymerase comprising a mutation as defined herein. A "mutant" DNA polymerase of the invention can encompass a "chimeric" DNA polymerase of the invention.

As used herein, "chemically modified" refers to a nucleic acid that is chemically or biochemically modified or contains non-natural or derivatized nucleotide bases. Such modifications include, for example, labels, methylation, substitution of one or more of the naturally occurring nucleotides with an analog, internucleotide modifications such as uncharged linkages (e.g. methyl phosphonates, phosphorodithioates, etc.), pendent moieties (e.g., polypeptides), intercalators, (e.g. acridine, psoralen, etc.) chelators, alkylators, and modified linkages (e.g. alpha anomeric nucleic acids, etc.) Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

As used herein, "thermostable" refers to an enzyme which is stable and active at temperatures as great as preferably between about 90-100° C. and more preferably between about 70-980 C to heat as compared, for example, to a non-thermostable form of an enzyme with a similar activity. For example, a thermostable nucleic acid polymerase derived from thermophilic organisms such as *P. furiosus, M. jannaschii, A. fulgidus* or *P. horikoshii* are more stable and active at elevated temperatures as compared to a nucleic acid polymerase from *E. coli*. A representative thermostable nucleic acid polymerase isolated from *P. furiosus* (Pfu) is described in Lundberg et al., 1991, *Gene,* 108:1-6. Additional representative temperature stable polymerases include, e.g., polymerases extracted from the thermophilic bacteria *Thermus flavus, Thermus ruber, Thermus thermophilus, Bacillus stearothermophilus* (which has a somewhat lower temperature optimum than the others listed), *Thermus lacteus, Thermus rubens, Thermotoga maritima*, or from thermophilic archaea *Thermococcus litoralis*, and *Methanothermus fervidus.*

Temperature stable polymerases are preferred in a thermocycling process wherein double stranded nucleic acids are denatured by exposure to a high temperature (about 95° C.) during the PCR cycle.

As used herein, the term "template DNA molecule" refers to that strand of a nucleic acid from which a complementary nucleic acid strand is synthesized by a DNA polymerase, for example, in a primer extension reaction.

As used herein, the term "template dependent manner" is intended to refer to a process that involves the template dependent extension of a primer molecule (e.g., DNA synthesis by DNA polymerase). The term "template dependent manner" refers to polynucleotide synthesis of RNA or DNA wherein the sequence of the newly synthesized strand of polynucleotide is dictated by the well-known rules of complementary base pairing (see, for example, Watson, J. D. et al., In: *Molecular Biology of the Gene,* 4th Ed., W. A. Benjamin, Inc., Menlo Park, Calif. (1987)).

As used herein, an "amplified product" refers to the double strand polynucleotide population at the end of a PCR amplification reaction. The amplified product contains the original polynucleotide template and polynucleotide synthesized by DNA polymerase using the polynucleotide template during the PCR reaction.

As used herein, "polynucleotide template" or "target polynucleotide template" or "template" refers to a polynucleotide containing an amplified region. The "amplified region," as used herein, is a region of a polynucleotide that is to be either synthesized by polymerase chain reaction (PCR). For example, an amplified region of a polynucleotide template resides between two sequences to which two PCR primers are complementary to.

As used herein, the term "primer" refers to a single stranded DNA or RNA molecule that can hybridize to a polynucleotide template and prime enzymatic synthesis of a second polynucleotide strand. A primer useful according to the invention is between 10 to 100 nucleotides in length, preferably 17-50 nucleotides in length and more preferably 17-45 nucleotides in length.

"Complementary" refers to the broad concept of sequence complementarity between regions of two polynucleotide strands or between two nucleotides through base-pairing. It is known that an adenine nucleotide is capable of forming specific hydrogen bonds ("base pairing") with a nucleotide which is thymine or uracil. Similarly, it is known that a cytosine nucleotide is capable of base pairing with a guanine nucleotide.

The term "wild-type" refers to a gene or gene product which has the characteristics of that gene or gene product when isolated from a naturally occurring source. In contrast, the term "modified" or "mutant" refers to a gene or gene product which displays altered characteristics when compared to the wild-type gene or gene product. For example, a mutant DNA polymerase in the present invention is a DNA polymerase which exhibits a reduced uracil detection activity.

As used herein "FEN-1 nuclease" refers to thermostable FEN-1 endonucleases useful according to the invention and includes, but is not limited to, FEN-1 endonuclease purified from the "hyperthermophiles", e.g., from *M. jannaschii, P. furiosus* and *P. woesei*. See U.S. Pat. No. 5,843,669, hereby incorporated by reference.

According to the methods of the present invention, the addition of FEN-1 in the amplification reaction dramatically increases the efficiency of the multi-site mutagenesis. 400 ng to 4000 ng of FEN-1 may be used in each amplification reaction. Preferably 400-1000 ng, more preferably, 400-600 ng of FEN-1 is used in the amplification reaction. In a preferred embodiment of the invention, 400 ng FEN-1 is used.

As used herein, "Thermus DNA ligase" refers to a thermostable DNA ligase that is used in the multi-site mutagenesis amplification reaction to ligate the mutant fragments synthesized by extending each mutagenic primer so to form a circular mutant strand. Tth and Taq DNA ligase require NAD as a cofactor.

Preferably, 1-20 U DNA ligase is used in each amplification reaction, more preferably, 2-15 U DNA ligase is used in each amplification reaction.

In a preferred embodiment, 15 U Taq DNA ligase is used in an amplification reaction. Taq DNA ligase cofactor NAD is used at a concentration of 0-1 mM, preferably between 0.02-0.2 mM, more preferably at 0.1 mM.

As used herein, a "PCR enhancing factor" or a "Polymerase Enhancing Factor" (PEF) refers to a complex or protein possessing polynucleotide polymerase enhancing activity including, but not limited to, PEF, dUTPase, ssbPCNA, RFC, helicases etc (Hogrefe et al., 1997, Strategies 10:93-96; and U.S. Pat. No. 6,183,997, both of which are hereby incorporated by reference). A "PCR enhancing factor" also includes non-protein factors, for example DMSO and betaine.

The invention also contemplates mutant archael DNA polymerases in combination with accessory factors, for example as described in U.S. Pat. No. 6,333,158, and WO 01/09347 A2, hereby incorporated by reference in its entirety.

The invention also relates to compositions made for carrying out the methods of the invention and compositions made while carrying out the methods of the invention. Such compositions may comprise one or more components selected from the group consisting of one or more polymerases of the invention, one or more nucleotides, one or more templates, one or more reaction buffers or buffering salts, one or more primers, one or more nucleic acid products made by the methods of the invention and the like.

BRIEF DESCRIPTION OF THE DRAWINGS

FIG. 1: Oligonucleotide Primers for QuikChange Mutagenesis (SEQ ID Nos: 5-26)

(b) PCR Amplification of Pfu V93R mutant extract in the presence of 100% dUTP.

Figure 3:
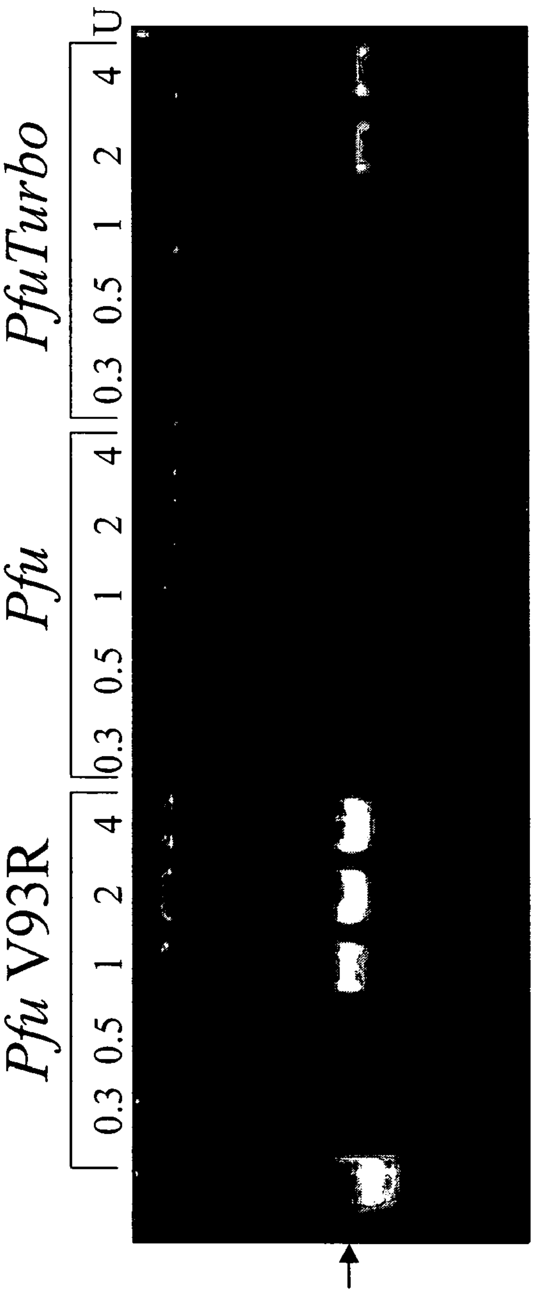

FIG. 3: Comparison of the efficacy of "long" PCR amplification of Pfu DNA polymerase mutants and wt enzyme.

Figure 4A:
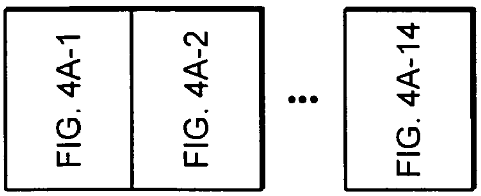

FIG. 4: 4A. DNA sequence of mutant archeael DNA polymerases

4B. Amino acid sequence of mutant archeael DNA polymerases

4C. DNA and Amino acid sequence of mutant Tgo DNA polymerase

FIG. 5: DNA and Amino acid sequence of wild type Pfu DNA polymerase

Figure 6A:
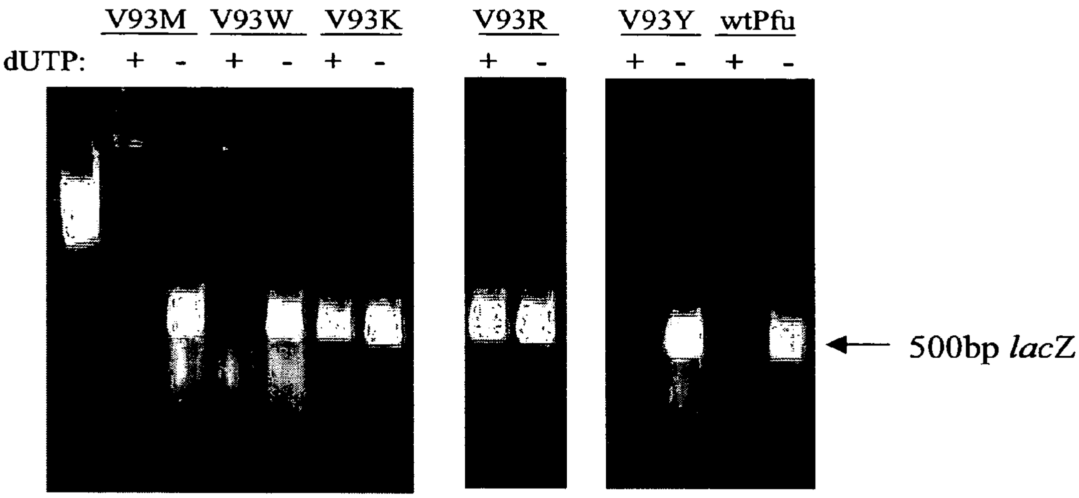
Figure 6B:
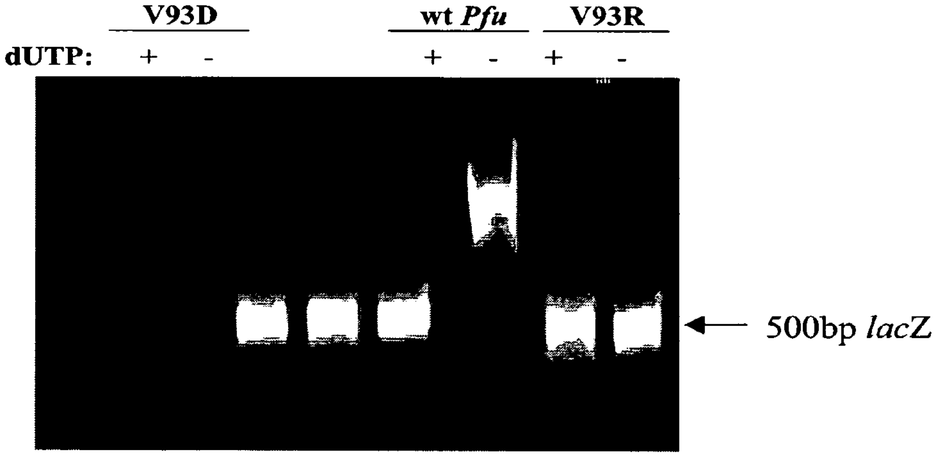
Figure 6C:
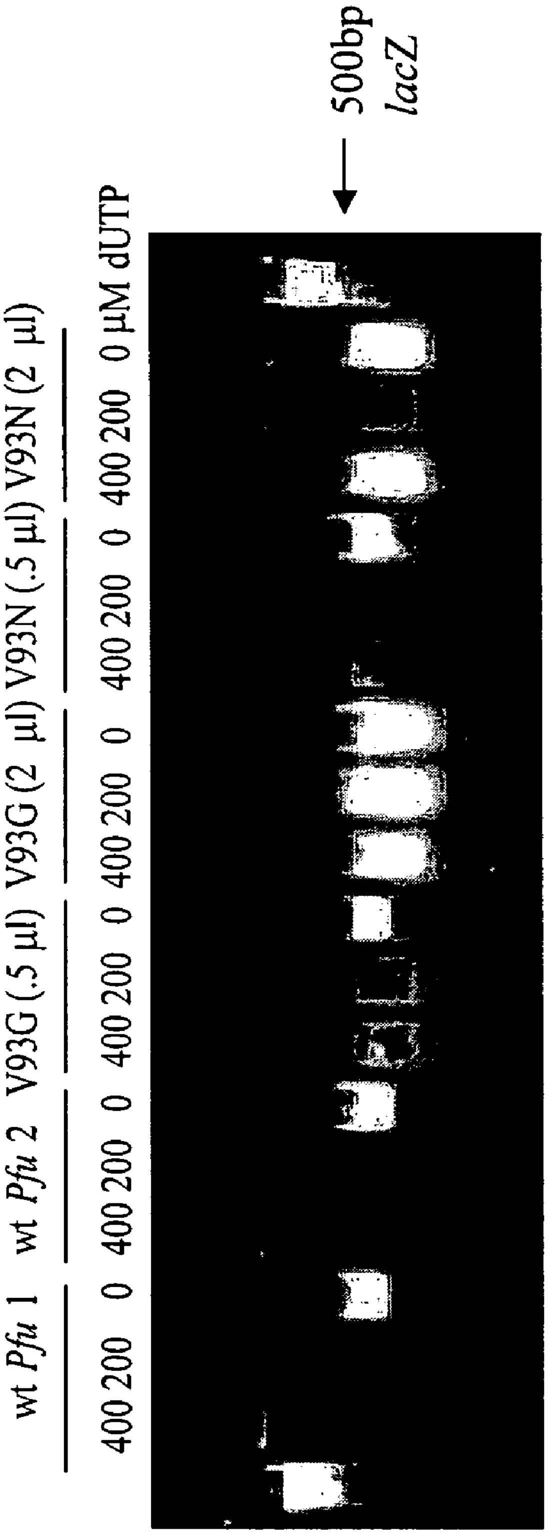

FIG. 6: dUTP incorporation of Pfu mutants compared to wild type Pfu DNA polymerase

6A. dUTP incorporation of Pfu mutants V93W, V93Y, V93M, V93K and V93R compared to wild type Pfu DNA polymerase

6B. dUTP incorporation of the Pfu V93D and V93R mutants compared to wild type Pfu DNA polymerase.

6C. dUTP incorporation of the Pfu V93N and V93G mutant compared to wild type Pfu DNA polymerase FIG. 7: DNA polymerase activity of N-terminal Pfu DNA polymerase truncation mutants.

FIG. 8: shows the sequence of

A. HMf-like protein
B. HMf-like protein-Taq fusion
C. HMf-like protein-Taq fusion
D. Pfu WT-HMf like protein fusion
E. Pfu WT-HMf like protein fusion
F. Pfu-V93 R or E-HMf-like protein fusion
G. Pfu-V93 R or E-HMf-like protein fusion
H. Pfu-G387P/V93 R or E-HMf-like protein fusion
I. Pfu-G387P/V93 R or E-HMf-like protein fusion
J. Pfu-D141A/E143A/V93 R or E-HMf-like protein fusion
K. Pfu-D141A/E143A/V93 R or E-HMf-like protein fusion
L. KOD-HMf-like protein fusion
M. KOD-HMf-like protein fusion
N. HMf-like protein-Vent fusion
O. HMf-like protein-Vent fusion
P. HMf-like protein-DeepVent fusion
Q. HMf-like protein-DeepVent fusion
R. HMf-like protein-JDF3 fusion
S. HMf-like protein-JDF3 fusion
T. PCNA
U. PCNA-Taq fusion
V. PCNA-Taq fusion
W. PCNA-PfuWT fusion
X. PCNA-PfuWT fusion
Y. Pfu-V93 R or E-PCNA fusion
Z. Pfu-V93 R or E-PCNA fusion
AA. Pfu-G387P/V93 R or E-PCNA fusion
BB. Pfu-G387P/V93 R or E-PCNA fusion
CC. Pfu-D141A/E143A/V93 R or E-PCNA fusion
DD. Pfu-D141A/E143A/V93 R or E-PCNA fusion
EE. KOD-PCNA fusion
FF. KOD-PCNA protein fusion
GG. PCNA-Vent fusion
HH. PCNA-Vent fusion
II. PCNA-DeepVent fusion
JJ. PCNA-DeepVent fusion
KK. PCNA-JDF3 fusion
LL. PCNA-JDF3 fusion
MM. Sac7d
NN. Sac7d-Taq fusion
OO. Sac7d-Taq fusion
PP. Sac7d-PfuWT fusion
QQ. Sac7d-PfuWT fusion
RR. Pfu-V93 R or E-Sac7d-like protein fusion
SS. Pfu-V93 R or E-Sac7d fusion
TT. Pfu-G387P/V93 R or E-Sac7d fusion
UU. Pfu-G387P/V93 R or E-Sac7d fusion
VV. Pfu-D141A/E143A/V93 R or E-Sac7d fusion
WW. KOD-Sac7d fusion
XX. KOD-Sac7d protein fusion
YY. Sac7d-Vent fusion
ZZ. Sac7d-Vent fusion
AAA. Sac7d-DeepVent fusion
BBB. Sac7d-DeepVent fusion
CCC. Sac7d-JDF3 fusion
DDD. Sac7d-JDF3 fusion
EEE. Sso7D
FFF. Sso7D-Taq fusion
GGG. Sso7D-PfuWT fusion
HHH. Pfu-V93 R or E-Sso7D fusion
III. Pfu-G387P/V93 R or E-Sso7D fusion
JJJ. Pfu-D141A/E143A/V93 R or E-Sso7D fusion
KKK. KOD-Sso7D fusion
LLL. KOD-Sso7D fusion
MMM. Sso7D-Vent fusion
NNN. Sso7D-Vent fusion
OOO. Sso7D-DeepVent fusion
PPP. Sso7D-DeepVent fusion
QQQ. Sso7D-JDF3 fusion
RRR. Sso7D-JDF3 fusion FIG. 9: HhH motif Sequences (a) Motifs conserved between topo V, RecA, and leucine-responsive regulator signature sequences. Topo V amino acid region 236-298 made no hits in databases and is not shown. A short region between positions 677-695 connecting repeats G and H and the 19-aa residues at the end of the sequence is not shown for simplicity. Invariant residues are shown on blue backgrounds with white lettering. Conservative positions are highlighted on the yellow background. (b) Structure of topo V HhH motifs. Backgrounds of Lys-68 and Lys-72 of -pol and corresponding positions in C and G repeats of topo V are colored cyan and magenta, respectively. Secondary structures in a and b were predicted by using JPRED (at web page address jura.ebi.ac.uk:8888/). Cylinders represent-helices, and lines between them (b) represent-hairpins. Tyrosines that have been substituted for phenylalanines by mutagenesis are boxed (see FIG. 2*a*). MkTpV, *M. kandleri* topo V; HTH asnC, the three-element fingerprint that provides a signature for the HTH motif of the asnC bacterial regulatory proteins; HTH SS, secondary structure of the HTH motif; A-L, topo V's HhH repeats; EcRuvA, *E. coli* RuvA protein, HsPolB, human polymerase; TaqPol, *T. aquaticus* polymerase I; HhH SS, secondary structure of HhH motifs. ALSCRIPT was used to illustrate the alignments.

DETAILED DESCRIPTION

The present invention discloses novel blends of chimeric and non-chimeric thermostable DNA polymerases for use in PCR, DNA sequencing and mutagenesis protocols. The invention allows for PCR reactions with shorter extension times that will facilitate PCR amplification of genomic DNA templates and improve the efficacy of long PCR.

I. DNA Polymerases According to the Invention

The invention provides for a blend of at least one chimeric DNA polymerase and at least one non-chimeric wild type, mutant or chemically modified DNA polymerase. The chimeric or non-chimeric DNA polymerases, useful according to the invention, can be with or without 3'-5' exonuclease activity, i.e., proofreading or non-proofreading, and are preferably thermostable. The invention provides for both chimeric and non chimeric DNA polymerase that harbor one or more mutations that modify one or more activities normally found in the wild-type DNA polymerase.

Additional nucleic acid polymerases useful according to the invention are listed below.

A. Bacteriophage DNA Polymerases (Useful for 37° C. assays):

Bacteriophage DNA polymerases are devoid of 5' to 3' exonuclease activity, as this activity is encoded by a separate polypeptide. Examples of suitable DNA polymerases are T4, T7, and Φ29 DNA polymerase. The enzymes available commercially are: T4 (available from many sources e.g., Epicentre) and T7 (available from many sources, e.g. Epicentre for unmodified and USB for 3' to 5' exo$^-$ T7 "Sequenase" DNA polymerase).

B. Archaeal DNA Polymerases:

There are 2 different classes of DNA polymerases which have been identified in archaea: 1. Family B/pol I type (homologs of Pfu from *Pyrococcus furiosus*) and 2. pol II type (homologs of *P. furiosus* DP1/DP2 2-subunit polymerase). DNA polymerases from both classes have been shown to naturally lack an associated 5' to 3' exonuclease activity and to possess 3' to 5' exonuclease (proofreading) activity. Suitable DNA polymerases (pol I or pol II) can be derived from archaea with optimal growth temperatures that are similar to the desired assay temperatures.

Thermostable archaeal DNA polymerases isolated from *Pyrococcus* species (*furiosus*, species GB-D, *woesii, abysii, horikoshii*), *Thermococcus* species (*kodakaraensis* KOD 1, *litoralis*, species 9 degrees North-7, species JDF-3, *gorgonarius*), *Pyrodictium occultum*, and *Archaeoglobus fulgidus*. It is estimated that suitable archaea would exhibit maximal growth temperatures of >80-85° C. or optimal growth temperatures of >70-80° C. Appropriate PCR enzymes from the archaeal pol I DNA polymerase group are commercially available, including Pfu (Stratagene), KOD (Toyobo), Pfx (Life Technologies, Inc.), Vent (New England BioLabs), Deep Vent (New England BioLabs), Tgo (Roche), and Pwo (Roche).

Additional archaea DNA polymerases related to those listed above are described in the following references: Archaea: A Laboratory Manual (Robb, F. T. and Place, A. R., eds.), Cold Spring Harbor Laboratory Press, Cold Spring Harbor, N.Y., 1995 and *Thermophilic Bacteria* (Kristjansson, J. K., ed.) CRC Press, Inc., Boca Raton, Fla., 1992.

The invention therefore provides for thermostable archaeal DNA polymerases of either Family B/pol I type or pol II type as well as mutants or derivatives thereof.

TABLE 1

ACCESSION INFORMATION FOR CLONED FAMILY B POLYMERASES

| | |
|---|---|
| Vent *Thermococcus litoralis* | |
| ACCESSION | AAA72101 |
| PID | g348689 |
| VERSION | AAA72101.1 GI:348689 |
| DBSOURCE | locus THCVDPE accession M74198.1 |
| THEST *THERMOCOCCUS* SP. (STRAIN TY) | |
| ACCESSION | O33845 |
| PID | g3913524 |
| VERSION | O33845 GI:3913524 |
| DBSOURCE | swissprot: locus DPOL_THEST, accession O33845 |
| Pab *Pyrococcus abyssi* | |
| ACCESSION | P77916 |
| PID | g3913529 |
| VERSION | P77916 GI:3913529 |
| DBSOURCE | swissprot: locus DPOL_PYRAB, accession P77916 |
| PYRHO | *Pyrococcus horikoshii* |
| ACCESSION | O59610 |
| PID | g3913526 |
| VERSION | O59610 GI:3913526 |
| DBSOURCE | swissprot: locus DPOL_PYRHO, accession O59610 |
| *PYRSE PYROCOCCUS* SP. (STRAIN GE23) | |
| ACCESSION | P77932 |
| PID | g3913530 |
| VERSION | P77932 GI:3913530 |
| DBSOURCE | swissprot: locus DPOL_PYRSE, accession P77932 |
| DeepVent *Pyrococcus* sp. | |
| ACCESSION | AAA67131 |
| PID | g436495 |
| VERSION | AAA67131.1 GI:436495 |
| DBSOURCE | locus PSU00707 accession U00707.1 |
| Pfu *Pyrococcus furiosus* | |
| ACCESSION | P80061 |
| PID | g399403 |
| VERSION | P80061 GI:399403 |
| DBSOURCE | swissprot: locus DPOL_PYRFU, accession P80061 |
| JDF-3 | *Thermococcus* sp. |
| Unpublished | |
| Baross gi\|2097756\|pat\|US\|5602011\|12 Sequence 12 from U.S. Pat. No. 5,602,011 9degN *THERMOCOCCUS* SP. (STRAIN 90N-7). | |

TABLE 1-continued

| ACCESSION INFORMATION FOR CLONED FAMILY B POLYMERASES | |
|---|---|
| ACCESSION | Q56366 |
| PID | g3913540 |
| VERSION | Q56366 GI:3913540 |
| DBSOURCE | swissprot: locus DPOL_THES9, accession Q56366 |
| KOD *Pyrococcus* sp. | |
| ACCESSION | BAA06142 |
| PID | g1620911 |
| VERSION | BAA06142.1 GI:1620911 |
| DBSOURCE | locus PYWKODPOL accession D29671.1 |
| Tgo *Thermococcus gorgonarius*. | |
| ACCESSION | 4699806 |
| PID | g4699806 |
| VERSION | GI:4699806 |
| DBSOURCE | pdb: chain 65, release Feb. 23, 1999 |
| THEFM Ther*mococcus fumicolans* | |
| ACCESSION | P74918 |
| PID | g3913528 |
| VERSION | P74918 GI:3913528 |
| DBSOURCE | swissprot: locus DPOL_THEFM, accession P74918 |
| METTH *Methanobacterium thermoautotrophicum* | |
| ACCESSION | O27276 |
| PID | g3913522 |
| VERSION | O27276 GI:3913522 |
| DBSOURCE | swissprot: locus DPOL_METTH, accession O27276 |
| Metja | *Methanococcus jannaschii* |
| ACCESSION | Q58295 |
| PID | g3915679 |
| VERSION | Q58295 GI:3915679 |
| DBSOURCE | swissprot: locus DPOL_METJA, accession Q58295 |
| POC *Pyrodictium occultum* | |
| ACCESSION | B56277 |
| PID | g1363344 |
| VERSION | B56277 GI:1363344 |
| DBSOURCE | pir: locus B56277 |
| Apel Aeropyrum pemix | |
| ACCESSION | BAA81109 |
| PID | g5105797 |
| VERSION | BAA81109.1 GI:5105797 |
| DBSOURCE | locus AP000063 accession AP000063.1 |
| ARCFU *Archaeoglobus fulgidus* | |
| ACCESSION | O29753 |
| PID | g3122019 |
| VERSION | O29753 GI:3122019 |
| DBSOURCE | swissprot: locus DPOL_ARCFU, accession O29753 |
| *Desulfurococcus* sp. Tok. | |
| ACCESSION | 6435708 |
| PID | g64357089 |
| VERSION GT: | 6435708 |
| DBSOURCE | pdb. chain 65, release Jun. 2, 1999 |

C. Eubacterial DNA Polymerases:

There are 3 classes of eubacterial DNA polymerases, pol I, II, and III. Enzymes in the Pol I DNA polymerase family possess 5' to 3' exonuclease activity, and certain members also exhibit 3' to 5' exonuclease activity. Pol II DNA polymerases naturally lack 5' to 3' exonuclease activity, but do exhibit 3' to 5' exonuclease activity. Pol III DNA polymerases represent the major replicative DNA polymerase of the cell and are composed of multiple subunits. The pol III catalytic subunit lacks 5' to 3' exonuclease activity, but in some cases 3' to 5' exonuclease activity is located in the same polypeptide.

There are no commercial sources of eubacterial pol II and pol III DNA polymerases.

There are a variety of commercially available Pol I DNA polymerases, some of which have been modified to reduce or abolish 5' to 3' exonuclease activity.

Suitable thermostable pol I DNA polymerases can be isolated from a variety of thermophilic eubacteria, including *Thermus* species and *Thermotoga maritima* such as *Thermus aquaticus* (Taq), *Thermus thermophilus* (Tth) and *Thermotoga maritima* (Tma UlTma).

Additional eubacteria related to those listed above are described in *Thermophilic Bacteria* (Kristjansson, J. K., ed.) CRC Press, Inc., Boca Raton, Fla., 1992.

The invention further provides for chimeric or non-chimeric DNA polymerases that are chemically modified according to methods disclosed in U.S. Pat. Nos. 5,677,152, 6,479,264 and 6,183, 998, the contents of which are hereby incorporated by reference in their entirety.

II. Preparing Mutant Non-Chimeric DNA Polymerases

According to the invention, non-chimeric DNA polymerases blended with DNA polymerase chimera can be generated from any DNA polymerase either wild-type or modified to contain one or more mutations, including but not limited to, one or more point mutations, N- and/or C-truncations, internal deletion or insertion that would cause the DNA polymerase to behave differently than the wild-type polymerase. DNA polymerase mutations useful to the invention include, but are not limited to, mutations that confer base analog or uracil insensitivity, increase fidelity, eliminate 3'-5' exonuclease activity or eliminate 5'-3' exonuclease activity or reduce polymerase activity. Specific examples of useful mutations or truncations include but are not limited to, V93R, K,E,D in Pfu DNA polymerase, which confer uracil insensitivity, D141A/E143A in Pfu DNA polymerase, which eliminates 3'-5' exonuclease activity, and the N-terminal truncation of Taq DNA polymerase to eliminate 5'-3' exonuclease activity(KlenTaq). Methods for generating non-chimeric DNA polymerase mutants are described below and other methods are known in the art.

Genetic Modifications—Mutagenesis

Direct comparison of DNA polymerases from diverse organisms indicates that the domain structure of these enzymes is highly conserved and in many instances, it is possible to assign a particular function to a well-defined domain of the enzyme. For example, the six most conserved C-terminal regions, spanning approximately 340 amino acids, are located in the same linear arrangement and contain highly conserved motifs that form the metal and dNTP binding sites and the cleft for holding the DNA template and are therefore essential for the polymerization function. In another example, the three amino acid regions containing the critical residues in the *E. coli* DNA polymerase I involved in metal binding, single-stranded DNA binding, and catalysis of the 3'-5' exonuclease reaction are located in the amino-terminal half and in the same linear arrangement in several prokaryotic and eukaryotic DNA polymerases. The location of these conserved regions provides a useful model to direct genetic modifications for preparing mutant DNA polymerase with modified activities whilst conserving essential functions e.g. DNA polymerization and proofreading activity.

For example, a non-chimeric mutant DNA polymerase can be generated by genetic modification (e.g., by modifying the DNA sequence of a wild-type DNA polymerase). A number of methods are known in the art that permit the random as well as targeted mutation of DNA sequences (see for example, Ausubel et. al. *Short Protocols in Molecular Biology* (1995) $3^{rd}$ Ed. John Wiley & Sons, Inc.). In addition, there are a number of commercially available kits for site-directed mutagenesis, including both conventional and PCR-based methods. Examples include the EXSITE™ PCR-Based Site-directed Mutagenesis Kit available from Stratagene (Catalog No. 200502) and the QUIKCHANGE™ Site-directed mutagenesis Kit from Stratagene (Catalog No. 200518), and the CHAMELEON® double-stranded Site-directed mutagenesis kit, also from Stratagene (Catalog No. 200509).

In addition non-chimeric mutant DNA polymerases may be generated by insertional mutation or truncation (N-terminal, internal or C-terminal) according to methodology known to a person skilled in the art.

Older methods of site-directed mutagenesis known in the art rely on sub-cloning of the sequence to be mutated into a vector, such as an M13 bacteriophage vector, that allows the isolation of single-stranded DNA template. In these methods, one anneals a mutagenic primer (i.e., a primer capable of annealing to the site to be mutated but bearing one or more mismatched nucleotides at the site to be mutated) to the single-stranded template and then polymerizes the complement of the template starting from the 3' end of the mutagenic primer. The resulting duplexes are then transformed into host bacteria and plaques are screened for the desired mutation.

More recently, site-directed mutagenesis has employed PCR methodologies, which have the advantage of not requiring a single-stranded template. In addition, methods have been developed that do not require sub-cloning. Several issues must be considered when PCR-based site-directed mutagenesis is performed. First, in these methods it is desirable to reduce the number of PCR cycles to prevent expansion of undesired mutations introduced by the polymerase. Second, a selection must be employed in order to reduce the number of non-mutated parental molecules persisting in the reaction. Third, an extended-length PCR method is preferred in order to allow the use of a single PCR primer set. And fourth, because of the non-template-dependent terminal extension activity of some thermostable polymerases it is often necessary to incorporate an end-polishing step into the procedure prior to blunt-end ligation of the PCR-generated mutant product.

The protocol described below accommodates these considerations through the following steps. First, the template concentration used is approximately 1000-fold higher than that used in conventional PCR reactions, allowing a reduction in the number of cycles from 25-30 down to 5-10 without dramatically reducing product yield. Second, the restriction endonuclease Dpn I (recognition target sequence: 5-Gm6ATC-3, where the A residue is methylated) is used to select against parental DNA, since most common strains of *E. coli* Dam methylate their DNA at the sequence 5-GATC-3. Third, Taq Extender is used in the PCR mix in order to increase the proportion of long (i.e., full plasmid length) PCR products. Finally, Pfu DNA polymerase is used to polish the ends of the PCR product prior to intramolecular ligation using T4 DNA ligase.

A non-limiting example for the isolation of non-chimeric mutant DNA polymerases is described in detail as follows:

Plasmid template DNA (approximately 0.5 pmole) is added to a PCR cocktail containing: 1× mutagenesis buffer (20 mM Tris HCl, pH 7.5; 8 mM $MgCl_2$; 40 μg/ml BSA); 12-20 pmole of each primer (one of skill in the art may design a mutagenic primer as necessary, giving consideration to those factors such as base composition, primer length and intended buffer salt concentrations that affect the annealing characteristics of oligonucleotide primers; one primer must contain the desired mutation, and one (the same or the other) must contain a 5' phosphate to facilitate later ligation), 250 μM each dNTP, 2.5 U Taq DNA polymerase, and 2.5 U of Taq Extender (Available from Stratagene; See Nielson et al. (1994) Strategies 7: 27, and U.S. Pat. No. 5,556,772). Primers can be prepared using the triester method of Matteucci et al., 1981, J. Am. Chem. Soc. 103:3185-3191, incorporated herein by reference. Alternatively automated synthesis may be preferred, for example, on a Biosearch 8700 DNA Synthesizer using cyanoethyl phosphoramidite chemistry.

The PCR cycling is performed as follows: 1 cycle of 4 min at 94° C., 2 min at 50° C. and 2 min at 72° C.; followed by 5-10 cycles of 1 min at 94° C., 2 min at 54° C. and 1 min at 72° C. The parental template DNA and the linear, PCR-generated DNA incorporating the mutagenic primer are treated with DpnI (10 U) and Pfu DNA polymerase (2.5 U). This results in the DpnI digestion of the in vivo methylated parental template and hybrid DNA and the removal, by Pfu DNA polymerase, of the non-template-directed Taq DNA polymerase-extended base(s) on the linear PCR product. The reaction is incubated at 37° C. for 30 min and then transferred to 72° C. for an additional 30 min. Mutagenesis buffer (115 ul of 1×) containing 0.5 mM ATP is added to the DpnI-digested, Pfu DNA polymerase-polished PCR products. The solution is mixed and 10 ul are removed to a new microfuge tube and T4 DNA ligase (2-4 U) is added. The ligation is incubated for greater than 60 min at 37° C. Finally, the treated solution is transformed into competent *E. coli* according to standard methods.

Methods of random mutagenesis, which will result in a panel of mutants bearing one or more randomly situated mutations, exist in the art. Such a panel of mutants may then be screened for improved activity such as those exhibiting properties including but not limited to reduced DNA polymerization activity, 3'-5' exonuclease deficiency, and/or reduced uracil detection activity relative to the wild-type polymerase (e.g., by measuring the incorporation of 10 nmoles of dNTPs into polymeric form in 30 minutes in the presence of 200 μM dUTP and at the optimal temperature for a given DNA polymerase). An example of a method for random mutagenesis is the so-called "error-prone PCR method". As the name implies, the method amplifies a given sequence under conditions in which the DNA polymerase does not support high fidelity incorporation. The conditions encouraging error-prone incorporation for different DNA polymerases vary, however one skilled in the art may determine such conditions for a given enzyme. A key variable for many DNA polymerases in the fidelity of amplification is, for example, the type and concentration of divalent metal ion in the buffer. The use of manganese ion and/or variation of the magnesium or manganese ion concentration may therefore be applied to influence the error rate of the polymerase.

Genes for desired mutant DNA polymerases generated by mutagenesis may be sequenced to identify the sites and number of mutations. For those mutants comprising more than one mutation, the effect of a given mutation may be evaluated by introduction of the identified mutation to the wild-type gene by site-directed mutagenesis in isolation from the other mutations borne by the particular mutant. Screening assays of the single mutant thus produced will then allow the determination of the effect of that mutation alone.

In one embodiment, the invention provides for blends of two or more DNA polymerases comprising one or more chimeric DNA polymerases or one or more mutant DNA polymerases, for example, at least one of which is derived from an archaeal DNA polymerase containing one or more mutations.

In a preferred embodiment, the invention provides for blends of two or more DNA polymerases comprising one or more chimeric DNA polymerases and one or more mutant DNA polymerases, at least one of which is derived from Pfu DNA polymerase.

In another preferred embodiment, the invention provides for blends of two or more DNA polymerases comprising one or more chimeric DNA polymerases and one or more non-chimeric DNA polymerases, at least one of which is derived from TaqDNA polymerase.

A person of average skill in the art having the benefit of this disclosure will recognize that DNA polymerases derived from other exo$^+$ DNA polymerases including Vent DNA polymerase, JDF-3 DNA polymerase, Tgo DNA polymerase, KOD DNA polymerase and the like may be suitably used in the subject compositions.

The amino acid and DNA coding sequence of a wild-type Pfu DNA polymerase are shown in FIG. 5 (Genbank Accession # P80061). A detailed description of the structure and function of Pfu DNA polymerase can be found, among other places in U.S. Pat. Nos. 5,948,663; 5,866,395; 5,545,552; 5,556,772, all of which are hereby incorporated in their entirety by reference. A non-limiting detailed procedure for preparing Pfu DNA polymerase with, for example, reduced uracil detection activity is provided in Example 1.

The enzyme of the subject composition may comprise DNA polymerases that have not yet been isolated.

The invention provides for blends of two or more DNA polymerases comprising one or more chimeric DNA polymerase and one or more non-chimeric mutant or wild type DNA polymerase.

The invention provides for blends of two or more DNA polymerases comprising one or more chimeric DNA polymerase and one or more non-chimeric mutant Pfu DNA polymerases containing one or more mutations that reduce base analog detection activity as disclosed in the pending U.S. patent application Ser. No. 10/280,962 (Hogrefe, et al.; filed: Oct. 25, 2002) and the pending U.S. patent application Ser. No. 10/298,680 (Hogrefe et al.; filed Nov. 18, 2002), the contents of which are hereby incorporated in their entirety.

In a preferred embodiment, the blend of two or more DNA polymerases comprises one or more chimeric DNA polymerase and one or more non-chimeric mutant Pfu DNA polymerase of the invention containing a Valine to Arginine, Valine to Glutamic acid, Valine to Lysine, Valine to Aspartic Acid or Valine to Asparagine substitution at amino acid position 93.

The invention further provides for a blend of two or more DNA polymerases comprising one or more chimeric DNA polymerase and one or more non-chimeric mutant archaeal DNA polymerases with reduced base analog detection activity that contain a Valine to Arginine, Valine to Glutamic acid, Valine to Lysine, Valine to Aspartic Acid or Valine to Asparagine substitution at amino acid position 93.

A Pfu DNA polymerase mutant with Reduced Uracil Detection can be prepared as follows. Mutations are introduced into Pfu DNA polymerase that are likely to reduce uracil detection, while having minimal effects on polymerase or proofreading activity. The DNA template used for mutagenesis contains the Pfu pol gene, cloned into pBluescript (pF72 clone described in U.S. Pat. No. 5,489,523). Point mutations are introduced using the QuikChange or the QuikChange Multi Site-Directed Mutagenesis Kit (Stratagene). With the QuikChange kit, point mutations are introduced using a pair of mutagenic primers (V93E, H, K, R, and N). With the QuikChange Multi kit, specific point mutations are introduced by incorporating one phosphorylated mutagenic primer or by selecting random mutants from a library of Pfu V93 variants, created by incorporating a degenerate codon (V93G and L). Clones are sequenced to identify the incorporated mutations.

Valine 93 in Pfu DNA polymerase was substituted with Glycine (G), asparagine (N), arginine [R], glutamic acid (E), histidine (H), and leucine (L) using the QuikChange primer sequences listed in FIG. 1.

Assessment of the activity of a mutant chimeric or non-chimeric Pfu DNA polymerase is done as follows.

Partially-purified Pfu mutant preparations (heat-treated bacterial extracts) were assayed for dUTP incorporation during PCR. In this example, a 2.3 kb fragment containing the Pfu pol gene was from plasmid DNA using PCR primers: (FPfuLIC) 5'-gACgACgACAAgATgATTTTAgATgTggAT-3'(SEQ ID NO: 1) and (RPfuLIC) 5'-ggAACAAgACCCgTCTAggATTTTTTAATg-3' (SEQ ID NO: 2). Amplification reactions consisted of 1× cloned Pfu PCR buffer, 7 ng plasmid DNA, 100 ng of each primer, 2.5 U of Pfu mutant (or wild type Pfu), and 200 μM each dGTP, dCTP, and dATP. To assess relative dUTP incorporation, various amounts of dUTP (0-400 μM) and/or TTP (0-200 μM) were added to the PCR reaction cocktail. The amplification reactions were cycled as described in example 6.

Figure 2A:
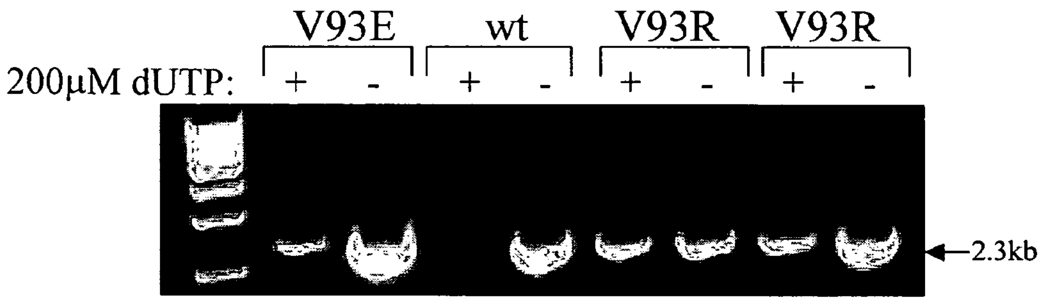
FIG. 2: (a) dUTP incorporation of V93E and V93R mutants compared to wild type Pfu DNA polymerase.
Figure 2B:
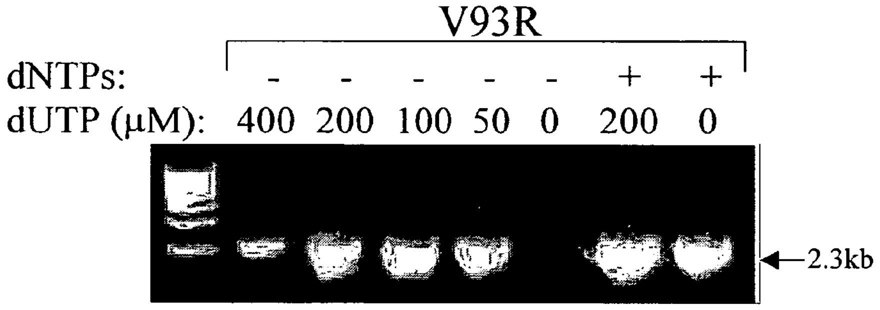

Results. Partially-purified preparations of the V93E and V93R chimeric or non-chimeric DNA polymerase mutants showed improved dUTP incorporation compared to wild type Pfu (FIG. 2*a*). Each mutant successfully amplified a 2.3 kb target in the presence of 200 μM dUTP (plus 200 μM each TTP, dATP, dCTP, dGTP). In contrast, extracts containing the V93R chimeric or non-chimeric Pfu V93N, V93G, V93H, and V93L mutants showed little-to-no amplification in the presence of 200 μM dUTP, similar to wild type Pfu (data not shown). Additional testing showed that the chimeric or non-chimeric Pfu V93R mutant extract amplified the 2.3 kb target in the presence of 100% dUTP (0% TTP)(FIG. 2*b*).

The invention further provides for a blend of two or more DNA polymerases comprising one or more chimeric DNA polymerase and one or more non-chimeric mutant archaeal DNA polymerases with a G387P mutant archaeal DNA polymerase with reduced DNA polymerization activity.

The invention further provides for a blend of two or more DNA polymerases comprising one or more chimeric DNA polymerase and one or more non-chimeric V93 mutant Pfu DNA polymerases with reduced uracil detection activity that contain one or more additional mutations that modulates one or more additional activities of V93 Pfu DNA polymerases, e.g., DNA polymerization activity or 3'-5' exonuclease activity. In one embodiment, the non-chimeric V93 mutant Pfu DNA polymerase according to the invention contains one or more mutations that renders the DNA polymerase 3'-5' exonuclease deficient. In another embodiment, the non-chimeric V93 mutant Pfu DNA polymerase according to the invention contains one or more mutations that reduce the DNA polymerization activity of the non-chimeric V93 Pfu DNA polymerase.

The invention further provides for a blend of two or more DNA polymerases comprising a one or more chimeric DNA polymerases and one or more non-chimeric V93 mutant Pfu DNA polymerases with reduced uracil detection activity that contain one or mutations that reduce DNA polymerization as disclosed in the pending U.S. patent application Ser. No. 10/035,091 (Hogrefe, et al.; filed: Dec. 21, 2001); the pending U.S. patent application Ser. No. 10/079,241 (Hogrefe, et al.; filed Feb. 20, 2002); the pending U.S. patent application Ser. No. 10/208,508 (Hogrefe et al.; filed Jul. 30, 2002); and the pending U.S. patent application Ser. No. 10/227,110 (Hogrefe et al.; filed Aug. 23, 2002), the contents of which are hereby incorporated in their entirety.

In one embodiment, the invention provides for a non-chimeric V93R/G387P, V93E/G387P, V93D/G387P, V93K/

G387P or V93N/G387P double mutant Pfu DNA polymerase with reduced DNA polymerization activity and reduced uracil detection activity.

The invention further provides for non-chimeric V93R, V93E, V93D, V93K or V93N mutant Pfu DNA polymerases with reduced uracil detection activity containing one or mutations that reduce or eliminate 3'-5' exonuclease activity as disclosed in the pending U.S. patent application Ser. No. 09/698,341 (Sorge et al; filed Oct. 27, 2000).

In one embodiment, the invention provides for a non-chimeric V93R/D141A/E143A triple mutant Pfu DNA polymerase with reduced 3'-5' exonuclease activity and reduced uracil detection activity.

The invention further provides for one or more non-chimeric Pfu DNA polymerase of the invention comprising any combination of one or more mutations that may increase or eliminate base analog detection activity of an archaeal DNA polymerase.

DNA polymerases containing additional mutations are generated by site directed mutagenesis using the DNA polymerases of the invention as a template DNA molecule, for example, the Pfu DNA polymerase or Pfu V93R cDNA, according to methods that are well known in the art and are described herein.

Methods used to generate non-chimeric Pfu DNA polymerases with reduced DNA polymerization activity of the invention are disclosed in the pending U.S. patent application Ser. No. 10/035,091 (Hogrefe, et al.; filed: Dec. 21, 2001); the pending U.S. patent application Ser. No. 10/079,241 (Hogrefe, et al.; filed Feb. 20, 2002); the pending U.S. patent application Ser. No. 10/208,508 (Hogrefe et al.; filed Jul. 30, 2002); and the pending U.S. patent application Ser. No. 10/227,110 (Hogrefe et al.; filed Aug. 23, 2002), the contents of which are hereby incorporated in their entirety.

Methods used to generate 3'-5' exonuclease deficient JDF-3 DNA polymerases including the D141A and E143A mutations are disclosed in the pending U.S. patent application Ser. No. 09/698,341 (Sorge et al; filed Oct. 27, 2000). A person skilled in the art in possession of the teachings of the pending U.S. patent application Ser. No. 09/698,341 (Sorge et at; filed Oct. 27, 2000) would have no difficulty introducing both the corresponding D141A and E143A mutations or other 3'-5' exonuclease mutations into a DNA polymerase of the invention including for example, the non-chimeric V93 Pfu DNA polymerase cDNA, as disclosed in the pending U.S. patent application Ser. No. 09/698,341, using established site-directed mutagenesis methodology.

Three 3' to 5' exonuclease motifs have been identified, and mutations in these regions have also been shown to abolish 3' to 5' exonuclease activity in Klenow, Φ29, T4, T7, and Vent DNA polymerases, yeast Pot α, Pot β, and Pot γ, and *Bacillus subtilis* Pot III (reviewed in Derbeyshire et al., 1995, Methods. Enzymol. 262:363) all of which can be used as the non chimeric DNA polymerase component in the blend of the invention disclosed herein. Methods for preparing additional non-chimeric DNA polymerase mutants, with reduced or abolished 3' to 5' exonuclease activity, are well known in the art.

Commercially-available enzymes that lack both 5' to 3' and 3' to 5' exonuclease activities include Sequenase ($exo^-$ T7; USB), Pfu $exo^-$ (Stratagene), $exo^-$ Vent (New England BioLabs), $exo^-$ DeepVent (New England BioLabs), $exo^-$ Klenow fragment (Stratagene), Bst (Bio-Rad), Isotherm (Epicentre), Ladderman (Panvera), KlenTaq1 (Ab Peptides), Stoffel fragment (Perkin-Elmer), ThermoSequenase (USB), and TaqFS (Hoffman-LaRoche), any one of which may be used as the non chimeric DNA polymerase component in the blend of the invention disclosed herein.

In accordance with the invention, in addition to the mutations described above, one or more additional mutations or modifications (or combinations thereof) may be made to the polymerases of interest. Mutations or modifications of particular interest include those modifications of mutations which (1) eliminate or reduce 5' to 3' exonuclease activity; and (2) reduce discrimination of dideoxynucleotides (that is, increase incorporation of dideoxynucleotides). The 5'-3' exonuclease activity of the polymerases can be reduced or eliminated by mutating the polymerase gene or by deleting the 5' to 3' exonuclease domain. Such mutations include point mutations, frame shift mutations, deletions, and insertions. Preferably, the region of the gene encoding an DNA polymerase activity is deleted using techniques well known in the art. For example, any one of six conserved amino acids that are associated with the 5'-3' exonuclease activity can be mutated. Examples of these conserved amino acids with respect to Taq DNA polymerase include $Asp^{18}$, $Glu^{117}$, $Asp^{119}$, $Asp^{120}$, $Asp^{142}$, and $Asp^{144}$.

Polymerase mutants can also be made to render the polymerase non-discriminating against non-natural nucleotides such as dideoxynucleotides (see U.S. Pat. No. 5,614,365), Changes within the O-helix, such as other point mutations, deletions, and insertions, can be made to render the polymerase non-discriminating. By way of example, one Tne DNA polymerase mutant having this property substitutes a non-natural amino acid such as Tyr for Phe730 in the O-helix.

Typically, the 5'-3' exonuclease activity, 3' to 5' exonuclease activity, discriminatory activity and fidelity can be affected by substitution of amino acids typically which have different properties. For example, an acidic amino acid such as Asp may be changed to a basic, neutral or polar but uncharged amino acid such as Lys, Arg, His (basic); Ala, Val, Leu, Ile, Pro, Met, Phe, Trp (neutral); or Gly, Ser, Thr, Cys, Tyr, Asn or Gln (polar but uncharged). Glu may be changed to Asp, Ala, Val Leu, Ile, Pro, Met, Phe, Trp, Gly, Ser, Thr, Cys, Tyr, Asn or Gln.

Preferably, oligonucleotide directed mutagenesis is used to create the mutant polymerases which allows for all possible classes of base pair changes at any determined site along the encoding DNA molecule. In general, this technique involves annealing a oligonucleotide complementary (except for one or more mismatches) to a single stranded nucleotide sequence coding for the DNA polymerase of interest. The mismatched oligonucleotide is then extended by DNA polymerase, generating a double stranded DNA molecule which contains the desired change in sequence on one strand. The changes in sequence can of course result in the deletion, substitution, or insertion of an amino acid. The double stranded polynucleotide can then be inserted into an appropriate expression vector, and a mutant polypeptide can thus be produced. The above-described oligonucleotide directed mutagenesis can of course be carried out via PCR.

In one embodiment, the non-chimeric mutant Pfu DNA polymerases are expressed and purified as described in U.S. Pat. No. 5,489,523, hereby incorporated by reference in its entirety.

III. Preparing Mutant Chimeric DNA Polymerases

The chimeric DNA polymerase of the invention is a DNA polymerase fusion polypeptide having at least two polypeptides covalently linked, in which one polypeptide comes from one protein sequence or domain and the other polypeptide comes from another protein sequence or domain. According to the invention, at least one of the domains of the chimeric DNA polymerase originates from a DNA polymerase of the invention. The polypeptides can be linked either directly or via a covalent linker, e.g., an amino acid linker, such as a polyglycine linker, or another type of chemical linker, e.g., a carbohydrate linker, a lipid linker, a fatty acid linker, a polyether linker, e.g., PEG, etc. (See, e.g., Hermanson, Bioconjugate techniques (1996)). The polypeptides forming the fusion polypeptide are typically linked C-terminus to N-terminus, although they can also be linked C-terminus to C-terminus, N-terminus to N-terminus, or N-terminus to C-terminus. One or more polypeptide domains may be inserted at an internal location within a DNA polymerase of the invention. The polypeptides of the fusion protein can be in any order. The term "fusion polypeptide" or "chimera" also refers to conservatively modified variants, polymorphic variants, alleles, mutant, subsequences and interspecies homologues of the polypeptides that make up the fusion protein. Fusion proteins may be produced by covalently linking a chain of amino acids from one protein sequence to a chain of amino acids from another protein sequence, e.g., by preparing a recombinant polynucleotide contiguously encoding the fusion protein. Fusion proteins can comprise 2, 3, 4 or more different chains of amino acids from the same or different species. The different chains of amino acids in a fusion protein may be directly spliced together or may be indirectly spliced together via a chemical linking group or an amino acid linking group, which can be about 200 amino acids or more in length, with 1 to 100 amino acids being typical. In some embodiments, proline residues are incorporated into the linker to prevent the formation of significant secondary structural elements by the linker. Linkers can often be flexible amino acid subsequences that are synthesized as part of a recombinant fusion protein. Such flexible linkers are known to persons of skill in the art.

In a preferred embodiment, the chimeric DNA polymerase, useful according to the invention, is a thermostable DNA polymerase with reduced DNA polymerization activity or with reduced uracil detection activity. In addition, the chimeric DNA polymerase of the invention may or may not have 3'-5' exonuclease activity.

In one embodiment, the chimeric component fused to the DNA polymerase is any non-native protein or protein domain fused to the DNA polymerase at the N- or C-terminus or at any internal position. The chimeric contribution to the activity of the DNA polymerase includes, but is not limited to, an increase in one or more of the following DNA polymerase activities: processivity, DNA binding, strand displacement activity, polymerase activity, nucleotide binding and recognition, proofreading, fidelity, and salt resistance and/or decreased DNA polymerase activity at room temperature.

A chimeric polymerase can be prepared by molecular biology techniques for preparing fusion proteins well known in the art.

Using techniques well known in the art (Sambrook et al., (1989) in: Molecular Cloning, A Laboratory Manual (2nd Ed.), Cold Spring Harbor Laboratory Press, Cold Spring Harbor, N.Y.), a protein domain of a DNA polymerase can be substituted with a domain from another polymerase which has the desired activity. Methods of preparing a chimeric DNA polymerases of the invention are also described in WO 01/92501 A1 and Pavlov et al., 2002, Proc. Natl. Acad. Sci. USA, 99:13510-13515, which are herein incorporated in its entirety.

In one embodiment, the chimeric DNA polymerase of the invention comprises a protein domain of one wild type DNA polymerase of the invention that is fused to a protein domain of a different DNA polymerase of the invention containing one or more mutations.

In another preferred embodiment, the chimeric DNA polymerase of the invention comprises all of or a part of Pfu or Taq DNA polymerase.

In one embodiment, the chimeric DNA polymerase of the invention comprises a Pfu DNA polymerase, or part thereof, having reduced DNA polymerization as disclosed in the pending U.S. patent application Ser. No. 10/035,091 (Hogrefe, et al.; filed: Dec. 21, 2001); the pending U.S. patent application Ser. No. 10/079,241 (Hogrefe, et al.; filed Feb. 20, 2002); the pending U.S. patent application Ser. No. 10/208,508 (Hogrefe et al.; filed Jul. 30, 2002); and the pending U.S. patent application Ser. No. 10/227,110 (Hogrefe et al.; filed Aug. 23, 2002), the contents of which are hereby incorporated by reference in their entirety.

In one embodiment, the chimeric DNA polymerase of the invention comprises a Pfu DNA polymerase, or part thereof, having one or mutations that reduce base analog detection activity as disclosed in the pending U.S. patent application Ser. No. 10/280,962 (Hogrefe, et al.; filed: Oct. 25, 2002) and the pending U.S. patent application Ser. No. 10/298,680 (Hogrefe et al.; filed Nov. 18, 2002), the contents of which are hereby incorporated by reference in their entirety.

In one embodiment, the chimeric DNA polymerase of the invention comprises a protein domain of one mutant DNA polymerase of the invention that is fused to a protein domain of a different DNA polymerase of the invention containing one or more mutations.

In one embodiment, the chimeric DNA polymerase of the invention comprises a protein domain of one DNA polymerase that replaces an analogous protein domain within another DNA polymerase of the invention. As used herein, two protein domains are said to be "analogous" if they share in common a domain that confers at least one DNA polymerase activity such as processivity, DNA binding, strand displacement activity, nucleotide binding and recognition, proofreading, e.g. 3'-5' exonuclease activity, fidelity, e.g. 5'-3' exonuclease activity, or salt resistance.

In one embodiment, the chimeric DNA polymerase of the invention comprises the helix-hairpin-helix DNA binding motifs from DNA topoisomerase V that increases processivity, salt resistance and thermostability as described in Pavlov et al., 2002, Proc. Natl. Acad. Sci USA, 99:13510-13515.

In another embodiment, the chimeric DNA polymerase of the invention comprises the thioredoxin binding domain that enhances the processivity of the chimeric DNA polymerase as described in WO 97/29209.

In another embodiment, the chimeric DNA polymerase of the invention comprises the archaeal PCNA binding domain fused to Taq DNA polymerase or a related eubacterial DNA polymerase. Addition of PCNA to the PCR reaction containing the PCNA binding domain-Taq DNA polymerase chimera results in enhanced processivity of the chimeric DNA polymerase and higher yields of PCR amplified DNA (Motz, M., et al., J. Biol. Chem. 2002 May 3; 277 (18); 16179-88).

In another embodiment, the chimeric DNA polymerase of the invention comprises the sequence non-specific DNA binding protein Sso7d or Sac7d from (for example, from *Sulfolobus sulfataricus* fused to a DNA polymerase of the invention. The fusion of the DNA binding protein Sso7d or Sac7d to chimeric DNA polymerases of the invention, such as Pfu or Taq DNA polymerase, greatly enhances the processivity of these DNA polymerases as disclosed in WO 01/92501 A1 which is hereby incorporated by reference in its entirety.

The invention contemplates chimeras wherein any of the HhH domains known in the art (see Belova et al., 2001, Proc. Natl. Acad. Sci. USA, 98:6015 and FIG. 9) are fused to any of the wildtype or mutant DNA polymerases included herein.

The HhH can be fused directly to the N or C terminus or at any internal site of any of the wildtype or mutant DNA polymerases included herein. One of more (for example the H-L or E-L) HhH domains can be used to create a chimera.

In another embodiment, the chimeric DNA polymerase of the invention comprises a Pfu DNA polymerase, or part thereof, having reduced 3'-5' exonuclease activity. Methods used to generate 3'-5' exonuclease deficient JDF-3 DNA polymerases including the D141A and E143A mutations are disclosed in the pending U.S. patent application Ser. No. 09/698,341 (Sorge et al; filed Oct. 27, 2000), the contents of which are hereby incorporated by reference in their entirety. A person skilled in the art in possession of the teachings of the pending U.S. patent application Ser. No. 09/698,341 (Sorge et al; filed Oct. 27, 2000) would have no difficulty introducing both the corresponding D141A and E143A mutations or other 3'-5' exonuclease mutations into anyone of the chimeric DNA polymerases of the invention i.e. a chimeric DNA polymerase with reduced base analog detection activity or reduced DNA polymerization activity as disclosed herein.

In another embodiment, the chimeric DNA polymerase of the invention comprises a DNA polymerase, or part thereof, that lacks both 5' to 3' and 3' to 5' exonuclease activities including, but not limited to, Sequenase (exo$^-$ T7; USB), Pfu exo$^-$ (Stratagene), exo$^-$ Vent (New England BioLabs), exo$^-$ DeepVent (New England BioLabs), exo$^-$ Klenow fragment (Stratagene), Bst (Bio-Rad), Isotherm (Epicentre), Ladderman (Panvera), KlenTaq1 (Ab Peptides), Stoffel fragment (Perkin-Elmer), ThermoSequenase (USB), and TaqFS (Hoffman-LaRoche), any one of which may be used as the chimeric DNA polymerase component in the blend of the invention disclosed herein.

In another embodiment, the chimeric DNA polymerase of the invention comprises a thermostable DNA polymerase, or part thereof, that has enhanced 3' to 5' exonuclease activity that confers enhanced fidelity to the chimeric DNA polymerase of the invention as disclosed in U.S. Pat. No. 5,795,762, the contents of which are hereby incorporated by reference in their entirety.

IV. Expression of Wild-Type or Mutant Enzymes According to the Invention

Methods known in the art may be applied to express and isolate DNA polymerases of the invention. Many bacterial expression vectors contain sequence elements or combinations of sequence elements allowing high level inducible expression of the protein encoded by a foreign sequence. For example, as mentioned above, bacteria expressing an integrated inducible form of the T7 RNA polymerase gene may be transformed with an expression vector bearing a mutated DNA polymerase gene linked to the T7 promoter. Induction of the T7 RNA polymerase by addition of an appropriate inducer, for example, isopropyl-β-D-thiogalactopyranoside (IPTG) for a lac-inducible promoter, induces the high level expression of the mutated gene from the T7 promoter.

Appropriate host strains of bacteria may be selected from those available in the art by one of skill in the art. As a non-limiting example, *E. coli* strain BL-21 is commonly used for expression of exogenous proteins since it is protease deficient relative to other strains of *E. coli*. BL-21 strains bearing an inducible T7 RNA polymerase gene include WJ56 and ER2566 (Gardner & Jack, 1999, supra). For situations in which codon usage for the particular polymerase gene differs from that normally seen in *E. coli* genes, there are strains of BL-21 that are modified to carry tRNA genes encoding tRNAs with rarer anticodons (for example, argu, ileY, leuW, and proL tRNA genes), allowing high efficiency expression of cloned protein genes, for example, cloned archaeal enzyme genes (several BL21-CODON PLUSTM cell strains carrying rare-codon tRNAs are available from Stratagene, for example).

There are many methods known to those of skill in the art that are suitable for the purification of a DNA polymerase of the invention. For example, the method of Lawyer et al. (1993, *PCR Meth. & App.* 2: 275) is well suited for the isolation of DNA polymerases expressed in *E. coli*, as it was designed originally for the isolation of Taq polymerase. Alternatively, the method of Kong et al. (1993, J. Biol. Chem. 268: 1965, incorporated herein by reference) may be used, which employs a heat denaturation step to destroy host proteins, and two column purification steps (over DEAE-Sepharose and heparin-Sepharose columns) to isolate highly active and approximately 80% pure DNA polymerase. Further, DNA polymerases may be isolated by an ammonium sulfate fractionation, followed by Q Sepharose and DNA cellulose columns, or by adsorption of contaminants on a HiTrap Q column, followed by gradient elution from a HiTrap heparin column.

V. Blends of Non Chimeric and Chimeric DNA Polymerases

A chimeric DNA polymerase blend formulation, according to the invention, can include at least one chimeric DNA polymerase and: (1) a proofreading or a non-proofreading non-chimeric DNA polymerase; or (2) a proofreading plus non-proofreading, non-proofreading plus non-proofreading or a proofreading plus proofreading non-chimeric DNA polymerase blend, e.g., Pfu, Taq, Pfu/Taq, Pfu/exo-Pfu, Taqlexo-Pfu, Pfu/JDF3, or any of these combinations with pol-Pfu (Pfu G387P). The ratio of DNA polymerase enzymes in a "blend" comprising one chimeric and one non-chimeric polymerase is in the range of 1:1-1:5-5:1, or 1:1-1:10-10:1, or 1:1-1:25-25:1 or 1:1-1:100-100:1. For embodiments wherein a "blend" comprises one chimeric DNA polymerase and two non-chimeric polymerases the ratio of the first non-chimeric DNA polymerase to the second non-chimeric DNA polymerase is in the range of 1:1-1:5-5:1, or 1:1-1:10-10:1, or 1:1-1:25-25:1 or 1:1-1:100-100:1. The formulation of the invention has no limitations on the ratios of the individual components.

In one embodiment, the blend formulation of the invention is 2.5 U Pfu/0.25 U chimeric Pfu.

The wild type DNA polymerase that is blended with the DNA polymerase chimera can be any native or cloned DNA polymerase having native levels of polymerase activity and proofreading activity and preferably is thermostable such as Pfu or Taq. The chimeric DNA polymerase and wt DNA polymerase are blended in the ratio range described above and can be mixed with any replication accessory factor or PCR enhancing additives, e.g., Pfu dUTPase (PEF), PCNA, RPA, ssb, antibodies, DMSO, betaine, or 3'-5' exonuclease (e.g., Pfu G387P).

The mutant DNA polymerase that is blended with the DNA polymerase chimera of the invention is any DNA polymerase having introduced mutations and/or truncations that generates a DNA polymerase with an activity that is distinct from a wild type DNA polymerase. The mutant could have any amount of polymerase and/or proofreading activity. Specific examples of useful mutations or truncations include, but are not limited to, V93R,K,E, or D in Pfu DNA polymerase, which confer uracil insensitivity, D141A/E143A in Pfu DNA polymerase, which eliminates 3'-5' exonuclease activity, and the N-terminal truncation of Taq that eliminates 5'-3' exonuclease activity (KlenTaq).

The invention further provides for mutant V93R, V93E, V93D, V93K or V93N non-chimeric Pfu DNA polymerases that contain one or more additional mutations with improved reverse transcriptase activity.

The invention provides for a blend wherein the ratio of chimeric DNA polymerase to non-chimeric DNA polymerase is in the ratio range of 1:1-1:5-5:1, or 1:1-1:10-10:1, or 1:1-1:25-25:1 or 1:1-1:100-100: 1. The invention contemplates a blend comprising a mixture of a chimeric DNA polymerase and more than one non-chimeric DNA polymerase. For a blend comprising a chimeric DNA polymerase in combination with two non-chimeric DNA polymerases, the ratio range of the first non-chimeric DNA polymerases to the second non-chimeric DNA polymerase is 1:1-1:5-5:1, or 1:1-1: 10-10:1, or 1:1-1:25-25:1 or 1:1-1:100-100:1.

VI. Applications of the Subject Invention

In one aspect, the invention provides a method for DNA synthesis using the compositions of the subject invention. Typically, synthesis of a polynucleotide requires a synthesis primer, a synthesis template, polynucleotide precursors for incorporation into the newly synthesized polynucleotide, (e.g. dATP, dCTP, dGTP, dTTP), and the like. Detailed methods for carrying out polynucleotide synthesis are well known to the person of ordinary skill in the art and can be found, for example, in *Molecular Cloning second edition*, Sambrook et al., Cold Spring Harbor Laboratory Press, Cold Spring Harbor, N.Y. (1989).

A. Application in Amplification Reactions

"Polymerase chain reaction" or "PCR" refers to an in vitro method for amplifying a specific polynucleotide template sequence. The technique of PCR is described in numerous publications, including, PCR: A Practical Approach, M. J. McPherson, et al., IRL Press (1991), PCR Protocols: A Guide to Methods and Applications, by Innis, et al., Academic Press (1990), and PCR Technology: Principals and Applications for DNA Amplification, H. A. Erlich, Stockton Press (1989). PCR is also described in many U.S. Patents, including U.S. Pat. Nos. 4,683,195; 4,683,202; 4,800,159; 4,965,188; 4,889,818; 5,075,216; 5,079,352; 5,104,792; 5,023,171; 5,091,310; and 5,066,584, each of which is herein incorporated by reference.

For ease of understanding the advantages provided by the present invention, a summary of PCR is provided. The PCR reaction involves a repetitive series of temperature cycles and is typically performed in a volume of 50-100 μl. The reaction mix comprises dNTPs (each of the four deoxynucleotides dATP, dCTP, dGTP, and dTTP), primers, buffers, DNA polymerase, and polynucleotide template. PCR requires two primers that hybridize with the double-stranded target polynucleotide sequence to be amplified. In PCR, this double-stranded target sequence is denatured and one primer is annealed to each strand of the denatured target. The primers anneal to the target polynucleotide at sites removed from one another and in orientations such that the extension product of one primer, when separated from its complement, can hybridize to the other primer. Once a given primer hybridizes to the target sequence, the primer is extended by the action of a DNA polymerase. The extension product is then denatured from the target sequence, and the process is repeated.

In successive cycles of this process, the extension products produced in earlier cycles serve as templates for DNA synthesis. Beginning in the second cycle, the product of amplification begins to accumulate at a logarithmic rate. The amplification product is a discrete double-stranded DNA molecule comprising: a first strand which contains the sequence of the first primer, eventually followed by the sequence complementary to the second primer, and a second strand which is complementary to the first strand.

Due to the enormous amplification possible with the PCR process, small levels of DNA carryover from samples with high DNA levels, positive control templates or from previous amplifications can result in PCR product, even in the absence of purposefully added template DNA. If possible, all reaction mixes are set up in an area separate from PCR product analysis and sample preparation. The use of dedicated or disposable vessels, solutions, and pipettes (preferably positive displacement pipettes) for RNA/DNA preparation, reaction mixing, and sample analysis will minimize cross contamination. See also Higuchi and Kwok, 1989, Nature, 339:237-238 and Kwok, and Orrego, in: Innis et al. eds., 1990, *PCR Protocols: A Guide to Methods and Applications*, Academic Press, Inc., San Diego, Calif., which are incorporated herein by reference.

The enzymes provided herein are also useful for dUTP/UNG cleanup methods that require PCR enzymes that incorporate dUTP (Longo et al., Supra).

1. Thermostable Enzymes

For PCR amplifications, the enzymes used in the invention are preferably thermostable. As used herein, "thermostable" refers to an enzyme which is stable to heat, is heat resistant, and functions at high temperatures, e.g., 50 to 90° C. The thermostable enzyme according to the present invention must satisfy a single criterion to be effective for the amplification reaction, i.e., the enzyme must not become irreversibly denatured (inactivated) when subjected to the elevated temperatures for the time necessary to effect denaturation of double-stranded polynucleotides. By "irreversible denaturation" as used in this connection, is meant a process bringing a permanent and complete loss of enzymatic activity. The heating conditions necessary for denaturation will depend, e.g., on the buffer salt concentration and the length and nucleotide composition of the polynucleotides being denatured, but typically range from 85° C., for shorter polynucleotides, to 105° C. for a time depending mainly on the temperature and the polynucleotide length, typically from 0.25 minutes for shorter polynucleotides, to 4.0 minutes for longer pieces of DNA. Higher temperatures may be tolerated as the buffer salt concentration and/or GC composition of the polynucleotide is increased. Preferably, the enzyme will not become irreversibly denatured at 90 to 100° C. An enzyme that does not become irreversibly denatured, according to the invention, retains at least 10%, or at least 25%, or at least 50% or more function or activity during the amplification reaction.

2. PCR Reaction Mixture

In addition to the subject enzyme mixture, one of average skill in the art may also employ other PCR parameters to increase the fidelity of synthesis/amplification reaction. It has been reported PCR fidelity may be affected by factors such as changes in dNTP concentration, units of enzyme used per reaction, pH, and the ratio of $Mg^{2+}$ to dNTPs present in the reaction (Mattila et al., 1991, supra).

$Mg^{2+}$ concentration affects the annealing of the oligonucleotide primers to the template DNA by stabilizing the primer-template interaction, it also stabilizes the replication complex of polymerase with template-primer. It can therefore also increase non-specific annealing and produce undesirable PCR products (gives multiple bands in gel). When non-specific amplification occurs, $Mg^{2+}$ may need to be lowered or EDTA can be added to chelate $Mg^{2+}$ to increase the accuracy and specificity of the amplification.

Other divalent cations such as $Mn^{2+}$, or $Co^{2+}$ can also affect DNA polymerization. Suitable cations for each DNA polymerase are known in the art (e.g., in *DNA Replication* $2^{nd}$ edition, supra). Divalent cation is supplied in the form of a salt such $MgCl_2$, $Mg(OAc)_2$, $MgSO_4$, $MnCl_2$, $Mn(OAc)_2$, or $MnSO_4$. Usable cation concentrations in a Tris-HCl buffer are for $MnCl_2$ from 0.5 to 7 mM, preferably, between 0.5 and 2 mM, and for $MgCl_2$ from 0.5 to 10 mM. Usable cation concentrations in a Bicine/KOAc buffer are from 1 to 20 mM for $Mn(OAc)_2$, preferably between 2 and 5 mM.

Monovalent cation required by DNA polymerase may be supplied by the potassium, sodium, ammonium, or lithium salts of either chloride or acetate. For KCl, the concentration is between 1 and 200 mM, preferably the concentration is between 40 and 100 mM, although the optimum concentration may vary depending on the polymerase used in the reaction.

Deoxyribonucleotide triphosphates (dNTPs) are added as solutions of the salts of dATP, dCTP, dGTP, dUTP, and dTTP, such as disodium or lithium salts. In the present methods, a final concentration in the range of 1 μM to 2 mM each is suitable, and 100-600 μM is preferable, although the optimal concentration of the nucleotides may vary in the PCR reaction depending on the total dNTP and divalent metal ion concentration, and on the buffer, salts, particular primers, and template. For longer products, i.e., greater than 1500 bp, 500 μM each dNTP may be preferred when using a Tris-HCl buffer.

dNTPs chelate divalent cations, therefore amount of divalent cations used may need to be changed according to the dNTP concentration in the reaction. Excessive amount of dNTPs (e.g., larger than 1.5 mM) can increase the error rate and possibly inhibit DNA polymerases. Lowering the dNTP (e.g., to 10-50 μM) may therefore reduce error rate. PCR reaction for amplifying larger size template may need more dNTPs.

One suitable buffering agent is Tris-HCl, preferably pH 8.3, although the pH may be in the range 8.0-8.8. The Tris-HCl concentration is from 5-250 mM, although 10-100 mM is most preferred. A preferred buffering agent is Bicine-KOH, preferably pH 8.3, although pH may be in the range 7.8-8.7. Bicine acts both as a pH buffer and as a metal buffer. Tricine may also be used.

PCR is a very powerful tool for DNA amplification and therefore very little template DNA is needed. However, in some embodiments, to reduce the likelihood of error, a higher DNA concentration may be used, though too many templates may increase the amount of contaminants and reduce efficiency.

Usually, up to 3 μM of primers may be used, but high primer to template ratio can results in non-specific amplification and primer-dimer formation. Therefore it is usually necessary to check primer sequences to avoid primer-dimer formation.

The invention provides for Pfu V93R, V93E, V93K, V93D, or V93N non chimeric or chimeric DNA polymerases with reduced uracil detection activity that enhance PCR of GC rich DNA templates by minimizing the effect of cytosine deamination in the template and by allowing the use of higher denaturation times and denaturation temperatures.

3. Cycling Parameters

Denaturation time may be increased if template GC content is high. Higher annealing temperature may be needed for primers with high GC content or longer primers. Gradient PCR is a useful way of determining the annealing temperature. Extension time should be extended for larger PCR product amplifications. However, extension time may need to be reduced whenever possible to limit damage to enzyme.

The number of cycle can be increased if the number of template DNA is very low, and decreased if high amount of template DNA is used.

4. PCR Enhancing Factors and Additives

PCR enhancing factors may also be used to improve efficiency of the amplification. As used herein, a "PCR enhancing factor" or a "Polymerase Enhancing Factor" (PEF) refers to a complex or protein possessing polynucleotide polymerase enhancing activity (Hogrefe et al., 1997, Strategies 10:93-96; and U.S. Pat. No. 6,183,997, both of which are hereby incorporated by references). For Pfu DNA polymerase, PEF comprises either P45 in native form (as a complex of P50 and P45) or as a recombinant protein. In the native complex of Pfu P50 and P45, only P45 exhibits PCR enhancing activity. The P50 protein is similar in structure to a bacterial flavoprotein. The P45 protein is similar in structure to dCTP deaminase and dUTPase, but it functions only as a dUTPase converting dUTP to dUMP and pyrophosphate. PEF, according to the present invention, can also be selected from the group consisting of: an isolated or purified naturally occurring polymerase enhancing protein obtained from an archeabacteria source (e.g., *Pyrococcus furiosus*); a wholly or partially synthetic protein having the same amino acid sequence as Pfu P45, or analogs thereof possessing polymerase enhancing activity; polymerase-enhancing mixtures of one or more of said naturally occurring or wholly or partially synthetic proteins; polymerase-enhancing protein complexes of one or more of said naturally occurring or wholly or partially synthetic proteins; or polymerase-enhancing partially purified cell extracts containing one or more of said naturally occurring proteins (U.S. Pat. No. 6,183,997, supra). The PCR enhancing activity of PEF is defined by means well known in the art. The unit definition for PEF is based on the dUTPase activity of PEF (P45), which is determined by monitoring the production of pyrophosphate (PPi) from dUTP. For example, PEF is incubated with dUTP (10 mM dUTP in 1× cloned Pfu PCR buffer) during which time PEF hydrolyzes dUTP to dUMP and PPi. The amount of PPi formed is quantitated using a coupled enzymatic assay system that is commercially available from Sigma (#P7275). One unit of activity is functionally defined as 4.0 nmole of PPi formed per hour (at 85° C.).

Other PCR additives may also affect the accuracy and specificity of PCR reactions. EDTA less than 0.5 mM may be present in the amplification reaction mix. Detergents such as Tween-20™ and Nonidet™ P-40 are present in the enzyme dilution buffers. A final concentration of non-ionic detergent approximately 0.1% or less is appropriate, however, 0.01-0.05% is preferred and will not interfere with polymerase activity. Similarly, glycerol is often present in enzyme preparations and is generally diluted to a concentration of 1-20% in the reaction mix. Glycerol (5-10%), formamide (1-5%) or DMSO (2-10%) can be added in PCR for template DNA with high GC content or long length (e.g., >1 kb). These additives change the Tm (melting temperature) of primer-template hybridization reaction and the thermostability of polymerase enzyme. BSA (up to 0.8 μg/μl) can improve efficiency of PCR reaction. Betaine (0.5-2M) is also useful for PCR over high GC content and long fragments of DNA. Tetramethylammonium chloride (TMAC, >50 mM), Tetraethylammonium chloride (TEAC), and Trimethlamine N-oxide (TMANO) may also be used. Test PCR reactions may be performed to determine optimum concentration of each additive mentioned above.

The invention provides for additive including, but not limited to antibodies (for hot start PCR) and ssb (single strand DNA binding protein; higher specificity). The invention also contemplates mutant archael DNA polymerases in combination with accessory factors, for example as described in U.S.

Pat. No. 6,333,158, and WO 01/09347 A2, hereby incorporated by reference in its entirety.

Various specific PCR amplification applications are available in the art (for reviews, see for example, Erlich, 1999, *Rev Immunogenet.,* 1: 127-34; Prediger 2001, *Methods Mol. Biol.* 160:49-63; Jurecic et al., 2000, *Curr. Opin. Microbiol.* 3:316-21; Triglia, 2000, *Methods Mol. Biol.* 130:79-83; MaClelland et al., 1994, *PCR Methods Appl.* 4:S66-81; Abramson and Myers, 1993, *Current Opinion in Biotechnology* 4:41-47; each of which is incorporated herein by references).

The subject invention can be used in PCR applications including, but not limited to, i) hot-start PCR which reduces non-specific amplification; ii) touch-down PCR which starts at high annealing temperature, then decreases annealing temperature in steps to reduce non-specific PCR product; iii) nested PCR which synthesizes more reliable product using an outer set of primers and an inner set of primers; iv) inverse PCR for amplification of regions flanking a known sequence. In this method, DNA is digested, the desired fragment is circularized by ligation, then PCR using primer complementary to the known sequence extending outwards; v) AP-PCR (arbitrary primed)/RAPD (random amplified polymorphic DNA). These methods create genomic fingerprints from species with little-known target sequences by amplifying using arbitrary oligonucleotides; vi) RT-PCR which uses RNA-directed DNA polymerase (e.g., reverse transcriptase) to synthesize cDNAs which is then used for PCR. This method is extremely sensitive for detecting the expression of a specific sequence in a tissue or cells. It may also be used to quantify mRNA transcripts; vii) RACE (rapid amplification of cDNA ends). This is used where information about DNA/protein sequence is limited. The method amplifies 3' or 5' ends of cDNAs generating fragments of cDNA with only one specific primer each (plus one adaptor primer). Overlapping RACE products can then be combined to produce full length cDNA; viii) DD-PCR (differential display PCR) which is used to identify differentially expressed genes in different tissues. First step in DD-PCR involves RT-PCR, then amplification is performed using short, intentionally nonspecific primers; ix) Multiplex-PCR in which two or more unique targets of DNA sequences in the same specimen are amplified simultaneously. One DNA sequence can be used as a control to verify the quality of PCR; x) Q/C-PCR (Quantitative comparative) which uses an internal control DNA sequence (but of a different size) which competes with the target DNA (competitive PCR) for the same set of primers; xi) Recusive PCR which is used to synthesize genes. Oligonucleotides used in this method are complementary to stretches of a gene (>80 bases), alternately to the sense and to the antisense strands with ends overlapping (~20 bases); xii) Asymmetric PCR; xiii) In Situ PCR; xiv) Site-directed PCR Mutagenesis.

It should be understood that this invention is not limited to any particular amplification system. As other systems are developed, those systems may benefit by practice of this invention.

B. Application in Direct Cloning of PCR Amplified Product

It is understood that the amplified product produced using the subject enzyme can be cloned by any method known in the art. In one embodiment, the invention provides a composition which allows direct cloning of PCR amplified product.

The most common method for cloning PCR products involves incorporation of flanking restriction sites onto the ends of primer molecules. The PCR cycling is carried out and the amplified DNA is then purified, restricted with an appropriate endonuclease(s) and ligated to a compatible vector preparation.

A method for directly cloning PCR products eliminates the need for preparing primers having restriction recognition sequences and it would eliminate the need for a restriction step to prepare the PCR product for cloning. Additionally, such method would preferably allow cloning PCR products directly without an intervening purification step.

U.S. Pat. Nos. 5,827,657 and 5,487,993 (hereby incorporated by their entirety) disclose methods for direct cloning of PCR products using a DNA polymerase which takes advantage of the single 3'-deoxy-adenosine monophosphate (dAMP) residues attached to the 3' termini of PCR generated nucleic acids. Vectors are prepared with recognition sequences that afford single 3'-terminal deoxy-thymidine monophosphate (dTMP) residues upon reaction with a suitable restriction enzyme. Thus, PCR generated copies of genes can be directly cloned into the vectors without need for preparing primers having suitable restriction sites therein.

Taq DNA polymerase exhibits terminal transferase activity that adds a single dATP to the 3' ends of PCR products in the absence of template. This activity is the basis for the TA cloning method in which PCR products amplified with Taq are directly ligated into vectors containing single 3'dT overhangs. Pfu DNA polymerase, on the other hand, lacks terminal transferase activity, and thus produces blunt-ended PCR products that are efficiently cloned into blunt-ended vectors. The invention also encompasses an Easy A composition that contains a blend of Taq (5 U/ul), recombinant PEF (4 U/ul), and Pfu G387P(40 ng/ul) as disclosed in the pending U.S. patent application Ser. No. 10/035,091 (Hogrefe, et al.; filed: Dec. 21, 2001); the pending U.S. patent application Ser. No. 10/079,241 (Hogrefe, et al.; filed Feb. 20, 2002); the pending U.S. patent application Ser. No. 10/208,508 (Hogrefe et al.; filed Jul. 30, 2002); and the pending U.S. patent application Ser. No. 10/227,110 (Hogrefe et al.; filed Aug. 23, 2002), the contents of which are hereby incorporated in their entirety. With cloned archaeal DNA polymerase with reduced base analog detection activity at 2.5 U/ul i.e. ~20-50 ng per ul, the ratio of Taq:Pfu is preferably 1:1 or more preferably 2:1 or more.

In one embodiment, the invention provides for a PCR product, generated in the presence of a mutant DNA polymerase with reduced uracil detection activity, that is subsequently incubated with Taq DNA polymerase in the presence of DATP at 72° C. for 15-30 minutes. Addition of 3'-dAMP to the ends of the amplified DNA product then permits cloning into TA cloning vectors according to methods that are well known to a person skilled in the art.

C. Application in DNA Sequencing

The invention further provides for dideoxynucleotide DNA sequencing methods using thermostable DNA polymerases having a reduced base analog detection activity to catalyze the primer extension reactions. Methods for dideoxynucleotide DNA sequencing are well known in the art and are disclosed in U.S. Pat. Nos. 5,075,216, 4,795,699 and 5,885,813, the contents of which are hereby incorporated in their entirety. The invention encompasses exo-Pfu (for example D141A/E143A double mutant) or the JDF3 P410L/A485T mutant with reduced ddNTP discrimination.

D. Application in Mutagenesis

The DNA polymerase blends of the invention also provide enhanced efficacy for PCR-based or linear amplification-based mutagenesis. The invention therefore provides for blends of chimeric and non-chimeric polymerases for site-directed mutagenesis and their incorporation into commercially available kits, for example, QuikChange Site-directed Mutagenesis, QuikChange Multi-Site-Directed Mutagenesis (Stratagene). Site-directed mutagenesis methods and reagents are disclosed in the pending U.S. patent application Ser. No. 10/198,449 (Hogrefe et al.; filed Jul. 18, 2002), the contents of which are hereby incorporated in its entirety. The invention also encompasses Mutazyme (exo$^-$Pfu in combination with PEF, GeneMorph Kit). The GeneMorph kits are disclosed in the pending U.S. patent application Ser. No. 10/154,206 (filed May 23, 2002), the contents of which are hereby incorporated in its entirety.

The chimeric blends described herein are used in the same way as conventional DNA polymerase/DNA polymerase formulations and can be used in any primer extension application, including PCR, to produce high product yields with shortened extension times. Amplification of genomic targets, in particular, which typically require extension times of 1-2 min./kb and take hours to amplify, is greatly facilitated by the disclosed invention because extension times are reduced to 5-30 sec./kb, or shorter, with the chimeric blends described herein.

Other applications of the present invention include RT-PCR, site-directed mutagenesis and random mutagenesis. The chimera blend of the invention used in all of these applications increases length capability, shortens reaction times and greatly improves overall performance in all standard protocols.

Blends with proofreading components (3'-5' exonuclease activity) are useful for high fidelity PCR: A blend that is useful for high fidelity PCR will demonstrate an increase of >10 3'-5' exonuclease activity and PCR fidelity, and accuracy of incorporation as compared to the non-chimeric component of the blend (with 3'-5' exonuclease activity) alone for complex genomic and/or plasmid template.

Blends with higher misinsertion and/or mispair extension frequency are useful for PCR random mutagenesis. A blend that is useful for PCR random mutagenesis preferably demonstrates an increase of ≧10% of the mutagenic properties or changes in mutational spectra as compared to the non-chimeric component of the blend for plasmid template.

By "mutagenic properties" is meant mutation rate and the overall number of mutation instances per kb of amplicon.

By "mutational spectra" is meant the number of transition and transversion mutations. "Mutational spectra" also encompasses the ratio of transitions to transversions. Preferably the ratio of transitions to transversion is 1:1.

All of the blends contemplated herein are useful for PCR and RT-PCR:

Blends with proofreading components that are used for PCR amplification and linear amplification are useful for Site Directed Mutagenesis.

Blends without 3'-5' exonuclease activity are useful for sequencing applications. A blend useful for sequencing will demonstrate one or more of shorter extension times, higher efficiency, higher specificity, higher fidelity (more accurate incorporation), and higher processivity (an increase of ≧10% above the non-chimeric component of the blend for sequencing template).

Kits

The invention herein also contemplates a kit format which comprises a package unit having one or more containers of the subject composition and in some embodiments including containers of various reagents used for polynucleotide synthesis, including synthesis in PCR. The kit may also contain one or more of the following items: polynucleotide precursors, primers, buffers, instructions, and controls. Kits may include containers of reagents mixed together in suitable proportions for performing the methods in accordance with the invention. Reagent containers preferably contain reagents in unit quantities that obviate measuring steps when performing the subject methods.

The invention contemplates a kit comprising a combination of chimeric and non-chimeric DNA polymerases according to the invention, PCR enhancing reagents and reagents for PCR amplification, DNA sequencing or mutagenesis.

A kit for sequencing DNA will comprise a number of container means. A first container means may, for example, comprise a substantially purified sample of the polymerases of the invention, A second container means may comprise one or a number of types of nucleotides needed to synthesize a DNA molecule complementary to DNA template. A third container means may comprise one or a number of different types of terminators (such as dideoxynucleoside triphosphates). A fourth container means may comprise pyrophosphatase. In addition to the above container means, additional container means may be included in the kit which comprise one or a number of primers and/or a suitable sequencing buffer.

A kit used for amplifying or synthesis of nucleic acids will comprise, for example, a first container means comprising a substantially pure polymerase of the invention and one or a number of additional container means which comprise a single type of nucleotide or mixtures of nucleotides.

Various primers may be included in a kit as well as a suitable amplification or synthesis buffers.

When desired, the kit of the present invention may also include container means which comprise detectably labeled nucleotides which may be used during the synthesis or sequencing of a nucleic acid molecule, One of a number of labels may be used to detect such nucleotides. Illustrative labels include, but are not limited to, radioactive isotopes, fluorescent labels, chemiluminescent labels, bioluminescent labels and enzyme labels.

Having now generally described the invention, the same will be more readily understood through reference to the following Examples which are provided by way of illustration, and are not intended to be limiting of the present invention, unless specified.

EXAMPLES

Example 1

Construction of Chimeric Pfu DNA Polymerases

A chimeric DNA polymerase is constructed by combining the domains of different DNA polymerases or a non DNA polymerase domain with a DNA polymerase of the invention using methods that are well known to a person of skill in the art.

For example, the thioredoxin processivity factor binding domain of bacteriophage T7 DNA polymerase was inserted into the homologous site in *E. coli* DNA polymerase I. The resulting chimeric thioredoxin binding domain-DNA polymerase exhibits a substantial increase in the processivity of the chimeric *E. coli* DNA polymerase I in the presence of thioredoxin. (Bedford, E., et al., PNAS, USA vol. 94, pp. 479-484, January 1997, WO 97/29209, U.S. Pat. No. 5,972, 603).

Alternatively, the Sso7 domain or the topoisomerase V HhH domain can be added to the N-terminus of Tag or the N-terminus of N-truncated Tag (Stoffel fragment) or the C-terminus of Pfu (as described in WO ol/92501 and Pavlov et al., supra).

Example 2

Purification of Chimeric Pfu

Plasmid DNA was purified with the StrataPrep® Plasmid Miniprep Kit (Stratagene), and used to transform BL26-CodonPlus-RIL cells. Ampicillin resistant colonies were grown up in 1-5 liters of LB media containing Turbo Amp™ (100 μg/μl) and chloramphenicol (30 μg/μl) at 30° C. with moderate aeration. The cells were collected by centrifugation and stored at −80° C. until use.

Cell pellets (12-24 grams) were resuspended in 3 volumes of lysis buffer (buffer A: 50 mM Tris HCl (pH 8.2), 1 mM EDTA, and 10 mM βME). Lysozyme (1 mg/g cells) and PMSF (1 mM) were added and the cells were lysed for 1 hour at 4° C. The cell mixture was sonicated, and the debris removed by centrifugation at 15,000 rpm for 30 minutes (4° C.). Tween 20 and Igepal CA-630 were added to final concentrations of 0.1% and the supernatant was heated at 72° C. for 10 minutes. Heat denatured *E. coli* proteins were then removed by centrifugation at 15,000 rpm for 30 minutes (4° C.).

Chimeric Pfu is also purified as described in PCT/USO1 17492 or Pavlov et al., supra.

Example 3

Purification of Pfu DNA Polymerase Mutants

Bacterial expression of Pfu mutants. Pfu mutants can be purified as described in U.S. Pat. No. 5,489,523 (purification of the $exo^-$ Pfu D141A/E143A DNA polymerase mutant) or as follows. Clarified, heat-treated bacterial extracts were chromatographed on a Q-Sepharose™ Fast Flow column (~20 ml column), equilibrated in buffer B (buffer A plus 0.1% (v/v) Igepal CA-630, and 0.1% (v/v) Tween 20). Flow-through fractions were collected and then loaded directly onto a P11 Phosphocellulose column (~20 ml), equilibrated in buffer C (same as buffer B, except pH 7.5). The column was washed and then eluted with a 0-0.7M KCl gradient/Buffer C. Fractions containing Pfu DNA polymerase mutants (95 kD by SDS-PAGE) were dialyzed overnight against buffer D (50 mM Tris HCl (pH 7.5), 5 mM βME, 5% (v/v) glycerol, 0.2% (v/v) Igepal CA-630, 0.2% (v/v) Tween 20, and 0.5M NaCl) and then applied to a Hydroxyapatite column (~5 ml), equilibrated in buffer D. The column was washed and Pfu DNA polymerase mutants were eluted with buffer D2 containing 400 mM $KPO_4$, (pH 7.5), 5 mM βME, 5% (v/v) glycerol, 0.2% (v/v) Igepal CA-630, 0.2% (v/v) Tween 20, and 0.5 M NaCl. Purified proteins were spin concentrated using Centricon YM30 devices, and exchanged into Pfu final dialysis buffer (50 mM Tris-HCl (pH 8.2), 0.1 mM EDTA, 1 mM dithiothreitol (DTT), 50% (v/v) glycerol, 0.1% (v/v) Igepal CA-630, and 0.1% (v/v) Tween 20).

Protein samples were evaluated for size, purity, and approximate concentration by SDS-PAGE using Tris-Glycine 4-20% acrylamide gradient gels. Gels were stained with silver stain or Sypro Orange (Molecular Probes). Protein concentration was determined relative to a BSA standard (Pierce) using the BCA assay (Pierce).

Purification is determined by SDS-PAGE.

Example 4

Determining Pfu Chimeric or Non-Chimeric Mutant Polymerase Unit Concentration and Specific Activity The unit concentration of purified Pfu mutant preparations was determined by PCR. In this assay, a 500 bp lacZ target is amplified from transgenic mouse genomic DNA using the forward primer: 5'-GACAGTCACTCCGGCCCG-3' (SEQ ID NO: 3) and the reverse primer: 5'-CGACGACTCGTGGAGCCC-3' (SEQ ID NO: 4). Amplification reactions consisted of 1× cloned Pfu PCR buffer, 100 ng genomic DNA, 150 ng each primer, 200 μM each dNTP, and varying amounts of either wild type Pfu (1.25 U to 5 U) or Pfu mutant (0.625-12.5 U). Amplification was performed using a RoboCycler® temperature cycler (Stratagene) with the following program: (1 cycle) 95° C. for 2 minute; (30 cycles) 95° C. for 1 minute, 58° C. for 1 minute, 72° C. for 1.5 minutes; (1 cycle) 72° C. for 7 minutes. PCR products were examined on 1% agarose gels containing ethidium bromide.

Example 5

Preparing a Chimeric DNA Polymerase Blend Formulation

A chimeric DNA polymerase blend formulation is comprised of a chimeric DNA polymerase and: (1) a proofreading or a non-proofreading DNA polymerase; or (2) a proofreading plus non-proofreading, non-proofreading plus non-proofreading or a proofreading plus proofreading DNA polymerase blend, e.g., Pfu, Taq, Pfu/Taq, Pfu/exo-Pfu, Taq/exo-Pfu, Pfu/JDF3, or any of these combinations with pol-Pfu (Pfu G387P). The ratios of the individual components are in the ratio range as described above. A specific example of a blend formulation includes, but is not limited to, 2.5 U Pfu/0.25 U chimeric Pfu.

A wild type DNA polymerase that is blended with the DNA polymerase chimera is any native or cloned DNA polymerase having native levels of polymerase activity and proofreading activity and preferably is thermostable, for example Pfu or Taq. The chimeric DNA polymerase and wt DNA polymerase could be blended and mixed with any replication accessory factor or PCR enhancing additives, e.g., Pfu dUTPase (PEF), PCNA, RPA, ssb, antibodies, DMSO, betaine, or 3'-5' exonuclease (e.g., Pfu G387P). The mutant DNA polymerase that is blended with the DNA polymerase chimera is any DNA polymerase having any introduced mutations and/or truncations that would cause the DNA polymerase to behave differently than the wt polymerase. The mutant could have any amount of polymerase and/or proofreading activity. Specific examples of commercially useful mutations or truncations would be, but not limited to, V93R,K,E or D in Pfu, which confer uracil insensitivity, D141A/E143A in Pfu, which eliminates 3'-5' exonuclease activity, and the N-terminal truncation of Taq to eliminate 5'-3' exonuclease activity(KlenTaq). The chimeric DNA polymerase and mutant DNA polymerase are blended in the ratio range described herein and, in embodiment, are mixed with any replication accessory factor or PCR additives. The DNA polymerase formulation is any mixture of wt, wt and mutant, mutant and mutant DNA polymerase, and in certain embodiments, further comprising any replication accessory factor or PCR additives.

Example 6

PCR Amplification with Pfu DNA Polymerase Blends Containing a Chimeric Pfu DNA Polymerase Pfu blends (for High Fidelity PCR). PCR reactions are conducted under standard conditions in 1× cloned Pfu PCR buffer (10 mM KCl, 10 mM $(NH4)_2SO_4$, 20 mM Tris HCl (pH 8.8), 2 mM Mg $SO_4$, 0.1% Triton X-100, and 100 μg/ml BSA) with 2.5-5 U PfuTurbo DNA polymerase (2.5 U/μl cloned Pfu DNA polymerase plus 1 U/1 μl native or 2 U/μl cloned *Pyrococcus furiosus* dUTPase (PEF)) and varying concentrations of chimeric DNA polymerases (e.g., 0.001-5.0 U). For genomic targets 0.9-9 kb in length, PCR reactions contained 1× cloned Pfu PCR buffer, 2.5 U PfuTurbo DNA polymerase, 100 ng of human genomic DNA, 200 μM each dNTP, and 100 ng of each primer. For genomic targets 12 kb and 17 kb in length, PCR reactions contained 1.5× cloned Pfu PCR buffer, 5 U PfuTurbo DNA polymerase, 250 ng of human genomic DNA, 500 μM each dNTP, and 200 ng of each primer.

Cycling Conditions:

| Target size (kb) | Target gene | Cycling Parameters |
|---|---|---|
| 0.9 | Hα1AT | (1 cycle) 95° C. 2 min<br>(30 cycles) 95° C. 5 sec,<br>58° C. 5 sec, 72° C. 5 sec<br>(1 cycle) 72° C. 7 min |
| 2.6 | Hα1AT | (1 cycle) 95° C. 2 min<br>(30 cycles) 95° C. 20 sec,<br>58° C. 20 sec, 72° C. 39 sec.<br>(1 cycle) 72° C. 7 min |
| 4 | β globin | (1 cycle) 95° C. 2 min<br>(30 cycles) 95° C. 30 sec,<br>54° C. 30 sec, 72° C. 1 min<br>(1 cycle) 72° C. 7 min |
| 9 | β globin | (1 cycle) 95° C. 2 min<br>(30 cycles) 95° C. 40 sec,<br>58° C. 30 sec, 72° C. 4.5 min<br>(1 cycle) 72° C. 10 min |
| 12 | β globin | (1 cycle) 95° C. 2 min<br>(30 cycles) 95° C. 40 sec,<br>58° C. 30 sec, 72° C. 6 min<br>(1 cycle) 72° C. 10 min |
| 17 | β globin | (one cycle) 92° C. 2 min<br>(10 cycles) 92° C. 10 sec,<br>63° C. 30 sec, 68° C. 8.5 min<br>(20 cycles) 92° C. 10 sec,<br>63° C. 30 sec, 68° C. 8.5 min (plus 10 sec/cycle) (one cycle) 68° C. 10 min |

By adding 0.001-5.0 U of a processive chimeric Pfu DNA polymerase to Pfu (in the presence of PEF/dUTPase), PCR extension times are expected to be substantially reduced for the amplification of genomic targets. For genomic targets of between 1-12 kb, an extension time of 1 min/kb for a non-chimeric DNA polymerase/DNA polymerase formulation is reduced to 15-45 sec/kb by adding a chimeric DNA polymerase. For genomic targets between 17-19 kb, an extension time of 2 min/kb for a non-chimeric DNA polymerase/polymerase formulation is reduced to 30-90 sec/kb. With 1-2 min per kb extension times, chimeric blends with improved activity exhibit >10% increase in product yields.

One of skill in the art will appreciate that reaction conditions (e.g., buffer composition etc. . . . ) are optimized depending on the components of the blend of the invention.

The chimeras useful for the invention also increase yield, rate, and length capability of a blend compared to equivalent mixtures prepared with non-chimeric DNA polymerases. The chimera blend generates higher yields with shorter extension times than the conventional non-chimeric DNA polymerase/polymerase blends alone. The mixture of chimeric DNA polymerase and non-chimeric DNA polymerase/DNA polymerase formulation also have a synergistic effect. The chimera blend reaction produces more amplicon template than the chimera alone. Therefore the replication reaction generates higher yields for complex targets than the chimera alone.

The practice of the present invention will employ, unless otherwise indicated, conventional techniques of molecular biology, cell biology, microbiology and recombinant DNA techniques, which are within the skill of the art. Such techniques are explained fully in the literature. See, e.g., Sambrook, Fritsch & Maniatis, 1989, *Molecular Cloning: A Laboratory Manual*, Second Edition; *Oligonucleotide Synthesis* (M. J. Gait, ed., 1984); *Nucleic Acid Hybridization* (B. D. Hames & S. J. Higgins, eds., 1984); *A Practical Guide to Molecular Cloning* (B. Perbal, 1984); (Harlow, E. and Lane, D.) Using Antibodies: A Laboratory Manual (1999) Cold Spring Harbor Laboratory Press; and a series, *Methods in Enzymology* (Academic Press, Inc.); *Short Protocols In Molecular Biology*, (Ausubel et al., ed., 1995).

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

What is claimed is:

1. A blend of two or more DNA polymerases, comprising at least one fusion polypeptide DNA polymerase and at least one non-fusion polypeptide DNA polymerase, wherein said fusion polypeptide DNA polymerase has a proofreading activity and consists of a first polypeptide covalently linked to a second polypeptide, wherein said first polypeptide is a DNA polymerase selected from archaeal DNA polymerases and eubacterial DNA polymerases, and the second polypeptide is a DNA binding polypeptide, wherein the first and second polypeptides are not fused to each other in nature; and wherein said non-fusion polypeptide is a DNA polymerase selected from archaeal DNA polymerases and eubacterial DNA polymerases, said non-fusion polypeptide having a proofreading activity.

2. The blend of claim 1, wherein at least one of said fusion polypeptide and one non-fusion polypeptide DNA polymerase is thermostable.

3. The blend of claim 1, wherein at least one of said fusion polypeptide and non-fusion polypeptide DNA polymerase comprises a Pfu DNA polymerase, wherein the Pfu DNA polymerase is a wild-type Pfu DNA polymerase or a mutant Pfu DNA polymerase that is the same as a wild-type Pfu DNA polymerase except for one or more mutations selected from the group consisting of amino acid positions 93 and 387.

4. The blend of claim 1, wherein both said fusion polypeptide and non-fusion polypeptide DNA polymerases comprise a Pfu DNA polymerase, wherein the pfu DNA polymerases in the fusion polypeptide and non-fusion polypeptide DNA polymerases are independently a wild-type Pfu DNA polymerase or a mutant Pfu DNA polymerase that is the same as a wild-type Pfu DNA polymerase except for one or more mutations selected from the group of amino acid positions 93 and 387.

5. The blend of claim 3, wherein said Pfu DNA polymerase comprises a Glycine to a Proline substitution at amino acid position 387 (G387P).

6. The blend of claim 5, wherein the Pfu DNA polymerase further comprises a mutation at position V93, wherein said mutation is a Valine to Arginine substitution, a Valine to Glutamic acid substitution, a Valine to Lysine substitution, a Valine to Aspartic acid substitution or a Valine to Asparagine substitution.

7. The blend of claim 1, wherein the DNA polymerase in said fusion polypeptide is selected from the group consisting of Pfu, KOD, Tgo, Pfx, Pwo, Vent and DeepVent.

8. The blend of claim 1, wherein said non-fusion polypeptide is selected from the group consisting of Pfu, KOD, Tgo, Pfx, Pwo, Vent and DeepVent.

9. The blend of claim 1, wherein said fusion or non-fusion polypeptide DNA polymerase comprises a mutation selected from the group consisting of PfuV93R, PfuV93E, PfuV93D, PfuV93K, PfuV93N, PfuG387P, PfuV93R/G387P, PfuV93E/G387P, PfuV93D/G387P, PfuV93K/G387P and PfuV93N/G387P.

10. The blend of claim 1, wherein said blend comprises a combination of two or more non-fusion DNA polymerases.

11. The blend of claim 1, wherein said DNA binding polypeptide is selected from the group consisting of thioredoxin processivity factor binding domain of bacteriophage T7, archaeal PCNA binding domain, PCNA, the helix-hairpin-helix DNA binding motifs from DNA topoisomerase V, and the DNA binding protein Sso7d and Sac7d.

12. A composition comprising the blend according to claim 1.

13. The composition of claim 12, further comprising a PCR enhancing factor and/or an additive.

14. A kit comprising the blend according to claim 1 and packaging materials therefore.

15. The kit of claim 14, further comprising a PCR enhancing factor and/or an additive.

16. A method for DNA synthesis comprising: a) providing a blend of two or more DNA polymerases according to claim 1; and contacting said blend with a nucleic acid template, wherein said blend permits DNA synthesis.

17. The method of claim 16, further comprising a PCR enhancing factor and/or an additive.

18. A method for DNA synthesis comprising:

providing a blend of two or more DNA polymerases, according to claim 1; and contacting said blend with a nucleic acid template, wherein said blend permits DNA synthesis.

19. The method of claim 18, further comprising a PCR enhancing factor and/or an additive.

20. A method for cloning of a DNA synthesis product comprising:

a) providing a blend of two or more DNA polymerases, according to claim 1;

b) contacting said blend with a nucleic acid template, wherein said blend permits DNA synthesis to generate a synthesized DNA product; and c) inserting said synthesized DNA product into a cloning vector.

21. The method of claim 20, further comprising a PCR enhancing factor and/or an additive.

22. A method for sequencing DNA comprising the steps of:

contacting a template DNA strand with a sequencing DNA primer;

contacting said DNA of step (a) with the blend of two or more DNA polymerases according to claim 1 with deoxyribonucleoside triphosphates, and a chain-terminating nucleotide analog;

incubating the mixture of step (b) under conditions sufficient to synthesize a random population of DNA molecules complementary to said first DNA molecule, wherein said synthesized DNA molecules are shorter in length than said first DNA molecule and wherein said synthesized DNA molecules comprise a terminator nucleotide at their 5' termini; and separating said synthesized DNA molecules by size so that at least a part of the nucleotide sequence of said firth DNA molecule can be determined.

23. The method of claim 22, further comprising a PCR enhancing factor and/or an additive.

24. A method of linear or exponential PCR amplification for site-directed or random mutagenesis comprising the steps of: incubating a reaction mixture comprising a nucleic acid template, at least two PCR primers, and the blend of claim 1 under conditions which permit amplification of said nucleic acid template by said blend to produce a mutated amplified product.

25. The method of claim 24, further comprising a PCR enhancing factor and/or an additive.

* * * * *

UNITED STATES PATENT AND TRADEMARK OFFICE

CERTIFICATE OF CORRECTION

PATENT NO. : 7,960,157 B2
APPLICATION NO. : 10/702400
DATED : June 14, 2011
INVENTOR(S) : Borns It is certified that error appears in the above-identified patent and that said Letters Patent is hereby corrected as shown below:

In column 213, line 5, in Claim 4, delete "pfu" and insert -- Pfu --, therefor.

In column 214, line 37, in Claim 22, delete "firth" and insert -- first --, therefor.

Signed and Sealed this
Thirteenth Day of September, 2011

David J. Kappos
*Director of the United States Patent and Trademark Office*

SEQUENCE LISTING

```
<160> NUMBER OF SEQ ID NOS: 120

<210> SEQ ID NO 1
<211> LENGTH: 30
<212> TYPE: DNA
<213> ORGANISM: Artificial sequence
<220> FEATURE:
<223> OTHER INFORMATION: Description of Artificial Sequence: Synthetic
      primer

<400> SEQUENCE: 1

gacgacgaca agatgatttt agatgtggat                                       30


<210> SEQ ID NO 2
<211> LENGTH: 30
<212> TYPE: DNA
<213> ORGANISM: Artificial sequence
<220> FEATURE:
<223> OTHER INFORMATION: Description of Artificial Sequence: Synthetic
```

primer

<400> SEQUENCE: 2
ggaacaagac ccgtctagga ttttttaatg 30

<210> SEQ ID NO 3
<211> LENGTH: 18
<212> TYPE: DNA
<213> ORGANISM: Artificial sequence
<220> FEATURE:
<223> OTHER INFORMATION: Description of Artificial Sequence: Synthetic
primer

<400> SEQUENCE: 3
gacagtcact ccggcccg 18

<210> SEQ ID NO 4
<211> LENGTH: 18
<212> TYPE: DNA
<213> ORGANISM: Artificial sequence
<220> FEATURE:
<223> OTHER INFORMATION: Description of Artificial Sequence: Synthetic
primer

<400> SEQUENCE: 4
cgacgactcg tggagccc 18

<210> SEQ ID NO 5
<211> LENGTH: 37
<212> TYPE: DNA
<213> ORGANISM: Artificial sequence
<220> FEATURE:
<223> OTHER INFORMATION: Description of Artificial Sequence: Synthetic
primer

<400> SEQUENCE: 5
gaacatcccc aagatgaacc cactattaga gaaaaag 37

<210> SEQ ID NO 6
<211> LENGTH: 37
<212> TYPE: DNA
<213> ORGANISM: Artificial sequence
<220> FEATURE:
<223> OTHER INFORMATION: Description of Artificial Sequence: Synthetic
primer

<400> SEQUENCE: 6
ctttttctct aatagtgggt tcatcttggg gatgttc 37

<210> SEQ ID NO 7
<211> LENGTH: 37
<212> TYPE: DNA
<213> ORGANISM: Artificial sequence
<220> FEATURE:
<223> OTHER INFORMATION: Description of Artificial Sequence: Synthetic
primer

<400> SEQUENCE: 7
gaacatcccc aagatagacc cactattaga gaaaaag 37

<210> SEQ ID NO 8
<211> LENGTH: 37
<212> TYPE: DNA
<213> ORGANISM: Artificial sequence
<220> FEATURE:
<223> OTHER INFORMATION: Description of Artificial Sequence: Synthetic
primer -continued

<400> SEQUENCE: 8 cttttctct aatagtgggt ctatcttggg gatgttc 37

<210> SEQ ID NO 9
<211> LENGTH: 37
<212> TYPE: DNA
<213> ORGANISM: Artificial sequence
<220> FEATURE:
<223> OTHER INFORMATION: Description of Artificial Sequence: Synthetic primer

<400> SEQUENCE: 9
gaacatcccc aagataaccc cactattaga gaaaaag 37

<210> SEQ ID NO 10
<211> LENGTH: 37
<212> TYPE: DNA
<213> ORGANISM: Artificial sequence
<220> FEATURE:
<223> OTHER INFORMATION: Description of Artificial Sequence: Synthetic primer

<400> SEQUENCE: 10 cttttctct aatagtgggg ttatcttggg gatgttc 37

<210> SEQ ID NO 11
<211> LENGTH: 37
<212> TYPE: DNA
<213> ORGANISM: Artificial sequence
<220> FEATURE:
<223> OTHER INFORMATION: Description of Artificial Sequence: Synthetic primer

<400> SEQUENCE: 11
gaacatcccc aagatcaccc cactattaga gaaaaag 37

<210> SEQ ID NO 12
<211> LENGTH: 37
<212> TYPE: DNA
<213> ORGANISM: Artificial sequence
<220> FEATURE:
<223> OTHER INFORMATION: Description of Artificial Sequence: Synthetic primer

<400> SEQUENCE: 12 cttttctct aatagtgggg tgatcttggg gatgttc 37

<210> SEQ ID NO 13
<211> LENGTH: 37
<212> TYPE: DNA
<213> ORGANISM: Artificial sequence
<220> FEATURE:
<223> OTHER INFORMATION: Description of Artificial Sequence: Synthetic primer
<220> FEATURE:
<221> NAME/KEY: misc_feature
<222> LOCATION: (1)..(1)
<223> OTHER INFORMATION: 5'-phosphate
<220> FEATURE:
<221> NAME/KEY: modified_base
<222> LOCATION: (16)..(17)
<223> OTHER INFORMATION: a, c, g, t, unknown or other

<400> SEQUENCE: 13
gaacatcccc aagatnnkcc cactattaga gaaaaag 37

<210> SEQ ID NO 14
<211> LENGTH: 31

```
<212> TYPE: DNA
<213> ORGANISM: Artificial sequence
<220> FEATURE:
<223> OTHER INFORMATION: Description of Artificial Sequence: Synthetic
      primer

<400> SEQUENCE: 14

gaacatcccc aagataaacc cactattaga g                                   31


<210> SEQ ID NO 15
<211> LENGTH: 31
<212> TYPE: DNA
<213> ORGANISM: Artificial sequence
<220> FEATURE:
<223> OTHER INFORMATION: Description of Artificial Sequence: Synthetic
      primer

<400> SEQUENCE: 15

ctctaatagt gggtttatct tggggatgtt c                                   31


<210> SEQ ID NO 16
<211> LENGTH: 37
<212> TYPE: DNA
<213> ORGANISM: Artificial sequence
<220> FEATURE:
<223> OTHER INFORMATION: Description of Artificial Sequence: Synthetic
      primer
<220> FEATURE:
<221> NAME/KEY: misc_feature
<222> LOCATION: (1)..(1)
<223> OTHER INFORMATION: 5'-phosphate

<400> SEQUENCE: 16

gaacatcccc aagatgcacc cactattaga gaaaaag                             37


<210> SEQ ID NO 17
<211> LENGTH: 37
<212> TYPE: DNA
<213> ORGANISM: Artificial sequence
<220> FEATURE:
<223> OTHER INFORMATION: Description of Artificial Sequence: Synthetic
      primer
<220> FEATURE:
<221> NAME/KEY: misc_feature
<222> LOCATION: (1)..(1)
<223> OTHER INFORMATION: 5'-phosphate

<400> SEQUENCE: 17

gaacatcccc aagatgaccc cactattaga gaaaaag                             37


<210> SEQ ID NO 18
<211> LENGTH: 38
<212> TYPE: DNA
<213> ORGANISM: Artificial sequence
<220> FEATURE:
<223> OTHER INFORMATION: Description of Artificial Sequence: Synthetic
      primer
<220> FEATURE:
<221> NAME/KEY: misc_feature
<222> LOCATION: (1)..(1)
<223> OTHER INFORMATION: 5'-phosphate

<400> SEQUENCE: 18

gaacatcccc aagattgccc ccactattag agaaaaag                            38


<210> SEQ ID NO 19
<211> LENGTH: 37
<212> TYPE: DNA
<213> ORGANISM: Artificial sequence
<220> FEATURE:
```

<223> OTHER INFORMATION: Description of Artificial Sequence: Synthetic
primer
<220> FEATURE:
<221> NAME/KEY: misc_feature
<222> LOCATION: (1)..(1)
<223> OTHER INFORMATION: 5'-phosphate

<400> SEQUENCE: 19
gaacatcccc aagatatacc cactattaga gaaaaag 37

<210> SEQ ID NO 20
<211> LENGTH: 37
<212> TYPE: DNA
<213> ORGANISM: Artificial sequence
<220> FEATURE:
<223> OTHER INFORMATION: Description of Artificial Sequence: Synthetic
primer
<220> FEATURE:
<221> NAME/KEY: misc_feature
<222> LOCATION: (1)..(1)
<223> OTHER INFORMATION: 5'-phosphate

<400> SEQUENCE: 20
gaacatcccc aagatatgcc cactattaga gaaaaag 37

<210> SEQ ID NO 21
<211> LENGTH: 37
<212> TYPE: DNA
<213> ORGANISM: Artificial sequence
<220> FEATURE:
<223> OTHER INFORMATION: Description of Artificial Sequence: Synthetic
primer
<220> FEATURE:
<221> NAME/KEY: misc_feature
<222> LOCATION: (1)..(1)
<223> OTHER INFORMATION: 5'-phosphate

<400> SEQUENCE: 21
gaacatcccc aagatttccc cactattaga gaaaaag 37

<210> SEQ ID NO 22
<211> LENGTH: 37
<212> TYPE: DNA
<213> ORGANISM: Artificial sequence
<220> FEATURE:
<223> OTHER INFORMATION: Description of Artificial Sequence: Synthetic
primer
<220> FEATURE:
<221> NAME/KEY: misc_feature
<222> LOCATION: (1)..(1)
<223> OTHER INFORMATION: 5'-phosphate

<400> SEQUENCE: 22
gaacatcccc aagatcctcc cactattaga gaaaaag 37

<210> SEQ ID NO 23
<211> LENGTH: 37
<212> TYPE: DNA
<213> ORGANISM: Artificial sequence
<220> FEATURE:
<223> OTHER INFORMATION: Description of Artificial Sequence: Synthetic
primer
<220> FEATURE:
<221> NAME/KEY: misc_feature
<222> LOCATION: (1)..(1)
<223> OTHER INFORMATION: 5'-phosphate

<400> SEQUENCE: 23
gaacatcccc aagatagccc cactattaga gaaaaag 37

<210> SEQ ID NO 24
<211> LENGTH: 37
<212> TYPE: DNA
<213> ORGANISM: Artificial sequence
<220> FEATURE:
<223> OTHER INFORMATION: Description of Artificial Sequence: Synthetic primer
<220> FEATURE:
<221> NAME/KEY: misc_feature
<222> LOCATION: (1)..(1)
<223> OTHER INFORMATION: 5'-phosphate

<400> SEQUENCE: 24
gaacatcccc aagatacacc cactattaga gaaaaag 37

<210> SEQ ID NO 25
<211> LENGTH: 37
<212> TYPE: DNA
<213> ORGANISM: Artificial sequence
<220> FEATURE:
<223> OTHER INFORMATION: Description of Artificial Sequence: Synthetic primer
<220> FEATURE:
<221> NAME/KEY: misc_feature
<222> LOCATION: (1)..(1)
<223> OTHER INFORMATION: 5'-phosphate

<400> SEQUENCE: 25
gaacatcccc aagattaccc cactattaga gaaaaag 37

<210> SEQ ID NO 26
<211> LENGTH: 37
<212> TYPE: DNA
<213> ORGANISM: Artificial sequence
<220> FEATURE:
<223> OTHER INFORMATION: Description of Artificial Sequence: Synthetic primer
<220> FEATURE:
<221> NAME/KEY: misc_feature
<222> LOCATION: (1)..(1)
<223> OTHER INFORMATION: 5'-phosphate

<400> SEQUENCE: 26
gaacatcccc aagattggcc cactattaga gaaaaag 37

<210> SEQ ID NO 27
<211> LENGTH: 2328
<212> TYPE: DNA
<213> ORGANISM: Pyrococcus furiosus
<220> FEATURE:
<221> NAME/KEY: modified_base
<222> LOCATION: (277)..(279)
<223> OTHER INFORMATION: region may encompass AGA, AGG, CGA, CGC, CGG, or CGT

<400> SEQUENCE: 27
atgattttag atgtggatta cataactgaa gaaggaaaac ctgttattag gctattcaaa 60
aaagagaacg gaaaatttaa gatagagcat gatagaactt ttagaccata catttacgct 120
cttctcaggg atgattcaaa gattgaagaa gttaagaaaa taacggggga aaggcatgga 180
aagattgtga gaattgttga tgtagagaag gttgagaaaa agtttctcgg caagcctatt 240
accgtgtgga aactttattt ggaacatccc caagatnnnc ccactattag agaaaaagtt 300
agagaacatc cagcagttgt ggacatcttc gaatacgata ttccatttgc aaagagatac 360
ctcatcgaca aaggcctaat accaatggag gggaagaag agctaaagat tcttgccttc 420
gatatagaaa ccctctatca cgaaggagaa gagtttggaa aaggcccaat tataatgatt 480
agttatgcag atgaaaatga agcaaaggtg attacttgga aaaacataga tcttccatac 540

```
gttgaggttg tatcaagcga gagagagatg ataaagagat ttctcaggat tatcagggag    600

aaggatcctg acattatagt tacttataat ggagactcat tcgcattccc atatttagcg    660

aaaagggcag aaaaacttgg gattaaatta accattggaa gagatggaag cgagcccaag    720

atgcagagaa taggcgatat gacggctgta gaagtcaagg gaagaataca tttcgacttg    780

tatcatgtaa taacaaggac aataaatctc ccaacataca cactagaggc tgtatatgaa    840

gcaatttttg gaaagccaaa ggagaaggta tacgccgacg agatagcaaa agcctgggaa    900

agtggagaga accttgagag agttgccaaa tactcgatgg aagatgcaaa ggcaacttat    960

gaactcggga aagaattcct tccaatggaa attcagcttt caagattagt tggacaacct   1020

ttatgggatg tttcaaggtc aagcacaggg aaccttgtag agtggttctt acttaggaaa   1080

gcctacgaaa gaaacgaagt agctccaaac aagccaagtg aagaggagta tcaaagaagg   1140

ctcagggaga gctacacagg tggattcgtt aaagagccag aaaaggggtt gtgggaaaac   1200

atagtatacc tagattttag agccctatat ccctcgatta taattaccca caatgtttct   1260

cccgatactc taaatcttga gggatgcaag aactatgata tcgctcctca agtaggccac   1320

aagttctgca aggacatccc tggttttata ccaagtctct tgggacattt gttagaggaa   1380

agacaaaaga ttaagacaaa aatgaaggaa actcaagatc ctatagaaaa aatactcctt   1440

gactatagac aaaaagcgat aaaactctta gcaaattctt tctacggata ttatggctat   1500

gcaaaagcaa gatggtactg taaggagtgt gctgagagcg ttactgcctg ggaagaaag    1560

tacatcgagt tagtatggaa ggagctcgaa gaaaagtttg gatttaaagt cctctacatt   1620

gacactgatg gtctctatgc aactatccca ggaggagaaa gtgaggaaat aaagaaaaag   1680

gctctagaat ttgtaaaata cataaattca aagctccctg gactgctaga gcttgaatat   1740

gaagggtttt ataagagggg attcttcgtt acgaagaaga ggtatgcagt aatagatgaa   1800

gaaggaaaag tcattactcg tggtttagag atagttagga gagattggag tgaaattgca   1860

aaagaaactc aagctagagt tttggagaca atactaaaac acggagatgt tgaagaagct   1920

gtgagaatag taaaagaagt aatacaaaag cttgccaatt atgaaattcc accagagaag   1980

ctcgcaatat atgagcagat aacaagacca ttacatgagt ataaggcgat aggtcctcac   2040

gtagctgttg caaagaaact agctgctaaa ggagttaaaa taaagccagg aatggtaatt   2100

ggatacatag tacttagagg cgatggtcca attagcaata gggcaattct agctgaggaa   2160

tacgatccca aaaagcacaa gtatgacgca gaatattaca tggagaacca ggttcttcca   2220

gcggtactta ggatattgga gggatttgga tacagaaagg aagacctcag ataccaaaag   2280

acaagacaag tcggcctaac ttcctggctt aacattaaaa aatcctag                2328
```

<210> SEQ ID NO 28
<211> LENGTH: 2328
<212> TYPE: DNA
<213> ORGANISM: Pyrococcus furiosus
<220> FEATURE:
<221> NAME/KEY: modified_base
<222> LOCATION: (277)..(279)
<223> OTHER INFORMATION: region may encompass GAA or GAG

<400> SEQUENCE: 28

```
atgattttag atgtggatta cataactgaa gaaggaaaac ctgttattag gctattcaaa     60

aaagagaacg gaaaatttaa gatagagcat gatagaactt ttagaccata catttacgct    120

cttctcaggg atgattcaaa gattgaagaa gttaagaaaa taacggggga aaggcatgga    180

aagattgtga gaattgttga tgtagagaag gttgagaaaa agtttctcgg caagcctatt    240
```

-continued

```
accgtgtgga aactttattt ggaacatccc caagatnnnc ccactattag agaaaaagtt    300
agagaacatc cagcagttgt ggacatcttc gaatacgata ttccatttgc aaagagatac    360
ctcatcgaca aaggcctaat accaatggag ggggaagaag agctaaagat tcttgccttc    420
gatatagaaa ccctctatca cgaaggagaa gagtttggaa aaggcccaat tataatgatt    480
agttatgcag atgaaaatga agcaaaggtg attacttgga aaaacataga tcttccatac    540
gttgaggttg tatcaagcga gagagagatg ataaagagat ttctcaggat tatcagggag    600
aaggatcctg acattatagt tacttataat ggagactcat tcgcattccc atatttagcg    660
aaaagggcag aaaaacttgg gattaaatta accattggaa gagatggaag cgagcccaag    720
atgcagagaa taggcgatat gacggctgta gaagtcaagg gaagaataca tttcgacttg    780
tatcatgtaa taacaaggac aataaatctc ccaacataca cactagaggc tgtatatgaa    840
gcaatttttg gaaagccaaa ggagaaggta tacgccgacg agatagcaaa agcctgggaa    900
agtggagaga accttgagag agttgccaaa tactcgatgg aagatgcaaa ggcaacttat    960
gaactcggga aagaattcct tccaatggaa attcagcttt caagattagt tggacaacct   1020
ttatgggatg tttcaaggtc aagcacaggg aaccttgtag agtggttctt acttaggaaa   1080
gcctacgaaa gaaacgaagt agctccaaac aagccaagtg aagaggagta tcaaagaagg   1140
ctcagggaga gctacacagg tggattcgtt aaagagccag aaaaggggtt gtgggaaaac   1200
atagtatacc tagattttag agccctatat ccctcgatta taattaccca caatgtttct   1260
cccgatactc taaatcttga gggatgcaag aactatgata tcgctcctca agtaggccac   1320
aagttctgca aggacatccc tggttttata ccaagtctct tgggacattt gttagaggaa   1380
agacaaaaga ttaagacaaa aatgaaggaa actcaagatc ctatagaaaa aatactcctt   1440
gactatagac aaaaagcgat aaaactctta gcaaattctt tctacggata ttatggctat   1500
gcaaaagcaa gatggtactg taaggagtgt gctgagagcg ttactgcctg gggaagaaag   1560
tacatcgagt tagtatggaa ggagctcgaa gaaaagtttg gatttaaagt cctctacatt   1620
gacactgatg gtctctatgc aactatccca ggaggagaaa gtgaggaaat aaagaaaaag   1680
gctctagaat ttgtaaaata cataaattca aagctccctg gactgctaga gcttgaatat   1740
gaagggtttt ataagagggg attcttcgtt acgaagaaga ggtatgcagt aatagatgaa   1800
gaaggaaaag tcattactcg tggtttagag atagttagga gagattggag tgaaattgca   1860
aaagaaactc aagctagagt tttggagaca atactaaaac acggagatgt tgaagaagct   1920
gtgagaatag taaaagaagt aatacaaaag cttgccaatt atgaaattcc accagagaag   1980
ctcgcaatat atgagcagat aacaagacca ttacatgagt ataaggcgat aggtcctcac   2040
gtagctgttg caaagaaact agctgctaaa ggagttaaaa taaagccagg aatggtaatt   2100
ggatacatag tacttagagg cgatggtcca attagcaata gggcaattct agctgaggaa   2160
tacgatccca aaaagcacaa gtatgacgca gaatattaca tggagaacca ggttcttcca   2220
gcggtactta ggatattgga gggatttgga tacagaaagg aagacctcag ataccaaaag   2280
acaagacaag tcggcctaac ttcctggctt aacattaaaa aatcctag                2328
```

<210> SEQ ID NO 29
<211> LENGTH: 2328
<212> TYPE: DNA
<213> ORGANISM: Pyrococcus furiosus
<220> FEATURE:
<221> NAME/KEY: modified_base
<222> LOCATION: (1161)..(1161)
<223> OTHER INFORMATION: a, c, g, t, unknown or other
<220> FEATURE:
<221> NAME/KEY: modified_base
<222> LOCATION: (277)..(279)
<223> OTHER INFORMATION: region may encompass AGA, AGG, CGA, CGC, CGG or CGT

<400> SEQUENCE: 29

```
atgattttag atgtggatta cataactgaa gaaggaaaac ctgttattag gctattcaaa     60

aaagagaacg gaaaatttaa gatagagcat gatagaactt ttagaccata catttacgct    120

cttctcaggg atgattcaaa gattgaagaa gttaagaaaa taacgggga aaggcatgga    180

aagattgtga gaattgttga tgtagagaag gttgagaaaa agtttctcgg caagcctatt    240

accgtgtgga aactttattt ggaacatccc caagatnnnc ccactattag agaaaaagtt    300

agagaacatc cagcagttgt ggacatcttc gaatacgata ttccatttgc aaagagatac    360

ctcatcgaca aaggcctaat accaatggag ggggaagaag agctaaagat tcttgccttc    420

gatatagaaa ccctctatca cgaaggagaa gagtttggaa aaggcccaat tataatgatt    480

agttatgcag atgaaaatga agcaaaggtg attacttgga aaaacataga tcttccatac    540

gttgaggttg tatcaagcga gagagagatg ataaagagat ttctcaggat tatcagggag    600

aaggatcctg acattatagt tacttataat ggagactcat tcgcattccc atatttagcg    660

aaaagggcag aaaaacttgg gattaaatta accattggaa gagatggaag cgagcccaag    720

atgcagagaa taggcgatat gacggctgta gaagtcaagg gaagaataca tttcgacttg    780

tatcatgtaa taacaaggac aataaatctc ccaacataca cactagaggc tgtatatgaa    840

gcaatttttg gaaagccaaa ggagaaggta tacgccgacg agatagcaaa agcctgggaa    900

agtggagaga accttgagag agttgccaaa tactcgatgg aagatgcaaa ggcaacttat    960

gaactcggga aagaattcct tccaatggaa attcagcttt caagattagt tggacaacct   1020

ttatgggatg tttcaaggtc aagcacaggg aaccttgtag agtggttctt acttaggaaa   1080

gcctacgaaa gaaacgaagt agctccaaac aagccaagtg aagaggagta tcaaagaagg   1140

ctcagggaga gctacacacc nggattcgtt aaagagccag aaaaggggtt gtgggaaaac   1200

atagtatacc tagattttag agccctatat ccctcgatta taattaccca caatgtttct   1260

cccgatactc taaatcttga gggatgcaag aactatgata tcgctcctca agtaggccac   1320

aagttctgca aggacatccc tggttttata ccaagtctct tgggacattt gttagaggaa   1380

agacaaaaga ttaagacaaa aatgaaggaa actcaagatc ctatagaaaa aatactcctt   1440

gactatagac aaaaagcgat aaaactctta gcaaattctt tctacggata ttatggctat   1500

gcaaaagcaa gatggtactg taaggagtgt gctgagagcg ttactgcctg gggaagaaag   1560

tacatcgagt tagtatggaa ggagctcgaa gaaaagtttg gatttaaagt cctctacatt   1620

gacactgatg gtctctatgc aactatccca ggaggagaaa gtgaggaaat aaagaaaaag   1680

gctctagaat ttgtaaaata cataaattca aagctccctg gactgctaga gcttgaatat   1740

gaagggtttt ataagagggg attcttcgtt acgaagaaga ggtatgcagt aatagatgaa   1800

gaaggaaaag tcattactcg tggtttagag atagttagga gagattggag tgaaattgca   1860

aaagaaactc aagctagagt tttggagaca atactaaaac acggagatgt tgaagaagct   1920

gtgagaatag taaaagaagt aatacaaaag cttgccaatt atgaaattcc accagagaag   1980

ctcgcaatat atgagcagat aacaagacca ttacatgagt ataaggcgat aggtcctcac   2040

gtagctgttg caaagaaact agctgctaaa ggagttaaaa taaagccagg aatggtaatt   2100

ggatacatag tacttagagg cgatggtcca attagcaata gggcaattct agctgaggaa   2160
```

-continued tacgatccca aaaagcacaa gtatgacgca gaatattaca tggagaacca ggttcttcca 2220
gcggtactta ggatattgga gggatttgga tacagaaagg aagacctcag ataccaaaag 2280
acaagacaag tcggcctaac ttcctggctt aacattaaaa aatcctag 2328

<210> SEQ ID NO 30
<211> LENGTH: 2328
<212> TYPE: DNA
<213> ORGANISM: Pyrococcus furiosus
<220> FEATURE:
<221> NAME/KEY: modified_base
<222> LOCATION: (1161)..(1161)
<223> OTHER INFORMATION: a, c, g, t, unknown or other
<220> FEATURE:
<221> NAME/KEY: modified_base
<222> LOCATION: (277)..(279)
<223> OTHER INFORMATION: region may encompass GAA or GAG

<400> SEQUENCE: 30
atgattttag atgtggatta cataactgaa gaaggaaaac ctgttattag gctattcaaa 60
aaagagaacg gaaaatttaa gatagagcat gatagaactt ttagaccata catttacgct 120
cttctcaggg atgattcaaa gattgaagaa gttaagaaaa taacgggga aaggcatgga 180 aagattgtga gaattgttga tgtagagaag gttgagaaaa agtttctcgg caagcctatt 240
accgtgtgga aactttattt ggaacatccc caagatnnnc ccactattag agaaaaagtt 300
agagaacatc cagcagttgt ggacatcttc gaatacgata ttccatttgc aaagagatac 360
ctcatcgaca aaggcctaat accaatggag ggggaagaag agctaaagat tcttgccttc 420
gatatagaaa ccctctatca cgaaggagaa gagtttggaa aaggcccaat tataatgatt 480
agttatgcag atgaaaatga agcaaaggtg attacttgga aaaacataga tcttccatac 540
gttgaggttg tatcaagcga gagagagatg ataaagagat ttctcaggat tatcagggag 600
aaggatcctg acattatagt tacttataat ggagactcat tcgcattccc atatttagcg 660
aaaagggcag aaaaacttgg gattaaatta accattggaa gagatggaag cgagcccaag 720
atgcagagaa taggcgatat gacggctgta gaagtcaagg gaagaataca tttcgacttg 780
tatcatgtaa taacaaggac aataaatctc ccaacataca cactagaggc tgtatatgaa 840
gcaatttttg gaaagccaaa ggagaaggta tacgccgacg agatagcaaa agcctgggaa 900
agtggagaga accttgagag agttgccaaa tactcgatgg aagatgcaaa ggcaacttat 960
gaactcggga aagaattcct tccaatggaa attcagcttt caagattagt tggacaacct 1020
ttatgggatg tttcaaggtc aagcacaggg aaccttgtag agtggttctt acttaggaaa 1080
gcctacgaaa gaaacgaagt agctccaaac aagccaagtg aagaggagta tcaaagaagg 1140
ctcagggaga gctacacacc nggattcgtt aaagagccag aaaaggggtt gtgggaaaac 1200
atagtatacc tagattttag agccctatat ccctcgatta taattaccca caatgtttct 1260
cccgatactc taaatcttga gggatgcaag aactatgata tcgctcctca agtaggccac 1320
aagttctgca aggacatccc tggttttata ccaagtctct tgggacattt gttagaggaa 1380
agacaaaaga ttaagacaaa aatgaaggaa actcaagatc ctatagaaaa aatactcctt 1440
gactatagac aaaaagcgat aaaactctta gcaaattctt tctacggata ttatggctat 1500
gcaaaagcaa gatggtactg taaggagtgt gctgagagcg ttactgcctg ggggaagaaag 1560 tacatcgagt tagtatggaa ggagctcgaa gaaaagtttg gatttaaagt cctctacatt 1620
gacactgatg gtctctatgc aactatccca ggaggagaaa gtgaggaaat aaagaaaaag 1680
gctctagaat ttgtaaaata cataaattca aagctccctg gactgctaga gcttgaatat 1740

```
gaagggtttt ataagagggg attcttcgtt acgaagaaga ggtatgcagt aatagatgaa   1800

gaaggaaaag tcattactcg tggtttagag atagttagga gagattggag tgaaattgca   1860

aaagaaactc aagctagagt tttggagaca atactaaaac acggagatgt tgaagaagct   1920

gtgagaatag taaaagaagt aatacaaaag cttgccaatt atgaaattcc accagagaag   1980

ctcgcaatat atgagcagat aacaagacca ttacatgagt ataaggcgat aggtcctcac   2040

gtagctgttg caaagaaact agctgctaaa ggagttaaaa taaagccagg aatggtaatt   2100

ggatacatag tacttagagg cgatggtcca attagcaata gggcaattct agctgaggaa   2160

tacgatccca aaaagcacaa gtatgacgca gaatattaca tggagaacca ggttcttcca   2220

gcggtactta ggatattgga gggatttgga tacagaaagg aagacctcag ataccaaaag   2280

acaagacaag tcggcctaac ttcctggctt aacattaaaa aatcctag               2328


<210> SEQ ID NO 31
<211> LENGTH: 2328
<212> TYPE: DNA
<213> ORGANISM: Pyrococcus furiosus
<220> FEATURE:
<221> NAME/KEY: modified_base
<222> LOCATION: (423)..(423)
<223> OTHER INFORMATION: a, c, g, t, unknown or other
<220> FEATURE:
<221> NAME/KEY: modified_base
<222> LOCATION: (429)..(429)
<223> OTHER INFORMATION: a, c, g, t, unknown or other
<220> FEATURE:
<221> NAME/KEY: modified_base
<222> LOCATION: (277)..(279)
<223> OTHER INFORMATION: region may encompass AGA, AGG, CGA, CGC, CGG or
      CGT

<400> SEQUENCE: 31

atgattttag atgtggatta cataactgaa gaaggaaaac ctgttattag gctattcaaa     60

aaagagaacg gaaaatttaa gatagagcat gatagaactt ttagaccata catttacgct    120

cttctcaggg atgattcaaa gattgaagaa gttaagaaaa taacgggggga aaggcatgga    180

aagattgtga gaattgttga tgtagagaag gttgagaaaa agtttctcgg caagcctatt    240

accgtgtgga aactttattt ggaacatccc caagatnnnc ccactattag agaaaaagtt    300

agagaacatc cagcagttgt ggacatcttc gaatacgata ttccatttgc aaagagatac    360

ctcatcgaca aaggcctaat accaatggag ggggaagaag agctaaagat tcttgccttc    420

gcnatagcna ccctctatca cgaaggagaa gagtttggaa aaggcccaat tataatgatt    480

agttatgcag atgaaaatga agcaaaggtg attacttgga aaaacataga tcttccatac    540

gttgaggttg tatcaagcga gagagagatg ataaagagat ttctcaggat tatcagggag    600

aaggatcctg acattatagt tacttataat ggagactcat tcgcattccc atatttagcg    660

aaaagggcag aaaaacttgg gattaaatta accattggaa gagatggaag cgagcccaag    720

atgcagagaa taggcgatat gacggctgta gaagtcaagg gaagaataca tttcgacttg    780

tatcatgtaa taacaaggac aataaatctc ccaacataca cactagaggc tgtatatgaa    840

gcaatttttg gaaagccaaa ggagaaggta tacgccgacg agatagcaaa agcctgggaa    900

agtggagaga accttgagag agttgccaaa tactcgatgg aagatgcaaa ggcaacttat    960

gaactcggga aagaattcct tccaatggaa attcagcttt caagattagt tggacaacct   1020

ttatgggatg tttcaaggtc aagcacaggg aaccttgtag agtggttctt acttaggaaa   1080

gcctacgaaa gaaacgaagt agctccaaac aagccaagtg aagaggagta tcaaagaagg   1140

ctcagggaga gctacacagg tggattcgtt aaagagccag aaaaggggtt gtgggaaaac   1200
```

atagtatacc tagattttag agccctatat ccctcgatta taattaccca caatgtttct 1260
cccgatactc taaatcttga gggatgcaag aactatgata tcgctcctca agtaggccac 1320
aagttctgca aggacatccc tggttttata ccaagtctct tgggacattt gttagaggaa 1380
agacaaaaga ttaagacaaa aatgaaggaa actcaagatc ctatagaaaa aatactcctt 1440
gactatagac aaaaagcgat aaaactctta gcaaattctt tctacggata ttatggctat 1500
gcaaaagcaa gatggtactg taaggagtgt gctgagagcg ttactgcctg gggaagaaag 1560
tacatcgagt tagtatggaa ggagctcgaa gaaaagtttg gatttaaagt cctctacatt 1620
gacactgatg gtctctatgc aactatccca ggaggagaaa gtgaggaaat aaagaaaaag 1680
gctctagaat ttgtaaaata cataaattca aagctccctg gactgctaga gcttgaatat 1740
gaagggtttt ataagagggg attcttcgtt acgaagaaga ggtatgcagt aatagatgaa 1800
gaaggaaaag tcattactcg tggtttagag atagttagga gagattggag tgaaattgca 1860
aaagaaactc aagctagagt tttggagaca atactaaaac acggagatgt tgaagaagct 1920
gtgagaatag taaaagaagt aatacaaaag cttgccaatt atgaaattcc accagagaag 1980
ctcgcaatat atgagcagat aacaagacca ttacatgagt ataaggcgat aggtcctcac 2040
gtagctgttg caaagaaact agctgctaaa ggagttaaaa taaagccagg aatggtaatt 2100
ggatacatag tacttagagg cgatggtcca attagcaata gggcaattct agctgaggaa 2160
tacgatccca aaaagcacaa gtatgacgca gaatattaca tggagaacca ggttcttcca 2220
gcggtactta ggatattgga gggatttgga tacagaaagg aagacctcag ataccaaaag 2280
acaagacaag tcggcctaac ttcctggctt aacattaaaa aatcctag 2328

<210> SEQ ID NO 32
<211> LENGTH: 2328
<212> TYPE: DNA
<213> ORGANISM: Pyrococcus furiosus
<220> FEATURE:
<221> NAME/KEY: modified_base
<222> LOCATION: (423)..(423)
<223> OTHER INFORMATION: a, c, g, t, unknown or other
<220> FEATURE:
<221> NAME/KEY: modified_base
<222> LOCATION: (429)..(429)
<223> OTHER INFORMATION: a, c, g, t, unknown or other
<220> FEATURE:
<221> NAME/KEY: modified_base
<222> LOCATION: (277)..(279)
<223> OTHER INFORMATION: region may encompass GAA or GAG

<400> SEQUENCE: 32
atgattttag atgtggatta cataactgaa gaaggaaaac ctgttattag gctattcaaa 60
aaagagaacg gaaaatttaa gatagagcat gatagaactt ttagaccata catttacgct 120
cttctcaggg atgattcaaa gattgaagaa gttaagaaaa taacggggga aaggcatgga 180
aagattgtga gaattgttga tgtagagaag gttgagaaaa agtttctcgg caagcctatt 240
accgtgtgga aactttattt ggaacatccc caagatnnnc ccactattag agaaaaagtt 300
agagaacatc cagcagttgt ggacatcttc gaatacgata ttccatttgc aaagagatac 360
ctcatcgaca aaggcctaat accaatggag ggggaagaag agctaaagat tcttgccttc 420
gcnatagcna ccctctatca cgaaggagaa gagtttggaa aaggcccaat tataatgatt 480
agttatgcag atgaaaatga agcaaaggtg attacttgga aaaacataga tcttccatac 540
gttgaggttg tatcaagcga gagagagatg ataaagagat ttctcaggat tatcagggag 600
aaggatcctg acattatagt tacttataat ggagactcat tcgcattccc atatttagcg 660

```
aaaagggcag aaaaacttgg gattaaatta accattggaa gagatggaag cgagcccaag    720
atgcagagaa taggcgatat gacggctgta gaagtcaagg gaagaataca tttcgacttg    780
tatcatgtaa taacaaggac aataaatctc ccaacataca cactagaggc tgtatatgaa    840
gcaatttttg gaaagccaaa ggagaaggta tacgccgacg agatagcaaa agcctgggaa    900
agtggagaga accttgagag agttgccaaa tactcgatgg aagatgcaaa ggcaacttat    960
gaactcggga aagaattcct tccaatggaa attcagcttt caagattagt tggacaacct   1020
ttatgggatg tttcaaggtc aagcacaggg aaccttgtag agtggttctt acttaggaaa   1080
gcctacgaaa gaaacgaagt agctccaaac aagccaagtg aagaggagta tcaaagaagg   1140
ctcagggaga gctacacagg tggattcgtt aaagagccag aaaaggggtt gtgggaaaac   1200
atagtatacc tagattttag agccctatat ccctcgatta taattaccca caatgtttct   1260
cccgatactc taaatcttga gggatgcaag aactatgata tcgctcctca agtaggccac   1320
aagttctgca aggacatccc tggttttata ccaagtctct tgggacattt gttagaggaa   1380
agacaaaaga ttaagacaaa aatgaaggaa actcaagatc ctatagaaaa aatactcctt   1440
gactatagac aaaaagcgat aaaactctta gcaaattctt tctacggata ttatggctat   1500
gcaaaagcaa gatggtactg taaggagtgt gctgagagcg ttactgcctg ggaagaaag    1560
tacatcgagt tagtatggaa ggagctcgaa gaaaagtttg gatttaaagt cctctacatt   1620
gacactgatg gtctctatgc aactatccca ggaggagaaa gtgaggaaat aaagaaaaag   1680
gctctagaat ttgtaaaata cataaattca aagctccctg gactgctaga gcttgaatat   1740
gaagggtttt ataagagggg attcttcgtt acgaagaaga ggtatgcagt aatagatgaa   1800
gaaggaaaag tcattactcg tggtttagag atagttagga gagattggag tgaaattgca   1860
aaagaaactc aagctagagt tttggagaca atactaaaac acggagatgt tgaagaagct   1920
gtgagaatag taaaagaagt aatacaaaag cttgccaatt atgaaattcc accagagaag   1980
ctcgcaatat atgagcagat aacaagacca ttacatgagt ataaggcgat aggtcctcac   2040
gtagctgttg caaagaaact agctgctaaa ggagttaaaa taaagccagg aatggtaatt   2100
ggatacatag tacttagagg cgatggtcca attagcaata gggcaattct agctgaggaa   2160
tacgatccca aaaagcacaa gtatgacgca gaatattaca tggagaacca ggttcttcca   2220
gcggtactta ggatattgga gggatttgga tacagaaagg aagacctcag ataccaaaag   2280
acaagacaag tcggcctaac ttcctggctt aacattaaaa aatcctag                2328
```

<210> SEQ ID NO 33
<211> LENGTH: 2325
<212> TYPE: DNA
<213> ORGANISM: Thermococcus kodakaraensis
<220> FEATURE:
<221> NAME/KEY: modified_base
<222> LOCATION: (277)..(279)
<223> OTHER INFORMATION: region may encompass AGA, AGG, CGA, CGC, CGG or CGT

<400> SEQUENCE: 33

```
atgatcctcg acactgacta cataaccgag gatggaaagc ctgtcataag aattttcaag     60
aaggaaaacg gcgagtttaa gattgagtac gaccggactt ttgaacccta cttctacgcc    120
ctcctgaagg acgattctgc cattgaggaa gtcaagaaga taaccgccga gaggcacggg    180
acggttgtaa cggttaagcg ggttgaaaag gttcagaaga agttcctcgg gagaccagtt    240
gaggtctgga aactctactt tactcatccg caggacnnnc cagcgataag ggacaagata    300
```

-continued

```
cgagagcatc cagcagttat tgacatctac gagtacgaca tacccttcgc caagcgctac    360

ctcatagaca agggattagt gccaatggaa ggcgacgagg agctgaaaat gctcgccttc    420

gacattgaaa ctctctacca tgagggcgag gagttcgccg aggggccaat ccttatgata    480

agctacgccg acgaggaagg ggccagggtg ataacttgga agaacgtgga tctcccctac    540

gttgacgtcg tctcgacgga gagggagatg ataaagcgct tcctccgtgt tgtgaaggag    600

aaagacccgg acgttctcat aacctacaac ggcgacaact tcgacttcgc ctatctgaaa    660

aagcgctgtg aaaagctcgg aataaacttc gccctcggaa gggatggaag cgagccgaag    720

attcagagga tgggcgacag gtttgccgtc gaagtgaagg gacggataca cttcgatctc    780

tatcctgtga taagacggac gataaacctg cccacataca cgcttgaggc cgtttatgaa    840

gccgtcttcg gtcagccgaa ggagaaggtt tacgctgagg aaataaccac agcctgggaa    900

accggcgaga accttgagag agtcgcccgc tactcgatgg aagatgcgaa ggtcacatac    960

gagcttggga aggagttcct tccgatggag gcccagcttt ctcgcttaat cggccagtcc   1020

ctctgggacg tctcccgctc cagcactggc aacctcgttg agtggttcct cctcaggaag   1080

gcctatgaga ggaatgagct ggccccgaac aagcccgatg aaaaggagct ggccagaaga   1140

cggcagagct atgaaggagg ctatgtaaaa gagcccgaga gagggttgtg ggagaacata   1200

gtgtacctag attttagatc cctgtacccc tcaatcatca tcacccacaa cgtctcgccg   1260

gatacgctca acagagaagg atgcaaggaa tatgacgttg ccccacaggt cggccaccgc   1320

ttctgcaagg acttcccagg atttatcccg agcctgcttg gagacctcct agaggagagg   1380

cagaagataa agaagaagat gaaggccacg attgacccga tcgagaggaa gctcctcgat   1440

tacaggcaga gggccatcaa gatcctggca aacagctact acggttacta cggctatgca   1500

agggcgcgct ggtactgcaa ggagtgtgca gagagcgtaa cggcctgggg aagggagtac   1560

ataacgatga ccatcaagga gatagaggaa aagtacggct ttaaggtaat ctacagcgac   1620

accgacggat tttttgccac aatacctgga gccgatgctg aaaccgtcaa aaagaaggct   1680

atggagttcc tcaagtatat caacgccaaa cttccgggcg cgcttgagct cgagtacgag   1740

ggcttctaca aacgcggctt cttcgtcacg aagaagaagt atgcggtgat agacgaggaa   1800

ggcaagataa caacgcgcgg acttgagatt gtgaggcgtg actggagcga gatagcgaaa   1860

gagacgcagg cgagggttct tgaagctttg ctaaaggacg gtgacgtcga gaaggccgtg   1920

aggatagtca aagaagttac cgaaaagctg agcaagtacg aggttccgcc ggagaagctg   1980

gtgatccacg agcagataac gagggattta aaggactaca aggcaaccgg tccccacgtt   2040

gccgttgcca agaggttggc cgcgagagga gtcaaaatac gccctggaac ggtgataagc   2100

tacatcgtgc tcaagggctc tgggaggata ggcgacaggg cgataccgtt cgacgagttc   2160

gacccgacga agcacaagta cgacgccgag tactacattg agaaccaggt tctcccagcc   2220

gttgagagaa ttctgagagc cttcggttac cgcaaggaag acctgcgcta ccagaagacg   2280

agacaggttg gtttgagtgc ttggctgaag ccgaagggaa cttga                   2325
```

<210> SEQ ID NO 34
<211> LENGTH: 2325
<212> TYPE: DNA
<213> ORGANISM: Thermococcus kodakaraensis
<220> FEATURE:
<221> NAME/KEY: modified_base
<222> LOCATION: (277)..(279)
<223> OTHER INFORMATION: region may encompass GAA or GAG

<400> SEQUENCE: 34

-continued

```
atgatcctcg acactgacta cataaccgag gatggaaagc ctgtcataag aattttcaag      60
aaggaaaacg gcgagtttaa gattgagtac gaccggactt ttgaacccta cttctacgcc     120
ctcctgaagg acgattctgc cattgaggaa gtcaagaaga taaccgccga gaggcacggg     180
acggttgtaa cggttaagcg ggttgaaaag gttcagaaga agttcctcgg gagaccagtt     240
gaggtctgga aactctactt tactcatccg caggacnnnc cagcgataag ggacaagata     300
cgagagcatc cagcagttat tgacatctac gagtacgaca tacccttcgc caagcgctac     360
ctcatagaca agggattagt gccaatggaa ggcgacgagg agctgaaaat gctcgccttc     420
gacattgaaa ctctctacca tgagggcgag gagttcgccg aggggccaat ccttatgata     480
agctacgccg acgaggaagg ggccagggtg ataacttgga agaacgtgga tctcccctac     540
gttgacgtcg tctcgacgga gagggagatg ataaagcgct tcctccgtgt tgtgaaggag     600
aaagacccgg acgttctcat aacctacaac ggcgacaact tcgacttcgc ctatctgaaa     660
aagcgctgtg aaaagctcgg aataaacttc gccctcggaa gggatggaag cgagccgaag     720
attcagagga tgggcgacag gtttgccgtc gaagtgaagg gacggataca cttcgatctc     780
tatcctgtga taagacggac gataaacctg cccacataca cgcttgaggc cgtttatgaa     840
gccgtcttcg gtcagccgaa ggagaaggtt tacgctgagg aaataaccac agcctgggaa     900
accggcgaga accttgagag agtcgcccgc tactcgatgg aagatgcgaa ggtcacatac     960
gagcttggga aggagttcct tccgatggag gcccagcttt ctcgcttaat cggccagtcc    1020
ctctgggacg tctcccgctc cagcactggc aacctcgttg agtggttcct cctcaggaag    1080
gcctatgaga ggaatgagct ggccccgaac aagcccgatg aaaaggagct ggccagaaga    1140
cggcagagct atgaaggagg ctatgtaaaa gagcccgaga gagggttgtg ggagaacata    1200
gtgtacctag attttagatc cctgtacccc tcaatcatca tcacccacaa cgtctcgccg    1260
gatacgctca acagagaagg atgcaaggaa tatgacgttg ccccacaggt cggccaccgc    1320
ttctgcaagg acttcccagg atttatcccg agcctgcttg gagacctcct agaggagagg    1380
cagaagataa agaagaagat gaaggccacg attgacccga tcgagaggaa gctcctcgat    1440
tacaggcaga gggccatcaa gatcctggca aacagctact acggttacta cggctatgca    1500
agggcgcgct ggtactgcaa ggagtgtgca gagagcgtaa cggcctgggg aagggagtac    1560
ataacgatga ccatcaagga gatagaggaa aagtacggct ttaaggtaat ctacagcgac    1620
accgacggat tttttgccac aatacctgga gccgatgctg aaaccgtcaa aaagaaggct    1680
atggagttcc tcaagtatat caacgccaaa cttccgggcg cgcttgagct cgagtacgag    1740
ggcttctaca aacgcggctt cttcgtcacg aagaagaagt atgcggtgat agacgaggaa    1800
ggcaagataa caacgcgcgg acttgagatt gtgaggcgtg actggagcga gatagcgaaa    1860
gagacgcagg cgagggttct tgaagctttg ctaaaggacg gtgacgtcga gaaggccgtg    1920
aggatagtca aagaagttac cgaaaagctg agcaagtacg aggttccgcc ggagaagctg    1980
gtgatccacg agcagataac gagggattta aaggactaca aggcaaccgg tccccacgtt    2040
gccgttgcca agaggttggc cgcgagagga gtcaaaatac gccctggaac ggtgataagc    2100
tacatcgtgc tcaagggctc tgggaggata ggcgacaggg cgataccgtt cgacgagttc    2160
gacccgacga agcacaagta cgacgccgag tactacattg agaaccaggt tctcccagcc    2220
gttgagagaa ttctgagagc cttcggttac cgcaaggaag acctgcgcta ccagaagacg    2280
agacaggttg gtttgagtgc ttggctgaag ccgaaggaa cttga                     2325
```

<210> SEQ ID NO 35

<211> LENGTH: 2325
<212> TYPE: DNA
<213> ORGANISM: Thermococcus litoralis
<220> FEATURE:
<221> NAME/KEY: modified_base
<222> LOCATION: (277)..(279)
<223> OTHER INFORMATION: region may encompass AGA, AGG, CGA, CGC, CGG or CGT

<400> SEQUENCE: 35

```
atgatactgg acactgatta cataacaaaa gatggcaagc ctataatccg aatttttaag     60

aaagagaacg ggagtttaa aatagaactt gaccctcatt ttcagcccta tatatatgct    120

cttctcaaag atgactccgc tattgaggag ataaaggcaa taaagggcga gagacatgga    180

aaaactgtga gagtgctcga tgcagtgaaa gtcaggaaaa aatttttggg aagggaagtt    240

gaagtctgga agctcatttt cgagcatccc caagacnnnc cagctatgcg gggcaaaata    300

agggaacatc cagctgtggt tgacatttac gaatatgaca taccctttgc caagcgttat    360

ctcatagaca agggcttgat tcccatggag ggagacgagg agcttaagct ccttgccttt    420

gatattgaaa cgttttatca tgagggagat gaatttggaa agggcgagat aataatgatt    480

agttatgccg atgaagaaga ggccagagta atcacatgga aaaatatcga tttgccgtat    540

gtcgatgttg tgtccaatga aagagaaatg ataaagcgtt ttgttcaagt tgttaaagaa    600

aaagaccccg atgtgataat aacttacaat ggggacaatt ttgatttgcc gtatctcata    660

aaacgggcag aaaagctggg agttcggctt gtcttaggaa gggacaaaga acatcccgaa    720

cccaagattc agaggatggg tgatagtttt gctgtggaaa tcaagggtag aatccacttt    780

gatcttttcc cagttgtgcg aaggacgata aacctcccaa cgtatacgct tgaggcagtt    840

tatgaagcag ttttaggaaa aaccaaaagc aaattaggag cagaggaaat tgccgctata    900

tgggaaacag aagaaagcat gaaaaaacta gcccagtact caatggaaga tgctagggca    960

acgtatgagc tcgggaagga attcttcccc atggaagctg agctggcaaa gctgataggt   1020

caaagtgtat gggacgtctc gagatcaagc accggcaacc tcgtggagtg gtatctttta   1080

agggtggcat acgcgaggaa tgaacttgca ccgaacaaac ctgatgagga agagtataaa   1140

cggcgcttaa gaacaactta cctgggagga tatgtaaaag agccagaaaa aggtttgtgg   1200

gaaaatatca tttatttgga tttccgcagt ctgtaccctt caataatagt tactcacaac   1260

gtatccccag ataccettga aaaagagggc tgtaagaatt acgatgttgc tccgatagta   1320

ggatataggt tctgcaagga ctttccgggc tttattccct ccatactcgg ggacttaatt   1380

gcaatgaggc aagatataaa gaagaaaatg aaatccacaa ttgacccgat cgaaaagaaa   1440

atgctcgatt ataggcaaag ggctattaaa ttgcttgcaa acagctatta cggctatatg   1500

gggtatccta aggcaagatg gtactcgaag gaatgtgctg aaagcgttac cgcatggggg   1560

agacactaca tagagatgac gataagagaa atagaggaaa agttcggctt taaggttctt   1620

tatgcggaca ctgacggctt ttatgccaca atacccgggg aaaagcctga actcattaaa   1680

aagaaagcca aggaattcct aaactacata aactccaaac ttccaggtct gcttgagctt   1740

gagtatgagg gcttttactt gagaggattc tttgttacaa aaaagcgcta tgcagtcata   1800

gatgaagagg gcaggataac aacaaggggc ttggaagtag taaggagaga ttggagtgag   1860

atagctaagg agactcaggc aaaggtttta gaggctatac ttaaagaggg aagtgttgaa   1920

aaagctgtag aagttgttag agatgttgta gagaaaatag caaaatacag ggttccactt   1980

gaaaagcttg ttatccatga gcagattacc agggatttaa aggactacaa agccattggc   2040

cctcatgtcg cgatagcaaa aagacttgcc gcaagaggga taaaagtgaa accgggcaca   2100
```

```
ataataagct atatcgttct caaagggagc ggaaagataa gcgatagggt aattttactt   2160

acagaatacg atcctagaaa acacaagtac gatccggact actacataga aaaccaagtt   2220

ttgccggcag tacttaggat actcgaagcg tttggataca gaaaggagga tttaaggtat   2280

caaagctcaa aacaaaccgg cttagatgca tggctcaaga ggtag                   2325
```

<210> SEQ ID NO 36
<211> LENGTH: 2325
<212> TYPE: DNA
<213> ORGANISM: Thermococcus litoralis
<220> FEATURE:
<221> NAME/KEY: modified_base
<222> LOCATION: (277)..(279)
<223> OTHER INFORMATION: region may encompass GAA or GAG

<400> SEQUENCE: 36

```
atgatactgg acactgatta cataacaaaa gatggcaagc ctataatccg aatttttaag     60

aaagagaacg ggagtttaa aatagaactt gaccctcatt ttcagcccta tatatatgct    120

cttctcaaag atgactccgc tattgaggag ataaaggcaa taaagggcga gagacatgga    180

aaaactgtga gagtgctcga tgcagtgaaa gtcaggaaaa aatttttggg aagggaagtt    240

gaagtctgga agctcatttt cgagcatccc caagacnnnc cagctatgcg gggcaaaata    300

agggaacatc cagctgtggt tgacatttac gaatatgaca taccctttgc caagcgttat    360

ctcatagaca agggcttgat tcccatggag ggagacgagg agcttaagct ccttgccttt    420

gatattgaaa cgttttatca tgagggagat gaatttggaa agggcgagat aataatgatt    480

agttatgccg atgaagaaga ggccagagta atcacatgga aaaatatcga tttgccgtat    540

gtcgatgttg tgtccaatga aagagaaatg ataaagcgtt ttgttcaagt tgttaaagaa    600

aaagaccccg atgtgataat aacttacaat ggggacaatt ttgatttgcc gtatctcata    660

aaacgggcag aaaagctggg agttcggctt gtcttaggaa gggacaaaga acatcccgaa    720

cccaagattc agaggatggg tgatagtttt gctgtggaaa tcaagggtag aatccacttt    780

gatcttttcc cagttgtgcg aaggacgata aacctcccaa cgtatacgct tgaggcagtt    840

tatgaagcag ttttaggaaa aaccaaaagc aaattaggag cagaggaaat tgccgctata    900

tgggaaacag aagaaagcat gaaaaaacta gcccagtact caatggaaga tgctagggca    960

acgtatgagc tcgggaagga attcttcccc atggaagctg agctggcaaa gctgataggt   1020

caaagtgtat gggacgtctc gagatcaagc accggcaacc tcgtggagtg gtatctttta   1080

agggtggcat acgcgaggaa tgaacttgca ccgaacaaac ctgatgagga agagtataaa   1140

cggcgcttaa gaacaactta cctgggagga tatgtaaaag agccagaaaa aggtttgtgg   1200

gaaaatatca tttatttgga tttccgcagt ctgtaccctt caataatagt tactcacaac   1260

gtatccccag ataccttga aaaagagggc tgtaagaatt acgatgttgc tccgatagta   1320

ggatataggt tctgcaagga ctttccgggc tttattccct ccatactcgg ggacttaatt   1380

gcaatgaggc aagatataaa gaagaaaatg aaatccacaa ttgacccgat cgaaaagaaa   1440

atgctcgatt ataggcaaag ggctattaaa ttgcttgcaa acagctatta cggctatatg   1500

ggtatcccta aggcaagatg gtactcgaag gaatgtgctg aaagcgttac cgcatggggg   1560

agacactaca tagagatgac gataagagaa atagaggaaa agttcggctt taaggttctt   1620

tatgcggaca ctgacggctt ttatgccaca atacccgggg aaaagcctga actcattaaa   1680

aagaaagcca aggaattcct aaactacata aactccaaac ttccaggtct gcttgagctt   1740

gagtatgagg gcttttactt gagaggattc tttgttacaa aaaagcgcta tgcagtcata   1800
```

gatgaagagg gcaggataac aacaaggggc ttggaagtag taaggagaga ttggagtgag 1860
atagctaagg agactcaggc aaaggtttta gaggctatac ttaaagaggg aagtgttgaa 1920
aaagctgtag aagttgttag agatgttgta gagaaaatag caaaatacag ggttccactt 1980
gaaaagcttg ttatccatga gcagattacc agggatttaa aggactacaa agccattggc 2040
cctcatgtcg cgatagcaaa aagacttgcc gcaagaggga taaaagtgaa accgggcaca 2100
ataataagct atatcgttct caaagggagc ggaaagataa gcgatagggt aattttactt 2160
acagaatacg atcctagaaa acacaagtac gatccggact actacataga aaaccaagtt 2220
ttgccggcag tacttaggat actcgaagcg tttggataca gaaaggagga tttaaggtat 2280
caaagctcaa aacaaaccgg cttagatgca tggctcaaga ggtag 2325

<210> SEQ ID NO 37
<211> LENGTH: 2328
<212> TYPE: DNA
<213> ORGANISM: Pyrococcus GB-D
<220> FEATURE:
<221> NAME/KEY: modified_base
<222> LOCATION: (277)..(279)
<223> OTHER INFORMATION: region may encompass AGA, AGG, CGA, CGC, CGG or CGT

<400> SEQUENCE: 37
atgatacttg acgctgacta catcaccgag gatgggaagc cgattataag gattttcaag 60
aaagaaaacg gcgagtttaa ggttgagtac gacagaaact ttagacctta catttacgct 120
ctcctcaaag atgactcgca gattgatgag gttaggaaga taaccgccga gaggcatggg 180
aagatagtga gaattataga tgccgaaaag gtaaggaaga agttcctggg gaggccgatt 240
gaggtatgga ggctgtactt tgaacaccct caggacnnnc ccgcaataag ggataagata 300
agagagcatt ccgcagttat tgacatcttt gagtacgaca ttccgttcgc gaagaggtac 360
ctaatagaca aaggcctaat tccaatggaa ggcgatgaag agctcaagtt gctcgcattt 420
gacatagaaa ccctctatca cgaaggggag gagttcgcga aggggcccat tataatgata 480
agctatgctg atgaggaaga agccaaagtc ataacgtgga aaaagatcga tctcccgtac 540
gtcgaggtag tttccagcga gagggagatg ataaagcggt tcctcaaggt gataagggag 600
aaagatcccg atgttataat tacctacaac ggcgattctt tcgaccttcc ctatctagtt 660
aagagggccg aaaagctcgg gataaagcta cccctgggaa gggacggtag tgagccaaag 720
atgcagaggc ttggggatat gacagcggtg gagataaagg gaaggataca ctttgacctc 780
taccacgtga ttaggagaac gataaacctc ccaacataca ccctcgaggc agtttatgag 840
gcaatcttcg gaaagccaaa ggagaaagtt tacgctcacg agatagctga ggcctgggag 900
actggaaagg gactggagag agttgcaaag tattcaatgg aggatgcaaa ggtaacgtac 960
gagctcggta gggagttctt cccaatggag gcccagcttt caaggttagt cggccagccc 1020
ctgtgggatg tttctaggtc ttcaactggc aacttggtgg agtggtacct cctcaggaag 1080
gcctacgaga ggaatgaatt ggctccaaac aagccggatg agagggagta cgagagaagg 1140
ctaagggaga gctacgctgg gggatacgtt aaggagccgg agaaagggct ctgggagggg 1200
ttagtttccc tagatttcag gagcctgtac ccctcgataa taatcaccca taacgtctca 1260
ccggatacgc tgaacaggga agggtgtagg gaatacgatg tcgccccaga ggttgggcac 1320
aagttctgca aggacttccc ggggtttatc cccagcctgc tcaagaggtt attggatgaa 1380
aggcaagaaa taaaaaggaa gatgaaagct tctaaagacc caatcgagaa gaagatgctt 1440

```
gattacaggc aacgggcaat caaaatcctg gcaaacagct attatgggta ttatgggtac   1500

gcaaaagccc gttggtactg taaggagtgc gcagagagcg ttacggcctg gggagggaa   1560

tatatagagt tcgtaaggaa ggaactggag gaaaagttcg ggttcaaagt cttatacata   1620

gacacagatg gactctacgc cacaattcct ggggcaaaac ccgaggagat aaagaagaaa   1680

gccctagagt tcgtagatta tataaacgcc aagctcccag ggctgttgga gcttgagtac   1740

gagggcttct acgtgagagg gttcttcgtg acgaagaaga agtatgcgtt gatagatgag   1800

gaagggaaga taatcactag ggggcttgaa atagtcagga gggactggag cgaaatagcc   1860

aaagaaaccc aagcaaaagt cctagaggct atcctaaagc atggcaacgt tgaggaggca   1920

gtaaagatag ttaaggaggt aactgaaaag ctgagcaagt acgaaatacc tccagaaaag   1980

ctagttattt acgagcagat cacgaggccc cttcacgagt acaaggctat aggtccgcac   2040

gttgccgtgg caaaaaggtt agccgctaga ggagtaaagg tgaggcctgg catggtgata   2100

gggtacatag tgctgagggg agacgggcca ataagcaaga gggctatcct tgcagaggag   2160

ttcgatctca ggaagcataa gtatgacgct gagtattaca tagaaaatca ggttttacct   2220

gccgttctta gaatattaga ggcctttggg tacaggaaag aagacctcag gtggcagaag   2280

actaaacaga caggtcttac ggcatggctt aacatcaaga agaagtaa                2328
```

```
<210> SEQ ID NO 38
<211> LENGTH: 2328
<212> TYPE: DNA
<213> ORGANISM: Pyrococcus GB-D
<220> FEATURE:
<221> NAME/KEY: modified_base
<222> LOCATION: (277)..(279)
<223> OTHER INFORMATION: region may encompass GAA or GAG

<400> SEQUENCE: 38
```

```
atgatacttg acgctgacta catcaccgag gatgggaagc cgattataag gattttcaag     60

aaagaaaacg gcgagtttaa ggttgagtac gacagaaact ttagacctta catttacgct    120

ctcctcaaag atgactcgca gattgatgag gttaggaaga taaccgccga gaggcatggg    180

aagatagtga gaattataga tgccgaaaag gtaaggaaga agttcctggg gaggccgatt    240

gaggtatgga ggctgtactt tgaacaccct caggacnnnc ccgcaataag ggataagata    300

agagagcatt ccgcagttat tgacatcttt gagtacgaca ttccgttcgc gaagaggtac    360

ctaatagaca aaggcctaat tccaatggaa ggcgatgaag agctcaagtt gctcgcattt    420

gacatagaaa ccctctatca cgaaggggag gagttcgcga aggggcccat tataatgata    480

agctatgctg atgaggaaga agccaaagtc ataacgtgga aaaagatcga tctcccgtac    540

gtcgaggtag tttccagcga gagggagatg ataaagcggt tcctcaaggt gataagggag    600

aaagatcccg atgttataat tacctacaac ggcgattctt tcgaccttcc ctatctagtt    660

aagagggccg aaaagctcgg gataaagcta cccctgggaa gggacggtag tgagccaaag    720

atgcagaggc ttggggatat gacagcggtg gagataaagg gaaggataca ctttgacctc    780

taccacgtga ttaggagaac gataaacctc ccaacataca ccctcgaggc agtttatgag    840

gcaatcttcg gaaagccaaa ggagaaagtt tacgctcacg agatagctga ggcctgggag    900

actggaaagg gactggagag agttgcaaag tattcaatgg aggatgcaaa ggtaacgtac    960

gagctcggta gggagttctt cccaatggag gcccagcttt caaggttagt cggccagccc   1020

ctgtgggatg tttctaggtc ttcaactggc aacttggtgg agtggtacct cctcaggaag   1080

gcctacgaga ggaatgaatt ggctccaaac aagccggatg agagggagta cgagagaagg   1140
```

-continued

```
ctaagggaga gctacgctgg gggatacgtt aaggagccgg agaaagggct ctgggagggg   1200

ttagtttccc tagatttcag gagcctgtac ccctcgataa taatcaccca taacgtctca   1260

ccggatacgc tgaacaggga agggtgtagg gaatacgatg tcgccccaga ggttgggcac   1320

aagttctgca aggacttccc ggggtttatc cccagcctgc tcaagaggtt attggatgaa   1380

aggcaagaaa taaaaaggaa gatgaaagct tctaaagacc caatcgagaa gaagatgctt   1440

gattacaggc aacgggcaat caaaatcctg gcaaacagct attatgggta ttatgggtac   1500

gcaaaagccc gttggtactg taaggagtgc gcagagagcg ttacggcctg gggagggaa   1560

tatatagagt tcgtaaggaa ggaactggag gaaaagttcg ggttcaaagt cttatacata   1620

gacacagatg gactctacgc cacaattcct ggggcaaaac ccgaggagat aaagaagaaa   1680

gccctagagt tcgtagatta tataaacgcc aagctcccag ggctgttgga gcttgagtac   1740

gagggcttct acgtgagagg gttcttcgtg acgaagaaga agtatgcgtt gatagatgag   1800

gaagggaaga taatcactag ggggcttgaa atagtcagga gggactggag cgaaatagcc   1860

aaagaaaccc aagcaaaagt cctagaggct atcctaaagc atggcaacgt tgaggaggca   1920

gtaaagatag ttaaggaggt aactgaaaag ctgagcaagt acgaaatacc tccagaaaag   1980

ctagttattt acgagcagat cacgaggccc cttcacgagt acaaggctat aggtccgcac   2040

gttgccgtgg caaaaaggtt agccgctaga ggagtaaagg tgaggcctgg catggtgata   2100

gggtacatag tgctgagggg agacgggcca ataagcaaga gggctatcct tgcagaggag   2160

ttcgatctca ggaagcataa gtatgacgct gagtattaca tagaaaatca ggttttacct   2220

gccgttctta gaatattaga ggcctttggg tacaggaaag aagacctcag gtggcagaag   2280

actaaacaga caggtcttac ggcatggctt aacatcaaga agaagtaa               2328
```

```
<210> SEQ ID NO 39
<211> LENGTH: 2331
<212> TYPE: DNA
<213> ORGANISM: Thermococcus sp.
<220> FEATURE:
<221> NAME/KEY: modified_base
<222> LOCATION: (277)..(279)
<223> OTHER INFORMATION: region may encompass AGA, AGG, CGA, CGC, CGG or
      CGT

<400> SEQUENCE: 39

atgatccttg acgttgatta catcaccgag aatggaaagc ccgtcatcag ggtcttcaag     60

aaggagaacg gcgagttcag gattgaatac gaccgcgagt tcgagcccta cttctacgcg    120

ctcctcaggg acgactctgc catcgaagaa atcaaaaaga taaccgcgga gaggcacggc    180

agggtcgtta aggttaagcg cgcggagaag gtgaagaaaa agttcctcgg caggtctgtg    240

gaggtctggg tcctctactt cacgcacccg caggacnnnc cggcaatccg cgacaaaata    300

aggaagcacc ccgcggtcat cgacatctac gagtacgaca taccettcgc caagcgctac    360

ctcatagaca agggcctaat cccgatggaa ggtgaggaag agcttaaact catgtccttc    420

gacatcgaga cgctctacca cgagggagaa gagtttggaa ccgggccgat tctgatgata    480

agctacgccg atgaaagcga ggcgcgcgtg ataacctgga agaagatcga ccttccttac    540

gttgaggttg tctccaccga gaaggagatg attaagcgct tcttgagggt cgttaaggag    600

aaggacccgg acgtgctgat aacatacaac ggcgacaact tcgacttcgc ctacctgaaa    660

aagcgctgtg agaagcttgg cgtgagcttt accctcggga gggacgggag cgagccgaag    720

atacagcgca tgggggacag gtttgcggtc gaggtgaagg gcagggtaca cttcgacctt    780

tatccagtca taaggcgcac cataaacctc ccgacctaca cccttgaggc tgtatacgag    840
```

-continued

```
gcggttttcg gcaagcccaa ggagaaggtc tacgccgagg agatagccac cgcctgggag     900

accggcgagg ggcttgagag ggtcgcgcgc tactcgatgg aggacgcgag ggttacctac     960

gagcttggca gggagttctt cccgatggag gcccagcttt ccaggctcat cggccaaggc    1020

ctctgggacg tttcccgctc cagcaccggc aacctcgtcg agtggttcct cctaaggaag    1080

gcctacgaga ggaacgaact cgctcccaac aagcccgacg agagggagct ggcgaggaga    1140

aggggggggct acgccggtgg ctacgtcaag gagccggagc ggggactgtg ggacaatatc   1200

gtgtatctag actttcgtag tctctaccct tcaatcataa tcacccacaa cgtctcgcca    1260

gatacgctca accgcgaggg gtgtaggagc tacgacgttg cccccgaggt cggtcacaag    1320

ttctgcaagg acttccccgg cttcattccg agcctgctcg gaaacctgct ggaggaaagg    1380

cagaagataa agaggaagat gaaggcaact ctcgacccgc tggagaagaa tctcctcgat    1440

tacaggcaac gcgccatcaa gattctcgcc aacagctact acggctacta cggctatgcc    1500

agggcaagat ggtactgcag ggagtgcgcc gagagcgtta cggcatgggg aagggagtac    1560

atcgaaatgg tcatcagaga gcttgaggaa aagttcggtt ttaaagtcct ctatgcagac    1620

acagacggtc tccatgccac cattcctgga gcggacgctg aaacagtcaa gaaaaaggca    1680

atggagttct taaactatat caatcccaaa ctgcccggcc ttctcgaact cgaatacgag    1740

ggcttctacg tcaggggctt cttcgtcacg aagaaaaagt acgcggtcat cgacgaggag    1800

ggcaagataa ccacgcgcgg gcttgagata gtcaggcgcg actggagcga gatagcgaag    1860

gagacgcagg cgagggtttt ggaggcgata ctcaggcacg gtgacgttga agaggccgtc    1920

agaattgtca gggaagtcac cgaaaagctg agcaagtacg aggttccgcc ggagaagctg    1980

gttatccacg agcagataac gcgcgagctc aaggactaca aggccaccgg cccgcacgta    2040

gccatagcga agcgtttggc cgccagaggt gttaaaatcc ggcccggaac tgtgataagc    2100

tacatcgttc tgaagggctc cggaaggata ggcgacaggg cgattccctt cgacgagttc    2160

gacccgacga agcacaagta cgatgcggac tactacatcg agaaccaggt tctgccggca    2220

gttgagagaa tcctcagggc cttcggctac cgcaaggaag acctgcgcta ccagaagacg    2280

aggcaggtcg ggcttggcgc gtggctgaag ccgaagggga agaagaagtg a             2331
```

<210> SEQ ID NO 40
<211> LENGTH: 2331
<212> TYPE: DNA
<213> ORGANISM: Thermococcus sp.
<220> FEATURE:
<221> NAME/KEY: modified_base
<222> LOCATION: (277)..(279)
<223> OTHER INFORMATION: region may encompass GAA or GAG

<400> SEQUENCE: 40

```
atgatccttg acgttgatta catcaccgag aatggaaagc ccgtcatcag ggtcttcaag      60

aaggagaacg gcgagttcag gattgaatac gaccgcgagt tcgagcccta cttctacgcg     120

ctcctcaggg acgactctgc catcgaagaa atcaaaaaga taaccgcgga gaggcacggc     180

agggtcgtta aggttaagcg cgcggagaag gtgaagaaaa agttcctcgg caggtctgtg     240

gaggtctggg tcctctactt cacgcacccg caggacnnnc cggcaatccg cgacaaaata     300

aggaagcacc ccgcggtcat cgacatctac gagtacgaca taccccttcgc caagcgctac    360

ctcatagaca agggcctaat cccgatggaa ggtgaggaag agcttaaact catgtccttc     420

gacatcgaga cgctctacca cgagggagaa gagtttggaa ccgggccgat tctgatgata     480

agctacgccg atgaaagcga ggcgcgcgtg ataacctgga agaagatcga ccttccttac     540
```

-continued

```
gttgaggttg tctccaccga gaaggagatg attaagcgct tcttgagggt cgttaaggag    600

aaggacccgg acgtgctgat aacatacaac ggcgacaact tcgacttcgc ctacctgaaa    660

aagcgctgtg agaagcttgg cgtgagcttt accctcggga gggacgggag cgagccgaag    720

atacagcgca tgggggacag gtttgcggtc gaggtgaagg gcagggtaca cttcgacctt    780

tatccagtca taaggcgcac cataaacctc ccgacctaca cccttgaggc tgtatacgag    840

gcggttttcg gcaagcccaa ggagaaggtc tacgccgagg agatagccac cgcctgggag    900

accggcgagg ggcttgagag ggtcgcgcgc tactcgatgg aggacgcgag ggttacctac    960

gagcttggca gggagttctt cccgatggag gcccagcttt ccaggctcat cggccaaggc   1020

ctctgggacg tttcccgctc cagcaccggc aacctcgtcg agtggttcct cctaaggaag   1080

gcctacgaga ggaacgaact cgctcccaac aagcccgacg agagggagct ggcgaggaga   1140

aggggggcgt acgccggtgg ctacgtcaag gagccggagc ggggactgtg ggacaatatc   1200

gtgtatctag actttcgtag tctctaccct tcaatcataa tcacccacaa cgtctcgcca   1260

gatacgctca accgcgaggg gtgtaggagc tacgacgttg cccccgaggt cggtcacaag   1320

ttctgcaagg acttccccgg cttcattccg agcctgctcg gaaacctgct ggaggaaagg   1380

cagaagataa agaggaagat gaaggcaact ctcgacccgc tggagaagaa tctcctcgat   1440

tacaggcaac gcgccatcaa gattctcgcc aacagctact acggctacta cggctatgcc   1500

agggcaagat ggtactgcag ggagtgcgcc gagagcgtta cggcatgggg aagggagtac   1560

atcgaaatgg tcatcagaga gcttgaggaa aagttcggtt ttaaagtcct ctatgcagac   1620

acagacggtc tccatgccac cattcctgga gcggacgctg aaacagtcaa gaaaaaggca   1680

atggagttct taaactatat caatcccaaa ctgcccggcc ttctcgaact cgaatacgag   1740

ggcttctacg tcaggggctt cttcgtcacg aagaaaaagt acgcggtcat cgacgaggag   1800

ggcaagataa ccacgcgcgg gcttgagata gtcaggcgcg actggagcga gatagcgaag   1860

gagacgcagg cgagggtttt ggaggcgata ctcaggcacg gtgacgttga agaggccgtc   1920

agaattgtca gggaagtcac cgaaaagctg agcaagtacg aggttccgcc ggagaagctg   1980

gttatccacg agcagataac gcgcgagctc aaggactaca aggccaccgg cccgcacgta   2040

gccatagcga agcgtttggc cgccagaggt gttaaaatcc ggcccggaac tgtgataagc   2100

tacatcgttc tgaagggctc cggaaggata ggcgacaggg cgattccctt cgacgagttc   2160

gacccgacga agcacaagta cgatgcggac tactacatcg agaaccaggt tctgccggca   2220

gttgagagaa tcctcagggc cttcggctac cgcaaggaag acctgcgcta ccagaagacg   2280

aggcaggtcg ggcttggcgc gtggctgaag ccgaagggga agaagaagtg a            2331
```

```
<210> SEQ ID NO 41
<211> LENGTH: 775
<212> TYPE: PRT
<213> ORGANISM: Pyrococcus furiosus

<400> SEQUENCE: 41

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60
```

```
Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Arg Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Glu Tyr Gln Arg Arg Leu Arg Glu Ser
    370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
```

485 490 495

Tyr Tyr Gly Tyr Ala Lys Ala Arg Trp Tyr Cys Lys Glu Cys Ala Glu
500 505 510

Ser Val Thr Ala Trp Gly Arg Lys Tyr Ile Glu Leu Val Trp Lys Glu
515 520 525

Leu Glu Glu Lys Phe Gly Phe Lys Val Leu Tyr Ile Asp Thr Asp Gly
530 535 540

Leu Tyr Ala Thr Ile Pro Gly Gly Glu Ser Glu Glu Ile Lys Lys Lys
545 550 555 560

Ala Leu Glu Phe Val Lys Tyr Ile Asn Ser Lys Leu Pro Gly Leu Leu
565 570 575

Glu Leu Glu Tyr Glu Gly Phe Tyr Lys Arg Gly Phe Phe Val Thr Lys
580 585 590

Lys Arg Tyr Ala Val Ile Asp Glu Glu Gly Lys Val Ile Thr Arg Gly
595 600 605

Leu Glu Ile Val Arg Arg Asp Trp Ser Glu Ile Ala Lys Glu Thr Gln
610 615 620

Ala Arg Val Leu Glu Thr Ile Leu Lys His Gly Asp Val Glu Glu Ala
625 630 635 640

Val Arg Ile Val Lys Glu Val Ile Gln Lys Leu Ala Asn Tyr Glu Ile
645 650 655

Pro Pro Glu Lys Leu Ala Ile Tyr Glu Gln Ile Thr Arg Pro Leu His
660 665 670

Glu Tyr Lys Ala Ile Gly Pro His Val Ala Val Ala Lys Lys Leu Ala
675 680 685

Ala Lys Gly Val Lys Ile Lys Pro Gly Met Val Ile Gly Tyr Ile Val
690 695 700

Leu Arg Gly Asp Gly Pro Ile Ser Asn Arg Ala Ile Leu Ala Glu Glu
705 710 715 720

Tyr Asp Pro Lys Lys His Lys Tyr Asp Ala Glu Tyr Tyr Ile Glu Asn
725 730 735

Gln Val Leu Pro Ala Val Leu Arg Ile Leu Glu Gly Phe Gly Tyr Arg
740 745 750

Lys Glu Asp Leu Arg Tyr Gln Lys Thr Arg Gln Val Gly Leu Thr Ser
755 760 765

Trp Leu Asn Ile Lys Lys Ser
770 775

<210> SEQ ID NO 42
<211> LENGTH: 775
<212> TYPE: PRT
<213> ORGANISM: Pyrococcus furiosus

<400> SEQUENCE: 42

Met Ile Leu Asp Val Asp Tyr Ile Thr Glu Glu Gly Lys Pro Val Ile
1 5 10 15

Arg Leu Phe Lys Lys Glu Asn Gly Lys Phe Lys Ile Glu His Asp Arg
20 25 30

Thr Phe Arg Pro Tyr Ile Tyr Ala Leu Leu Arg Asp Asp Ser Lys Ile
35 40 45

Glu Glu Val Lys Lys Ile Thr Gly Glu Arg His Gly Lys Ile Val Arg
50 55 60

Ile Val Asp Val Glu Lys Val Glu Lys Lys Phe Leu Gly Lys Pro Ile
65 70 75 80

Thr Val Trp Lys Leu Tyr Leu Glu His Pro Gln Asp Glu Pro Thr Ile

```
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Glu Tyr Gln Arg Arg Leu Arg Glu Ser
    370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510
```

```
Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser
    770                 775


<210> SEQ ID NO 43
<211> LENGTH: 775
<212> TYPE: PRT
<213> ORGANISM: Pyrococcus furiosus

<400> SEQUENCE: 43

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Arg Pro Thr Ile
                85                  90                  95

Arg Glu Lys Val Arg Glu His Pro Ala Val Val Asp Ile Phe Glu Tyr
            100                 105                 110
```

```
Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Glu Tyr Gln Arg Arg Leu Arg Glu Ser
    370                 375                 380

Tyr Thr Pro Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
    530                 535                 540
```

Leu Tyr Ala Thr Ile Pro Gly Gly Glu Ser Glu Glu Ile Lys Lys Lys
545 550 555 560

Ala Leu Glu Phe Val Lys Tyr Ile Asn Ser Lys Leu Pro Gly Leu Leu
565 570 575

Glu Leu Glu Tyr Glu Gly Phe Tyr Lys Arg Gly Phe Phe Val Thr Lys
580 585 590

Lys Arg Tyr Ala Val Ile Asp Glu Glu Gly Lys Val Ile Thr Arg Gly
595 600 605

Leu Glu Ile Val Arg Arg Asp Trp Ser Glu Ile Ala Lys Glu Thr Gln
610 615 620

Ala Arg Val Leu Glu Thr Ile Leu Lys His Gly Asp Val Glu Glu Ala
625 630 635 640

Val Arg Ile Val Lys Glu Val Ile Gln Lys Leu Ala Asn Tyr Glu Ile
645 650 655

Pro Pro Glu Lys Leu Ala Ile Tyr Glu Gln Ile Thr Arg Pro Leu His
660 665 670

Glu Tyr Lys Ala Ile Gly Pro His Val Ala Val Ala Lys Lys Leu Ala
675 680 685

Ala Lys Gly Val Lys Ile Lys Pro Gly Met Val Ile Gly Tyr Ile Val
690 695 700

Leu Arg Gly Asp Gly Pro Ile Ser Asn Arg Ala Ile Leu Ala Glu Glu
705 710 715 720

Tyr Asp Pro Lys Lys His Lys Tyr Asp Ala Glu Tyr Tyr Ile Glu Asn
725 730 735

Gln Val Leu Pro Ala Val Leu Arg Ile Leu Glu Gly Phe Gly Tyr Arg
740 745 750

Lys Glu Asp Leu Arg Tyr Gln Lys Thr Arg Gln Val Gly Leu Thr Ser
755 760 765

Trp Leu Asn Ile Lys Lys Ser
770 775

<210> SEQ ID NO 44
<211> LENGTH: 775
<212> TYPE: PRT
<213> ORGANISM: Pyrococcus furiosus

<400> SEQUENCE: 44

Met Ile Leu Asp Val Asp Tyr Ile Thr Glu Glu Gly Lys Pro Val Ile
1 5 10 15

Arg Leu Phe Lys Lys Glu Asn Gly Lys Phe Lys Ile Glu His Asp Arg
20 25 30

Thr Phe Arg Pro Tyr Ile Tyr Ala Leu Leu Arg Asp Asp Ser Lys Ile
35 40 45

Glu Glu Val Lys Lys Ile Thr Gly Glu Arg His Gly Lys Ile Val Arg
50 55 60

Ile Val Asp Val Glu Lys Val Glu Lys Lys Phe Leu Gly Lys Pro Ile
65 70 75 80

Thr Val Trp Lys Leu Tyr Leu Glu His Pro Gln Asp Arg Pro Thr Ile
85 90 95

Arg Glu Lys Val Arg Glu His Pro Ala Val Val Asp Ile Phe Glu Tyr
100 105 110

Asp Ile Pro Phe Ala Lys Arg Tyr Leu Ile Asp Lys Gly Leu Ile Pro
115 120 125

Met Glu Gly Glu Glu Glu Leu Lys Ile Leu Ala Phe Ala Ile Ala Thr
130 135 140

```
Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Glu Tyr Gln Arg Arg Leu Arg Glu Ser
    370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
```

```
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser
    770                 775


<210> SEQ ID NO 45
<211> LENGTH: 775
<212> TYPE: PRT
<213> ORGANISM: Pyrococcus furiosus

<400> SEQUENCE: 45

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Glu Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
```

```
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Glu Tyr Gln Arg Arg Leu Arg Glu Ser
    370                 375                 380

Tyr Thr Pro Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590
```

```
Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser
    770                 775


<210> SEQ ID NO 46
<211> LENGTH: 775
<212> TYPE: PRT
<213> ORGANISM: Pyrococcus furiosus

<400> SEQUENCE: 46

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Arg Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Ala Ile Ala Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190
```

```
Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Glu Tyr Gln Arg Arg Leu Arg Glu Ser
    370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
    610                 615                 620
```

```
Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655

Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
                725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser
    770                 775


<210> SEQ ID NO 47
<211> LENGTH: 775
<212> TYPE: PRT
<213> ORGANISM: Thermococcus sp.

<400> SEQUENCE: 47

Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
            20                  25                  30

Asn Phe Arg Pro Tyr Ile Tyr Ala Leu Leu Lys Asp Asp Ser Gln Ile
        35                  40                  45

Asp Glu Val Arg Lys Ile Thr Ala Glu Arg His Gly Lys Ile Val Arg
    50                  55                  60

Ile Ile Asp Ala Glu Lys Val Arg Lys Lys Phe Leu Gly Arg Pro Ile
65                  70                  75                  80

Glu Val Trp Arg Leu Tyr Phe Glu His Pro Gln Asp Arg Pro Ala Ile
                85                  90                  95

Arg Asp Lys Ile Arg Glu His Ser Ala Val Ile Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Leu Tyr His Glu Gly Glu Glu Phe Ala Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190

Arg Phe Leu Lys Val Ile Arg Glu Lys Asp Pro Asp Val Ile Ile Thr
        195                 200                 205

Tyr Asn Gly Asp Ser Phe Asp Leu Pro Tyr Leu Val Lys Arg Ala Glu
    210                 215                 220
```

-continued

```
Lys Leu Gly Ile Lys Leu Pro Leu Gly Arg Asp Gly Ser Glu Pro Lys
225                 230                 235                 240

Met Gln Arg Leu Gly Asp Met Thr Ala Val Glu Ile Lys Gly Arg Ile
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala His Glu Ile Ala Glu Ala Trp Glu Thr Gly Lys Gly
    290                 295                 300

Leu Glu Arg Val Ala Lys Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Tyr Leu Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
    370                 375                 380

Tyr Ala Gly Gly Tyr Val Lys Glu Pro Glu Lys Gly Leu Trp Glu Gly
385                 390                 395                 400

Leu Val Ser Leu Asp Phe Arg Ser Leu Tyr Pro Ser Ile Ile Ile Thr
                405                 410                 415

His Asn Val Ser Pro Asp Thr Leu Asn Arg Glu Gly Cys Arg Glu Tyr
            420                 425                 430

Asp Val Ala Pro Glu Val Gly His Lys Phe Cys Lys Asp Phe Pro Gly
        435                 440                 445

Phe Ile Pro Ser Leu Leu Lys Arg Leu Leu Asp Glu Arg Gln Glu Ile
    450                 455                 460

Lys Arg Lys Met Lys Ala Ser Lys Asp Pro Ile Glu Lys Lys Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Arg Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Ala Lys Pro Glu Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Val Arg Gly Phe Phe Val Thr Lys
            580                 585                 590

Lys Lys Tyr Ala Leu Ile Asp Glu Glu Gly Lys Ile Ile Thr Arg Gly
        595                 600                 605

Leu Glu Ile Val Arg Arg Asp Trp Ser Glu Ile Ala Lys Glu Thr Gln
    610                 615                 620

Ala Lys Val Leu Glu Ala Ile Leu Lys His Gly Asn Val Glu Glu Ala
625                 630                 635                 640

Val Lys Ile Val Lys Glu Val Thr Glu Lys Leu Ser Lys Tyr Glu Ile
```

```
                645                 650                 655

Pro Pro Glu Lys Leu Val Ile Tyr Glu Gln Ile Thr Arg Pro Leu His
            660                 665                 670

Glu Tyr Lys Ala Ile Gly Pro His Val Ala Val Ala Lys Arg Leu Ala
        675                 680                 685

Ala Arg Gly Val Lys Val Arg Pro Gly Met Val Ile Gly Tyr Ile Val
    690                 695                 700

Leu Arg Gly Asp Gly Pro Ile Ser Lys Arg Ala Ile Leu Ala Glu Glu
705                 710                 715                 720

Phe Asp Leu Arg Lys His Lys Tyr Asp Ala Glu Tyr Tyr Ile Glu Asn
                725                 730                 735

Gln Val Leu Pro Ala Val Leu Arg Ile Leu Glu Ala Phe Gly Tyr Arg
            740                 745                 750

Lys Glu Asp Leu Arg Trp Gln Lys Thr Lys Gln Thr Gly Leu Thr Ala
        755                 760                 765

Trp Leu Asn Ile Lys Lys Lys
    770                 775


<210> SEQ ID NO 48
<211> LENGTH: 775
<212> TYPE: PRT
<213> ORGANISM: Thermococcus sp.

<400> SEQUENCE: 48

Met Ile Leu Asp Ala Asp Tyr Ile Thr Glu Asp Gly Lys Pro Ile Ile
1               5                   10                  15

Arg Ile Phe Lys Lys Glu Asn Gly Glu Phe Lys Val Glu Tyr Asp Arg
            20                  25                  30

Asn Phe Arg Pro Tyr Ile Tyr Ala Leu Leu Lys Asp Asp Ser Gln Ile
        35                  40                  45

Asp Glu Val Arg Lys Ile Thr Ala Glu Arg His Gly Lys Ile Val Arg
    50                  55                  60

Ile Ile Asp Ala Glu Lys Val Arg Lys Lys Phe Leu Gly Arg Pro Ile
65                  70                  75                  80

Glu Val Trp Arg Leu Tyr Phe Glu His Pro Gln Asp Glu Pro Ala Ile
                85                  90                  95

Arg Asp Lys Ile Arg Glu His Ser Ala Val Ile Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Leu Tyr His Glu Gly Glu Glu Phe Ala Lys Gly Pro Ile Ile Met Ile
145                 150                 155                 160

Ser Tyr Ala Asp Glu Glu Glu Ala Lys Val Ile Thr Trp Lys Lys Ile
                165                 170                 175

Asp Leu Pro Tyr Val Glu Val Val Ser Ser Glu Arg Glu Met Ile Lys
            180                 185                 190

Arg Phe Leu Lys Val Ile Arg Glu Lys Asp Pro Asp Val Ile Ile Thr
        195                 200                 205

Tyr Asn Gly Asp Ser Phe Asp Leu Pro Tyr Leu Val Lys Arg Ala Glu
    210                 215                 220

Lys Leu Gly Ile Lys Leu Pro Leu Gly Arg Asp Gly Ser Glu Pro Lys
225                 230                 235                 240

Met Gln Arg Leu Gly Asp Met Thr Ala Val Glu Ile Lys Gly Arg Ile
```

```
                245                 250                 255

His Phe Asp Leu Tyr His Val Ile Arg Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala His Glu Ile Ala Glu Ala Trp Glu Thr Gly Lys Gly
    290                 295                 300

Leu Glu Arg Val Ala Lys Tyr Ser Met Glu Asp Ala Lys Val Thr Tyr
305                 310                 315                 320

Glu Leu Gly Arg Glu Phe Phe Pro Met Glu Ala Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Tyr Leu Leu Arg Lys Ala Tyr Glu Arg Asn Glu Leu Ala
        355                 360                 365

Pro Asn Lys Pro Asp Glu Arg Glu Tyr Glu Arg Arg Leu Arg Glu Ser
    370                 375                 380

Tyr Ala Gly Gly Tyr Val Lys Glu Pro Glu Lys Gly Leu Trp Glu Gly
385                 390                 395                 400

Leu Val Ser Leu Asp Phe Arg Ser Leu Tyr Pro Ser Ile Ile Ile Thr
                405                 410                 415

His Asn Val Ser Pro Asp Thr Leu Asn Arg Glu Gly Cys Arg Glu Tyr
            420                 425                 430

Asp Val Ala Pro Glu Val Gly His Lys Phe Cys Lys Asp Phe Pro Gly
        435                 440                 445

Phe Ile Pro Ser Leu Leu Lys Arg Leu Leu Asp Glu Arg Gln Glu Ile
    450                 455                 460

Lys Arg Lys Met Lys Ala Ser Lys Asp Pro Ile Glu Lys Lys Met Leu
465                 470                 475                 480

Asp Tyr Arg Gln Arg Ala Ile Lys Ile Leu Ala Asn Ser Tyr Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Glu Tyr Ile Glu Phe Val Arg Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Ala Lys Pro Glu Glu Ile Lys Lys Lys
545                 550                 555                 560

Ala Leu Glu Phe Val Asp Tyr Ile Asn Ala Lys Leu Pro Gly Leu Leu
                565                 570                 575

Glu Leu Glu Tyr Glu Gly Phe Tyr Val Arg Gly Phe Phe Val Thr Lys
            580                 585                 590

Lys Lys Tyr Ala Leu Ile Asp Glu Glu Gly Lys Ile Ile Thr Arg Gly
        595                 600                 605

Leu Glu Ile Val Arg Arg Asp Trp Ser Glu Ile Ala Lys Glu Thr Gln
    610                 615                 620

Ala Lys Val Leu Glu Ala Ile Leu Lys His Gly Asn Val Glu Glu Ala
625                 630                 635                 640

Val Lys Ile Val Lys Glu Val Thr Glu Lys Leu Ser Lys Tyr Glu Ile
                645                 650                 655

Pro Pro Glu Lys Leu Val Ile Tyr Glu Gln Ile Thr Arg Pro Leu His
            660                 665                 670
```

```
Glu Tyr Lys Ala Ile Gly Pro His Val Ala Val Ala Lys Arg Leu Ala
        675                 680                 685

Ala Arg Gly Val Lys Val Arg Pro Gly Met Val Ile Gly Tyr Ile Val
    690                 695                 700

Leu Arg Gly Asp Gly Pro Ile Ser Lys Arg Ala Ile Leu Ala Glu Glu
705                 710                 715                 720

Phe Asp Leu Arg Lys His Lys Tyr Asp Ala Glu Tyr Tyr Ile Glu Asn
                725                 730                 735

Gln Val Leu Pro Ala Val Leu Arg Ile Leu Glu Ala Phe Gly Tyr Arg
            740                 745                 750

Lys Glu Asp Leu Arg Trp Gln Lys Thr Lys Gln Thr Gly Leu Thr Ala
        755                 760                 765

Trp Leu Asn Ile Lys Lys Lys
    770                 775


<210> SEQ ID NO 49
<211> LENGTH: 773
<212> TYPE: PRT
<213> ORGANISM: Thermococcus gorgonarius

<400> SEQUENCE: 49

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Lys Phe Leu Gly Arg Pro Ile
65                  70                  75                  80

Glu Val Trp Lys Leu Tyr Phe Thr His Pro Gln Asp Arg Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270
```

```
Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Arg Glu Ser Tyr
    370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Ile Asp Pro Ile Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile Tyr Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700
```

```
Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Thr
    770


<210> SEQ ID NO 50
<211> LENGTH: 773
<212> TYPE: PRT
<213> ORGANISM: Thermococcus gorgonarius

<400> SEQUENCE: 50

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Lys Phe Leu Gly Arg Pro Ile
65                  70                  75                  80

Glu Val Trp Lys Leu Tyr Phe Thr His Pro Gln Asp Glu Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300
```

```
Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Arg Glu Ser Tyr
    370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Ile Asp Pro Ile Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile Tyr Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
```

```
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Thr
    770


<210> SEQ ID NO 51
<211> LENGTH: 774
<212> TYPE: PRT
<213> ORGANISM: Thermococcus kodakaraensis

<400> SEQUENCE: 51

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Glu Val Lys Lys Ile Thr Ala Glu Arg His Gly Thr Val Val Thr
    50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Arg Pro Ala Ile
                85                  90                  95

Arg Asp Lys Ile Arg Glu His Gly Ala Val Ile Asp Ile Tyr Glu Tyr
            100                 105                 110

Asp Ile Pro Phe Ala Lys Arg Tyr Leu Ile Asp Lys Gly Leu Val Pro
        115                 120                 125

Met Glu Gly Asp Glu Glu Leu Lys Met Leu Ala Phe Asp Ile Gln Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
        275                 280                 285

Lys Val Tyr Ala Glu Glu Ile Thr Pro Ala Trp Glu Thr Gly Glu Asn
    290                 295                 300

Leu Glu Arg Val Ala Arg Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
```

-continued

```
            325                 330                 335

Ile Gly Gln Ser Leu Trp Asp Val Ser Arg Ser Ser Thr Gly Asn Leu
        340                 345                 350

Val Glu Trp Phe Leu Leu Arg Lys Ala Tyr Glu Arg Asn Glu Leu Ala
    355                 360                 365

Pro Asn Lys Pro Asp Glu Lys Glu Leu Ala Arg Arg Arg Gln Ser Tyr
    370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
            405                 410                 415

Asn Val Ser Pro Asp Thr Leu Asn Arg Glu Gly Cys Lys Glu Tyr Asp
        420                 425                 430

Val Ala Pro Gln Val Gly His Arg Phe Cys Lys Asp Phe Pro Gly Phe
    435                 440                 445

Ile Pro Ser Leu Leu Gly Asp Leu Leu Glu Glu Arg Gln Lys Ile Lys
    450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
            485                 490                 495

Tyr Gly Tyr Ala Arg Ala Arg Trp Tyr Cys Lys Glu Cys Ala Glu Ser
        500                 505                 510

Val Thr Ala Trp Gly Arg Glu Tyr Ile Thr Met Thr Ile Lys Glu Ile
    515                 520                 525

Glu Glu Lys Tyr Gly Phe Lys Val Ile Tyr Ser Asp Thr Asp Gly Phe
    530                 535                 540

Phe Ala Thr Ile Pro Gly Ala Asp Ala Glu Thr Val Lys Lys Lys Ala
545                 550                 555                 560

Met Glu Phe Leu Asn Tyr Ile Asn Ala Lys Leu Pro Gly Ala Leu Glu
            565                 570                 575

Leu Glu Tyr Glu Gly Phe Tyr Lys Arg Gly Phe Phe Val Thr Lys Lys
        580                 585                 590

Lys Tyr Ala Val Ile Asp Glu Glu Gly Lys Ile Thr Thr Arg Gly Leu
    595                 600                 605

Glu Ile Val Arg Arg Asp Trp Ser Glu Ile Ala Lys Glu Thr Gln Ala
    610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
            645                 650                 655

Pro Glu Lys Leu Val Ile His Glu Gln Ile Thr Arg Asp Leu Lys Asp
        660                 665                 670

Tyr Lys Ala Thr Gly Pro His Val Ala Val Ala Lys Arg Leu Ala Ala
    675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
            725                 730                 735

Val Leu Pro Ala Val Glu Arg Ile Leu Arg Ala Phe Gly Tyr Arg Lys
        740                 745                 750
```

```
Glu Asp Leu Arg Tyr Gln Lys Thr Arg Gln Val Gly Leu Ser Ala Trp
        755                 760                 765

Leu Lys Pro Lys Gly Thr
    770


<210> SEQ ID NO 52
<211> LENGTH: 774
<212> TYPE: PRT
<213> ORGANISM: Thermococcus kodakaraensis

<400> SEQUENCE: 52

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Glu Val Lys Lys Ile Thr Ala Glu Arg His Gly Thr Val Val Thr
    50                  55                  60

Val Lys Arg Val Glu Lys Val Gln Lys Lys Phe Leu Gly Arg Pro Val
65                  70                  75                  80

Glu Val Trp Lys Leu Tyr Phe Thr His Pro Gln Asp Glu Pro Ala Ile
                85                  90                  95

Arg Asp Lys Ile Arg Glu His Gly Ala Val Ile Asp Ile Tyr Glu Tyr
            100                 105                 110

Asp Ile Pro Phe Ala Lys Arg Tyr Leu Ile Asp Lys Gly Leu Val Pro
        115                 120                 125

Met Glu Gly Asp Glu Glu Leu Lys Met Leu Ala Phe Asp Ile Gln Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Val
                165                 170                 175

Asp Leu Pro Tyr Val Asp Val Val Ser Thr Glu Arg Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Ile Asn Phe Ala Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Gln Pro Lys Glu
        275                 280                 285

Lys Val Tyr Ala Glu Glu Ile Thr Pro Ala Trp Glu Thr Gly Glu Asn
    290                 295                 300

Leu Glu Arg Val Ala Arg Tyr Ser Met Glu Asp Ala Lys Val Thr Tyr
305                 310                 315                 320

Glu Leu Gly Lys Glu Phe Leu Pro Met Glu Ala Gln Leu Ser Arg Leu
                325                 330                 335

Ile Gly Gln Ser Leu Trp Asp Val Ser Arg Ser Ser Thr Gly Asn Leu
            340                 345                 350
```

-continued

```
Val Glu Trp Phe Leu Leu Arg Lys Ala Tyr Glu Arg Asn Glu Leu Ala
        355                 360                 365

Pro Asn Lys Pro Asp Glu Lys Glu Leu Ala Arg Arg Arg Gln Ser Tyr
    370                 375                 380

Glu Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Lys Glu Tyr Asp
            420                 425                 430

Val Ala Pro Gln Val Gly His Arg Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Lys Lys Met Lys Ala Thr Ile Asp Pro Ile Glu Arg Lys Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Lys Glu Cys Ala Glu Ser
            500                 505                 510

Val Thr Ala Trp Gly Arg Glu Tyr Ile Thr Met Thr Ile Lys Glu Ile
        515                 520                 525

Glu Glu Lys Tyr Gly Phe Lys Val Ile Tyr Ser Asp Thr Asp Gly Phe
    530                 535                 540

Phe Ala Thr Ile Pro Gly Ala Asp Ala Glu Thr Val Lys Lys Lys Ala
545                 550                 555                 560

Met Glu Phe Leu Asn Tyr Ile Asn Ala Lys Leu Pro Gly Ala Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Leu Leu Lys Asp Gly Asp Val Glu Lys Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Ser Ala Trp
        755                 760                 765

Leu Lys Pro Lys Gly Thr
    770
```

<210> SEQ ID NO 53
<211> LENGTH: 774
<212> TYPE: PRT
<213> ORGANISM: Thermococcus litoralis

<400> SEQUENCE: 53

```
Met Ile Leu Asp Thr Asp Tyr Ile Thr Lys Asp Gly Lys Pro Ile Ile
1               5                   10                  15

Arg Ile Phe Lys Lys Glu Asn Gly Glu Phe Lys Ile Glu Leu Asp Pro
            20                  25                  30

His Phe Gln Pro Tyr Ile Tyr Ala Leu Leu Lys Asp Asp Ser Ala Ile
        35                  40                  45

Glu Glu Ile Lys Ala Ile Lys Gly Glu Arg His Gly Lys Thr Val Arg
    50                  55                  60

Val Leu Asp Ala Val Lys Val Arg Lys Lys Phe Leu Gly Arg Glu Val
65                  70                  75                  80

Glu Val Trp Lys Leu Ile Phe Glu His Pro Gln Asp Arg Pro Ala Met
                85                  90                  95

Arg Gly Lys Ile Arg Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Phe Tyr His Glu Gly Asp Glu Phe Gly Lys Gly Glu Ile Ile Met Ile
145                 150                 155                 160

Ser Tyr Ala Asp Glu Glu Glu Ala Arg Val Ile Thr Trp Lys Asn Ile
                165                 170                 175

Asp Leu Pro Tyr Val Asp Val Val Ser Asn Glu Arg Glu Met Ile Lys
            180                 185                 190

Arg Phe Val Gln Val Val Lys Glu Lys Asp Pro Asp Val Ile Ile Thr
        195                 200                 205

Tyr Asn Gly Asp Asn Phe Asp Leu Pro Tyr Leu Ile Lys Arg Ala Glu
    210                 215                 220

Lys Leu Gly Val Arg Leu Val Leu Gly Arg Asp Lys Glu His Pro Glu
225                 230                 235                 240

Pro Lys Ile Gln Arg Met Gly Asp Ser Phe Ala Val Glu Ile Lys Gly
                245                 250                 255

Arg Ile His Phe Asp Leu Phe Pro Val Val Arg Arg Thr Ile Asn Leu
            260                 265                 270

Pro Thr Tyr Thr Leu Glu Ala Val Tyr Glu Ala Val Leu Gly Lys Thr
        275                 280                 285

Lys Ser Lys Leu Gly Ala Glu Glu Ile Ala Ala Ile Trp Glu Thr Glu
    290                 295                 300

Glu Ser Met Lys Lys Leu Ala Gln Tyr Ser Met Glu Asp Ala Arg Ala
305                 310                 315                 320

Thr Tyr Glu Leu Gly Lys Glu Phe Phe Pro Met Glu Ala Glu Leu Ala
                325                 330                 335

Lys Leu Ile Gly Gln Ser Val Trp Asp Val Ser Arg Ser Ser Thr Gly
            340                 345                 350

Asn Leu Val Glu Trp Tyr Leu Leu Arg Val Ala Tyr Ala Arg Asn Glu
        355                 360                 365

Leu Ala Pro Asn Lys Pro Asp Glu Glu Glu Tyr Lys Arg Arg Leu Arg
    370                 375                 380
```

Thr Thr Tyr Leu Gly Gly Tyr Val Lys Glu Pro Glu Lys Gly Leu Trp
385 390 395 400

Glu Asn Ile Ile Tyr Leu Asp Phe Arg Ser Leu Tyr Pro Ser Ile Ile
405 410 415

Val Thr His Asn Val Ser Pro Asp Thr Leu Glu Lys Glu Gly Cys Lys
420 425 430

Asn Tyr Asp Val Ala Pro Ile Val Gly Tyr Arg Phe Cys Lys Asp Phe
435 440 445

Pro Gly Phe Ile Pro Ser Ile Leu Gly Asp Leu Ile Ala Met Arg Gln
450 455 460

Asp Ile Lys Lys Lys Met Lys Ser Thr Ile Asp Pro Ile Glu Lys Lys
465 470 475 480

Met Leu Asp Tyr Arg Gln Arg Ala Ile Lys Leu Leu Ala Asn Ser Tyr
485 490 495

Tyr Gly Tyr Met Gly Tyr Pro Lys Ala Arg Trp Tyr Ser Lys Glu Cys
500 505 510

Ala Glu Ser Val Thr Ala Trp Gly Arg His Tyr Ile Glu Met Thr Ile
515 520 525

Arg Glu Ile Glu Glu Lys Phe Gly Phe Lys Val Leu Tyr Ala Asp Thr
530 535 540

Asp Gly Phe Tyr Ala Thr Ile Pro Gly Glu Lys Pro Glu Leu Ile Lys
545 550 555 560

Lys Lys Ala Lys Glu Phe Leu Asn Tyr Ile Asn Ser Lys Leu Pro Gly
565 570 575

Leu Leu Glu Leu Glu Tyr Glu Gly Phe Tyr Leu Arg Gly Phe Phe Val
580 585 590

Thr Lys Lys Arg Tyr Ala Val Ile Asp Glu Glu Gly Arg Ile Thr Thr
595 600 605

Arg Gly Leu Glu Val Val Arg Arg Asp Trp Ser Glu Ile Ala Lys Glu
610 615 620

Thr Gln Ala Lys Val Leu Glu Ala Ile Leu Lys Glu Gly Ser Val Glu
625 630 635 640

Lys Ala Val Glu Val Val Arg Asp Val Val Glu Lys Ile Ala Lys Tyr
645 650 655

Arg Val Pro Leu Glu Lys Leu Val Ile His Glu Gln Ile Thr Arg Asp
660 665 670

Leu Lys Asp Tyr Lys Ala Ile Gly Pro His Val Ala Ile Ala Lys Arg
675 680 685

Leu Ala Ala Arg Gly Ile Lys Val Lys Pro Gly Thr Ile Ile Ser Tyr
690 695 700

Ile Val Leu Lys Gly Ser Gly Lys Ile Ser Asp Arg Val Ile Leu Leu
705 710 715 720

Thr Glu Tyr Asp Pro Arg Lys His Lys Tyr Asp Pro Asp Tyr Tyr Ile
725 730 735

Glu Asn Gln Val Leu Pro Ala Val Leu Arg Ile Leu Glu Ala Phe Gly
740 745 750

Tyr Arg Lys Glu Asp Leu Arg Tyr Gln Ser Ser Lys Gln Thr Gly Leu
755 760 765

Asp Ala Trp Leu Lys Arg
770

<210> SEQ ID NO 54
<211> LENGTH: 774
<212> TYPE: PRT

<213> ORGANISM: Thermococcus litoralis

<400> SEQUENCE: 54

Met Ile Leu Asp Thr Asp Tyr Ile Thr Lys Asp Gly Lys Pro Ile Ile
1               5                   10                  15

Arg Ile Phe Lys Lys Glu Asn Gly Glu Phe Lys Ile Glu Leu Asp Pro
            20                  25                  30

His Phe Gln Pro Tyr Ile Tyr Ala Leu Leu Lys Asp Asp Ser Ala Ile
        35                  40                  45

Glu Glu Ile Lys Ala Ile Lys Gly Glu Arg His Gly Lys Thr Val Arg
    50                  55                  60

Val Leu Asp Ala Val Lys Val Arg Lys Lys Phe Leu Gly Arg Glu Val
65                  70                  75                  80

Glu Val Trp Lys Leu Ile Phe Glu His Pro Gln Asp Glu Pro Ala Met
                85                  90                  95

Arg Gly Lys Ile Arg Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Phe Tyr His Glu Gly Asp Glu Phe Gly Lys Gly Glu Ile Ile Met Ile
145                 150                 155                 160

Ser Tyr Ala Asp Glu Glu Glu Ala Arg Val Ile Thr Trp Lys Asn Ile
                165                 170                 175

Asp Leu Pro Tyr Val Asp Val Val Ser Asn Glu Arg Glu Met Ile Lys
            180                 185                 190

Arg Phe Val Gln Val Val Lys Glu Lys Asp Pro Asp Val Ile Ile Thr
        195                 200                 205

Tyr Asn Gly Asp Asn Phe Asp Leu Pro Tyr Leu Ile Lys Arg Ala Glu
    210                 215                 220

Lys Leu Gly Val Arg Leu Val Leu Gly Arg Asp Lys Glu His Pro Glu
225                 230                 235                 240

Pro Lys Ile Gln Arg Met Gly Asp Ser Phe Ala Val Glu Ile Lys Gly
                245                 250                 255

Arg Ile His Phe Asp Leu Phe Pro Val Val Arg Arg Thr Ile Asn Leu
            260                 265                 270

Pro Thr Tyr Thr Leu Glu Ala Val Tyr Glu Ala Val Leu Gly Lys Thr
        275                 280                 285

Lys Ser Lys Leu Gly Ala Glu Glu Ile Ala Ala Ile Trp Glu Thr Glu
    290                 295                 300

Glu Ser Met Lys Lys Leu Ala Gln Tyr Ser Met Glu Asp Ala Arg Ala
305                 310                 315                 320

Thr Tyr Glu Leu Gly Lys Glu Phe Phe Pro Met Glu Ala Glu Leu Ala
                325                 330                 335

Lys Leu Ile Gly Gln Ser Val Trp Asp Val Ser Arg Ser Ser Thr Gly
            340                 345                 350

Asn Leu Val Glu Trp Tyr Leu Leu Arg Val Ala Tyr Ala Arg Asn Glu
        355                 360                 365

Leu Ala Pro Asn Lys Pro Asp Glu Glu Glu Tyr Lys Arg Arg Leu Arg
    370                 375                 380

Thr Thr Tyr Leu Gly Gly Tyr Val Lys Glu Pro Glu Lys Gly Leu Trp
385                 390                 395                 400

Glu Asn Ile Ile Tyr Leu Asp Phe Arg Ser Leu Tyr Pro Ser Ile Ile

```
                405                 410                 415

Val Thr His Asn Val Ser Pro Asp Thr Leu Glu Lys Glu Gly Cys Lys
            420                 425                 430

Asn Tyr Asp Val Ala Pro Ile Val Gly Tyr Arg Phe Cys Lys Asp Phe
        435                 440                 445

Pro Gly Phe Ile Pro Ser Ile Leu Gly Asp Leu Ile Ala Met Arg Gln
    450                 455                 460

Asp Ile Lys Lys Lys Met Lys Ser Thr Ile Asp Pro Ile Glu Lys Lys
465                 470                 475                 480

Met Leu Asp Tyr Arg Gln Arg Ala Ile Lys Leu Leu Ala Asn Ser Tyr
                485                 490                 495

Tyr Gly Tyr Met Gly Tyr Pro Lys Ala Arg Trp Tyr Ser Lys Glu Cys
            500                 505                 510

Ala Glu Ser Val Thr Ala Trp Gly Arg His Tyr Ile Glu Met Thr Ile
        515                 520                 525

Arg Glu Ile Glu Glu Lys Phe Gly Phe Lys Val Leu Tyr Ala Asp Thr
    530                 535                 540

Asp Gly Phe Tyr Ala Thr Ile Pro Gly Glu Lys Pro Glu Leu Ile Lys
545                 550                 555                 560

Lys Lys Ala Lys Glu Phe Leu Asn Tyr Ile Asn Ser Lys Leu Pro Gly
                565                 570                 575

Leu Leu Glu Leu Glu Tyr Glu Gly Phe Tyr Leu Arg Gly Phe Phe Val
            580                 585                 590

Thr Lys Lys Arg Tyr Ala Val Ile Asp Glu Glu Gly Arg Ile Thr Thr
        595                 600                 605

Arg Gly Leu Glu Val Val Arg Arg Asp Trp Ser Glu Ile Ala Lys Glu
    610                 615                 620

Thr Gln Ala Lys Val Leu Glu Ala Ile Leu Lys Glu Gly Ser Val Glu
625                 630                 635                 640

Lys Ala Val Glu Val Val Arg Asp Val Val Glu Lys Ile Ala Lys Tyr
                645                 650                 655

Arg Val Pro Leu Glu Lys Leu Val Ile His Glu Gln Ile Thr Arg Asp
            660                 665                 670

Leu Lys Asp Tyr Lys Ala Ile Gly Pro His Val Ala Ile Ala Lys Arg
        675                 680                 685

Leu Ala Ala Arg Gly Ile Lys Val Lys Pro Gly Thr Ile Ile Ser Tyr
    690                 695                 700

Ile Val Leu Lys Gly Ser Gly Lys Ile Ser Asp Arg Val Ile Leu Leu
705                 710                 715                 720

Thr Glu Tyr Asp Pro Arg Lys His Lys Tyr Asp Pro Asp Tyr Tyr Ile
                725                 730                 735

Glu Asn Gln Val Leu Pro Ala Val Leu Arg Ile Leu Glu Ala Phe Gly
            740                 745                 750

Tyr Arg Lys Glu Asp Leu Arg Tyr Gln Ser Ser Lys Gln Thr Gly Leu
        755                 760                 765

Asp Ala Trp Leu Lys Arg
    770

<210> SEQ ID NO 55
<211> LENGTH: 776
<212> TYPE: PRT
<213> ORGANISM: Pyrococcus GB-D

<400> SEQUENCE: 55

Met Ile Leu Asp Val Asp Tyr Ile Thr Glu Asn Gly Lys Pro Val Ile
```

-continued

```
1               5                   10                  15

Arg Val Phe Lys Lys Glu Asn Gly Glu Phe Arg Ile Glu Tyr Asp Arg
            20                  25                  30

Glu Phe Glu Pro Tyr Phe Tyr Ala Leu Leu Arg Asp Asp Ser Ala Ile
        35                  40                  45

Glu Glu Ile Lys Lys Ile Thr Ala Glu Arg His Gly Arg Val Val Lys
    50                  55                  60

Val Lys Arg Ala Glu Lys Val Lys Lys Lys Phe Leu Gly Arg Ser Val
65                  70                  75                  80

Glu Val Trp Val Leu Tyr Phe Thr His Pro Gln Asp Arg Pro Ala Ile
                85                  90                  95

Arg Asp Lys Ile Arg Lys His Pro Ala Val Ile Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Leu Met Ser Phe Asp Ile Glu Thr
    130                 135                 140

Leu Tyr His Glu Gly Glu Glu Phe Gly Thr Gly Pro Ile Leu Met Ile
145                 150                 155                 160

Ser Tyr Ala Asp Glu Ser Glu Ala Arg Val Ile Thr Trp Lys Lys Ile
                165                 170                 175

Asp Leu Pro Tyr Val Glu Val Val Ser Thr Glu Lys Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Val Ser Phe Thr Leu Gly Arg Asp Gly Ser Glu Pro Lys
225                 230                 235                 240

Ile Gln Arg Met Gly Asp Arg Phe Ala Val Glu Val Lys Gly Arg Val
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Thr Ala Trp Glu Thr Gly Glu Gly
    290                 295                 300

Leu Glu Arg Val Ala Arg Tyr Ser Met Glu Asp Ala Arg Val Thr Tyr
305                 310                 315                 320

Glu Leu Gly Arg Glu Phe Phe Pro Met Glu Ala Gln Leu Ser Arg Leu
                325                 330                 335

Ile Gly Gln Gly Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Arg Gly Gly Tyr
    370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Arg Ser Tyr Asp
            420                 425                 430
```

```
Val Ala Pro Glu Val Gly His Lys Phe Cys Lys Asp Phe Pro Gly Phe
        435                 440                 445

Ile Pro Ser Leu Leu Gly Asn Leu Leu Glu Glu Arg Gln Lys Ile Lys
    450                 455                 460

Arg Lys Met Lys Ala Thr Leu Asp Pro Leu Glu Lys Asn Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Arg Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
    530                 535                 540

His Ala Thr Ile Pro Gly Ala Asp Ala Glu Thr Val Lys Lys Lys Ala
545                 550                 555                 560

Met Glu Phe Leu Asn Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Arg His Gly Asp Val Glu Glu Ala Val
625                 630                 635                 640

Arg Ile Val Arg Glu Val Thr Glu Lys Leu Ser Lys Tyr Glu Val Pro
                645                 650                 655

Pro Glu Lys Leu Val Ile His Glu Gln Ile Thr Arg Glu Leu Lys Asp
            660                 665                 670

Tyr Lys Ala Thr Gly Pro His Val Ala Ile Ala Lys Arg Leu Ala Ala
        675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Asp Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Gly Lys Lys Lys
    770                 775


<210> SEQ ID NO 56
<211> LENGTH: 776
<212> TYPE: PRT
<213> ORGANISM: Pyrococcus GB-D

<400> SEQUENCE: 56

Met Ile Leu Asp Val Asp Tyr Ile Thr Glu Asn Gly Lys Pro Val Ile
1               5                   10                  15

Arg Val Phe Lys Lys Glu Asn Gly Glu Phe Arg Ile Glu Tyr Asp Arg
            20                  25                  30
```

-continued

```
Glu Phe Glu Pro Tyr Phe Tyr Ala Leu Leu Arg Asp Asp Ser Ala Ile
        35                  40                  45

Glu Glu Ile Lys Lys Ile Thr Ala Glu Arg His Gly Arg Val Val Lys
    50                  55                  60

Val Lys Arg Ala Glu Lys Val Lys Lys Lys Phe Leu Gly Arg Ser Val
65                  70                  75                  80

Glu Val Trp Val Leu Tyr Phe Thr His Pro Gln Asp Glu Pro Ala Ile
                85                  90                  95

Arg Asp Lys Ile Arg Lys His Pro Ala Val Ile Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Leu Met Ser Phe Asp Ile Glu Thr
    130                 135                 140

Leu Tyr His Glu Gly Glu Glu Phe Gly Thr Gly Pro Ile Leu Met Ile
145                 150                 155                 160

Ser Tyr Ala Asp Glu Ser Glu Ala Arg Val Ile Thr Trp Lys Lys Ile
                165                 170                 175

Asp Leu Pro Tyr Val Glu Val Val Ser Thr Glu Lys Glu Met Ile Lys
            180                 185                 190

Arg Phe Leu Arg Val Val Lys Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Lys Leu Gly Val Ser Phe Thr Leu Gly Arg Asp Gly Ser Glu Pro Lys
225                 230                 235                 240

Ile Gln Arg Met Gly Asp Arg Phe Ala Val Glu Val Lys Gly Arg Val
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Val Phe Gly Lys Pro Lys Glu
        275                 280                 285

Lys Val Tyr Ala Glu Glu Ile Ala Thr Ala Trp Glu Thr Gly Glu Gly
    290                 295                 300

Leu Glu Arg Val Ala Arg Tyr Ser Met Glu Asp Ala Arg Val Thr Tyr
305                 310                 315                 320

Glu Leu Gly Arg Glu Phe Phe Pro Met Glu Ala Gln Leu Ser Arg Leu
                325                 330                 335

Ile Gly Gln Gly Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Arg Gly Gly Tyr
    370                 375                 380

Ala Gly Gly Tyr Val Lys Glu Pro Glu Arg Gly Leu Trp Asp Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Arg Ser Tyr Asp
            420                 425                 430

Val Ala Pro Glu Val Gly His Lys Phe Cys Lys Asp Phe Pro Gly Phe
        435                 440                 445

Ile Pro Ser Leu Leu Gly Asn Leu Leu Glu Glu Arg Gln Lys Ile Lys
    450                 455                 460
```

```
Arg Lys Met Lys Ala Thr Leu Asp Pro Leu Glu Lys Asn Leu Leu Asp
465                 470                 475                 480

Tyr Arg Gln Arg Ala Ile Lys Ile Leu Ala Asn Ser Tyr Tyr Gly Tyr
                485                 490                 495

Tyr Gly Tyr Ala Arg Ala Arg Trp Tyr Cys Arg Glu Cys Ala Glu Ser
            500                 505                 510

Val Thr Ala Trp Gly Arg Glu Tyr Ile Glu Met Val Ile Arg Glu Leu
        515                 520                 525

Glu Glu Lys Phe Gly Phe Lys Val Leu Tyr Ala Asp Thr Asp Gly Leu
    530                 535                 540

His Ala Thr Ile Pro Gly Ala Asp Ala Glu Thr Val Lys Lys Lys Ala
545                 550                 555                 560

Met Glu Phe Leu Asn Tyr Ile Asn Pro Lys Leu Pro Gly Leu Leu Glu
                565                 570                 575

Leu Glu Tyr Glu Gly Phe Tyr Val Arg Gly Phe Phe Val Thr Lys Lys
            580                 585                 590

Lys Tyr Ala Val Ile Asp Glu Glu Gly Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Arg His Gly Asp Val Glu Glu Ala Val
625                 630                 635                 640

Arg Ile Val Arg Glu Val Thr Glu Lys Leu Ser Lys Tyr Glu Val Pro
                645                 650                 655

Pro Glu Lys Leu Val Ile His Glu Gln Ile Thr Arg Glu Leu Lys Asp
            660                 665                 670

Tyr Lys Ala Thr Gly Pro His Val Ala Ile Ala Lys Arg Leu Ala Ala
        675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Asp Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Gly Lys Lys Lys
    770                 775


<210> SEQ ID NO 57
<211> LENGTH: 2322
<212> TYPE: DNA
<213> ORGANISM: Thermococcus gorgonarius
<220> FEATURE:
<221> NAME/KEY: modified_base
<222> LOCATION: (277)..(279)
<223> OTHER INFORMATION: region may encompass AGA, AGG, CGA, CGC, CGG or
      CGT
<220> FEATURE:
<221> NAME/KEY: CDS
<222> LOCATION: (1)..(2322)

<400> SEQUENCE: 57

atg atc ctc gat aca gac tac ata act gag gat gga aag ccc gtc atc       48
Met Ile Leu Asp Thr Asp Tyr Ile Thr Glu Asp Gly Lys Pro Val Ile
1               5                   10                  15
```

```
agg atc ttc aag aag gag aac ggc gag ttc aaa ata gac tac gac aga        96
Arg Ile Phe Lys Lys Glu Asn Gly Glu Phe Lys Ile Asp Tyr Asp Arg
            20                  25                  30

aac ttt gag cca tac atc tac gcg ctc ttg aag gac gac tct gcg att       144
Asn Phe Glu Pro Tyr Ile Tyr Ala Leu Leu Lys Asp Asp Ser Ala Ile
        35                  40                  45

gag gac gtc aag aag ata act gcc gag agg cac ggc act acc gtt agg       192
Glu Asp Val Lys Lys Ile Thr Ala Glu Arg His Gly Thr Thr Val Arg
    50                  55                  60

gtt gtc agg gcc gag aaa gtg aag aag aag ttc cta ggc agg ccg ata       240
Val Val Arg Ala Glu Lys Val Lys Lys Lys Phe Leu Gly Arg Pro Ile
65                  70                  75                  80

gag gtc tgg aag ctc tac ttc act cac ccc cag gac nnn ccc gca atc       288
Glu Val Trp Lys Leu Tyr Phe Thr His Pro Gln Asp Xaa Pro Ala Ile
                85                  90                  95

agg gac aag ata aag gag cat cct gcc gtt gtg gac atc tac gag tac       336
Arg Asp Lys Ile Lys Glu His Pro Ala Val Val Asp Ile Tyr Glu Tyr
            100                 105                 110

gac atc ccc ttc gcg aag cgc tac ctc ata gac aaa ggc tta atc ccg       384
Asp Ile Pro Phe Ala Lys Arg Tyr Leu Ile Asp Lys Gly Leu Ile Pro
        115                 120                 125

atg gag ggc gac gag gaa ctt aag atg ctc gcc ttc gac atc gag acg       432
Met Glu Gly Asp Glu Glu Leu Lys Met Leu Ala Phe Asp Ile Glu Thr
    130                 135                 140

ctc tat cac gag ggc gag gag ttc gcc gaa ggg cct atc ctg atg ata       480
Leu Tyr His Glu Gly Glu Glu Phe Ala Glu Gly Pro Ile Leu Met Ile
145                 150                 155                 160

agc tac gcc gac gag gaa ggg gcg cgc gtt att acc tgg aag aat atc       528
Ser Tyr Ala Asp Glu Glu Gly Ala Arg Val Ile Thr Trp Lys Asn Ile
                165                 170                 175

gac ctt ccc tat gtc gac gtc gtt tcc acc gag aag gag atg ata aag       576
Asp Leu Pro Tyr Val Asp Val Val Ser Thr Glu Lys Glu Met Ile Lys
            180                 185                 190

cgc ttc ctc aag gtc gtc aag gaa aag gat ccc gac gtc ctc ata acc       624
Arg Phe Leu Lys Val Val Lys Glu Lys Asp Pro Asp Val Leu Ile Thr
        195                 200                 205

tac aac ggc gac aac ttc gac ttc gcc tac ctc aag aag cgc tcc gag       672
Tyr Asn Gly Asp Asn Phe Asp Phe Ala Tyr Leu Lys Lys Arg Ser Glu
    210                 215                 220

aag ctc gga gtc aag ttc atc ctc gga agg gaa ggg agc gag ccg aaa       720
Lys Leu Gly Val Lys Phe Ile Leu Gly Arg Glu Gly Ser Glu Pro Lys
225                 230                 235                 240

atc cag cgc atg ggc gat cgc ttt gcg gtg gag gtc aag gga agg att       768
Ile Gln Arg Met Gly Asp Arg Phe Ala Val Glu Val Lys Gly Arg Ile
                245                 250                 255

cac ttc gac ctc tac ccc gtc att agg aga acg att aac ctc ccc act       816
His Phe Asp Leu Tyr Pro Val Ile Arg Arg Thr Ile Asn Leu Pro Thr
            260                 265                 270

tac acc ctt gag gca gta tat gaa gcc atc ttt gga cag ccg aag gag       864
Tyr Thr Leu Glu Ala Val Tyr Glu Ala Ile Phe Gly Gln Pro Lys Glu
        275                 280                 285

aag gtc tac gct gag gag ata gcg cag gcc tgg gaa acg ggc gag gga       912
Lys Val Tyr Ala Glu Glu Ile Ala Gln Ala Trp Glu Thr Gly Glu Gly
    290                 295                 300

tta gaa agg gtg gcc cgc tac tcg atg gag gac gca aag gta acc tat       960
Leu Glu Arg Val Ala Arg Tyr Ser Met Glu Asp Ala Lys Val Thr Tyr
305                 310                 315                 320

gaa ctc gga aaa gag ttc ttc cct atg gaa gcc cag ctc tcg cgc ctc      1008
Glu Leu Gly Lys Glu Phe Phe Pro Met Glu Ala Gln Leu Ser Arg Leu
                325                 330                 335
```

US 7,960,157 B2

153 154

-continued

```
gta ggc cag agc ctc tgg gat gta tct cgc tcg agt acc gga aac ctc      1056
Val Gly Gln Ser Leu Trp Asp Val Ser Arg Ser Ser Thr Gly Asn Leu
            340                 345                 350

gtc gag tgg ttt ttg ctg agg aag gcc tac gag agg aat gaa ctt gca      1104
Val Glu Trp Phe Leu Leu Arg Lys Ala Tyr Glu Arg Asn Glu Leu Ala
        355                 360                 365

cca aac aag ccg gac gag agg gag ctg gca aga aga agg gag agc tac      1152
Pro Asn Lys Pro Asp Glu Arg Glu Leu Ala Arg Arg Arg Glu Ser Tyr
    370                 375                 380

gcg ggt gga tac gtc aag gag ccc gaa agg gga ctg tgg gag aac atc      1200
Ala Gly Gly Tyr Val Lys Glu Pro Glu Arg Gly Leu Trp Glu Asn Ile
385                 390                 395                 400

gtg tat ctg gac ttc cgc tcc ctg tat cct tcg ata ata atc acc cat      1248
Val Tyr Leu Asp Phe Arg Ser Leu Tyr Pro Ser Ile Ile Ile Thr His
                405                 410                 415

aac gtc tcc cct gat aca ctc aac agg gag ggt tgt gag gag tac gac      1296
Asn Val Ser Pro Asp Thr Leu Asn Arg Glu Gly Cys Glu Glu Tyr Asp
            420                 425                 430

gtg gct cct cag gta ggc cat aag ttc tgc aag gac ttc ccc ggc ttc      1344
Val Ala Pro Gln Val Gly His Lys Phe Cys Lys Asp Phe Pro Gly Phe
        435                 440                 445

atc cca agc ctc ctc gga gac ctc ttg gag gag aga cag aag gta aag      1392
Ile Pro Ser Leu Leu Gly Asp Leu Leu Glu Glu Arg Gln Lys Val Lys
    450                 455                 460

aag aag atg aag gcc act ata gac cca atc gag aag aaa ctc ctc gat      1440
Lys Lys Met Lys Ala Thr Ile Asp Pro Ile Glu Lys Lys Leu Leu Asp
465                 470                 475                 480

tac agg caa cga gca atc aaa atc ctt gct aat agc ttc tac ggt tac      1488
Tyr Arg Gln Arg Ala Ile Lys Ile Leu Ala Asn Ser Phe Tyr Gly Tyr
                485                 490                 495

tac ggc tat gca aag gcc cgc tgg tac tgc aag gag tgc gcc gag agc      1536
Tyr Gly Tyr Ala Lys Ala Arg Trp Tyr Cys Lys Glu Cys Ala Glu Ser
            500                 505                 510

gtt acc gct tgg ggc agg cag tac atc gag acc acg ata agg gaa ata      1584
Val Thr Ala Trp Gly Arg Gln Tyr Ile Glu Thr Thr Ile Arg Glu Ile
        515                 520                 525

gag gag aaa ttt ggc ttt aaa gtc ctc tac gcg gac aca gat gga ttt      1632
Glu Glu Lys Phe Gly Phe Lys Val Leu Tyr Ala Asp Thr Asp Gly Phe
    530                 535                 540

ttc gca aca ata cct gga gcg gac gcc gaa acc gtc aaa aag aag gca      1680
Phe Ala Thr Ile Pro Gly Ala Asp Ala Glu Thr Val Lys Lys Lys Ala
545                 550                 555                 560

aag gag ttc ctg gac tac atc aac gcc aaa ctg ccc ggc ctg ctc gaa      1728
Lys Glu Phe Leu Asp Tyr Ile Asn Ala Lys Leu Pro Gly Leu Leu Glu
                565                 570                 575

ctc gaa tac gag ggc ttc tac aag cgc ggc ttc ttc gtg acg aag aag      1776
Leu Glu Tyr Glu Gly Phe Tyr Lys Arg Gly Phe Phe Val Thr Lys Lys
            580                 585                 590

aag tac gcg gtt ata gac gag gag gac aag ata acg acg cgc ggg ctt      1824
Lys Tyr Ala Val Ile Asp Glu Glu Asp Lys Ile Thr Thr Arg Gly Leu
        595                 600                 605

gaa ata gtt agg cgt gac tgg agc gag ata gcg aag gag acg cag gcg      1872
Glu Ile Val Arg Arg Asp Trp Ser Glu Ile Ala Lys Glu Thr Gln Ala
    610                 615                 620

agg gtt ctt gag gcg ata cta aag cac ggt gac gtt gaa gaa gcg gta      1920
Arg Val Leu Glu Ala Ile Leu Lys His Gly Asp Val Glu Glu Ala Val
625                 630                 635                 640

agg att gtc aaa gag gtt acg gag aag ctg agc aag tac gag gtt cca      1968
Arg Ile Val Lys Glu Val Thr Glu Lys Leu Ser Lys Tyr Glu Val Pro
                645                 650                 655
```

```
ccg gag aag ctg gtc atc tac gag cag ata acc cgc gac ctg aag gac     2016
Pro Glu Lys Leu Val Ile Tyr Glu Gln Ile Thr Arg Asp Leu Lys Asp
            660                 665                 670

tac aag gcc acc ggg ccg cat gtg gct gtt gca aaa cgc ctc gcc gca     2064
Tyr Lys Ala Thr Gly Pro His Val Ala Val Ala Lys Arg Leu Ala Ala
        675                 680                 685

agg ggg ata aaa atc cgg ccc gga acg gtc ata agc tac atc gtg ctc     2112
Arg Gly Ile Lys Ile Arg Pro Gly Thr Val Ile Ser Tyr Ile Val Leu
    690                 695                 700

aaa ggc tcg gga agg att ggg gac agg gct ata ccc ttt gac gaa ttt     2160
Lys Gly Ser Gly Arg Ile Gly Asp Arg Ala Ile Pro Phe Asp Glu Phe
705                 710                 715                 720

gac ccg gca aag cac aag tac gat gca gaa tac tac atc gag aac cag     2208
Asp Pro Ala Lys His Lys Tyr Asp Ala Glu Tyr Tyr Ile Glu Asn Gln
                725                 730                 735

gtt ctt cca gct gtg gag agg att ctg agg gcc ttt ggt tac cgt aaa     2256
Val Leu Pro Ala Val Glu Arg Ile Leu Arg Ala Phe Gly Tyr Arg Lys
            740                 745                 750

gaa gat tta agg tat cag aaa acg cgg cag gtt ggc ttg ggg gcg tgg     2304
Glu Asp Leu Arg Tyr Gln Lys Thr Arg Gln Val Gly Leu Gly Ala Trp
        755                 760                 765

cta aaa cct aag aca tga                                             2322
Leu Lys Pro Lys Thr
    770


<210> SEQ ID NO 58
<211> LENGTH: 773
<212> TYPE: PRT
<213> ORGANISM: Thermococcus gorgonarius
<220> FEATURE:
<221> NAME/KEY: MOD_RES
<222> LOCATION: (93)..(93)
<223> OTHER INFORMATION: Lys, Asn, Arg, Ser, Thr, Ile, Met, Glu, Asp,
      Gly, Ala, Val, Gln, His, Pro, Leu, Tyr, Trp, Cys, or Phe.

<400> SEQUENCE: 58

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Lys Phe Leu Gly Arg Pro Ile
65                  70                  75                  80

Glu Val Trp Lys Leu Tyr Phe Thr His Pro Gln Asp Xaa Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
```

```
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Arg Glu Ser Tyr
    370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Ile Asp Pro Ile Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605
```

```
Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile Tyr Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765

Leu Lys Pro Lys Thr
    770


<210> SEQ ID NO 59
<211> LENGTH: 2322
<212> TYPE: DNA
<213> ORGANISM: Thermococcus gorgonarius
<220> FEATURE:
<221> NAME/KEY: CDS
<222> LOCATION: (1)..(2322)
<220> FEATURE:
<221> NAME/KEY: modified_base
<222> LOCATION: (277)..(279)
<223> OTHER INFORMATION: region may encompass GAA or GAG

<400> SEQUENCE: 59

atg atc ctc gat aca gac tac ata act gag gat gga aag ccc gtc atc       48
Met Ile Leu Asp Thr Asp Tyr Ile Thr Glu Asp Gly Lys Pro Val Ile
1               5                   10                  15

agg atc ttc aag aag gag aac ggc gag ttc aaa ata gac tac gac aga       96
Arg Ile Phe Lys Lys Glu Asn Gly Glu Phe Lys Ile Asp Tyr Asp Arg
            20                  25                  30

aac ttt gag cca tac atc tac gcg ctc ttg aag gac gac tct gcg att      144
Asn Phe Glu Pro Tyr Ile Tyr Ala Leu Leu Lys Asp Asp Ser Ala Ile
        35                  40                  45

gag gac gtc aag aag ata act gcc gag agg cac ggc act acc gtt agg      192
Glu Asp Val Lys Lys Ile Thr Ala Glu Arg His Gly Thr Thr Val Arg
    50                  55                  60

gtt gtc agg gcc gag aaa gtg aag aag aag ttc cta ggc agg ccg ata      240
Val Val Arg Ala Glu Lys Val Lys Lys Lys Phe Leu Gly Arg Pro Ile
65                  70                  75                  80

gag gtc tgg aag ctc tac ttc act cac ccc cag gac nnn ccc gca atc      288
Glu Val Trp Lys Leu Tyr Phe Thr His Pro Gln Asp Xaa Pro Ala Ile
                85                  90                  95

agg gac aag ata aag gag cat cct gcc gtt gtg gac atc tac gag tac      336
Arg Asp Lys Ile Lys Glu His Pro Ala Val Val Asp Ile Tyr Glu Tyr
            100                 105                 110

gac atc ccc ttc gcg aag cgc tac ctc ata gac aaa ggc tta atc ccg      384
Asp Ile Pro Phe Ala Lys Arg Tyr Leu Ile Asp Lys Gly Leu Ile Pro
        115                 120                 125
```

-continued

```
atg gag ggc gac gag gaa ctt aag atg ctc gcc ttc gac atc gag acg      432
Met Glu Gly Asp Glu Glu Leu Lys Met Leu Ala Phe Asp Ile Glu Thr
    130                 135                 140

ctc tat cac gag ggc gag gag ttc gcc gaa ggg cct atc ctg atg ata      480
Leu Tyr His Glu Gly Glu Glu Phe Ala Glu Gly Pro Ile Leu Met Ile
145                 150                 155                 160

agc tac gcc gac gag gaa ggg gcg cgc gtt att acc tgg aag aat atc      528
Ser Tyr Ala Asp Glu Glu Gly Ala Arg Val Ile Thr Trp Lys Asn Ile
                165                 170                 175

gac ctt ccc tat gtc gac gtc gtt tcc acc gag aag gag atg ata aag      576
Asp Leu Pro Tyr Val Asp Val Val Ser Thr Glu Lys Glu Met Ile Lys
            180                 185                 190

cgc ttc ctc aag gtc gtc aag gaa aag gat ccc gac gtc ctc ata acc      624
Arg Phe Leu Lys Val Val Lys Glu Lys Asp Pro Asp Val Leu Ile Thr
        195                 200                 205

tac aac ggc gac aac ttc gac ttc gcc tac ctc aag aag cgc tcc gag      672
Tyr Asn Gly Asp Asn Phe Asp Phe Ala Tyr Leu Lys Lys Arg Ser Glu
    210                 215                 220

aag ctc gga gtc aag ttc atc ctc gga agg gaa ggg agc gag ccg aaa      720
Lys Leu Gly Val Lys Phe Ile Leu Gly Arg Glu Gly Ser Glu Pro Lys
225                 230                 235                 240

atc cag cgc atg ggc gat cgc ttt gcg gtg gag gtc aag gga agg att      768
Ile Gln Arg Met Gly Asp Arg Phe Ala Val Glu Val Lys Gly Arg Ile
                245                 250                 255

cac ttc gac ctc tac ccc gtc att agg aga acg att aac ctc ccc act      816
His Phe Asp Leu Tyr Pro Val Ile Arg Arg Thr Ile Asn Leu Pro Thr
            260                 265                 270

tac acc ctt gag gca gta tat gaa gcc atc ttt gga cag ccg aag gag      864
Tyr Thr Leu Glu Ala Val Tyr Glu Ala Ile Phe Gly Gln Pro Lys Glu
        275                 280                 285

aag gtc tac gct gag gag ata gcg cag gcc tgg gaa acg ggc gag gga      912
Lys Val Tyr Ala Glu Glu Ile Ala Gln Ala Trp Glu Thr Gly Glu Gly
    290                 295                 300

tta gaa agg gtg gcc cgc tac tcg atg gag gac gca aag gta acc tat      960
Leu Glu Arg Val Ala Arg Tyr Ser Met Glu Asp Ala Lys Val Thr Tyr
305                 310                 315                 320

gaa ctc gga aaa gag ttc ttc cct atg gaa gcc cag ctc tcg cgc ctc     1008
Glu Leu Gly Lys Glu Phe Phe Pro Met Glu Ala Gln Leu Ser Arg Leu
                325                 330                 335

gta ggc cag agc ctc tgg gat gta tct cgc tcg agt acc gga aac ctc     1056
Val Gly Gln Ser Leu Trp Asp Val Ser Arg Ser Ser Thr Gly Asn Leu
            340                 345                 350

gtc gag tgg ttt ttg ctg agg aag gcc tac gag agg aat gaa ctt gca     1104
Val Glu Trp Phe Leu Leu Arg Lys Ala Tyr Glu Arg Asn Glu Leu Ala
        355                 360                 365

cca aac aag ccg gac gag agg gag ctg gca aga aga agg gag agc tac     1152
Pro Asn Lys Pro Asp Glu Arg Glu Leu Ala Arg Arg Arg Glu Ser Tyr
    370                 375                 380

gcg ggt gga tac gtc aag gag ccc gaa agg gga ctg tgg gag aac atc     1200
Ala Gly Gly Tyr Val Lys Glu Pro Glu Arg Gly Leu Trp Glu Asn Ile
385                 390                 395                 400

gtg tat ctg gac ttc cgc tcc ctg tat cct tcg ata ata atc acc cat     1248
Val Tyr Leu Asp Phe Arg Ser Leu Tyr Pro Ser Ile Ile Ile Thr His
                405                 410                 415

aac gtc tcc cct gat aca ctc aac agg gag ggt tgt gag gag tac gac     1296
Asn Val Ser Pro Asp Thr Leu Asn Arg Glu Gly Cys Glu Glu Tyr Asp
            420                 425                 430

gtg gct cct cag gta ggc cat aag ttc tgc aag gac ttc ccc ggc ttc     1344
Val Ala Pro Gln Val Gly His Lys Phe Cys Lys Asp Phe Pro Gly Phe
        435                 440                 445
```

-continued

```
atc cca agc ctc ctc gga gac ctc ttg gag gag aga cag aag gta aag      1392
Ile Pro Ser Leu Leu Gly Asp Leu Leu Glu Glu Arg Gln Lys Val Lys
    450                 455                 460

aag aag atg aag gcc act ata gac cca atc gag aag aaa ctc ctc gat      1440
Lys Lys Met Lys Ala Thr Ile Asp Pro Ile Glu Lys Lys Leu Leu Asp
465                 470                 475                 480

tac agg caa cga gca atc aaa atc ctt gct aat agc ttc tac ggt tac      1488
Tyr Arg Gln Arg Ala Ile Lys Ile Leu Ala Asn Ser Phe Tyr Gly Tyr
                485                 490                 495

tac ggc tat gca aag gcc cgc tgg tac tgc aag gag tgc gcc gag agc      1536
Tyr Gly Tyr Ala Lys Ala Arg Trp Tyr Cys Lys Glu Cys Ala Glu Ser
            500                 505                 510

gtt acc gct tgg ggc agg cag tac atc gag acc acg ata agg gaa ata      1584
Val Thr Ala Trp Gly Arg Gln Tyr Ile Glu Thr Thr Ile Arg Glu Ile
        515                 520                 525

gag gag aaa ttt ggc ttt aaa gtc ctc tac gcg gac aca gat gga ttt      1632
Glu Glu Lys Phe Gly Phe Lys Val Leu Tyr Ala Asp Thr Asp Gly Phe
    530                 535                 540

ttc gca aca ata cct gga gcg gac gcc gaa acc gtc aaa aag aag gca      1680
Phe Ala Thr Ile Pro Gly Ala Asp Ala Glu Thr Val Lys Lys Lys Ala
545                 550                 555                 560

aag gag ttc ctg gac tac atc aac gcc aaa ctg ccc ggc ctg ctc gaa      1728
Lys Glu Phe Leu Asp Tyr Ile Asn Ala Lys Leu Pro Gly Leu Leu Glu
                565                 570                 575

ctc gaa tac gag ggc ttc tac aag cgc ggc ttc ttc gtg acg aag aag      1776
Leu Glu Tyr Glu Gly Phe Tyr Lys Arg Gly Phe Phe Val Thr Lys Lys
            580                 585                 590

aag tac gcg gtt ata gac gag gag gac aag ata acg acg cgc ggg ctt      1824
Lys Tyr Ala Val Ile Asp Glu Glu Asp Lys Ile Thr Thr Arg Gly Leu
        595                 600                 605

gaa ata gtt agg cgt gac tgg agc gag ata gcg aag gag acg cag gcg      1872
Glu Ile Val Arg Arg Asp Trp Ser Glu Ile Ala Lys Glu Thr Gln Ala
    610                 615                 620

agg gtt ctt gag gcg ata cta aag cac ggt gac gtt gaa gaa gcg gta      1920
Arg Val Leu Glu Ala Ile Leu Lys His Gly Asp Val Glu Glu Ala Val
625                 630                 635                 640

agg att gtc aaa gag gtt acg gag aag ctg agc aag tac gag gtt cca      1968
Arg Ile Val Lys Glu Val Thr Glu Lys Leu Ser Lys Tyr Glu Val Pro
                645                 650                 655

ccg gag aag ctg gtc atc tac gag cag ata acc cgc gac ctg aag gac      2016
Pro Glu Lys Leu Val Ile Tyr Glu Gln Ile Thr Arg Asp Leu Lys Asp
            660                 665                 670

tac aag gcc acc ggg ccg cat gtg gct gtt gca aaa cgc ctc gcc gca      2064
Tyr Lys Ala Thr Gly Pro His Val Ala Val Ala Lys Arg Leu Ala Ala
        675                 680                 685

agg ggg ata aaa atc cgg ccc gga acg gtc ata agc tac atc gtg ctc      2112
Arg Gly Ile Lys Ile Arg Pro Gly Thr Val Ile Ser Tyr Ile Val Leu
    690                 695                 700

aaa ggc tcg gga agg att ggg gac agg gct ata ccc ttt gac gaa ttt      2160
Lys Gly Ser Gly Arg Ile Gly Asp Arg Ala Ile Pro Phe Asp Glu Phe
705                 710                 715                 720

gac ccg gca aag cac aag tac gat gca gaa tac tac atc gag aac cag      2208
Asp Pro Ala Lys His Lys Tyr Asp Ala Glu Tyr Tyr Ile Glu Asn Gln
                725                 730                 735

gtt ctt cca gct gtg gag agg att ctg agg gcc ttt ggt tac cgt aaa      2256
Val Leu Pro Ala Val Glu Arg Ile Leu Arg Ala Phe Gly Tyr Arg Lys
            740                 745                 750

gaa gat tta agg tat cag aaa acg cgg cag gtt ggc ttg ggg gcg tgg      2304
Glu Asp Leu Arg Tyr Gln Lys Thr Arg Gln Val Gly Leu Gly Ala Trp
        755                 760                 765
```

```
cta aaa cct aag aca tga                                            2322
Leu Lys Pro Lys Thr
    770


<210> SEQ ID NO 60
<211> LENGTH: 773
<212> TYPE: PRT
<213> ORGANISM: Thermococcus gorgonarius
<220> FEATURE:
<221> NAME/KEY: MOD_RES
<222> LOCATION: (93)..(93)
<223> OTHER INFORMATION: Lys, Asn, Arg, Ser, Thr, Ile, Met, Glu, Asp,
      Gly, Ala, Val, Gln, His, Pro, Leu, Tyr, Trp, Cys, or Phe.

<400> SEQUENCE: 60

Met Ile Leu Asp Thr Asp Tyr Ile Thr Glu Asp Gly Lys Pro Val Ile
1               5                   10                  15

Arg Ile Phe Lys Lys Glu Asn Gly Glu Phe Lys Ile Asp Tyr Asp Arg
            20                  25                  30

Asn Phe Glu Pro Tyr Ile Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Lys Phe Leu Gly Arg Pro Ile
65                  70                  75                  80

Glu Val Trp Lys Leu Tyr Phe Thr His Pro Gln Asp Xaa Pro Ala Ile
                85                  90                  95

Arg Asp Lys Ile Lys Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Lys Val Val Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Glu Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Ala Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335
```

-continued

```
Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Arg Glu Leu Ala Arg Arg Arg Glu Ser Tyr
    370                 375                 380

Ala Gly Gly Tyr Val Lys Glu Pro Glu Arg Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Glu Glu Tyr Asp
            420                 425                 430

Val Ala Pro Gln Val Gly His Lys Phe Cys Lys Asp Phe Pro Gly Phe
        435                 440                 445

Ile Pro Ser Leu Leu Gly Asp Leu Leu Glu Glu Arg Gln Lys Val Lys
    450                 455                 460

Lys Lys Met Lys Ala Thr Ile Asp Pro Ile Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Lys Glu Cys Ala Glu Ser
            500                 505                 510

Val Thr Ala Trp Gly Arg Gln Tyr Ile Glu Thr Thr Ile Arg Glu Ile
        515                 520                 525

Glu Glu Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ala
545                 550                 555                 560

Lys Glu Phe Leu Asp Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
            580                 585                 590

Lys Tyr Ala Val Ile Asp Glu Glu Asp Lys Ile Thr Thr Arg Gly Leu
        595                 600                 605

Glu Ile Val Arg Arg Asp Trp Ser Glu Ile Ala Lys Glu Thr Gln Ala
    610                 615                 620

Arg Val Leu Glu Ala Ile Leu Lys His Gly Asp Val Glu Glu Ala Val
625                 630                 635                 640

Arg Ile Val Lys Glu Val Thr Glu Lys Leu Ser Lys Tyr Glu Val Pro
                645                 650                 655

Pro Glu Lys Leu Val Ile Tyr Glu Gln Ile Thr Arg Asp Leu Lys Asp
            660                 665                 670

Tyr Lys Ala Thr Gly Pro His Val Ala Val Ala Lys Arg Leu Ala Ala
        675                 680                 685

Arg Gly Ile Lys Ile Arg Pro Gly Thr Val Ile Ser Tyr Ile Val Leu
    690                 695                 700

Lys Gly Ser Gly Arg Ile Gly Asp Arg Ala Ile Pro Phe Asp Glu Phe
705                 710                 715                 720

Asp Pro Ala Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
            740                 745                 750

Glu Asp Leu Arg Tyr Gln Lys Thr Arg Gln Val Gly Leu Gly Ala Trp
        755                 760                 765
```

```
Leu Lys Pro Lys Thr
    770


<210> SEQ ID NO 61
<211> LENGTH: 3499
<212> TYPE: DNA
<213> ORGANISM: Pyrococcus furiosus
<220> FEATURE:
<221> NAME/KEY: modified_base
<222> LOCATION: (2788)..(2789)
<223> OTHER INFORMATION: a, c, g, t, unknown or other
<220> FEATURE:
<221> NAME/KEY: modified_base
<222> LOCATION: (3287)..(3292)
<223> OTHER INFORMATION: a, c, g, t, unknown or other
<220> FEATURE:
<221> NAME/KEY: modified_base
<222> LOCATION: (3473)..(3473)
<223> OTHER INFORMATION: a, c, g, t, unknown or other
<220> FEATURE:
<221> NAME/KEY: modified_base
<222> LOCATION: (3478)..(3478)
<223> OTHER INFORMATION: a, c, g, t, unknown or other
<220> FEATURE:
<221> NAME/KEY: CDS
<222> LOCATION: (224)..(2551)

<400> SEQUENCE: 61

ccctggtcct gggtccacat atatgttctt actcgccttt atgaagaatc ccccagtcgc      60

tctaacctgg gttatagtga caaatcttcc tccaccaccg cccaagaagg ttatttctat     120

caactctaca cctcccctat tttctctctt atgagatttt taagtatagt tatagagaag     180

gttttatact ccaaactgag ttagtagata tgtggggagc ata atg att tta gat       235
                                                Met Ile Leu Asp
                                                1

gtg gat tac ata act gaa gaa gga aaa cct gtt att agg cta ttc aaa       283
Val Asp Tyr Ile Thr Glu Glu Gly Lys Pro Val Ile Arg Leu Phe Lys
5                   10                  15                  20

aaa gag aac gga aaa ttt aag ata gag cat gat aga act ttt aga cca       331
Lys Glu Asn Gly Lys Phe Lys Ile Glu His Asp Arg Thr Phe Arg Pro
                25                  30                  35

tac att tac gct ctt ctc agg gat gat tca aag att gaa gaa gtt aag       379
Tyr Ile Tyr Ala Leu Leu Arg Asp Asp Ser Lys Ile Glu Glu Val Lys
            40                  45                  50

aaa ata acg ggg gaa agg cat gga aag att gtg aga att gtt gat gta       427
Lys Ile Thr Gly Glu Arg His Gly Lys Ile Val Arg Ile Val Asp Val
        55                  60                  65

gag aag gtt gag aaa aag ttt ctc ggc aag cct att acc gtg tgg aaa       475
Glu Lys Val Glu Lys Lys Phe Leu Gly Lys Pro Ile Thr Val Trp Lys
    70                  75                  80

ctt tat ttg gaa cat ccc caa gat gtt ccc act att aga gaa aaa gtt       523
Leu Tyr Leu Glu His Pro Gln Asp Val Pro Thr Ile Arg Glu Lys Val
85                  90                  95                  100

aga gaa cat cca gca gtt gtg gac atc ttc gaa tac gat att cca ttt       571
Arg Glu His Pro Ala Val Val Asp Ile Phe Glu Tyr Asp Ile Pro Phe
                105                 110                 115

gca aag aga tac ctc atc gac aaa ggc cta ata cca atg gag ggg gaa       619
Ala Lys Arg Tyr Leu Ile Asp Lys Gly Leu Ile Pro Met Glu Gly Glu
            120                 125                 130

gaa gag cta aag att ctt gcc ttc gat ata gaa acc ctc tat cac gaa       667
Glu Glu Leu Lys Ile Leu Ala Phe Asp Ile Glu Thr Leu Tyr His Glu
        135                 140                 145

gga gaa gag ttt gga aaa ggc cca att ata atg att agt tat gca gat       715
Gly Glu Glu Phe Gly Lys Gly Pro Ile Ile Met Ile Ser Tyr Ala Asp
    150                 155                 160
```

-continued

```
gaa aat gaa gca aag gtg att act tgg aaa aac ata gat ctt cca tac      763
Glu Asn Glu Ala Lys Val Ile Thr Trp Lys Asn Ile Asp Leu Pro Tyr
165                 170                 175                 180

gtt gag gtt gta tca agc gag aga gag atg ata aag aga ttt ctc agg      811
Val Glu Val Val Ser Ser Glu Arg Glu Met Ile Lys Arg Phe Leu Arg
                185                 190                 195

att atc agg gag aag gat cct gac att ata gtt act tat aat gga gac      859
Ile Ile Arg Glu Lys Asp Pro Asp Ile Ile Val Thr Tyr Asn Gly Asp
            200                 205                 210

tca ttc gac ttc cca tat tta gcg aaa agg gca gaa aaa ctt ggg att      907
Ser Phe Asp Phe Pro Tyr Leu Ala Lys Arg Ala Glu Lys Leu Gly Ile
        215                 220                 225

aaa tta acc att gga aga gat gga agc gag ccc aag atg cag aga ata      955
Lys Leu Thr Ile Gly Arg Asp Gly Ser Glu Pro Lys Met Gln Arg Ile
    230                 235                 240

ggc gat atg acg gct gta gaa gtc aag gga aga ata cat ttc gac ttg     1003
Gly Asp Met Thr Ala Val Glu Val Lys Gly Arg Ile His Phe Asp Leu
245                 250                 255                 260

tat cat gta ata aca agg aca ata aat ctc cca aca tac aca cta gag     1051
Tyr His Val Ile Thr Arg Thr Ile Asn Leu Pro Thr Tyr Thr Leu Glu
                265                 270                 275

gct gta tat gaa gca att ttt gga aag cca aag gag aag gta tac gcc     1099
Ala Val Tyr Glu Ala Ile Phe Gly Lys Pro Lys Glu Lys Val Tyr Ala
            280                 285                 290

gac gag ata gca aaa gcc tgg gaa agt gga gag aac ctt gag aga gtt     1147
Asp Glu Ile Ala Lys Ala Trp Glu Ser Gly Glu Asn Leu Glu Arg Val
        295                 300                 305

gcc aaa tac tcg atg gaa gat gca aag gca act tat gaa ctc ggg aaa     1195
Ala Lys Tyr Ser Met Glu Asp Ala Lys Ala Thr Tyr Glu Leu Gly Lys
    310                 315                 320

gaa ttc ctt cca atg gaa att cag ctt tca aga tta gtt gga caa cct     1243
Glu Phe Leu Pro Met Glu Ile Gln Leu Ser Arg Leu Val Gly Gln Pro
325                 330                 335                 340

tta tgg gat gtt tca agg tca agc aca ggg aac ctt gta gag tgg ttc     1291
Leu Trp Asp Val Ser Arg Ser Ser Thr Gly Asn Leu Val Glu Trp Phe
                345                 350                 355

tta ctt agg aaa gcc tac gaa aga aac gaa gta gct cca aac aag cca     1339
Leu Leu Arg Lys Ala Tyr Glu Arg Asn Glu Val Ala Pro Asn Lys Pro
            360                 365                 370

agt gaa gag gag tat caa aga agg ctc agg gag agc tac aca ggt gga     1387
Ser Glu Glu Glu Tyr Gln Arg Arg Leu Arg Glu Ser Tyr Thr Gly Gly
        375                 380                 385

ttc gtt aaa gag cca gaa aag ggg ttg tgg gaa aac ata gta tac cta     1435
Phe Val Lys Glu Pro Glu Lys Gly Leu Trp Glu Asn Ile Val Tyr Leu
    390                 395                 400

gat ttt aga gcc cta tat ccc tcg att ata att acc cac aat gtt tct     1483
Asp Phe Arg Ala Leu Tyr Pro Ser Ile Ile Ile Thr His Asn Val Ser
405                 410                 415                 420

ccc gat act cta aat ctt gag gga tgc aag aac tat gat atc gct cct     1531
Pro Asp Thr Leu Asn Leu Glu Gly Cys Lys Asn Tyr Asp Ile Ala Pro
                425                 430                 435

caa gta ggc cac aag ttc tgc aag gac atc cct ggt ttt ata cca agt     1579
Gln Val Gly His Lys Phe Cys Lys Asp Ile Pro Gly Phe Ile Pro Ser
            440                 445                 450

ctc ttg gga cat ttg tta gag gaa aga caa aag att aag aca aaa atg     1627
Leu Leu Gly His Leu Leu Glu Glu Arg Gln Lys Ile Lys Thr Lys Met
        455                 460                 465

aag gaa act caa gat cct ata gaa aaa ata ctc ctt gac tat aga caa     1675
Lys Glu Thr Gln Asp Pro Ile Glu Lys Ile Leu Leu Asp Tyr Arg Gln
    470                 475                 480
```

```
aaa gcg ata aaa ctc tta gca aat tct ttc tac gga tat tat ggc tat     1723
Lys Ala Ile Lys Leu Leu Ala Asn Ser Phe Tyr Gly Tyr Tyr Gly Tyr
485                 490                 495                 500

gca aaa gca aga tgg tac tgt aag gag tgt gct gag agc gtt act gcc     1771
Ala Lys Ala Arg Trp Tyr Cys Lys Glu Cys Ala Glu Ser Val Thr Ala
                505                 510                 515

tgg gga aga aag tac atc gag tta gta tgg aag gag ctc gaa gaa aag     1819
Trp Gly Arg Lys Tyr Ile Glu Leu Val Trp Lys Glu Leu Glu Glu Lys
            520                 525                 530

ttt gga ttt aaa gtc ctc tac att gac act gat ggt ctc tat gca act     1867
Phe Gly Phe Lys Val Leu Tyr Ile Asp Thr Asp Gly Leu Tyr Ala Thr
        535                 540                 545

atc cca gga gga gaa agt gag gaa ata aag aaa aag gct cta gaa ttt     1915
Ile Pro Gly Gly Glu Ser Glu Glu Ile Lys Lys Lys Ala Leu Glu Phe
    550                 555                 560

gta aaa tac ata aat tca aag ctc cct gga ctg cta gag ctt gaa tat     1963
Val Lys Tyr Ile Asn Ser Lys Leu Pro Gly Leu Leu Glu Leu Glu Tyr
565                 570                 575                 580

gaa ggg ttt tat aag agg gga ttc ttc gtt acg aag aag agg tat gca     2011
Glu Gly Phe Tyr Lys Arg Gly Phe Phe Val Thr Lys Lys Arg Tyr Ala
                585                 590                 595

gta ata gat gaa gaa gga aaa gtc att act cgt ggt tta gag ata gtt     2059
Val Ile Asp Glu Glu Gly Lys Val Ile Thr Arg Gly Leu Glu Ile Val
            600                 605                 610

agg aga gat tgg agt gaa att gca aaa gaa act caa gct aga gtt ttg     2107
Arg Arg Asp Trp Ser Glu Ile Ala Lys Glu Thr Gln Ala Arg Val Leu
        615                 620                 625

gag aca ata cta aaa cac gga gat gtt gaa gaa gct gtg aga ata gta     2155
Glu Thr Ile Leu Lys His Gly Asp Val Glu Glu Ala Val Arg Ile Val
    630                 635                 640

aaa gaa gta ata caa aag ctt gcc aat tat gaa att cca cca gag aag     2203
Lys Glu Val Ile Gln Lys Leu Ala Asn Tyr Glu Ile Pro Pro Glu Lys
645                 650                 655                 660

ctc gca ata tat gag cag ata aca aga cca tta cat gag tat aag gcg     2251
Leu Ala Ile Tyr Glu Gln Ile Thr Arg Pro Leu His Glu Tyr Lys Ala
                665                 670                 675

ata ggt cct cac gta gct gtt gca aag aaa cta gct gct aaa gga gtt     2299
Ile Gly Pro His Val Ala Val Ala Lys Lys Leu Ala Ala Lys Gly Val
            680                 685                 690

aaa ata aag cca gga atg gta att gga tac ata gta ctt aga ggc gat     2347
Lys Ile Lys Pro Gly Met Val Ile Gly Tyr Ile Val Leu Arg Gly Asp
        695                 700                 705

ggt cca att agc aat agg gca att cta gct gag gaa tac gat ccc aaa     2395
Gly Pro Ile Ser Asn Arg Ala Ile Leu Ala Glu Glu Tyr Asp Pro Lys
    710                 715                 720

aag cac aag tat gac gca gaa tat tac att gag aac cag gtt ctt cca     2443
Lys His Lys Tyr Asp Ala Glu Tyr Tyr Ile Glu Asn Gln Val Leu Pro
725                 730                 735                 740

gcg gta ctt agg ata ttg gag gga ttt gga tac aga aag gaa gac ctc     2491
Ala Val Leu Arg Ile Leu Glu Gly Phe Gly Tyr Arg Lys Glu Asp Leu
                745                 750                 755

aga tac caa aag aca aga caa gtc ggc cta act tcc tgg ctt aac att     2539
Arg Tyr Gln Lys Thr Arg Gln Val Gly Leu Thr Ser Trp Leu Asn Ile
            760                 765                 770

aaa aaa tcc tag aaaagcgata gatatcaact tttattcttt ctaacctttt         2591
Lys Lys Ser
        775

tctatgaaag aagaactgag caggaattac cagttcttcc gttattttat gggtaattaa   2651

aaacccatgc tcttgggaga atcttcgaat aaaatcccta acttcaggct ttgctaagtg   2711
```

```
aatagaataa acaacatcac tcacttcaaa cgccttcgtt agaaatggtc tatctgcatg   2771

cttctctggc tcggaanngg aggattcata acaacagtat caacattctc agagaattga   2831

gaaacatcag aaactttgac ttctacaaca tttctaactt tgcaactctt caagattttc   2891

taaaagaatt ttaacggcct cctcgtcaat ttcgacgacg tagatctttt ttgctccaag   2951

cagagccgct ccaatggata acacccctgt tcccgcaccc aagtccgcta caatttttttc  3011

cttgtatctc ctaatgtata agcaagccaa aggagagtag atgctacctt tccgggagtt   3071

ttgtattgct ctagccaagg tttgggattt ttgaatcctt taactctgga aagtataatt   3131

tcaagctcct tcttcttcat gacagatgaa aaattgtttt gtctcttttt aacttttaca   3191

gaaataactg tctcaaatta tgacaactct tgacattttt acttcattac cagggtaatg   3251

tttttaagta tgaaattttt ctttcataga ggaggnnnnn ngtcctctcc tcgatttcct   3311

tggttgtgct ccatatgata agcttccaaa gtgggtgttc agacttttag acactcaaat   3371

accagacgac aatggtgtgc tcactcaagc cccatatggg ttgagaaaag tagaagcggc   3431

actactcaga tgcttcccca ggaatgaggt tgttgtagct cntcccngaa agattgagat   3491

gttcttgg                                                            3499
```

```
<210> SEQ ID NO 62
<211> LENGTH: 775
<212> TYPE: PRT
<213> ORGANISM: Pyrococcus furiosus

<400> SEQUENCE: 62

Met Ile Leu Asp Val Asp Tyr Ile Thr Glu Glu Gly Lys Pro Val Ile
1               5                   10                  15

Arg Leu Phe Lys Lys Glu Asn Gly Lys Phe Lys Ile Glu His Asp Arg
            20                  25                  30

Thr Phe Arg Pro Tyr Ile Tyr Ala Leu Leu Arg Asp Asp Ser Lys Ile
        35                  40                  45

Glu Glu Val Lys Lys Ile Thr Gly Glu Arg His Gly Lys Ile Val Arg
    50                  55                  60

Ile Val Asp Val Glu Lys Val Glu Lys Lys Phe Leu Gly Lys Pro Ile
65                  70                  75                  80

Thr Val Trp Lys Leu Tyr Leu Glu His Pro Gln Asp Val Pro Thr Ile
                85                  90                  95

Arg Glu Lys Val Arg Glu His Pro Ala Val Val Asp Ile Phe Glu Tyr
            100                 105                 110

Asp Ile Pro Phe Ala Lys Arg Tyr Leu Ile Asp Lys Gly Leu Ile Pro
        115                 120                 125

Met Glu Gly Glu Glu Glu Leu Lys Ile Leu Ala Phe Asp Ile Glu Thr
    130                 135                 140

Leu Tyr His Glu Gly Glu Glu Phe Gly Lys Gly Pro Ile Ile Met Ile
145                 150                 155                 160

Ser Tyr Ala Asp Glu Asn Glu Ala Lys Val Ile Thr Trp Lys Asn Ile
                165                 170                 175

Asp Leu Pro Tyr Val Glu Val Val Ser Ser Glu Arg Glu Met Ile Lys
            180                 185                 190

Arg Phe Leu Arg Ile Ile Arg Glu Lys Asp Pro Asp Ile Ile Val Thr
        195                 200                 205

Tyr Asn Gly Asp Ser Phe Asp Phe Pro Tyr Leu Ala Lys Arg Ala Glu
    210                 215                 220

Lys Leu Gly Ile Lys Leu Thr Ile Gly Arg Asp Gly Ser Glu Pro Lys
```

-continued

```
225                 230                 235                 240

Met Gln Arg Ile Gly Asp Met Thr Ala Val Glu Val Lys Gly Arg Ile
                245                 250                 255

His Phe Asp Leu Tyr His Val Ile Thr Arg Thr Ile Asn Leu Pro Thr
            260                 265                 270

Tyr Thr Leu Glu Ala Val Tyr Glu Ala Ile Phe Gly Lys Pro Lys Glu
        275                 280                 285

Lys Val Tyr Ala Asp Glu Ile Ala Lys Ala Trp Glu Ser Gly Glu Asn
    290                 295                 300

Leu Glu Arg Val Ala Lys Tyr Ser Met Glu Asp Ala Lys Ala Thr Tyr
305                 310                 315                 320

Glu Leu Gly Lys Glu Phe Leu Pro Met Glu Ile Gln Leu Ser Arg Leu
                325                 330                 335

Val Gly Gln Pro Leu Trp Asp Val Ser Arg Ser Ser Thr Gly Asn Leu
            340                 345                 350

Val Glu Trp Phe Leu Leu Arg Lys Ala Tyr Glu Arg Asn Glu Val Ala
        355                 360                 365

Pro Asn Lys Pro Ser Glu Glu Glu Tyr Gln Arg Arg Leu Arg Glu Ser
    370                 375                 380

Tyr Thr Gly Gly Phe Val Lys Glu Pro Glu Lys Gly Leu Trp Glu Asn
385                 390                 395                 400

Ile Val Tyr Leu Asp Phe Arg Ala Leu Tyr Pro Ser Ile Ile Ile Thr
                405                 410                 415

His Asn Val Ser Pro Asp Thr Leu Asn Leu Glu Gly Cys Lys Asn Tyr
            420                 425                 430

Asp Ile Ala Pro Gln Val Gly His Lys Phe Cys Lys Asp Ile Pro Gly
        435                 440                 445

Phe Ile Pro Ser Leu Leu Gly His Leu Leu Glu Glu Arg Gln Lys Ile
    450                 455                 460

Lys Thr Lys Met Lys Glu Thr Gln Asp Pro Ile Glu Lys Ile Leu Leu
465                 470                 475                 480

Asp Tyr Arg Gln Lys Ala Ile Lys Leu Leu Ala Asn Ser Phe Tyr Gly
                485                 490                 495

Tyr Tyr Gly Tyr Ala Lys Ala Arg Trp Tyr Cys Lys Glu Cys Ala Glu
            500                 505                 510

Ser Val Thr Ala Trp Gly Arg Lys Tyr Ile Glu Leu Val Trp Lys Glu
        515                 520                 525

Leu Glu Glu Lys Phe Gly Phe Lys Val Leu Tyr Ile Asp Thr Asp Gly
    530                 535                 540

Leu Tyr Ala Thr Ile Pro Gly Gly Glu Ser Glu Glu Ile Lys Lys Lys
545                 550                 555                 560

Ala Leu Glu Phe Val Lys Tyr Ile Asn Ser Lys Leu Pro Gly Leu Leu
                565                 570                 575

Glu Leu Glu Tyr Glu Gly Phe Tyr Lys Arg Gly Phe Phe Val Thr Lys
            580                 585                 590

Lys Arg Tyr Ala Val Ile Asp Glu Glu Gly Lys Val Ile Thr Arg Gly
        595                 600                 605

Leu Glu Ile Val Arg Arg Asp Trp Ser Glu Ile Ala Lys Glu Thr Gln
    610                 615                 620

Ala Arg Val Leu Glu Thr Ile Leu Lys His Gly Asp Val Glu Glu Ala
625                 630                 635                 640

Val Arg Ile Val Lys Glu Val Ile Gln Lys Leu Ala Asn Tyr Glu Ile
                645                 650                 655
```

```
Pro Pro Glu Lys Leu Ala Ile Tyr Glu Gln Ile Thr Arg Pro Leu His
            660                 665                 670

Glu Tyr Lys Ala Ile Gly Pro His Val Ala Val Ala Lys Lys Leu Ala
        675                 680                 685

Ala Lys Gly Val Lys Ile Lys Pro Gly Met Val Ile Gly Tyr Ile Val
    690                 695                 700

Leu Arg Gly Asp Gly Pro Ile Ser Asn Arg Ala Ile Leu Ala Glu Glu
705                 710                 715                 720

Tyr Asp Pro Lys Lys His Lys Tyr Asp Ala Glu Tyr Tyr Ile Glu Asn
            725                 730                 735

Gln Val Leu Pro Ala Val Leu Arg Ile Leu Glu Gly Phe Gly Tyr Arg
            740                 745                 750

Lys Glu Asp Leu Arg Tyr Gln Lys Thr Arg Gln Val Gly Leu Thr Ser
        755                 760                 765

Trp Leu Asn Ile Lys Lys Ser
    770                 775


<210> SEQ ID NO 63
<211> LENGTH: 207
<212> TYPE: DNA
<213> ORGANISM: Pyrococcus furiosus
<220> FEATURE:
<221> NAME/KEY: CDS
<222> LOCATION: (1)..(207)

<400> SEQUENCE: 63

atg atg gga gaa tta cca att gcc cca gtt gac aga ctt ata aga aag        48
Met Met Gly Glu Leu Pro Ile Ala Pro Val Asp Arg Leu Ile Arg Lys
1               5                   10                  15

gct ggt gct cag aga gtt agc gag caa gca gct aag gta ctt gca gag        96
Ala Gly Ala Gln Arg Val Ser Glu Gln Ala Ala Lys Val Leu Ala Glu
            20                  25                  30

cac ctt gag gaa aaa gct att gag atc gca aaa aag gca gta gat ctt       144
His Leu Glu Glu Lys Ala Ile Glu Ile Ala Lys Lys Ala Val Asp Leu
        35                  40                  45

gca aag cac gca ggt aga aag acc gtt aag gtc gaa gac att aag ctc       192
Ala Lys His Ala Gly Arg Lys Thr Val Lys Val Glu Asp Ile Lys Leu
    50                  55                  60

gca att aag agc tga                                                   207
Ala Ile Lys Ser
65


<210> SEQ ID NO 64
<211> LENGTH: 68
<212> TYPE: PRT
<213> ORGANISM: Pyrococcus furiosus

<400> SEQUENCE: 64

Met Met Gly Glu Leu Pro Ile Ala Pro Val Asp Arg Leu Ile Arg Lys
1               5                   10                  15

Ala Gly Ala Gln Arg Val Ser Glu Gln Ala Ala Lys Val Leu Ala Glu
            20                  25                  30

His Leu Glu Glu Lys Ala Ile Glu Ile Ala Lys Lys Ala Val Asp Leu
        35                  40                  45

Ala Lys His Ala Gly Arg Lys Thr Val Lys Val Glu Asp Ile Lys Leu
    50                  55                  60

Ala Ile Lys Ser
65


<210> SEQ ID NO 65
```

<211> LENGTH: 2556
<212> TYPE: DNA
<213> ORGANISM: Thermus aquaticus
<220> FEATURE:
<221> NAME/KEY: CDS
<222> LOCATION: (1)..(2556)

<400> SEQUENCE: 65

```
ggc ggc ggt gtc act agt ggg atg ctg ccc ctc ttt gag ccc aag ggc       48
Gly Gly Gly Val Thr Ser Gly Met Leu Pro Leu Phe Glu Pro Lys Gly
1               5                   10                  15

cgg gtc ctc ctg gtg gac ggc cac cac ctg gcc tac cgc acc ttc cac       96
Arg Val Leu Leu Val Asp Gly His His Leu Ala Tyr Arg Thr Phe His
            20                  25                  30

gcc ctg aag ggc ctc acc acc agc cgg ggg gag ccg gtg cag gcg gtc      144
Ala Leu Lys Gly Leu Thr Thr Ser Arg Gly Glu Pro Val Gln Ala Val
        35                  40                  45

tac ggc ttc gcc aag agc ctc ctc aag gcc ctc aag gag gac ggg gac      192
Tyr Gly Phe Ala Lys Ser Leu Leu Lys Ala Leu Lys Glu Asp Gly Asp
    50                  55                  60

gcg gtg atc gtg gtc ttt gac gcc aag gcc ccc tcc ttc cgc cac gag      240
Ala Val Ile Val Val Phe Asp Ala Lys Ala Pro Ser Phe Arg His Glu
65                  70                  75                  80

gcc tac ggg ggg tac aag gcg ggc cgg gcc ccc acg cca gag gac ttt      288
Ala Tyr Gly Gly Tyr Lys Ala Gly Arg Ala Pro Thr Pro Glu Asp Phe
                85                  90                  95

ccc cgg caa ctc gcc ctc atc aag gag ctg gtg gac ctc ctg ggg ctg      336
Pro Arg Gln Leu Ala Leu Ile Lys Glu Leu Val Asp Leu Leu Gly Leu
            100                 105                 110

gcg cgc ctc gag gtc ccg ggc tac gag gcg gac gac gtc ctg gcc agc      384
Ala Arg Leu Glu Val Pro Gly Tyr Glu Ala Asp Asp Val Leu Ala Ser
        115                 120                 125

ctg gcc aag aag gcg gaa aag gag ggc tac gag gtc cgc atc ctc acc      432
Leu Ala Lys Lys Ala Glu Lys Glu Gly Tyr Glu Val Arg Ile Leu Thr
    130                 135                 140

gcc gac aaa gac ctt tac cag ctc ctt tcc gac cgc atc cac gtc ctc      480
Ala Asp Lys Asp Leu Tyr Gln Leu Leu Ser Asp Arg Ile His Val Leu
145                 150                 155                 160

cac ccc gag ggg tac ctc atc acc ccg gcc tgg ctt tgg gaa aag tac      528
His Pro Glu Gly Tyr Leu Ile Thr Pro Ala Trp Leu Trp Glu Lys Tyr
                165                 170                 175

ggc ctg agg ccc gac cag tgg gcc gac tac cgg gcc ctg acc ggg gac      576
Gly Leu Arg Pro Asp Gln Trp Ala Asp Tyr Arg Ala Leu Thr Gly Asp
            180                 185                 190

gag tcc gac aac ctt ccc ggg gtc aag ggc atc ggg gag aag acg gcg      624
Glu Ser Asp Asn Leu Pro Gly Val Lys Gly Ile Gly Glu Lys Thr Ala
        195                 200                 205

agg aag ctt ctg gag gag tgg ggg agc ctg gaa gcc ctc ctc aag aac      672
Arg Lys Leu Leu Glu Glu Trp Gly Ser Leu Glu Ala Leu Leu Lys Asn
    210                 215                 220

ctg gac cgg ctg aag ccc gcc atc cgg gag aag atc ctg gcc cac atg      720
Leu Asp Arg Leu Lys Pro Ala Ile Arg Glu Lys Ile Leu Ala His Met
225                 230                 235                 240

gac gat ctg aag ctc tcc tgg gac ctg gcc aag gtg cgc acc gac ctg      768
Asp Asp Leu Lys Leu Ser Trp Asp Leu Ala Lys Val Arg Thr Asp Leu
                245                 250                 255

ccc ctg gag gtg gac ttc gcc aaa agg cgg gag ccc gac cgg gag agg      816
Pro Leu Glu Val Asp Phe Ala Lys Arg Arg Glu Pro Asp Arg Glu Arg
            260                 265                 270

ctt agg gcc ttt ctg gag agg ctt gag ttt ggc agc ctc ctc cac gag      864
Leu Arg Ala Phe Leu Glu Arg Leu Glu Phe Gly Ser Leu Leu His Glu
        275                 280                 285
```

-continued

```
ttc ggc ctt ctg gaa agc ccc aag gcc ctg gag gag gcc ccc tgg ccc       912
Phe Gly Leu Leu Glu Ser Pro Lys Ala Leu Glu Glu Ala Pro Trp Pro
    290                 295                 300

ccg ccg gaa ggg gcc ttc gtg ggc ttt gtg ctt tcc cgc aag gag ccc       960
Pro Pro Glu Gly Ala Phe Val Gly Phe Val Leu Ser Arg Lys Glu Pro
305                 310                 315                 320

atg tgg gcc gat ctt ctg gcc ctg gcc gcc gcc agg ggg ggc cgg gtc      1008
Met Trp Ala Asp Leu Leu Ala Leu Ala Ala Ala Arg Gly Gly Arg Val
                325                 330                 335

cac cgg gcc ccc gag cct tat aaa gcc ctc agg gac ctg aag gag gcg      1056
His Arg Ala Pro Glu Pro Tyr Lys Ala Leu Arg Asp Leu Lys Glu Ala
            340                 345                 350

cgg ggg ctt ctc gcc aaa gac ctg agc gtt ctg gcc ctg agg gaa ggc      1104
Arg Gly Leu Leu Ala Lys Asp Leu Ser Val Leu Ala Leu Arg Glu Gly
        355                 360                 365

ctt ggc ctc ccg ccc ggc gac gac ccc atg ctc ctc gcc tac ctc ctg      1152
Leu Gly Leu Pro Pro Gly Asp Asp Pro Met Leu Leu Ala Tyr Leu Leu
    370                 375                 380

gac cct tcc aac acc acc ccc gag ggg gtg gcc cgg cgc tac ggc ggg      1200
Asp Pro Ser Asn Thr Thr Pro Glu Gly Val Ala Arg Arg Tyr Gly Gly
385                 390                 395                 400

gag tgg acg gag gag gcg ggg gag cgg gcc gcc ctt tcc gag agg ctc      1248
Glu Trp Thr Glu Glu Ala Gly Glu Arg Ala Ala Leu Ser Glu Arg Leu
                405                 410                 415

ttc gcc aac ctg tgg ggg agg ctt gag ggg gag gag agg ctc ctt tgg      1296
Phe Ala Asn Leu Trp Gly Arg Leu Glu Gly Glu Glu Arg Leu Leu Trp
            420                 425                 430

ctt tac cgg gag gtg gag agg ccc ctt tcc gct gtc ctg gcc cac atg      1344
Leu Tyr Arg Glu Val Glu Arg Pro Leu Ser Ala Val Leu Ala His Met
        435                 440                 445

gag gcc acg ggg gtg cgc ctg gac gtg gcc tat ctc agg gcc ttg tcc      1392
Glu Ala Thr Gly Val Arg Leu Asp Val Ala Tyr Leu Arg Ala Leu Ser
    450                 455                 460

ctg gag gtg gcc gag gag atc gcc cgc ctc gag gcc gag gtc ttc cgc      1440
Leu Glu Val Ala Glu Glu Ile Ala Arg Leu Glu Ala Glu Val Phe Arg
465                 470                 475                 480

ctg gcc ggc cac ccc ttc aac ctc aac tcc cgg gac cag ctg gaa agg      1488
Leu Ala Gly His Pro Phe Asn Leu Asn Ser Arg Asp Gln Leu Glu Arg
                485                 490                 495

gtc ctc ttt gac gag cta ggg ctt ccc gcc atc ggc aag acg gag aag      1536
Val Leu Phe Asp Glu Leu Gly Leu Pro Ala Ile Gly Lys Thr Glu Lys
            500                 505                 510

acc ggc aag cgc tcc acc agc gcc gcc gtc ctg gag gcc ctc cgc gag      1584
Thr Gly Lys Arg Ser Thr Ser Ala Ala Val Leu Glu Ala Leu Arg Glu
        515                 520                 525

gcc cac ccc atc gtg gag aag atc ctg cag tac cgg gag ctc acc aag      1632
Ala His Pro Ile Val Glu Lys Ile Leu Gln Tyr Arg Glu Leu Thr Lys
    530                 535                 540

ctg aag agc acc tac att gac ccc ttg ccg gac ctc atc cac ccc agg      1680
Leu Lys Ser Thr Tyr Ile Asp Pro Leu Pro Asp Leu Ile His Pro Arg
545                 550                 555                 560

acg ggc cgc ctc cac acc cgc ttc aac cag acg gcc acg gcc acg ggc      1728
Thr Gly Arg Leu His Thr Arg Phe Asn Gln Thr Ala Thr Ala Thr Gly
                565                 570                 575

agg cta agt agc tcc gat ccc aac ctc cag aac atc ccc gtc cgc acc      1776
Arg Leu Ser Ser Ser Asp Pro Asn Leu Gln Asn Ile Pro Val Arg Thr
            580                 585                 590

ccg ctt ggg cag agg atc cgc cgg gcc ttc atc gcc gag gag ggg tgg      1824
Pro Leu Gly Gln Arg Ile Arg Arg Ala Phe Ile Ala Glu Glu Gly Trp
        595                 600                 605
```

```
cta ttg gtg gcc ctg gac tat agc cag ata gag ctc agg gtg ctg gcc      1872
Leu Leu Val Ala Leu Asp Tyr Ser Gln Ile Glu Leu Arg Val Leu Ala
    610                 615                 620

cac ctc tcc ggc gac gag aac ctg atc cgg gtc ttc cag gag ggg cgg      1920
His Leu Ser Gly Asp Glu Asn Leu Ile Arg Val Phe Gln Glu Gly Arg
625                 630                 635                 640

gac atc cac acg gag acc gcc agc tgg atg ttc ggc gtc ccc cgg gag      1968
Asp Ile His Thr Glu Thr Ala Ser Trp Met Phe Gly Val Pro Arg Glu
                645                 650                 655

gcc gtg gac ccc ctg atg cgc cgg gcg gcc aag acc atc aac ttc ggg      2016
Ala Val Asp Pro Leu Met Arg Arg Ala Ala Lys Thr Ile Asn Phe Gly
            660                 665                 670

gtc ctc tac ggc atg tcg gcc cac cgc ctc tcc cag gag cta gcc atc      2064
Val Leu Tyr Gly Met Ser Ala His Arg Leu Ser Gln Glu Leu Ala Ile
        675                 680                 685

cct tac gag gag gcc cag gcc ttc att gag cgc tac ttt cag agc ttc      2112
Pro Tyr Glu Glu Ala Gln Ala Phe Ile Glu Arg Tyr Phe Gln Ser Phe
    690                 695                 700

ccc aag gtg cgg gcc tgg att gag aag acc ctg gag gag ggc agg agg      2160
Pro Lys Val Arg Ala Trp Ile Glu Lys Thr Leu Glu Glu Gly Arg Arg
705                 710                 715                 720

cgg ggg tac gtg gag acc ctc ttc ggc cgc cgc cgc tac gtg cca gac      2208
Arg Gly Tyr Val Glu Thr Leu Phe Gly Arg Arg Arg Tyr Val Pro Asp
                725                 730                 735

cta gag gcc cgg gtg aag agc gtg cgg gag gcg gcc gag cgc atg gcc      2256
Leu Glu Ala Arg Val Lys Ser Val Arg Glu Ala Ala Glu Arg Met Ala
            740                 745                 750

ttc aac atg ccc gtc cag ggc acc gcc gcc gac ctc atg aag ctg gct      2304
Phe Asn Met Pro Val Gln Gly Thr Ala Ala Asp Leu Met Lys Leu Ala
        755                 760                 765

atg gtg aag ctc ttc ccc agg ctg gag gaa atg ggg gcc agg atg ctc      2352
Met Val Lys Leu Phe Pro Arg Leu Glu Glu Met Gly Ala Arg Met Leu
    770                 775                 780

ctt cag gtc cac gac gag ctg gtc ctc gag gcc cca aaa gag agg gcg      2400
Leu Gln Val His Asp Glu Leu Val Leu Glu Ala Pro Lys Glu Arg Ala
785                 790                 795                 800

gag gcc gtg gcc cgg ctg gcc aag gag gtc atg gag ggg gtg tat ccc      2448
Glu Ala Val Ala Arg Leu Ala Lys Glu Val Met Glu Gly Val Tyr Pro
                805                 810                 815

ctg gcc gtg ccc ctg gag gtg gag gtg ggg ata ggg gag gac tgg ctc      2496
Leu Ala Val Pro Leu Glu Val Glu Val Gly Ile Gly Glu Asp Trp Leu
            820                 825                 830

tcc gcc aag gag ggc att gat ggc cgc ggc gga ggc ggg cat cat cat      2544
Ser Ala Lys Glu Gly Ile Asp Gly Arg Gly Gly Gly Gly His His His
        835                 840                 845

cat cat cat taa                                                      2556
His His His
    850


<210> SEQ ID NO 66
<211> LENGTH: 851
<212> TYPE: PRT
<213> ORGANISM: Thermus aquaticus

<400> SEQUENCE: 66

Gly Gly Gly Val Thr Ser Gly Met Leu Pro Leu Phe Glu Pro Lys Gly
1               5                   10                  15

Arg Val Leu Leu Val Asp Gly His His Leu Ala Tyr Arg Thr Phe His
            20                  25                  30

Ala Leu Lys Gly Leu Thr Thr Ser Arg Gly Glu Pro Val Gln Ala Val
```

-continued

```
        35                  40                  45

Tyr Gly Phe Ala Lys Ser Leu Leu Lys Ala Leu Lys Glu Asp Gly Asp
    50                  55                  60

Ala Val Ile Val Val Phe Asp Ala Lys Ala Pro Ser Phe Arg His Glu
65                  70                  75                  80

Ala Tyr Gly Gly Tyr Lys Ala Gly Arg Ala Pro Thr Pro Glu Asp Phe
                85                  90                  95

Pro Arg Gln Leu Ala Leu Ile Lys Glu Leu Val Asp Leu Leu Gly Leu
            100                 105                 110

Ala Arg Leu Glu Val Pro Gly Tyr Glu Ala Asp Asp Val Leu Ala Ser
        115                 120                 125

Leu Ala Lys Lys Ala Glu Lys Glu Gly Tyr Glu Val Arg Ile Leu Thr
    130                 135                 140

Ala Asp Lys Asp Leu Tyr Gln Leu Leu Ser Asp Arg Ile His Val Leu
145                 150                 155                 160

His Pro Glu Gly Tyr Leu Ile Thr Pro Ala Trp Leu Trp Glu Lys Tyr
                165                 170                 175

Gly Leu Arg Pro Asp Gln Trp Ala Asp Tyr Arg Ala Leu Thr Gly Asp
            180                 185                 190

Glu Ser Asp Asn Leu Pro Gly Val Lys Gly Ile Gly Glu Lys Thr Ala
        195                 200                 205

Arg Lys Leu Leu Glu Glu Trp Gly Ser Leu Glu Ala Leu Leu Lys Asn
    210                 215                 220

Leu Asp Arg Leu Lys Pro Ala Ile Arg Glu Lys Ile Leu Ala His Met
225                 230                 235                 240

Asp Asp Leu Lys Leu Ser Trp Asp Leu Ala Lys Val Arg Thr Asp Leu
                245                 250                 255

Pro Leu Glu Val Asp Phe Ala Lys Arg Arg Glu Pro Asp Arg Glu Arg
            260                 265                 270

Leu Arg Ala Phe Leu Glu Arg Leu Glu Phe Gly Ser Leu Leu His Glu
        275                 280                 285

Phe Gly Leu Leu Glu Ser Pro Lys Ala Leu Glu Glu Ala Pro Trp Pro
    290                 295                 300

Pro Pro Glu Gly Ala Phe Val Gly Phe Val Leu Ser Arg Lys Glu Pro
305                 310                 315                 320

Met Trp Ala Asp Leu Leu Ala Leu Ala Ala Ala Arg Gly Gly Arg Val
                325                 330                 335

His Arg Ala Pro Glu Pro Tyr Lys Ala Leu Arg Asp Leu Lys Glu Ala
            340                 345                 350

Arg Gly Leu Leu Ala Lys Asp Leu Ser Val Leu Ala Leu Arg Glu Gly
        355                 360                 365

Leu Gly Leu Pro Pro Gly Asp Asp Pro Met Leu Leu Ala Tyr Leu Leu
    370                 375                 380

Asp Pro Ser Asn Thr Thr Pro Glu Gly Val Ala Arg Arg Tyr Gly Gly
385                 390                 395                 400

Glu Trp Thr Glu Glu Ala Gly Glu Arg Ala Ala Leu Ser Glu Arg Leu
                405                 410                 415

Phe Ala Asn Leu Trp Gly Arg Leu Glu Gly Glu Glu Arg Leu Leu Trp
            420                 425                 430

Leu Tyr Arg Glu Val Glu Arg Pro Leu Ser Ala Val Leu Ala His Met
        435                 440                 445

Glu Ala Thr Gly Val Arg Leu Asp Val Ala Tyr Leu Arg Ala Leu Ser
    450                 455                 460
```

```
Leu Glu Val Ala Glu Glu Ile Ala Arg Leu Glu Ala Glu Val Phe Arg
465                 470                 475                 480

Leu Ala Gly His Pro Phe Asn Leu Asn Ser Arg Asp Gln Leu Glu Arg
                485                 490                 495

Val Leu Phe Asp Glu Leu Gly Leu Pro Ala Ile Gly Lys Thr Glu Lys
            500                 505                 510

Thr Gly Lys Arg Ser Thr Ser Ala Ala Val Leu Glu Ala Leu Arg Glu
        515                 520                 525

Ala His Pro Ile Val Glu Lys Ile Leu Gln Tyr Arg Glu Leu Thr Lys
    530                 535                 540

Leu Lys Ser Thr Tyr Ile Asp Pro Leu Pro Asp Leu Ile His Pro Arg
545                 550                 555                 560

Thr Gly Arg Leu His Thr Arg Phe Asn Gln Thr Ala Thr Ala Thr Gly
                565                 570                 575

Arg Leu Ser Ser Ser Asp Pro Asn Leu Gln Asn Ile Pro Val Arg Thr
            580                 585                 590

Pro Leu Gly Gln Arg Ile Arg Arg Ala Phe Ile Ala Glu Glu Gly Trp
        595                 600                 605

Leu Leu Val Ala Leu Asp Tyr Ser Gln Ile Glu Leu Arg Val Leu Ala
    610                 615                 620

His Leu Ser Gly Asp Glu Asn Leu Ile Arg Val Phe Gln Glu Gly Arg
625                 630                 635                 640

Asp Ile His Thr Glu Thr Ala Ser Trp Met Phe Gly Val Pro Arg Glu
                645                 650                 655

Ala Val Asp Pro Leu Met Arg Arg Ala Ala Lys Thr Ile Asn Phe Gly
            660                 665                 670

Val Leu Tyr Gly Met Ser Ala His Arg Leu Ser Gln Glu Leu Ala Ile
        675                 680                 685

Pro Tyr Glu Glu Ala Gln Ala Phe Ile Glu Arg Tyr Phe Gln Ser Phe
    690                 695                 700

Pro Lys Val Arg Ala Trp Ile Glu Lys Thr Leu Glu Glu Gly Arg Arg
705                 710                 715                 720

Arg Gly Tyr Val Glu Thr Leu Phe Gly Arg Arg Arg Tyr Val Pro Asp
                725                 730                 735

Leu Glu Ala Arg Val Lys Ser Val Arg Glu Ala Ala Glu Arg Met Ala
            740                 745                 750

Phe Asn Met Pro Val Gln Gly Thr Ala Ala Asp Leu Met Lys Leu Ala
        755                 760                 765

Met Val Lys Leu Phe Pro Arg Leu Glu Glu Met Gly Ala Arg Met Leu
    770                 775                 780

Leu Gln Val His Asp Glu Leu Val Leu Glu Ala Pro Lys Glu Arg Ala
785                 790                 795                 800

Glu Ala Val Ala Arg Leu Ala Lys Glu Val Met Glu Gly Val Tyr Pro
                805                 810                 815

Leu Ala Val Pro Leu Glu Val Glu Val Gly Ile Gly Glu Asp Trp Leu
            820                 825                 830

Ser Ala Lys Glu Gly Ile Asp Gly Arg Gly Gly Gly Gly His His His
        835                 840                 845

His His His
    850
```

<210> SEQ ID NO 67
<211> LENGTH: 750
<212> TYPE: DNA
<213> ORGANISM: Pyrococcus furiosus

```
<220> FEATURE:
<221> NAME/KEY: CDS
<222> LOCATION: (1)..(750)

<400> SEQUENCE: 67

atg cca ttt gaa atc gta ttt gaa ggt gca aaa gag ttt gcc caa ctt       48
Met Pro Phe Glu Ile Val Phe Glu Gly Ala Lys Glu Phe Ala Gln Leu
1               5                   10                  15

ata gac acc gca agt aag tta ata gat gag gcc gcg ttt aaa gtt aca       96
Ile Asp Thr Ala Ser Lys Leu Ile Asp Glu Ala Ala Phe Lys Val Thr
            20                  25                  30

gaa gat ggg ata agc atg agg gcc atg gat cca agt aga gtt gtc ctg      144
Glu Asp Gly Ile Ser Met Arg Ala Met Asp Pro Ser Arg Val Val Leu
        35                  40                  45

att gac cta aat ctc ccg tca agc ata ttt agc aaa tat gaa gtt gtt      192
Ile Asp Leu Asn Leu Pro Ser Ser Ile Phe Ser Lys Tyr Glu Val Val
    50                  55                  60

gaa cca gaa aca att gga gtt aac atg gac cac cta aag aag atc cta      240
Glu Pro Glu Thr Ile Gly Val Asn Met Asp His Leu Lys Lys Ile Leu
65                  70                  75                  80

aag aga ggt aaa gca aag gac acc tta ata ctc aag aaa gga gag gaa      288
Lys Arg Gly Lys Ala Lys Asp Thr Leu Ile Leu Lys Lys Gly Glu Glu
                85                  90                  95

aac ttc tta gag ata aca att caa gga act gca aca aga aca ttt aga      336
Asn Phe Leu Glu Ile Thr Ile Gln Gly Thr Ala Thr Arg Thr Phe Arg
            100                 105                 110

gtt ccc cta ata gat gta gaa gag atg gaa gtt gac ctc cca gaa ctt      384
Val Pro Leu Ile Asp Val Glu Glu Met Glu Val Asp Leu Pro Glu Leu
        115                 120                 125

cca ttc act gca aag gtt gta gtt ctt gga gaa gtc cta aaa gat gct      432
Pro Phe Thr Ala Lys Val Val Val Leu Gly Glu Val Leu Lys Asp Ala
    130                 135                 140

gtt aaa gat gcc tct cta gtg agt gac agc ata aaa ttt att gcc agg      480
Val Lys Asp Ala Ser Leu Val Ser Asp Ser Ile Lys Phe Ile Ala Arg
145                 150                 155                 160

gaa aat gaa ttt ata atg aag gca gag gga gaa acc cag gaa gtt gag      528
Glu Asn Glu Phe Ile Met Lys Ala Glu Gly Glu Thr Gln Glu Val Glu
                165                 170                 175

ata aag cta act ctt gaa gat gag gga tta ttg gac atc gag gtt caa      576
Ile Lys Leu Thr Leu Glu Asp Glu Gly Leu Leu Asp Ile Glu Val Gln
            180                 185                 190

gag gag aca aag agc gca tat gga gtc agc tat ctc tcc gac atg gtt      624
Glu Glu Thr Lys Ser Ala Tyr Gly Val Ser Tyr Leu Ser Asp Met Val
        195                 200                 205

aaa gga ctt gga aag gcc gat gaa gtt aca ata aag ttt gga aat gaa      672
Lys Gly Leu Gly Lys Ala Asp Glu Val Thr Ile Lys Phe Gly Asn Glu
    210                 215                 220

atg ccc atg caa atg gag tat tac att aga gat gaa gga aga ctt aca      720
Met Pro Met Gln Met Glu Tyr Tyr Ile Arg Asp Glu Gly Arg Leu Thr
225                 230                 235                 240

ttc cta ctg gct cca aga gtt gaa gag tga                              750
Phe Leu Leu Ala Pro Arg Val Glu Glu
                245


<210> SEQ ID NO 68
<211> LENGTH: 249
<212> TYPE: PRT
<213> ORGANISM: Pyrococcus furiosus

<400> SEQUENCE: 68

Met Pro Phe Glu Ile Val Phe Glu Gly Ala Lys Glu Phe Ala Gln Leu
1               5                   10                  15
```

```
Ile Asp Thr Ala Ser Lys Leu Ile Asp Glu Ala Ala Phe Lys Val Thr
            20                  25                  30

Glu Asp Gly Ile Ser Met Arg Ala Met Asp Pro Ser Arg Val Val Leu
        35                  40                  45

Ile Asp Leu Asn Leu Pro Ser Ser Ile Phe Ser Lys Tyr Glu Val Val
    50                  55                  60

Glu Pro Glu Thr Ile Gly Val Asn Met Asp His Leu Lys Lys Ile Leu
65                  70                  75                  80

Lys Arg Gly Lys Ala Lys Asp Thr Leu Ile Leu Lys Lys Gly Glu Glu
                85                  90                  95

Asn Phe Leu Glu Ile Thr Ile Gln Gly Thr Ala Thr Arg Thr Phe Arg
            100                 105                 110

Val Pro Leu Ile Asp Val Glu Glu Met Glu Val Asp Leu Pro Glu Leu
        115                 120                 125

Pro Phe Thr Ala Lys Val Val Val Leu Gly Glu Val Leu Lys Asp Ala
    130                 135                 140

Val Lys Asp Ala Ser Leu Val Ser Asp Ser Ile Lys Phe Ile Ala Arg
145                 150                 155                 160

Glu Asn Glu Phe Ile Met Lys Ala Glu Gly Glu Thr Gln Glu Val Glu
                165                 170                 175

Ile Lys Leu Thr Leu Glu Asp Glu Gly Leu Leu Asp Ile Glu Val Gln
            180                 185                 190

Glu Glu Thr Lys Ser Ala Tyr Gly Val Ser Tyr Leu Ser Asp Met Val
        195                 200                 205

Lys Gly Leu Gly Lys Ala Asp Glu Val Thr Ile Lys Phe Gly Asn Glu
    210                 215                 220

Met Pro Met Gln Met Glu Tyr Tyr Ile Arg Asp Glu Gly Arg Leu Thr
225                 230                 235                 240

Phe Leu Leu Ala Pro Arg Val Glu Glu
                245


<210> SEQ ID NO 69
<211> LENGTH: 201
<212> TYPE: DNA
<213> ORGANISM: Sulfolobus acidocaldarius
<220> FEATURE:
<221> NAME/KEY: CDS
<222> LOCATION: (1)..(201)

<400> SEQUENCE: 69

atg gtg aag gta aag ttc aag tat aag ggt gaa gag aaa gaa gta gac       48
Met Val Lys Val Lys Phe Lys Tyr Lys Gly Glu Glu Lys Glu Val Asp
1               5                   10                  15

act tca aag ata aag aag gtt tgg aga gta ggc aaa atg gtg tcc ttt       96
Thr Ser Lys Ile Lys Lys Val Trp Arg Val Gly Lys Met Val Ser Phe
            20                  25                  30

acc tat gac gac aat ggt aag aca ggt aga gga gct gta agc gag aaa      144
Thr Tyr Asp Asp Asn Gly Lys Thr Gly Arg Gly Ala Val Ser Glu Lys
        35                  40                  45

gat gct cca aaa gaa tta tta gac atg tta gca aga gca gaa aga gag      192
Asp Ala Pro Lys Glu Leu Leu Asp Met Leu Ala Arg Ala Glu Arg Glu
    50                  55                  60

aag aaa taa                                                          201
Lys Lys
65


<210> SEQ ID NO 70
<211> LENGTH: 66
```

```
<212> TYPE: PRT
<213> ORGANISM: Sulfolobus acidocaldarius

<400> SEQUENCE: 70

Met Val Lys Val Lys Phe Lys Tyr Lys Gly Glu Glu Lys Glu Val Asp
1               5                   10                  15

Thr Ser Lys Ile Lys Lys Val Trp Arg Val Gly Lys Met Val Ser Phe
            20                  25                  30

Thr Tyr Asp Asp Asn Gly Lys Thr Gly Arg Gly Ala Val Ser Glu Lys
        35                  40                  45

Asp Ala Pro Lys Glu Leu Leu Asp Met Leu Ala Arg Ala Glu Arg Glu
    50                  55                  60

Lys Lys
65


<210> SEQ ID NO 71
<211> LENGTH: 189
<212> TYPE: DNA
<213> ORGANISM: Sulfolobus solfactaricus
<220> FEATURE:
<221> NAME/KEY: CDS
<222> LOCATION: (1)..(189)

<400> SEQUENCE: 71

gca acc gta aag ttc aag tac aaa ggc gaa gaa aaa gag gta gac atc       48
Ala Thr Val Lys Phe Lys Tyr Lys Gly Glu Glu Lys Glu Val Asp Ile
1               5                   10                  15

tcc aag atc aag aaa gta tgg cgt gtg ggc aag atg atc tcc ttc acc       96
Ser Lys Ile Lys Lys Val Trp Arg Val Gly Lys Met Ile Ser Phe Thr
            20                  25                  30

tac gac gag ggc ggt ggc aag acc ggc cgt ggt gcg gta agc gaa aag      144
Tyr Asp Glu Gly Gly Gly Lys Thr Gly Arg Gly Ala Val Ser Glu Lys
        35                  40                  45

gac gcg ccg aag gag ctg ctg cag atg ctg gag aag cag aaa aag          189
Asp Ala Pro Lys Glu Leu Leu Gln Met Leu Glu Lys Gln Lys Lys
    50                  55                  60


<210> SEQ ID NO 72
<211> LENGTH: 63
<212> TYPE: PRT
<213> ORGANISM: Sulfolobus solfactaricus

<400> SEQUENCE: 72

Ala Thr Val Lys Phe Lys Tyr Lys Gly Glu Glu Lys Glu Val Asp Ile
1               5                   10                  15

Ser Lys Ile Lys Lys Val Trp Arg Val Gly Lys Met Ile Ser Phe Thr
            20                  25                  30

Tyr Asp Glu Gly Gly Gly Lys Thr Gly Arg Gly Ala Val Ser Glu Lys
        35                  40                  45

Asp Ala Pro Lys Glu Leu Leu Gln Met Leu Glu Lys Gln Lys Lys
    50                  55                  60


<210> SEQ ID NO 73
<211> LENGTH: 57
<212> TYPE: PRT
<213> ORGANISM: Methanopyrus kandleri

<400> SEQUENCE: 73

Val Ala Leu Val Tyr Asp Ala Glu Phe Val Gly Ser Glu Arg Glu Phe
1               5                   10                  15

Glu Glu Glu Arg Glu Thr Phe Leu Lys Gly Val Lys Ala Tyr Asp Gly
            20                  25                  30
```

```
Val Leu Ala Thr Arg Tyr Leu Met Glu Arg Ser Ser Ser Ala Lys Asn
        35                  40                  45

Asp Glu Glu Leu Leu Glu Leu His Gln
    50                  55


<210> SEQ ID NO 74
<211> LENGTH: 29
<212> TYPE: PRT
<213> ORGANISM: Escherichia coli

<400> SEQUENCE: 74

Gly Gly Asn Ala Leu Lys Phe Tyr Ala Ser Val Arg Leu Asp Ile Arg
1               5                   10                  15

Arg Ile Gly Ala Ile Lys Asp Gly Asp Glu Val Val Gly
            20                  25


<210> SEQ ID NO 75
<211> LENGTH: 57
<212> TYPE: PRT
<213> ORGANISM: Methanopyrus kandleri

<400> SEQUENCE: 75

Val Pro Ile Asp Glu Lys Glu Glu Arg Ile Leu Glu Ile Leu Arg Glu
1               5                   10                  15

Asn Pro Trp Thr Pro His Asp Glu Ile Ala Arg Arg Gly Gly Leu Ser
            20                  25                  30

Val Ser Glu Val Glu Gly Glu Lys Asp Pro Glu Ser Ser Gly Ile Tyr
        35                  40                  45

Ser Leu Trp Ser Arg Val Val Val Asn
    50                  55


<210> SEQ ID NO 76
<211> LENGTH: 40
<212> TYPE: PRT
<213> ORGANISM: Escherichia coli

<400> SEQUENCE: 76

Ile Asp Arg Ile Asp Arg Lys Ile Leu Asn Glu Leu Gln Lys Asp Gly
1               5                   10                  15

Arg Arg Ile Ser Asn Glu Leu Ala Lys Arg Val Gly Leu Ser Val Ser
            20                  25                  30

Thr Val Arg Glu Arg Val Arg Arg
        35                  40


<210> SEQ ID NO 77
<211> LENGTH: 40
<212> TYPE: PRT
<213> ORGANISM: Methanopyrus kandleri

<400> SEQUENCE: 77

Leu Lys Leu Gln Asp Arg Tyr Gly Ile Arg Glu Asp Val Ala Leu Cys
1               5                   10                  15

Leu Ala Arg Ala Phe Asp Gly Ser Ile Ser Met Ile Ala Thr Thr Pro
            20                  25                  30

Tyr Arg Thr Leu Lys Asp Val Cys
        35                  40


<210> SEQ ID NO 78
<211> LENGTH: 15
<212> TYPE: PRT
<213> ORGANISM: Methanopyrus kandleri
```

<400> SEQUENCE: 78

Pro Asp Leu Thr Leu Glu Glu Ala Lys Ser Val Asn Arg Thr Leu
1 5 10 15

<210> SEQ ID NO 79
<211> LENGTH: 30
<212> TYPE: PRT
<213> ORGANISM: Methanopyrus kandleri

<400> SEQUENCE: 79

Ala Thr Leu Ile Asp Glu His Gly Leu Ser Pro Ala Asp Ala Ala Asp
1 5 10 15

Glu Leu Ile Glu His Phe Glu Ser Ile Ala Gly Ile Leu Ala
20 25 30

<210> SEQ ID NO 80
<211> LENGTH: 11
<212> TYPE: PRT
<213> ORGANISM: Methanopyrus kandleri

<400> SEQUENCE: 80

Thr Asp Leu Glu Glu Ile Glu Arg Met Tyr Glu
1 5 10

<210> SEQ ID NO 81
<211> LENGTH: 15
<212> TYPE: PRT
<213> ORGANISM: Methanopyrus kandleri

<400> SEQUENCE: 81

Glu Gly Arg Leu Ser Glu Glu Ala Tyr Arg Ala Ala Val Glu Ile
1 5 10 15

<210> SEQ ID NO 82
<211> LENGTH: 57
<212> TYPE: PRT
<213> ORGANISM: Thermococcus kodakaraensis

<400> SEQUENCE: 82

Ala Glu Leu Thr Lys Lys Glu Gly Val Gly Arg Lys Thr Ala Glu Arg
1 5 10 15

Leu Leu Arg Ala Phe Gly Asn Pro Glu Arg Val Lys Gln Leu Ala Arg
20 25 30

Glu Phe Glu Ile Glu Lys Leu Ala Ser Val Glu Gly Val Gly Glu Arg
35 40 45

Val Leu Arg Ser Leu Val Pro Gly Tyr
50 55

<210> SEQ ID NO 83
<211> LENGTH: 27
<212> TYPE: PRT
<213> ORGANISM: Methanopyrus kandleri

<400> SEQUENCE: 83

Ala Ser Leu Ile Ser Ile Arg Gly Ile Asp Arg Glu Arg Ala Glu Arg
1 5 10 15

Leu Leu Lys Lys Tyr Gly Gly Tyr Ser Lys Val
20 25

<210> SEQ ID NO 84
<211> LENGTH: 10
<212> TYPE: PRT

<213> ORGANISM: Methanopyrus kandleri

<400> SEQUENCE: 84

```
Arg Glu Ala Gly Val Glu Glu Leu Arg Glu
1               5                   10
```

<210> SEQ ID NO 85
<211> LENGTH: 13
<212> TYPE: PRT
<213> ORGANISM: Methanopyrus kandleri

<400> SEQUENCE: 85

```
Asp Gly Leu Thr Asp Ala Gln Ile Arg Glu Leu Lys Gly
1               5                   10
```

<210> SEQ ID NO 86
<211> LENGTH: 27
<212> TYPE: PRT
<213> ORGANISM: Methanopyrus kandleri

<400> SEQUENCE: 86

```
Leu Lys Thr Leu Glu Ser Ile Val Gly Asp Leu Glu Lys Ala Asp Glu
1               5                   10                  15

Leu Lys Arg Lys Tyr Gly Ser Ala Ser Ala Val
            20                  25
```

<210> SEQ ID NO 87
<211> LENGTH: 10
<212> TYPE: PRT
<213> ORGANISM: Methanopyrus kandleri

<400> SEQUENCE: 87

```
Arg Arg Leu Pro Val Glu Glu Leu Arg Glu
1               5                   10
```

<210> SEQ ID NO 88
<211> LENGTH: 13
<212> TYPE: PRT
<213> ORGANISM: Methanopyrus kandleri

<400> SEQUENCE: 88

```
Leu Gly Phe Ser Asp Asp Glu Ile Ala Glu Ile Lys Gly
1               5                   10
```

<210> SEQ ID NO 89
<211> LENGTH: 28
<212> TYPE: PRT
<213> ORGANISM: Methanopyrus kandleri

<400> SEQUENCE: 89

```
Ile Pro Lys Lys Leu Arg Glu Ala Phe Asp Leu Glu Thr Ala Ala Glu
1               5                   10                  15

Leu Tyr Glu Arg Tyr Gly Ser Leu Lys Glu Ile Gly
            20                  25
```

<210> SEQ ID NO 90
<211> LENGTH: 10
<212> TYPE: PRT
<213> ORGANISM: Methanopyrus kandleri

<400> SEQUENCE: 90

```
Arg Arg Leu Ser Tyr Asp Asp Leu Leu Glu
1               5                   10
```

```
<210> SEQ ID NO 91
<211> LENGTH: 15
<212> TYPE: PRT
<213> ORGANISM: Methanopyrus kandleri

<400> SEQUENCE: 91

Leu Gly Ala Thr Pro Lys Ala Ala Ala Glu Ile Lys Gly Pro Glu
1               5                   10                  15


<210> SEQ ID NO 92
<211> LENGTH: 28
<212> TYPE: PRT
<213> ORGANISM: Methanopyrus kandleri

<400> SEQUENCE: 92

Lys Phe Leu Leu Asn Ile Glu Gly Val Gly Pro Lys Leu Ala Glu Arg
1               5                   10                  15

Ile Leu Glu Ala Val Asp Tyr Asp Leu Glu Arg Leu
            20                  25


<210> SEQ ID NO 93
<211> LENGTH: 26
<212> TYPE: PRT
<213> ORGANISM: Methanopyrus kandleri

<400> SEQUENCE: 93

Ala Ser Leu Asn Pro Glu Glu Leu Ala Glu Val Glu Gly Leu Gly Glu
1               5                   10                  15

Glu Leu Ala Glu Arg Val Val Tyr Ala Ala
            20                  25


<210> SEQ ID NO 94
<211> LENGTH: 40
<212> TYPE: PRT
<213> ORGANISM: Methanopyrus kandleri

<400> SEQUENCE: 94

Trp Lys Glu Trp Leu Glu Arg Lys Val Gly Glu Gly Arg Ala Arg Arg
1               5                   10                  15

Leu Ile Glu Tyr Phe Gly Ser Ala Gly Glu Val Gly Lys Leu Val Glu
            20                  25                  30

Asn Ala Glu Val Ser Lys Leu Leu
        35                  40


<210> SEQ ID NO 95
<211> LENGTH: 15
<212> TYPE: PRT
<213> ORGANISM: Methanopyrus kandleri

<400> SEQUENCE: 95

Val Pro Gly Ile Gly Asp Glu Ala Val Ala Arg Leu Val Pro Gly
1               5                   10                  15


<210> SEQ ID NO 96
<211> LENGTH: 28
<212> TYPE: PRT
<213> ORGANISM: Methanopyrus kandleri

<400> SEQUENCE: 96

Tyr Lys Thr Leu Arg Asp Ala Gly Leu Thr Pro Ala Glu Ala Glu Arg
1               5                   10                  15

Val Leu Lys Arg Tyr Gly Ser Val Ser Lys Val Gln
            20                  25
```

<210> SEQ ID NO 97
<211> LENGTH: 10
<212> TYPE: PRT
<213> ORGANISM: Methanopyrus kandleri

<400> SEQUENCE: 97

Glu Gly Ala Thr Pro Asp Glu Leu Arg Glu
1 5 10

<210> SEQ ID NO 98
<211> LENGTH: 13
<212> TYPE: PRT
<213> ORGANISM: Methanopyrus kandleri

<400> SEQUENCE: 98

Leu Gly Leu Gly Asp Ala Lys Ile Ala Arg Ile Leu Gly
1 5 10

<210> SEQ ID NO 99
<211> LENGTH: 27
<212> TYPE: PRT
<213> ORGANISM: Methanopyrus kandleri

<400> SEQUENCE: 99

Leu Arg Ser Leu Val Asn Lys Arg Leu Asp Val Asp Thr Ala Tyr Glu
1 5 10 15

Leu Lys Arg Arg Tyr Gly Ser Val Ser Ala Val
20 25

<210> SEQ ID NO 100
<211> LENGTH: 10
<212> TYPE: PRT
<213> ORGANISM: Methanopyrus kandleri

<400> SEQUENCE: 100

Arg Lys Ala Pro Val Lys Glu Leu Arg Glu
1 5 10

<210> SEQ ID NO 101
<211> LENGTH: 15
<212> TYPE: PRT
<213> ORGANISM: Methanopyrus kandleri

<400> SEQUENCE: 101

Leu Gly Leu Ser Asp Arg Lys Ile Ala Arg Ile Lys Gly Ile Pro
1 5 10 15

<210> SEQ ID NO 102
<211> LENGTH: 27
<212> TYPE: PRT
<213> ORGANISM: Methanopyrus kandleri

<400> SEQUENCE: 102

Glu Thr Met Leu Gln Val Arg Gly Met Ser Val Glu Lys Ala Glu Arg
1 5 10 15

Leu Leu Glu Arg Phe Asp Thr Trp Thr Lys Val
20 25

<210> SEQ ID NO 103
<211> LENGTH: 9
<212> TYPE: PRT
<213> ORGANISM: Methanopyrus kandleri

<400> SEQUENCE: 103

Lys Glu Ala Pro Val Ser Glu Leu Val
1 5

<210> SEQ ID NO 104
<211> LENGTH: 16
<212> TYPE: PRT
<213> ORGANISM: Methanopyrus kandleri

<400> SEQUENCE: 104

Val Pro Gly Val Gly Leu Ser Leu Val Lys Glu Ile Lys Ala Gln Val
1 5 10 15

<210> SEQ ID NO 105
<211> LENGTH: 27
<212> TYPE: PRT
<213> ORGANISM: Methanopyrus kandleri

<400> SEQUENCE: 105

Lys Ala Leu Leu Asp Val Lys Gly Val Ser Pro Glu Leu Ala Asp Arg
1 5 10 15

Leu Val Glu Glu Leu Gly Ser Pro Tyr Arg Val
20 25

<210> SEQ ID NO 106
<211> LENGTH: 9
<212> TYPE: PRT
<213> ORGANISM: Methanopyrus kandleri

<400> SEQUENCE: 106

Leu Thr Ala Lys Lys Ser Asp Leu Met
1 5

<210> SEQ ID NO 107
<211> LENGTH: 16
<212> TYPE: PRT
<213> ORGANISM: Methanopyrus kandleri

<400> SEQUENCE: 107

Val Glu Arg Val Gly Pro Lys Leu Ala Glu Arg Ile Arg Ala Ala Gly
1 5 10 15

<210> SEQ ID NO 108
<211> LENGTH: 27
<212> TYPE: PRT
<213> ORGANISM: Escherichia coli

<400> SEQUENCE: 108

Lys Glu Leu Ile Lys Thr Asn Gly Val Gly Pro Lys Leu Ala Leu Ala
1 5 10 15

Ile Leu Ser Gly Met Ser Ala Gln Gln Phe Val
20 25

<210> SEQ ID NO 109
<211> LENGTH: 26
<212> TYPE: PRT
<213> ORGANISM: Escherichia coli

<400> SEQUENCE: 109

Asn Ala Val Glu Arg Glu Glu Val Gly Ala Leu Pro Gly Ile Gly Lys
1 5 10 15

Lys Thr Ala Glu Arg Leu Ile Val Glu Met
20 25

<210> SEQ ID NO 110

<211> LENGTH: 57
<212> TYPE: PRT
<213> ORGANISM: Homo sapiens

<400> SEQUENCE: 110

```
Ala Glu Ala Lys Lys Leu Pro Gly Val Gly Thr Lys Ile Ala Glu Lys
1               5                   10                  15

Ile Asp Glu Phe Leu Ala Thr Gly Lys Leu Arg Lys Leu Glu Lys Ile
            20                  25                  30

Arg Gln Asp Asp Thr Ser Ser Ser Ile Val Ser Gly Ile Gly Pro Ser
        35                  40                  45

Ala Ala Arg Lys Phe Val Asp Glu Gly
    50                  55
```

<210> SEQ ID NO 111
<211> LENGTH: 27
<212> TYPE: PRT
<213> ORGANISM: Escherichia coli

<400> SEQUENCE: 111

```
Leu Glu Val Met Glu Val Pro Gly Val Gly Pro Lys Thr Ala Arg Gly
1               5                   10                  15

Leu Tyr Glu Ala Leu Gly Ile Asp Ser Leu Glu
            20                  25
```

<210> SEQ ID NO 112
<211> LENGTH: 12
<212> TYPE: PRT
<213> ORGANISM: Escherichia coli

<400> SEQUENCE: 112

```
Lys Leu Lys Glu Ala Leu Glu Arg Gly Asp Leu Leu
1               5                   10
```

<210> SEQ ID NO 113
<211> LENGTH: 16
<212> TYPE: PRT
<213> ORGANISM: Escherichia coli

<400> SEQUENCE: 113

```
Leu Lys Gly Phe Gly Ala Lys Lys Ala Glu Arg Ile Lys Glu Gly Leu
1               5                   10                  15
```

<210> SEQ ID NO 114
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 114

```
cctgctctgc cgcttcacgc                                                  20
```

<210> SEQ ID NO 115
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 115

```
gcacagcggc tggctgagga                                                  20
```

```
<210> SEQ ID NO 116
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116

cacatggtac agcaagcctg gc                                            22


<210> SEQ ID NO 117
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117

cccgtatctg ctgggatact ggc                                           23


<210> SEQ ID NO 118
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118

cagcggtgct gactgaatca tgg                                           23


<210> SEQ ID NO 119
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119

cctgcctgcc gcttcacgc                                                19


<210> SEQ ID NO 120
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120

ccaatacccg tttcatcgcg gc                                            22
```